(12) United States Patent
Wang et al.

(10) Patent No.: US 9,090,593 B2
(45) Date of Patent: Jul. 28, 2015

(54) BICYCLIC COMPOUNDS AS PIM INHIBITORS

(75) Inventors: Hui-Ling Wang, Thousand Oaks, CA (US); Kaustav Biswas, Agoura Hills, CA (US); Victor J. Cee, Thousand Oaks, CA (US); Frank Chavez, Jr., Camarillo, CA (US); Bradley J. Herberich, Newbury Park, CA (US); Claire L. M. Jackson, Thousand Oaks, CA (US); Brian A. Lanman, Woodland Hills, CA (US); Matthew Lee, Calabasas, CA (US); Thomas Nixey, Newbury Park, CA (US); Liping H. Pettus, Thousand Oaks, CA (US); Anthony B. Reed, Newbury Park, CA (US); Robert M. Rzasa, Ventura, CA (US); Shannon Rumfelt, Camarillo, CA (US); Andrew Tasker, Simi Valley, CA (US); Bin Wu, Thousand Oaks, CA (US); Ryan Wurz, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 13/991,603

(22) PCT Filed: Dec. 7, 2011

(86) PCT No.: PCT/US2011/063776
§ 371 (c)(1),
(2), (4) Date: Sep. 30, 2013

(87) PCT Pub. No.: WO2012/078777
PCT Pub. Date: Jun. 14, 2012

(65) Prior Publication Data
US 2014/0031360 A1   Jan. 30, 2014

Related U.S. Application Data

(60) Provisional application No. 61/421,569, filed on Dec. 9, 2010.

(51) Int. Cl.
| C07D 401/14 | (2006.01) |
| C07D 403/04 | (2006.01) |
| C07D 403/14 | (2006.01) |
| C07D 405/14 | (2006.01) |
| C07D 413/14 | (2006.01) |
| C07D 417/14 | (2006.01) |
| C07D 471/04 | (2006.01) |
| C07D 405/04 | (2006.01) |

(52) U.S. Cl.
CPC ............ *C07D 401/14* (2013.01); *C07D 403/04* (2013.01); *C07D 403/14* (2013.01); *C07D 405/04* (2013.01); *C07D 405/14* (2013.01); *C07D 413/14* (2013.01); *C07D 417/14* (2013.01); *C07D 471/04* (2013.01)

(58) Field of Classification Search
CPC .. C07D 401/04; C07D 403/04; C07D 403/14; C07D 405/14
USPC ................................ 548/362.5, 466; 546/113
See application file for complete search history.

(56) References Cited

U.S. PATENT DOCUMENTS

| 5,744,488 | A | 4/1998 | Cross et al. |
| 6,180,643 | B1 | 1/2001 | Zablocki et al. |
| 6,184,238 | B1 | 2/2001 | Takano et al. |
| 6,358,972 | B1 | 3/2002 | Filla et al. |
| 7,399,780 | B2 | 7/2008 | Berg et al. |
| 2004/0127536 | A1 | 7/2004 | Bhagwat et al. |
| 2004/0127538 | A1 | 7/2004 | Oinuma et al. |
| 2005/0090529 | A1 | 4/2005 | McAlpine et al. |
| 2005/0137201 | A1 | 6/2005 | Aronov et al. |
| 2005/0153987 | A1 | 7/2005 | Berg et al. |
| 2005/0282880 | A1 | 12/2005 | Oinuma et al. |
| 2007/0043048 | A1 | 2/2007 | Bollbuck et al. |
| 2007/0191604 | A1 | 8/2007 | Cooper et al. |

(Continued)

FOREIGN PATENT DOCUMENTS

| WO | 00/43393 A1 | 7/2000 |
| WO | 01/53268 A2 | 7/2001 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Michels, et al. Document No. 153:359014, retrieved from CAPLUS; Aug. 26, 2010.*

(Continued)

*Primary Examiner* — Shawquia Jackson
(74) *Attorney, Agent, or Firm* — Bernard P. Friedrichsen

(57) ABSTRACT

The invention relates to bicyclic compounds of formula (1'), and salts thereof. In some embodiments, the invention relates to inhibitors or modulators of Pim-1 and/or Pim-2, and/or Pim-3 protein kinase activity or enzyme function. In still further embodiments, the invention relates to pharmaceutical compositions comprising compounds disclosed herein, and their use in the prevention and treatment of Pim kinase related conditions and diseases, preferably cancer.

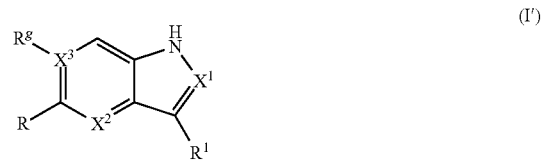

51 Claims, No Drawings

(56) References Cited

U.S. PATENT DOCUMENTS

| | | |
|---|---|---|
| 2008/0113988 A1 | 5/2008 | Andres-Gil et al. |
| 2008/0176833 A1 | 7/2008 | Adler et al. |
| 2009/0118284 A1 | 5/2009 | Cooper et al. |
| 2009/0203690 A1 | 8/2009 | Akritopoulou-Zane et al. |
| 2009/0203691 A1 | 8/2009 | Oinuma et al. |
| 2009/0318446 A1 | 12/2009 | Fischer et al. |
| 2010/0160287 A1 | 6/2010 | Wannamaker et al. |
| 2010/0267707 A1 | 10/2010 | Kozina et al. |
| 2011/0033417 A1 | 2/2011 | Anilkumar et al. |
| 2011/0086834 A1 | 4/2011 | Chen et al. |
| 2011/0104110 A1 | 5/2011 | Anikumar et al. |
| 2011/0130384 A1 | 6/2011 | Setah et al. |
| 2011/0172221 A1 | 7/2011 | Michels et al. |

FOREIGN PATENT DOCUMENTS

| | | |
|---|---|---|
| WO | 02/10137 A2 | 2/2002 |
| WO | 2005/009997 A1 | 2/2005 |
| WO | 2009/149836 A1 | 12/2009 |
| WO | 2010/002933 A1 | 1/2010 |
| WO | 2010/094405 A1 | 8/2010 |
| WO | 2011/067189 A2 | 6/2011 |

OTHER PUBLICATIONS

John L. Lamattina et al: "Antiulcer agents. 4-Substituted 2-guanidinothiazoles: reversible, competitive, and selective inhibitors of gastric H+, K+-ATPase", Journal of Medicinal Chemistry, vol. 33, No. 2, Feb. 1, 1990, pp. 543-552.

Matzen L et al: "5-HT Reuptake Inhibitors 1 with 5-HT1B/1D Antagonistic Activity: A New Approach toward Efficient Antidepressants", Journal of Medicinal Chemistry, American Chemical Society, US, vol. 43, Jan. 1, 2000, pp. 1149-1157.

Francisco-Javier Gamo et al: "Thousands of chemical starting points for antimalarial lead identification", Nature, Nature Publishing Group, United Kingdom, vol. 465, No. 7296 May 20, 2010, pp. 305-310.

European Patent Office Communication—European Search Report Dated Sep. 29, 2014.

Lu et al., Pim2 is required for maintaining multiple myeloma cell growth through modulating TSC2 phosphorylation, Blood, August 29, 2013 x No. 122, No. 9.

Keeton et al, AZD1208, a potent and selective pan-Pim kinase inhibitor, demonstrates efficacy in preclinical models of acute myeloid leukemia, Blood, Feb. 6, 2014 x vol. 123, No. 6.

Garcia et al, Pan-PIM Kinase Inhibition Provides a Novel Therapy for Treating Hematologic Cancers, Clin Cancer Res; 20(7) Apr. 1, 2014.

Nawijn et al., For better or for worse: the role of Pim oncogenes in tumorigenesis, Nature Reviews, Cancer, vol. 11, Jan. 2011.

Fay Tonsiengsom, et al: "Reduction of 2,5-Bis(3¢-indolyl)pyrazines to 2,5-Bis(3¢-indolyl)piperazines: Synthesis of Bisindolylpiperazine Marine Alkaloids Dragmacidin A, B, and C", Synthesis vol. 2006, No. 01 , Jan. 1, 2006, pp. 49-54.

Karl-Heinz Pfoertner et al: "Herstellungder 1H-IH-Indazole durch Photolyse von 2-Aminophenylketon-)-(Methoxycarbonyl)oximen und von 3,1,4-Benzoxadiazepin-2(1H)-onen"Helvetica Chimica Acta, vol. 65, No. 3, May 5, 1982 pp. 798-806.

Rufine Akue-Gedu et al: "Synthesis and Biological activities of aminopyrimidyl-indoles structurallyrelated to meridianins" Bioorganic & Medicinal Chemistry, vol. 17, No. 13, Jul. 1, 2009.

CAS rn: 1176535-07-1.

CAS rn: 1177100-99-0.

\* cited by examiner

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Oligonucleotide PCR primer

<400> SEQUENCE: 1
tggctgatca atgctcttgt ccaaaatc                                           28

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide PCR primer

<400> SEQUENCE: 2
attagaattc tatttgctgg gccccggc                                           28

<210> SEQ ID NO 3
<211> LENGTH: 29
<212> TYPE: DNA
<213> ORGANISM: Artificial Sequence
<220> FEATURE:
<223> OTHER INFORMATION: Oligonucleotide PCR primer
```

```
<400> SEQUENCE: 3
tgcaggatcc atgttgacca agcctctac                              29

<210> SEQ ID NO 4
<211> LENGTH: 28
<212> TYPE: DNA
<213> ORGANISM: Artificial Sequence
<220> FEATURE:
<223> OTHER INFORMATION: Oligonucleotide PCR primer

<400> SEQUENCE: 4
acgtgaattc tatccctgtg acatggcc                               28
```

BICYCLIC COMPOUNDS AS PIM INHIBITORS

FIELD OF THE INVENTION

The present invention relates to certain bicyclic compounds that are Pim inhibitors, pharmaceutical compositions containing such compounds, and processes for preparing such compounds. Provided herein also are methods of treating disorders or diseases treatable by inhibition of Pims, such as cancer, and the like.

BACKGROUND

The role of Pim serine/threonine kinases in the pathogenesis and therapy of hematological malignancies and solid cancers is of interest to the medical community. Pim proteins are constitutively active and are over-expressed in a subset of human cancers, many of hematological origin. Pim kinases also regulate aspects of transformation and drug resistance in hematological malignancies such as DLBCL, MM, and AML where they are overexpressed or mutated. Aberrant expression of Pim-1 or Pim-2 promotes tumor development in mouse models of lymphoma and prostate cancer. Elevated Pim-1 levels correlate with poor prognosis in DLBCL and mantle cell lymphoma. Pims play a role in some solid tumors (prostate cancer, and head and neck cancer). Whereas elevated levels of Pim-1 and Pim-2 were mostly found in hematological malignancies and prostate cancer, increased Pim-3 expression was observed in different solid tumors. Pim kinases are constitutively active and their activity supports in vitro and in vivo tumour cell growth and survival through modification of an increasing number of common as well as isoform-specific substrates including several cell cycle regulators and apoptosis mediators. Pim-1 but not Pim-2 mediates homing and migration of normal and malignant hematopoietic cells by regulating chemokine receptor surface expression. Knockdown experiments by RNA interference or dominant-negative acting mutants suggested that Pim kinases are important for maintenance of a transformed phenotype and therefore potential therapeutic targets.

There exists a need for compounds that inhibit the growth of tumors, treat cancer, modulate cell cycle arrest, and/or inhibit molecules such as Pim-1, Pim-2, or Pim-3 and pharmaceutical formulations and medicaments that contain such compounds.

SUMMARY OF THE INVENTION

The present invention comprises a new class of bicyclic compounds useful in the treatment of diseases, such as Pim-mediated diseases, for example cancer. Accordingly, the invention also comprises pharmaceutical compositions comprising the compounds, methods for the treatment of Pim-mediated diseases and other maladies, such as treatment of hematological malignancies and of solid tumors, for example prostate cancer, and head and neck cancer, using the compounds and compositions of the invention, and intermediates and processes useful for the preparation of the compounds of the invention.

The compounds of the invention are represented by the following general structure:

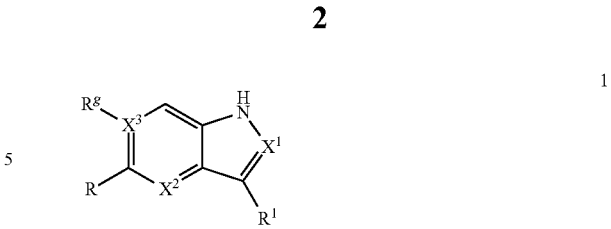

and a pharmaceutically acceptable salt thereof; wherein $X^1$; $X^2$; $X^3$; R; $R^1$; and $R^g$ are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

One aspect of the current invention relates to compounds having the general structure of formula (I):
(I);

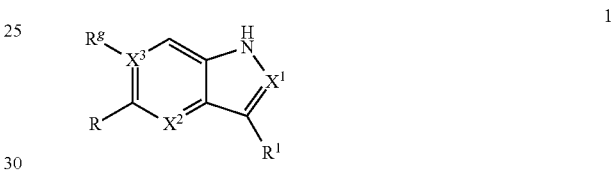

wherein $X^1$ is CH or N;
wherein $X^2$ is CH or N;
wherein $X^3$ is C or N;
wherein R is optionally substituted aryl or optionally substituted 5-membered heterocyclyl or optionally substituted 6-membered heterocyclyl or optionally substituted 9 membered heterocyclyl or optionally substituted 10 membered heterocyclyl or cycloalkylalkenyl or halo, or 1,2,2',3',5',6'-hexahydrospiro[indole-3,4'-pyranyl] or alkoxycarbonyl, or HOOC—, or alkylcarbonylamino, or phenylaminocarbonyl, or aminocarbonyl, alkylaminocarbonyl, or phenylcarbonylamino, or benzylaminocarbonyl, or nitro or amino; provided R is not oxadiazolyl or thiadiazolyl;
wherein $R^1$ is optionally substituted 5-membered heterocyclyl, optionally substituted 6-membered heterocyclyl, or optionally substituted 9 membered heterocyclyl;
$R^g$ is H or F;
and a pharmaceutically acceptable salt thereof;
provided $R^1$ is not 4-pyridyl when R is 3-pyridyl, when $X^1$ is CH, $X^2$ is CH and $X^3$ is C; further provided R is not 2,6-dimethyl-3,5-dicyano-dihydropyridyl when $X^1$ is N, $X^2$ is CH and $X^3$ is C; further provided $R^1$ is not 2-(4-morpholinyl-4-phenylamino)-4-pyrimidyl when $X^1$ is CH, $X^2$ is CH and $X^3$ is C; further provided R is not 2-(3-furyl)-(5-phenyl-2-aminopropoxy)-3-pyridyl when $X^1$ is N, $X^2$ is CH and $X^3$ is C; further provided R is not triazolyl or tetrazolyl when $R^1$ is 4-pyridyl or 3-pyridyl or 3-quinolinyl, when $X^1$ is N, $X^2$ is CH and $X^3$ is C; further provided R is not 7,9-dicyano-[1,3,4,8-tetrahydropyrido[2,1-c][1,4]oxazin-8-yl when $X^1$ is N, $X^2$ is CH and $X^3$ is C.

In another embodiment, wherein $X^1$ is CH; wherein $X^2$ is CH; wherein $X^3$ is C; and wherein $R^g$ is H; and a pharmaceutically acceptable salt thereof.

In another embodiment, the group $X^1$ is N; wherein $X^2$ is CH; wherein $X^3$ is C; and wherein $R^g$ is H; and a pharmaceutically acceptable salt thereof.

In another embodiment, the group $X^1$ is CH; wherein $X^2$ is N; wherein $X^3$ is C; and wherein $R^g$ is H; and a pharmaceutically acceptable salt thereof.

In another embodiment, the group $R^1$ is

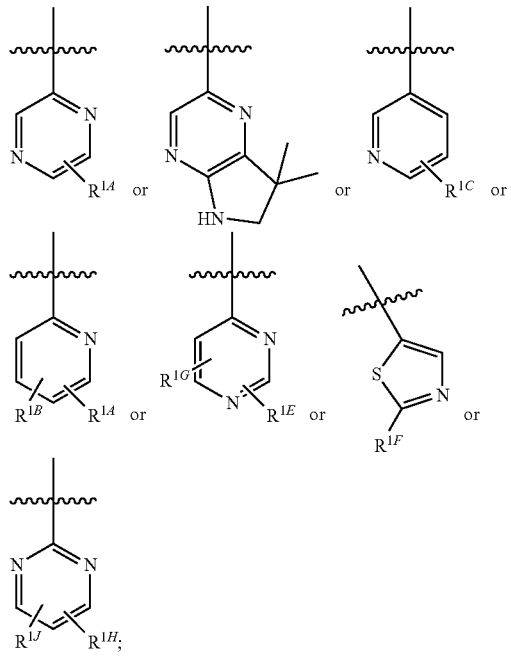

Wherein $R^{1A}$ is H, hydroxy, $C_1$-$C_3$-alkoxy, optionally substituted 5-6-membered heterocyclyl, or optionally substituted 5-6-membered heterocyclyl-amino or optionally substituted 5-6-membered heterocyclyl-(alkyl)amino or optionally substituted 5-6-membered heterocyclyloxy or alkylamino or optionally substituted 5-6-membered heterocyclyl-S—, or optionally substituted phenylamino or 9-10 membered nitrogen containing heterocyclyl;

Wherein $R^{1B}$ is H hydroxy or $C_1$-$C_3$-alkoxy;

Wherein $R^{1C}$ is H, hydroxy, $C_1$-$C_3$-alkoxy, optionally substituted 5-6-membered heterocyclyl, or optionally substituted 5-6-membered heterocyclyl-amino;

Wherein $R^{1E}$ is H, hydroxy, $C_1$-$C_3$-alkoxy, optionally substituted 5-6-membered heterocyclyl, optionally substituted 5-6-membered heterocyclyl-amino, optionally substituted 5-6-membered heterocyclyl-(alkyl)amino, optionally substituted 5-6-membered heterocyclyloxy or alkylamino;

Wherein $R^{1F}$ is H, or optionally substituted 6-membered heterocyclyl;

Wherein $R^{1G}$ is H, hydroxy, or $C_1$-$C_3$-alkoxy;

Wherein $R^{1J}$ is H, hydroxy, $C_1$-$C_3$-alkoxy, optionally substituted 5-6-membered heterocyclyl, or optionally substituted 5-6-membered heterocyclyl-amino or optionally substituted 5-6-membered heterocyclyl-(alkyl)amino or optionally substituted 5-6-membered heterocyclyloxy or alkylamino or optionally substituted 5-6-membered heterocyclyl-S—, or optionally substituted phenyl or 9-10 membered nitrogen containing heterocyclyl;

Wherein $R^{1H}$ is H, hydroxy, or $C_1$-$C_3$-alkoxy; and a pharmaceutically acceptable salt thereof.

In another embodiment, the group R is halo, $C_3$-$C_6$-cycloalkyl-$C_2$-$C_3$-alkenyl, $C_{1-4}$ alkoxycarbonyl, HOOC—, $C_{1-4}$ alkylcarbonylamino, phenylcarbonylamino, aminocarbonyl, $C_{1-4}$ alkylaminocarbonyl, phenylcarbonylamino, benzylaminocarbonyl, nitro or amino; and a pharmaceutically acceptable salt thereof.

In another embodiment, the group R is bromo, cyclopropylethenyl, methoxycarbonyl, nitro, amino, aminocarbonyl, ethylcarbonylamino, phenylcarbonylamino, isopropylaminocarbonyl, HOOC—, phenylaminocarbonyl, or benzylaminocarbonyl; and a pharmaceutically acceptable salt thereof.

In another embodiment, R is optionally substituted phenyl or optionally substituted 5-membered heterocyclyl or optionally substituted 6-membered heteroaryl or optionally substituted 9 membered heteroaryl or optionally substituted 10 membered heteroaryl; and a pharmaceutically acceptable salt thereof.

In another embodiment, R is optionally substituted phenyl, optionally substituted pyrrolidinyl, optionally substituted piperidinyl, optionally substituted thiazolyl, optionally substituted pyrazolyl, optionally substituted pyrazinyl, optionally substituted pyridazinyl, optionally substituted pyrimidinyl, optionally substituted pyridyl, optionally substituted indazolyl or optionally substituted quinolyl; and a pharmaceutically acceptable salt thereof.

In another embodiment, R is 2-oxo-1-pyrrolidinyl, 2-oxo-1-piperidinyl, thiazol-2-yl, 2-(2-methylpiperidin-1-yl)thiazol-4-yl, 2-(pyrrolidin-1-yl)thiazol-4-yl, 2-fluorophenyl, 2,6-difluorophenyl, 2-chloro-6-fluorophenyl, 2-pyrazinyl, 2-aminopyrazin-5-yl, 2-aminopyrazin-6-yl, 2-(isopropoxy)-pyrazin-6-yl, 3-methoxypyrazin-6-yl, 2-cyclopropyl-pyrazin-6-yl, 3-pyridazinyl, 4-amino-6-pyridazinyl, 3-amino-6-pyridazinyl, 2-pyrimidinyl, 3-cyclopropylaminopyrid-5-yl, 2-aminopyrid-5-yl, 2-methoxy-3-quinolyl or 2-oxopyrid-4-yl; and a pharmaceutically acceptable salt thereof.

In another embodiment, $R^{1A}$ is piperidin-3-ylamino, piperidin-4-ylamino, piperidin-4-yl-N-methylamino, piperidin-3-yl-N-methylamino, pyrrolidin-3-ylamino, 3-azetidinylamino, 3-azetidinyloxy, pyrrolidin-3-yloxy, piperidin-3-yloxy, 4-fluoro-piperidin-3-yloxy, 3-fluoro-piperidin-5-yloxy, 4-methyl-piperidin-3-yloxy, piperidin-4-yloxy, azaspiro[2.5]oct-4-yloxy), methylamino, ethylamino, isopropylamino, tert-butylamino, dimethylamino, phenylamino, piperidin-3-ylthio, ((3S)-4-methylidene-3-piperidinyl)oxy, 3-pyridyl, 5-indazolyl, 1,4-diazepan-1-yl, 1-pyrrolidinyl, 3-hydroxypyrrolidin-1-yl, 3-aminopyrrolidinyl, 4-aminopiperidinyl, 3-aminopiperidinyl, 3-hydroxypiperidin-1-yl, 4-hydroxypiperidinyl, 4-morpholinyl, 3-pyrazolyl, 3-azetidinyl, 1-piperazinyl or 1-piperidinyl; $R^{1B}$ is H, hydroxy or methoxy; $R^{1C}$ is H, hydroxy, methoxy, piperidin-3-ylamino, piperidin-4-ylamino, piperidin-4-yl-N-methylamino, piperidin-3-yl-N-methylamino, pyrrolidin-3-ylamino, 3-azetidinylamino, 3-pyridyl, 1-pyrrolidinyl, 3-hydroxypyrrolidin-1-yl, 3-aminopyrrolidinyl, 4-aminopiperidinyl, 3-aminopiperidinyl, 3-hydroxypiperidin-1-yl, 4-hydroxypiperidinyl, 4-morpholinyl, 3-pyrazolyl, 3-azetidinyl, 1-piperazinyl or 1-piperidinyl; $R^{1E}$ is H, hydroxy, methoxy, piperidin-3-yloxy, isopropylamino, 4-amino-piperidin-1-yl, methylamino, piperidin-3-ylamino or piperidin-4-ylamino; $R^{1F}$ is 4-amino-piperidin-1-yl; $R^{1G}$ is H, hydroxy or methoxy; $R^{1H}$ is H, hydroxy or methoxy; and $R^{1J}$ is H, hydroxy, methoxy, piperidin-3-yloxy, isopropylamino, 4-amino-piperidin-1-yl, methylamino, piperidin-3-ylamino or piperidin-4-ylamino; and a pharmaceutically acceptable salt thereof.

Another aspect of the current invention relates to compounds having the general structure of formula (2):

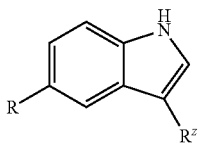

Wherein R$^z$ is optionally substituted 5-membered heteroaryl or optionally substituted 6-membered heteroaryl or optionally substituted 9 membered heterocyclyl or optionally substituted 10 membered heterocyclyl;

Wherein R is optionally substituted 2-fluorophenyl, optionally substituted pyrazinyl, optionally substituted pyridazinyl, optionally substituted pyrimidinyl, optionally substituted pyridyl, or optionally substituted thiazolyl;

and a pharmaceutically acceptable salt thereof;

provided R$^z$ is not 4-pyridyl when R is 3-pyridyl.

In another embodiment, the group R$^z$ is optionally substituted thiazolyl, optionally substituted pyrazinyl, optionally substituted pyridyl, optionally substituted pyrimidinyl or optionally substituted indazolyl; and a pharmaceutically acceptable salt thereof.

In another embodiment, R$^z$ is optionally substituted thiazol-4-yl; and a pharmaceutically acceptable salt thereof.

In another embodiment, R is optionally substituted 2-fluorophenyl; and a pharmaceutically acceptable salt thereof.

In another embodiment, R is optionally substituted pyrazinyl, optionally substituted pyridazinyl, optionally substituted pyrimidinyl, or optionally substituted pyridyl, and a pharmaceutically acceptable salt thereof.

In another embodiment, R$^z$ is 2-(1-imidazolyl)thiazol-4-yl, 2-(2-oxo-pyrid-1-yl)thiazol-4-yl, 2-dimethylaminopyrazin-6-yl, 2-(cyclohexylamino)pyrazin-6-yl, 2-(pyrrolidin-3-ylamino)pyrazin-6-yl, 2-(piperidin-3-ylamino)pyrazin-6-yl, 2-(piperidin-4-ylamino)pyrazin-6-yl, 2-(2-oxopiperazin-4-ylamino)pyrazin-6-yl, 2-(3-amino-pyrrolidin-1-yl)pyrazin-6-yl, 2-(4-aminopiperidin-1-yl)pyrazin-6-yl, 2-(3-aminopiperidin-1-yl)pyrazin-6-yl, 2-(morpholin-4-yl)pyrazin-6-yl, 2-methoxy-pyrazin-6-yl, 2-methoxy-pyrazin-5-yl, 2-isopropoxy-pyrazin-6-yl, 2-(piperidin-3-yloxy)pyrazin-6-yl, 2-(piperidin-4-yloxy)pyrazin-6-yl, 2-(morpholin-4-yl)pyrid-6-yl, 2-(2-oxo-pyrrolidin-1-yl)pyrid-6-yl, 2-(pyrazol-1-yl)pyrid-6-yl, 3-fluoro-6-pyridyl, 2-amino-6-pyridyl, 2-amino-4-pyridyl, 4-amino-2-pyridyl, 2-amino-3-chloropyrid-5-yl, 4-methyl-2-pyridyl, 3-methyl-6-pyridyl, 2-isopropoxy-pyrid-6-yl, 4-(piperidin-3-ylamino)pyrimidin-2-yl, 2-(4-aminopiperidin-1-yl)-4-methoxypyrimidin-6-yl, 2-(4-aminopiperidin-1-yl)-4-oxypyrimidin-6-yl, 4-(piperidin-3-yloxy)pyrimidin-2-yl, 4-(piperidin-4-yloxy)pyrimidin-2-yl, 4-(piperidin-4-ylamino)pyrimidin-2-yl, or 6-indazolyl; and a pharmaceutically acceptable salt thereof.

In another embodiment, R is 2,6-difluorophenyl, 2-chloro-6-fluorophenyl, or 2-(isopropoxy)-pyrazin-6-yl; and a pharmaceutically acceptable salt thereof.

In another embodiment, R is 2,6-difluorophenyl, or 2-chloro-6-fluorophenyl; and a pharmaceutically acceptable salt thereof.

In another embodiment, R is 2-(isopropoxy)-pyrazin-6-yl; and a pharmaceutically acceptable salt thereof.

In another embodiment, R$^z$ is thiazol-4-yl substituted with 5-membered nitrogen-containing heteroaryl or 6-membered nitrogen-containing heteroaryl, pyrazin-2-yl substituted with dialkylamino, substituted or unsubstituted 5-membered nitrogen-containing heterocyclyl, substituted or unsubstituted 6-membered nitrogen-containing heterocyclyl, $C_1$-$C_3$ alkoxy, 6-membered nitrogen-containing heterocyclyloxy, 6-membered nitrogen-containing heterocyclylamino, 5-membered nitrogen-containing heterocyclylamino, pyrid-2-yl substituted with 5-membered nitrogen-containing heterocyclyl, 6-membered nitrogen-containing heterocyclyl, $C_1$-$C_3$ alkoxy, $C_1$-$C_3$ alkyl, amino, fluoro, pyrid-4-yl substituted with amino, pyrimidin-2-yl substituted with 6-membered nitrogen-containing heterocyclyloxy, or 6-membered nitrogen-containing heterocyclylamino, or indazolyl;

wherein the substituted 5-membered nitrogen-containing heterocyclyl, or substituted 6-membered nitrogen-containing heterocyclyl are substituted with one or more substituents selected from amino, oxo, methyl, fluoro, =CH$_2$, and a pharmaceutically acceptable salt thereof.

Another aspect of the current invention relates to compounds having the general structure of formula (3):

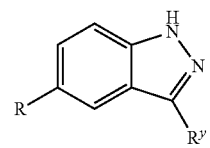

Wherein R$^y$ is

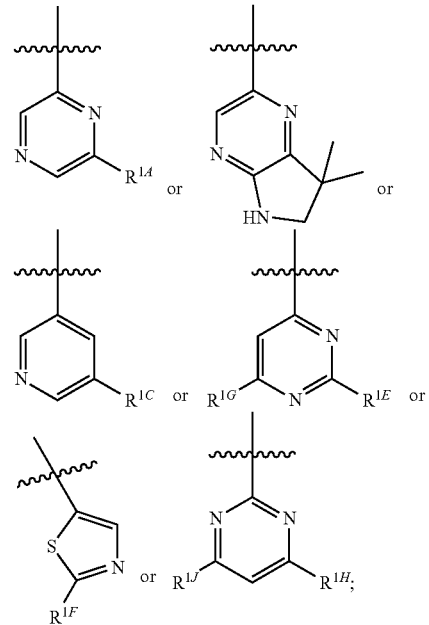

Wherein R is optionally substituted $C_6$-$C_{10}$-aryl, optionally substituted 5-6-membered heterocyclyl, optionally substituted 9-10-membered heterocyclyl, 1,2,2',3',5',6'-hexahydrospiro[indole-3,4'-pyran]-4-yl, halo, $C_3$-$C_6$-cycloalkyl-$C_2$-$C_3$-alkenyl, halo, $C_{1-4}$ alkoxycarbonyl, HOOC—, $C_{1-4}$ alkylcarbonylamino, aminocarbonyl, phenylaminocarbonyl, $C_{1-4}$ alkylaminocarbonyl, phenylcarbonylamino, nitro, benzylaminocarbonyl or amino; provided R is not 2-methoxypyridyl when R$^y$ is 2-(4-amino-1-piperidyl)-6-pyrazinyl;

Wherein $R^{1A}$ is H, hydroxy, $C_1$-$C_3$-alkoxy, optionally substituted 5-6-membered heterocyclyl, or optionally substituted 5-6-membered heterocyclyl-amino or optionally substituted 5-6-membered heterocyclyl-(alkyl)amino or optionally substituted 5-6-membered heterocyclyloxy or alkylamino or optionally substituted 5-6-membered heterocyclyl-S—, or optionally substituted phenylamino or 9-10 membered nitrogen containing heterocyclyl;

Wherein $R^{1C}$ is H, hydroxy, $C_1$-$C_3$-alkoxy, optionally substituted 5-6-membered heterocyclyl, or optionally substituted 5-6-membered heterocyclyl-amino;

Wherein $R^{1E}$ is H, hydroxy, $C_1$-$C_3$-alkoxy, optionally substituted 5-6-membered heterocyclyl, optionally substituted 5-6-membered heterocyclyl-amino, optionally substituted 5-6-membered heterocyclyl-(alkyl)amino, optionally substituted 5-6-membered heterocyclyloxy or alkylamino;

Wherein $R^{1F}$ is H, or optionally substituted 6-membered heterocyclyl;

Wherein $R^{1G}$ is H, hydroxy or $C_1$-$C_3$-alkoxy;

Wherein $R^{1H}$ is H, hydroxy or $C_1$-$C_3$-alkoxy;

Wherein $R^{1J}$ is H, hydroxy, $C_1$-$C_3$-alkoxy, optionally substituted 5-6-membered heterocyclyl, or optionally substituted 5-6-membered heterocyclyl-amino or optionally substituted 5-6-membered heterocyclyl-(alkyl)amino or optionally substituted 5-6-membered heterocyclyloxy or alkylamino or optionally substituted 5-6-membered heterocyclyl-S—, or optionally substituted phenyl or 9-10 membered nitrogen containing heterocyclyl;

and a pharmaceutically acceptable salt thereof;

provided R is not 2,6-dimethyl-3,5-dicyano-dihydropyridyl.

In another embodiment, R is optionally substituted nitrogen containing-6 membered heteroaryl or optionally substituted phenyl; and a pharmaceutically acceptable salt thereof.

In another embodiment, R is phenyl optionally substituted with one or more substituents selected from fluoro, chloro, nitro, amino, cyano, methyl, oxo, hydroxy, methoxy, isopropoxy, trifluoromethoxy, methylsulfonyl, dimethylamino, morpholine, isopropylaminocarbonyl, cyclopropylaminocarbonyl, phenylaminocarbonyl, diethylaminocarbonyl, dimethylaminocarbonyl, benzylaminocarbonyl, tert-butylaminocarbonyl, butylaminocarbonyl, propylaminocarbonyl, ethylaminocarbonyl, cyclopropylaminocarbonyl, cyclohexylaminocarbonyl, piperidinylcarbonyl or morpholinylcarbonyl; and a pharmaceutically acceptable salt thereof.

In another embodiment, R is pyridyl, or pyrimidinyl, or pyrazinyl, or pyridazinyl, wherein R is optionally substituted with one or more substituents selected from hydroxy, amino, cyclopropyl, fluoro, methoxy, chloro, isopropoxy, ethoxy, methyl, trifluoromethyl, tert-butylaminocarbonyl, tert-butylcarbonylamino, 4-cyclopropylaminocarbonyl, oxo, isopropyl, morpholinyl, or cyclopentylamino; and a pharmaceutically acceptable salt thereof.

In another embodiment, R is quinolyl, or isoquinolinyl, or quinoxalinyl, or pyrazolo[3,4-b]pyridinyl, or 2,3-dihydro-indolyl, or indazolyl or benzothiazolyl, or 3,4-dihydro-2H-pyrido[3,2-b][1,4]oxazinyl, or 3,4-dihydro-2H-1,4-benzoxazinyl, or 1H-pyrrolo[2,3-b]pyridinyl, or imidazo[1,2-a]pyrazinyl, or [1,2,4]triazolo[4,3-a]pyridinyl, or 1,2,2',3',5',6'-hexahydrospiro[indole-3,4'-pyran] or 2,3-dihydro-1,4-benzodioxinyl; wherein R is optionally substituted with one or more substituents selected from hydroxy, cyano, chloro, methoxy, fluoro, trifluoromethoxy, methyl, oxo, trifluoromethyl or 2-aminopyrimidin-4-yl; and a pharmaceutically acceptable salt thereof.

In another embodiment, R is pyran, 5,6-dihydro-2H-pyranyl, 3,6-dihydro-2H-pyranyl, tetrahydropyran, pyrrolidinyl, piperidinyl, morpholinyl, and imidazolidinyl; wherein R is optionally substituted with one or more substituents selected from methyl, or oxo; and a pharmaceutically acceptable salt thereof.

In another embodiment, the group R is $C_3$-$C_6$-cycloalkyl-$C_2$-$C_3$-alkenyl or bromo; and a pharmaceutically acceptable salt thereof.

In another embodiment, the group R is cyclopropylethenyl, bromo, $C_{1-4}$ alkoxycarbonyl, HOOC—, $C_{1-4}$ alkylcarbonylamino, aminocarbonyl, phenylaminocarbonyl, $C_{1-4}$ alkylaminocarbonyl, phenylcarbonylamino, nitro, benzylaminocarbonyl or amino; and a pharmaceutically acceptable salt thereof.

In another embodiment, the group R is cyclopropylethenyl, bromo, methoxycarbonyl, nitro, amino, aminocarbonyl, ethylcarbonylamino, phenylcarbonylamino, isopropylaminocarbonyl, HOOC—, phenylaminocarbonyl, or benzylaminocarbonyl; and a pharmaceutically acceptable salt thereof.

In another embodiment, R is phenyl, 2,6-difluorophenyl, 2,3-difluorophenyl, 2-fluorophenyl, 3-fluorophenyl, 2-fluoro-5-nitrophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(pipendin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-hydroxyphenyl, 3-hydroxyphenyl, 3-methoxyphenyl, 3,5-dimethoxyphenyl, 3-isopropoxyphenyl, 3-trifluoromethoxyphenyl, 2-cyanophenyl, 3-aminophenyl, 3-amino-2-methylphenyl, 2-cyanophenyl, 3-cyanophenyl, 2-chlorophenyl, 2-chloro-6-fluorophenyl, 3-methylsulfonylphenyl, 4-methylsulfonylphenyl, 3-dimethylaminophenyl, 3-amino-4-morpholinophenyl, 3-amino-6-trifluoromethoxyphenyl, 2-pyridyl, 3-pyridyl, 4-pyridyl, 2-hydroxy-3-pyridyl, 2-amino-4-pyridyl, 3-amino-5-pyridyl, 3-amino-2-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 3-fluoro-2-pyridyl, 3-fluoro-5-pyridyl, 3-methyl-2-pyridyl, 2-trifluoromethyl-6-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 2-amino-4-cyclopentylamino-pyrimidin-5-yl, 4-cyclopropylpyrimidin-2-yl, 4-oxo-pyrimidin-5-yl, 2-methoxy-pyrimidin-4-yl, 2-isopropoxypyrimidin-4-yl, 3-pyrazinyl, 2-cyclopropyl-6-pyrazinyl, 2-cyclopropylamino-6-pyrazinyl, 2-isopropoxy-6-pyrazinyl, 3-pyridazinyl, 4-amino-pyridazin-6-yl, 3-quinolyl, 2-hydroxy-3-quinolyl, 2-chloro-3-quinolyl, 7-methoxy-4-quinolyl, 7-fluoro-4-quinolyl, 7-cyano-4-quinolyl, 7-trifluoromethoxy-4-quinolyl, 2-methoxy-3-quinolyl, 1-methyl-2-oxo-quinolin-4-yl, 1-methyl-2-oxoisoquinolin-6-yl, 6-quinoxalinyl, 3-trifluoromethyl-1H-pyrazolo[3,4-b]pyridin-5-yl, 3-trifluoromethyl-5-indazolyl, 1-methyl-2-oxo-2,3-dihydro-indol-5-yl, 1-(2-aminopyrimidin-4-yl)-2,3-dihydro-indol-6-yl, benzothiazol-5-yl, benzothiazol-6-yl, 4-methyl-3,4-dihydro-2H-pyrido[3,2-b][1,4]oxazin-7-yl, 4-methyl-3,4-dihydro-2H-1,4-benzoxazin-7-yl, 1H-pyrrolo[2,3-b]pyridin-5-yl, 1H-pyrrolo[2,3-b]pyridin-6-yl, imidazo[1,2-a]pyrazin-5-yl, [1,2,4]triazolo[4,3-a]pyridin-5-yl, 1,2,2',3',5',6'-hexahydrospiro[indole-3,4'-pyran]-4-yl and 2,3-dihydro-1,4-benzodioxin-6-yl, 1H-pyrazol-5-yl, 1-methyl-1H-pyrazol-4-yl, thiazol-2-yl, 2-(2-methylpiperidin-1-yl)thiazol-4-yl, 2-(pyrrolidin-1-yl)thiazol-4-yl, 4-pyran, 3-pyran, 5,6-dihydro-2H-pyran-3-yl, 3,6-dihydro-2H-pyran-4-yl, tetrahydro-4-pyran, tetrahydro-3-pyran, 2-oxo-pyrrolidin-1-yl, 2-oxo-piperidin-1-yl, morpholin-4-yl, 1-methyl-2-oxo-imidazolidin-3-yl, 1-piperidinyl, amino, —COOH, methoxycarbonyl, nitro, bromo, ethylcarbonylamino, phenylaminocarbonyl, aminocarbonyl, methylaminocarbonyl, phenylcarbonylamino, benzylaminocarbonyl or cyclopropylethenyl; and a pharmaceutically acceptable salt thereof.

In another embodiment, $R^{1E}$ is H, hydroxy, methoxy, piperidin-3-yloxy, isopropylamino, 4-amino-piperidin-1-yl, methylamino, piperidin-3-ylamino, or piperidin-4-ylamino; wherein $R^{1G}$ is H, hydroxy, or methoxy; and a pharmaceutically acceptable salt thereof.

In another embodiment, $R^{1A}$ is piperidin-3-ylamino, piperidin-4-ylamino, piperidin-4-yl-N-methylamino, piperidin-3-yl-N-methylamino, pyrrolidin-3-ylamino, 3-azetidinylamino, 3-azetidinyloxy, pyrrolidin-3-yloxy, piperidin-3-yloxy, 4-fluoro-piperidin-3-yloxy, 3-fluoro-piperidin-5-yloxy, 4-methyl-piperidin-3-yloxy, piperidin-4-yloxy, azaspiro[2.5]oct-4-yloxy), methylamino, ethylamino, isopropylamino, tert-butylamino, dimethylamino, phenylamino, piperidin-3-ylthio, ((3S)-4-methylidene-3-piperidinyl)oxy, 3-pyridyl, 5-indazolyl, 1,4-diazepan-1-yl, 1-pyrrolidinyl, 3-hydroxypyrrolidin-1-yl, 3-aminopyrrolidinyl, 4-aminopiperidinyl, 3-aminopiperidinyl, 3-hydroxypiperidin-1-yl, 4-hydroxypiperidinyl, 4-morpholinyl, 3-pyrazolyl, 3-azetidinyl, 1-piperazinyl, or 1-piperidinyl; and a pharmaceutically acceptable salt thereof In another embodiment, $R^y$ is

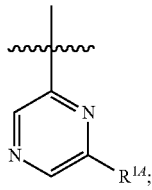

and a pharmaceutically acceptable salt thereof.

In another embodiment, $R^{1C}$ is H, hydroxy, methoxy, piperidin-3-ylamino, piperidin-4-ylamino, piperidin-4-yl-N-methylamino, piperidin-3-yl-N-methylamino, pyrrolidin-3-ylamino, 3-azetidinylamino, 3-pyridyl, 1-pyrrolidinyl, 3-hydroxypyrrolidin-1-yl, 3-aminopyrrolidinyl, 4-aminopiperidinyl, 3-aminopiperidinyl, 3-hydroxypiperidin-1-yl, 4-hydroxypiperidinyl, 4-morpholinyl, 3-pyrazolyl, 3-azetidinyl, 1-piperazinyl, or 1-piperidinyl; and a pharmaceutically acceptable salt thereof.

In another embodiment, R is 5-membered heteroaryl; and a pharmaceutically acceptable salt thereof.

In another embodiment, R is unsubstituted or substituted thiazolyl or unsubstituted or substituted pyrazolyl; and a pharmaceutically acceptable salt thereof.

In another embodiment, $R^y$ is

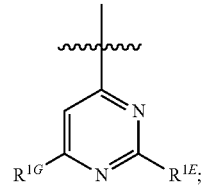

and a pharmaceutically acceptable salt thereof.

In another embodiment, $R^y$ is

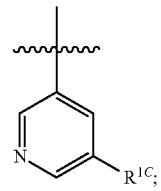

wherein $R^{1C}$ is H, hydroxy, methoxy or 4-aminopiperidin-1-yl; and a pharmaceutically acceptable salt thereof.

Another aspect of the current invention relates to compounds having the general structure of formula (4):

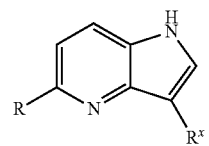

4

Wherein $R^x$ is

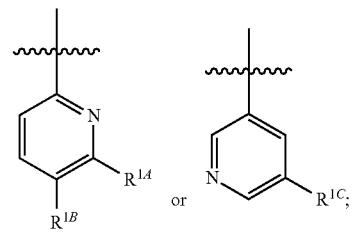

Wherein R is optionally substituted phenyl or optionally substituted 5-membered heteroaryl or optionally substituted 6-membered heteroaryl, or halo;

Wherein $R^{1A}$ is H, methoxy, 6-membered heterocyclylamino or optionally substituted 6-membered heterocyclyl;

Wherein $R^{1B}$ is H or methoxy; and

Wherein $R^{1C}$ is H, methoxy, optionally substituted 6-membered heterocyclyl, or optionally substituted 6-membered heterocyclyl-amino;

and a pharmaceutically acceptable salt thereof.

In another embodiment, the group R is substituted or unsubstituted phenyl; and a pharmaceutically acceptable salt thereof.

In another embodiment, the group R is 2-fluorophenyl, or 2,6-difluorophenyl; and a pharmaceutically acceptable salt thereof.

In another embodiment, the group $R^x$ is

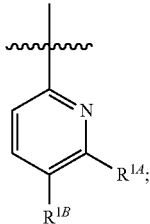

and a pharmaceutically acceptable salt thereof.

In another embodiment, $R^x$ is

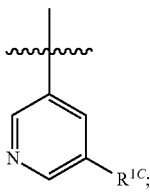

and a pharmaceutically acceptable salt thereof.

In another embodiment, $R^{1C}$ is piperid-3-ylamino or 4-amino-piperidyl; and a pharmaceutically acceptable salt thereof.

In another embodiment, $R^{1A}$ is H, methoxy, piperid-3-ylamino or 4-amino-piperidyl; wherein $R^{1B}$ is H or methoxy and a pharmaceutically acceptable salt thereof.

Another aspect of the current invention relates to compounds having the general structure of Formula 1a

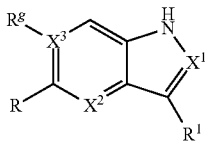

wherein $X^1$ is CH or N;
wherein $X^2$ is CH or N;
wherein $X^3$ is C or N;
wherein R is substituted or unsubstituted aryl, substituted or unsubstituted 5-membered heterocyclyl, substituted or unsubstituted 6-membered heterocyclyl, substituted or unsubstituted 9 membered heterocyclyl, substituted or unsubstituted 10 membered heterocyclyl, cycloalkylalkenyl, halo, 1,2,2',3',5',6'-hexahydrospiro[indole-3,4'-pyranyl], alkoxycarbonyl, HOOC—, alkylcarbonylamino, phenylaminocarbonyl, aminocarbonyl, alkylaminocarbonyl, phenylcarbonylamino, benzylaminocarbonyl, alkylcarbonyl, hydroxyalkyl, haloalkyl, cyanoalkyl, substituted or unsubstituted cycloalkyl, substituted or unsubstituted arylamino, alkenyl, haloalkenyl, cyano, nitro or amino;
wherein $R^1$ is optionally substituted 5-membered heterocyclyl, optionally substituted 6-membered heterocyclyl, or optionally substituted 9-10 membered heterocyclyl;
$R^g$ is H or F;
and a pharmaceutically acceptable salt thereof;
provided R is not oxadiazolyl or thiadiazolyl; further provided $R^1$ is not 4-pyridyl when R is 3-pyridyl, when $X^1$ is CH, $X^2$ is CH and $X^3$ is C; further provided R is not 2,6-dimethyl-3,5-dicyano-dihydropyridyl when $X^1$ is N, $X^2$ is CH and $X^3$ is C; further provided $R^1$ is not 2-(4-morpholinyl-4-phenylamino)-4-pyrimidyl when $X^1$ is CH, $X^2$ is CH and $X^3$ is C; further provided R is not 2-(3-furyl)-(5-phenyl-2-aminopropoxy)-3-pyridyl when $X^1$ is N, $X^2$ is CH and $X^3$ is C; further provided R is not triazolyl or tetrazolyl when $R^1$ is 4-pyridyl or 3-pyridyl or 3-quinolinyl, when $X^1$ is N, $X^2$ is CH and $X^3$ is C; further provided R is not 7,9-dicyano-[1,3,4,8-tetrahydropyrido[2,1-c][1,4]oxazin-8-yl when $X^1$ is N, $X^2$ is CH and $X^3$ is C; and further provided R is not 0.3-cyano-2-methyl-5-oxo-1,4,5,7-tetrahydrofuro[3,4-b]pyridin-4-yl when $X^1$ is N, $X^2$ is CH, $X^3$ is C, $R^g$ is H and $R^1$ is 2-isopropoxypyridin-5-yl.

In another embodiment, $X^1$ is CH; wherein $X^2$ is CH; wherein $X^3$ is C; and wherein $R^g$ is H; and a pharmaceutically acceptable salt thereof.

In another embodiment, $X^1$ is N; wherein $X^2$ is CH; wherein $X^3$ is C; and wherein $R^g$ is H; and a pharmaceutically acceptable salt thereof.

In another embodiment, $X^1$ is CH; wherein $X^2$ is N; wherein $X^3$ is C; and wherein $R^g$ is H; and a pharmaceutically acceptable salt thereof.

In another embodiment, $R^1$ is

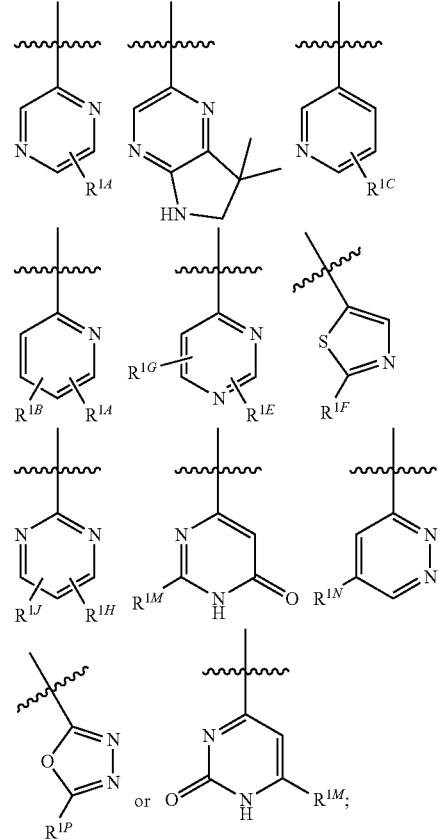

Wherein $R^{1A}$ is H, hydroxy, $C_1$-$C_3$-alkoxy, $C_1$-$C_3$-haloalkoxy, optionally substituted 5-6-membered heterocyclyl, optionally substituted 5-6-membered heterocyclyl-amino, optionally substituted 5-6-membered heterocyclyl-(alkyl)amino, optionally substituted 5-6-membered heterocycly-loxy, alkylamino, $C_3$-$C_6$ cycloalkylamino, optionally substituted 5-6-membered heterocyclyl-S—, optionally substituted phenylamino or 9-10 membered nitrogen containing heterocyclyl;

Wherein $R^{1B}$ is H, hydroxy or $C_1$-$C_3$-alkoxy;

Wherein $R^{1C}$ is H, hydroxy, $C_1$-$C_3$-alkoxy, optionally substituted 5-6-membered heterocyclyl, or optionally substituted 5-6-membered heterocyclyl-amino;

Wherein $R^{1E}$ is H, hydroxy, $C_1$-$C_3$-alkoxy, optionally substituted 5-6-membered heterocyclyl, optionally substituted 5-6-membered heterocyclyl-amino, optionally substituted 5-6-membered heterocyclyl-(alkyl)amino, optionally substituted 5-6-membered heterocyclyloxy or alkylamino;

Wherein $R^{1F}$ is H, or optionally substituted 6-membered heterocyclyl;

Wherein $R^{1G}$ is H, hydroxy or $C_1$-$C_3$-alkoxy;

Wherein $R^{1J}$ is H, hydroxy, $C_1$-$C_3$-alkoxy, optionally substituted 5-6-membered heterocyclyl, or optionally substituted 5-6-membered heterocyclyl-amino or optionally substituted 5-6-membered heterocyclyl-(alkyl)amino or optionally substituted 5-6-membered heterocyclyloxy or alkylamino or optionally substituted 5-6-membered heterocyclyl-S—, or optionally substituted phenyl or 9-10 membered nitrogen containing heterocyclyl;

Wherein $R^{1H}$ is H, hydroxy or $C_1$-$C_3$-alkoxy;

Wherein $R^{1M}$ is H, lower alkyl, lower alkoxy, lower alkylamino, lower dialkylamino, substituted or unsubstituted 5-6-membered heterocyclyloxy, substituted or unsubstituted 5-6-membered heterocyclyl or substituted or unsubstituted 5-6-membered heterocyclylamino;

Wherein $R^{1N}$ is H, or $C_1$-$C_3$-alkoxy; and

Wherein $R^{1P}$ substituted or unsubstituted phenylamino, lower alkylamino, substituted or unsubstituted 5-membered nitrogen-containing heterocyclyl, substituted or unsubstituted 5-membered nitrogen-containing heterocyclylamino, substituted or unsubstituted 6-membered nitrogen-containing heterocyclylamino, or substituted or unsubstituted 6-membered nitrogen-containing heterocyclyl;

and a pharmaceutically acceptable salt thereof.

In another embodiment, R is halo, $C_{1-4}$ hydroxyalkyl, $C_{1-4}$ haloalkyl, $C_{1-4}$ cyanoalkyl, $C_3$-$C_6$-cycloalkyl-$C_2$-$C_3$-alkenyl, $C_{1-4}$ alkylcarbonyl, $C_{1-4}$ alkoxycarbonyl, HOOC—, $C_{1-4}$ alkylcarbonylamino, phenylaminocarbonyl, aminocarbonyl, $C_{1-4}$ alkylaminocarbonyl, $C_{1-4}$ dialkylaminocarbonyl, phenylcarbonylamino, benzylaminocarbonyl, substituted or unsubstituted $C_6$-$C_{10}$-arylamino, $C_{2-4}$ alkenyl, $C_{2-4}$ haloalkenyl, nitro or amino; and a pharmaceutically acceptable salt thereof.

In another embodiment, R is methoxycarbonyl, isopropoxycarbonyl, methylcarbonyl, cyano, cyanomethyl, nitro, amino, 2,6-difluorophenylamino, aminocarbonyl, ethylcarbonylamino, phenylcarbonylamino, isopropylaminocarbonyl, methylaminocarbonyl, dimethylaminocarbonyl, HOOC—, phenylaminocarbonyl, benzylaminocarbonyl, bromo, hydroxyethyl, 1-hydroxy-2-propyl, isopropyl, 1-methylcyclopropyl, 1-trifluoromethylcyclopropyl, 3,3,3-trifluoroprop-2-yl, prop-1-en-2-yl, 3,3,3-trifluoroprop-1-en-2-yl or cyclopropylethenyl; and a pharmaceutically acceptable salt thereof.

In another embodiment, R is substituted or unsubstituted $C_3$-$C_6$ cycloalkyl, substituted or unsubstituted phenyl or substituted or unsubstituted 5-membered heterocyclyl or substituted or unsubstituted 6-membered heteroaryl or substituted or unsubstituted 9 membered heteroaryl or substituted or unsubstituted 10 membered heteroaryl; and a pharmaceutically acceptable salt thereof.

In another embodiment, R is substituted or unsubstituted phenyl, substituted or unsubstituted pyrrolidinyl, substituted or unsubstituted piperidinyl, substituted or unsubstituted pyranyl, substituted or unsubstituted 5,6-dihydro-2H-pyranyl, substituted or unsubstituted 3,6-dihydro-2H-pyranyl, substituted or unsubstituted tetrahydro-pyranyl, substituted or unsubstituted morpholinyl, substituted or unsubstituted imidazolidinyl, substituted or unsubstituted cyclopropyl, substituted or unsubstituted cyclobutyl, substituted or unsubstituted cyclopentyl, substituted or unsubstituted thiazolyl, substituted or unsubstituted pyrazolyl, substituted or unsubstituted imidazolyl, substituted or unsubstituted oxazolyl, substituted or unsubstituted pyrazinyl, substituted or unsubstituted pyridazinyl, substituted or unsubstituted pyrimidinyl, substituted or unsubstituted pyridyl, substituted or unsubstituted indazolyl, substituted or unsubstituted quinoxalinyl, substituted or unsubstituted 1H-pyrazolo[3,4-b]pyridinyl, substituted or unsubstituted 2,3-dihydro-indolyl, substituted or unsubstituted benzothiazolyl, substituted or unsubstituted 3,4-dihydro-2H-pyrido[3,2-b][1,4]oxazinyl, substituted or unsubstituted 3,4-dihydro-2H-1,4-benzoxazinyl, substituted or unsubstituted 1H-pyrrolo[2,3-b]pyridinyl, substituted or unsubstituted 1H-pyrrolo[3,2-c]pyridinyl, substituted or unsubstituted imidazo[1,2-a]pyrazinyl, substituted or unsubstituted [1,2,4]triazolo[4,3-a]pyridinyl, substituted or unsubstituted 1,2,2',3',5',6'-hexahydrospiro[indole-3,4'-pyran]yl, substituted or unsubstituted 2,3-dihydro-1,4-benzodioxinyl, or substituted or unsubstituted quinolyl; and a pharmaceutically acceptable salt thereof In another embodiment, R is phenyl, 2,6-difluorophenyl, 2,5-difluorophenyl, 2,4-difluorophenyl, 2,3-difluorophenyl, 2-fluorophenyl, 3-fluorophenyl, 2-fluoro-5-nitrophenyl, 4-aminocarbonyl-2-fluorophenyl, 3-aminocarbonyl-6-fluorophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(piperidin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-fluoro-4-hydroxyphenyl, 2-hydroxyphenyl, 3-hydroxyphenyl, 3-methoxyphenyl, 3,5-dimethoxyphenyl, 3-isopropoxyphenyl, 3-trifluoromethoxyphenyl, 2-trifluoromethylphenyl, 3-aminophenyl, 3-amino-2-methylphenyl, 3-(1-hydroxyethyl)phenyl, 2-cyanophenyl, 3-cyanophenyl, 4-cyano-2-fluorophenyl, 2-cyano-6-fluorophenyl, 2-chlorophenyl, 2-chloro-6-fluorophenyl, 3-chloro-6-fluorophenyl, 4-chloro-2-fluorophenyl, 3-methylsulfonylphenyl, 2-fluoro-4-methylsulfonylphenyl, 4-methylsulfonylphenyl, 2,6-difluoro-4-methylsulfonylphenyl, 2-fluoro-4-methylsulfonylamino-phenyl, 4-aminosulfonyl-2-fluorophenyl, 3-dimethylaminophenyl, 3-amino-4-morpholinophenyl, 3-amino-6-trifluoromethoxyphenyl, 4-amino-2-fluorophenyl, 2-fluoro 4-methylcarbonylaminophenyl, ethynylphenyl, (1-chlorovinyl)benzene, 2-methylphenyl, 2-pyridyl, 3-pyridyl, 4-pyridyl, 2-hydroxy-3-pyridyl, 2-amino-4-pyridyl, 3-amino-5-pyridyl, 3-amino-2-pyridyl, 2-amino-6-fluoro-5-pyridyl, 4-cyano-3-pyridyl, 2-cyano-3-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 2-fluoro-3-pyridyl, 4-fluoro-3-pyridyl, 2,4-difluoro-3-pyridyl, 3-fluoro-2-pyridyl, 3-fluoro-4-pyridyl, 3-fluoro-5-pyridyl, 3-methyl-2-pyridyl, 2-trifluoromethyl-6-pyridyl, 4-trifluoromethyl-2-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 4-(3-methylmorpholin-4-yl)-pyrimidin-2-yl, 2-amino-4-cyclopentylamino-pyrimidin-5-yl, 4-cyclopropylaminopyrimidin-2-yl, 4-isobutylpyrimidin-2-yl, 4-cyclopropylpyrimidin-2-yl, 2-cyclopropylpyrimidin-4-yl, 4-oxo-pyrimidin-5-yl, 2-methoxy-pyrimidin-4-yl, 2-isopropoxypyrimidin-4-yl, 3-pyrazinyl, 2-aminopyrazin-6-yl, 2-cyclopropyl-6-pyrazinyl, 2-cyclopropylamino-6-pyrazinyl, 2-isopropoxy-6-pyrazinyl, 3-pyridazinyl, 4-amino-pyridazin-6-yl, 3-quinolyl, 2-hydroxy-3-quinolyl, 2-chloro-3-quinolyl, 7-methoxy-4-quinolyl, 7-fluoro-4-quinolyl, 7-cyano-4-quinolyl, 7-trifluoromethoxy-4-quinolyl, 2-methoxy-3-quinolyl, 1-methyl-2-oxo-quinolin-4-yl, 1-methyl-2-oxo-isoquinolin-6-yl, 6-quinoxalinyl, 3-trifluoromethyl-1H-pyrazolo[3,4-b]pyridin-5-yl, 3-trifluoromethyl-5-indazolyl, 1-methyl-2-oxo-2,3-dihydro-indol-5-yl, 1-(2-aminopyrimidin-4-yl)-2,3-dihydro-indol-6-yl, benzothiazol-5-yl, benzothiazol-6-yl, 4-methyl-3,4-dihydro-2H-pyrido[3,2-b][1,4]oxazin-7-yl, 4-methyl-3,4-dihydro-2H-1,4-benzoxazin-7-yl, 1H-pyrrolo[2,3-b]pyridin-5-yl, 1H-pyrrolo[3,2-c]pyridin-4-yl, 1H-pyrrolo[3,2-c]pyridin-6-yl, 1H-pyrrolo[2,3-b]pyridin-6-yl, imidazo[1,2-a]pyrazin-5-yl, [1,2,4]triazolo[4,3-a]pyridin-5-yl, 1,2,2',3',5',6'-hexahydrospiro[indole-3,4'-pyran]-4-yl and 2,3-dihydro-1,4-benzodioxin-6-yl, 1H-pyrazol-5-yl, 1-methyl-1H-pyrazol-4-yl, 1-methyl-1H-pyrazol-5-yl, 1-isopropyl-1H-pyrazol-4-yl, thiazol-2-yl, 2-(2-methylpiperidin-1-yl)thiazol-4-yl, 2-(pyrrolidin-1-yl)thiazol-4-yl, 1-methyl-5-imidazolyl, 2-oxazolyl, 4-pyranyl, 3-pyranyl, 5,6-dihydro-2H-pyran-3-yl, 3,6-dihydro-2H-pyran-4-yl, tetrahydro-4-pyranyl, tetrahydro-3-pyranyl, 2-oxo-pyrrolidin-1-yl, 2-oxo-piperidin-1-yl, morpholin-4-yl, 1-methyl-2-oxo-imidazolidin-3-yl, 1-piperidinyl, cyclopropyl, cyclobutyl, cyclopentyl, 3-methyl-morpholin-4-yl, 2-methyl-morpholin-4-yl, 3-oxo-morpholin-4-yl, morpholin-4-yl; and a pharmaceutically acceptable salt thereof.

In another embodiment, $R^{1A}$ is piperidin-3-ylamino, piperidin-4-ylamino, piperidin-4-yl-N-methylamino, piperidin-3-yl-N-methylamino, pyrrolidin-3-ylamino, 3-azetidinylamino, cyclopropylamino, hydroxy, methoxy, isopropoxy, trifluoroethoxy, fluoroethoxy, 3-pyridyloxy, 3-azetidinyloxy, pyrrolidin-3-yloxy, piperidin-3-yloxy, 4-fluoro-piperidin-3-yloxy, 3-fluoro-piperidin-4-yloxy, 3-fluoro-piperidin-5-yloxy, 3-methyl-piperidin-3-yloxy, 3-methyl-piperidin-5-yloxy, 1-methyl-piperidin-4-yloxy, 4-isopropyl-piperidin-3-yloxy, 4-ethyl-piperidin-3-yloxy, 4-methyl-piperidin-3-yloxy, 4,4-dimethyl-piperidin-3-yloxy, 3,3-dimethyl-piperidin-4-yloxy, piperidin-4-yloxy, 1,2,3,6-tetrahydro-3-pyridinyloxy, 6-azaspiro[2.5]oct-4-yloxy, 5-azaspiro[2.5]oct-8-yloxy, 3-azabicyclo[4.1.0]hept-5-yloxy, ((3S)-4-methylidene-3-piperidinyl)oxy, piperidin-3-ylthio, methylamino, ethylamino, isopropylamino, tert-butylamino, dimethylamino, phenylamino, piperidin-3-ylmethyl, piperidin-4-ylmethyl, cyclopropyl, 3-pyridyl, 5-indazolyl, 1,4-diazepan-1-yl, 1-pyrrolidinyl, 3-hydroxypyrrolidin-1-yl, 3,4-dihydroxypyrrolidin-1-yl, 3-aminopyrrolidinyl, 4-aminopiperidin-1-yl, 3-aminopiperidinyl, 3-hydroxypiperidin-1-yl, 3,4-dihydroxypiperidin-1-yl, 4-hydroxypiperidinyl, 4-morpholinyl, 3-pyrazolyl, 3-azetidinyl, 1-piperazinyl, or 1-piperidinyl; $R^{1E}$ is 4-aminopiperidin-1-yl, piperidin-3-ylamino, piperidin-4-ylamino, piperidin-4-yloxy or piperidin-3-yl; $R^{1G}$ is H, hydroxy or methoxy; $R^{1H}$ is H, hydroxy or methoxy; $R^{1J}$ is 4-aminopiperidin-1-yl, piperidin-3-ylamino, piperidin-4-ylamino or piperidin-3-yl; $R^{1M}$ is butyl, dimethylamino, isopropylamino, isopropoxy, 3-fluoro-piperidin-4-yloxy, 4-fluoro-piperidin-3-yloxy, piperidin-3-yloxy, 6-azaspiro[2.5]octan-4-yloxy, 4-aminopiperidin-1-yl, 3-hydroxypyrrolidin-1-yl, piperidin-3-ylamino, piperidin-4-ylamino or 3-methylpiperidin-5-ylamino; wherein $R^{1N}$ is H or methoxy; and wherein $R^{1P}$ phenylamino, isopropylamino, 3-aminopiperidin-1-yl, 4-aminopiperidin-1-yl, piperidin-3-ylamino, pyrrolidin-3-ylamino, or pyrrolidin-1-yl; and a pharmaceutically acceptable salt thereof.

Another aspect of the current invention relates to compounds having the general structure of Formula 2'

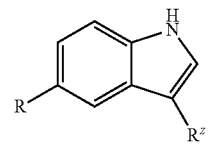

2'

$R^z$ is substituted or unsubstituted 5-membered heterocyclyl or substituted or unsubstituted 6-membered heterocyclyl or substituted or unsubstituted 9 membered heterocyclyl or substituted or unsubstituted 10 membered heterocyclyl;

Wherein R is —$CO_2$H, cyano, lower alkoxycarbonyl, lower alkylaminocarbonyl, substituted or unsubstituted cycloalkyl, substituted or unsubstituted phenyl, substituted or unsubstituted 7-azaindolyl, substituted or unsubstituted 1,2,3,4-tetrahydro-1,8-naphthyridyl, substituted or unsubstituted 1H-pyrazolo[3,4-b]pyridyl, substituted or unsubstituted benzomorpholinyl, substituted or unsubstituted pyrazinyl, substituted or unsubstituted pyridazinyl, substituted or unsubstituted pyrimidinyl, substituted or unsubstituted pyridyl, substituted or unsubstituted thiazolyl, substituted or unsubstituted pyrazolyl, or substituted or unsubstituted oxazolyl;

and a pharmaceutically acceptable salt thereof;
provided $R^z$ is not 4-pyridyl when R is 3-pyridyl.

In another embodiment, $R^z$ is substituted or unsubstituted thiazolyl, oxadiazolyl; substituted or unsubstituted pyrazinyl, substituted or unsubstituted pyridyl, substituted or unsubstituted pyrimidinyl, substituted or unsubstituted oxo-pyrimidinyl or substituted or unsubstituted indazolyl; and a pharmaceutically acceptable salt thereof.

In another embodiment, $R^z$ is substituted or unsubstituted thiazol-4-yl or substituted or unsubstituted oxadiazol-2-yl; and a pharmaceutically acceptable salt thereof.

In another embodiment, R is substituted or unsubstituted phenyl; and a pharmaceutically acceptable salt thereof.

In another embodiment, R is substituted or unsubstituted pyrazinyl, substituted or unsubstituted pyridazinyl, substituted or unsubstituted pyrimidinyl, or substituted or unsubstituted pyridyl; and a pharmaceutically acceptable salt thereof.

In another embodiment, $R^z$ is 2-(1-imidazolyl)thiazol-4-yl, 2-(2-oxo-pyrid-1-yl)thiazol-4-yl, 5-isopropylamino-oxadiazol-2-yl, 5-phenylamino-oxadiazol-2-yl, 5-(3-aminopiperidin-1-yl)oxadiazol-2-yl, 5-(4-aminopiperidin-1-yl)oxadiazol-2-yl, 5-(piperidin-3-ylamino)oxadiazol-2-yl, 5-(pyrrolidin-3-ylamino)oxadiazol-2-yl, 5-pyrrolidin-1-yloxadiazol-2-yl, pyrazin-2-yl, 2-dimethylaminopyrazin-6-yl, 2-(cyclohexylamino)pyrazin-6-yl, 2-(pyrrolidin-3-ylamino)pyrazin-6-yl, 2-(piperidin-3-ylamino)pyrazin-6-yl, 2-(piperidin-4-ylamino)pyrazin-6-yl, 2-(2-oxopiperazin-4-ylamino)pyrazin-6-yl, 2-(piperidin-3-yloxy)pyrazin-6-yl, 2-(3-amino-pyrrolidin-1-yl)pyrazin-6-yl, 2-(4-aminopiperidin-1-yl)pyrazin-6-yl, 2-isopropylaminopyrazin-6-yl, 2-(3-aminopiperidin-1-yl)pyrazin-6-yl, 2-(morpholin-4-yl)pyrazin-6-yl, 2-methoxy-pyrazin-6-yl, 2-methoxy-pyrazin-5-yl, 2-isopropoxy-pyrazin-6-yl, 2-(piperidin-3-yloxy)pyrazin-6-yl, 2-(piperidin-4-yloxy)pyrazin-6-yl, 2-cyclopropylpyrazin-6-yl, 2-(morpholin-4-yl)pyrid-6-yl, 2-(2-oxo-pyrrolidin-1-yl)pyrid-6-yl, 2-(pyrazol-1-yl)pyrid-6-yl, 3-fluoro-6-pyridyl, 2-amino-6-pyridyl, 2-amino-4-pyridyl, 4-amino-2-pyridyl, 2-amino-3-chloropyrid-5-yl, 4-methyl-2-pyridyl, 3-methyl-6-pyridyl, 2-isopropoxy-pyrid-6-yl, 4-(piperidin-3-ylamino)pyrimidin-2-yl, 4-(piperidin-3-ylamino)-6-methoxypyrimidin-2-yl, 2-(4-aminopiperidin-1-yl)-4-methoxypyrimidin-6-yl, 2-(4-aminopiperidin-1-yl)-4-oxypyrimidin-6-yl, 4-(piperidin-3-yloxy)pyrimidin-2-yl, 4-(piperidin-4-yloxy)pyrimidin-2-yl, 4-(piperidin-4-ylamino)pyrimidin-2-yl, 4-(piperidin-3-ylamino)-6-hydroxypyrimidin-2-yl, 2-(piperidin-3-ylamino)-6-hydroxypyrimidin-4-yl, 2-(morpholinin-4-yl)-6-hydroxypyrimidin-4-yl, 2-(morpholinin-4-yl)-4-hydroxypyrimidin-6-yl, 2-(morpholinin-4-yl)-4-methoxypyrimidin-6-yl, 4-(morpholinin-4-yl)-6-methoxypyrimidin-2-yl, 2-(piperidin-3-yloxy)-6-methoxypyrimidin-4-yl, 2-(piperidin-3-ylamino)-6-methoxypyrimidin-4-yl, 2-(4-aminopiperidin-1-yl)-4-methoxypyrimidin-6-yl, 2-(4-aminopiperidin-1-yl)-4-hydroxypyrimidin-6-yl, 4-(4-aminopiperidin-1-yl)-6-hydroxypyrimidin-2-yl, 4-cyclopropylpyrimidin-2-yl, 6-(4-aminopiperidin-1-yl)-2-oxopyrimidin-4-yl, 2-(4-aminopiperidin-1-yl)-4-oxopyrimidin-6-yl, 2-isopropylamino-4-oxopyrimidin-6-yl, 4-isopropylamino-2-oxopyrimidin-6-yl, 2-dimethylamino-4-oxopyrimidin-6-yl, 4-dimethylamino-6-oxopyrimidin-2-yl, or 6-indazolyl; and a pharmaceutically acceptable salt thereof.

In another embodiment, R is phenyl, 2-fluorophenyl, 2,6-difluorophenyl, 2-chloro-6-fluorophenyl, 3-fluoro-4-methoxyphenyl, 3-fluoro-4-cyanophenyl, 4-fluoro-3-cyanophenyl, 3-chloro-6-methoxyphenyl, 3,4-dimethoxyphenyl, 3,5-dimethoxyphenyl, 2,5-dimethoxyphenyl, 3-methoxyphenyl, 4-methoxyphenyl, 3-cyano-5,6-dimethoxyphenyl, 3-cyano-4-isopropoxyphenyl, 4-isopropoxyphenyl, 3-isopropoxyphenyl, 3-cyano-5-methoxy-6-propoxyphenyl, 3-cyano-6-isopropoxy 5-methoxyphenyl, 2-cyano-5-isopropoxy-4-methoxyphenyl, 4-isopropylphenyl, 4-isobutylphenyl, 2,3-dimethylphenyl, 3,5-dimethyl-4-methoxyphenyl, 3-hydroxymethylphenyl, 4-hydroxymethylphenyl, 3-(2-hydroxyethyl)phenyl, 2-methyl-5-trifluoromethylphenyl, 3-carboxyphenyl, 2-cyanophenyl, 4-(methylcarbonylamino)phenyl, 4-(cyclopropylcarbonylamino)phenyl, 3-(cyclobutylaminocarbonyl)-6-methylphenyl, 3-(methylcarbonylamino)-5-trifluoromethylphenyl, 3-(ethylaminocarbonyl)-6-methylphenyl, 3-difluoromethoxyphenyl, 4-amino-3-trifluoromethoxyphenyl, benzodioxolyl, 3-(pyrazol-3-yl)phenyl, 3-tetrazol-5-ylphenyl, 3-isoxazol-5-ylphenyl, 3-(2-methylthiazol-4-yl)phenyl, 3-(1-cyanocyclobutyl)phenyl, or 4-(morpholin-4-yl)phenyl; and a pharmaceutically acceptable salt thereof.

In another embodiment, $R^z$ is thiazol-4-yl substituted with substituted or unsubstituted 5-membered nitrogen-containing heterocyclyl or substituted or unsubstituted 6-membered nitrogen-containing heterocyclyl, oxadiazol-2-yl substituted with phenylamino, lower alkylamino, 5-membered nitrogen-containing heterocyclyl, substituted or unsubstituted 5-membered nitrogen-containing heterocyclylamino, substituted or unsubstituted 6-membered nitrogen-containing heterocyclylamino, or substituted or unsubstituted 6-membered nitrogen-containing heterocyclyl, pyrazin-2-yl substituted with alkylamino, dialkylamino, lower cycloalkylamino, substituted or unsubstituted 5-membered nitrogen-containing heterocyclyl, substituted or unsubstituted 6-membered nitrogen-containing heterocyclyl, $C_1$-$C_3$ alkoxy, substituted or unsubstituted 6-membered nitrogen-containing heterocyclyloxy, substituted or unsubstituted 6-membered nitrogen-containing heterocyclylamino, substituted or unsubstituted 5-membered nitrogen-containing heterocyclylamino, substituted or unsubstituted $C_3$-$C_6$ cycloalkyl, pyrid-2-yl substituted with substituted or unsubstituted 5-membered nitrogen-containing heterocyclyl, substituted or unsubstituted 6-membered nitrogen-containing heterocyclyl, $C_1$-$C_3$ alkoxy, $C_1$-$C_3$ alkyl, amino, fluoro, pyrid-4-yl substituted with amino, pyrimidin-2-yl substituted with substituted or unsubstituted 6-membered nitrogen-containing heterocyclyloxy, or substituted or unsubstituted 6-membered nitrogen-containing heterocyclylamino, 2-oxo-pyrimidin-4-yl unsubstituted or substituted with substituted or unsubstituted 6-membered nitrogen-containing heterocyclyloxy, or substituted or unsubstituted 6-membered nitrogen-containing heterocyclylamino, or substituted or unsubstituted indazolyl;

wherein the substituted 5-membered nitrogen-containing heterocyclyl, or substituted 6-membered nitrogen-containing heterocyclyl are substituted with one or more substituents selected from amino, oxo, methyl, fluoro, $=CH_2$, and a pharmaceutically acceptable salt thereof.

In another embodiment, R is oxazolyl, 1-cyclopropyl-3-pyrazolyl, 2-(2-methylpiperidin-1-yl)thiazol-4-yl, or 1-isopropylpyrazol-4-yl; and a pharmaceutically acceptable salt thereof.

In another embodiment, R is $CO_2H$, or methoxycarbonyl; and a pharmaceutically acceptable salt thereof.

In another embodiment, R is 2-(isopropoxy)-pyrazin-6-yl, 2-cyclopentyloxypyrazin-6-yl, 2-cyclopropylpyrazin-6-yl, 2-cyclopropylaminopyrazin-6-yl, 2-dimethylamino-pyrazin-5-yl, 2-isopropoxypyrazin-6-yl, 2-(pyrazol-1-yl)pyrazin-5-yl, 2-(pyrrolidin-1-yl)pyrazin-6-yl, 2-(3-methylpiperidin-1-yl)pyrazin-5-yl, 3-chloropyrid-5-yl, 3-chloropyrid-4-yl, 3-cyclopropylaminopyrid-5-yl, 3-fluoro-6-methoxypyrid-4-yl, 2-methoxypyrid-3-yl, 2-methoxypyrid-5-yl, 2-cyclopentyloxy-pyrid-6-yl, 2-cyclobutyloxy-pyrid-6-yl, 2-cyclopropylmethoxy-pyrid-5-yl, 2-(piperazin-1-yl)pyrid-6-yl, 2-(4-methylpiperidin-1-yl)-6-pyridyl, 2-(2-methyl-imidazol-1-yl)pyrid-6-yl, 2-(3-methylpyrazol-1-yl)pyrid-6-yl, 3-(pyrrolidin-2-yl)pyrid-5-yl, 2-cyanopyrid-3-yl, 2-chloro-3-methylsulfonylamino-pyrid-5-yl, 2-(4-aminophenyloxy)pyrid-3-yl, 2-(morpholin-4-yl)pyrid-3-yl, 4-dihydroxypyrimidin-5-yl, 4-cyclopropylpyrimidin-2-yl, and a pharmaceutically acceptable salt thereof.

In another embodiment, R is 2,2-dimethylcyclopropyl; and a pharmaceutically acceptable salt thereof.

In another embodiment, R is 3-methyl-1H-pyrazolo[3,4-b]pyrid-5-yl, 7-azaindol-5-yl, 4-methylbenzomorpholin-7-yl, or 1,2,3,4-tetrahydro-1,8-naphthyrid-6-yl; and a pharmaceutically acceptable salt thereof.

Another aspect of the current invention relates to compounds having the general structure of Formula 3'

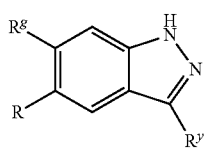

Wherein $R^g$ is H or F;
Wherein $R^y$ is

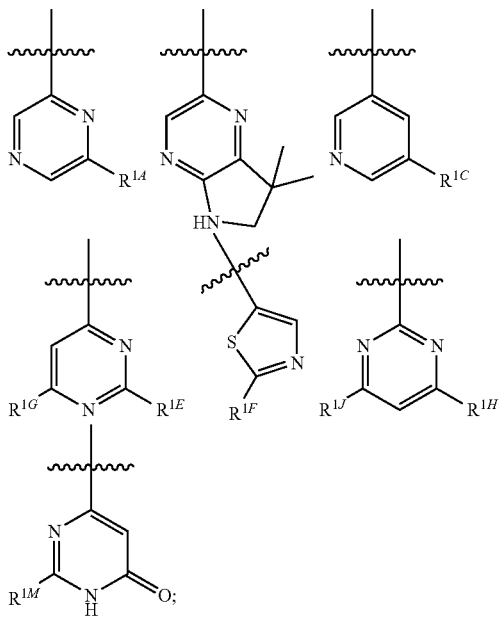

Wherein R is substituted or unsubstituted $C_6$-$C_{10}$-aryl, substituted or unsubstituted 5-6-membered heterocyclyl, substituted or unsubstituted 9-10-membered heterocyclyl, 1,2,2',3',5',6'-hexahydrospiro[indole-3,4'-pyran]-4-yl, halo, $C_{1-4}$ hydroxyalkyl, $C_{1-4}$ haloalkyl, substituted or unsubstituted $C_3$-$C_6$ cycloalkyl, $C_3$-$C_6$-cycloalkyl-$C_2$-$C_3$-alkenyl, halo, $C_{1-4}$ alkylcarbonyl, $C_{1-4}$ alkoxycarbonyl, HOOC—, $C_{1-4}$ alkylcarbonylamino, aminocarbonyl, phenylaminocarbonyl, $C_{1-4}$ alkylaminocarbonyl, $C_{1-4}$ dialkylaminocarbonyl, phenylcarbonylamino, nitro, cyano, $C_{1-4}$ cyanoalkyl, benzylaminocarbonyl, substituted or unsubstituted $C_6$-$C_{10}$-arylamino, $C_{2-4}$ alkenyl, $C_{2-4}$ haloalkenyl or amino; provided R is not 2-methoxypyridyl when Ry is 2-(4-amino-1-piperidyl)-6-pyrazinyl;

Wherein $R^{1A}$ is H, hydroxy, $C_1$-$C_3$-alkoxy, $C_1$-$C_3$-haloalkoxy, substituted or unsubstituted 5-6-membered heterocyclyl, substituted or unsubstituted 5-6-membered heterocyclyl-amino, substituted or unsubstituted 5-6-membered heterocyclyl-(alkyl)amino, substituted or unsubstituted 5-6-membered heterocyclyloxy, alkylamino, $C_3$-$C_6$ cycloalkylamino, substituted or unsubstituted 5-6-membered heterocyclyl-S—, or substituted or unsubstituted phenylamino or 9-10 membered nitrogen containing heterocyclyl;

Wherein $R^{1C}$ is H, $C_1$-$C_3$-alkoxy, substituted or unsubstituted 5-6-membered heterocyclyl, or substituted or unsubstituted 5-6-membered heterocyclyl-amino;

Wherein $R^{1E}$ is H, $C_1$-$C_3$-alkoxy, substituted or unsubstituted 5-6-membered heterocyclyl, substituted or unsubstituted 5-6-membered heterocyclyl-amino, substituted or unsubstituted 5-6-membered heterocyclyl-(alkyl)amino, substituted or unsubstituted 5-6-membered heterocyclyloxy or alkylamino;

Wherein $R^{1F}$ is H, or substituted or unsubstituted 6-membered heterocyclyl;

Wherein $R^{1G}$ is H, hydroxy or $C_1$-$C_3$-alkoxy;

Wherein $R^{1H}$ is H, hydroxy or $C_1$-$C_3$-alkoxy;

Wherein $R^{1J}$ is H, hydroxy, $C_1$-$C_3$-alkoxy, substituted or unsubstituted 5-6-membered heterocyclyl, or substituted or unsubstituted 5-6-membered heterocyclyl-amino, or substituted or unsubstituted 5-6-membered heterocyclyl-(alkyl)amino or substituted or unsubstituted 5-6-membered heterocyclyloxy or alkylamino or substituted or unsubstituted 5-6-membered heterocyclyl-S—, or substituted or unsubstituted phenyl or 9-10 membered nitrogen containing heterocyclyl; and Wherein $R^{1M}$ is H, lower alkyl, lower alkoxy, lower alkylamino, lower dialkylamino, substituted or unsubstituted 5-6-membered heterocyclyloxy, substituted or unsubstituted 5-6-membered heterocyclyl or substituted or unsubstituted 5-6-membered heterocyclylam;

and a pharmaceutically acceptable salt thereof; provided R is not 2,6-dimethyl-3,5-dicyano-dihydropyridyl.

In another embodiment, $R^{1A}$ is piperidin-3-ylamino, piperidin-4-ylamino, piperidin-4-yl-N-methylamino, piperidin-3-yl-N-methylamino, pyrrolidin-3-ylamino, 3-azetidinylamino, cyclopropylamino, hydroxy, methoxy, isopropoxy, trifluoroethoxy, fluoroethoxy, 3-pyridyloxy, 3-azetidinyloxy, pyrrolidin-3-yloxy, piperidin-3-yloxy, 4-fluoro-piperidin-3-yloxy, 3-fluoro-piperidin-4-yloxy, 3-fluoro-piperidin-5-yloxy, 3-methyl-piperidin-3-yloxy, 3-methyl-piperidin-5-yloxy, 1-methyl-piperidin-4-yloxy, 4-isopropyl-piperidin-3-yloxy, 4-ethyl-piperidin-3-yloxy, 4-methyl-piperidin-3-yloxy, 4,4-dimethyl-piperidin-3-yloxy, 3,3-dimethyl-piperidin-4-yloxy, piperidin-4-yloxy, 1,2,3,6-tetrahydro-3-pyridinyloxy, 6-azaspiro[2.5]oct-4-yloxy, 5-azaspiro[2.5]oct-8-yloxy, 3-azabicyclo[4.1.0]hept-5-yloxy, ((3S)-4-methylidene-3-piperidinyl)oxy, piperidin-3-ylthio, methylamino, ethylamino, isopropylamino, tert-butylamino, dimethylamino, phenylamino, piperidin-3-ylmethyl, piperidin-4-ylmethyl, cyclopropyl, 3-pyridyl, 5-indazolyl, 1,4-diazepan-1-yl, 1-pyrrolidinyl, 3-hydroxypyrrolidin-1-yl, 3,4-dihydroxypyrrolidin-1-yl, 3-aminopyrrolidinyl, 4-aminopiperidin-1-yl, 3-aminopiperidinyl, 3-hydroxypiperidin-1-yl, 3,4-dihydroxypiperidin-1-yl, 4-hydroxypiperidinyl, 4-morpholinyl, 3-pyrazolyl, 3-azetidinyl, 1-piperazinyl, or 1-piperidinyl; $R^{1E}$ is 4-aminopiperidin-1-yl, piperidin-3-ylamino, piperidin-4-ylamino, piperidin-4-yloxy or piperidin-3-yl; $R^{1G}$ is H, hydroxy or methoxy; $R^{1H}$ is H, hydroxy or methoxy; $R^{1J}$ is 4-aminopiperidin-1-yl, piperidin-3-ylamino, piperidin-4-ylamino or piperidin-3-yl; and $R^{1M}$ is butyl, dimethylamino, isopropylamino, isopropoxy, 3-fluoro-piperidin-4-yloxy, 4-fluoro-piperidin-3-yloxy, piperidin-3-yloxy, 6-azaspiro[2.5]octan-4-yloxy, 4-aminopiperidin-1-yl, 3-hydroxypyrrolidin-1-yl, piperidin-3-ylamino, piperidin-4-ylamino or 3-methylpiperidin-5-ylamino;

and a pharmaceutically acceptable salt thereof.

In another embodiment, R is substituted or unsubstituted nitrogen containing-6 membered heteroaryl or substituted or unsubstituted phenyl; and a pharmaceutically acceptable salt thereof.

In another embodiment, R is phenyl substituted or unsubstituted with one or more substituents selected from fluoro, chloro, nitro, amino, cyano, methyl, trifluoromethyl, 1-hydroxyethyl, ethynyl, 1-chlorovinyl, oxo, hydroxy, methoxy, isopropoxy, trifluoromethoxy, methylsulfonyl, dimethylamino, morpholinyl, aminosulfonyl, methylsulfonylamino, aminocarbonyl, methylcarbonylamino, isopropylaminocarbonyl, cyclopropylaminocarbonyl, phenylaminocarbonyl, diethylaminocarbonyl, dimethylaminocarbonyl, benzylaminocarbonyl, tert-butylaminocarbonyl, butylaminocarbonyl, propylaminocarbonyl, ethylaminocarbonyl, cyclopropylaminocarbonyl, cyclohexylaminocarbonyl, piperidinylcarbonyl or morpholinylcarbonyl;

and a pharmaceutically acceptable salt thereof.

In another embodiment, R is pyridyl, or pyrimidinyl, or pyrazinyl, or pyridazinyl, wherein R is substituted or unsubstituted with one or more substituents selected from hydroxy, amino, cyano, cyclopropyl, fluoro, chloro, methoxy, isopropoxy, ethoxy, methyl, isopropyl, isobutyltrifluoromethyl, tert-butylaminocarbonyl, tert-butylcarbonylamino, 4-cyclopropylaminocarbonyl, oxo, morpholinyl, 3-methylmorpholinyl, cyclopropylamino or cyclopentylamino; and a pharmaceutically acceptable salt thereof.

In another embodiment, R is R is quinolyl, isoquinolinyl, quinoxalinyl, pyrazolo[3,4-b]pyridinyl, 2,3-dihydro-indolyl, indazolyl, benzothiazolyl, 3,4-dihydro-2H-pyrido[3,2-b][1,4]oxazinyl, 3,4-dihydro-2H-1,4-benzoxazinyl, 1H-pyrrolo[2,3-b]pyridinyl, 1H-pyrrolo[3,2-c]pyridinyl, imidazo[1,2-a]pyrazinyl, [1,2,4]triazolo[4,3-a]pyridinyl, 1,2,2',3',5',6'-hexahydrospiro[indole-3,4'-pyranyl] or 2,3-dihydro-1,4-benzodioxinyl; wherein R is substituted or unsubstituted with one or more substituents selected from hydroxy, cyano, chloro, methoxy, fluoro, trifluoromethoxy, methyl, oxo, trifluoromethyl or 2-aminopyrimidin-4-yl; and a pharmaceutically acceptable salt thereof.

In another embodiment, R is cyclopropyl, cyclobutyl, cyclopentyl, pyranyl, 5,6-dihydro-2H-pyranyl, 3,6-dihydro-2H-pyranyl, tetrahydropyran, pyrrolidinyl, piperidinyl, morpholinyl, or imidazolidinyl; wherein R is substituted or unsubstituted with one or more substituents selected from methyl, or oxo; and a pharmaceutically acceptable salt thereof.

In another embodiment, R is methoxycarbonyl, isopropoxycarbonyl, methylcarbonyl, cyano, cyanomethyl, nitro, amino, 2,6-difluorophenylamino, aminocarbonyl, ethylcarbonylamino, phenylcarbonylamino, isopropylaminocarbonyl, methylaminocarbonyl, dimethylaminocarbonyl, HOOC—, phenylaminocarbonyl, benzylaminocarbonyl, bromo, hydroxyethyl, 1-hydroxy-2-propyl, isopropyl, 1-methylcyclopropyl, 1-trifluoromethylcyclopropyl, 3,3,3-trifluoroprop-2-yl, prop-1-en-2-yl, 3,3,3-trifluoroprop-1-en-2-yl or cyclopropylethenyl; and a pharmaceutically acceptable salt thereof.

In another embodiment, R is phenyl, 2,6-difluorophenyl, 2,5-difluorophenyl, 2,4-difluorophenyl, 2,3-difluorophenyl, 2-fluorophenyl, 3-fluorophenyl, 2-fluoro-5-nitrophenyl, 4-aminocarbonyl-2-fluorophenyl, 3-aminocarbonyl-6-fluorophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(piperidin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-fluoro-4-hydroxyphenyl, 2-hydroxyphenyl, 3-hydroxyphenyl, 3-methoxyphenyl, 3,5-dimethoxyphenyl, 3-isopropoxyphenyl, 3-trifluoromethoxyphenyl, 2-trifluoromethylphenyl, 3-aminophenyl, 3-amino-2-methylphenyl, 3-(1-hydroxyethyl)phenyl, 2-cyanophenyl, 3-cyanophenyl, 4-cyano-2-fluorophenyl, 2-cyano-6-fluorophenyl, 2-chlorophenyl, 2-chloro-6-fluorophenyl, 3-chloro-6-fluorophenyl, 4-chloro-2-fluorophenyl, 3-methylsulfonylphenyl, 2-fluoro-4-methylsulfonylphenyl, 4-methylsulfonylphenyl, 2,6-difluoro-4-methylsulfonylphenyl, 2-fluoro-4-methylsulfonylamino-phenyl, 4-aminosulfonyl-2-fluorophenyl, 3-dimethylaminophenyl, 3-amino-4-morpholinophenyl, 3-amino-6-trifluoromethoxyphenyl, 4-amino-2-fluorophenyl, 2-fluoro 4-methylcarbonylaminophenyl, ethynylphenyl, (1-chlorovinyl)benzene, 2-methylphenyl, 2-pyridyl, 3-pyridyl, 4-pyridyl, 2-hydroxy-3-pyridyl, 2-amino-4-pyridyl, 3-amino-5-pyridyl, 3-amino-2-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 3-fluoro-2-pyridyl, 3-fluoro-5-pyridyl, 3-methyl-2-pyridyl, 2-trifluoromethyl-6-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 2-amino-4-cyclopentylamino-pyrimidin-5-yl, 4-cyclopropylpyrimidin-2-yl, 4-oxo-pyrimidin-5-yl, 2-methoxy-pyrimidin-4-yl, 2-isopropoxypyrimidin-4-yl, 3-pyrazinyl, 2-cyclopropyl-6-pyrazinyl, 2-cyclopropylamino-6-pyrazinyl, 2-isopropoxy-6-pyrazinyl, 3-pyridazinyl, 4-amino-pyridazin-6-yl, 3-quinolyl, 2-hydroxy-3-quinolyl, 2-chloro-3-quinolyl, 7-methoxy-4-quinolyl, 7-fluoro-4-quinolyl, 7-cyano-4-quinolyl, 7-trifluoromethoxy-4-quinolyl, 2-methoxy-3-quinolyl, 1-methyl-2-oxo-quinolin-4-yl, 1-methyl-2-oxo-isoquinolin-6-yl, 6-quinoxalinyl, 3-trifluoromethyl-1H-pyrazolo[3,4-b]pyridin-5-yl, 3-trifluoromethyl-5-indazolyl, 1-methyl-2-oxo-2,3-dihydro-indol-5-yl, 1-(2-aminopyrimidin-4-yl)-2,3-dihydro-indol-6-yl, benzothiazol-5-yl, benzothiazol-6-yl, 4-methyl-3,4-dihydro-2H-pyrido[3,2-b][1,4]oxazin-7-yl, 4-methyl-3,4-dihydro-2H-1,4-benzoxazin-7-yl, 1H-pyrrolo[2,3-b]pyridin-5-yl, 1H-pyrrolo[2,3-b]pyridin-6-yl, imidazo[1,2-a]pyrazin-5-yl, [1,2,4]triazolo[4,3-a]pyridin-5-yl, 1,2,2',3',5',6'-hexahydrospiro[indole-3,4'-pyran]-4-yl and 2,3-dihydro-1,4-benzodioxin-6-yl, 1H-pyrazol-5-yl, 1-methyl-1H-pyrazol-4-yl, thiazol-2-yl, 2-(2-methylpiperidin-1-yl)thiazol-4-yl, 2-(pyrrolidin-1-yl) thiazol-4-yl, 4-pyranyl, 3-pyranyl, 5,6-dihydro-2H-pyran-3-yl, 3,6-dihydro-2H-pyran-4-yl, tetrahydro-4-pyranyl, tetrahydro-3-pyranyl, 2-oxo-pyrrolidin-1-yl, 2-oxo-piperidin-1-yl, morpholin-4-yl, 1-methyl-2-oxo-imidazolidin-3-yl, 1-piperidinyl, methoxycarbonyl, nitro, amino, aminocarbonyl, ethylcarbonylamino, phenylcarbonylamino, isopropylaminocarbonyl, HOOC—, phenylaminocarbonyl, benzylaminocarbonyl, bromo, or cyclopropylethenyl; and a pharmaceutically acceptable salt thereof.

In another embodiment, $R^{1E}$ is H, hydroxy, methoxy, piperidin-3-yloxy, isopropylamino, 4-amino-piperidin-1-yl, methylamino, piperidin-3-ylamino, piperidin-4-ylamino, 4-aminopiperidin-1-yl, piperidin-4-yloxy or piperidin-3-yl; wherein $R^{1G}$ is H, hydroxy, or methoxy; and a pharmaceutically acceptable salt thereof.

In another embodiment, $R^{1A}$ is piperidin-3-ylamino, piperidin-4-ylamino, piperidin-4-yl-N-methylamino, piperidin-3-yl-N-methylamino, pyrrolidin-3-ylamino, 3-azetidinylamino, cyclopropylamino, hydroxy, methoxy, isopropoxy, trifluoroethoxy, fluoroethoxy, 3-pyridyloxy, 3-azetidinyloxy, pyrrolidin-3-yloxy, piperidin-3-yloxy, 4-fluoro-piperidin-3-yloxy, 3-fluoro-piperidin-4-yloxy, 3-fluoro-piperidin-5-yloxy, 3-methyl-piperidin-3-yloxy, 3-methyl-piperidin-5-yloxy, 1-methyl-piperidin-4-yloxy, 4-isopropyl-piperidin-3-yloxy, 4-ethyl-piperidin-3-yloxy, 4-methyl-piperidin-3-yloxy, 4,4-dimethyl-piperidin-3-yloxy, 3,3-dimethyl-piperidin-4-yloxy, piperidin-4-yloxy, 1,2,3,6-tetrahydro-3-pyridinyloxy, 6-azaspiro[2.5]oct-4-yloxy, 5-azaspiro[2.5]oct-8-yloxy, 3-azabicyclo[4.1.0]hept-5-yloxy, ((3S)-4-methylidene-3-piperidinyl)oxy, piperidin-3-ylthio, methylamino, ethylamino, isopropylamino, tert-butylamino, dimethylamino, phenylamino, piperidin-3-ylmethyl, piperidin-4-ylmethyl, cyclopropyl, 3-pyridyl, 5-indazolyl, 1,4-diazepan-1-yl, 1-pyrrolidinyl, 3-hydroxypyrrolidin-1-yl, 3,4-dihydroxypyrrolidin-1-yl, 3-aminopyrrolidinyl, 4-aminopiperidin-1-yl, 3-aminopiperidinyl, 3-hydroxypiperidin-1-yl, 3,4-dihydroxypiperidin-1-yl, 4-hydroxypiperidinyl, 4-morpholinyl, 3-pyrazolyl, 3-azetidinyl, 1-piperazinyl, or 1-piperidinyl; and a pharmaceutically acceptable salt thereof.

In another embodiment, $R^{1F}$ is 4-amino-piperidin-1-yl; and a pharmaceutically acceptable salt thereof In another embodiment, $R^y$ is

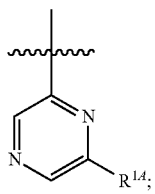

and a pharmaceutically acceptable salt thereof.

In another embodiment, $R^{1C}$ is H, hydroxy, methoxy, piperidin-3-ylamino, piperidin-4-ylamino, piperidin-4-yl-N-methylamino, piperidin-3-yl-N-methylamino, pyrrolidin-3-ylamino, 3-azetidinylamino, 3-pyridyl, 1-pyrrolidinyl, 3-hydroxypyrrolidin-1-yl, 3-aminopyrrolidinyl, 4-aminopiperidinyl, 3-aminopiperidinyl, 3-hydroxypiperidin-1-yl, 4-hydroxypiperidinyl, 4-morpholinyl, 3-pyrazolyl, 3-azetidinyl, 1-piperazinyl, or 1-piperidinyl; and a pharmaceutically acceptable salt thereof.

In another embodiment, R is unsubstituted or substituted 5-membered heteroaryl; and a pharmaceutically acceptable salt thereof.

In another embodiment, R is unsubstituted or substituted thiazolyl, unsubstituted or substituted imidazolyl, unsubstituted or substituted oxazolyl or unsubstituted or substituted pyrazolyl; and a pharmaceutically acceptable salt thereof.

In another embodiment, R is pyrazolyl, thiazolyl, imidazolyl, or oxazolyl; wherein R is substituted or unsubstituted with one or more substituents selected from methyl, isopropyl, 2-methylpiperidin-1-yl, pyrrolidin-1-yl or oxo; and a pharmaceutically acceptable salt thereof In another embodiment, $R^y$ is

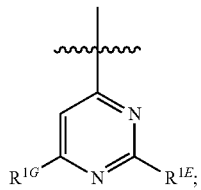

and a pharmaceutically acceptable salt thereof.

In another embodiment, $R^y$ is

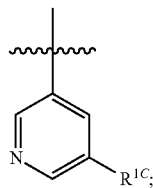

wherein $R^{1C}$ is H, hydroxy, methoxy or 4-aminopiperidin-1-yl; and a pharmaceutically acceptable salt thereof.

In another embodiment, $R^y$ is

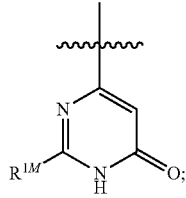

wherein $R^{1M}$ is butyl, dimethylamino, isopropylamino, isopropoxy, 3-fluoro-piperidin-4-yloxy, 4-fluoro-piperidin-3-yloxy, piperidin-3-yloxy, 6-azaspiro[2.5]octan-4-yloxy, 4-aminopiperidin-1-yl, 3-hydroxypyrrolidin-1-yl, piperidin-3-ylamino, piperidin-4-ylamino or 3-methylpiperidin-5-ylamino; and a pharmaceutically acceptable salt thereof.

Another aspect of the current invention relates to compounds having the general structure of formula 4':

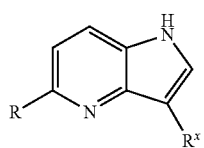

4'

Wherein $R^x$ is

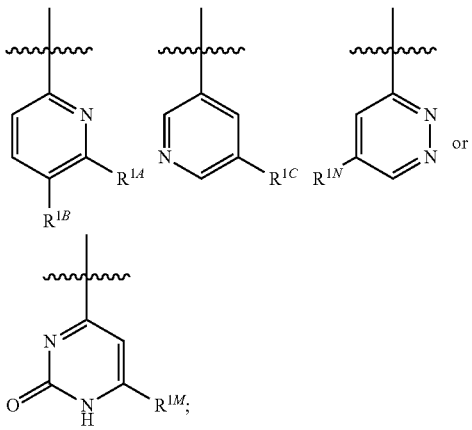

Wherein R is substituted or unsubstituted phenyl or substituted or unsubstituted 5-membered heteroaryl or substituted or unsubstituted 6-membered heteroaryl, or halo;

Wherein $R^{1A}$ is H, methoxy, substituted or unsubstituted 6-membered heterocyclyl-amino or substituted or unsubstituted 6-membered heterocyclyl;

Wherein $R^{1B}$ is H or methoxy;

Wherein $R^{1C}$ is H, methoxy, substituted or unsubstituted 6-membered heterocyclyl, or substituted or unsubstituted 6-membered heterocyclyl-amino;

Wherein $R^{1M}$ is H, methoxy or substituted or unsubstituted 6-membered heterocyclyl; and Wherein $R^{1N}$ is H or methoxy; and and a pharmaceutically acceptable salt thereof.

In another embodiment, the group R is substituted or unsubstituted phenyl; and a pharmaceutically acceptable salt thereof.

In another embodiment, the group R is 2-fluorophenyl, or 2,6-difluorophenyl; and a pharmaceutically acceptable salt thereof.

In another embodiment, the group $R^x$ is

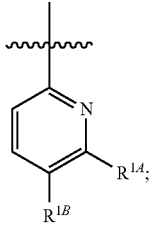

and a pharmaceutically acceptable salt thereof.

In another embodiment, $R^x$ is

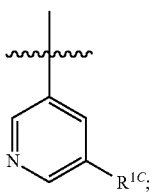

and a pharmaceutically acceptable salt thereof.

In another embodiment, $R^{1C}$ is piperid-3-ylamino or 4-amino-piperidyl; and a pharmaceutically acceptable salt thereof.

In another embodiment, $R^{1A}$ is H, methoxy, piperid-3-ylamino or 4-amino-piperidyl; wherein $R^{1B}$ is H or methoxy and a pharmaceutically acceptable salt thereof.

In another embodiment, $R^x$ is

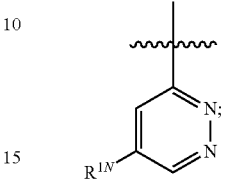

and a pharmaceutically acceptable salt thereof.

In another embodiment, $R^{1N}$ is H or methoxy; and a pharmaceutically acceptable salt thereof.

In another embodiment, $R^x$ is

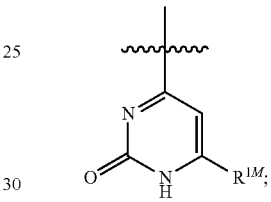

and a pharmaceutically acceptable salt thereof.

In another embodiment, $R^{1M}$ is H, methoxy or 4-amino-piperidyl; and a pharmaceutically acceptable salt thereof.

A family of specific compounds of particular interest within Formula 1 consists of compounds and pharmaceutically-acceptable derivatives thereof as follows:

1-(5-(5-(2-fluorophenyl)-1H-pyrrolo[3,2-b]pyridin-3-yl)pyridin-3-yl)piperidin-4-amine;

5-(5-(2,6-difluorophenyl)-1H-pyrrolo[3,2-b]pyridin-3-yl)-N-(piperidin-3-yl)pyridin-3-amine;

1-(5-(5-(2,6-difluorophenyl)-1H-pyrrolo[3,2-b]pyridin-3-yl)pyridin-3-yl)piperidin-4-amine;

1-(6-(5-bromo-1H-indazol-3-yl)pyrazin-2-yl)piperidin-4-amine hydrochloride salt;

1-(6-(5-(2-methoxyquinolin-3-yl)-1H-indazol-3-yl)pyrazin-2-yl)piperidin-4-amine;

3-(3-(6-(4-aminopiperidin-1-yl)pyrazin-2-yl)-1H-indazol-5-yl)-N-cyclopropyl-4-fluorobenzamide;

1-(6-(5-(2-fluoro-3-methoxyphenyl)-1H-indazol-3-yl) pyrazin-2-yl)piperidin-4-amine;

1-(6-(5-(6-isopropoxypyrazin-2-yl)-1H-indazol-3-yl) pyrazin-2-yl)piperidin-4-amine;

1-(6-(5-(3-(trifluoromethyl)-1H-pyrazolo[3,4-b]pyridin-5-yl)-1H-indazol-3-yl)pyrazin-2-yl)piperidin-4-amine;

1-(6-(5-(3-Fluorophenyl)-1H-indazol-3-yl)pyrazin-2-yl)piperidin-4-amine;

1-(3-(6-(4-Aminopiperidin-1-yl)pyrazin-2-yl)-1H-indazol-5-yl)pyrrolidin-2-one;

1-(6-(5-(2,6-dimethoxypyrimidin-4-yl)-1H-indazol-3-yl) pyrazin-2-yl)piperidin-4-amine;

(R)-5-(5-chloro-2-fluoropyridin-3-yl)-3-(6-(piperidin-3-yloxy)pyrazin-2-yl)-1H-indazole;

5-(6-(1-Methylethoxy)-2-pyrazinyl)-3-(6-((3R)-3-piperidinyloxy)-2-pyrazinyl)-1H-indazole;

5-(6-Cyclopropyl-2-pyrazinyl)-3-(6-((3R)-3-piperidinyloxy)-2-pyrazinyl)-1H-indazole;

5-(2,6-Difluoro-phenyl)-3-iodo-1-(tetrahydro-pyran-2-yl)-1H-indazole;
1-(6-(5-(2,6-difluorophenyl)-1H-indazol-3-yl)pyrazin-2-yl)piperidin-3-amine;
(R)-6-(5-(2,6-difluorophenyl)-1H-indazol-3-yl)-N-(pyrrolidin-3-yl)pyrazin-2-amine;
6-(5-(2,6-Difluorophenyl)-1H-indazol-3-yl)-N-methyl-N-(piperidin-4-yl)pyrazin-2-amine;
5-(2,6-difluorophenyl)-3-(6-(trans-4-fluoropiperidin-3-yloxy)pyrazin-2-yl)-1H-indazole;
(R)-4-(5-(2,6-difluorophenyl)-1H-indazol-3-yl)-N-(piperidin-3-yl)pyrimidin-2-amine;
3,5-Bis(5-methoxypyridin-3-yl)-1H-indazole;
1-(4-(5-(5-Methoxypyridin-3-yl)-1H-indazol-3-yl)pyrimidin-2-yl)piperidin-4-amine;
1-(5-(5-(5-Methoxypyridin-3-yl)-1H-indazol-3-yl)thiazol-2-yl)piperidin-4-amine;
1-(5-(5-(2,6-difluorophenyl)-1H-indazol-3-yl)pyridin-3-yl)piperidin-4-amine;
3-(3-(6-(4-amino-1-piperidinyl)-2-pyrazinyl)-1H-indazol-5-yl)-N-benzyl-4-fluorobenzamide;
3-(3-(6-(4-amino-1-piperidinyl)-2-pyrazinyl)-1H-indazol-5-yl)-N-tert-butyl-4-fluorobenzamide;
3-(3-(6-(4-amino-1-piperidinyl)-2-pyrazinyl)-1H-indazol-5-yl)-N-butyl-4-fluorobenzamide;
3-(3-(6-(4-amino-1-piperidinyl)-2-pyrazinyl)-1H-indazol-5-yl)-4-fluoro-N-propylbenzamide;
3-(3-(6-(4-amino-1-piperidinyl)-2-pyrazinyl)-1H-indazol-5-yl)-4-fluoro-N,N-dimethylbenzamide;
1-(6-(5-(2-fluoro-5-(1-piperidinylcarbonyl)phenyl)-1H-indazol-3-yl)-2-pyrazinyl)-4-piperidinamine;
1-(6-(5-(2-fluoro-5-(4-morpholinylcarbonyl)phenyl)-1H-indazol-3-yl)-2-pyrazinyl)-4-piperidinamine;
3-(3-(6-(4-amino-1-piperidinyl)-2-pyrazinyl)-1H-indazol-5-yl)-N-ethyl-4-fluorobenzamide;
3-(3-(6-(4-amino-1-piperidinyl)-2-pyrazinyl)-1H-indazol-5-yl)-4-fluoro-N-(1-methylethyl)benzamide;
3-(3-(6-(4-amino-1-piperidinyl)-2-pyrazinyl)-1H-indazol-5-yl)-4-fluoro-N-phenylbenzamide;
3-(3-(6-(4-amino-1-piperidinyl)-2-pyrazinyl)-1H-indazol-5-yl)-N,N-diethyl-4-fluorobenzamide;
3-(3-(6-(4-amino-1-piperidinyl)-2-pyrazinyl)-1H-indazol-5-yl)-N,N-diethyl-2-fluorobenzamide;
1-(6-(5-(2-chloro-3-quinolinyl)-1H-indazol-3-yl)-2-pyrazinyl)-4-piperidinamine;
6-(3-(6-(4-amino-1-piperidinyl)-2-pyrazinyl)-1H-indazol-5-yl)-2-methyl-1 (2H)-isoquinolinone;
4-(3-(6-(4-amino-1-piperidinyl)-2-pyrazinyl)-1H-indazol-5-yl)-1-methyl-2 (1H)-quinolinone;
5-(3-(6-(4-amino-1-piperidinyl)-2-pyrazinyl)-1H-indazol-5-yl)-1-methyl-1,3-dihydro-2H-indol-2-one;
1-(6-(5-(1,3-benzothiazol-6-yl)-1H-indazol-3-yl)-2-pyrazinyl)-4-piperidinamine;
1-(6-(5-(1,3-benzothiazol-5-yl)-1H-indazol-3-yl)-2-pyrazinyl)-4-piperidinamine;
3-(3-(6-(4-amino-1-piperidinyl)-2-pyrazinyl)-1H-indazol-5-yl)-2-quinolinol;
1-(6-(5-(3-quinolinyl)-1H-indazol-3-yl)-2-pyrazinyl)-4-piperidinamine;
1-(6-(5-(6-quinoxalinyl)-1H-indazol-3-yl)-2-pyrazinyl)-4-piperidinamine;
1-(6-(5-(1H-pyrrolo[2,3-b]pyridin-5-yl)-1H-indazol-3-yl)-2-pyrazinyl)-4-piperidinamine;
1-(6-(5-(4-methyl-3,4-dihydro-2H-pyrido[3,2-b][1,4]oxazin-7-yl)-1H-indazol-3-yl)-2-pyrazinyl)-4-piperidinamine;
1-(6-(5-(4-(methylsulfonyl)phenyl)-1H-indazol-3-yl)-2-pyrazinyl)-4-piperidinamine;
2-(3-(6-(4-amino-1-piperidinyl)-2-pyrazinyl)-1H-indazol-5-yl)benzonitrile;
1-(6-(5-(2-fluoro-5-methoxyphenyl)-1H-indazol-3-yl)-2-pyrazinyl)-4-piperidinamine;
3-(3-(6-(4-amino-1-piperidinyl)-2-pyrazinyl)-1H-indazol-5-yl)benzonitrile;
1-(6-(5-(6-methoxy-2-pyridinyl)-1H-indazol-3-yl)-2-pyrazinyl)-4-piperidinamine;
1-(6-(5-(6-(1-methylethoxy)-2-pyridinyl)-1H-indazol-3-yl)-2-pyrazinyl)-4-piperidinamine;
1-(6-(5-(6-ethoxy-2-pyridinyl)-1H-indazol-3-yl)-2-pyrazinyl)-4-piperidinamine;
1-(6-(5-(6-fluoro-2-pyridinyl)-1H-indazol-3-yl)-2-pyrazinyl)-4-piperidinamine;
1-(6-(5-(2-fluorophenyl)-1H-indazol-3-yl)-2-pyrazinyl)-4-piperidinamine;
3-(3-(6-(4-amino-1-piperidinyl)-2-pyrazinyl)-1H-indazol-5-yl)-2-pyridinol;
1-(6-(5-(3-fluorophenyl)-1H-indazol-3-yl)-2-pyrazinyl)-4-piperidinamine;
1-(6-(5-(5-fluoro-2-methoxy-4-pyridinyl)-1H-indazol-3-yl)-2-pyrazinyl)-4-piperidinamine;
1-(6-(5-(2,3-difluorophenyl)-1H-indazol-3-yl)-2-pyrazinyl)-4-piperidinamine;
2-(3-(6-(4-amino-1-piperidinyl)-2-pyrazinyl)-1H-indazol-5-yl)phenol;
5-(3-(6-(4-amino-1-piperidinyl)-2-pyrazinyl)-1H-indazol-5-yl)-3-pyridinamine;
4-(3-(6-(4-amino-1-piperidinyl)-2-pyrazinyl)-1H-indazol-5-yl)-5-chloro-2(1H)-pyridinone;
1-(6-(5-phenyl-1H-indazol-3-yl)-2-pyrazinyl)-4-piperidinamine;
1-(6-(5-(3-(methylsulfonyl)phenyl)-1H-indazol-3-yl)-2-pyrazinyl)-4-piperidinamine;
1-(6-(5-(3-methoxyphenyl)-1H-indazol-3-yl)-2-pyrazinyl)-4-piperidinamine;
3-(3-(6-(4-amino-1-piperidinyl)-2-pyrazinyl)-1H-indazol-5-yl)phenol;
1-(6-(5-(5-methoxy-3-pyridinyl)-1H-indazol-3-yl)-2-pyrazinyl)-4-piperidinamine;
1-(6-(5-(1H-pyrazol-5-yl)-1H-indazol-3-yl)-2-pyrazinyl)-4-piperidinamine;
1-(6-(5-(3-aminophenyl)-1H-indazol-3-yl)-2-pyrazinyl)-4-piperidinamine;
1-(6-(5-(3-pyridinyl)-1H-indazol-3-yl)-2-pyrazinyl)-4-piperidinamine;
1-(6-(5-(2-chlorophenyl)-1H-indazol-3-yl)-2-pyrazinyl)-4-piperidinamine;
1-(6-(5-(2-fluoro-5-nitrophenyl)-1H-indazol-3-yl)-2-pyrazinyl)-4-piperidinamine;
1-(6-(5-(5-fluoro-3-pyridinyl)-1H-indazol-3-yl)-2-pyrazinyl)-4-piperidinamine;
1-(6-(5-(3,5-dimethoxyphenyl)-1H-indazol-3-yl)-2-pyrazinyl)-4-piperidinamine;
1-(6-(5-(5-pyrimidinyl)-1H-indazol-3-yl)-2-pyrazinyl)-4-piperidinamine;
1-(6-(5-(2-pyridinyl)-1H-indazol-3-yl)-2-pyrazinyl)-4-piperidinamine;
1-(6-(5-(4-morpholinyl)-1H-indazol-3-yl)-2-pyrazinyl)-4-piperidinamine;
1-(6-(5-(1-piperidinyl)-1H-indazol-3-yl)-2-pyrazinyl)-4-piperidinamine;
1-(3-(6-(4-amino-1-piperidinyl)-2-pyrazinyl)-1H-indazol-5-yl)-2-piperidinone;

1-(3-(6-(4-amino-1-piperidinyl)-2-pyrazinyl)-1H-indazol-5-yl)-3-methyl-2-imidazolidinone;
N-(6-(3-(6-(4-amino-1-piperidinyl)-2-pyrazinyl)-1H-indazol-5-yl)-2-pyridinyl)-2,2-dimethylpropanamide;
2-(3-(6-(4-amino-1-piperidinyl)-2-pyrazinyl)-1H-indazol-5-yl)-3-pyridinamine;
1-(6-(5-(1H-pyrrolo[2,3-b]pyridin-6-yl)-1H-indazol-3-yl)-2-pyrazinyl)-4-piperidinamine;
5-(3-(6-(4-amino-1-piperidinyl)-2-pyrazinyl)-1H-indazol-5-yl)-N~4~-cyclopentyl-2,4-pyrimidinediamine;
5-(3-(6-(4-amino-1-piperidinyl)-2-pyrazinyl)-1H-indazol-5-yl)-2-pyrimidinamine;
1-(6-(5-(2-(4-morpholinyl)-4-pyrimidinyl)-1H-indazol-3-yl)-2-pyrazinyl)-4-piperidinamine;
1-(6-(5-imidazo[1,2-a]pyrazin-6-yl-1H-indazol-3-yl)-2-pyrazinyl)-4-piperidinamine;
4-(3-(6-(4-amino-1-piperidinyl)-2-pyrazinyl)-1H-indazol-5-yl)-2-pyridinamine;
1-(6-(5-(7-methoxy-4-quinolinyl)-1H-indazol-3-yl)-2-pyrazinyl)-4-piperidinamine;
1-(6-(5-(4-pyridinyl)-1H-indazol-3-yl)-2-pyrazinyl)-4-piperidinamine,
1-(6-(5-(3-amino-2-methylphenyl)-1H-indazol-3-yl)-2-pyrazinyl)-4-piperidinamine,
6-(3-(6-(4-amino-1-piperidinyl)-2-pyrazinyl)-1H-indazol-5-yl)-4-pyridazinamine,
1-(6-(5-(3-amino-4-(4-morpholinyl)phenyl)-1H-indazol-3-yl)-2-pyrazinyl)-4-piperidinamine,
1-(6-(5-(1,2,2',3',5',6'-hexahydrospiro[indole-3,4'-pyran]-4-yl)-1H-indazol-3-yl)-2-pyrazinyl)-4-piperidinamine,
1-(6-(5-(5-amino-2-(trifluoromethoxy)phenyl)-1H-indazol-3-yl)-2-pyrazinyl)-4-piperidinamine,
1-(6-(5-(3-(dimethylamino)phenyl)-1H-indazol-3-yl)-2-pyrazinyl)-4-piperidinamine,
1-(6-(5-(6-cyclopropyl-2-pyrazinyl)-1H-indazol-3-yl)-2-pyrazinyl)-4-piperidinamine,
1-(6-(5-(7-fluoro-4-quinolinyl)-1H-indazol-3-yl)-2-pyrazinyl)-4-piperidinamine,
1-(6-(5-(7-(trifluoromethoxy)-4-quinolinyl)-1H-indazol-3-yl)-2-pyrazinyl)-4-piperidinamine,
4-(3-(6-(4-amino-1-piperidinyl)-2-pyrazinyl)-1H-indazol-5-yl)-7-quinolinecarbonitrile,
4-(6-(3-(6-(4-amino-1-piperidinyl)-2-pyrazinyl)-1H-indazol-5-yl)-2,3-dihydro-1H-indol-1-yl)-2-pyrimidinamine,
5-(5-methoxy-3-pyridinyl)-3-(6-((3R)-3-piperidinyloxy)-2-pyrazinyl)-1H-indazole,
5-(5-fluoro-3-pyridinyl)-3-(6-((3R)-3-piperidinyloxy)-2-pyrazinyl)-1H-indazole,
N-tert-butyl-4-fluoro-3-(3-(6-((3R)-3-piperidinyloxy)-2-pyrazinyl)-1H-indazol-5-yl)benzamide,
5-(5-chloro-2-fluoro-3-pyridinyl)-3-(6-((3R)-3-piperidinyloxy)-2-pyrazinyl)-1H-indazole,
5-(6-cyclopropyl-2-pyrazinyl)-3-(6-((3R)-3-piperidinyloxy)-2-pyrazinyl)-1H-indazole,
5-(6-(1-methylethoxy)-2-pyrazinyl)-3-(6-((3R)-3-piperidinyloxy)-2-pyrazinyl)-1H-indazole,
5-(5-(1-methylethoxy)-3-pyridinyl)-3-(6-((3R)-3-piperidinyloxy)-2-pyrazinyl)-1H-indazole,
3-(6-((3R)-3-piperidinyloxy)-2-pyrazinyl)-5-(1H-pyrrolo[2,3-b]pyridin-5-yl)-1H-indazole,
4-fluoro-N-(1-methylethyl)-3-(3-(6-((3R)-3-piperidinyloxy)-2-pyrazinyl)-1H-indazol-5-yl)benzamide,
4-methyl-7-(3-(6-((3R)-3-piperidinyloxy)-2-pyrazinyl)-1H-indazol-5-yl)-3,4-dihydro-2H-1,4-benzoxazine,
5-(3-fluoro-2-pyridinyl)-3-(6-((3R)-3-piperidinyloxy)-2-pyrazinyl)-1H-indazole,
5-(3-(6-((3R)-3-piperidinyloxy)-2-pyrazinyl)-1H-indazol-5-yl)-4(3H)-pyrimidinone,
5-(4-(1-methylethyl)-2-pyrimidinyl)-3-(6-((3R)-3-piperidinyloxy)-2-pyrazinyl)-1H-indazole,
5-(4-cyclopropyl-2-pyrimidinyl)-3-(6-((3R)-3-piperidinyloxy)-2-pyrazinyl)-1H-indazole,
5-chloro-4-(3-(6-((3R)-3-piperidinyloxy)-2-pyrazinyl)-1H-indazol-5-yl)-2(1H)-pyridinone,
5-(1-methyl-1H-pyrazol-4-yl)-3-(6-((3R)-3-piperidinyloxy)-2-pyrazinyl)-1H-indazole,
4-methyl-7-(3-(6-((3R)-3-piperidinyloxy)-2-pyrazinyl)-1H-indazol-5-yl)-3,4-dihydro-2H-pyrido[3,2-b][1,4]oxazine,
5-(2-fluoro-3-methoxyphenyl)-3-(6-((3R)-3-piperidinyloxy)-2-pyrazinyl)-1H-indazole,
N-cyclopropyl-3-(3-(6-((3R)-3-piperidinyloxy)-2-pyrazinyl)-1H-indazol-5-yl)benzamide,
5-(2-fluorophenyl)-3-(6-((3R)-3-piperidinyloxy)-2-pyrazinyl)-1H-indazole,
5-phenyl-3-(6-((3R)-3-piperidinyloxy)-2-pyrazinyl)-1H-indazole,
5-bromo-3-(6-((3R)-3-piperidinyloxy)-2-pyrazinyl)-1H-indazole,
5-(6-cyclopropyl-2-pyridinyl)-3-(6-((3R)-3-piperidinyloxy)-2-pyrazinyl)-1H-indazole,
5-(6-methoxy-2-pyridinyl)-3-(6-((3R)-3-piperidinyloxy)-2-pyrazinyl)-1H-indazole,
6-(3-(6-((3R)-3-piperidinyloxy)-2-pyrazinyl)-1H-indazol-5-yl)imidazo[1,2-a]pyrazine,
N-cyclopropyl-4-fluoro-3-(3-(6-((3R)-3-piperidinyloxy)-2-pyrazinyl)-1H-indazol-5-yl)benzamide,
5-(2,3-dihydro-1,4-benzodioxin-6-yl)-3-(6-((3R)-3-piperidinyloxy)-2-pyrazinyl)-1H-indazole,
5-(4-cyclopropyl-2-pyridinyl)-3-(6-((3R)-3-piperidinyloxy)-2-pyrazinyl)-1H-indazole,
3-(6-((3R)-3-piperidinyloxy)-2-pyrazinyl)-5-(6-(trifluoromethyl)-2-pyridinyl)-1H-indazole,
5-(2-(1-methylethoxy)-4-pyridinyl)-3-(6-((3R)-3-piperidinyloxy)-2-pyrazinyl)-1H-indazole,
5-(6-(1-methylethoxy)-2-pyridinyl)-3-(6-((3R)-3-piperidinyloxy)-2-pyrazinyl)-1H-indazole,
6-(3-(6-((3R)-3-piperidinyloxy)-2-pyrazinyl)-1H-indazol-5-yl)[1,2,4]triazolo[4,3-a]pyridine,
5-(3-(1-methylethoxy)phenyl)-3-(6-((3R)-3-piperidinyloxy)-2-pyrazinyl)-1H-indazole,
5-((E)-2-cyclopropylethenyl)-3-(6-((3R)-3-piperidinyloxy)-2-pyrazinyl)-1H-indazole,
5-(3,6-dihydro-2H-pyran-4-yl)-3-(6-((3R)-3-piperidinyloxy)-2-pyrazinyl)-1H-indazole,
3-(6-((3R)-3-piperidinyloxy)-2-pyrazinyl)-5-(3-pyridazinyl)-1H-indazole,
3-(6-((3R)-3-piperidinyloxy)-2-pyrazinyl)-5-(3-(trifluoromethoxy)phenyl)-1H-indazole,
3-(6-((3R)-3-piperidinyloxy)-2-pyrazinyl)-5-(tetrahydro-2H-pyran-4-yl)-1H-indazole,
5-(2-methoxy-4-pyrimidinyl)-3-(6-((3R)-3-piperidinyloxy)-2-pyrazinyl)-1H-indazole,
5-(2-(1-methylethoxy)-4-pyrimidinyl)-3-(6-((3R)-3-piperidinyloxy)-2-pyrazinyl)-1H-indazole,
5-(5,6-dihydro-2H-pyran-3-yl)-3-(6-((3R)-3-piperidinyloxy)-2-pyrazinyl)-1H-indazole,
4-(3-(6-((3R)-3-piperidinyloxy)-2-pyrazinyl)-1H-indazol-5-yl)-2-pyrimidinol,
3-(6-((3R)-3-piperidinyloxy)-2-pyrazinyl)-5-(tetrahydro-2H-pyran-3-yl)-1H-indazole,
N-cyclopropyl-2-(3-(6-((3R)-3-piperidinyloxy)-2-pyrazinyl)-1H-indazol-5-yl)-4-pyridinecarboxamide, N-cyclopropyl-6-(3-(6-((3R)-3-piperidinyloxy)-2-pyrazinyl)-1H-indazol-5-yl)-2-pyrazinamine,
N-cyclopropyl-5-(3-(6-((3R)-3-piperidinyloxy)-2-pyrazinyl)-1H-indazol-5-yl)-3-pyridinecarboxamide,
5-(2-methoxy-4-pyridinyl)-3-(6-((3R)-3-piperidinyloxy)-2-pyrazinyl)-1H-indazole,
1-(6-(5-(2,6-difluorophenyl)-1H-indazol-3-yl)-2-pyrazinyl)-4-piperidinamine,
(3R)-1-(6-(5-(2,6-difluorophenyl)-1H-indazol-3-yl)-2-pyrazinyl)-3-pyrrolidinamine,
(3S)-1-(6-(5-(2,6-difluorophenyl)-1H-indazol-3-yl)-2-pyrazinyl)-3-piperidinol,
6-(5-(2,6-difluorophenyl)-1H-indazol-3-yl)-N-((3S)-3-piperidinyl)-2-pyrazinamine,
5-(2,6-difluorophenyl)-3-(6-(1-piperazinyl)-2-pyrazinyl)-1H-indazole,
5-(2,6-difluorophenyl)-3-(6-(1-piperidinyl)-2-pyrazinyl)-1H-indazole,
6-(5-(2,6-difluorophenyl)-1H-indazol-3-yl)-N-((3S)-3-piperidinyl)-2-pyrazinamine,
6-(5-(2,6-difluorophenyl)-1H-indazol-3-yl)-N-((3R)-3-piperidinyl)-2-pyrazinamine,
5-(2,6-difluorophenyl)-3-(6-(4-morpholinyl)-2-pyrazinyl)-1H-indazole,
5-(2,6-difluorophenyl)-3-(6-(1-pyrrolidinyl)-2-pyrazinyl)-1H-indazole,
3-(6-(1,4-diazepan-1-yl)-2-pyrazinyl)-5-(2,6-difluorophenyl)-1H-indazole,
6-(5-(2,6-difluorophenyl)-1H-indazol-3-yl)-N-4-piperidinyl-2-pyrazinamine,
1-(6-(5-(2,6-difluorophenyl)-1H-indazol-3-yl)-2-pyrazinyl)-4-piperidinol,
6-(5-(2,6-difluorophenyl)-1H-indazol-3-yl)-N-((3S)-3-pyrrolidinyl)-2-pyrazinamine,
(3S)-1-(6-(5-(2,6-difluorophenyl)-1H-indazol-3-yl)-2-pyrazinyl)-3-pyrrolidinol,
N-3-azetidinyl-6-(5-(2,6-difluorophenyl)-1H-indazol-3-yl)-2-pyrazinamine,
6-(5-(2,6-difluorophenyl)-1H-indazol-3-yl)-N-((3S)-3-pyrrolidinyl)-2-pyrazinamine,
6-(5-(2,6-difluorophenyl)-1H-indazol-3-yl)-N-methyl-N-3-piperidinyl-2-pyrazinamine,
6-(5-(2,6-difluorophenyl)-1H-indazol-3-yl)-N-methyl-2-pyrazinamine,
6-(5-(2,6-difluorophenyl)-1H-indazol-3-yl)-N-ethyl-2-pyrazinamine,
6-(5-(2,6-difluorophenyl)-1H-indazol-3-yl)-N,N-dimethyl-2-pyrazinamine,
6-(5-(2,6-difluorophenyl)-1H-indazol-3-yl)-N-(1-methylethyl)-2-pyrazinamine,
N-tert-butyl-6-(5-(2,6-difluorophenyl)-1H-indazol-3-yl)-2-pyrazinamine,
6-(5-(2,6-difluorophenyl)-1H-indazol-3-yl)-N-phenyl-2-pyrazinamine,
5-(2,6-difluorophenyl)-3-(6-((3R)-3-piperidinyloxy)-2-pyrazinyl)-1H-indazole,
5-(2,6-difluorophenyl)-3-(6-(4-piperidinyloxy)-2-pyrazinyl)-1H-indazole,
5-(2,6-difluorophenyl)-3-(6-(3-pyrrolidinyloxy)-2-pyrazinyl)-1H-indazole,
5-(2,6-difluorophenyl)-3-(6-((3R)-3-piperidinyloxy)-2-pyrazinyl)-1H-indazole,
5-(2,6-difluorophenyl)-3-(6-((3S)-3-piperidinyloxy)-2-pyrazinyl)-1H-indazole,
5-(2,6-difluorophenyl)-3-(2-((3R)-3-piperidinyloxy)-4-pyrimidinyl)-1H-indazole,
4-(5-(2,6-difluorophenyl)-1H-indazol-3-yl)-N-((3R)-3-piperidinyl)-2-pyrimidinamine,
4-(5-(2,6-difluorophenyl)-1H-indazol-3-yl)-N-methyl-2-pyrimidinamine,
4-(5-(2,6-difluorophenyl)-1H-indazol-3-yl)-N-(1-methylethyl)-2-pyrimidinamine,
1-(4-(5-(2,6-difluorophenyl)-1H-indazol-3-yl)-2-pyrimidinyl)-4-piperidinamine,
5-(2,6-difluorophenyl)-3-(6-(((3R,4S)-4-methyl-3-piperidinyl)oxy)-2-pyrazinyl)-1H-indazole,
5-(2,6-difluorophenyl)-3-(6-(((3R,5S)-5-fluoro-3-piperidinyl)oxy)-2-pyrazinyl)-1H-indazole,
5-(2,6-difluorophenyl)-3-(6-(((3S,4R)-4-methyl-3-piperidinyl)oxy)-2-pyrazinyl)-1H-indazole,
5-(2,6-difluorophenyl)-3-(6-(((3R,4S)-4-methyl-3-piperidinyl)oxy)-2-pyrazinyl)-1H-indazole,
5-(2,6-difluorophenyl)-3-(6-(((3S,4S)-4-methyl-3-piperidinyl)oxy)-2-pyrazinyl)-1H-indazole,
3-(6-((4R)-6-azaspiro[2.5]oct-4-yloxy)-2-pyrazinyl)-5-(2,6-difluorophenyl)-1H-indazole,
5-(2,6-difluorophenyl)-3-(6-(((3S)-4-methylidene-3-piperidinyl)oxy)-2-pyrazinyl)-1H-indazole,
3-(6-((4R)-6-azaspiro[25]oct-4-yloxy)-2-pyrazinyl)-5-(2,6-difluorophenyl)-1H-indazole;
1-(6-(5-nitro-1H-indol-3-yl)-2-pyrazinyl)-4-piperidinamine;
3-(6-(4-amino-1-piperidinyl)-2-pyrazinyl)-1H-indol-5-amine;
N-(3-(6-(4-amino-1-piperidinyl)-2-pyrazinyl)-1H-indol-5-yl)benzamide;
N-(3-(6-(4-amino-1-piperidinyl)-2-pyrazinyl)-1H-indol-5-yl)propanamide;
3-(6-(4-amino-1-piperidinyl)-2-pyrazinyl)-1H-indole-5-carboxylic acid;
methyl 3-(6-(4-amino-1-piperidinyl)-2-pyrazinyl)-1H-indole-5-carboxylate;
3-(6-(4-amino-1-piperidinyl)-2-pyrazinyl)-1H-indole-5-carboxamide;
3-(6-(4-amino-1-piperidinyl)-2-pyrazinyl)-N-(1-methylethyl)-1H-indole-5-carboxamide;
3-(6-(4-amino-1-piperidinyl)-2-pyrazinyl)-N-phenyl-1H-indole-5-carboxamide;
3-(6-(4-amino-1-piperidinyl)-2-pyrazinyl)-N-benzyl-1H-indole-5-carboxamide;
1-(6-(5-(2,6-difluorophenyl)-1H-indol-3-yl)pyrazin-2-yl)piperidin-3-amine;
1-(6-(5-(2,6-difluorophenyl)-1H-indol-3-yl)pyrazin-2-yl)piperidin-4-amine;
(R)-5-(2,6-difluorophenyl)-3-(6-(piperidin-3-yloxy)pyrazin-2-yl)-1H-indole;
(R)-2-(5-(2,6-difluorophenyl)-1H-indol-3-yl)-N-(piperidin-3-yl)pyrimidin-4-amine;
(R)-6-(5-(6-isopropoxypyrazin-2-yl)-1H-indol-3-yl)-N-(piperidin-3-yl)pyrazin-2-amine;
(R)-5-(2-chloro-6-fluorophenyl)-3-(6-(piperidin-3-yloxy)pyrazin-2-yl)-1H-indole bis(2,2,2-trifluoroacetate);
1-(6-(5-(2-chloro-6-fluorophenyl)-1H-indol-3-yl)pyrazin-2-yl)piperidin-4-amine bis(2,2,2-trifluoroacetate);
4-(5-(6-(1-methylethoxy)-2-pyrazinyl)-1H-indol-3-yl)-2-pyridinamine,
(3S)-1-(6-(5-(2,6-difluorophenyl)-1H-indol-3-yl)-2-pyrazinyl)-3-piperidinamine,
N-cyclohexyl-6-(5-(2,6-difluorophenyl)-1H-indol-3-yl)-2-pyrazinamine,
(3R)-1-(6-(5-(2,6-difluorophenyl)-1H-indol-3-yl)-2-pyrazinyl)-3-piperidinamine, 4-(6-(5-(2,6-difluorophenyl)-1H-indol-3-yl)-2-pyrazinyl)-2-piperazinone,
6-(5-(2,6-difluorophenyl)-1H-indol-3-yl)-N-4-piperidinyl-2-pyrazinamine,
5-(2,6-difluorophenyl)-3-(6-(4-piperidinyloxy)-2-pyrazinyl)-1H-indole,
6-(5-(2,6-difluorophenyl)-1H-indol-3-yl)-N-((3R)-3-piperidinyl)-2-pyrazinamine,
6-(5-(2,6-difluorophenyl)-1H-indol-3-yl)-N-((3R)-3-pyrrolidinyl)-2-pyrazinamine,
5-(2,6-difluorophenyl)-3-(4-((3R)-3-piperidinyloxy)-2-pyrimidinyl)-1H-indole,
2-(5-(2,6-difluorophenyl)-1H-indol-3-yl)-N-4-piperidinyl-4-pyrimidinamine,
5-(2,6-difluorophenyl)-3-(4-(4-piperidinyloxy)-2-pyrimidinyl)-1H-indole,
(3R)-1-(6-(5-(2,6-difluorophenyl)-1H-indol-3-yl)-2-pyrazinyl)-3-pyrrolidinamine,
5-(6-(1-methylethoxy)-2-pyrazinyl)-3-(6-((3R)-3-piperidinyloxy)-2-pyrazinyl)-1H-indole,
5-(2,6-difluorophenyl)-3-(6-((3S)-3-piperidinyloxy)-2-pyrazinyl)-1H-indole,
3-(5-fluoro-2-pyridinyl)-5-(6-(1-methylethoxy)-2-pyrazinyl)-1H-indole,
5-(6-(1-methylethoxy)-2-pyrazinyl)-3-(4-methyl-2-pyridinyl)-1H-indole,
6-(5-(6-(1-methylethoxy)-2-pyrazinyl)-1H-indol-3-yl)-2-pyridinamine,
2-(5-(6-(1-methylethoxy)-2-pyrazinyl)-1H-indol-3-yl)-4-pyridinamine,
5-(6-(1-methylethoxy)-2-pyrazinyl)-3-(5-methyl-2-pyridinyl)-1H-indole,
5-(6-(1-methylethoxy)-2-pyrazinyl)-3-(6-(4-morpholinyl)-2-pyridinyl)-1H-indole,
6-(5-(6-(1-methylethoxy)-2-pyrazinyl)-1H-indol-3-yl)-1H-indazole,
3-(5-methoxy-2-pyrazinyl)-5-(6-(1-methylethoxy)-2-pyrazinyl)-1H-indole,
5-(6-(1-methylethoxy)-2-pyrazinyl)-3-(6-(1H-pyrazol-1-yl)-2-pyridinyl)-1H-indole,
3-(6-methoxy-2-pyrazinyl)-5-(6-(1-methylethoxy)-2-pyrazinyl)-1H-indole,
5-(6-(1-methylethoxy)-2-pyrazinyl)-3-(6-(4-morpholinyl)-2-pyrazinyl)-1H-indole,
5-(6-(1-methylethoxy)-2-pyrazinyl)-3-(6-(1-methylethoxy)-2-pyridinyl)-1H-indole,
1-(4-(5-(6-(1-methylethoxy)-2-pyrazinyl)-1H-indol-3-yl)-1,3-thiazol-2-yl)-2(1H)-pyridinone,
3-(2-(1H-imidazol-1-yl)-1,3-thiazol-4-yl)-5-(6-(1-methylethoxy)-2-pyrazinyl)-1H-indole,
1-(6-(5-(6-(1-methylethoxy)-2-pyrazinyl)-1H-indol-3-yl)-2-pyridinyl)-2-pyrrolidinone, or
N,N-dimethyl-6-(5-(6-(1-methylethoxy)-2-pyrazinyl)-1H-indol-3-yl)-2-pyrazinamine;
and a pharmaceutically acceptable salt thereof.

Another aspect of the invention includes a family of specific compounds of particular interest within Formulas 1 and 1' as follows:
5-(6-cyclopropyl-2-pyrazinyl)-3-(6-(4-piperidinyloxy)-2-pyrazinyl)-1H-indazole;
6-(5-(6-cyclopropyl-2-pyrazinyl)-1H-indazol-3-yl)-N-(1-methylethyl)-2-pyrazinamine;
N-cyclopropyl-6-(3-(6-methoxy-2-pyrazinyl)-1H-indazol-5-yl)-2-pyrazinamine;
5-(6-cyclopropyl-2-pyrazinyl)-3-(6-(((3R,4S)-3-fluoro-4-piperidinyl)oxy)-2-pyrazinyl)-1H-indazole;
5-(6-cyclopropyl-2-pyrazinyl)-3-(6-(((3S,4R)-3-fluoro-4-piperidinyl)oxy)-2-pyrazinyl)-1H-indazole;
5-(6-cyclopropyl-2-pyrazinyl)-3-(6-(((3R,4R)-3-fluoro-4-piperidinyl)oxy)-2-pyrazinyl)-1H-indazole;
5-(6-cyclopropyl-2-pyrazinyl)-3-(6-(((3S,4S)-3-fluoro-4-piperidinyl)oxy)-2-pyrazinyl)-1H-indazole;
6-(3-(6-(4-amino-1-piperidinyl)-2-pyrazinyl)-1H-indazol-5-yl)-N-cyclopropyl-2-pyrazinamine;
6-(3-(6-(2-fluoroethoxy)-2-pyrazinyl)-1H-indazol-5-yl)-2-pyrazinamine;
1-(6-(5-(6-cyclopropyl-2-pyrazinyl)-1H-indazol-3-yl)-2-pyrazinyl)-4-piperidinamine;
6-(5-(6-cyclopropyl-2-pyrazinyl)-1H-indazol-3-yl)-N-4-piperidinyl-2-pyrazinamine;
6-(5-(6-cyclopropyl-2-pyrazinyl)-1H-indazol-3-yl)-N-((3R)-3-piperidinyl)-2-pyrazinamine;
(4-(3-(6-((3R)-3-piperidinyloxy)-2-pyrazinyl)-1H-indol-5-yl)phenyl)methanol;
1-methylethyl 3-(6-((3R)-3-piperidinylamino)-2-pyrazinyl)-1H-indazole-5-carboxylate;
1-(6-(5-(6-cyclopropyl-2-pyrazinyl)-1H-indol-3-yl)-2-pyrazinyl)-4-piperidinamine;
5-(4-(4-morpholinyl)phenyl)-3-(6-((3R)-3-piperidinyloxy)-2-pyrazinyl)-1H-indole;
3-(6-((8R)-5-azaspiro[2.5]oct-8-yloxy)-2-pyrazinyl)-5-(6-cyclopropyl-2-pyrazinyl)-1H-indazole;
5-(1-cyclopropyl-1H-pyrazol-4-yl)-3-(6-((3R)-3-piperidinyloxy)-2-pyrazinyl)-1H-indole;
5-(1-(1-methylethyl)-1H-pyrazol-4-yl)-3-(6-((3R)-3-piperidinyloxy)-2-pyrazinyl)-1H-indole;
5-(3-fluoro-4-pyridinyl)-3-(6-((3R)-3-piperidinyloxy)-2-pyrazinyl)-1H-indole;
3,5-bis(6-cyclopropyl-2-pyrazinyl)-1H-indazole;
1-(6-(5-(6-cyclopropyl-2-pyrazinyl)-1H-indol-3-yl)-2-pyrazinyl)-4-piperidinamine;
3-(6-((4R)-6-azaspiro[2.5]oct-4-yloxy)-2-pyrazinyl)-5-(3,6-dihydro-2H-pyran-4-yl)-1H-indazole;
3-(6-((4R)-6-azaspiro[2.5]oct-4-yloxy)-2-pyrazinyl)-5-(2,6-difluorophenyl)-1H-indole;
3-(6-((4S)-6-azaspiro[2.5]oct-4-yloxy)-2-pyrazinyl)-5-(2,6-difluorophenyl)-1H-indole;
5-(6-cyclopropyl-2-pyrazinyl)-3-(6-(4-piperidinyloxy)-2-pyrazinyl)-1H-indazole;
6-(5-(6-cyclopropyl-2-pyrazinyl)-1H-indazol-3-yl)-N-(1-methylethyl)-2-pyrazinamine;
N-cyclopropyl-6-(3-(6-methoxy-2-pyrazinyl)-1H-indazol-5-yl)-2-pyrazinamine;
5-(6-cyclopropyl-2-pyrazinyl)-3-(6-(((3R,4S)-3-fluoro-4-piperidinyl)oxy)-2-pyrazinyl)-1H-indazole;
5-(6-cyclopropyl-2-pyrazinyl)-3-(6-(((3S,4R)-3-fluoro-4-piperidinyl)oxy)-2-pyrazinyl)-1H-indazole;
5-(6-cyclopropyl-2-pyrazinyl)-3-(6-(((3R,4R)-3-fluoro-4-piperidinyl)oxy)-2-pyrazinyl)-1H-indazole;
5-(6-cyclopropyl-2-pyrazinyl)-3-(6-(((3S,4S)-3-fluoro-4-piperidinyl)oxy)-2-pyrazinyl)-1H-indazole;
6-(3-(6-(4-amino-1-piperidinyl)-2-pyrazinyl)-1H-indazol-5-yl)-N-cyclopropyl-2-pyrazinamine;
6-(3-(6-(2-fluoroethoxy)-2-pyrazinyl)-1H-indazol-5-yl)-2-pyrazinamine;
1-(6-(5-(6-cyclopropyl-2-pyrazinyl)-1H-indazol-3-yl)-2-pyrazinyl)-4-piperidinamine;
6-(5-(6-cyclopropyl-2-pyrazinyl)-1H-indazol-3-yl)-N-4-piperidinyl-2-pyrazinamine;
6-(5-(6-cyclopropyl-2-pyrazinyl)-1H-indazol-3-yl)-N-((3R)-3-piperidinyl)-2-pyrazinamine;
(4-(3-(6-((3R)-3-piperidinyloxy)-2-pyrazinyl)-1H-indol-5-yl)phenyl)methanol;

1-methylethyl 3-(6-((3R)-3-piperidinylamino)-2-pyrazinyl)-1H-indazole-5-carboxylate;

N-cyclopropyl-6-(5-(6-cyclopropyl-2-pyrazinyl)-1H-indazol-3-yl)-2-pyrazinamine;

5-(4-(4-morpholinyl)phenyl)-3-(6-((3R)-3-piperidinyloxy)-2-pyrazinyl)-1H-indole;

3-(6-((8R)-5-azaspiro[2.5]oct-8-yloxy)-2-pyrazinyl)-5-(6-cyclopropyl-2-pyrazinyl)-1H-indazole;

5-(1-cyclopropyl-1H-pyrazol-4-yl)-3-(6-((3R)-3-piperidinyloxy)-2-pyrazinyl)-1H-indole;

methyl 3-(6-(4-amino-1-piperidinyl)-2-pyrazinyl)-1H-indazole-5-carboxylate;

5-(1-(1-methylethyl)-1H-pyrazol-4-yl)-3-(6-((3R)-3-piperidinyloxy)-2-pyrazinyl)-1H-indole;

5-(3-fluoro-4-pyridinyl)-3-(6-((3R)-3-piperidinyloxy)-2-pyrazinyl)-1H-indole;

1-(6-(5-(6-cyclopropyl-2-pyrazinyl)-1H-indol-3-yl)-2-pyrazinyl)-4-piperidinamine;

3-(6-((4R)-6-azaspiro[25]oct-4-yloxy)-2-pyrazinyl)-5-(3,6-dihydro-2H-pyran-4-yl)-1H-indazole;

3-(6-((4R)-6-azaspiro[2.5]oct-4-yloxy)-2-pyrazinyl)-5-(2,6-difluorophenyl)-1H-indole;

3-(6-((4S)-6-azaspiro[2.5]oct-4-yloxy)-2-pyrazinyl)-5-(2,6-difluorophenyl)-1H-indole;

3-(6-((8R)-5-azaspiro[2.5]oct-8-yloxy)-2-pyrazinyl)-5-(6-cyclopropyl-2-pyrazinyl)-1H-indazole; 3,5-bis(6-cyclopropyl-2-pyrazinyl)-1H-indazole; and 3-(6-((8S)-5-azaspiro[2.5]oct-8-yloxy)-2-pyrazinyl)-5-(6-cyclopropyl-2-pyrazinyl)-1H-indazole;

and a pharmaceutically acceptable salt thereof.

Another aspect of the invention relates to a pharmaceutical composition comprising a compound of formula (I) and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of cancer.

The compounds of this invention may have in general several asymmetric centers and are typically depicted in the form of racemic mixtures. This invention is intended to encompass racemic mixtures, partially racemic mixtures and separate enantiomers and diasteromers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof. Unless otherwise specified, the following definitions apply to terms found in the specification and claims:

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "haloalkenyl" embraces radicals wherein any one or more of the alkenyl carbon atoms is substituted with halo as defined above. Specifically embraced are monohaloalkenyl, dihaloalkenyl and polyhaloalkenyl radicals including perhaloalkenyl. "Lower haloalkenyl" embraces radicals having 2-6 carbon atoms. Even more preferred are lower haloalkenyl radicals having two to three carbon atoms. Examples of haloalkenyl radicals include trifluoropropenyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "cyanoalkyl" embraces linear or branched alkyl radicals having one to about ten carbon atoms any one of which may be substituted with one or more cyano radicals. More preferred hydroxyalkyl radicals are "lower cyanoalkyl" radicals having one to six carbon atoms and one cyano radical. Examples of such radicals include cyanomethyl. Even more preferred are lower cyanoalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

"Heterocycle" means a ring comprising at least one carbon atom and at least one other atom selected from N, O and S. Examples of heterocycles that may be found in the claims include, but are not limited to, the following:

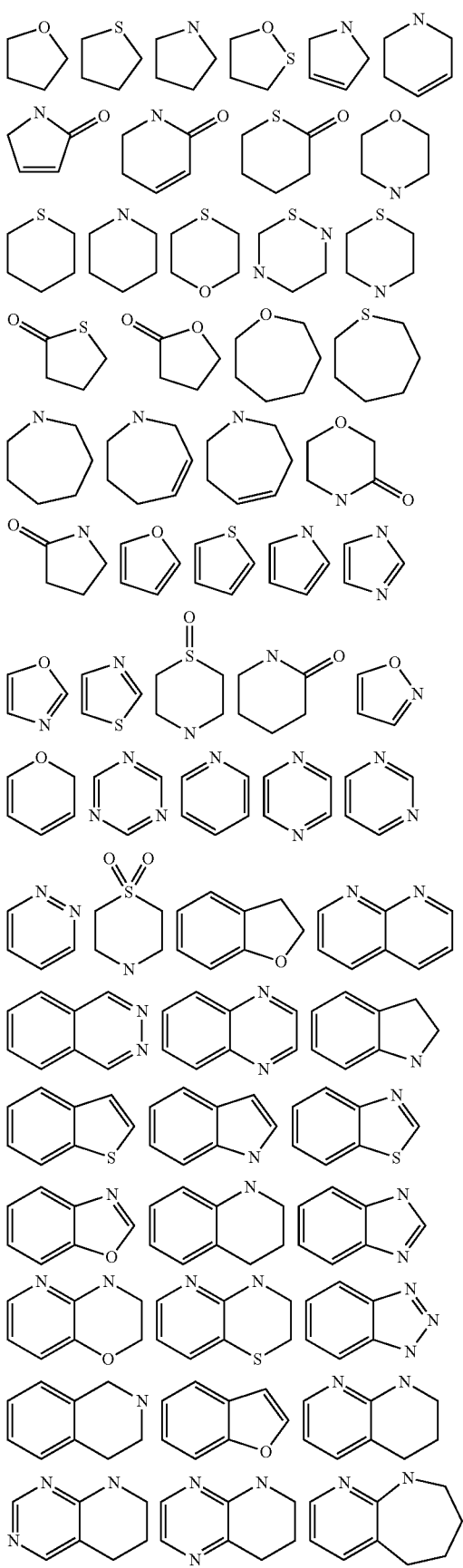
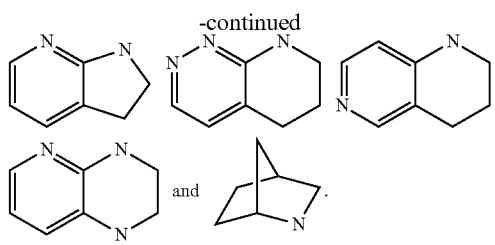

and

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "alkylcarbonyl" denotes an carbonyl radical substituted with an alkyl group.

The term "alkoxycarbonyl" denotes an ester group, containing an alkoxy substituted carbonyl.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical. More preferred are phenylaminocarbonyl and substituted phenylaminocarbonyl.

The term "cycloalkylalkenyl" embraces cycloalkyl-substituted alkenyl radicals. More preferred cycloalkylalkenyl radicals are "5- or 6-membered cycloalkylalkenyl" radicals having alkenyl portions of two to four carbon atoms and a 5- or 6-membered cycloalkyl radical. Even more preferred are lower cycloalkylalkenyl radicals having alkyl portions of two to three carbon atoms. Examples include such radicals as cyclohexylethenyl.

The term "heterocyclylalkylenyl" embraces heterocyclic-substituted alkyl radicals. More preferred heterocyclylalkylenyl radicals are "5- or 6-membered heteroarylalkylenyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylamino" embraces "N-alkylamino" and "N,N-dialkylamino" where amino groups are substituted with one alkyl radical and with two independent alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "cycloalkylamino" denotes amino groups which have been substituted with one or two cycloalkyl radicals, such as N-cyclohexylamino. The cycloalkylamino radicals may be further substituted on the cycloalkyl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "heterocyclylamino" denotes amino groups which have been substituted with one or two heterocyclyl radicals, such as N-piperidinylamino. The "heterocyclylamino" radicals may be further substituted on the heterocyclyl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "alkylcarbonylamino" denotes amino radicals independently substituted with an alkylcarbonyl radicals, respectively. More preferred are "lower alkylcarbonylamino" having lower alkyl radicals as described above attached to an carbonylamino radical.

The term "arylcarbonylamino" denotes amino radicals independently substituted with an arylcarbonyl radicals, respectively. More preferred are "phenylcarbonylamino".

The term "aralkylcarbonylamino" denotes amino radicals independently substituted with an aralkylcarbonyl radicals, respectively. More preferred are "lower aralkylcarbonylamino" having lower alkyl radicals as described above attached to an carbonylamino radical. More preferred are benzylcarbonylamino radicals.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heterocyclyloxy" embraces optionally substituted heterocyclyl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

The term "oxo" represents the groups =O (as in carbonyl).

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups, and the like, for example as illustrated in the following examples:

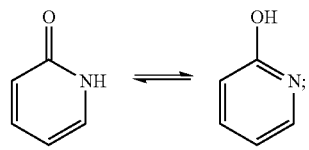 [SMILES: O=c1cccc[nH]1 ; Oc1ccccn1]

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Utility and Methods of Use

An aspect of the present invention is a method for inhibiting Pim kinase activity in a cell, comprising contacting the cell with an effective amount of a compound of Formula 1-4.

Another aspect of the present invention provides a method for treating a condition by modulation of Pim kinase activity comprising administering to a patient in need of such treatment an effective amount of a compound of Formula 1-4.

Another embodiment of the present invention provides a method for treating a cancer disorder in a patient, comprising administering to the patient a composition comprising an amount of a compound of Formula 1-4 effective to inhibit Pim kinase activity in the patient.

Another embodiment of the present invention provides a method for treating a cancer disorder in a patient, wherein the cancer is prostate, head and neck or lymphoma, comprising administering to the patient a composition comprising an amount of a compound of Formula 1-4 effective to inhibit Pim kinase activity in the patient.

Another aspect of the present invention provides the use of any one of the compounds of Formula I-4 in the manufacture of a medicament for the treatment of cancer.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (I) may range from approximately 0.1-1000 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

COMBINATIONS

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimeterxate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitertinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimeterxate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bc1-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemeterxed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other agents, such as other kinase inhibitors including CDK inhibitors, mTor inhibitors, Pi3k inhibitors, and Aurora kinase inhibitors.

Synthetic Methods

The compounds of the invention can be prepared according to the following procedures of Schemes 1-14, wherein the substituents are as defined for Formulas 1-4, above, except where noted.

Scheme 1

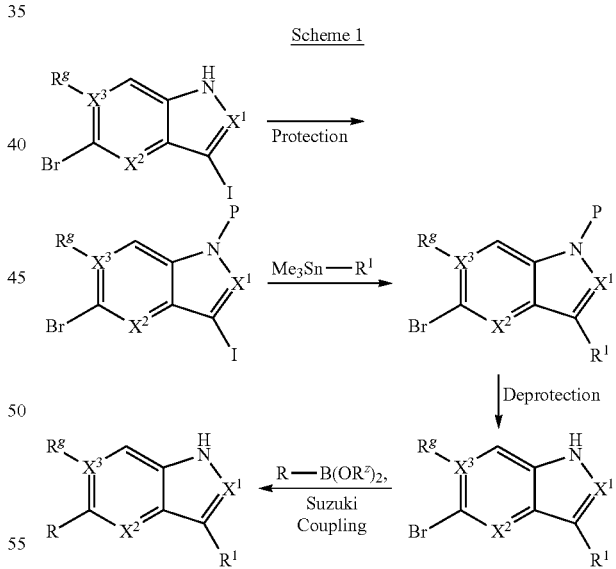

Substituted heterocyclic compounds can be prepared according to the method set out in Scheme 1. Protection of any labile heteroatoms (where P is a protecting group), can be achieved with known protecting group chemistry, such as with THP via reaction with 3,4-dihydro-2H-pyran in the presence of p-TSA in THF. Coupling with substituted (alkyl tin) compounds (e.g. $Me_3Sn—R^1$) with copper (I) iodide and $Pd(PPh_3)_4$ in DMF provide the initial substitution. Deprotection, such as with HCl, followed by Suzuki coupling provides the desired compounds.

Scheme 2

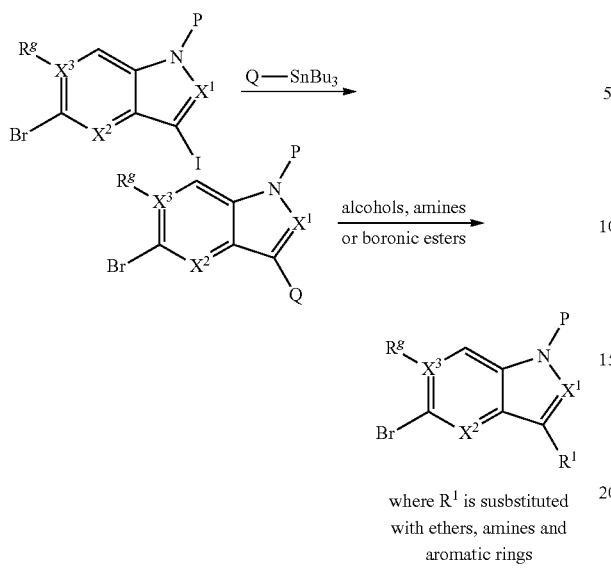

where $R^1$ is susbstituted with ethers, amines and aromatic rings

The compounds of the invention can be prepared by the following general methods. Coupling with substituted (alkyl tin) compounds with copper (I) iodide and Pd(PPh$_3$)$_4$ in DMF provide the initial substitution (where Q is a chloro substituted ring such as phenyl, 5-membered heteroaryl, 6-membered heteroaryl, or 9 membered heteroaryl). Substitutions on $R^1$ can be achieved using standard aromatic substitution chemistry. For example, amination of chloro substituted aromatic rings can be provided by treatment with dicyclohexyl (2',6'-diisopropoxybiphenyl-2-yl)phosphine, RuPhos precatalyst, base, e.g. sodium tert-butoxide and the secondary amine in a suitable solvent such as THF provides the desired compounds. For primary amines, treatment with the amine BrettPhos precatalyst, base, e.g. sodium tert-butoxide, and dicyclohexyl(2',4',6'-triisopropyl-3,6-dimethoxybiphenyl-2-yl)phosphine in suitable solvent such as p-dioxane provides the desired compounds.

Scheme 3

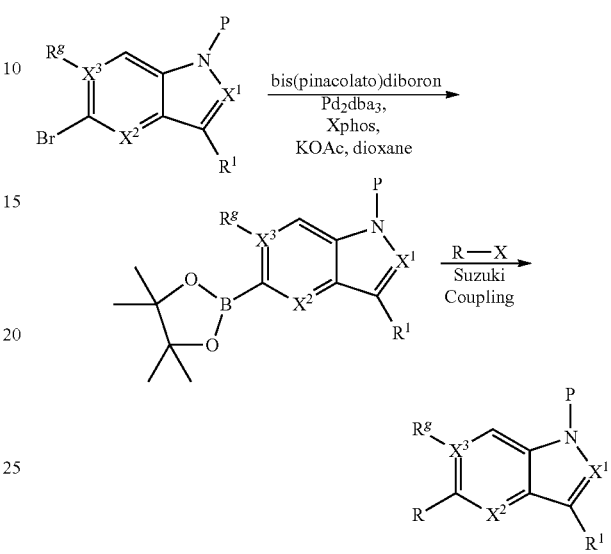

The compounds of the invention can be prepared by the following general methods. Treatment of the bromo compounds with bis(pinacolato)-diboron, Pd$_2$dba$_3$, Xphos and KOAc in anhydrous solvent such as 1,4-dioxane provides the boronic ester intermediate. Suzuki coupling with aryl halides or heteroaryl halides provides the desired compounds.

Scheme 4

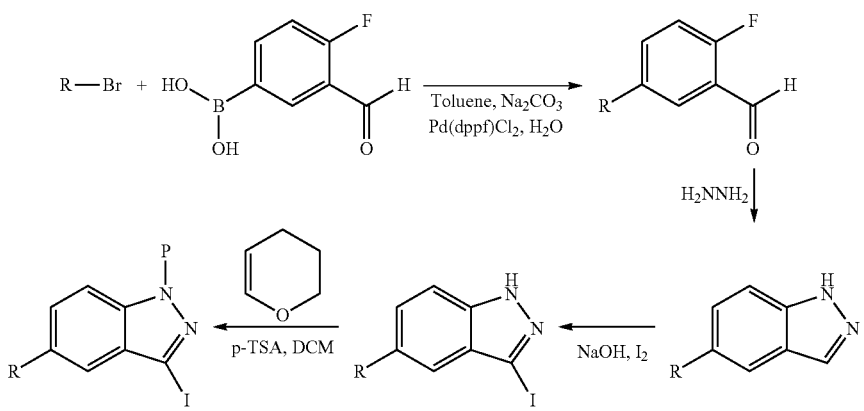

Indazoles can be prepared by the following general methods. Coupling of the bromo substituted ring starting material with a boronic acid, such as with 4-fluoro-3-formylphenylboronic acid, Na$_2$CO$_3$ and a palladium catalyst, such as PdCl$_2$(dppf), in a solvent such as toluene at temperature about RT, provides the R substituted benzaldehyde. Conversion of the formyl derivative to the indazoles is accomplished such as by treatment with hydrazine hydrate at a temperature of greater than 50° C., preferably greater than 100° C. and more preferably about 120° C. Iodination, such as by treatment with a basic solution of I$_2$, preferably where the base is NaOH at a temperature of about RT, provides the 3-iodoindazole. Protection of the labile nitrogen, such as with THP via reaction with 3,4-dihydro-2H-pyran in the presence of p-TSA in THF provides the protected indazole.

Scheme 5

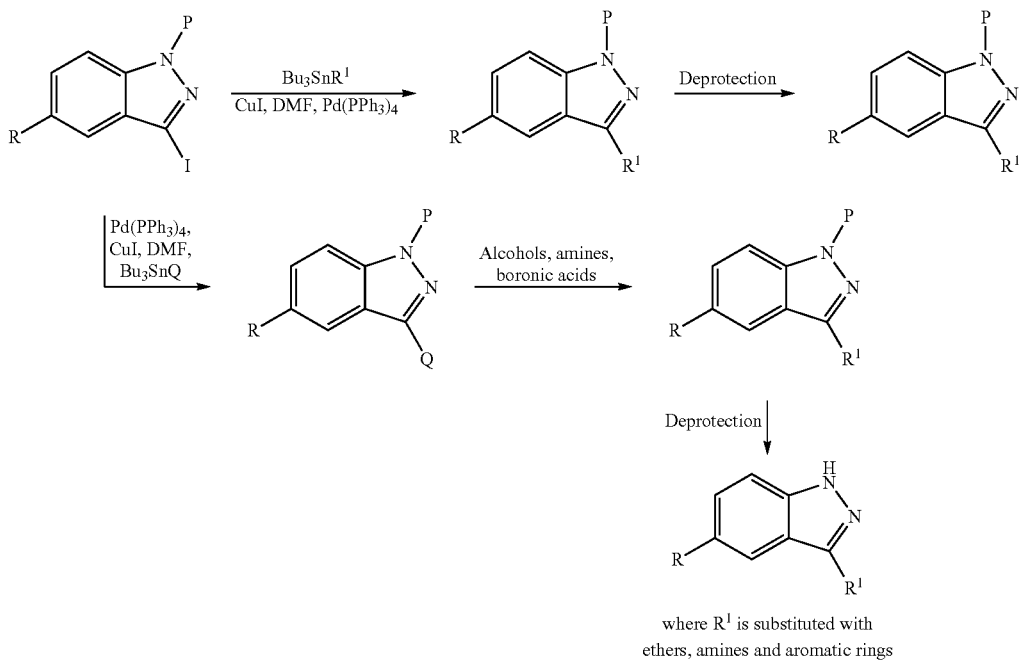

where R¹ is substituted with ethers, amines and aromatic rings

Preparation of the substituted indazoles can be prepared by the following general methods. Coupling 3-iodopyrazoles with substituted (alkyl tin) compounds with CuI and a palladium catalyst such as $Pd(PPh_3)_4$, in DMF provide the initial substitution (where Q is a chloro substituted ring such as phenyl, 5-membered heteroaryl, 6-membered heteroaryl, or 9 membered heteroaryl). Substitutions on R¹ can be achieved using standard aromatic substitution chemistry. For example, amination of chloro substituted aromatic rings can be provided by treatment with dicyclohexyl(2',6'-diisopropoxybiphenyl-2-yl)phosphine, RuPhos precatalyst, base, e.g. sodium tert-butoxide and the secondary amine in a suitable solvent such as THF provides the desired compounds. For primary amines, treatment with the amine BrettPhos precatalyst, base, e.g. sodium tert-butoxide, and dicyclohexyl(2',4',6'-triisopropyl-3,6-dimethoxybiphenyl-2-yl)phosphine in suitable solvent such as p-dioxane provides the protected compounds. Deprotection, such as with HCl, provides the desired compounds. Alternatively, coupling 3-iodo-pyrazoles with R¹-substituted (alkyl tin) compounds with CuI and a palladium catalyst such as $Pd(PPh_3)_4$, in DMF provide the protected indazoles. Deprotection, such as with HCl, provides the desired compounds.

Scheme 6

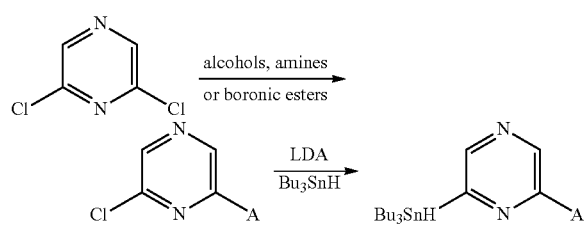

Preparation of the substituted pyrazine tin compounds (where A is an ether, an amine, an aromatic ring) can be prepared by the following general methods. For example, a mixture of 2,6-dichloropyrazine, an amine, base, such as potassium carbonate, in a solvent such as DMF is reacted at a temperature of about RT, to provide the A-substituted pyrazine. Addition of tri-n-butyltin hydride and LDA to the substituted pyrazine in a solvent such as THF at a temperature of less than RT, preferably at about 0° C. provides the desired tin compounds.

Scheme 7

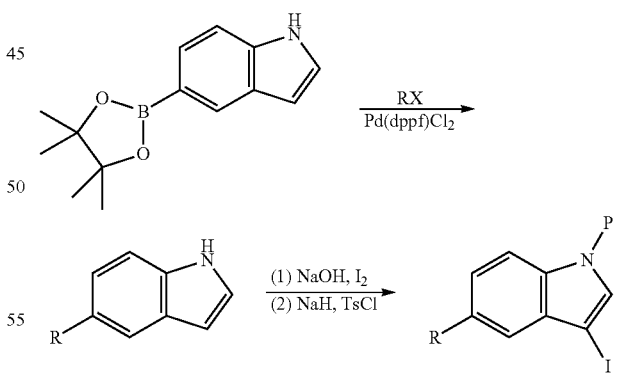

Protected indoles can be prepared by the following methods. Treatment of a boronic ester with RX (where X is bromo), together with a palladium catalyst, such as Pd(dppf)Cl₂ and a base, e.g. $Na_2CO_3$, in a solvent such as toluene, at a temperature of over 50° C., preferably over about 100° C., and more preferably at about 125° C. provides the desired intermediate. Iodination as described above (Scheme 4) and protection, such as with TsCl, and a base such as NaH, provides the desired protected 3-iodo indoles (P=tosyl).

Scheme 8

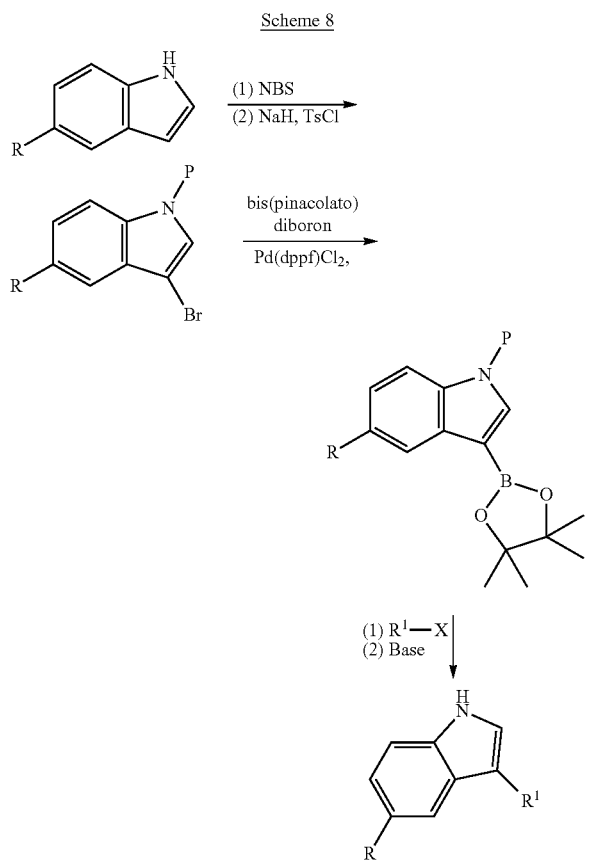

Scheme 9

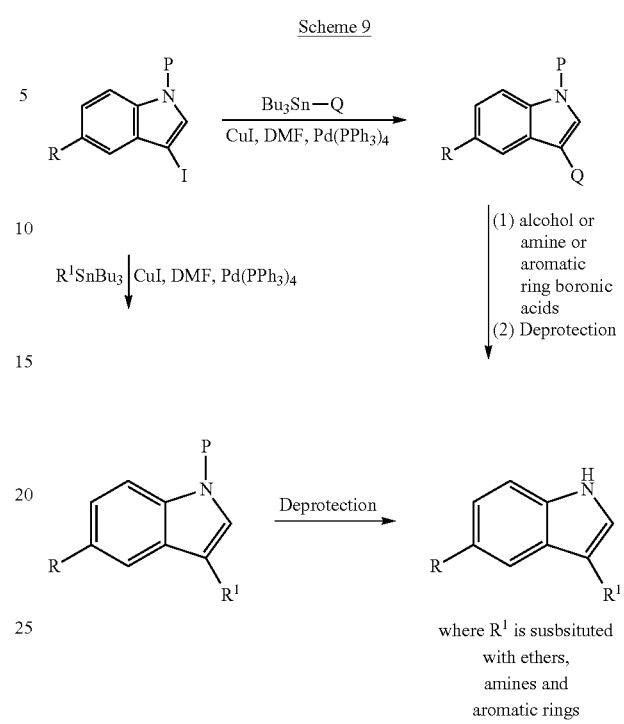

Preparation of substituted indoles can be prepared by the following methods. The protected 3-bromoindoles can be prepared by bromination, such as by addition of base, e.g. potassium hydroxide and NBS in a solvent, such as DMF at a temperature of about RT. Treatment of base, such as NaH, and TsCl provides the protected indole (P=tosyl). Conversion into the boronic derivative as described in Scheme 3 and coupling with the haloaryl compound (where X is chloro) followed by deprotection, provides the desired indoles.

Preparation of substituted indoles can be prepared by the following methods. $R^1$ substituted trialkyl tin compounds, such as tributylstannyl compounds in a solvent such as DMF, together with CuI and a palladium catalyst, such as Pd$(PPh_3)_4$, provides the desired protected $R^1$ substituted indoles. The reaction is maintained at a temperature over RT, preferably at a temperature above about 50° C., more preferably at about 80° C. Alternatively, Q-substituted tributylstannyl-compounds can be incorporated using similar chemistry (where Q is a chloro substituted ring such as phenyl, 5-membered heteroaryl, 6-membered heteroaryl, or 9 membered heteroaryl). The substitution at the chloro group can be accomplished using methods described in Scheme 5. Deprotection provides the desired compounds of the invention.

Scheme 10

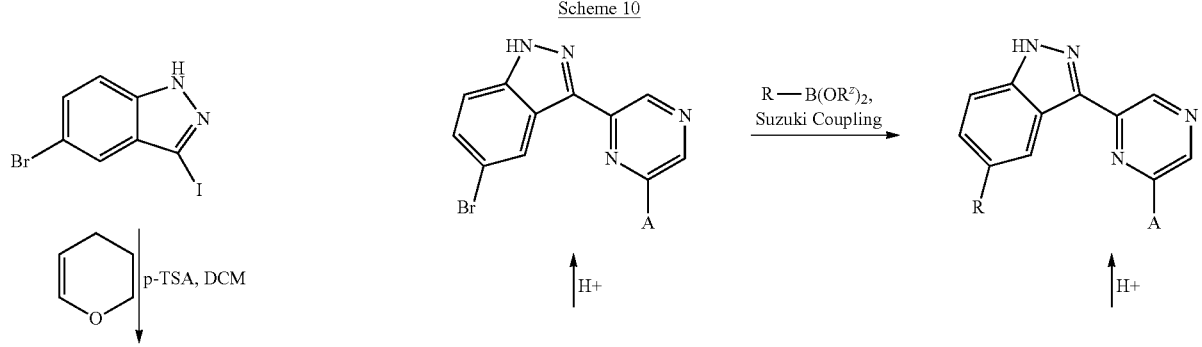

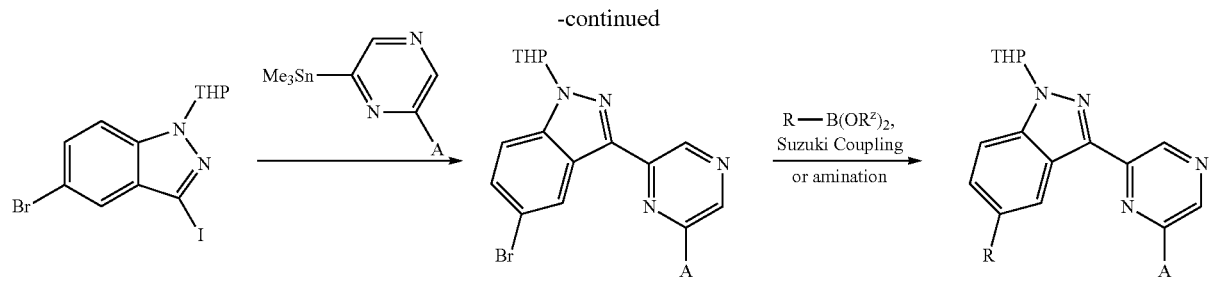

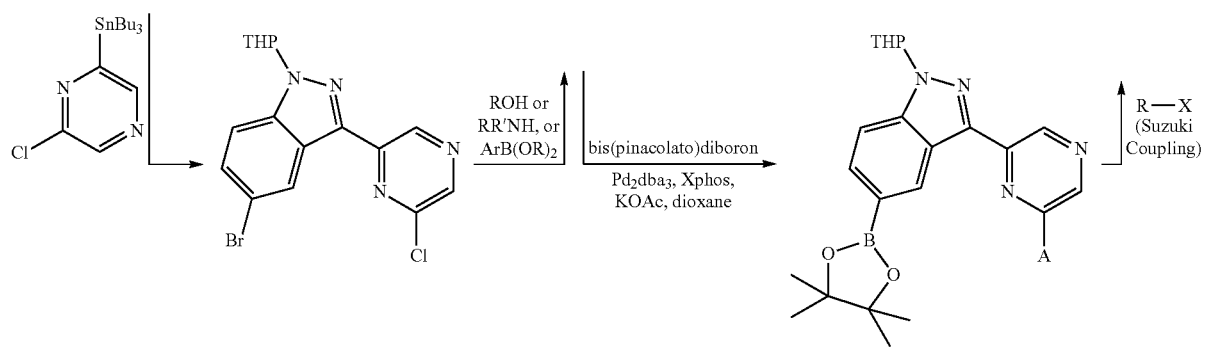

The compounds of the invention can be prepared by the following general methods. Substituted heterocyclic compounds can be prepared according to the method set out in Scheme 1. Protection of any labile nitrogen atom, such as THP via the reaction with 3,4-dihydro-2H-pyran in the presence of p-toluenesulfonic acid in THF provides the protected halo substituted indazole. Alternatively, other amino protecting groups known in the art can be used. Coupling with substituted (alkyl tin) compounds with copper (I) iodide and Pd(PPh$_3$)$_4$ in DMF provide the pyrazine substitution at position 3 (where A is an ether, an amine, an aromatic or a ring). Deprotection, such as with HCl, followed by Susuki coupling provides the desired compounds.

The compounds of the invention can be prepared by the alternative general methods. Coupling with substituted (alkyl tin) compounds with CuI and Pd(PPh$_3$)$_4$ in DMF provide the initial substitution. Substitutions on the pyrazine ring (where A is an ether, an amine, an aromatic or a ring) can be achieved using standard aromatic substitution chemistry. For example, amination of chloro substituted aromatic rings can be provided by treatment with dicyclohexyl(2',6'-diisopropoxybiphenyl-2-yl)phosphine, RuPhos precatalyst, base, e.g. sodium tert-butoxide and the secondary amine in a suitable solvent such as THF provides the desired compounds. For primary amines, treatment with the amine BrettPhos precatalyst, base, e.g. sodium tert-butoxide, and dicyclohexyl(2',4',6'-triisopropyl-3,6-dimethoxybiphenyl-2-yl)phosphine in suitable solvent such as p-dioxane provides the desired compounds.

The compounds of the invention can be prepared by the following alternative general method. Treatment of the 5-bromo-3-pyrazine compounds with bis(pinacolato)-diboron, Pd$_2$dba$_3$, Xphos and KOAc in anhydrous solvent such as 1,4-dioxane provides the 5-boronic ester intermediate. Suzuki coupling followed by deprotection, provides the desired compounds.

Scheme 11

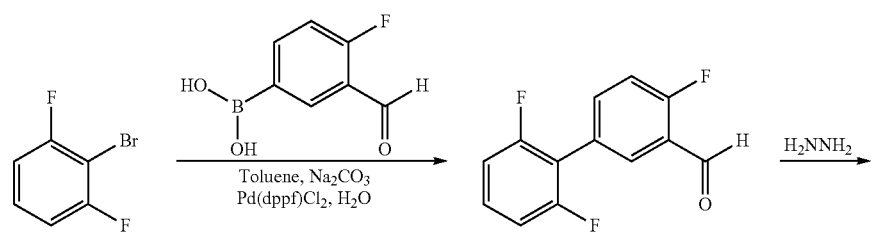

-continued

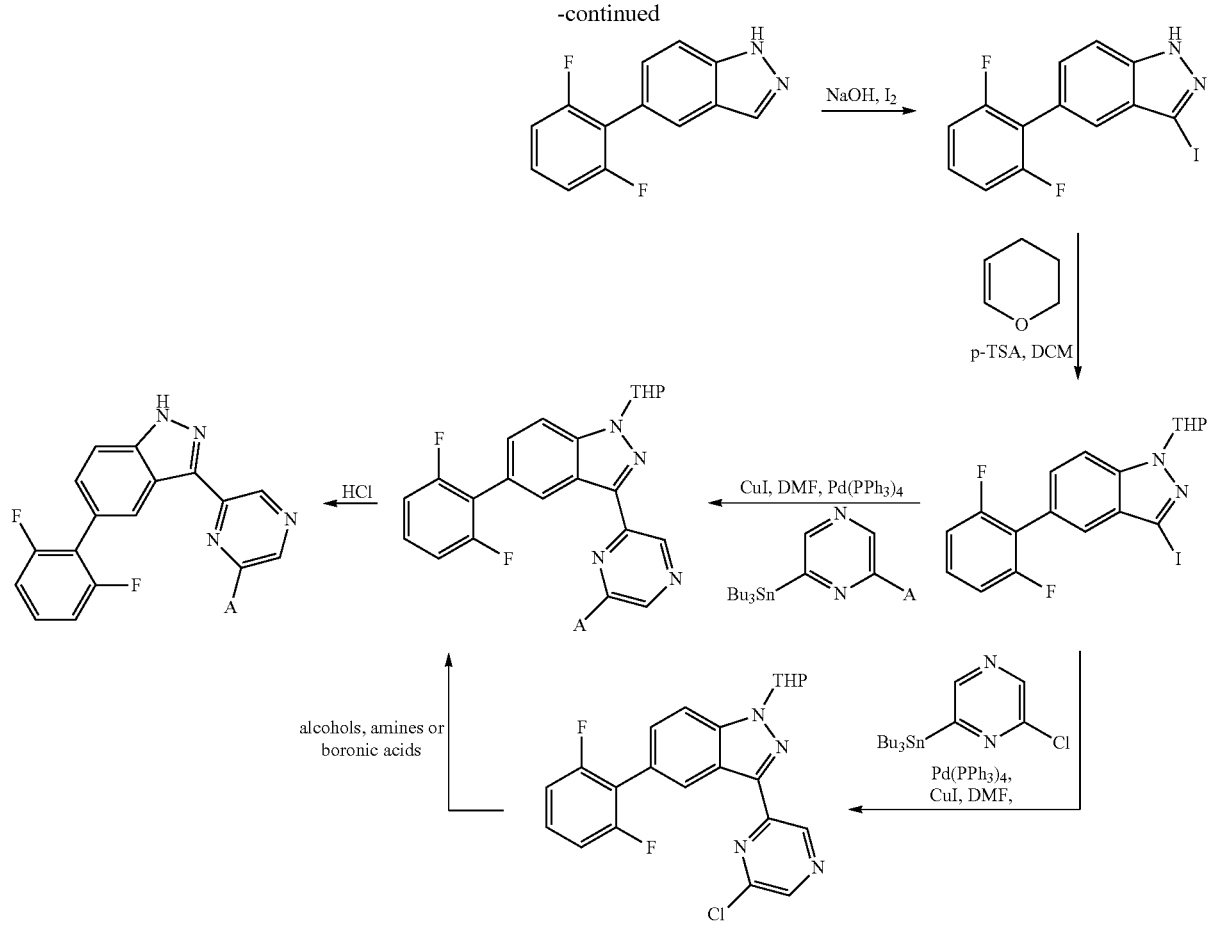

Indazoles of the present invention can be prepared by the following general methods. Coupling of the bromophenyl starting material with a boronic acid, such as 4-fluoro-3-formylphenylboronic acid, and sodium carbonate and a palladium catalyst, such as PdCl$_2$(dppf), in a solvent such as toluene at temperature about RT, yields the formyl substituted biphenyl. Cyclization of the formyl derivative to the indazole is accomplished by treatment with hydrazine hydrate at a temperature of greater than 50° C., preferably greater than 100° C. and more preferably about 120° C. Iodination, such as by treatment with a basic solution of iodine, preferably where the base is sodium hydroxide at a temperature of about RT, provides the 3-iodo-indazole. Protection of the labile nitrogen, such as where P is THP, via the reaction with 3,4-dihydro-2H-pyran in the presence of p-toluenesulfonic acid in THF provides the protected indazole. Coupling with substituted (alkyl tin) compounds with CuI and Pd(PPh$_3$)$_4$ in DMF provide the initial substitution. Alternatively, substitutions on R$^1$ (where R$^1$ is substituted pyrazine) can be achieved using standard aromatic substitution chemistry. For example, amination of chloro substituted pyrazine rings can be provided by treatment with dicyclohexyl(2',6'-diisopropoxybiphenyl-2-yl)phosphine, RuPhos precatalyst, base, e.g. sodium tert-butoxide and the secondary amine in a suitable solvent such as THF provides the desired compounds. For primary amines, treatment with the amine BrettPhos precatalyst, base, e.g. sodium tert-butoxide, and dicyclohexyl(2',4',6'-triisopropyl-3,6-dimethoxybiphenyl-2-yl)phosphine in suitable solvent such as p-dioxane provides the protected compounds. Deprotection, such as with treatment with acid, preferably HCl, provides the desired compounds.

Scheme 12

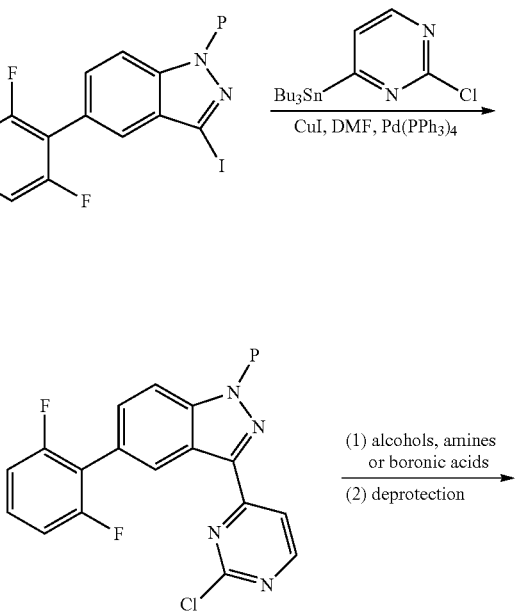

-continued

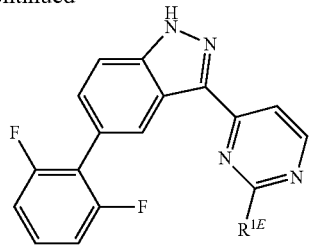

The compounds of the invention can be prepared by the following general methods. Coupling of the 3-iodoindazole with substituted (alkyl tin) pyrimidines with CuI and palladium catalysts, such as Pd(PPh$_3$)$_4$, in DMF provide the initial 3-pyrimidinylindazoles. Substitutions on R$^1$ can be achieved using standard aromatic substitution chemistry. For example, amination of chloro substituted pyrimidines can be provided by treatment with dicyclohexyl(2',6'-diisopropoxybiphenyl-2-yl)phosphine, RuPhos precatalyst, base, e.g. sodium tert-butoxide and the secondary amine in a suitable solvent such as THF provides the desired compounds. For primary amines, treatment with the amine BrettPhos precatalyst, base, e.g. sodium tert-butoxide, and dicyclohexyl(2',4',6'-triisopropyl-3,6-dimethoxybiphenyl-2-yl)phosphine in suitable solvent such as p-dioxane provides the desired protected compounds. Deprotection, such as with treatment with acid, preferably HCl, provides the desired compounds.

Preparation of the substituted indoles (where R$^{1A}$ is described above), can be prepared by the following methods. Treatment of 3-iodoindoles from Scheme 7 with tributyl stannyl-2-chloropyrazines in a solvent such as DMF, together with CuI and a palladium catalyst, e.g. Pd(PPh$_3$)$_4$, provides the 2-chloropyrazine substituted indoles. The reaction is maintained at a temperature above RT, preferably at a temperature above about 50° C., more preferably at about 80° C. Alternatively, substituted pyrazinyl tributylstannyl-compounds can be incorporated using similar chemistry. The chloro group can be replaced using chemistry described in Scheme 5. Deprotection provides the desired compounds of the invention.

Scheme 14

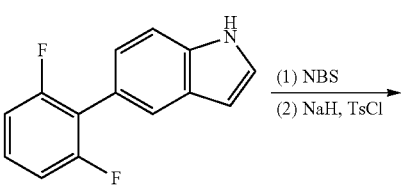

Scheme 13

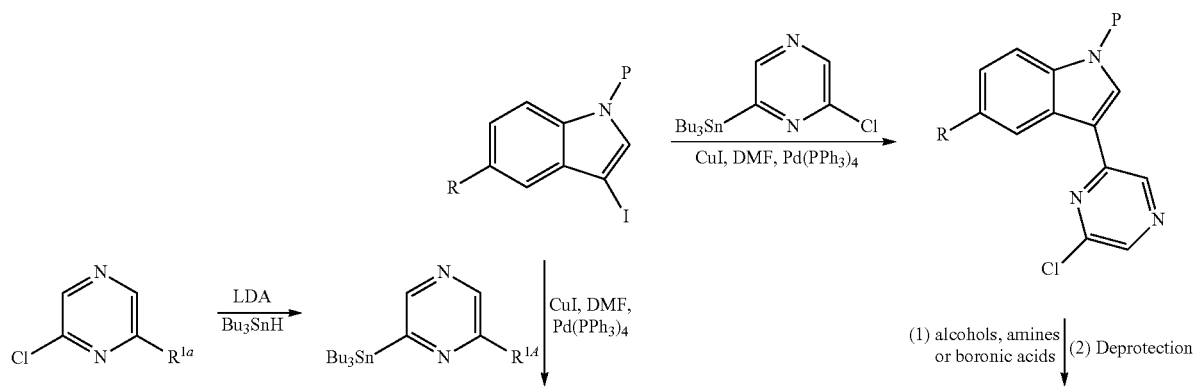

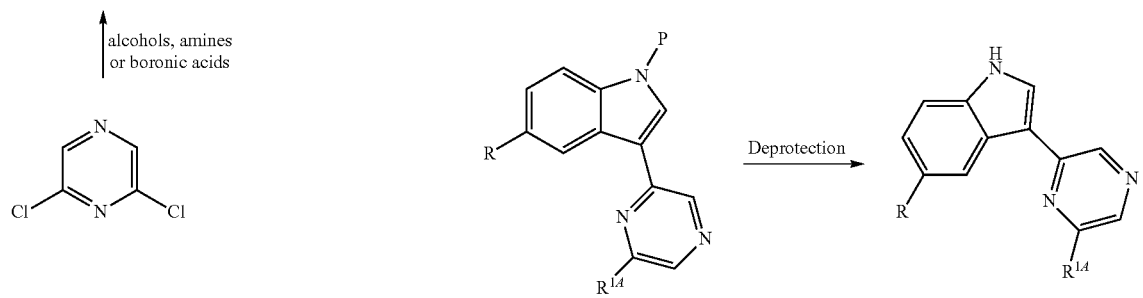

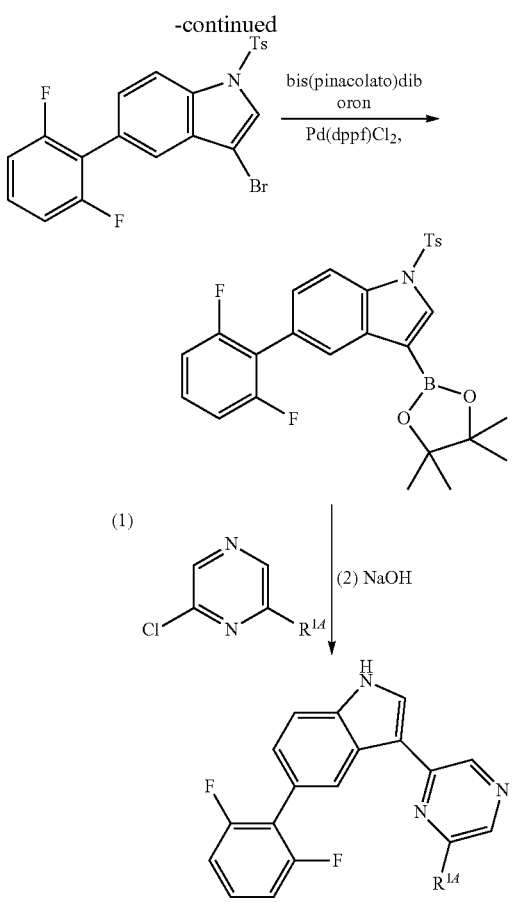

Preparation of the 3-substituted pyrazinyl-5-difluorophenylindoles can be prepared by the following methods. The protected 3-bromoindoles can be prepared by bromination of 5-(2,6-difluorophenyl)indole, such as by addition of base, e.g. potassium hydroxide, and NBS in a polar aprotic solvent, such as DMF at a temperature of about RT. Protection of the $N^1$ nitrogen, such as with treatment with base, e.g. NaH, and TsCl provides the tosyl protected indole. Conversion of the 3-bromo-indole into the corresponding boronic derivative proceeds as described in Scheme 8. Coupling with the substituted pyrazine (Scheme 13) provides the desired indoles.

The starting compounds defined in Schemes 1-14 may also be present with functional groups in protected form if necessary and/or in the form of salts, provided a salt-forming group is present and the reaction in salt form is possible. If so desired, one compound of formulas 1-4 can be converted into another compound of formulas 1-4 or a N-oxide thereof; a compound of formulas 1-4 can be converted into a salt; a salt of a compound of formulas 1-4 can be converted into the free compound or another salt; and/or a mixture of isomeric compounds of formulas 1-4 can be separated into the individual isomers.

N-Oxides can be obtained in a known manner by reacting a compound of formulas 1-4 with hydrogen peroxide or a peracid, e.g. 3-chloroperoxy-benzoic acid, in an inert solvent, e.g. dichloromethane, at a temperature between about −10-35° C., such as about 0° C.-RT.

If one or more other functional groups, for example carboxy, hydroxy, amino, or mercapto, are or need to be protected in a compound of formulas 1-4 or in the synthesis of a compound of formulas 1-4, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide and Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formulas 1-4 with a salt-forming group may be prepared in a manner known per se. Acid addition salts of compounds of formulas 1-4 may thus be obtained by treatment with an acid or with a suitable anion exchange reagent. A salt with two acid molecules (for example a dihalogenide of a compound of formulas 1-4) may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formulas 1-4.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150°

C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., ethyl acetate, ethers, typically aliphatic ethers, e.g., diethyl-ether, or cyclic ethers, e.g., THF, liquid aromatic hydrocarbons, typically benzene or toluene, alcohols, typically MeOH, EtOH or 1-propanol, 2-propanol, nitriles, typically $CH_3CN$, halogenated hydrocarbons, typically DCM, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formulas 1-4, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); A. Katritzky and A. Pozharski, Handbook of Heterocyclic Chemistry, $2^{nd}$ Ed. (2001); M. Bodanszky, A. Bodanszky: *The practice of Peptide Synthesis* Springer-Verlag, Berlin Heidelberg 1984; J. Seyden-Penne: *Reductions by the Alumino- and Borohydrides in Organic Synthesis*, $2^{nd}$ Ed., Wiley-VCH, 1997; and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas 1-4. These detailed descriptions fall within the scope, and serve to exemplify, the above described General Synthetic Procedures which form part of the invention. These detailed descriptions are presented for illustrative purposes only and are not intended as a restriction on the scope of the invention.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. MS data was determined by electrospray ionization technique. All examples were purified to >90% purity as determined by high-performance liquid chromatography. Unless otherwise stated, reactions were run at RT.

Analytical Methods:

Unless otherwise indicated, HPLC analyses were run on an Agilent Model 1100 system with an Agilent Technologies Zorbax SB-$C_8$ (5μ) reverse phase column (4.6×150 mm) run at 30° C. with a flow rate of about 1.50 mL/min (Agilent Technologies, Santa Clara, Calif.). The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Methods:

Unless otherwise indicated, samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min. The mobile phase used a mixture of solvent A ($H_2O$/0.1% $HCO_2H$ or TFA) and solvent B (ACN/0.1% $HCO_2H$ or TFA) with a 5 to for a gradient from 10% to 90% solvent B. The gradient was followed by a 0.5 min period 9 min time period to return to 10% solvent B and a 2.5 min 10% solvent B re-equilibration (flush) of the column Preparative HPLC Methods:

Where indicated, compounds of the present invention were purified via reverse phase HPLC using a Gilson (Gilson, Middleton, Wis.) or Shimadzu (Columbia, Md.) workstation utilizing one of the following two protocols: (A) Using a 50×100 mm column (Waters, Externa, C18, 5μ) (Waters, Milford, Mass.) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a ≥10 min gradient from 40% to 100% solvent B followed by a 5 min flow of 100% solvent B. The gradient was followed by a 2 min return to 40% solvent B; or (B) Using a Waters 20×50 mm column at 20 mL/min or Phenomenex Gemni 5μ C18 100×30 mm (Phenomenex, Torrance, Calif.). The mobile phase used was a mixture of solvent A ($H_2O$/0.1% TFA) and solvent B (ACN/0.1% TFA) with a ≥10 min gradient from 5% to 100% solvent B. The gradient is followed by a 2 min return to 5% ACN.

Mass Spectra (MS)

Unless otherwise indicated, all mass spectral data for starting materials, intermediates and/or exemplary compounds are reported as mass/charge (m/z), having an (M+H$^+$) or (M−H$^-$) molecular ion, depending on the ionization mode (positive or negative). The molecular ion reported was obtained by electrospray detection method. Compounds having an isotopic atom, such as bromine and the like, are reported according to the detected isotopic pattern, as appreciated by those skilled in the art.

The following abbreviations may be used herein:
$Ac_2O$ acetic anhydride
ACN acetonitrile
(A-Phos)$_2$PdCl$_2$ bis[(di-tert-butyl(4-dimethylaminophenyl)-phosphine)]palladium dichloride
PdCl$_2$(Amphos) bis[(di-tert-butyl(4-dimethylaminophenyl)-phosphine)]palladium dichloride
aq aqueous
ATP adenosine 5'-triphosphate
nBuLi n-butyllithium
Calcd or Calc'd calculated
Conc. concentrated
CuI copper (I) iodide
DCM dichloromethane
DIPEA diisopropylethyl amine
DMAP dimethyl aminopyridine
DME dimethoxyl ethyl ether
DMF N,N-dimethylformamide
DMSO dimethyl sulfoxide
dppf 1,1'-bis(diphenylphosphino)ferrocene
DTT dithiothreitol
ESI electrospray ionization
Et$_2$O diethyl ether
Et$_3$N triethylamine
EtOAc ethyl acetate
EtOH ethyl alcohol
FBS fetal bovine serum
g grams
h hour
HBTU- 2-(1H-benzotriazole-1-yl)-1,1,3,3-tetramethylaminium hexafluorophosphate
HATU O-(7-azobenzotriazol-1-yl)-1,1,3,3-tetramethyluronium hexafluorophosphate
HCl hydrochloric acid
HCO$_2$H formic acid
H$_2$NNH$_2$ hydrazine
H$_2$O water Hex hexanes
HOAc acetic acid
HOBt 1-hydroxybenzotriazole
HPLC high pressure liquid chromatography
$I_2$ iodine
IPA or iPrOH or iPr isopropyl alcohol
$iPr_2NEt$ N-ethyl diisopropylamine
KF potassium fluoride
KOAc potassium hydroxyacetate
KOH potassium hydroxide
L liter
LCMS, LC-MS or LC/MS liquid chromatography mass spectroscopy
LDA lithium diisopropylamide
m/z mass divided by charge
Me- methyl
MTBE- methyl tert-butyl ether
MeCN acetonitrile
MeI iodomethane
MeOH methyl alcohol
mg milligrams
min minutes
mL milliliters
$MgSO_4$ magnesium sulfate
MS mass spectra
MsCl mesylchloride
$N_2$ nitrogen
$NH_3$ ammonia
$NH_4OH$ ammonium hydroxide
$NH_4Cl$ ammonium chloride
NaH sodium hydride
NaOH sodium hydroxide
$Na_2CO_3$ sodium carbonate
$Na_2SO_4$ sodium sulfate
NBS N-bromosuccinimide
NMP 1-methyl-2-pyrrolidinone
NMR nuclear magnetic resonance
$Pd(PPh_3)_4$ tetrakis(triphenylphosphine)-palladium (0)
$Pd_2 dba_3$ tris(dibenzylideneacetone)dipalladium (0)
$Pd(dppf)Cl_2$ [(1,1-bis(diphenylphosphino)ferrocene]dichloropalladium(II)
$PdCl_2$ palladium chloride
P protecting group
Pos. ion positive ion
py or pyr pyridine
rt or RT room temperature
Sat. saturated
TFA trifluoroacetic acid
TFAA trifluoroacetic anhydride
THF tetrahydrofuran
THP tetrahydropyran
TMS tetramethylsilane
Ts or tosyl para-toluene sulfonyl
TSA or PTSA p-toluenesulfonic acid
TsCl para-toluene sulfonyl chloride
wt Weight
Xantphos 9,9-dimethyl-4,5-bis(diphenylphosphino)xanthene
Xphos 2-dicyclohexylphosphino-2',4',6'-triisopropylbiphenyl Example 1

1-(6-(5-bromo-1H-indazol-3-yl)pyrazin-2-yl)piperidin-4-amine

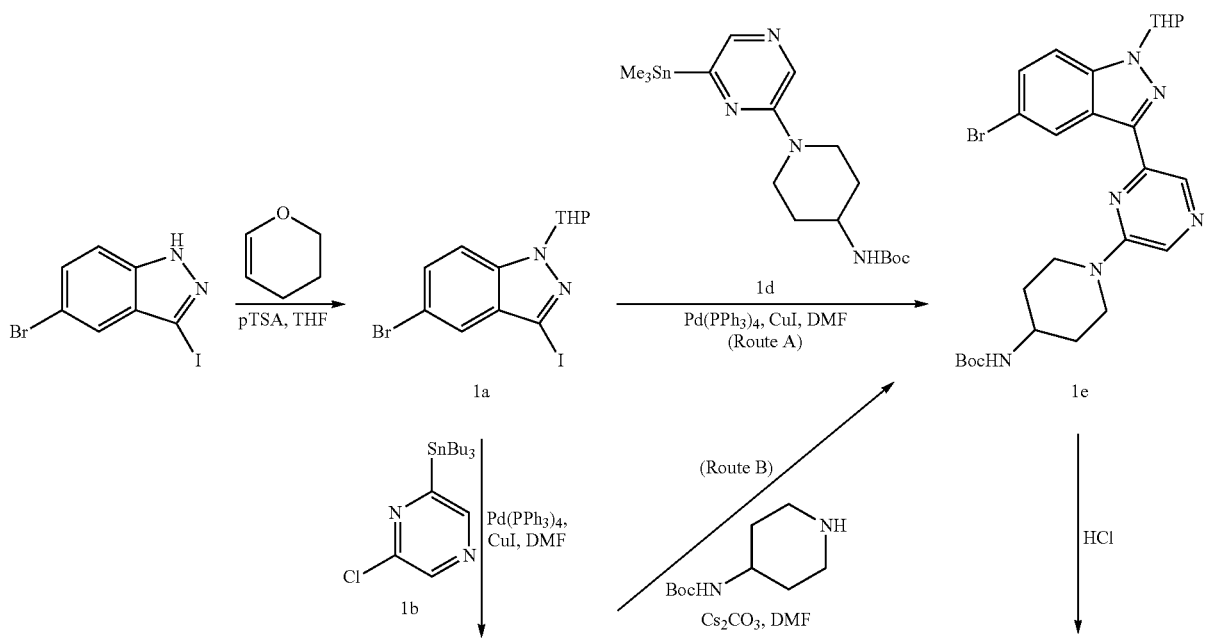

-continued

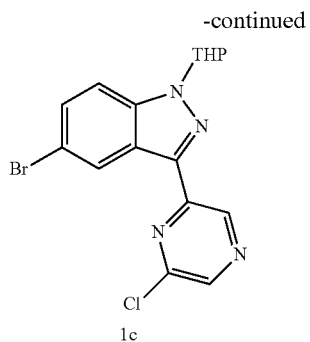

1c

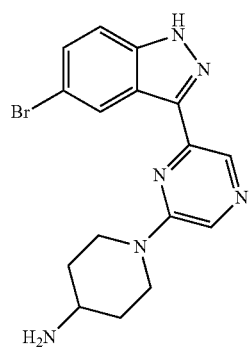

1

Preparation of Compound 1a: 5-bromo-3-iodo-1-(tetrahydro-2H-pyran-2-yl)-1H-indazole To a solution of 5-bromo-3-iodo-1H-indazole (800 g, 2.50 mol, 1 eq) and TSA monohydrate (105 g, 0.55 mol, 0.22 eq) in THF (15 L) was added 3,4-dihydro-2H-pyran (791 mL, 8.70 mol, 3.5 eq). The reaction mixture was stirred at 70° C. overnight. LC-MS analysis showed that 5-bromo-3-iodo-1H-indazole was consumed. The reaction was cooled to RT and quenched with aqueous saturated NaHCO$_3$. After phase separation, the aqueous layer was extracted with EtOAc (4 L×2). The combined organics were washed with brine, dried over anhydrous Na$_2$SO$_4$, and concentrated in vacuo. The residue was dissolved in hot hexanes (2 L). After cooling to RT, a yellow solid precipitated out. This was collected by filtration to give 600 g (>96% purity) of 1a. The mother liquor was purified by column chromatography eluting with hexanes/EtOAc (20/1), affording 1a (160 g, >98% purity). The total yield in this step is 75%. MS (ESI, pos. ion) m/z: 408.8 (M+1)

Preparation of Compound 1b: 2-chloro-6-(tributylstannyl)pyrazine

22 L Three-neck flask was charged with anhydrous THF (4 L) and cooled to −40° C., and to it was added n-BuLi (2.5M in hexanes, 1100 mL, 2.75 mol, 3.15 eq) followed by slow addition of 2,2,6,6-tetramethylpiperidine (467 mL, 2.75 mol, 3.15 eq) keeping the internal temperature below −40° C. The reaction mixture was warmed to 0° C. and stirred for 20 min and then cooled to −78° C. A mixture of 2-chloropyrazine (100 g, 0.87 mol, 1.0 eq) and tri-n-butyltin chloride (284 g, 0.87 mol, 1.0 eq) in anhydrous THF (2 L) was added slowly to the above reaction mixture keeping the internal temperature below −73° C. The reaction mixture was then stirred for 3 h (temperature was slowly increased from −78° C. to −40° C.). Hydrolysis was then carried out at −40° C. using a solution of conc. HCl, EtOH and THF (1:4:5, total; 4500 mL). The reaction mixture was warmed to RT, neutralized with aqueous saturated NaHCO$_3$, and concentrated under reduced pressure. The residue was partitioned between DCM (4 L) and water (4 L). After phase separation, the aqueous layer was extracted with DCM (3 L×2). The combined organic extracts were dried over Na$_2$SO$_4$ and filtered. Similarly, other two batches on 100 g scale (0.87 mol) each were carried out. The combined organic extracts of these three batches were concentrated and purified by column chromatography (100%→0% hexanes in DCM) to give 392 g (37% yield) of the compound 1b as a light yellow oil with >98% purity by LC-MS analysis.

Preparation of Compound 1c: 5-bromo-3-(6-chloropyrazin-2-yl)-1-(tetrahydro-2H-pyran-2-yl)-1H-indazole A mixture of compound 1a (278 g, 0.68 mol, 1.0 eq), compound 1b (358 g, 0.89 mol, 1.3 eq) and CuI (14.3 g, 0.075 mol, 0.11 eq) was dissolved in anhydrous DMF (2 L) under N$_2$. The reaction mixture was degassed for 15 min and Pd(PPh$_3$)$_4$ (79 g, 0.068 mol, 0.1 eq) was added into it. The mixture was degassed for an additional 15 min. The reaction mixture was heated to 100° C. and stirred overnight. The reaction mixture was cooled to RT, filtered, and washed with EtOAc to give crude product as a yellow solid. The crude product was purified by column chromatography (50% DCM in hexanes→100% DCM→5% EtOAc in DCM) to give 65 g of compound 1c as a light yellow solid with >96% purity by LC-MS. Similarly, another batch was carried out on 30 g scale (0.074 mol) to give 12 g of compound 1c after purification. The mother liquor of these two batches were combined and concentrated under reduced pressure. The crude material was dissolved in DCM (2 L), washed with water (1 L×3), dried over Na$_2$SO$_4$, filtered, and concentrated. The crude material was purified by column chromatography to give 100 g of compound 1c, with ~85% purity by $^1$H NMR (Impurity is triphenylphosphine oxide residue). This material was further purified using trituration with EtOAc to give 79 g of compound 1c with >96% purity by LC-MS. 156 g of compound 1c was obtained from these two batches (51% yield). MS (ESI, pos. ion) m/z: 393.0 (M+1), 395.0 (M+3)

Preparation of Compound 1d: tert-butyl 1-(6-(trimethylstannyl)pyrazin-2-yl)piperidin-4-ylcarbamate A suspension of 2,6-dichloropyrazine (223.5 g, 1.5 mol, 1.0 eq), 4-N-boc-aminopiperidine (300 g, 1.5 mol, 1.0 eq) and K$_2$CO$_3$ (228 g, 1.65 mol, 1.1 eq) in DMF (900 mL) was heated to 85° C. for 20 h. LC-MS analysis showed that tert-butyl 1-(6-(trimethylstannyl)pyrazin-2-yl)piperidin-4-ylcarbamate was formed as the major product. The reaction mixture was cooled to RT and poured into ice-water (3 L). The resulting precipitate was collected by filtration, washed with water (1 L×2) and hexane (1 L×2), and dried at 50° C. under vacuum affording tert-butyl 1-(6-chloropyrazin-2-yl)piperidin-4-ylcarbamate (252 g, >98% purity) in 54% yield. MS (ESI, pos. ion) m/z: 393.0 (M+1). A suspension of tert-butyl 1-(6-chloropyrazin-2-yl)piperidin-4-ylcarbamate (245 g, 0.75 mol, 1.0 eq), hexamethylditin (492 g, 1.5 mol, 2.0 eq) and Pd(PPh$_3$)$_4$ (87 g, 0.075 mol, 0.1 eq) in anhydrous toluene (2 L) was degassed with N$_2$ for 30 min and heated to 110° C. for 24 h.

LC-MS analysis showed around 50% conversion and no more further reaction. The reaction mixture was cooled to RT, quenched with water (2 L), and stirred well. After filtration through a celite pad and phase separation, the aqueous layer was extracted with EtOAc (1 L×2). The combined organics were washed with brine, dried over anhydrous Na$_2$SO$_4$, and concentrated in vacuo. The residue was purified by column chromatography eluting with DCM/EtOAc (20/1), affording title compound 1d (150 g, >96% purity) in 45% yield. MS (ESI, pos. ion) m/z: 443.2 (M+1)

Preparation of Compound 1e: tert-butyl 1-(6-(5-bromo-1-(tetrahydro-2H-pyran-2-yl)-1H-indazol-3-yl)pyrazin-2-yl)piperidin-4-ylcarbamate Route A: A suspension of 1d (150 g, 0.34 mol, 1.0 eq), 1a (138 g, 0.34 mol, 1.0 eq), Pd(PPh$_3$)$_4$ (39.3 g, 0.034 mol, 0.1 eq) and Cu(I)I (6.5 g, 0.034 mol, 0.1 eq) in anhydrous DMF (2 L) was degassed with N$_2$ for 30 min and heated to 90° C. for 4 h. LC-MS analysis showed that 1d was consumed and 1e was formed as a major product. The reaction mixture was cooled to RT and diluted with EtOAc (1 L) and sat. NaHCO$_3$ (2 L). After phase separation, the aqueous layer was extracted with EtOAc (2×1 L). The combined organics were washed with water and brine, dried over MgSO$_4$, concentrated in vacuo, and purified by column chromatography eluting with DCM/EtOAc (20/1), affording 125 g of title compound 1e (>97% purity) in 62% yield. MS (ESI, pos. ion) m/z: 557.2, 559.2 (M+1, M+3).

Route B: A mixture of 5-bromo-3-(6-chloropyrazin-2-yl)-1-(tetrahydro-2H-pyran-2-yl)-1H-indazole 1c (8.5395 g, 21.69 mmol), 4-(N-boc-amino)-piperidine (6.52 g, 32.5 mmol, Sigma Aldrich), and cesium carbonate (3.47 mL, 43.4 mmol, Alfa Aesar) in DMF (54.2 mL) was stirred and heated at 90° C. overnight. Reaction mixture was cooled to RT and solvent was evaporated. The crude product was adsorbed onto a plug of silica gel and purified by chromatography through a Biotage SNAP cartridge (KP-Sil 340 g), eluting with a gradient of 10% to 100% EtOAc in hexanes, to provide title compound 1e (3.99 g, 7.16 mmol, 33.0% yield).

Preparation of Compound 1: 1-(6-(5-bromo-1H-indazol-3-yl)pyrazin-2-yl)piperidin-4-amine hydrochloride salt A glass scintillation vial containing tert-butyl 1-(6-(5-bromo-1-(tetrahydro-2H-pyran-2-yl)-1H-indazol-3-yl)pyrazin-2-yl)piperidin-4-ylcarbamate 1e (0.338 g, 0.606 mmol) and HCl, 5-6N in IPA (12 mL, 60.0 mmol) was stirred vigorously at 50° C. for 4 h. The reaction mixture was cooled to RT and the solvent was removed in vacuo. The residue was concentrated to dryness to give a yellow solid that was used in the next step without further purification. MS (ESI, pos. ion) m/z: 373 (M+1).

Example 2

1-(6-(5-(2-methoxyquinolin-3-yl)-1H-indazol-3-yl)pyrazin-2-yl)piperidin-4-amine

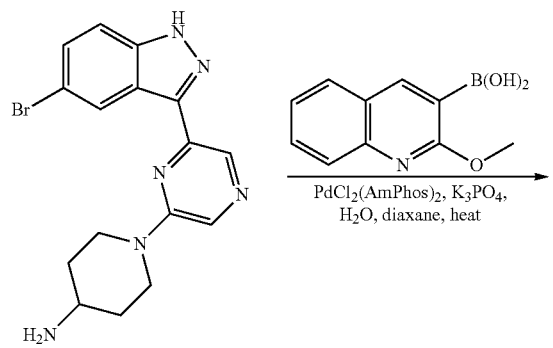

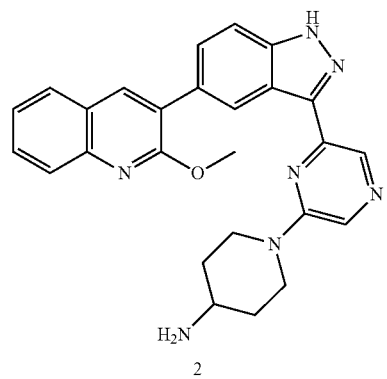

To a 5 mL conical vial was added 2-methoxyquinolin-3-ylboronic acid (Frontier Scientific, 89 mg, 0.437 mmol), potassium phosphate (Aldrich, 285 mg, 1.345 mmol), PdCl$_2$ (AmPhos) (23.80 mg, 0.034 mmol), and 1-(6-(5-bromo-1H-indazol-3-yl)pyrazin-2-yl)piperidin-4-amine dihydrochloride salt (Example 1) (150 mg, 0.336 mmol) which was sealed, evacuated and back-filled with N$_2$ 3×. Dioxane (2.8 mL) and water (0.6 mL) were added, and the reaction mixture was heated at 150° C. for 30 min with microwave irradiation. After the reaction mixtures were filtered, the crude reaction mixture was concentrated and purified on silica gel (eluent: 0 to 4% MeOH (with 2M NH$_3$) in DCM) to afford the title compound. MS (ESI, pos. ion) m/z: 438 (M+1).

Example 3

3-(3-(6-(4-aminopiperidin-1-yl)pyrazin-2-yl)-1H-indazol-5-yl)-N-cyclopropyl-4-fluorobenzamide

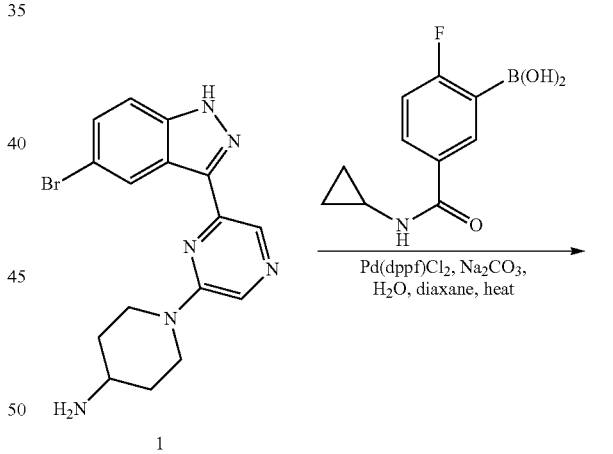

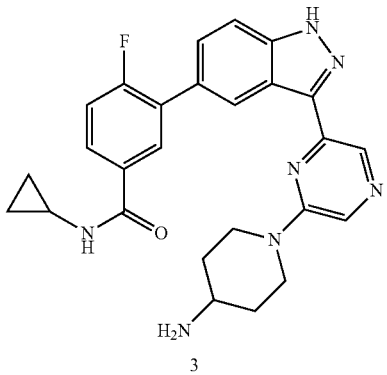

To a 5 mL conical microwave vial was added Pd(dppf)Cl₂ (15.53 mg, 0.02 mmol), 1-(6-(5-bromo-1H-indazol-3-yl)pyrazin-2-yl)piperidin-4-amine dihydrochloride salt (Example 1) (71 mg, 0.19 mmol), and 5-(cyclopropylcarbamoyl)-2-fluorophenylboronic acid (46.7 mg, 0.21 mmol), capped, degassed and backfilled with argon (3×). Dioxane (1.9 mL) and 2N Na₂CO₃ aqueous solution (0.2 mL, 0.48 mmol) were added. The reaction mixture was stirred at 80° C. for 16 h. After cooling to RT, the reaction mixtures were filtered before concentrating under reduced pressure. The crude reaction mixture was purified by preparative HPLC using water with 0.1% NH₄OH and ACN with 0.1% NH₄OH (Column: Phenomenex Gemini-NX C18 110 A 5 μm, 21×100 mm) to afford the title compound. MS (ESI, pos. ion) m/z: 472 (M+1).

Example 4

1-(6-(5-(2-fluoro-3-methoxyphenyl)-1H-indazol-3-yl)pyrazin-2-yl)piperidin-4-amine

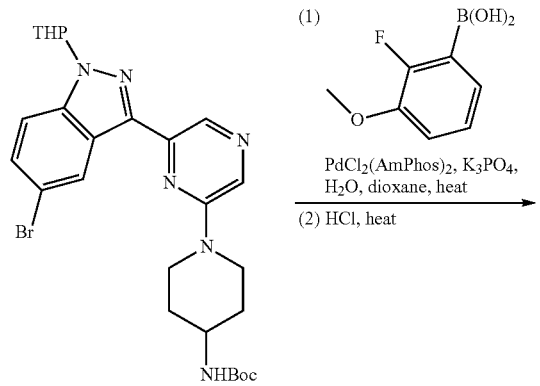

To a 5 mL conical microwave vial was added potassium phosphate (Aldrich, 129 mg, 0.61 mmol), PdCl₂AmPhos (17.1 mg, 0.02 mmol), tert-butyl 1-(6-(5-bromo-1-(tetrahydro-2H-pyran-2-yl)-1H-indazol-3-yl)pyrazin-2-yl)piperidin-4-ylcarbamate (compound 1e, 135 mg, 0.24 mmol), and 2-fluoro-3-methoxyphenylboronic acid (Frontier Scientific, 45.3 mg, 0.27 mmol) which was sealed, evacuated and backfilled with N₂ 3×. Dioxane (2.0 mL) and water (0.4 mL) were added and the resulting mixture was heated at 150° C. for 30 min with microwave irradiation. After the reaction mixtures were filtered, the crude reaction mixture was concentrated under reduced pressure. The dark brown residue was dissolved with DMSO, filtered, and purified by HPLC (5% 0.1% TFA in water to 95% 0.1% TFA in ACN over 20 min) to give tert-butyl 1-(6-(5-(2-fluoro-3-methoxyphenyl)-1-(tetrahydro-2H-pyran-2-yl)-1H-indazol-3-yl)pyrazin-2-yl)piperidin-4-ylcarbamate (78.1 mg, 53.5%). MS (ESI, pos. ion) m/z: 603 (M+1). A mixture of 5N HCl in IPA (25.9 μL, 0.13 mmol), tert-butyl 1-(6-(5-(2-fluoro-3-methoxyphenyl)-1-(tetrahydro-2H-pyran-2-yl)-1H-indazol-3-yl)pyrazin-2-yl)piperidin-4-ylcarbamate (78.1 mg, 0.13 mmol), DCM (1.3 mL) and MeOH (1.3 mL) was heated at 80° C. for 30 min with stirring. The resulting reaction mixture was cooled to RT and concentrated to a yellow solid. The above solid was stirred with a 1:1 mixture of DCM:MeOH and applied to a pre-washed (10 mL MeOH) column of Si-propylsulfonic acid (Silicycle, Cat# R51230B). The compound was released with 30 mL of MeOH (with 2M NH₃) to yield the title compound product as a yellow oil. MS (ESI, pos. ion) m/z: 419 (M+1).

Example 5

1-(6-(5-(6-isopropoxypyrazin-2-yl)-1H-indazol-3-yl)pyrazin-2-yl)piperidin-4-amine

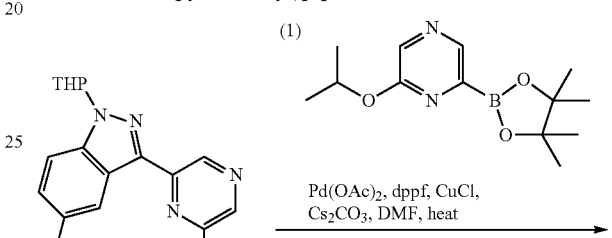

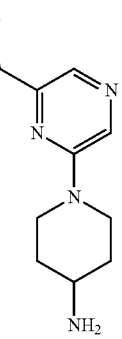

A mixture of CuI (Aldrich, 26.6 mg, 0.27 mmol), cesium carbonate (Aldrich, 351 mg, 1.08 mmol), 1,1'-bis(diphenylphosphino)ferrocene (14.9 mg, 0.03 mmol), palladium(II) acetate (Strem Chemicals, 3.0 mg, 0.01 mmol), 2-isopropoxy-6-(4,4,5,5-tetramethyl-1,3,2-dioxaborolan-2-yl)pyrazine (Combi-Phos, 142 mg, 0.54 mmol), and tert-butyl 1-(6-(5-bromo-1-(tetrahydro-2H-pyran-2-yl)-1H-indazol-3-yl)pyrazin-2-yl)piperidin-4-ylcarbamate (compound 1e, 150 mg, 0.27 mmol) in a 5 mL conical microwave vial was sealed, evacuated and back-filled with N₂ 3×. DMF (2.7 mL) was added, and the reaction mixture was stirred at 80° C. for 16 h. The resulting reaction mixture was cooled to RT, filtered, and concentrated to dryness. The crude product was purified by HPLC (5 to 80% 0.1% TFA:Water:0.1% TFA:ACN over 25 min). The fractions were combined, washed with sat. aq. NaHCO₃ and extracted with 20% IPA in chloroform. The

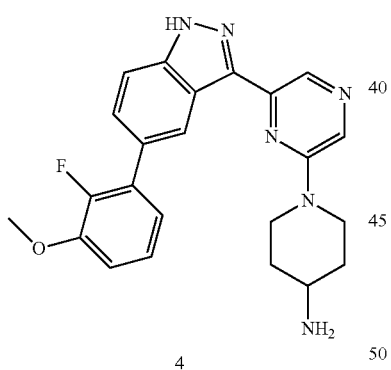

combined organics were dried over Na₂SO₄, filtered, and concentrated under reduced pressure to a tan oil. The oil was dissolved in MeOH/DCM before adding 6 N HCl in IPA and stirring at 80° C. for 2 h. The reaction mixture was concentrated under reduced pressure before resolubilizing with MeOH and passing through a MeOH washed plug of Si-propylsulfonic acid. The compound was released with 2M NH₃ in MeOH (30 mL) to afford 1-(6-(5-(6-isopropoxy-pyrazin-2-yl)-1H-indazol-3-yl)pyrazin-2-yl)piperidin-4-amine as a dark tan solid. MS (ESI, pos. ion) m/z: 431 (M+1).

Example 6

1-(6-(5-(3-(trifluoromethyl)-1H-pyrazolo[3,4-b]pyridin-5-yl)-1H-indazol-3-yl)pyrazin-2-yl)piperidin-4-amine

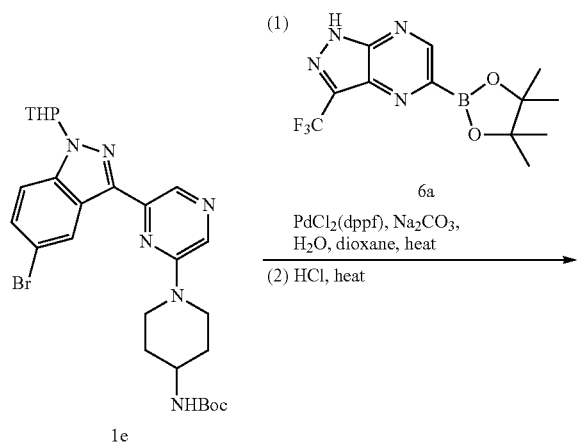

Preparation of Compound 6a: 5-(4,4,5,5-tetramethyl-1,3,2-dioxaborolan-2-yl)-3-(trifluoromethyl)-1H-pyrazolo[3,4-b]pyridine LDA, 2.0 M (15.63 mL, 31.3 mmol, Aldrich) was added to THF (35 ml) that was precooled to −78° C. under argon. The mixture was stirred for 5 min before 5-bromo-2-fluoropyridine (5.0 g, 28.4 mmol, Aldrich) was added dropwise. This mixture was stirred at −78° C. for 1.5 h and then ethyl 2,2,2-trifluoroacetate (5.65 g, 39.8 mmol, Aldrich) was added. The cooling bath was removed and the mixture was stirred for 1 h before 1N HCl and EtOAc were added. The layers were separated and the organic layer was dried with MgSO₄, filtered, and concentrated to give a red oil. The oil was dissolved in EtOH (100 mL) and hydrazine (1.78 mL, 56.8 mmol, Aldrich) was added. This mixture was stirred at reflux for 2 h, cooled to RT, and diluted with EtOAc. The mixture was then washed with water, brine, dried (MgSO₄), filtered, and concentrated in vacuo to give an oil that was precipitated with DCM. The solid was collected and the filtrate was concentrated and suspended in DCM again. The solid was collected and this time the filtrate was concentrated to give an oil which was purified by silica gel chromatography (0 to 50% EtOAc/hexane) affording 5-bromo-3-(trifluoromethyl)-1H-pyrazolo[3,4-b]pyridine (4.4 g, 59%). MS (ESI, pos. ion) m/z: =266.1 (M+1). A mixture of 5-bromo-3-(trifluoromethyl)-1H-pyrazolo[3,4-b]pyridine (158 mg, 0.59 mmol), bis(pinacolato)diboron (181 mg, 0.71 mmol), Pd(dppf)Cl₂ (48.5 mg, 0.06 mmol, Strem) and potassium acetate (233 mg, 2.38 mmol, Aldrich) was capped, degassed and backfilled with argon (3×). Dioxane (5 mL) was added, and the reaction was heated at 100° C. After 22 h, the reaction mixture was cooled to 23° C., and filtered through celite. The crude reaction mixture of 5-(4,4,5,5-tetramethyl-1,3,2-dioxaborolan-2-yl)-3-(trifluoromethyl)-1H-pyrazolo[3,4-b]pyridine was concentrated to dryness and taken forward to the next step.

Preparation of Compound 6: 1-(6-(5-(3-(trifluoromethyl)-1H-pyrazolo[3,4-b]pyridin-5-yl)-1H-indazol-3-yl)pyrazin-2-yl)piperidin-4-amine A suspension of tert-butyl 1-(6-(5-bromo-1-(tetrahydro-2H-pyran-2-yl)-1H-indazol-3-yl)pyrazin-2-yl)piperidin-4-ylcarbamate (compound 1e) (150 mg, 0.269 mmol), crude 5-(4,4,5,5-tetramethyl-1,3,2-dioxaborolan-2-yl)-3-(trifluoromethyl)-1H-pyrazolo[3,4-b]pyridine 6a (177 mg, 0.57 mmol), Pd(dppf)Cl₂ (22 mg, 0.03 mmol, Strem) and aqueous Na₂CO₃, 2.0 M (0.27 mL, 0.54 mmol) in dioxane (3 mL) was capped, degassed and backfilled with argon. The reaction was heated at 120° C. in a microwave for 45 min. The reaction mixture was diluted with EtOAc (75 mL) and washed with saturated NaHCO₃ solution (50 mL) and brine (75 mL), dried over MgSO4, concentrated in vacuo and purified by silica gel chromatography (eluent: 0.5-3.5% MeOH/DCM), affording tert-butyl 1-(6-(1-(tetrahydro-2H-pyran-2-yl)-5-(3-(trifluoromethyl)-1H-pyrazolo[3,4-b]pyridin-5-yl)-1H-indazol-3-yl)pyrazin-2-yl)piperidin-4-ylcarbamate (94 mg, 52% yield). MS (ESI, pos. ion) m/z: 664.3 (M+1). A solution of tert-butyl 1-(6-(1-(tetrahydro-2H-pyran-2-yl)-5-(3-(trifluoromethyl)-1H-pyrazolo[3,4-b]pyridin-5-yl)-1H-indazol-3-yl)pyrazin-2-yl)piperidin-4-ylcarbamate (87 mg, 0.13 mmol) in dioxane (3 mL) was treated with HCl, 36.5-38.0% (0.11 mL, 1.31 mmol). The reaction mixture was heated at 90° C. After 3 h, the reaction mixture was cooled to 23° C. and concentrated. The residue (as HCl salt) was free-based using a Silicycle Si-propylsulfonic acid ion exchange column (catalog # R51230B). The compound was diluted in MeOH and added to a pad of the resin (wetted and flushed with 10 mL MeOH). It was flushed with MeOH (50 mL), and then the product was "released" using 2.0 M NH₃ in MeOH solution (50 ml). The final filtrate was concentrated, affording 1-(6-(5-(3-(trifluo-

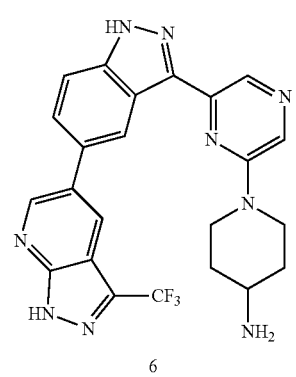

romethyl)-1H-pyrazolo[3,4-b]pyridin-5-yl)-1H-indazol-3-yl)pyrazin-2-yl)piperidin-4-amine. MS (ESI, pos. ion) m/z: 480.2 (M+1).

Example 7

1-(6-(5-(3-Fluorophenyl)-1H-indazol-3-yl)pyrazin-2-yl)piperidin-4-amine

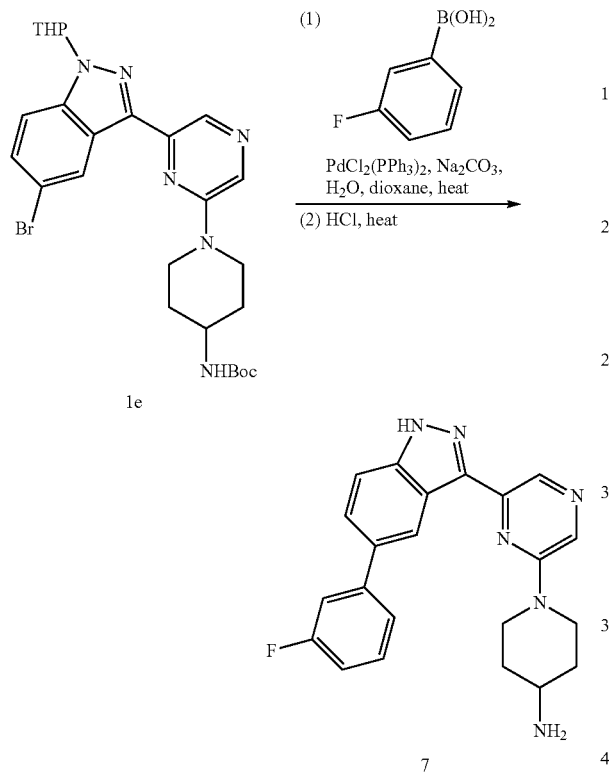

A glass microwave reaction vessel was charged with tert-butyl 1-(6-(5-bromo-1-(tetrahydro-2H-pyran-2-yl)-1H-indazol-3-yl)pyrazin-2-yl)piperidin-4-ylcarbamate (0.200 g, 0.359 mmol), 3-fluorophenylboronic acid (0.072 g, 0.515 mmol, Aldrich), $Na_2CO_3$ (0.210 g, 1.981 mmol, J. T. Baker) and trans-dichlorobis(triphenyl-phosphine)palladium (II) (0.022 g, 0.031 mmol, Strem). Dioxane (3 mL) and water (1 mL) were added and the reaction mixture was sealed under argon and heated in a Emrys Optmizer microwave reactor (Personal Chemistry, Biotage AB, Inc., Uppsala, Sweden) at 140° C. for 15 min. The mixture was partitioned between EtOAc/water. The aqueous layer was extracted with EtOAc (3×) and the combined organic layers were evaporated onto silica gel and purified by flash chromatography (Isco, (40 gram)) eluting with 2M $NH_3$ in MeOH:DCM (0:1→1:49) to give 119 mg of tert-Butyl 1-(6-(5-(3-fluorophenyl)-1-(tetrahydro-2H-pyran-2-yl)-1H-indazol-3-yl)pyrazin-2-yl)piperidin-4-ylcarbamate as a yellow amorphous solid. MS (ESI, pos. ion) m/z: 573.2 (M+1). A solution of tert-butyl 1-(6-(5-(3-fluorophenyl)-1-(tetrahydro-2H-pyran-2-yl)-1H-indazol-3-yl)pyrazin-2-yl)piperidin-4-ylcarbamate (0.119 g, 0.208 mmol) in HCl, 5-6 N in IPA (5.00 mL, 25.00 mmol) and water (0.5 mL) was heated at 80° C. for 2.5 h. The reaction mixture was cooled to RT and the solid was filtered and washed with IPA. The material was dissolved in DMSO and purified by reverse-phase HPLC (Gilson; Gemini-NX 10µ C18 110 A AXIA, 100×50 mm column) eluting with 0.1% TFA-$H_2O$: 0.1% TFA ACN (9:1→1:9). The fractions containing the desired product were combined and concentrated in vacuo. The residue was dissolved in MeOH and loaded onto an SCX II cartridge eluting with MeOH then 2M $NH_3$ in MeOH to give the title compound as a yellow crystalline solid. MS (ESI, pos. ion) m/z: 389.1 (M+1).

Example 8

1-(3-(6-(4-Aminopiperidin-1-yl)pyrazin-2-yl)-1H-indazol-5-yl)pyrrolidin-2-one

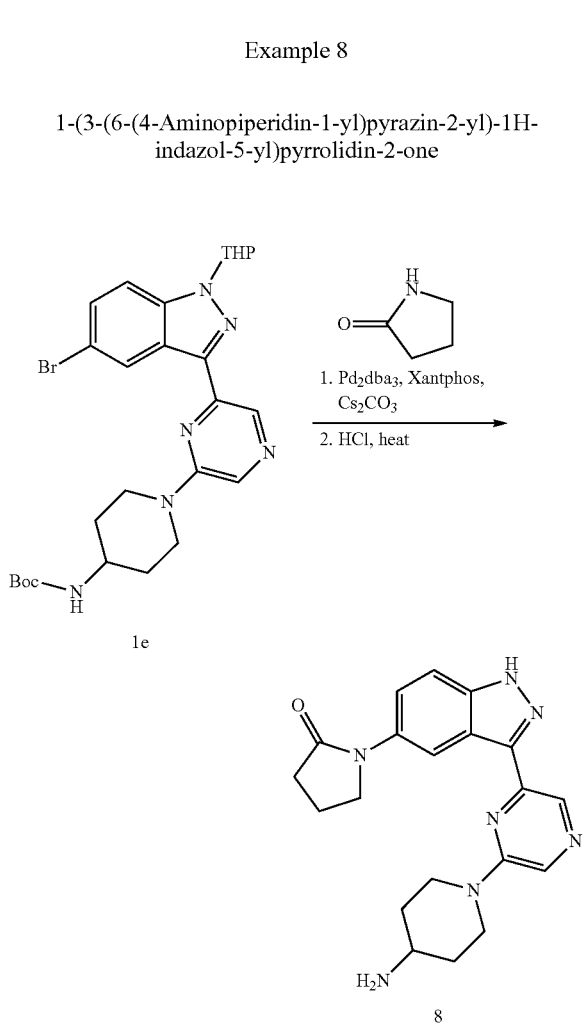

A glass microwave reaction vessel was charged with tert-butyl 1-(6-(5-bromo-1-(tetrahydro-2H-pyran-2-yl)-1H-indazol-3-yl)pyrazin-2-yl)piperidin-4-ylcarbamate (0.200 g, 0.359 mmol), cesium carbonate (0.044 mL, 0.546 mmol, Strem), tris(dibenzylideneacetone)dipalladium (0) (0.012 g, 0.013 mmol, Strem) and 9,9-dimethyl-4,5-bis(diphenylphosphino)xanthene (0.022 g, 0.038 mmol, Strem). The vessel was capped and evacuated/purged with argon (3×). Dioxane (2 mL) and 2-pyrrolidinone (0.050 mL, 0.658 mmol, Aldrich) were added and the reaction mixture was heated thermally at 110° C. for 54 h. The mixture was cooled to RT, treated with HCl, 5-6 N in IPA (10 mL, 50.0 mmol) and heated at 80° C. for 3 h. The mixture was treated with water, filtered and purified by reverse-phase HPLC (Gilson; Gemini-NX 10µ C18 110 A AXIA, 100×50 mm column) eluting with 0.1% TFA-$H_2O$:0.1% TFA ACN (9:1→1:9). The fractions containing the desired product were combined and concentrated in vacuo. The residue was dissolved in MeOH and loaded onto an SCX II cartridge eluting with MeOH then 2M NH₃ in MeOH to give a yellow crystalline solid. MS (ESI, pos. ion) m/z: 378.2 (M+1).

Example 9

1-(6-(5-(2,6-dimethoxypyrimidin-4-yl)-1H-indazol-3-yl)pyrazin-2-yl)piperidin-4-amine

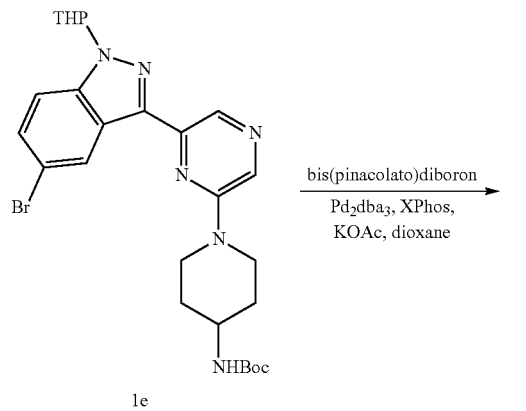

1e

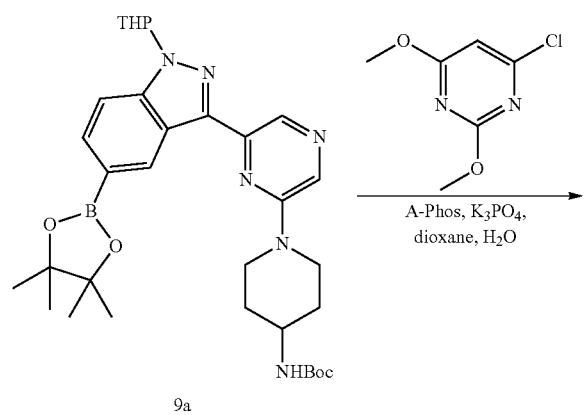

9a

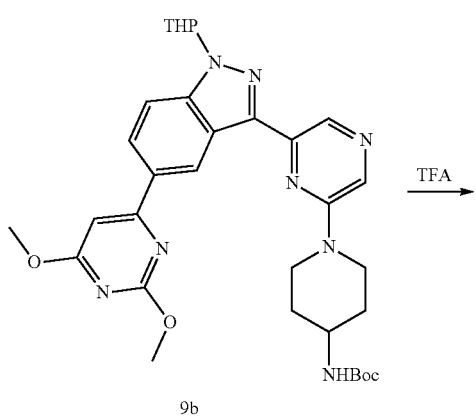

9b

-continued

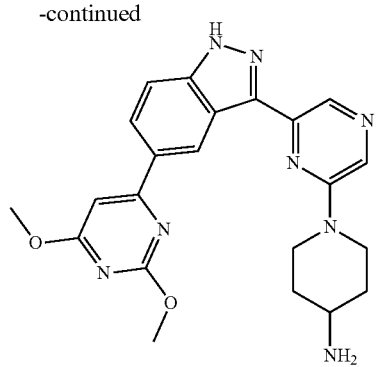

9

Preparation of Compound 9a: tert-butyl 1-(6-(1-(tetrahydro-2H-pyran-2-yl)-5-(4,4,5,5-tetramethyl-1,3,2-dioxaborolan-2-yl)-1H-indazol-3-yl)pyrazin-2-yl)piperidin-4-ylcarbamate A mixture of tert-butyl 1-(6-(5-bromo-1-(tetrahydro-2H-pyran-2-yl)-1H-indazol-3-yl)pyrazin-2-yl)piperidin-4-ylcarbamate 1e (115 g, 0.21 mol, 1 eq), bis(pinacolato)-diboron (78.6 g, 0.31 mol, 1.5 eq), Pd₂dba₃ (9.6 g, 0.011 mol, 0.05 eq), Xphos (12.2 g, 0.022 mol, 0.1 eq) and KOAc (61.8 g, 0.63 mol, 3 eq) in anhydrous 1,4-dioxane (1.5 L) was degassed with N₂ for 15 min and heated to 100° C. for 18 h. LC-MS analysis showed around 50% conversion. The reaction mixture was stirred at 100° C. for additional 14 h until 1e was consumed. The mixture was diluted with EtOAc (1 L) and water (1 L) and filtered through a Celite pad. After phase separation, the organic layer was washed with water and brine, dried over anhydrous MgSO₄, and concentrated under reduced pressure. The residue was dissolved in hot MTBE. While cooling to RT, a yellow solid was formed and removed by filtration. The mother liquor was purified by multiple flash column chromatography eluting with DCM/EtOAc (20/1) to give crude in 9a (50 g) containing an impurity (non-uv active), which was difficult to remove by chromatographic separation. Further purification of this material afforded 9a (27.5 g, ~90% purity) as a yellow solid in 22% yield. MS (ESI, pos. ion) m/z: 605.4 (M+1).

Preparation of Compound 9b: tert-butyl 1-(6-(5-(2,6-dimethoxypyrimidin-4-yl)-1-(tetrahydro-2H-pyran-2-yl)-1H-indazol-3-yl)pyrazin-2-yl)piperidin-4-ylcarbamate A glass microwave reaction vessel was charged with tert-butyl 1-(6-(1-(tetrahydro-2H-pyran-2-yl)-5-(4,4,5,5-tetramethyl-1,3,2-dioxaborolan-2-yl)-1H-indazol-3-yl)pyrazin-2-yl)piperidin-4-ylcarbamate (166 mg, 0.28 mmol), 4-chloro-2,6-dimethoxypyrimidine (40 mg, 0.23 mmol, ASDI) in p-dioxane/H₂O (4:1, 2 mL), potassium phosphate (47.4 µL, 0.57 mmol) and A-Phos (8.11 mg, 0.01 mmol). The reaction mixture was stirred and heated in a Initiator microwave reactor (Personal Chemistry, Biotage AB, Inc., Uppsala, Sweden) at 105° C. for 30 min, then the mixture was diluted with DCM and washed with water. The organic layer was dried, filtered and concentrated to give the crude product 9b. MS (ESI, pos. ion) m/z: 617 (M+1);

Preparation of Compound 9: 1-(6-(5-(2,6-dimethoxypyrimidin-4-yl)-1H-indazol-3-yl)pyrazin-2-yl)piperidin-4-amine A glass microwave reaction vessel was charged with tert-butyl 1-(6-(5-(2,6-dimethoxypyrimidin-4-yl)-1-(tetrahydro- 2H-pyran-2-yl)-1H-indazol-3-yl)pyrazin-2-yl)piperidin-4-ylcarbamate (141 mg, 0.229 mmol) in DCM (1 mL) and TFA (0.5 mL). The reaction mixture was stirred and heated in an Initiator microwave reactor (Personal Chemistry, Biotage AB, Inc., Uppsala, Sweden) at 85° C. for 20 min. The solvent was then removed and the residue was purified with RP-HPLC to give 1-(6-(5-(2,6-dimethoxypyrimidin-4-yl)-1H-indazol-3-yl)pyrazin-2-yl)piperidin-4-amine as a solid. MS (ESI, pos. ion) m/z: 433 (M+1).

Example 10

5-(5-methoxy-3-pyridinyl)-3-(6-((3R)-3-piperidinyloxy)-2-pyrazinyl)-1H-indazole

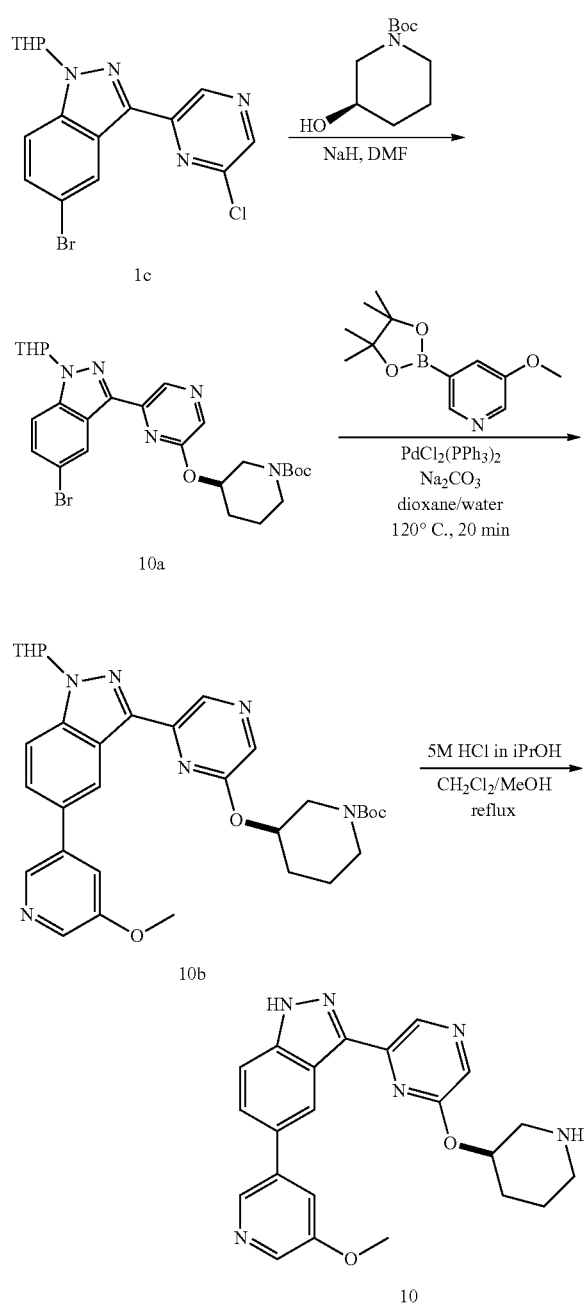

Preparation of Compound 10a: Tert-butyl (3R)-3-((6-(5-bromo-1-(tetrahydro-2H-pyran-2-yl)-1H-indazol-3-yl)-2-pyrazinyl)oxy)-1-piperidinecarboxylate NaH (60% in mineral oil, 0.081 g, 2.032 mmol) was added to a solution of (R)-tert-butyl 3-hydroxypiperidine-1-carboxylate (0.245 g, 1.219 mmol, Astatech, Inc.) in DMF (2.50 mL) at 0° C. The mixture was stirred for 15 min then 5-bromo-3-(6-chloropyrazin-2-yl)-1-(tetrahydro-2H-pyran-2-yl)-1H-indazole 1c (0.400 g, 1.016 mmol, Pharmacore) was added and the heterogenous mixture was warmed to RT. After 60 min at RT, ice was added and the mixture was extracted with EtOAc (3×). The combined organic layers were dried over anhydrous $Na_2SO_4$, filtered and concentrated. The crude material was absorbed onto a plug of silica gel and purified by chromatography through a Redi-Sep pre-packed silica gel column (12 g), eluting with a gradient of 0% to 50% EtOAc in hexane, to provide tert-butyl (3R)-3-((6-(5-bromo-1-(tetrahydro-2H-pyran-2-yl)-1H-indazol-3-yl)-2-pyrazinyl)oxy)-1-piperidinecarboxylate (0.562 g, 1.006 mmol, 99% yield) as a light-yellow foam. MS (ESI, pos. ion) m/z: 558.0, 560.0 (M+1).

Preparation of Compound 10b: Tert-butyl (3R)-3-((6-(5-(5-methoxy-3-pyridinyl)-1-(tetrahydro-2H-pyran-2-yl)-1H-indazol-3-yl)-2-pyrazinyl)oxy)-1-piperidinecarboxylate A glass microwave reaction vessel was charged with tert-butyl (3R)-3-((6-(5-bromo-1-(tetrahydro-2H-pyran-2-yl)-1H-indazol-3-yl)-2-pyrazinyl)oxy)-1-piperidinecarboxylate (0.100 g, 0.179 mmol), 5-methoxy-3-pyridineboronic acid pinacol ester (0.084 g, 0.358 mmol, Sigma-Aldrich), trans-dichlorobis(triphenyl-phosphine)palladium (II) (10.05 mg, 0.014 mmol) and $Na_2CO_3$ (0.095 g, 0.895 mmol) in dioxane (0.7 mL) and Water (0.175 mL). The reaction mixture was stirred and heated in an Initiator microwave reactor (Personal Chemistry, Biotage AB, Inc., Uppsala, Sweden) at 120° C. for 20 min. The layers were separated and the organic layer was dried over anhydrous $Na_2SO_4$, filtered and concentrated. The crude material was absorbed onto a plug of silica gel and purified by chromatography through a Redi-Sep pre-packed silica gel column (12 g), eluting with a gradient of 0% to 100% EtOAc in hexane, to provide tert-butyl (3R)-3-((6-(5-(5-methoxy-3-pyridinyl)-1-(tetrahydro-2H-pyran-2-yl)-1H-indazol-3-yl)-2-pyrazinyl)oxy)-1-piperidinecarboxylate (0.062 g, 0.106 mmol, 59.0% yield) as a brown oil. MS (ESI, pos. ion) m/z: 587.2 (M+1).

Preparation of Compound 10: 5-(5-Methoxy-3-pyridinyl)-3-(6-((3R)-3-piperidinyloxy)-2-pyrazinyl)-1H-indazole A mixture of tert-butyl (3R)-3-((6-(5-(5-methoxy-3-pyridinyl)-1-(tetrahydro-2H-pyran-2-yl)-1H-indazol-3-yl)-2-pyrazinyl)oxy)-1-piperidinecarboxylate (0.062 g, 0.106 mmol) and HCl (5 M in i-PrOH, 2.114 mL, 10.57 mmol, Acros) in 1 ml of MeOH and 1 mL of DCM was heated at reflux for 30 min. The crude reaction was cooled to RT and concentrated to a yellowish-green solid that was slurried with a 1/1 mixture of DCM/MeOH (2 mL) and applied to a pre-washed (5 mL MeOH) of Si-propylsulfonic acid (Silicycle, Cat# R51230B). The column was washed with MeOH (10 mL). The compound was released with 15 mL of 2 M $NH_3$ in MeOH to afford 5-(5-methoxy-3-pyridinyl)-3-(6-((3R)-3-piperidinyloxy)-2-pyrazinyl)-1H-indazole as an off-white foam. MS (ESI, pos. ion) m/z: 403.1 (M+1).

Example 11

(R)-5-(5-chloro-2-fluoropyridin-3-yl)-3-(6-(piperidin-3-yloxy)pyrazin-2-yl)-1H-indazole

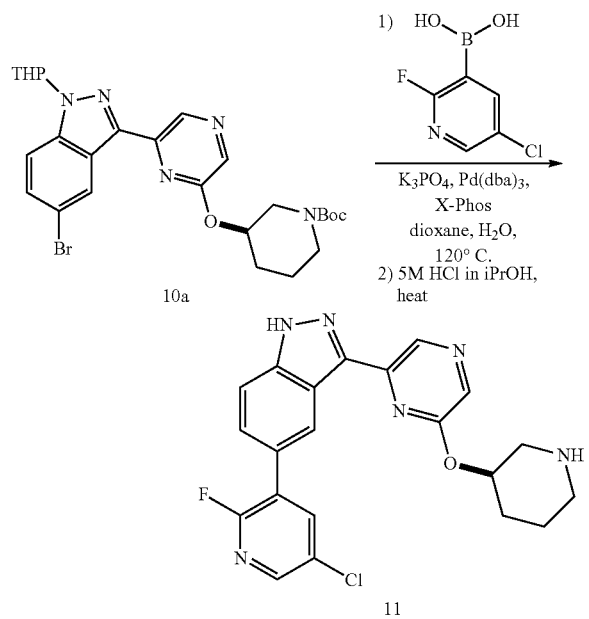

(3R)-tert-butyl 3-(6-(5-bromo-1-(tetrahydro-2H-pyran-2-yl)-1H-indazol-3-yl)pyrazin-2-yloxy)piperidine-1-carboxylate 10a (270 mg, 0.48 mmol), 5-chloro-2-fluoropyridin-3-ylboronic acid (97 mg, 0.56 mmol) (Combi-Blocks, Catalog# BB-3818), potassium phosphate tribasic (308 mg, 1.45 mmol) (Sigma-Aldrich, Catalog# P5629-25G, Lot#069K0110), dicyclohexyl(2',4',6'-triisopropylbiphenyl-2-yl)phosphine (13.8 mg, 0.03 mmol) (Strem, Catalog#15-1149, Batch# A0183078), and Pd$_2$(dba)$_3$ (13.3 mg, 0.02 mmol) (Strem, Catalog#46-3000, Lot# A8761089) were weighed into a 10 mL glass microwave vial. The vial was purged with argon, the solids were treated with dioxane (4 mL) and water (1 mL) and the vial was sealed. The contents were heated in Initiator microwave reactor (Personal Chemistry, Biotage AB, Inc., Uppsala, Sweden) at 115° C. for 30 min. The reaction mixture was treated with 2 mL of water and extracted with EtOAc (2×10 mL). The combined organic layers were dried over MgSO$_4$, filtered and concentrated, affording (3R)-tert-butyl 3-(6-(5-(5-chloro-2-fluoropyridin-3-yl)-1-(tetrahydro-2H-pyran-2-yl)-1H-indazol-3-yl)pyrazin-2-yloxy)piperidine-1-carboxylate as a light yellow solid. MS (ESI, pos. ion) m/z: 609.2 (M+1). The material was used without purification. To a solution of (3R)-tert-butyl 3-(6-(5-(5-chloro-2-fluoropyridin-3-yl)-1-(tetrahydro-2H-pyran-2-yl)-1H-indazol-3-yl)pyrazin-2-yloxy)piperidine-1-carboxylate (292 mg, 0.48 mmol) in THF (2.2 mL) and EtOH (2.2 mL) was added HCl, 5-6N in IPA (0.8 mL, 26.40 mmol). The solution was heated in an oil bath at 65° C. for 1 h. The crude reaction was concentrated to a yellow solid that was dissolved in 5 mL of DMSO and purified on a reverse phase HPLC, using a gradient of 10-90% [0.1% TFA in ACN] in [0.1% TFA in water]. The desired fractions were collected, concentrated, and basified with 1 N NaOH, extracted with EtOAc. The EtOAc solution was washed with brine, dried with Na$_2$SO$_4$ and concentrated to afford (R)-5-(5-chloro-2-fluoropyridin-3-yl)-3-(6-(piperidin-3-yloxy)pyrazin-2-yl)-1H-indazole as an off white crystalline solid. MS (ESI, pos. ion) m/z: 425.1 (M+1).

Example 12

5-(6-(1-methylethoxy)-2-pyrazinyl)-3-(6-((3R)-3-piperidinyloxy)-2-pyrazinyl)-1H-indazole

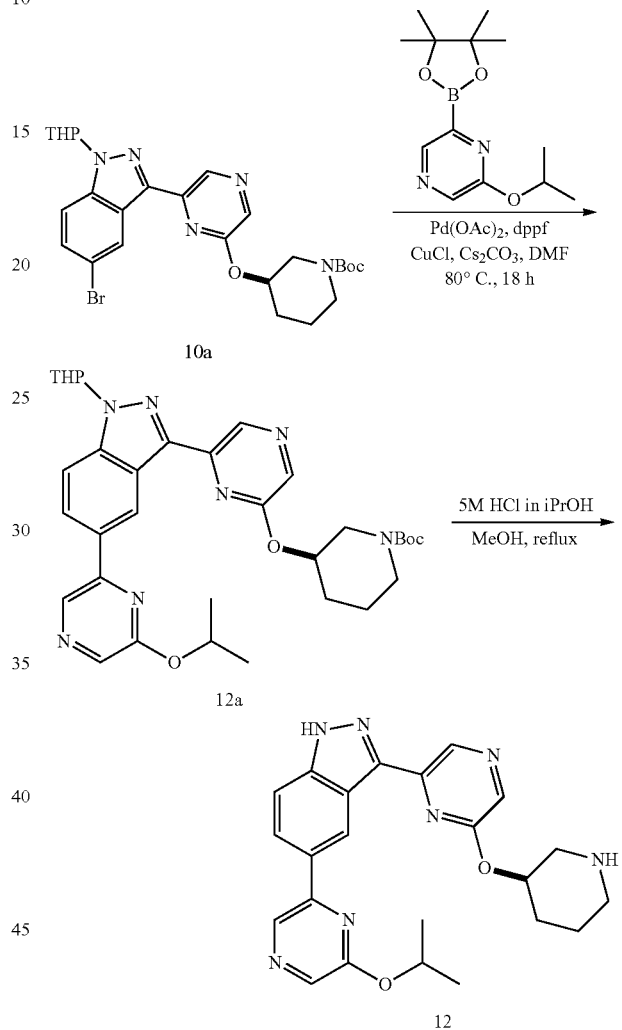

Preparation of Compound 12a: Tert-butyl (3R)-3-((6-(5-(6-(1-methylethoxy)-2-pyrazinyl)-1-(tetrahydro-2H-pyran-2-yl)-1H-indazol-3-yl)-2-pyrazinyl)oxy)-1-piperidinecarboxylate To a 50 mL round bottom flask was added CuCl (0.035 g, 0.36 mmol), Cs$_2$CO$_3$ (0.467 g, 1.43 mmol), 1,1'-bis(diphenylphosphino)ferrocene (0.020 g, 0.04 mmol), tert-butyl (3R)-3-((6-(5-bromo-1-(tetrahydro-2H-pyran-2-yl)-1H-indazol-3-yl)-2-pyrazinyl)oxy)-1-piperidinecarboxylate 10a (0.200 g, 0.36 mmol), Pd(OAc)$_2$ (4.02 mg, 0.02 mmol), and 2-isopropoxy-6-(4,4,5,5-tetramethyl-1,3,2-dioxaborolan-2-yl)pyrazine (0.189 g, 0.72 mmol, CombiPhos Catalysis). The flask was sealed and evacuated under vacuum and backfilled with N$_2$. DMF (2.7 mL) was added, and the reaction mixture was stirred at 80° C. for 18 h. The reaction was filtered through a 0.45 M filter and then diluted in water and extracted with EtOAc (3×). The combined organic layers were dried over anhydrous Na$_2$SO$_4$, filtered and concentrated. The crude material was absorbed onto a plug of silica gel and purified by chromatography through a Redi-Sep pre-packed silica gel column (12 g), eluting with a gradient of 0% to 50% EtOAc in hexane, to provide tert-butyl (3R)-3-((6-(5-(6-(1-methylethoxy)-2-pyrazinyl)-1-(tetrahydro-2H-pyran-2-yl)-1H-indazol-3-yl)-2-pyrazinyl)oxy)-1-piperidinecarboxylate (0.130 g, 0.21 mmol, 59% yield) as a light-yellow oil. MS (ESI, pos. ion) m/z: 616.2 (M+1).

Preparation of Compound 12: 5-(6-(1-Methylethoxy)-2-pyrazinyl)-3-(6-((3R)-3-piperidinyloxy)-2-pyrazinyl)-1H-indazole To a solution of tert-butyl (3R)-3-((6-(5-(6-(1-methylethoxy)-2-pyrazinyl)-1-(tetrahydro-2H-pyran-2-yl)-1H-indazol-3-yl)-2-pyrazinyl)oxy)-1-piperidinecarboxylate (0.130 g, 0.21 mmol) in MeOH (2.0 mL) was added HCl (5 M in IPA, 4.2 mL, 21.11 mmol, Acros). The mixture was heated at 80° C. for 30 min. The crude reaction was cooled to RT and concentrated to a yellow solid that was slurried with a 1/1 mixture of DCM/MeOH (2 mL) and applied to a pre-washed (5 mL MeOH) of Si-propylsulfonic acid (Silicycle, Cat# R51230B). The column was washed with MeOH (10 mL). The compound was released with 15 mL of 2 M NH$_3$ in MeOH to afford 5-(6-(1-methylethoxy)-2-pyrazinyl)-3-(6-((3R)-3-piperidinyloxy)-2-pyrazinyl)-1H-indazole as a pink solid. MS (ESI, pos. ion) m/z: 432.2 (M+1).

Example 13

5-(6-cyclopropyl-2-pyrazinyl)-3-(6-((3R)-3-piperidinyloxy)-2-pyrazinyl)-1H-indazole

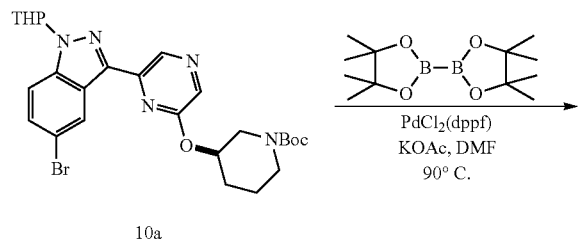

10a

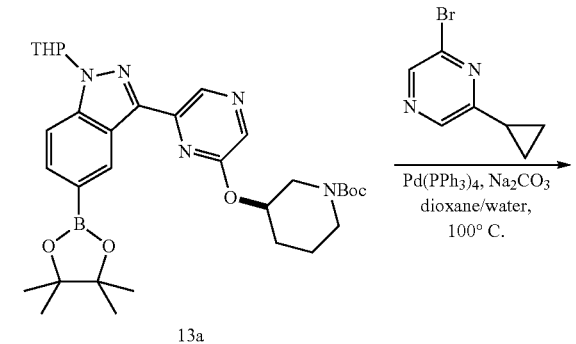

13a

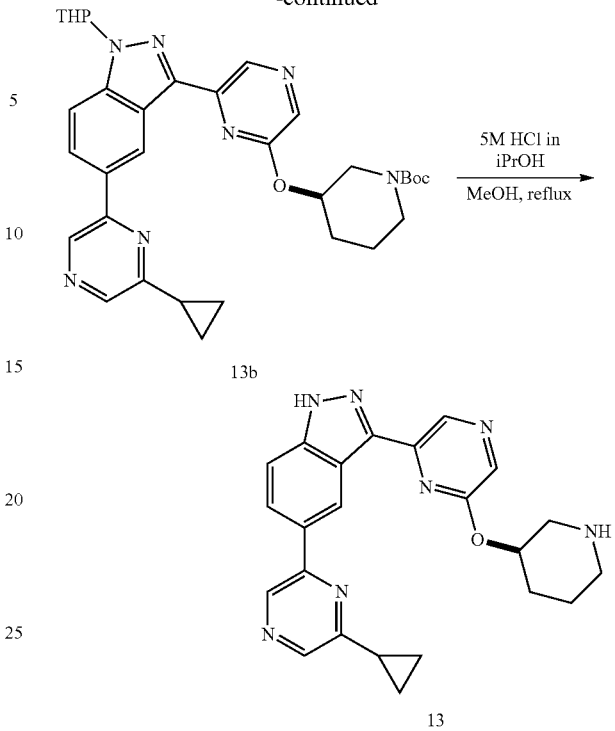

13b

13

Preparation of Compound 13a: Tert-butyl (3R)-3-((6-(1-(tetrahydro-2H-pyran-2-yl)-5-(4,4,5,5-tetramethyl-1,3,2-dioxaborolan-2-yl)-1H-indazol-3-yl)-2-pyrazinyl)oxy)-1-piperidinecarboxylate A mixture of (3R)-tert-butyl 3-(6-(5-bromo-1-(tetrahydro-2H-pyran-2-yl)-1H-indazol-3-yl)pyrazin-2-yloxy)piperidine-1-carboxylate 10a (7.14 g, 12.78 mmol), bis(pinacolato)diboron (4.87 g, 19.18 mmol), 1,1'-bis(diphenylphosphino)ferrocene-palladium dichloride (1.044 g, 1.28 mmol) and potassium acetate (6.27 g, 63.90 mmol) in DMF (40 mL) was stirred at 90° C. for 16 h. The reaction mixture was cooled to RT and concentrated. The thick oil was taken up in EtOAc and water and filtered through Celite. The layers were separated and the aqueous layer was extracted with EtOAc (2×). The combined organic layers were dried over anhydrous Na$_2$SO$_4$, filtered and concentrated. The crude material was absorbed onto a plug of silica gel and purified by chromatography through a Redi-Sep pre-packed silica gel column (330 g), eluting with a gradient of 0% to 50% EtOAc in hexane, to provide (3R)-tert-butyl 3-(6-(1-(tetrahydro-2H-pyran-2-yl)-5-(4,4,5,5-tetramethyl-1,3,2-dioxaborolan-2-yl)-1H-indazol-3-yl)pyrazin-2-yloxy)piperidine-1-carboxylate (5.97 g, 9.86 mmol, 77% yield) as a light yellow solid. MS (ESI, pos. ion) m/z: 606.2 (M+1).

Preparation of Compound 13b: Tert-butyl (3R)-3-((6-(5-(6-cyclopropyl-2-pyrazinyl)-1-(tetrahydro-2H-pyran-2-yl)-1H-indazol-3-yl)-2-pyrazinyl)oxy)-1-piperidinecarboxylate A glass microwave reaction vessel was charged with (3R)-tert-butyl 3-(6-(1-(tetrahydro-2H-pyran-2-yl)-5-(4,4,5,5-tetramethyl-1,3,2-dioxaborolan-2-yl)-1H-indazol-3-yl)pyrazin-2-yloxy)piperidine-1-carboxylate (1.315 g, 2.17 mmol) and Pd(PPh$_3$)$_4$ (0.125 g, 0.11 mmol). The tube was sealed and evacuated under vacuum and back-filled with N₂ (g). A solution of 2-bromo-6-cyclopropylpyrazine (0.562 g, 2.82 mmol) in dioxane (1.8 mL) and 2 M Na₂CO₃ (5.43 mL, 10.86 mmol) were added. The reaction mixture was stirred and heated at 100° C. for 2 h. After cooling to RT, the organic layer was separated and dried over anhydrous Na₂SO₄, filtered and concentrated. The crude material was absorbed onto a plug of silica gel and purified by chromatography through a Redi-Sep pre-packed silica gel column (80 g), eluting with a gradient of 0% to 40% EtOAc in hexanes, to provide (3R)-tert-butyl 3-(6-(5-(6-cyclopropylpyrazin-2-yl)-1-(tetrahydro-2H-pyran-2-yl)-1H-indazol-3-yl)pyrazin-2-yloxy)piperidine-1-carboxylate (0.910 g, 1.52 mmol, 70% yield) as a yellow foam. MS (ESI, pos. ion) m/z: 598.2 (M+1).

Preparation of Compound 13: 5-(6-Cyclopropyl-2-pyrazinyl)-3-(6-((3R)-3-piperidinyloxy)-2-pyrazinyl)-1H-indazole A solution of (3R)-tert-butyl 3-(6-(5-(6-cyclopropylpyrazin-2-yl)-1-(tetrahydro-2H-pyran-2-yl)-1H-indazol-3-yl)pyrazin-2-yloxy)piperidine-1-carboxylate (0.910 g, 1.522 mmol) in and HCl, 5-6N in IPA (30.4 mL, 152 mmol) in 15 mL of MeOH was heated at 80° C. for 3 h. The crude reaction was cooled to RT and concentrated to a yellow solid that was slurried with a 1/1 mixture of DCM/MeOH (12 mL) and applied to a pre-washed (45 mL MeOH) of Si-propylsulfonic acid (12 g, Silicycle, Cat# R51230B). The column was washed with MeOH (35 mL). The compound was released with 35 mL of 2 M NH₃ in MeOH to afford 450 mg of material that was 94% pure. The above material was suspended in EtOAC, filtered and washed with EtOAC to afford pure (R)-5-(6-cyclopropylpyrazin-2-yl)-3-(6-(piperidin-3-yloxy)pyrazin-2-yl)-1H-indazole as a pale yellow solid. MS (ESI, pos. ion) m/z: 414.1 (M+1).

Example 14

5-(2,6-difluorophenyl)-3-iodo-1-(tetrahydro-2H-pyran-2-yl)-1H-indazole

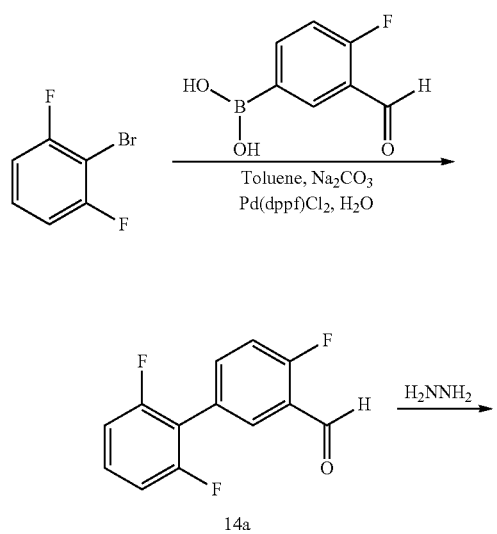

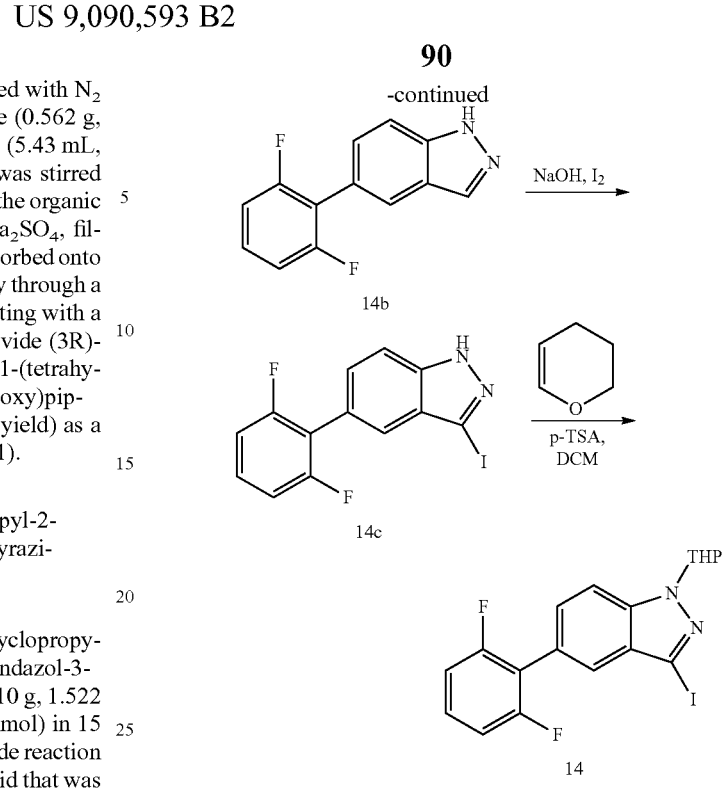

Preparation of Compound 14a: 2',4,6'-trifluorobiphenyl-3-carbaldehyde

To a solution of 2-bromo-1,3-difluorobenzene (100 g, 477.46 mmol) and 4-fluoro-3-formylphenylboronic acid (96.2 g, 572.95 mmol) in toluene (1432 mL) at RT was added Na₂CO₃ (2M in H₂O) (477.46 mL, 954.2 mmol) and PdCl₂(dppf) (7.798 g, 9.54 mmol). The reaction mixture was stirred at 100° C. for 8 h and cooled to RT. Water was added to the reaction mixture and extracted with EtOAc (2×500 mL). Organic layer was washed with brine and dried over Na₂SO₄. The organic layer was concentrated and purified by column using silica (100-200 mesh) and 0-5% EtOAc-hexane to provide 2',4,6'-trifluorobiphenyl-3-carbaldehyde (54.3 g, 49.4% yield).

Preparation of Compound 14b: 5-(2,6-difluorophenyl)-1H-indazole

2',4,6'-trifluorobiphenyl-3-carbaldehyde (160 g, 695.01 mmol) was taken in hydrazine hydrate (800 mL) and heated to 120° C. for 8 h. The reaction mixture was cooled to RT. Water was added to the reaction mixture and extracted with EtOAc (2×500 mL). Organic layer was washed with brine and dried over Na₂SO₄. The organic layer was concentrated and purified by column using silica (100-200 mesh) and 0-15% EtOAc-hexane to provide 5-(2,6-difluoro-phenyl)-1H-indazole (40.8 g, 25.4% yield). MS (ESI, pos. ion) m/z: 231.1 (M+1).

Preparation of Compound 14c: 5-(2,6-difluoro-phenyl)-3-iodo-1H-indazole

To a solution of 5-(2,6-difluoro-phenyl)-1H-indazole (40.8 g, 176.46 mmol) in DMF (441.1 mL) was added KOH (14.8 g, 246.69 mmol) and I₂ (98.5 g, 388.21 mmol) at RT. The reaction mixture was stirred for 6 h at RT. Water was added to the reaction mass and extracted with EtOAc (2×500 mL).

Organic layer was washed with brine and dried over Na₂SO₄. The organic layer was concentrated and purified by column using silica (100-200 mesh) and 0-15 EtOAc-hexane to provide 5-(2,6-difluoro-phenyl)-3-iodo-1H-indazole (45.5 g, 72.4% yield). MS (ESI, pos. ion) m/z: 357.1 (M+1).

Preparation of Compound 14: 5-(2,6-Difluoro-phenyl)-3-iodo-1-(tetrahydro-pyran-2-yl)-1H-indazole To a solution of 5-(2,6-difluoro-phenyl)-3-iodo-1H-indazole (45.5 g, 127.76 mmol) and TSA (4.86 g, 25.55 mmol) in THF (383.2 mL) was added 3,4-dihydro-2H-pyran (23.8 mL, 255.53 mmol) at RT. The mixture was stirred at 70° C. for 8 h. The reaction mixture was cooled to RT. Water was added to the reaction mixture and extracted with EtOAc (2×500 mL). The organic layer was washed with brine and dried over Na₂SO₄. The organic layer was concentrated under reduced pressure. The crude product was purified by column using (100-200 mesh) silica with 0-5% EtOAc in hexane to provide 5-(2,6-difluoro-phenyl)-3-iodo-1-(tetrahydro-pyran-2-yl)-1H-indazole (42.95 g, 78.2% yield). MS (ESI, pos. ion) m/z: 441.1 (M+1).

Example 15

1-(6-(5-(2,6-difluorophenyl)-1H-indazol-3-yl)pyrazin-2-yl)piperidin-4-amine

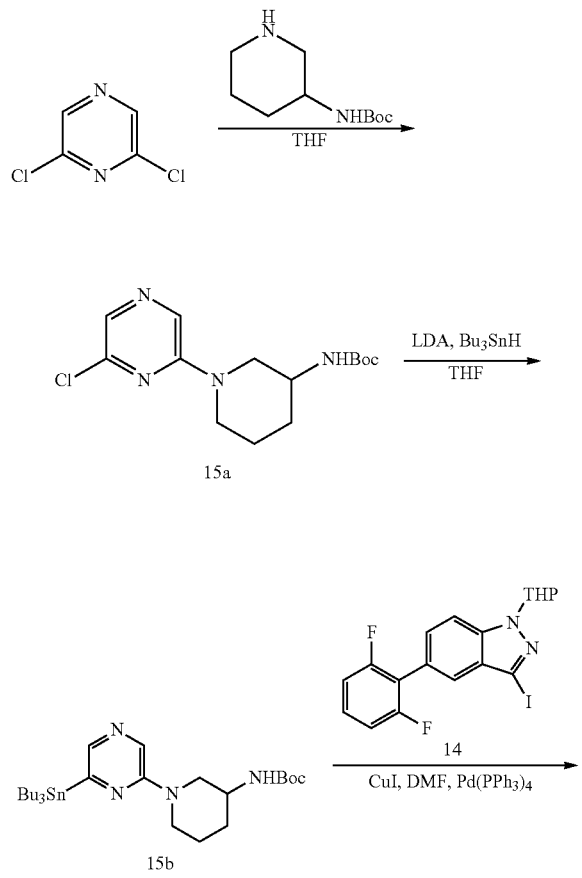

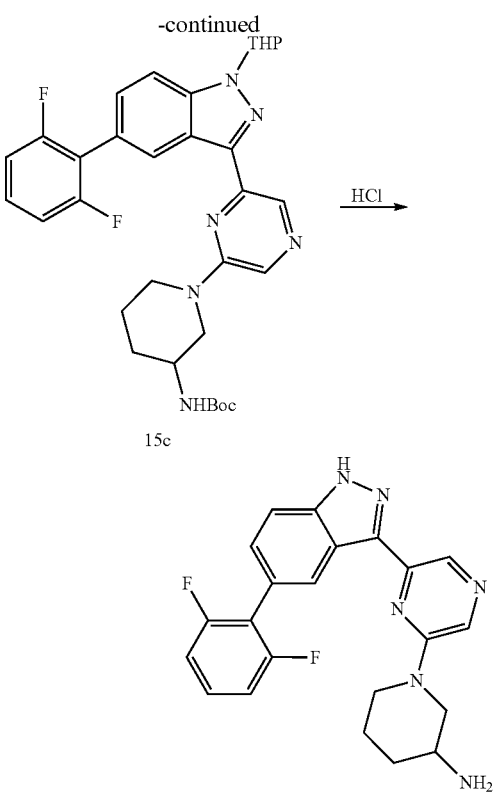

Preparation of Compound 15a: tert-butyl 1-(6-chloropyrazin-2-yl)piperidin-3-ylcarbamate A mixture of 2,6-dichloropyrazine (1.00 g, 6.71 mmol), tert-butyl 1-(6-chloropyrazin-2-yl)piperidin-3-ylcarbamate (1.747 g, 5.59 mmol), and potassium carbonate (0.405 mL, 6.71 mmol) in DMF (3.5 mL) was stirred at RT for 4 h. To the reaction mixture was added ice and white precipitate was formed. The precipitate was collected by filtration, washed with water and dried overnight to give tert-butyl 1-(6-chloropyrazin-2-yl)piperidin-3-ylcarbamate (1.75 g, 83%) as a white solid. MS (ESI, pos. ion) m/z: 313 (M+1).

Preparation of Compound 15b: tert-butyl 1-(6-(tributylstannyl)pyrazin-2-yl)piperidin-3-ylcarbamate To a solution of tri-n-butyltin hydride (1.686 mL, 6.39 mmol) in THF (10 mL) at 0° C. was added LDA (1.8 M solution in heptane/THF/ethylbenzene, 3.55 mL, 6.39 mmol) dropwise. The reaction mixture was stirred at 0° C. for 15 min and tert-butyl 1-(6-chloropyrazin-2-yl)piperidin-3-ylcarbamate (1.00 g, 3.20 mmol) was added. The reaction mixture was kept at 0° C. for 2 h, then quenched with 10% KF solution. The mixture was extracted with DCM and the combined organic layers were dried, filtered and concentrated. The residue was purified with silica gel chromatography (eluting with 10-25% EtOAc in Hexanes) to give tert-butyl 1-(6-(tributylstannyl)pyrazin-2-yl)piperidin-3-ylcarbamate (400 mg, 22.1% yield). MS (ESI, pos. ion) m/z: 569 (M+1).

Preparation of Compound 15c: tert-butyl 1-(6-(5-(2,6-difluorophenyl)-1-(tetrahydro-2H-pyran-2-yl)-1H-indazol-3-yl)pyrazin-2-yl)piperidin-3-ylcarbamate A solution of 5-(2,6-difluorophenyl)-3-iodo-1-(tetrahydro-2H-pyran-2-yl)-1H-indazole (400 mg, 0.91 mmol) and tert-butyl 1-(6-(tributylstannyl)pyrazin-2-yl)piperidin-3-yl-carbamate (520 mg, 0.91 mmol) in DMF (9.1 mL) was purged with N$_2$ for 15 min and added CuI (225 mg, 1.18 mmol) and Pd(PPh$_3$)$_4$ (105 mg, 0.09 mmol). The reaction mixture was heated at 80° C. for 2 h and cooled to RT. To the reaction mixture was added water and precipitate was formed. The precipitate was collected by filtration, washed with water and dried overnight to give crude product. The crude was purified by chromatography (eluting with 0-10% MeOH and DCM) to obtain the title compound (350 mg, 66% yield). MS (ESI, pos. ion) m/z: 591 (M+1).

Preparation of Compound 15: 1-(6-(5-(2,6-difluorophenyl)-1H-indazol-3-yl)pyrazin-2-yl)piperidin-3-amine To a solution of tert-butyl 1-(6-(5-(2,6-difluorophenyl)-1-(tetrahydro-2H-pyran-2-yl)-1H-indazol-3-yl)pyrazin-2-yl)piperidin-3-ylcarbamate (350 mg, 0.592 mmol) in Et$_2$O (6 mL) was added HCl in Et$_2$O (6 mL). The reaction mixture was heated at 80° C. overnight and cooled to RT. The resulting mixture was diluted with water and neutralized with K$_2$CO$_3$. The resulting precipitate was collected by filtration, washed with water and a mixture of EtOH/EtOA (1:10), and dried overnight to give 1-(6-(5-(2,6-difluorophenyl)-1H-indazol-3-yl)pyrazin-2-yl)piperidin-3-amine MS (ESI, pos. ion) m/z: 407 (M+1).

Example 16

(R)-6-(5-(2,6-difluorophenyl)-1H-indazol-3-yl)-N-(pyrrolidin-3-yl)pyrazin-2-amine

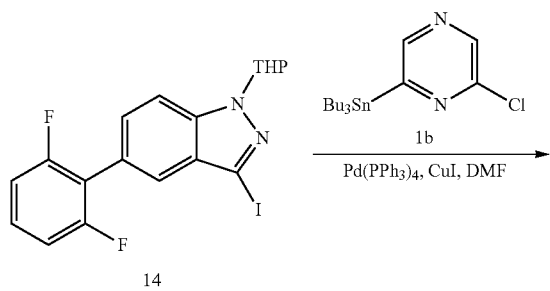

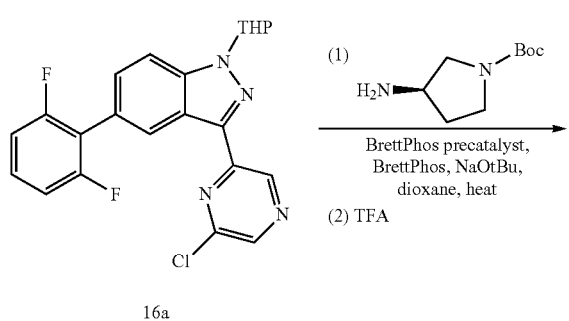

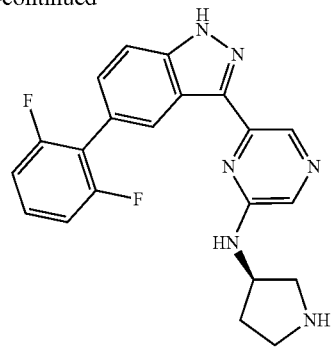

16

Preparation of Compound 16a: 3-(6-chloropyrazin-2-yl)-5-(2,6-difluorophenyl)-1-(tetrahydro-2H-pyran-2-yl)-1H-indazole A glass microwave reaction vessel was charged with 5-(2,6-difluorophenyl)-3-iodo-1-(tetrahydro-2H-pyran-2-yl)-1H-indazole 14 (1.00 g, 2.272 mmol) and 2-chloro-6-(tributylstannyl)pyrazine 1b (1.375 g, 3.41 mmol) in DMF (9 mL) followed by Pd(PPh$_3$)$_4$ (0.131 g, 0.114 mmol) and CuI (7.70 μL, 0.227 mmol). The reaction mixture was stirred and heated in an Initiator microwave reactor (Personal Chemistry, Biotage AB, Inc., Uppsala, Sweden) at 105° C. for 1 h. The resulting mixture was diluted with DCM. The organic layer was separated, washed with water, dried, filtered and concentrated. The residue was purified by silica gel chromatography (eluting with 0-15% EtOAc in Hexanes) to give 3-(6-chloropyrazin-2-yl)-5-(2,6-difluorophenyl)-1-(tetrahydro-2H-pyran-2-yl)-1H-indazole (0.95 g, 2.22 mmol, 98% yield) as a yellow solid. MS (ESI, pos. ion) m/z: 427.0 (M+1).

Preparation of Compound 16: (R)-6-(5-(2,6-difluorophenyl)-1H-indazol-3-yl)-N-(pyrrolidin-3-yl)pyrazin-2-amine A glass microwave reaction vessel was charged with 3-(6-chloropyrazin-2-yl)-5-(2,6-difluorophenyl)-1-(tetrahydro-2H-pyran-2-yl)-1H-indazole (250 mg, 0.586 mmol) and (R)-(+)-1-boc-3-aminopyrrolidine (149 μL, 0.879 mmol, CNH technologies) in p-dioxane (2.5 mL) followed by chloro[2-(dicyclohexylphosphino)-3,6-dimethoxy-2'-4'-6'-tri-1-propyl-1,1'-biphenyl][2-(2-aminoethyl)phenyl]palladium(II) (BrettPhos precatalyst) (23.39 mg, 0.029 mmol), sodium tert-butoxide (143 μL, 1.171 mmol) and BrettPhos precatalyst (15.72 mg, 0.029 mmol). The reaction mixture was stirred and heated in an oil bath at 85° C. for 2 h, and then solvent was removed. The residue was purified by silica gel chromatography (eluting with 5-30% EtOAc in DCM with 1% MeOH) to give (3R)-tert-butyl 3-(6-(5-(2,6-difluorophenyl)-1-(tetrahydro-2H-pyran-2-yl)-1H-indazol-3-yl)pyrazin-2-ylamino)pyrrolidine-1-carboxylate (280 mg, 83% yield). MS (ESI, pos. ion) m/z: 577 (M+1).

To a solution of (3R)-tert-butyl 3-(6-(5-(2,6-difluorophenyl)-1-(tetrahydro-2H-pyran-2-yl)-1H-indazol-3-yl)pyrazin-2-ylamino)pyrrolidine-1-carboxylate (280 mg, 0.486 mmol) in DCM was added TFA (0.5 ml, 6.49 mmol). The reaction was stirred at RT for 2 h, and then TFA was removed. The residue was purified with RP-HPLC to give (R)-6-(5-(2,6-difluorophenyl)-1H-indazol-3-yl)-N-(pyrrolidin-3-yl)pyrazin-2-amine as an orange solid. MS (ESI, pos.

ion) m/z: 393 (M+1); $^1$H NMR (400 MHz, DMSO-d6) δ ppm 8.71 (1 H, s), 8.47 (1 H, s), 7.87 (1 H, s), 7.72 (1 H, d, J=8.6 Hz), 7.41-7.55 (2 H, m), 7.18-7.31 (3 H, m), 4.22-4.36 (1 H, m), 2.88-3.05 (2 H, m), 2.61-2.82 (2 H, m), 1.97-2.12 (1 H, m), 1.57-1.73 (1 H, m).

Example 17

6-(5-(2,6-Difluorophenyl)-1H-indazol-3-yl)-N-methyl-N-(piperidin-4-yl)pyrazin-2-amine

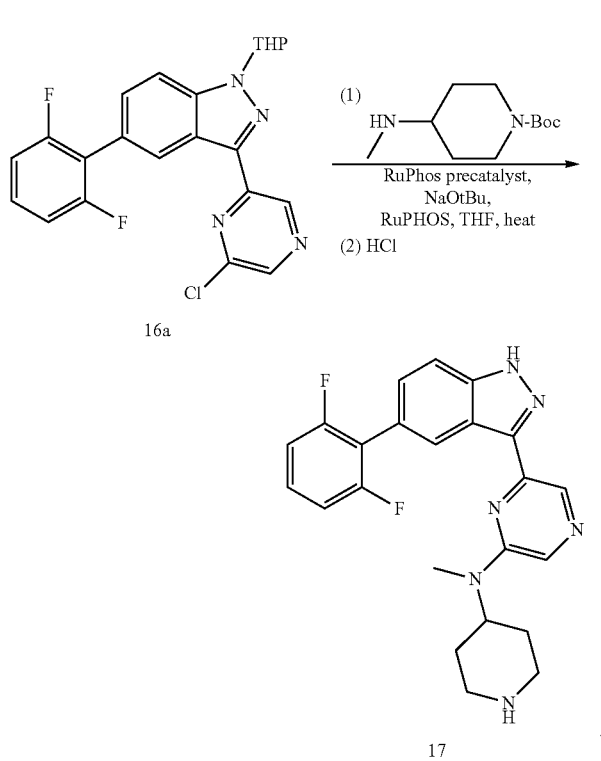

To a glass microwave vial was added 3-(6-chloropyrazin-2-yl)-5-(2,6-difluorophenyl)-1-(tetrahydro-2H-pyran-2-yl)-1H-indazole (0.200 g, 0.469 mmol), dicyclohexyl(2',6'-diisopropoxybiphenyl-2-yl)phosphine (RuPhos, 6.57 mg, 0.014 mmol), chloro(2-dicyclohexylphosphino-2',6'-dipropoxy-1,1'-biphenyl)[2-(2-aminoethylphenyl)]palladium(II), methyl-t-butylether adduct (6.57 mg, 0.014 mmol), RuPhos precatalyst (10.28 mg, 0.014 mmol), and sodium tert-butoxide (0.144 mL, 1.174 mmol). The vial was placed under vacuum and flushed with argon. tert-Butyl 4-(methylamino)piperidine-1-carboxylate (0.121 g, 0.563 mmol, CNH Technologies) and THF (1.565 mL) were added and the reaction mixture was stirred at 85° C. overnight. Reaction was cooled to RT. The crude product was adsorbed onto a plug of silica gel and chromatographed through a Biotage pre-packed silica gel column (40S), eluting with a gradient of 10% to 100% EtOAc in hexane. The desired tert-Butyl 4-((6-(5-(2,6-difluorophenyl)-1-(tetrahydro-2H-pyran-2-yl)-1H-indazol-3-yl) pyrazin-2-yl)(methyl)amino)piperidine-1-carboxylate was obtained and then treated with 5-6 M HCl in IPA. The reaction mixture was heated at 80° C. for 1 h and then contracted to dryness. The crude product was purified by reverse-phase preparative HPLC using a Phenomenex Synergi column, 4 micron, MAX-RP, 80 Å, 150×30 MM, 0.1% TFA in ACN/H$_2$O, gradient 15% to 100% over 15 min. The title compound was obtained. MS (ESI, pos. ion) m/z: 421.1 (M+1).

Example 18

Non-racemic 5-(2,6-difluorophenyl)-3-(6-(trans-4-fluoropiperidin-3-yloxy)pyrazin-2-yl)-1H-indazole, Enantiomer

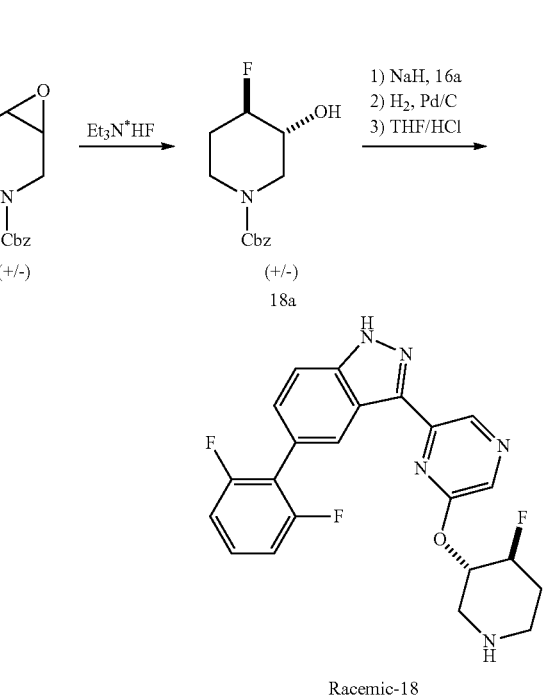

Preparation of Compound 18a: Racemic trans-benzyl 4-fluoro-3-hydroxypiperidine-1-carboxylate Racemic benzyl 7-oxa-3-azabicyclo[4.1.0]heptane-3-carboxylate (1.00 g, 4.29 mmol) (AMRI, Syracuse, N.Y. E00017 Lot IN-GBG-A-009B) and triethylamine trihydrofluoride (0.699 mL, 4.29 mmol) were combined in a sealed tube and heated to 100° C. overnight. The reaction was cooled and partitioned between water and EtOAc. The aqueous layer was extracted 3×EtOAc, and the organic layer was washed with water once, saturated aqueous NaCl once, and the organics were dried over anhydrous Na$_2$SO$_4$, filtered, and concentrated in vacuo. The material was treated with DCM and purified by silica gel chromatography (80 g column) using 15-50% EtOAc/hexane to give racemic trans-benzyl 4-fluoro-3-hydroxypiperidine-1-carboxylate (0.612 g, 2.42 mmol, 56% yield). MS (ESI, pos. ion) m/z: 254 (M+1).

Preparation of Compound 18: Non-racemic 5-(2,6-difluorophenyl)-3-(6-(trans-4-fluoropiperidin-3-yloxy)pyrazin-2-yl)-1H-indazole, Enantiomer 1

To a solution of racemic trans-benzyl 4-fluoro-3-hydroxypiperidine-1-carboxylate (0.309 g, 1.22 mmol) in 2 mL NMP at 0° C. was added NaH 60% in mineral oil (0.049 g, 1.22 mmol). Bubbling observed. The bath was removed. After 5 min, 3-(6-chloropyrazin-2-yl)-5-(2,6-difluorophenyl)-1-(tetrahydro-2H-pyran-2-yl)-1H-indazole (0.200 g, 0.469 mmol) was added and the purple slurry was sealed and placed in a 120° C. oil bath for 10 min. The reaction became a dark brown solution. The reaction was heated 10 min additional, and the reaction was cooled and partitioned between water and EtOAc. The aqueous layer was extracted 3×EtOAc. The combined organic layers were washed with water 2 times, saturated aqueous NaCl once, and the organics were dried over anhydrous Na₂SO₄, filtered, and concentrated in vacuo. The material was treated with DCM and purified by silica gel chromatography (40 g column) using 0-40% EtOAc/hexane. The product-containing fractions were concentrated to afford an yellow oil (0.366 g). The material was treated with 10% palladium on carbon (50% water wet) (0.499 g, 0.47 mmol), 2.5 mL MeOH and 2.5 mL THF, and stirred rapidly under a balloon of hydrogen gas. After 1.5 h, the reaction was flushed with N₂ and filtered through celite, rinsing with DCM. The filtrate was concentrated in vacuo to give an orange foam, which was treated with 2 mL THF and 2 mL 5 N aqueous HCl, sealed, and heated to 70° C. for 4 h. An additional 2 mL 5N aqueous HCl was added, and heating was continued for 2 h. The reaction was poured onto ice and treated with 10 N NaOH until basic. The aqueous layer was extracted with 3×DCM. The combined extracts were dried over anhydrous Na₂SO₄, filtered, and concentrated. The material was treated with DCM and purified by silica gel chromatography (40 g column) using 0-100% 90/10 DCM/MeOH in DCM. The product-containing fractions were concentrated to afford racemic 5-(2,6-difluorophenyl)-3-(6-(trans-4-fluoropiperidin-3-yloxy)pyrazin-2-yl)-1H-indazole (0.081 g, 0.19 mmol, 41% yield) as a light-yellow solid. MS (ESI, pos. ion) m/z: 426 (M+1). Non-racemic 5-(2,6-difluorophenyl)-3-(6-(trans-4-fluoropiperidin-3-yloxy)pyrazin-2-yl)-1H-indazole, Enantiomer 1 was obtained by SFC chromatography under the following conditions: racemic 5-(2,6-difluorophenyl)-3-(6-(trans-4-fluoropiperidin-3-yloxy)pyrazin-2-yl)-1H-indazole was dissolved in 13 mL MeOH and DCM (1:1) and injected on Chiralcel ODH (21×250 mm, 5 um) for supercritical fluid chromatography. Eluent: supercritical fluid CO₂ with 30% MeOH (20 mM NH₃) as additive. Total flow 65 mL/min. Column temperature 40° C., outlet pressure 100 bar. UV 238 nm, 1 ml injections. MS (ESI, pos. ion) m/z: 426 (M+1).

Example 19

Non-racemic 5-(2,6-difluorophenyl)-3-(6-(trans-4-fluoropiperidin-3-yloxy)pyrazin-2-yl)-1H-indazole, Enantiomer 2

The title compound was prepared according to the procedure for compound 18, using racemic 5-(2,6-difluorophenyl)-3-(6-(trans-4-fluoropiperidin-3-yloxy)pyrazin-2-yl)-1H-indazole.

Example 20

(R)-4-(5-(2,6-difluorophenyl)-1H-indazol-3-yl)-N-(piperidin-3-yl)pyrimidin-2-amine

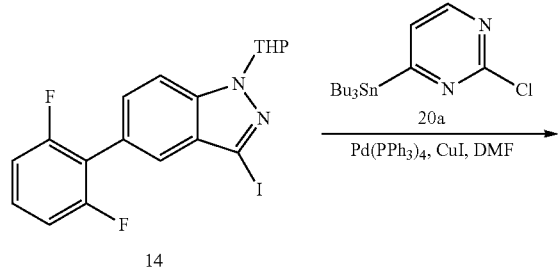

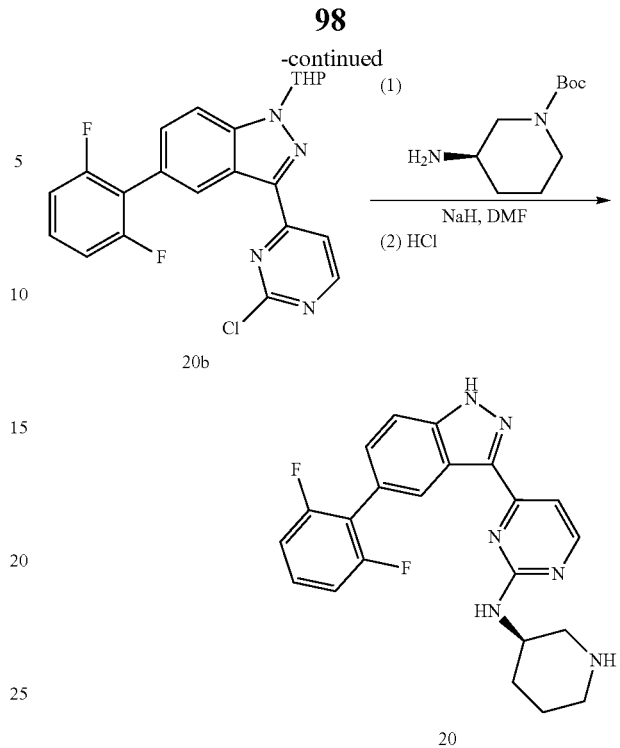

Preparation of Compound 20a: 2-chloro-4-(tributylstannyl)pyrimidine

To a mixture of THF (300 mL) and LDA (100 mL, 20.1 mmol) at −20° C. was added SnBu₃H (50 mL, 17.4 mmol) dropwise and stirred for 15 min. The reaction mixture was cooled to −78° C. and treated with 2,4-dichloro pyrimidine (20 g, 134 mmol) portionwise. The reaction mixture was stirred at −78° C. for 5 h with constant stirring under argon atmosphere. The cooling bath was removed and the reaction mixture was warmed up to 0° C. within 30 min. The resulting mixture was poured into 10% NH₄Cl aqueous solution, and extracted the compound with Et₂O. The organic layer was washed with brine, dried with Na₂SO₄, filtered, and evaporated. The residue was purified by column chromatography (1% EtOAc: 99% n-Hexane) to obtain 4-Chloro-2-tributylstannanyl-pyrimidine (13 g, 24% yield) as a pale yellow color syrup and 2-Chloro-4-tributylstannanyl-pyrimidine 20a (3 g, 5.5% yield) as a pale yellow color syrup.

Preparation of Compound 20b: 3-(2-chloropyrimidin-4-yl)-5-(2,6-difluorophenyl)-1-(tetrahydro-2H-pyran-2-yl)-1H-indazole To a solution of 5-(2,6-difluorophenyl)-3-iodo-1-(tetrahydro-2H-pyran-2-yl)-1H-indazole 14 (0.2 g, 0.45 mmol) and 2-Chloro-4-tributylstannanyl-pyrimidine 20a (0.27 g, 0.68 mmol) in DMF was bubbled N₂ for 15 min and added CuI (0.052 g, 0.54 mmol) and Pd(PPh₃)₄ (0.1 g, 0.025 mmol). The reaction mixture was heated at 90° C. for 2 h and cooled to RT. The reaction mixture was quenched with water and precipitate was formed. The resulting precipitate was collected by filtration, washed with water, and dried to yield crude product. Purification by silica gel column chromatography, eluting with 5-10% EtOAc and hexanes to obtain the title compound (0.1 g, 38%). MS (ESI, pos. ion) m/z: 427.0 (M+1).

Preparation of Compound 20: (R)-4-(5-(2,6-difluorophenyl)-1H-indazol-3-yl)-N-(piperidin-3-yl)pyrimidin-2-amine To a solution of (R)-tert-butyl 3-aminopiperidine-1-carboxylate (0.28 g, 1.32 mmol) in DMF (10 mL) was treated with NaH (0.056 g, 2.34 mmol) and stirred for 15 min. The reaction mixture was cooled to 0° C. and 3-(2-chloropyrimidin-4-yl)-5-(2,6-difluorophenyl)-1-(tetrahydro-2H-pyran-2-yl)-1H-indazole (0.5 g, 1.17 mmol) was added. The resulting mixture was stirred at RT for 2 h. The reaction mixture was quenched with ice cold water and extracted with EtOAc. The organic layer was dried over Na$_2$SO$_4$, filtered and concentrated to yield crude compound. Purification by silica gel column chromatography, eluting with 5-15% EtOAc and hexanes to obtain (3R)-tert-butyl 3-(4-(5-(2,6-difluorophenyl)-1-(tetrahydro-2H-pyran-2-yl)-1H-indazol-3-yl)pyrimidin-2-ylamino)piperidine-1-carboxylate (0.2 g, 18%). MS (ESI, pos. ion) m/z: 591.1 (M+1). To a solution of (3R)-tert-butyl 3-(4-(5-(2,6-difluorophenyl)-1-(tetrahydro-2H-pyran-2-yl)-1H-indazol-3-yl)pyrimidin-2-ylamino)piperidine-1-carboxylate (0.3 g, 0.5 mmol) in EtOAc (10 mL) was added EtOAc-HCl (10 mL) and stirred at RT for 16 h. The reaction mixture was quenched with saturated NaHCO$_3$ solution and extracted with EtOAc. The organic layer was washed with water and brine, dried over Na$_2$SO$_4$ and concentrated. The crude product was purified by reverse-phase preparative HPLC (using a AG/PP/C18-15/021 column, eluting with gradient, A: 5% TFE+0.01% TFA in Water; B: ACN). The title compound was obtained. MS (ESI, pos. ion) m/z: 407.2 (M+1).

Example 21

1-(6-(5-(2,6-difluorophenyl)-1H-indol-3-yl)pyrazin-2-yl)piperidin-3-amine

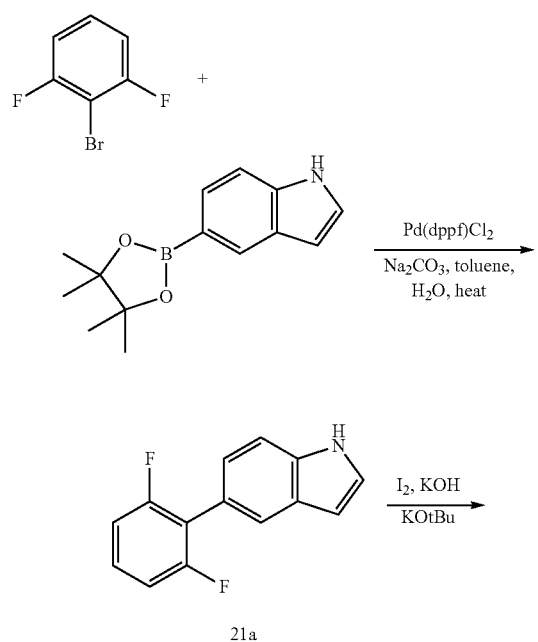

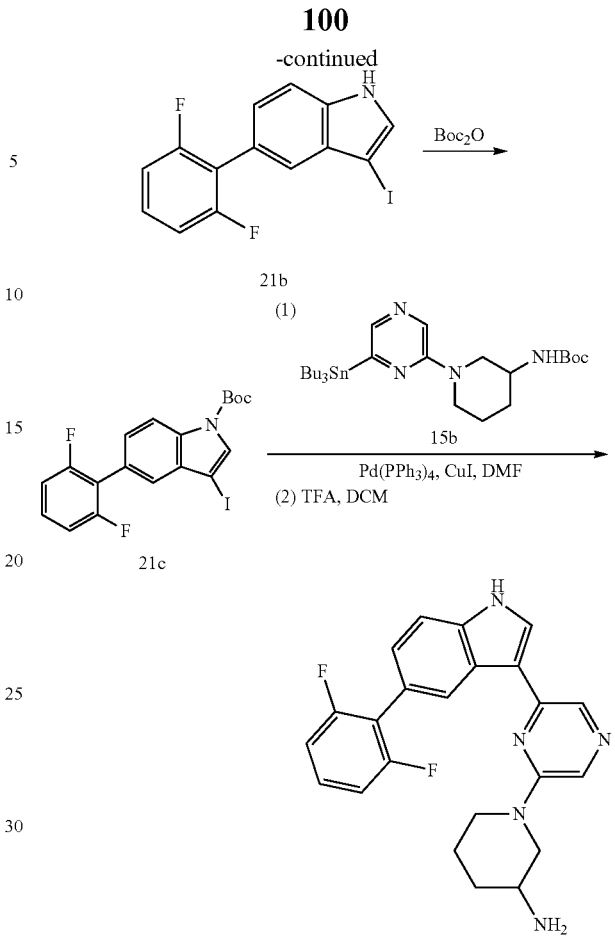

Preparation of Compound 21a:
5-(2,6-difluorophenyl)-1H-indole

A glass microwave reaction vessel was charged with 1-bromo-2,6-difluorobenzene (1.145 mL, 7.71 mmol) and 5-indoleboronic acid pinacol ester (1.50 g, 6.17 mmol) in toluene/H$_2$O (4:1, 15 mL) followed by dichloro(1,1-bis(diphenylphosphinoferrocene)) palladium(ii) complex with DCM (0.252 g, 0.309 mmol) and Na$_2$CO$_3$ (0.645 mL, 15.43 mmol). The reaction mixture was stirred and heated in a Initiator microwave reactor (Personal Chemistry, Biotage AB, Inc., Uppsala, Sweden) at 125° C. for 4 h, and then the mixture was diluted with DCM. The organic layer was separated, washed with water, dried over Na$_2$SO$_4$, filtered and concentrated. The residue was purified with silica gel chromatography (eluting with 10-15% EtOAc in Hexanes) to give 5-(2,6-difluorophenyl)-1H-indole (1.06 g, 4.62 mmol, 74.9% yield) as a light yellow oil. MS (ESI, pos. ion) m/z: 230 (M+1).

Preparation of Compound 21b:
5-(2,6-difluorophenyl)-3-iodo-1H-indole

To a solution of 5-(2,6-difluorophenyl)-1H-indole (1.06 g, 4.62 mmol) in DMF (10 mL) was added I$_2$ (0.262 mL, 5.09 mmol) followed by KOH (0.317 mL, 11.56 mmol). The reaction was stirred at RT for 1 h, and then poured into ice/water mixture with sodium bisulfite. The mixture was extracted with DCM and the combined organic layers were washed with water, brine, dried over Na₂SO₄, filtered and concentrated to give the crude product. MS (ESI, pos. ion) m/z: 355.0 (M+1).

Preparation of Compound 21c: tert-butyl 5-(2,6-difluorophenyl)-3-iodo-1H-indole-1-carboxylate To a solution of 5-(2,6-difluorophenyl)-3-iodo-1H-indole (1.46 g, 4.11 mmol) in DMF (8 mL) at 0° C. was added potassium t-butoxide (0.484 g, 4.32 mmol) followed by di-t-butyl dicarbonate (0.924 mL, 4.32 mmol). The reaction was warmed to RT and stirred for 30 min. The reaction was diluted with DCM (200 mL). The organic layer was separated, washed with water (3×50 mL) and brine, dried over Na₂SO₄, filtered and concentrated. The residue was purified with silica gel chromatography (eluting with 0-15% DCM in Hexanes) to give tert-butyl 5-(2,6-difluorophenyl)-3-iodo-1H-indole-1-carboxylate (1.23 g, 2.70 mmol, 65.7% yield) as a solid. MS (ESI, pos. ion) m/z: 456 (M+1).

Preparation of Compound 21: 1-(6-(5-(2,6-difluorophenyl)-1H-indol-3-yl)pyrazin-2-yl)piperidin-3-amine A glass microwave reaction vessel was charged with tert-butyl 5-(2,6-difluorophenyl)-3-iodo-1H-indole-1-carboxylate (350 mg, 0.769 mmol), tert-butyl 1-(6-(tributylstannyl)pyrazin-2-yl)piperidin-3-ylcarbamate (436 mg, 0.769 mmol), Pd(PPh₃)₄ (89 mg, 0.077 mmol), and CuI (15 mg, 0.077 mmol) in DMF (6 mL). The reaction mixture was stirred and heated in a Initiator microwave reactor (Personal Chemistry, Biotage AB, Inc., Uppsala, Sweden) at 100° C. for 30 min. The mixture was diluted with DCM and water. The organic layer was separated, washed with water and brine, dried over Na₂SO₄, filtered and concentrated to give the crude product, tert-butyl 3-(6-(3-(tert-butoxycarbonylamino)piperidin-1-yl)pyrazin-2-yl)-5-(2,6-difluorophenyl)-1H-indole-1-carboxylate. MS (ESI, pos. ion) m/z: 606 (M+1). To a solution of tert-butyl 3-(6-(3-(tert-butoxycarbonylamino)piperidin-1-yl)pyrazin-2-yl)-5-(2,6-difluorophenyl)-1H-indole-1-carboxylate (466 mg, 0.769 mmol) in DCM (6 mL) was added TFA (4 mL) and the reaction was stirred at RT for 3 h, then solvent was removed. The residue was diluted with DCM and washed with saturated NaHCO₃ aqueous solution twice. The organic layer was dried over Na₂SO₄, filtered and concentrated. The residue was purified with RP-HPLC to give 1-(6-(5-(2,6-difluorophenyl)-1H-indol-3-yl)pyrazin-2-yl)piperidin-3-amine as a light brown solid. MS (ESI, pos. ion) m/z: 406 (M+1).

Example 22

1-(6-(5-(2,6-difluorophenyl)-1H-indol-3-yl)pyrazin-2-yl)piperidin-4-amine

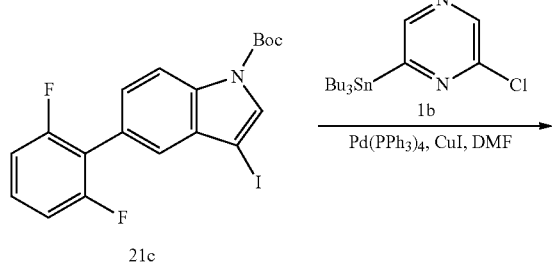

21c

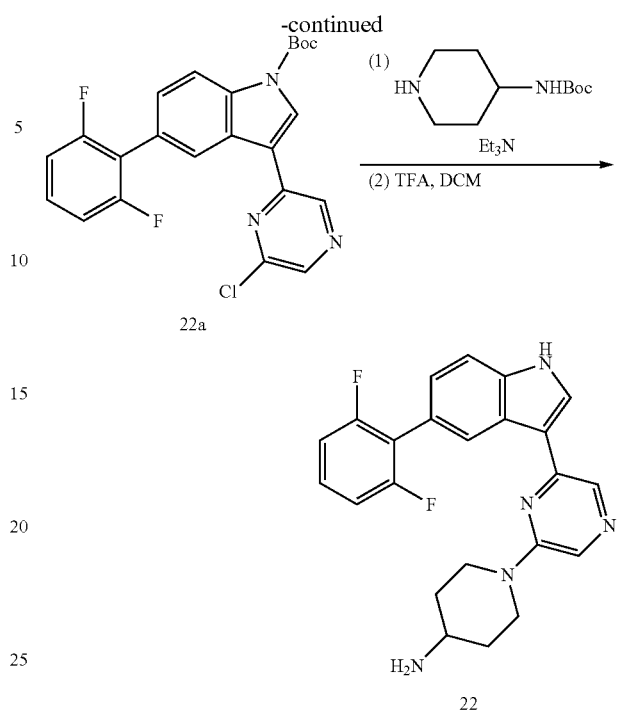

22a

22

Preparation of Compound 22a: tert-butyl 3-(6-chloropyrazin-2-yl)-5-(2,6-difluorophenyl)-1H-indole-1-carboxylate A glass microwave reaction vessel was charged with 2-chloro-6-(tributylstannyl)pyrazine (177 mg, 0.439 mmol) and tert-butyl 5-(2,6-difluorophenyl)-3-iodo-1H-indole-1-carboxylate (200 mg, 0.439 mmol) in DMF (2.5 mL) followed by CuI (18 mg, 0.044 mmol) and Pd(PPh₃)₄ (50.8 mg, 0.044 mmol). The reaction mixture was stirred and heated in a Initiator microwave reactor (Personal Chemistry, Biotage AB, Inc., Uppsala, Sweden) at 100° C. for 40 min, and then the mixture was diluted with DCM. The organic layer was separated, washed with water (20 mL×4), dried over Na₂SO₄, filtered and concentrated. The residue was purified with silica gel chromatography (eluting with 0-5% EtOAc in Hexanes) to give tert-butyl 3-(6-chloropyrazin-2-yl)-5-(2,6-difluorophenyl)-1H-indole-1-carboxylate (68.0 mg, 0.154 mmol, 35.0% yield) as a white solid. MS (ESI, pos. ion) m/z: 442 (M+1).

Preparation of Compound 22: 1-(6-(5-(2,6-difluorophenyl)-1H-indol-3-yl)pyrazin-2-yl)piperidin-4-amine A glass microwave reaction vessel was charged with tert-butyl 3-(6-chloropyrazin-2-yl)-5-(2,6-difluorophenyl)-1H-indole-1-carboxylate (50.0 mg, 0.113 mmol) and 4-boc-amino-1-piperidine (34.0 mg, 0.170 mmol) in NMP (0.6 mL), followed by Et₃N (0.047 mL, 0.339 mmol). The reaction mixture was stirred and heated in an oil bath at 150° C. for 16 h, and then the mixture was diluted with DCM and water. The organic layer was separated, dried over Na₂SO₄, filtered and concentrated. The residue was dissolved in DCM (2 mL) and treated with TFA (0.5 mL). The reaction mixture was stirred at RT for 2 h, and solvent was removed. The residue was purified with RP-HPLC to give 1-(6-(5-(2,6-difluorophenyl)-

1H-indol-3-yl)pyrazin-2-yl)piperidin-4-amine as a brown solid. MS (ESI, pos. ion) m/z: 406 (M+1).

Example 23

(R)-5-(2,6-difluorophenyl)-3-(6-(piperidin-3-yloxy)pyrazin-2-yl)-1H-indole

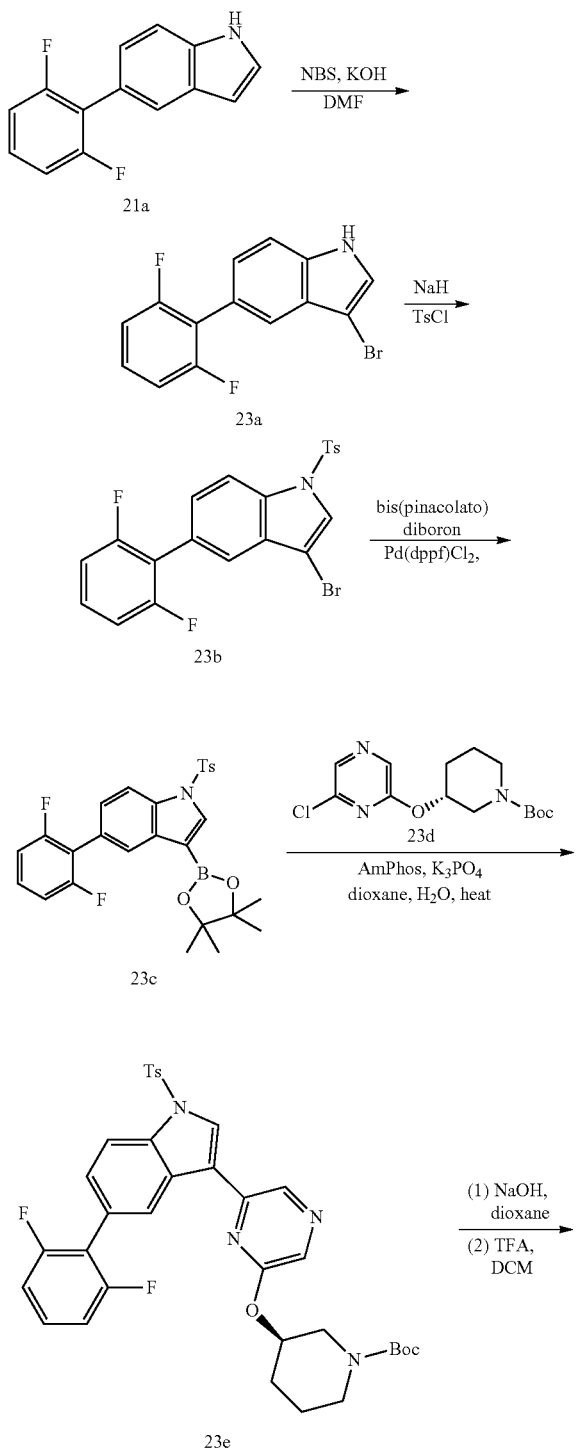

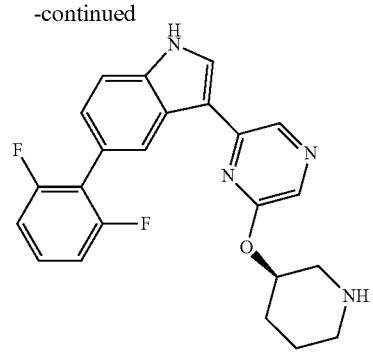

Preparation of Compound 23a: 3-bromo-5-(2,6-difluorophenyl)-1H-indole

To a stirred solution of 5-(2,6-difluorophenyl)-1H-indole (2.0 g, 8.7 mmol) in DMF (20 mL) was added KOH (0.98 g, 17.5 mmol) and NBS (1.55 g, 8.7 mmol) at RT and stirred for 1 h. The resulting mixture was diluted with water, extracted with DCM (20 mL), dried over $Na_2SO_4$, filtered, concentrated to give crude 3-bromo-5-(2,6-difluorophenyl)-1H-indole.

Preparation of Compound 23b: 3-bromo-5-(2,6-difluorophenyl)-1-tosyl-1H-indole

To a stirred solution of crude 3-bromo-5-(2,6-difluorophenyl)-1H-indole (14 g, 0.04 mol) in DMF (140 mL) was added NaH (60% suspended in mineral oil) (3 eq) and p-TsCl (13 g, 0.068 mol). The reaction mixture was stirred at RT for 8 h under argon atmosphere. Then ice cold water was added to the reaction mixture. The resulting precipitate was collected by filtration, washed with water and dried under vacuum. The crude product was purified by column chromatography (silica 60-120 mesh, eluted with 4% EtOAc in hexane) to obtain the title compound (8.6 g, 41%). MS (ESI, pos. ion) m/z: 462, 464 (M+1).

Preparation of Compound 23c: 5-(2,6-difluorophenyl)-3-(4,4,5,5-tetramethyl-1,3,2-dioxaborolan-2-yl)-1-tosyl-1H-indole A glass microwave reaction vessel was charged with 3-bromo-5-(2,6-difluorophenyl)-1-tosyl-1H-indole (2.50 g, 5.41 mmol) and bis(pinacolato)diboron (2.75 g, 10.82 mmol) in DMF (30 mL) followed by potassium acetate (1.33 g, 13.52 mmol) and 1,1'-bis(diphenylphosphino)ferrocene-palladium dichloride (0.221 g, 0.270 mmol). The reaction mixture was stirred and heated in a Initiator microwave reactor (Personal Chemistry, Biotage AB, Inc., Uppsala, Sweden) at 110° C. for 45 min. The mixture was diluted with water and extracted with EtOAc. The combined organic layers were washed with water, brine, dried, filtered and concentrated to give the crude 5-(2,6-difluorophenyl)-3-(4,4,5,5-tetramethyl-1,3,2-dioxaborolan-2-yl)-1-tosyl-1H-indole. MS (ESI, pos. ion) m/z: 510 (M+1). The material was used in the next step without further purification.

Preparation of Compound 23d: (R)-tert-butyl 3-(6-chloropyrazin-2-yloxy)piperidine-1-carboxylate To a 500-mL round-bottomed flask was added (R)-tert-butyl 3-hydroxypiperidine-1-carboxylate (2.5 g, 12.42 mmol) in DMF (80 mL) at 0° C. NaH (1.080 mL, 24.84 mmol) was added slowly and the mixture was stirred at 0° C. for 15 min. 2,6-dichloropyrazine (1.851 g, 12.42 mmol) was added and the mixture was warmed to RT and stirred for 2 h. The reaction mixture was quenched with water and extracted with DCM. The combined organic layers were washed with water, brine, dried, filtered and concentrated to give the crude title compound. The material was used in the next step without further purification Preparation of Compound 23e: (R)-tert-butyl 3-(6-(5-(2,6-difluorophenyl)-1-tosyl-1H-indol-3-yl)pyrazin-2-yloxy)piperidine-1-carboxylate A glass microwave reaction vessel was charged with 5-(2,6-difluorophenyl)-3-(4,4,5,5-tetramethyl-1,3,2-dioxaborolan-2-yl)-1-tosyl-1H-indole (2.75 g, 5.40 mmol) and (R)-tert-butyl 3-(6-chloropyrazin-2-yloxy)piperidine-1-carboxylate (1.694 g, 5.40 mmol) in p-dioxane/H$_2$O (4:1, 16 mL) followed by A-Phos (0.191 g, 0.270 mmol) and potassium phosphate (2.92 g, 10.80 mmol). The reaction mixture was stirred and heated in a Initiator microwave reactor (Personal Chemistry, Biotage AB, Inc., Uppsala, Sweden) at 110° C. for 80 min. The reaction mixture was diluted with water and extracted with DCM. The combined organic layers were dried, filtered and concentrated. The residue was purified with silica gel chromatography (eluting with 10-20% EtOAc in Hexanes) to give (R)-tert-butyl 3-(6-(5-(2,6-difluorophenyl)-1-tosyl-1H-indol-3-yl)pyrazin-2-yloxy)piperidine-1-carboxylate (3.15 g, 4.77 mmol, 88% yield) as a solid. MS (ESI, pos. ion) m/z: 661 (M+1).

Preparation of Compound 23: (R)-5-(2,6-difluorophenyl)-3-(6-(piperidin-3-yloxy)pyrazin-2-yl)-1H-indole A glass microwave reaction vessel was charged with (R)-tert-butyl 3-(6-(5-(2,6-difluorophenyl)-1-tosyl-1H-indol-3-yl)pyrazin-2-yloxy)piperidine-1-carboxylate (2.5 g, 3.78 mmol) and NaOH (1.513 mL, 7.57 mmol) in p-dioxane (12 mL). The reaction mixture was stirred and heated in a Initiator microwave reactor (Personal Chemistry, Biotage AB, Inc., Uppsala, Sweden) at 100° C. for 1 h, then the mixture was diluted with water, and extracted with DCM. The combined organic layers were dried, filtered and concentrated to give the crude (R)-tert-butyl 3-(6-(5-(2,6-difluorophenyl)-1H-indol-3-yl)pyrazin-2-yloxy)piperidine-1-carboxylate.

A glass microwave reaction vessel was charged with (R)-tert-butyl 3-(6-(5-(2,6-difluorophenyl)-1H-indol-3-yl)pyrazin-2-yloxy)piperidine-1-carboxylate (1.91 g, 3.77 mmol) in DCM (10 mL)/TFA (4 mL). The reaction mixture was stirred and heated in a Initiator microwave reactor (Personal Chemistry, Biotage AB, Inc., Uppsala, Sweden) at 80° C. for 15 min, and then the solvent was removed. The residue was purified with RP-HPLC to give (R)-5-(2,6-difluorophenyl)-3-(6-(piperidin-3-yloxy)pyrazin-2-yl)-1H-indole.

Example 24

(R)-2-(5-(2,6-difluorophenyl)-1H-indol-3-yl)-N-(piperidin-3-yl)pyrimidin-4-amine

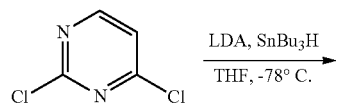

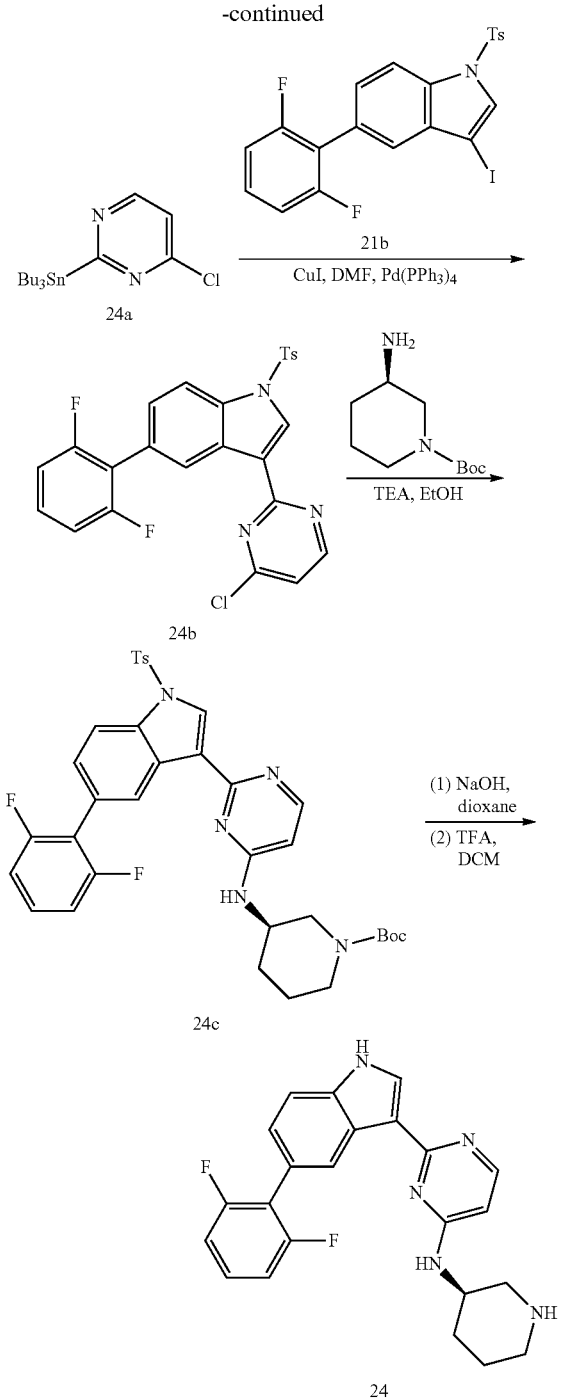

Preparation of Compound 24a: 4-chloro-2-(tributylstannyl)pyrimidine

To a mixture of THF (300 mL) and LDA (100 mL, 20.1 mmol) at −20° C. was added Bu$_3$SnH (50 mL, 17.4 mmol) dropwise and stirred for 15 min. The reaction mixture was cooled to −78° C. and treated with 2,4-dichloro pyrimidine (20 g, 134 mmol) portionwise. The reaction mixture was stirred at −78° C. for 5 h with constant stirring under argon atmosphere. The cooling bath was removed and the reaction mixture was warmed up to 0° C. within 30 min. The resulting mixture was poured into 10% NH₄Cl aqueous solution, and extracted the compound with Et₂O. The organic layer was washed with brine, dried with Na₂SO₄, filtered, and evaporated. The residue was purified by column chromatography (1% EtOAc: 99% n-Hexane) to obtain 2-chloro-4-tributyl-stannanyl-pyrimidine 20a (3 g, 5.5% yield) as a pale yellow color syrup and 4-chloro-2-tributylstannanyl-pyrimidine 24a (13 g, 24% yield) as a pale yellow color syrup. Compound 24a: MS (ESI, pos. ion) m/z: 405.3 (M+1).

Preparation of Compound 24b: 3-(4-chloropyrimidin-2-yl)-5-(2,6-difluorophenyl)-1-tosyl-1H-indole To a solution of 5-(2,6-difluorophenyl)-3-iodo-1-tosyl-1H-indole (2.0 g, 3.92 mmol) and 4-chloro-2-tributylstannanyl-pyrimidine (2.38 g, 5.98 mmol) in DMF (60 mL) was bubbled N₂ for 15 min and added CuI (0.898 g, 4.71 mmol) and Pd(PPh₃)₄ (0.226 g, 0.196 mmol). The reaction mixture was heated at 80° C. for 1 h and cooled to RT. The reaction mixture was quenched with water and precipitate was formed. The resulting precipitate was collected by filtration, washed with water, and dried to yield crude product. Purification by silica gel column chromatography, eluting with 10% EtOAc in hexanes obtained the title compound (0.50 g, 26%). MS (ESI, pos. ion) m/z: 496.0 (M+1).

Preparation of Compound 24c: (R)-tert-butyl 3-(2-(5-(2,6-difluorophenyl)-1-tosyl-1H-indol-3-yl)pyrimidin-4-ylamino)piperidine-1-carboxylate A mixture of 3-(4-chloropyrimidin-2-yl)-5-(2,6-difluorophenyl)-1-tosyl-1H-indole (500 mg, 10 mmol) and (R)-tert-butyl 3-aminopiperidine-1-carboxylate (404 mg, 2.02 mmol) in DMSO (10 mL) was heated at 110° C. for 12 h. The resulting mixture was cooled to at RT for 2 h. The reaction mixture was quenched with ice cold water and extracted with EtOAc. The organic layer was dried over Na₂SO₄, filtered and concentrated to yield crude compound. Purification by silica gel column chromatography, eluting with 5-15% EtOAc and hexanes to the title compound (500 mg, 75%). MS (ESI, pos. ion) m/z: 660 (M+1).

Preparation of Compound 24: (R)-2-(5-(2,6-difluorophenyl)-1H-indol-3-yl)-N-(piperidin-3-yl)pyrimidin-4-amine A solution of (R)-tert-butyl 3-(2-(5-(2,6-difluorophenyl)-1-tosyl-1H-indol-3-yl)pyrimidin-4-ylamino)piperidine-1-carboxylate (500 mg, 0.757 mmol) in dioxane (10 mL) was treated with aqueous 1N NaOH (5 mL) and heated at 100° C. for 2 h. The resulting mixture was cooled to RT, and quenched with ice cold water. The resulting precipitate was collected by filtration, washed with ice cold water and dried to obtain the pure (R)-tert-butyl 3-(2-(5-(2,6-difluorophenyl)-1H-indol-3-yl)pyrimidin-4-ylamino)piperidine-1-carboxylate (350 mg, 92%). (R)-tert-butyl 3-(2-(5-(2,6-difluorophenyl)-1H-indol-3-yl)pyrimidin-4-ylamino)piperidine-1-carboxylate (350 mg, 0.69 mmol) was treated with ethanolic HCl (10 mL). The reaction mixture was stirred at RT for 16 h and then extracted with DCM. The combined organic layers were dried; filtered and concentrated to give the crude product, which was purified by recrystallization using 10% MeOH in CHCl₃ to yield (R)-2-(5-(2,6-difluorophenyl)-1H-indol-3-yl)-N-(piperidin-3-yl)pyrimidin-4-amine MS (ESI, pos. ion) m/z: 406 (M+1).

Example 25

(R)-6-(5-(6-isopropoxypyrazin-2-yl)-1H-indol-3-yl)-N-(piperidin-3-yl)pyrazin-2-amine

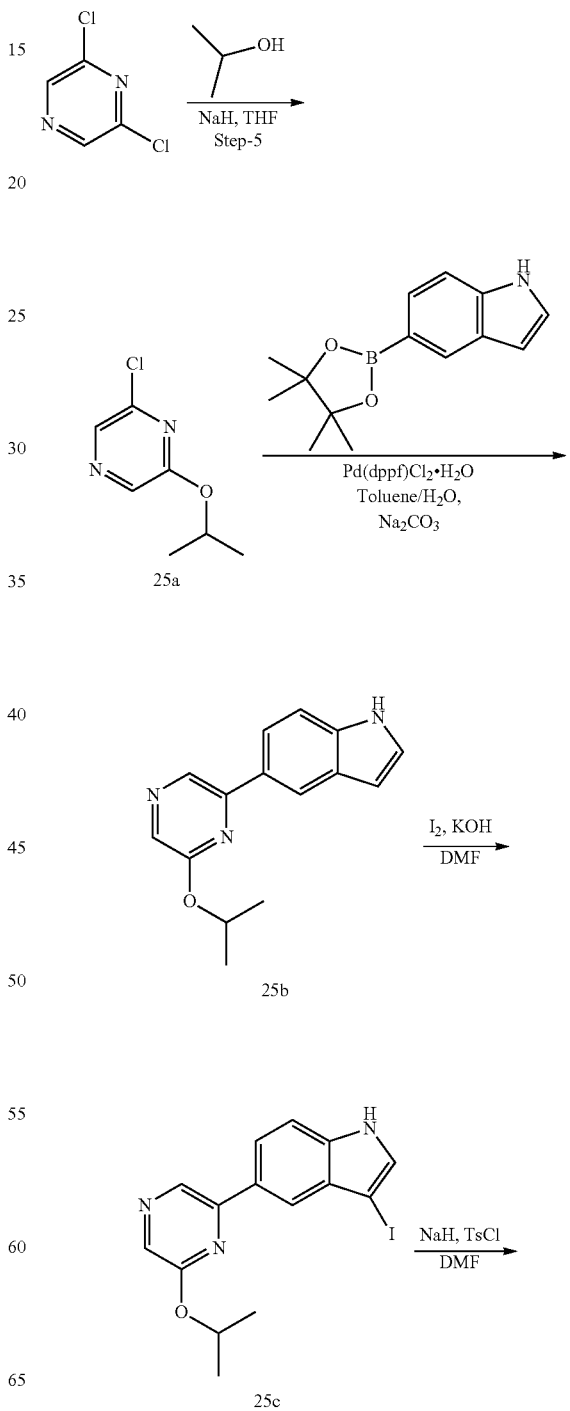

-continued

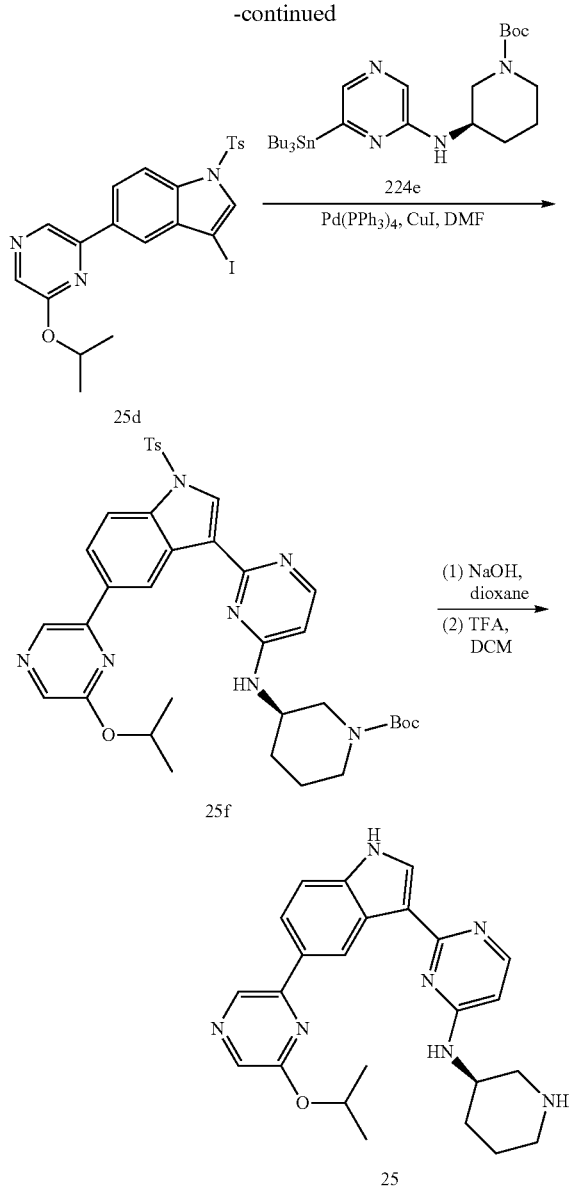

Preparation of Compound 25a:
2-chloro-6-isopropoxypyrazine

To a solution of IPA (50.0 g, 0.369 mol) in 500 mL of THF slowly was added 60% NaH (27.0 g, 0.671 mol) at RT under N₂ atmosphere and stirred at RT for 20 min. Then the reaction mixture was slowly treated with 2,6-dichloropyrazine (50 g, 0.336 mol) at RT and stirred at RT for 1 h. The resulting mixture was poured into ice water and extracted with EtOAc. The organic layer was separated, dried over anhydrous Na₂SO₄, and concentrated to afford crude 2-chloro-6-isopropoxypyrazine (53 g) as pale brown liquid. This material was used further step without purification. MS (ESI, m/z): 173 (M+1).

Preparation of Compound 25b:
5-(6-isopropoxypyrazin-2-yl)-1H-indole

A mixture of 5-Indole boronate ester (57 g, 0.234 mol), 2-chloro-6-isopropoxy pyrazine (49 g, 0.281 mol), Na₂CO₃ (62.1 g, 0.586 mol) and Pd(dppf)₂Cl₂.DCM complex in toluene (450 mL)/water (150 mL) was heated at reflux for 8 h. Then reaction mixture was cooled to RT and added ice water. The reaction was extracted with EtOAc. The organic layer was separated, dried over Na₂SO₄, and concentrated to afford crude compound. This crude was purified through column by using EtOAc and n-hexane to obtain the title compound (34 g, 56% yield) as pale brown solid. MS (ESI, m/z): 254.1 (M+1).

Preparation of Compound 25c:
3-iodo-5-(6-isopropoxypyrazin-2-yl)-1H-indole

To a solution of 5-(6-isopropoxy-pyrazin-2-yl)-1H-indole (32 g, 0.126 mol) in DMF (250 mL) was added KOH (17.8 g, 0.316 mol) and then stirred for 15 min at RT. I₂ (35.3 g, 0.139 mol) was added to the reaction mixture and stirred at RT for another 1 h. Then reaction mixture was poured into ice water and excess of I₂ was quenched with sodium thiosulfite. The resulting solid was collected by filtration, washed with water and dried under vacuum to afford crude 3-iodo-5-(6-isopropoxypyrazin-2-yl)-1H-indole (49 g) as pale brown solid. MS (ESI, m/z): 379.9 (M+1). This material was used to further step without purification.

Preparation of Compound 25d: 3-iodo-5-(6-isopropoxypyrazin-2-yl)-1-tosyl-1H-indole To a solution of 3-iodo-5-(6-isopropoxy-pyrazin-2-yl)-1H-indole (20 g, 0.053 mol) in DMF (200 mL) was added NaH (6.5 g, 0.158 mol) slowly at 0° C., and then stirred for 15 min. p-Toluenesulfonyl chloride (15.10 g, 0.079 mol) was added slowly to the reaction mixture and stirred for 1 h. The resulting mixture was poured into ice with stirring and the precipitate was formed. The resulting precipitate was collected by filtration, washed with water and dried under vacuum to give the crude product. The crude product was purified by column chromatography eluting with EtOAc and n-hexane to afford the desire 3-iodo-5-(6-isopropoxypyrazin-2-yl)-1-tosyl-1H-indole (15.5 g, 55%) as pale brown solid. MS (ESI, m/z): 533.6 (M+1).

Preparation of Compound 25e: (R)-tert-butyl 3-(6-(tributylstannyl)pyrazin-2-ylamino)piperidine-1-carboxylate To a solution of (R)-tert-butyl 3-aminopiperidine-1-carboxylate (1.53 g, 7.6 mmol) in DMF (76 mL) was added Et₃N (22 mmol) stirred for 15 min. 2-6-Dichloro pyrazine (1.14 g, 76 mmol) was added at RT and the reaction mixture was stirred at 100° C. overnight. The resulting reaction mixture was quenched with ice cold water and precipitate was formed. The precipitate was collected by filtration, washed with ice cold water and dried to obtain (R)-tert-butyl 3-(6-chloropyrazin-2-ylamino)piperidine-1-carboxylate (1.1 g, 43%). MS (ESI, pos. ion) m/z: 313 (M+1). To a solution of tributyltin hydride (1.39 g, 4.8 mmol) in THF (25 mL) at 0° C. was added LDA (1.8 M; 0.5 mL, 4.8 mmol) and stirred at the same temperature for 10 min. (R)-tert-butyl 3-(6-chloropyrazin-2-ylamino)piperidine-1-carboxylate (1.1 g) was added at 0° C. and the reaction mixture was stirred at RT for an additional 3 h. The resulting mixture was quenched with 10% KF aqueous solution and extracted with EtOAc. The organic layer was separated, dried over Na₂SO₄ and concentrated to dryness. The crude product was purified by column chromatography, using basic alumina, and eluting with 10% EtOAc/hexane to obtain pure (R)-tert-butyl 3-(6-(tributylstannyl)pyrazin-2-ylamino)piperidine-1-carboxylate (0.8 g, 48%). MS (ESI, pos. ion) m/z: 569.2 (M+1).

Preparation of Compound 25f: (R)-tert-butyl 3-(6-(5-(6-isopropoxypyrazin-2-yl)-1-tosyl-1H-indol-3-yl)pyrazin-2-ylamino)piperidine-1-carboxylate 3-Iodo-5-(6-isopropoxypyrazin-2-yl)-1-tosyl-1H-indole (0.4 g, 0.753 mmol) and (R)-tert-butyl 3-(6-(tributylstannyl)pyrazin-2-ylamino)piperidine-1-carboxylate (0.51 g, 0.903 mmol) in DMF (10 mL) was purged with argon for 15 min and added CuI (225 mg, 1.18 mmol) and Pd(PPh$_3$)$_4$ (105 mg, 0.09 mmol). The reaction mixture was heated at 100° C. for 2 h and cooled to RT. To the reaction mixture was added water and precipitate was formed. The precipitate was collected by filtration, washed with water and dried overnight. The crude product was purified by chromatography (eluting with 50% EtOAc/hexane) to obtain (R)-tert-butyl 3-(6-(5-(6-isopropoxy-pyrazin-2-yl)-1-tosyl-1H-indol-3-yl)pyrazin-2-ylamino)piperidine-1-carboxylate (0.2 g, 57%). MS (ESI, pos. ion) m/z: 684 (M+1).

Preparation of Compound 25: (R)-6-(5-(6-isopropoxypyrazin-2-yl)-1H-indol-3-yl)-N-(piperidin-3-yl)pyrazin-2-amine To a solution of (R)-tert-butyl 3-(6-(5-(6-isopropoxypyrazin-2-yl)-1-tosyl-1H-indol-3-yl)pyrazin-2-ylamino)piperidine-1-carboxylate (0.250 g, 0.365 mmol) in 1-4-dioxane (3.6 mL), 1N NaOH (3.6 mL) was added and heated at 100° C. for 2 h. The reaction mixture was quenched with ice cold water and precipitate was formed. The precipitate was collected by filtration, washed with ice cold water and dried to give pure (R)-tert-butyl 3-(6-(5-(6-isopropoxypyrazin-2-yl)-1H-indol-3-yl)pyrazin-2-ylamino)piperidine-1-carboxylate (180 mg, 93%). MS (ESI, pos. ion) m/z: 530.0 (M+1). To a solution of (R)-tert-butyl 3-(6-(5-(6-isopropoxypyrazin-2-yl)-1H-indol-3-yl)pyrazin-2-ylamino)piperidine-1-carboxylate (180 mg, 1.25 mmol) in EtOAc (5.0 mL) was treated with HCl in EtOAc (5.0 mL) and stirred at RT for 3 h. The reaction mixture was quenched with water, neutralized with NaHCO$_3$, extracted with EtOAc. The organic layer was separated, dried over Na$_2$SO$_4$ and evaporated to dryness. The crude solid was re-crystallized in acetone to obtain (R)-6-(5-(6-isopropoxypyrazin-2-yl)-1H-indol-3-yl)-N-(piperidin-3-yl)pyrazin-2-amine. MS (ESI, pos. ion) m/z: 430.0 (M+1).

Example 26

(R)-5-(2-chloro-6-fluorophenyl)-3-(6-(piperidin-3-yloxy)pyrazin-2-yl)-1H-indole bis(2,2,2-trifluoroacetate)

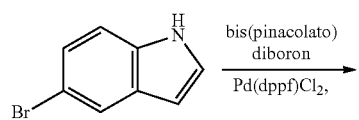

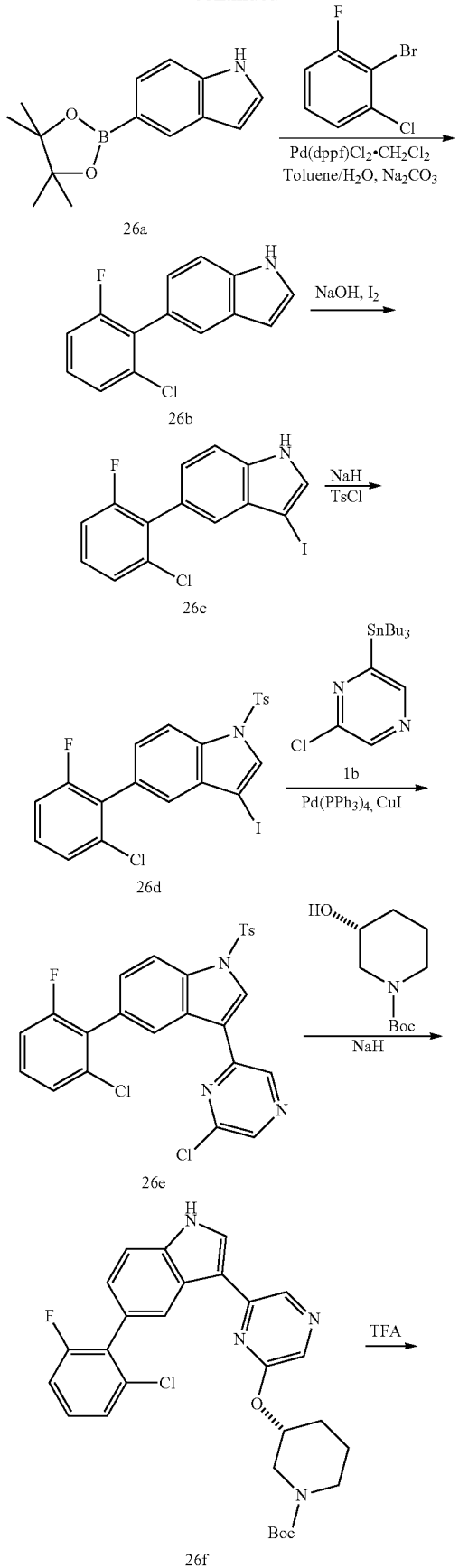

-continued

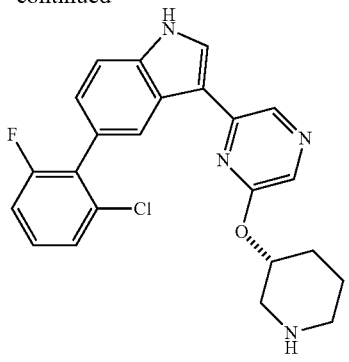

26

Preparation of Compound 26a: 5-(4,4,5,5-tetramethyl-1,3,2-dioxaborolan-2-yl)-1H-indole To 5-bromoindole (50 g, 0.26 mol) in DMF (500 mL) was added bis(pinacolato)diborane (97.2 g, 0.38 mol), potassium acetate (124.9 g, 1.28 mol) and Pd(dppf)Cl$_2$.DCM complex (2.8 g, 0.004 mol). The reaction mixture was degasified 2-3 times and heated at 90° C. for 16 h by maintaining argon atmosphere. The reaction mixture was warmed to RT. The resulting mixture was added water and extracted with Et$_2$O. The organic layer was separated and aqueous layer was extracted with Et$_2$O again. Combined organic layers was dried over anhydrous Na$_2$SO$_4$ and concentrated to obtain semi solid mixture, which was purified by column chromatography using EtOAc and hexane (50:50 ratio) to obtain the title compound (25 g, 40%). MS (ESI, m/z): 244.1 (M+1).

Preparation of Compound 26b: 5-(2-chloro-6-fluorophenyl)-1H-indole

This title compound was prepared analogously to compound 25b using 2-bromo-1-chloro-3-fluorobenzene (39.5 g, 0.19 mol) and 5-(4,4,5,5-tetramethyl-1,3,2-dioxaborolan-2-yl)-1H-indole (37.0 g, 0.15 mol). The title compound (23.1 g, 62%) was obtained. MS (ESI, m/z): 246.0 (M+1).

Preparation of Compound 26c: 5-(2-chloro-6-fluorophenyl)-3-iodo-1H-indole

This title compound was prepared analogously to compound 25c using 5-(2-chloro-6-fluorophenyl)-1H-indole (15 g, 0.06 mol) and I$_2$ (17.1 g, 0.15 mol) to obtain the crude title compound (23 g). MS (ESI, m/z): 370.8 (M+1).

Preparation of Compound 26d: 5-(2-chloro-6-fluorophenyl)-3-iodo-1-tosyl-1H-indole This title compound was prepared analogously to compound 25d using 5-(2-chloro-6-fluorophenyl)-3-iodo-1H-indole (23 g, 0.07 mol) and tosyl chloride (17.7 g, 0.09 mol) to obtain the title compound (17.2 g, 46%).

Preparation of Compound 26e: 5-(2-chloro-6-fluorophenyl)-3-(6-chloropyrazin-2-yl)-1-tosyl-1H-indole Argon was bubbled through a slurry of CuI (0.036 g, 0.190 mmol), Pd(PPh$_3$)$_4$ (0.110 g, 0.095 mmol), 2-chloro-6-(tributylstannyl)pyrazine (1.151 g, 2.85 mmol), 5-(2-chloro-6-fluorophenyl)-3-iodo-1-tosyl-1H-indole (1.00 g, 1.902 mmol) in 9 mL DMF for 2 min. The reaction was sealed and heated to 105° C. for 2 h. The reaction was cooled and partitioned between EtOAc and water. The organic layer was washed 1× brine, dried over Na$_2$SO$_4$, filtered, and concentrated in vacuo. The material was treated with DCM and purified by silica gel chromatography (80 g column) using 0-30% EtOAc/hexane. The product-containing fractions were concentrated to afford 5-(2-chloro-6-fluorophenyl)-3-(6-chloropyrazin-2-yl)-1-tosyl-1H-indole (0.88 g, 1.72 mmol, 91% yield) as a light-yellow solid. MS (ESI, pos. ion) m/z: 512 (M+1).

Preparation of Compound 26f: (R)-tert-butyl 3-(6-(5-(2-chloro-6-fluorophenyl)-1H-indol-3-yl)pyrazin-2-yloxy)piperidine-1-carboxylate To a slurry of NaH 60% in mineral oil (0.047 g, 1.171 mmol) in 2 mL DMF at 0° C. was added (R)-tert-butyl 3-hydroxypiperidine-1-carboxylate (0.236 g, 1.171 mmol). The reaction was warmed to RT. After 10 min, solid 5-(2-chloro-6-fluorophenyl)-3-(6-chloropyrazin-2-yl)-1-tosyl-1H-indole (0.200 g, 0.390 mmol) was added and the reaction became dark brown. After 30 min, the reaction was sealed and heated to 80° C. overnight. Additional NaH 60% in mineral oil (0.047 g, 1.171 mmol) and (R)-tert-butyl 3-hydroxypiperidine-1-carboxylate (0.236 g, 1.171 mmol) were added, the reaction was sealed, and heated to 120° C. for 1 h. The reaction was cooled and treated with ice, water, and EtOAc, and the aqueous layer was acidified with 1N aqueous HCl. The aqeuous layer was extracted 2×EtOAc, and the combined organics were washed 1× water, 1× brine, dried over Na$_2$SO$_4$, filtered, and concentrated in vacuo. The material was treated with DCM and purified by silica gel chromatography (40 g column) using 0-60% EtOAc/hexane. The product-containing fractions were concentrated to afford (R)-tert-butyl 3-(6-(5-(2-chloro-6-fluorophenyl)-1H-indol-3-yl)pyrazin-2-yloxy)piperidine-1-carboxylate (0.077 g, 0.147 mmol, 37.7% yield) as a light-yellow oil. MS (ESI, pos. ion) m/z: 523 (M+1).

Preparation of Compound 26: (R)-5-(2-chloro-6-fluorophenyl)-3-(6-(piperidin-3-yloxy)pyrazin-2-yl)-1H-indole bis(2,2,2-trifluoroacetate)

To a solution of (R)-tert-butyl 3-(6-(5-(2-chloro-6-fluorophenyl)-1H-indol-3-yl)pyrazin-2-yloxy)piperidine-1-carboxylate (0.077 g, 0.147 mmol) in 1.5 mL DCM was added TFA (0.170 mL, 2.208 mmol). After 30 min, the reaction was concentrated in vacuo, taken up in DMSO, and purified by RPHPLC, 10-100% ACN/H2O with 0.1% TFA; product-containing fractions were combined and concentrated in vacuo to give (R)-5-(2-chloro-6-fluorophenyl)-3-(6-(piperidin-3-yloxy)pyrazin-2-yl)-1H-indole bis(2,2,2-trifluoroacetate) as an orange solid. MS (ESI, pos. ion) m/z: 423 (M+1).

Example 27

1-(6-(5-(2-chloro-6-fluorophenyl)-1H-indol-3-yl)pyrazin-2-yl)piperidin-4-amine bis(2,2,2-trifluoroacetate)

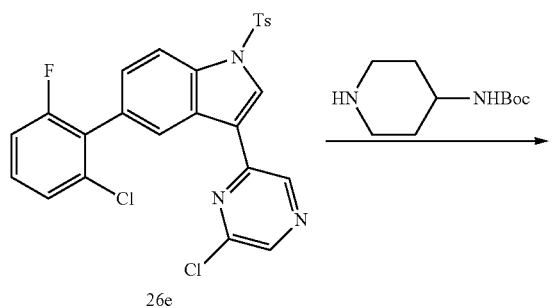

26e

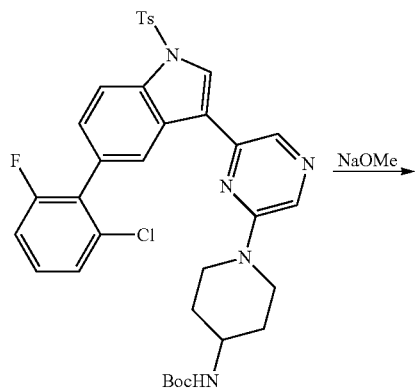

27a

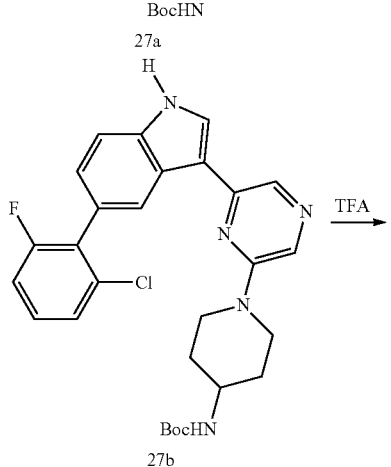

27b

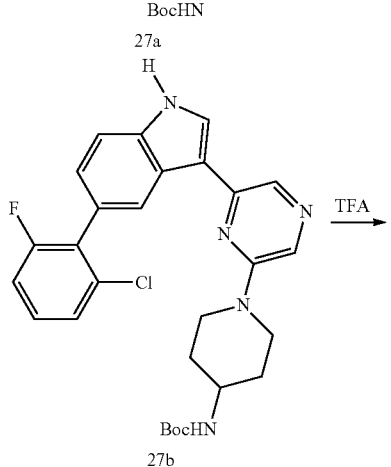

27

Preparation of Compound 27a: tert-butyl 1-(6-(5-(2-chloro-6-fluorophenyl)-1-tosyl-1H-indol-3-yl)pyrazin-2-yl)piperidin-4-ylcarbamate A slurry of 5-(2-chloro-6-fluorophenyl)-3-(6-chloropyrazin-2-yl)-1-tosyl-1H-indole (Ref, 0.200 g, 0.390 mmol) and tert-butyl piperidin-4-ylcarbamate (Combi-blocks Inc., 0.313 g, 1.561 mmol) in 2 mL DMSO in a sealed tube was heated to 130° C. The solids dissolved and the reaction became a yellow solution. After 1 h, reaction was complete by LCMS. The reaction was cooled and partitioned between water and EtOAc. The organic layer was washed with water once, satd $NaHCO_3$ once, satd NaCl once, and the organics were dried over anhydrous $Na_2SO_4$, filtered, and concentrated in vacuo. The residue was suspended in MeOH and filtered, rinsing 1×1 mL MeOH. The solid was collected and dried in vacuo to give tert-butyl 1-(6-(5-(2-chloro-6-fluorophenyl)-1-tosyl-1H-indol-3-yl)pyrazin-2-yl)piperidin-4-ylcarbamate (0.186 g, 0.275 mmol, 70.5% yield) as a light yellow solid. MS (ESI, pos. ion) m/z: 676 (M+1).

Preparation of Compound 27b: tert-butyl 1-(6-(5-(2-chloro-6-fluorophenyl)-1H-indol-3-yl)pyrazin-2-yl)piperidin-4-ylcarbamate To a slurry of tert-butyl 1-(6-(5-(2-chloro-6-fluorophenyl)-1-tosyl-1H-indol-3-yl)pyrazin-2-yl)piperidin-4-ylcarbamate (0.186 g, 0.275 mmol) in 2 mL MeOH was added sodium methanolate 25 wt % in MeOH (0.126 mL, 0.550 mmol). 2 mL THF was added. The cloudy mixture was sealed and stirred rapidly. After 1 h, additional sodium methanolate 25 wt % in MeOH (0.126 mL, 0.550 mmol) was added. The reaction became a clear, orange solution. After 2 h, the reaction was concentrated under a stream of $N_2$, and the solid was partitioned between saturated aqueous $NH_4Cl$ and DCM. 1 mL 1N HCl was added to acidify the aqueous layer. The aqueous layer was extracted with DCM 3 times, and the combined organics were dried over anhydrous $Na_2SO_4$, filtered, and concentrated in vacuo. The material was treated with DCM/MeOH and adsorbed onto 1.5 g silica gel, dried, and purified by silica gel chromatography (40 g column) using 20-80% EtOAc/hexane. The product-containing fractions were concentrated to afford tert-butyl 1-(6-(5-(2-chloro-6-fluorophenyl)-1H-indol-3-yl)pyrazin-2-yl)piperidin-4-ylcarbamate (0.104 g, 0.199 mmol, 72.4% yield) as a orange solid. MS (ESI, pos. ion) m/z: 522 (M+1).

Preparation of Compound 27: 1-(6-(5-(2-chloro-6-fluorophenyl)-1H-indol-3-yl)pyrazin-2-yl)piperidin-4-amine bis(2,2,2-trifluoroacetate)

A solution of tert-butyl 1-(6-(5-(2-chloro-6-fluorophenyl)-1H-indol-3-yl)pyrazin-2-yl)piperidin-4-ylcarbamate (0.104 g, 0.199 mmol) in 2 mL DCM and TFA (0.153 mL, 1.992 mmol) was stirred for 1 h. Additional TFA (0.153 mL, 1.992 mmol) was added. After 1 h additional, the reaction was concentrated, and the material suspended in $Et_2O$ to give a solid. The solid was collected by filtration, and was dried in vacuo overnight, to give 1-(6-(5-(2-chloro-6-fluorophenyl)-1H-indol-3-yl)pyrazin-2-yl)piperidin-4-amine bis(2,2,2-trifluoroacetate) as a yellow solid. MS (ESI, pos. ion) m/z: 422 (M+1).

Example 28

4-(5-(6-(1-methylethoxy)-2-pyrazinyl)-1H-indol-3-yl)-2-pyridinamine

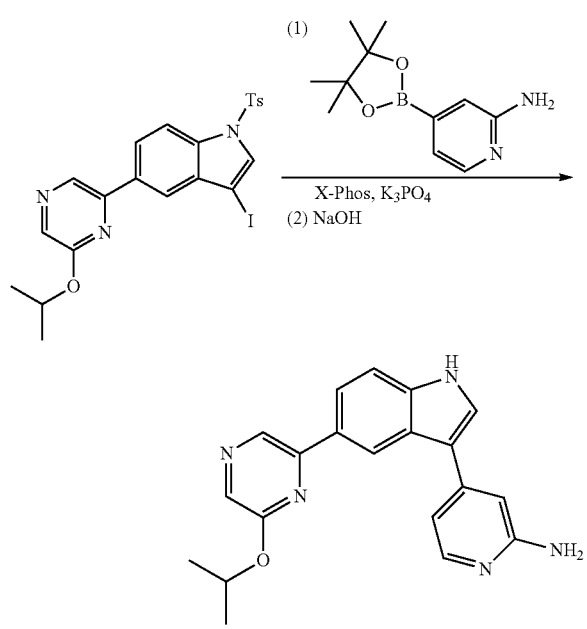

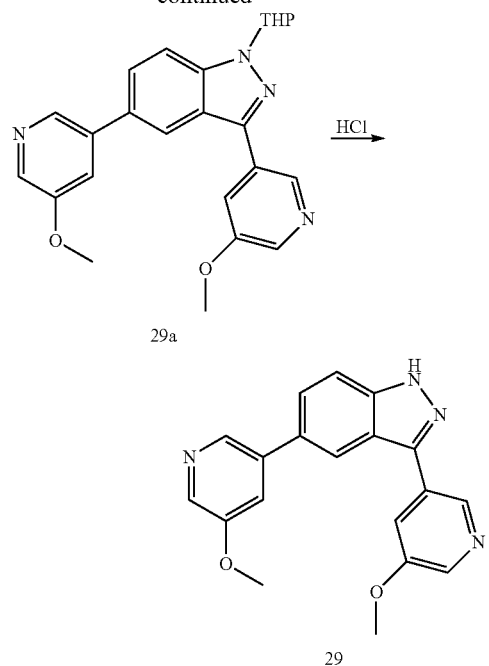

A solution of 3-iodo-5-(6-isopropoxypyrazin-2-yl)-1-tosyl-1H-indole (0.060 g, 0.11 mmol), 4-(4,4,5,5-tetramethyl-1,3,2-dioxaborolan-2-yl)pyridin-2-amine (39, 0.17 mmol), Potassium Phosphate (0.072 g, 0.34 mmol), Pd$_2$dba$_3$ (5 mg, 6 μmol), X-Phos (5 mg, 0.011 mmol), and dioxane/water (2/1, 1.5 mL) was heated in a microwave at 125° C. for 10 min. The solution was cooled, the aqueous layer was removed, and the organic layer was purified by prep HPLC (66-95% ACN/water/0.1% TFA). The resulting product was dissolved in dioxane (1 mL), 1M NaOH (0.2 mL) was added, and the mixture was heated in a microwave at 130° C. for 10 min. The resulting solution was purified by preparative HPLC (10-90% ACN/water/0.1% TFA) to give 4-(5-(6-(1-methylethoxy)-2-pyrazinyl)-1H-indol-3-yl)-2-pyridinamine. MS (ESI, pos. ion) m/z: 346 (M+1).

Example 29

3,5-Bis(5-methoxypyridin-3-yl)-1H-indazole

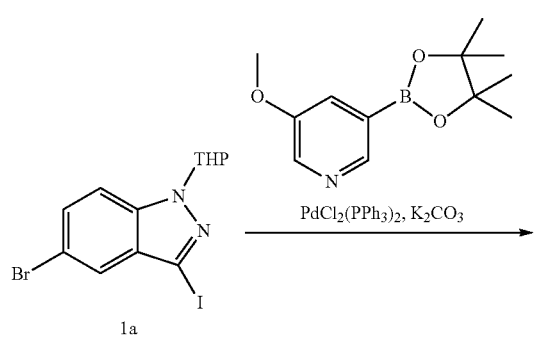

Preparation of Compound 29a: 3,5-Bis(5-methoxy-pyridin-3-yl)-1-(tetrahydro-2H-pyran-2-yl)-1H-indazole A glass microwave reaction vessel was charged with 5-bromo-3-iodo-1-(tetrahydro-2H-pyran-2-yl)-1H-indazole (0.419 g, 1.029 mmol), 5-methoxy-3-pyridineboronic acid pinacol ester (0.924 g, 3.93 mmol, Aldrich), potassium carbonate (1.124 g, 8.13 mmol, Aldrich) and Pd(PPh$_3$)$_4$ (0.114 g, 0.099 mmol, Strem). Toluene (10 mL) was added and the reaction mixture was sealed under argon and heated at 100° C. overnight. The reaction mixture was further heated in the Emrys Optmizer microwave reactor (Personal Chemistry, Biotage AB, Inc., Uppsala, Sweden) at 140° C. for 20 min. The reaction mixture was partitioned between DCM/water and the aqueous layer was extracted with DCM (3x). The combined organic layers were washed with brine, evaporated onto silica gel and purified by flash chromatography (Isco, (40 gram)) eluting with 2M NH$_3$ in MeOH:DCM (0:1→3:97) to give a yellow oil that was carried onto the next step.

Preparation of Compound 29: 3,5-Bis(5-methoxypyridin-3-yl)-1H-indazole

A mixture of 3,5-bis(5-methoxypyridin-3-yl)-1-(tetrahydro-2H-pyran-2-yl)-1H-indazole (0.429 g, 1.029 mmol) and HCl, 5-6 N in IPA (10 mL, 50.0 mmol) was heated at 50° C. for 2.5 h. The reaction was cooled to RT and the solvent was removed in vacuo. The material was basified with 5 N NaOH and diluted with MeOH. The solution was purified by reverse-phase HPLC (Gilson; Gemini-NX 14, C18 110 A AXIA, 100×50 mm column) eluting with 0.1% TFA-H$_2$O:0.1% TFA ACN (9:1→1:9). The fractions containing the desired product were combined and concentrated in vacuo to give a white crystalline solid. m/z: 333.2 (M+1).

Example 30

1-(4-(5-(5-Methoxypyridin-3-yl)-1H-indazol-3-yl)pyrimidin-2-yl)piperidin-4-amine

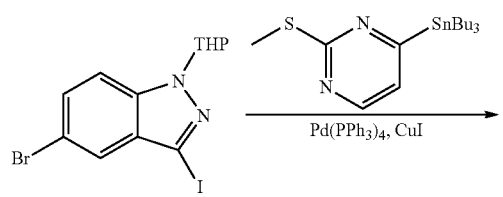

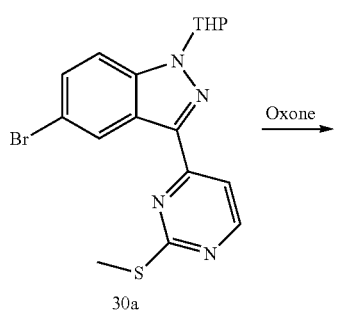

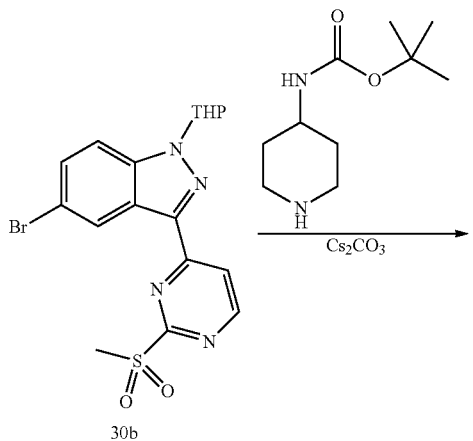

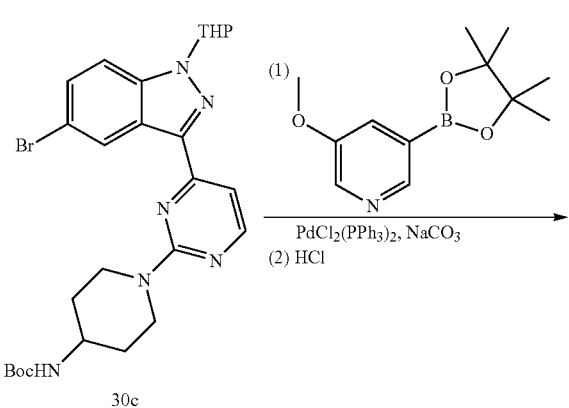

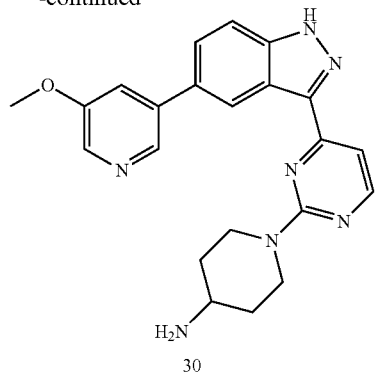

Preparation of Compound 30a: 5-Bromo-3-(2-(methylthio)pyrimidin-4-yl)-1-(tetrahydro-2H-pyran-2-yl)-1H-indazole A glass microwave reaction vessel was charged with 5-bromo-3-iodo-1-(tetrahydro-2H-pyran-2-yl)-1H-indazole (2.04 g, 5.01 mmol), Pd(PPh$_3$)$_4$ (0.555 g, 0.480 mmol), CuI (0.130 g, 0.683 mmol) and 2-(methylthio)-4-(tributylstannyl)pyrimidine (2.23 g, 5.37 mmol, Frontier Scientific). DMF (6 mL) was added and the reaction mixture was sealed under argon and heated thermally at 100° C. for 6.5 h. The solvent was removed in vacuo and the residue was dissolved in MeOH, evaporated onto silica gel and purified by flash chromatography (Isco, (80 gram)) eluting with 2M NH$_3$ in MeOH:DCM (0:1→1:19) to give 855 mg of a tan amorphous solid. m/z: 405.0 [M+1].

Preparation of Compound 30b: 5-Bromo-3-(2-(methylsulfonyl)pyrimidin-4-yl)-1-(tetrahydro-2H-pyran-2-yl)-1H-indazole To a RT slurry of 5-bromo-3-(2-(methylthio)pyrimidin-4-yl)-1-(tetrahydro-2H-pyran-2-yl)-1H-indazole (0.855 g, 2.109 mmol) in MeOH (40 mL) was added oxone, monopersulfate compound (6.46 g, 10.51 mmol, Aldrich) and the reaction was stirred overnight. The reaction mixture was concentrated to ~50% volume and diluted with water. The slurry was neutralized with 5 N NaOH and the solids were filtered, washed consecutively with water and MeOH, and dried in vacuo to give 795 mg of a light-yellow amorphous solid. m/z: 437.9, 439.0 [M+1].

Preparation of Compound 30c: tert-Butyl 1-(4-(5-bromo-1-(tetrahydro-2H-pyran-2-yl)-1H-indazol-3-yl)pyrimidin-2-yl)piperidin-4-ylcarbamate A glass microwave reaction vessel was charged with 5-bromo-3-(2-(methylsulfonyl)pyrimidin-4-yl)-1-(tetrahydro-2H-pyran-2-yl)-1H-indazole (0.795 g, 1.818 mmol), 4-Boc-aminopiperidine (0.665 g, 3.32 mmol, Combi-Blocks) and cesium carbonate (1.147 g, 3.52 mmol). DMF (4 mL) was added and the reaction mixture was sealed under argon and heated at 90° C. overnight. The reaction mixture was partitioned between DCM/brine and the aqueous layer was extracted with DCM (3×). The combined organic layers were, evaporated onto silica gel and purified by flash chromatography (Isco (80 gram)) eluting with EtOAc:hexanes (0:1→1:3) to give 360 mg (35%) of a white amorphous solid. m/z: 557.0 [M+1].

121

Preparation of Compound 30: 1-(4-(5-(5-Methoxy-pyridin-3-yl)-1H-indazol-3-yl)pyrimidin-2-yl)piperidin-4-amine A glass microwave reaction vessel was charged with tert-butyl 1-(4-(5-bromo-1-(tetrahydro-2H-pyran-2-yl)-1H-indazol-3-yl)pyrimidin-2-yl)piperidin-4-ylcarbamate (0.305 g, 0.547 mmol), 3-methoxypyridine-5-boronic acid pinacol ester (0.232 g, 0.987 mmol, Frontier Scientific), $Na_2CO_3$ (0.356 g, 3.36 mmol) and trans-dichlorobis(triphenyl-phosphine)palladium (II) (0.056 g, 0.080 mmol). Water (2 mL) and dioxane (5 mL) were added and the reaction mixture was sealed under argon and heated in an Emrys Optmizer microwave reactor (Personal Chemistry, Biotage AB, Inc., Uppsala, Sweden) at 145° C. for 20 min. The reaction mixture was partitioned between DCM/brine and the aqueous layer was extracted with DCM (3×). The combined organic layers were evaporated onto silica gel and purified by flash chromatography (Isco, (40 gram)) eluting with 2M $NH_3$ in MeOH:DCM (0:1→1:39) to give a white amorphous solid. The material was heated at 50° C. for 5 h in the presence of HCl, 5-6N in IPA (10 mL, 50.0 mmol). The mixture was cooled to RT and the solvent was removed in vacuo. The residue was dissolved in DMSO and purified by reverse-phase HPLC (Gilson; Gemini-NX 10μ C18 110 A AXIA, 100×50 mm column) eluting with 0.1% TFA-$H_2O$:0.1% TFA ACN (9:1→1:9). The fractions containing the desired product were combined and concentrated in vacuo to give an off-white amorphous solid. m/z: 402.2 [M+1].

Example 31

1-(5-(5-(5-Methoxypyridin-3-yl)-1H-indazol-3-yl)thiazol-2-yl)piperidin-4-amine

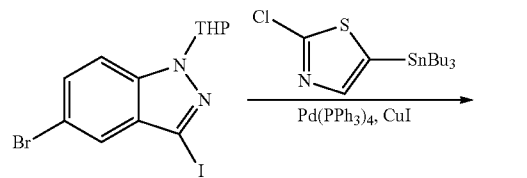

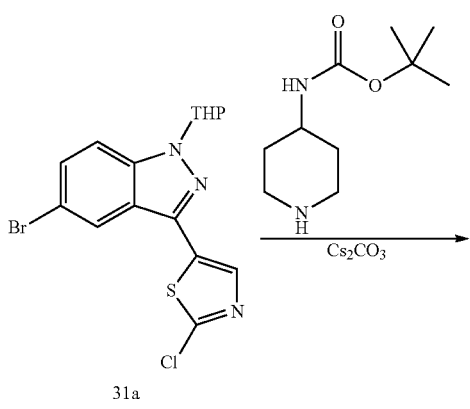

31a

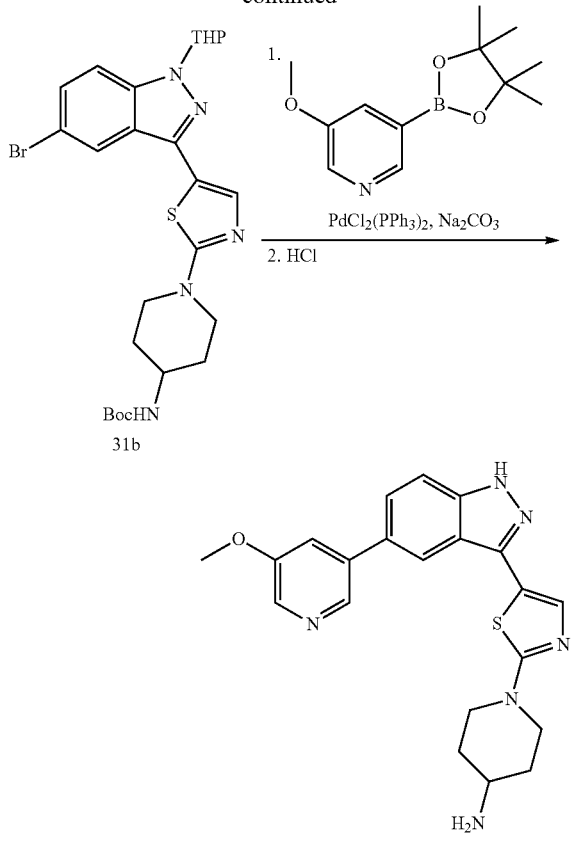

Preparation of Compound 31a: 5-(5-Bromo-1-(tetrahydro-2H-pyran-2-yl)-1H-indazol-3-yl)-2-chlorothiazole The title compound was prepared analogously to compound 30a, using 5-bromo-3-iodo-1-(tetrahydro-2H-pyran-2-yl)-1H-indazole (2.56 g, 6.29 mmol), 2-chloro-5-(tributylstannyl)thiazole (2.955 g, 7.23 mmol, Synthonix), CuI (0.12 g, 0.630 mmol) and Pd(PPh$_3$)$_4$ (0.74 g, 0.640 mmol). Purification by flash chromatography (Isco, (120 gram)) eluting with 2M $NH_3$ in MeOH:DCM (0:1→1:99) gave 2.12 g (85%) of a white amorphous solid. m/z: 397.8, 399.8 [M+1].

Preparation of Compound 31b: tert-Butyl 1-(5-(5-bromo-1-(tetrahydro-2H-pyran-2-yl)-1H-indazol-3-yl)thiazol-2-yl)piperidin-4-ylcarbamate The title compound was prepared analogously to compound 30c, using 5-(5-bromo-1-(tetrahydro-2H-pyran-2-yl)-1H-indazol-3-yl)-2-chlorothiazole (1.00 g, 2.508 mmol), 4-boc-aminopiperidine (0.927 g, 4.63 mmol, Combi-Blocks) and cesium carbonate (1.67 g, 5.13 mmol). Purification by flash chromatography (Isco, (120 gram)) eluting with 2M $NH_3$ in MeOH:DCM (0:1→1:39) gave a yellow amorphous solid. m/z: 562.1, 564.0 [M+1].

Preparation of Compound 31: 1-(5-(5-(5-Methoxypyridin-3-yl)-1H-indazol-3-yl)thiazol-2-yl)piperidin-4-amine TFA salt The title compound was prepared analogously to compound 30 using tert-butyl 1-(5-(5-bromo-1-(tetrahydro-2H- pyran-2-yl)-1H-indazol-3-yl)thiazol-2-yl)piperidin-4-ylcarbamate (0.400 g, 0.711 mmol), 3-methoxypyridine-5-boronic acid pinacol ester (0.262 g, 1.114 mmol, Frontier Scientific), $Na_2CO_3$ (0.412 g, 3.89 mmol) and trans-dichlorobis(triphenyl-phosphine)palladium (II) (0.052 g, 0.074 mmol). Purification by reverse-phase HPLC (Gilson; Gemini-NX 10μ C18 110 A AXIA, 100×50 mm column) eluting with 0.1% TFA-$H_2O$:0.1% TFA $CH_3CN$ (9:1→1:9). The fractions containing the desired product were combined and concentrated in vacuo to give a light-yellow amorphous solid. m/z: 407.1 [M+1].

Example 32

1-(5-(5-(2,6-difluorophenyl)-1H-pyrrolo[3,2-b]pyridin-3-yl)pyridin-3-yl)piperidin-4-amine

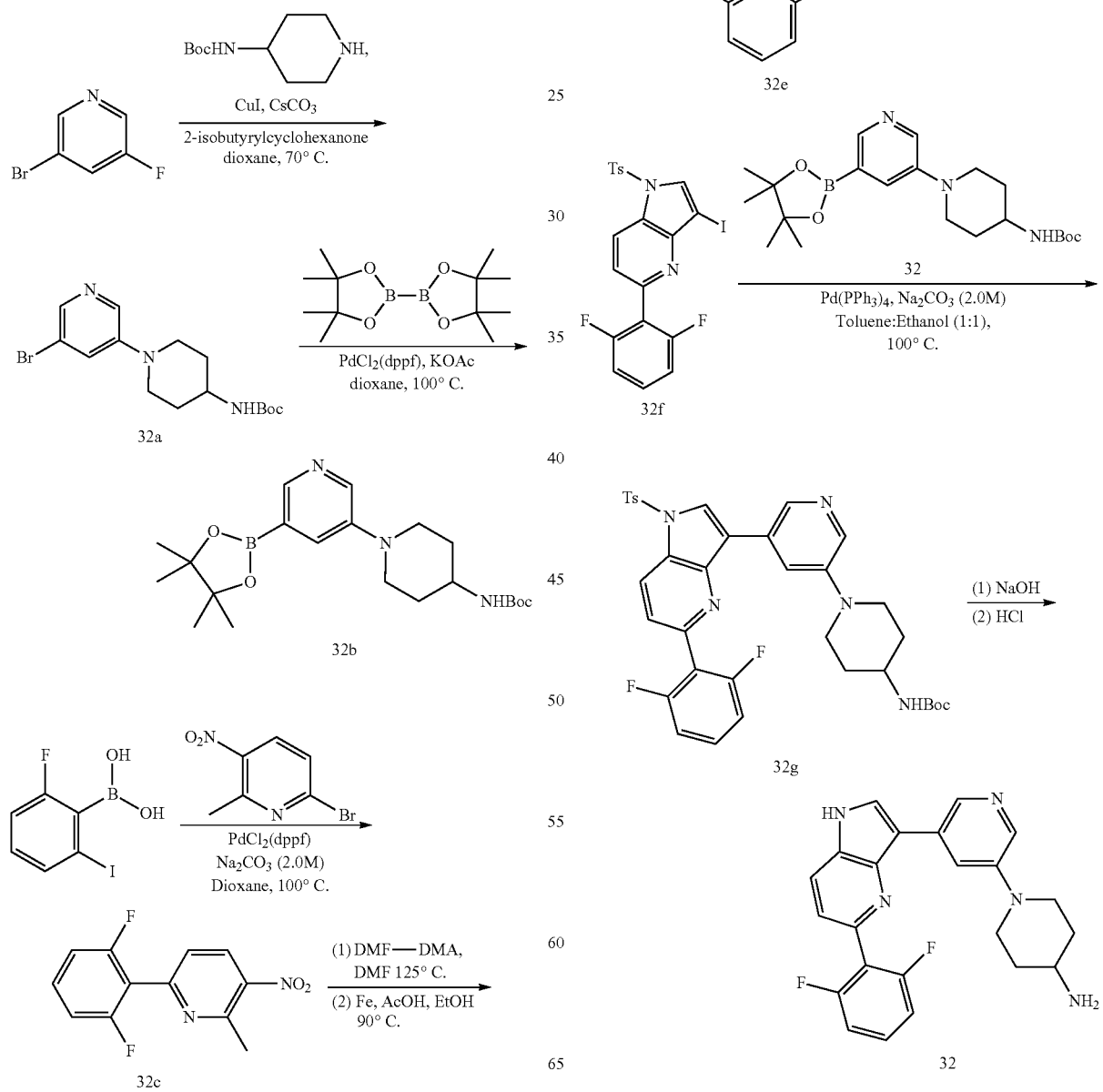

Preparation of Compound 32a: tert-butyl 1-(5-bromopyridin-3-yl)piperidin-4-ylcarbamate A mixture of 3-bromo-5-iodopyridine (600 mg, 2.113 mmol, Aldrich), 4-(n-boc-amino)-piperidine (466 mg, 2.325 mmol, Aldrich), CuI (40.3 mg, 0.211 mmol, Aldrich) and cesium carbonate (1377 mg, 4.23 mmol, Strem) was capped, degassed and backfilled with argon (3×). Dioxane (2 mL) and 2-isobutyrylcyclohexanone (0.141 mL, 0.845 mmol, Aldrich) were added, and the reaction was stirred at 70° C. After 43 h, the reaction mixture was cooled to 23° C., diluted with EtOAc (50 mL) and washed with brine (50 mL), dried over $MgSO_4$, concentrated in vacuo and purified by silica gel chromatography (eluent: 15-40% EtOAc/hexane), affording tert-butyl 1-(5-bromopyridin-3-yl)piperidin-4-ylcarbamate (198 mg, 26%). MS (ESI, pos. ion) m/z: 356.0 (M+1), 358.0 (M+3).

Preparation of Compound 32b: tert-butyl 1-(5-(4,4,5,5-tetramethyl-1,3,2-dioxaborolan-2-yl)pyridin-3-yl)piperidin-4-ylcarbamate A suspension of tert-butyl 1-(5-bromopyridin-3-yl)piperidin-4-ylcarbamate (109 mg, 0.306 mmol), bis(pinacolato)diboron (93 mg, 0.367 mmol, Aldrich), potassium acetate (120 mg, 1.224 mmol, Aldrich) and dichloro 1,1'-bis(diphenylphosphino)ferrocene palladium (II) (24.99 mg, 0.031 mmol, Strem) in Dioxane (2 mL) was capped, degassed and backfilled with argon (3×). The reaction was heated at 100° C. After 21 h, the reaction was cooled to 23° C., and filtered through celite. The filtrate was concentrated, affording the crude product as a dark brown solid. LCMS showed a peak at 322—corresponding to the desired product boronic acid (M+=321). Co-elutes with M+H=278, which is debrominated S.M. The crude boronate mixture was taken forward to Suzuki reaction.

Preparation of Compound 32c: 6-(2,6-difluorophenyl)-2-methyl-3-nitropyridine A suspension of 2-bromo-6-methyl-5-nitropyridine (3 g, 13.82 mmol, Matrix Scientific), 2,6-difluorobenzeneboronic acid (4.37 g, 27.6 mmol, Alfa Aesar) and [1,1'-bis(diphenylphosphino)ferrocene]dichloropalladium(II), complex with DCM (0.564 g, 0.691 mmol, Strem) in Dioxane (60 mL) (degassed with argon for 30 min) and $Na_2CO_3$, 2.0 M (20.74 mL, 41.5 mmol) was heated to 100° C. under $N_2$. After 3 h, 2,6-difluorobenzeneboronic acid (4.37 g, 27.6 mmol) was further added. After a total of 7 h, 2,6-difluorobenzeneboronic acid (2.18 g, 13.8 mmol) was further added. After a total of 9 h, the reaction mixture was cooled to 23° C., diluted with EtOAc (400 ml) and washed with brine (200 mL), dried over $MgSO_4$, concentrated in vacuo and purified by silica gel chromatography (eluent: 5-10% EtOAc/hexane), affording 6-(2,6-difluorophenyl)-2-methyl-3-nitropyridine (1.931 g, 56%).

Preparation of Compound 32d: 5-(2,6-difluorophenyl)-1H-pyrrolo[3,2-b]pyridine A solution of 6-(2,6-difluorophenyl)-2-methyl-3-nitropyridine (1.929 g, 7.71 mmol) in DMF (25 mL) was treated with n,n-dimethylformamide dimethyl acetal (1.331 mL, 10.02 mmol). The reaction was heated to 125° C. under $N_2$. After 3 h, the reaction was cooled to 23° C., diluted with EtOAc (200 ml) and washed with brine (150 ml), dried over $MgSO_4$, concentrated in vacuo, affording a purple solid that was carried forward to the next step without further manipulation. A suspension of that solid in ethanol (40.0 mL) and acetic acid (40 mL) was treated with iron powder—325 mesh (4.31 g, 77 mmol, Aldrich). The reaction was heated to 90° C. under $N_2$. After 2 h, the reaction was cooled to 23° C., filtered through Celite, concentrated in vacuo and purified by silica gel chromatography (eluent: 0.5-3% MeOH/DCM), affording 5-(2,6-difluorophenyl)-1H-pyrrolo[3,2-b]pyridine (1.271 g, 72%).

Preparation of Compound 32e: 5-(2,6-difluorophenyl)-3-iodo-1H-pyrrolo[3,2-b]pyridine A solution of 5-(2,6-difluorophenyl)-1H-pyrrolo[3,2-b]pyridine (700 mg, 3.04 mmol) in THF (25 mL) was treated with n-iodosuccinimide (753 mg, 3.34 mmol, Alfa-Aesar). The reaction was stirred at 23° C. under $N_2$. After 30 min, the solution was diluted with EtOAc (250 ml) and washed with brine (175 ml), dried over $MgSO_4$, concentrated in vacuo and purified by silica gel chromatography (eluent: 15-40% EtOAc/hexane), affording 5-(2,6-difluorophenyl)-3-iodo-1H-pyrrolo[3,2-b]pyridine (255 mg, 78%). MS (ESI, pos. ion) m/z: 356.9 (M+1).

Preparation of Compound 32f: 5-(2,6-difluorophenyl)-3-iodo-1-tosyl-1H-pyrrolo[3,2-b]pyridine A solution of 5-(2,6-difluorophenyl)-3-iodo-1H-pyrrolo[3,2-b]pyridine (657 mg, 1.845 mmol) in THF (18 mL) was treated with 4-toluenesulfonyl chloride (387 mg, 2.029 mmol, Aldrich) and solid NaOH (89 mg, 2.214 mmol, VWR). The reaction was stirred at 23° C. under $N_2$. After 45 min, the solution was diluted with EtOAc (200 ml) and washed with brine (150 mL), dried over $MgSO_4$, concentrated in vacuo and purified by silica gel chromatography (eluent: 10-30% EtOAc/hexane), affording 5-(2,6-difluorophenyl)-3-iodo-1-tosyl-1H-pyrrolo[3,2-b]pyridine.

Preparation of Compound 32 g: tert-butyl 1-(5-(5-(2,6-difluorophenyl)-1-tosyl-1H-pyrrolo[3,2-b]pyridin-3-yl)pyridin-3-yl)piperidin-4-ylcarbamate A solution of 5-(2,6-difluorophenyl)-3-iodo-1-tosyl-1H-pyrrolo[3,2-b]pyridine (92 mg, 0.180 mmol), crude tert-butyl 1-(5-(4,4,5,5-tetramethyl-1,3,2-dioxaborolan-2-yl)pyridin-3-yl)piperidin-4-ylcarbamate (127 mg, 0.316 mmol) and $Pd(PPh_3)_4$ (20.83 mg, 0.018 mmol, Strem) in toluene (1 mL) and Ethanol (1.000 mL) was treated with $Na_2CO_3$, 2.0 M (0.180 mL, 0.361 mmol). The reaction vessel was capped, degassed and backfilled with argon; and the reaction was heated to 100° C. After 20 h, the solution was cooled to 23° C., diluted with EtOAc (100 mL) and washed with brine (75 mL), dried over $MgSO_4$, concentrated in vacuo and purified by silica gel chromatography (eluent: 30-90% EtOAc/hexane), affording tert-butyl 1-(5-(5-(2,6-difluorophenyl)-1-tosyl-1H-pyrrolo[3,2-b]pyridin-3-yl)pyridin-3-yl)piperidin-4-ylcarbamate (85 mg, 71%). MS (ESI, pos. ion) m/z: 660.4 (M+1).

Preparation of Compound 32: 1-(5-(5-(2,6-difluorophenyl)-1H-pyrrolo[3,2-b]pyridin-3-yl)pyridin-3-yl)piperidin-4-amine A solution of tert-butyl 1-(5-(5-(2,6-difluorophenyl)-1-tosyl-1H-pyrrolo[3,2-b]pyridin-3-yl)pyridin-3-yl)piperidin-4-ylcarbamate (79 mg, 0.120 mmol, 88% pure) in THF (2 mL) was treated with NaOH 5M (0.048 mL, 0.239 mmol). The reaction mixture was heated to reflux (bath temperature 80° C.). After 1 h, NaOH 5M (0.45 mL, 0.96 mmol, 8.0 equiv) was further added. After 23 h, the solution was cooled to 23° C., concentrated in vacuo and purified by silica gel chromatography (eluent: 1-7% MeOH/DCM), affording tert-butyl 1-(5-(5-(2,6-difluorophenyl)-1H-pyrrolo[3,2-b]pyridin-3-yl)pyridin-3-yl)piperidin-4-ylcarbamate (31 mg, 51%). MS (ESI, pos. ion) m/z: 506.2 (M+1). A solution of tert-butyl 1-(5-(5-(2,6-difluorophenyl)-1H-pyrrolo[3,2-b]pyridin-3-yl)pyridin-3-yl)piperidin-4-ylcarbamate (31 mg, 0.061 mmol) in MeOH (0.5 mL) was treated with HCl, 5-6n in IPA (0.123 mL, 0.613 mmol). The reaction was heated to 50° C. under N$_2$. After 2 h, the reaction was cooled to 23° C. and the product (as HCl salt) was free-based using a Silicycle Si-propylsulfonic acid ion exchange column (catalog # R51230B). The compound was slurried in MeOH/DCM and added to a pad of the resin (wetted and flushed with 10 mL MeOH). It was flushed with MeOH (50 mL), and then the product was "released" using 2.0 M NH$_3$ in MeOH solution (50 ml). The final filtrate was concentrated, affording 1-(5-(5-(2,6-difluorophenyl)-1H-pyrrolo[3,2-b]pyridin-3-yl)pyridin-3-yl)piperidin-4-amine MS (ESI, pos. ion) m/z: 406.3 (M+1).

Example 33

5-(5-(2,6-difluorophenyl)-1H-pyrrolo[3,2-b]pyridin-3-yl)-N-(piperidin-3-yl)pyridin-3-amine

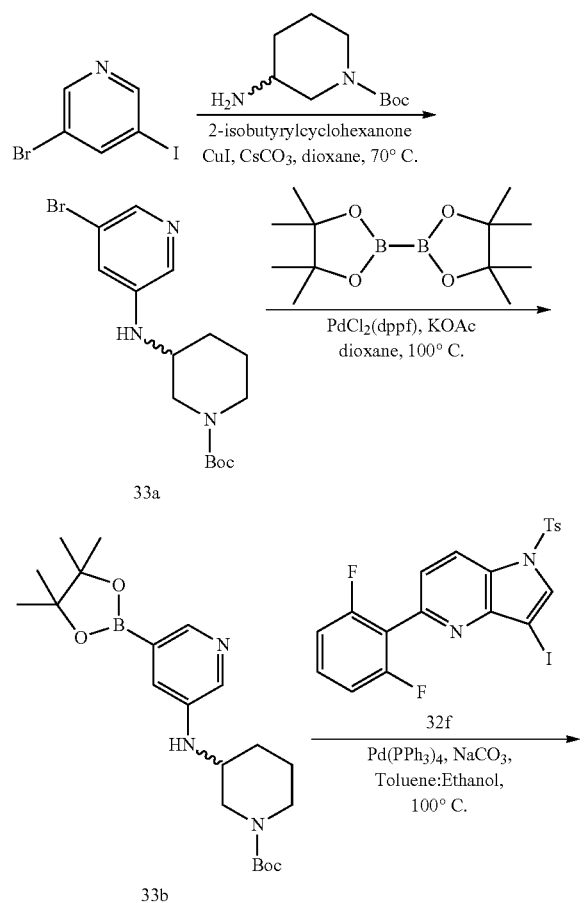

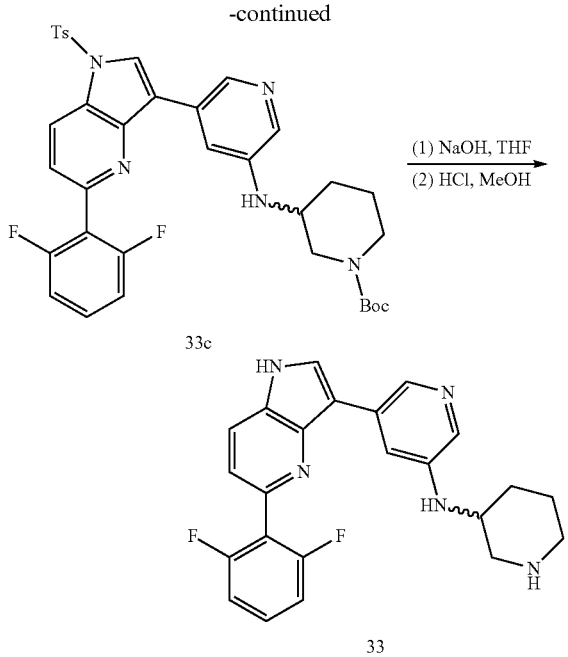

Preparation of Compound 33a: tert-butyl 3-(5-bromopyridin-3-ylamino)piperidine-1-carboxylate A mixture of 3-bromo-5-iodopyridine (500 mg, 1.761 mmol, Aldrich), tert-butyl 3-aminopiperidine-1-carboxylate (388 mg, 1.937 mmol, Combi-blocks), CuI (33.5 mg, 0.176 mmol, Aldrich) and cesium carbonate (1148 mg, 3.52 mmol, Fluka) was capped, degassed and backfilled with argon (3×). Dioxane (2 mL) and 2-isobutyrylcyclohexanone (0.118 mL, 0.704 mmol) were added, and the reaction was heated to 55° C. After 16 h, the temperature was raised to 70° C. After 60 h at 70° C., the reaction mixture was cooled to 23° C., diluted with EtOAc (75 mL) and washed with brine (50 mL), dried over MgSO$_4$, concentrated in vacuo and purified by silica gel chromatography (eluent: 25-60% EtOAc/hexane), affording tert-butyl 3-(5-bromopyridin-3-ylamino)piperidine-1-carboxylate (375 mg, 60%). MS (ESI, pos. ion) m/z: 356.1 (M+1), 358.1 (M+3).

Preparation of Compound 33b: tert-butyl 3-(5-(4,4,5,5-tetramethyl-1,3,2-dioxaborolan-2-yl)pyridin-3-ylamino)piperidine-1-carboxylate A mixture of tert-butyl 3-(5-bromopyridin-3-ylamino)piperidine-1-carboxylate (100 mg, 0.281 mmol), bis(pinacolato)diboron (86 mg, 0.337 mmol, Aldrich), dichloro 1,1'-bis(diphenylphosphino)ferrocene palladium (II) (22.92 mg, 0.028 mmol, Strem) and potassium acetate (110 mg, 1.123 mmol, Aldrich) was capped, degassed and backfilled with argon (3×). Dioxane (2 mL) was added, and the reaction was heated to 100° C. After 15 h, the reaction was cooled to 23° C., and filtered through celite. The filtrate was concentrated, affording the crude tert-butyl 3-(5-(4,4,5,5-tetramethyl-1,3,2-dioxaborolan-2-yl)pyridin-3-ylamino)piperidine-1-carboxylate (65% HPLC purity) as a dark brown solid. The crude boronate mixture was taken forward to Suzuki reaction.

Preparation of Compound 33c: tert-butyl 3-(5-(5-(2,6-difluorophenyl)-1-tosyl-1H-pyrrolo[3,2-b]pyridin-3-yl)pyridin-3-ylamino)piperidine-1-carboxylate A suspension of 5-(2,6-difluorophenyl)-3-iodo-1-tosyl-1H-pyrrolo[3,2-b]pyridine (73 mg, 0.143 mmol) and crude tert-butyl 3-(5-(4,4,5,5-tetramethyl-1,3,2-dioxaborolan-2-yl)pyridin-3-ylamino)piperidine-1-carboxylate (113 mg, 0.279 mmol) in toluene (1.000 mL) and EtOH (1 mL) was treated with Na$_2$CO$_3$, 2.0 M (0.143 mL, 0.286 mmol) and Pd(PPh$_3$)$_4$ (16.53 mg, 0.014 mmol, Strem). The reaction mixture was degassed, backfilled with argon and heated to 100° C. under N$_2$. After 15 h, the reaction was cooled to 23° C., filtered through celite, and purified by silica gel chromatography (eluent: 0.5-10% MeOH/DCM), affording tert-butyl 3-(5-(5-(2,6-difluorophenyl)-1-tosyl-1H-pyrrolo[3,2-b]pyridin-3-yl)pyridin-3-ylamino)piperidine-1-carboxylate (R$_f$=0.5 in 10% MeOH/DCM, desired product) (33 mg, 35%); along with a byproduct, tert-butyl 3-(5-(5-(2,6-difluorophenyl)-1H-pyrrolo[3,2-b]pyridin-3-yl)pyridin-3-ylamino)piperidine-1-carboxylate (R$_f$=0.2 in 10% MeOH/DCM, de-tosylated product) (31 mg, 43%). MS (ESI, pos. ion) m/z: 660.3 (M+1)

Preparation of Compound 33c: 5-(5-(2,6-difluorophenyl)-1H-pyrrolo[3,2-b]pyridin-3-yl)-N-(piperidin-3-yl)pyridin-3-amine A solution of tert-butyl 3-(5-(5-(2,6-difluorophenyl)-1-tosyl-1H-pyrrolo[3,2-b]pyridin-3-yl)pyridin-3-ylamino)piperidine-1-carboxylate (33 mg, 0.050 mmol) in THF (1 mL) was treated with NaOH 10N (0.050 mL, 0.500 mmol). The reaction was heated to reflux at 80° C. After 4 h, the solution was cooled to 23° C., concentrated in vacuo and purified by silica gel chromatography (eluent: 1-6% MeOH/DCM), affording tert-butyl 3-(5-(5-(2,6-difluorophenyl)-1H-pyrrolo[3,2-b]pyridin-3-yl)pyridin-3-ylamino)piperidine-1-carboxylate (21 mg, 83%). MS (ESI, pos. ion) m/z: 506.3 (M+1) A solution of tert-butyl 3-(5-(5-(2,6-difluorophenyl)-1H-pyrrolo[3,2-b]pyridin-3-yl)pyridin-3-ylamino)piperidine-1-carboxylate (21 mg, 0.042 mmol) in MeOH (1 mL) was treated with HCl, 5-6N in IPA (0.083 mL, 0.415 mmol). The reaction was heated to 50° After 1 h, the reaction was cooled to 23° C., and the product (as HCl salt) was free-based using a Silicycle Si-propylsulfonic acid ion exchange column (catalog # R51230B). The compound was diluted in MeOH and added to a pad of the resin (wetted and flushed with 10 mL MeOH). It was flushed with MeOH (50 mL), and then the product was "released" using 2.0 M NH$_3$ in MeOH solution (50 ml). The final filtrate was concentrated, affording 5-(5-(2,6-difluorophenyl)-1H-pyrrolo[3,2-b]pyridin-3-yl)-N-(piperidin-3-yl)pyridin-3-amine MS (ESI, pos. ion) m/z: 406.2 (M+1).

Example 34

1-(5-(5-(2-fluorophenyl)-1H-pyrrolo[3,2-t]pyridin-3-yl)pyridin-3-yl)piperidin-4-amine

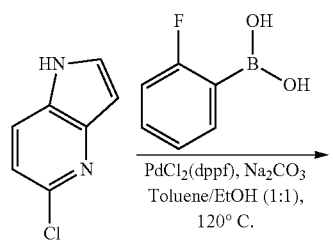

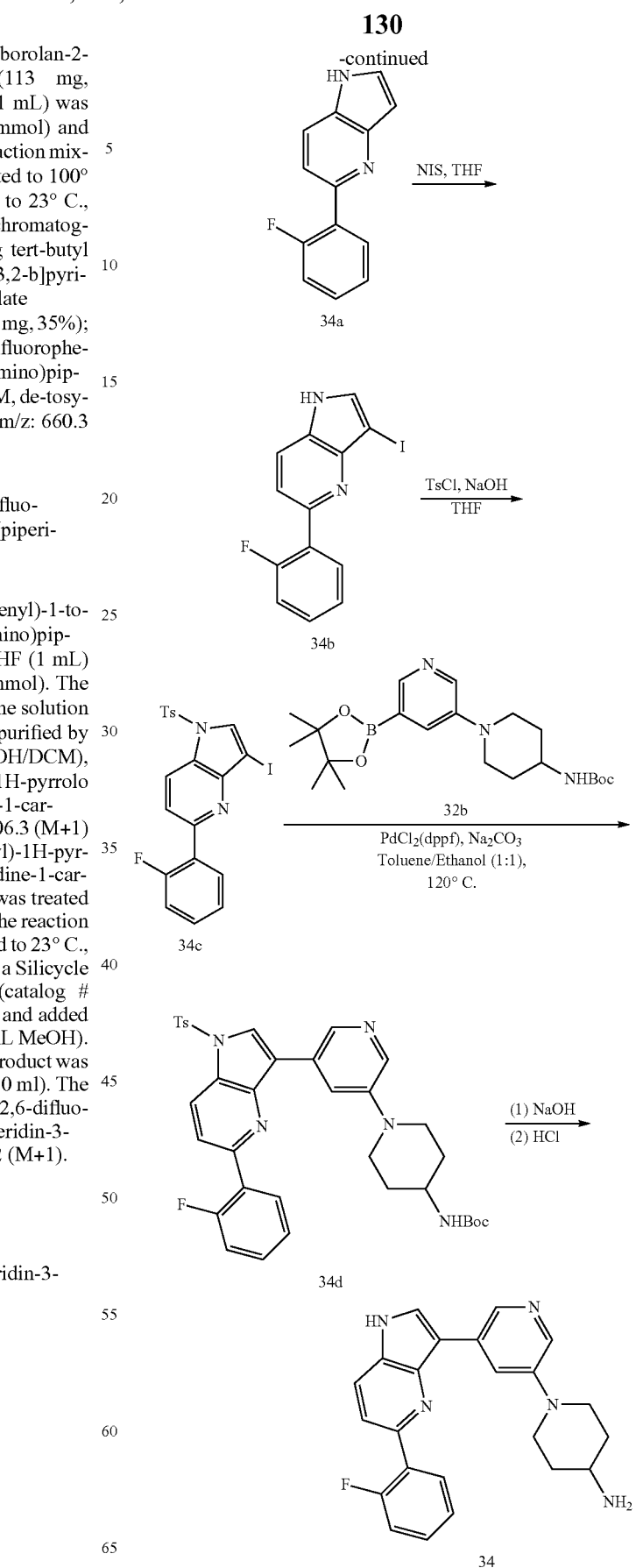

Preparation of Compound 34a:
5-(2-fluorophenyl)-1H-pyrrolo[3,2-t]pyridine

A mixture of 5-chloro-1H-pyrrolo[3,2-b]pyridine (150 mg, 0.983 mmol, Matrix Scientific), 2-fluorophenylboronic acid (275 mg, 1.966 mmol, Aldrich) and dichloro 1,1'-bis (diphenylphosphino)ferrocene palladium (II) (80 mg, 0.098 mmol, Strem) was capped, degassed and backfilled with argon (3×). Toluene (2 mL), EtOH (2 mL) and Na$_2$CO$_3$, 2.0 M (0.983 mL, 1.966 mmol) were added, and the reaction was heated to 120° C. in a microwave for 45 min. The solution was diluted with EtOAc (50 mL) and washed with brine (50 mL), dried over MgSO$_4$, concentrated in vacuo and purified by silica gel chromatography (eluent: 1-4% MeOH/DCM), affording 5-(2-fluorophenyl)-1H-pyrrolo[3,2-b]pyridine (200 mg, 96%). MS (ESI, pos. ion) m/z: 213.1 (M+1).

Preparation of Compound 34b: 5-(2-fluorophenyl)-3-iodo-1H-pyrrolo[3,2-b]pyridine A solution of 5-(2-fluorophenyl)-1H-pyrrolo[3,2-b]pyridine (199 mg, 0.938 mmol) in THF (10 mL) was treated with n-iodosuccinimide (232 mg, 1.031 mmol, Alfa-Aesar). The reaction was stirred at 23° C. under N$_2$. After 45 min, the solution was diluted with EtOAc (75 mL) and washed with brine (50 mL), dried over MgSO$_4$, concentrated in vacuo and purified by silica gel chromatography (eluent: 15-30% EtOAc/hexane), affording 5-(2-fluorophenyl)-3-iodo-1H-pyrrolo[3,2-b]pyridine (231 mg, 73%). MS (ESI, pos. ion) m/z: 339.1 (M+1).

Preparation of Compound 34c: 5-(2-fluorophenyl)-3-iodo-1-tosyl-1H-pyrrolo[3,2-b]pyridine A solution of 5-(2-fluorophenyl)-3-iodo-1H-pyrrolo[3,2-b]pyridine (227 mg, 0.671 mmol) in THF (7 mL) was treated with TsCl (141 mg, 0.738 mmol, Fluka) and solid NaOH (32.2 mg, 0.806 mmol, VWR). The reaction was stirred at 23° C. under N$_2$. After 45 min, the solution was diluted with EtOAc (100 ml) and washed with brine (75 mL), dried over MgSO$_4$, concentrated in vacuo and purified by silica gel chromatography (eluent: 10-25% EtOAc/hexane), affording 5-(2-fluorophenyl)-3-iodo-1-tosyl-1H-pyrrolo[3,2-b]pyridine (238 mg, 72%). MS (ESI, pos. ion) m/z: 493.0 (M+1).

Preparation of Compound 34d: tert-butyl 1-(5-(5-(2-fluorophenyl)-1-tosyl-1H-pyrrolo[3,2-b]pyridin-3-yl) pyridin-3-yl)piperidin-4-ylcarbamate A suspension of 5-(2-fluorophenyl)-3-iodo-1-tosyl-1H-pyrrolo[3,2-b]pyridine (155 mg, 0.315 mmol), tert-butyl 1-(5-(4,4,5,5-tetramethyl-1,3,2-dioxaborolan-2-yl)pyridin-3-yl)piperidin-4-ylcarbamate (222 mg, 0.551 mmol) Pd(PPh$_3$)$_4$ (36.4 mg, 0.031 mmol, Strem) and Na$_2$CO$_3$, 2.0 M (0.315 mL, 0.630 mmol) in Toluene (2 mL) and EtOH (2 mL) was capped, degassed and backfilled with argon. The reaction was heated to 100° C. After 18 h, the reaction was cooled to 23° C., diluted with EtOAc (75 mL) and washed with brine (50 mL), dried over MgSO$_4$, concentrated in vacuo and purified by silica gel chromatography (eluent: 0-4% MeOH/DCM), affording tert-butyl 1-(5-(5-(2-fluorophenyl)-1-tosyl-1H-pyrrolo[3,2-b]pyridin-3-yl)pyridin-3-yl)piperidin-4-ylcarbamate (134 mg, 66%). MS (ESI, pos. ion) m/z: 642.4 (M+1).

Preparation of Compound 34: 1-(5-(5-(2-fluorophenyl)-1H-pyrrolo[3,2-b]pyridin-3-yl)pyridin-3-yl)piperidin-4-amine A solution of tert-butyl 1-(5-(5-(2-fluorophenyl)-1-tosyl-1H-pyrrolo[3,2-b]pyridin-3-yl)pyridin-3-yl)piperidin-4-yl-carbamate (125 mg, 0.195 mmol) in THF (3 mL) was treated with NaOH 10N (0.195 mL, 1.948 mmol). The reaction was heated to reflux at 80° C. After 4 h, the solution was cooled to 23° C., concentrated in vacuo and purified by silica gel chromatography (eluent: 1-5% MeOH/DCM), affording tert-butyl 1-(5-(5-(2-fluorophenyl)-1H-pyrrolo[3,2-b]pyridin-3-yl) pyridin-3-yl)piperidin-4-ylcarbamate (69 mg, 73%). MS (ESI, pos. ion) m/z: 488.2 (M+1). A solution of tert-butyl 1-(5-(5-(2-fluorophenyl)-1H-pyrrolo[3,2-b]pyridin-3-yl)pyridin-3-yl)piperidin-4-ylcarbamate (64 mg, 0.131 mmol) in MeOH (3 mL) and DCM (0.500 mL) was treated with HCl, 36.5-38.0% (0.109 mL, 1.313 mmol). The reaction was heated to 50° C. After 2 h 30 min, the reaction was cooled to 23° C. and concentrated. The residue (as HCl salt) was freebased using a Silicycle Si-propylsulfonic acid ion exchange column (catalog # R51230B). The compound was diluted in MeOH and added to a pad of the resin (wetted and flushed with 10 mL MeOH). It was flushed with MeOH (50 mL), and then the product was "released" using 2.0 M NH$_3$ in MeOH solution (50 ml). The final filtrate was concentrated, affording 1-(5-(5-(2-fluorophenyl)-1H-pyrrolo[3,2-b]pyridin-3-yl)pyridin-3-yl)piperidin-4-amine. MS (ESI, pos. ion) m/z: 388.3 (M+1).

Example 35

1-(5-(5-(2,6-difluorophenyl)-1H-indazol-3-yl)pyridin-3-yl)piperidin-4-amine

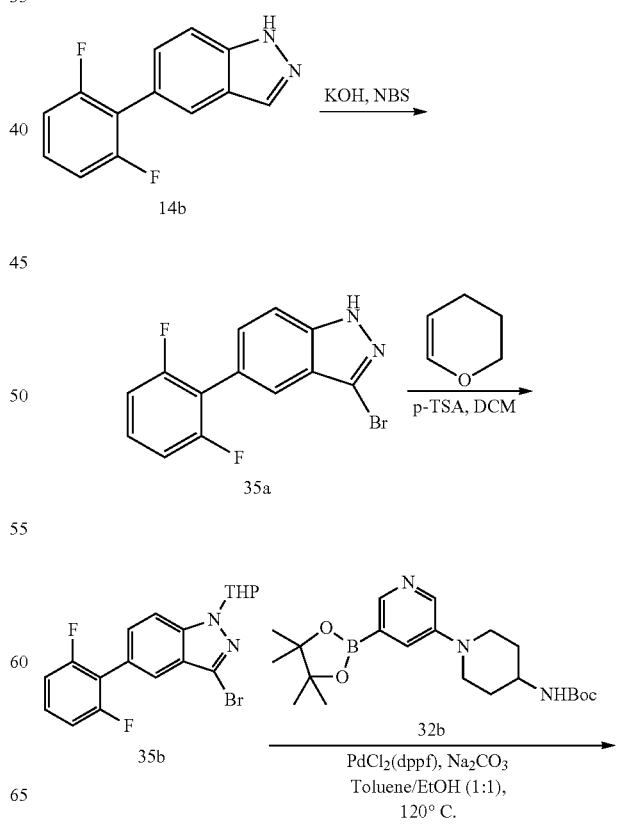

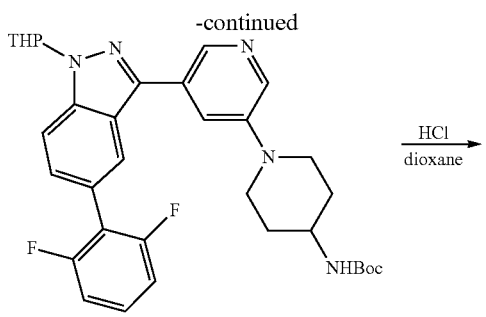

35c

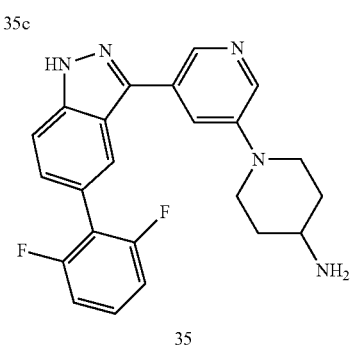

35

Preparation of Compound 35a:
3-Bromo-5-(2,6-difluoro-phenyl)-1H-indazole

To a solution of 5-(2,6-difluoro-phenyl)-1H-indazole (1 g, 4.35 mmol) in DMF (13 ml) were added KOH (488 mg, 8.7 mmol) and NBS (1.15 g, 6.48 mmol) at RT. The reaction mixture was stirred for 2 h at RT. Water was added to the reaction mixture and extracted with EtOAc (2×20 ml). Combined organic layers were washed with brine and dried over $Na_2SO_4$. The organic layer was concentrated and purified by column using silica (100-200 mesh) and 0-15 EtOAc-hexane to provide 3-bromo-5-(2,6-difluoro-phenyl)-1H-indazole (600 mg, 45% yield). MS (ESI, pos. ion) m/z: 306.9 (M−1).

Preparation of Compound 35b: 3-Bromo-5-(2,6-difluoro-phenyl)-1-(tetrahydro-pyran-2-yl)-1H-indazole To a solution of 3-bromo-5-(2,6-difluoro-phenyl)-1H-indazole (30.0 g, 97.05 mmol) and p-toluene sulfonic acid (3.7 g, 19.4 mmol) in THF (776 ml) was added 3,4-dihydro-2H-pyran (18.2 ml, 194.1 mmol) at RT. The mixture was stirred at 70° C. for 8 h. The reaction mixture was cooled to RT. Water was added to the reaction mixture and extracted with EtOAc (2×200 ml). The organic layer was washed with brine and dried over $Na_2SO_4$. The organic layer was concentrated under reduced pressure. The crude product was purified by column using (100-200 mesh) silica with 0-5% EtOAc in hexane to provide 3-bromo-5-(2,6-difluoro-phenyl)-1-(tetrahydro-pyran-2-yl)-1H-indazole (18.5 g, 48.4% yield). MS (ESI, pos. ion) m/z: 393.1 (M+1).

Preparation of Compound 35c: tert-butyl 1-(5-(5-(2,6-difluorophenyl)-1-(tetrahydro-2H-pyran-2-yl)-1H-indazol-3-yl)pyridin-3-yl)piperidin-4-ylcarbamate A mixture of 3-bromo-5-(2,6-difluorophenyl)-1-(tetrahydro-2H-pyran-2-yl)-1H-indazole (90 mg, 0.229 mmol), tert-butyl 1-(5-(4,4,5,5-tetramethyl-1,3,2-dioxaborolan-2-yl)pyridin-3-yl)piperidin-4-ylcarbamate (115 mg, 0.286 mmol), $Na_2CO_3$, 2.0 M (0.229 mL, 0.458 mmol) and dichloro 1,1'-bis(diphenylphosphino) ferrocene palladium (II) (18.69 mg, 0.023 mmol, Strem) in dioxane (3 mL) was capped, degassed and backfilled with argon. The reaction was heated to 135° C. in a microwave for 45 min. The reaction mixture was diluted with EtOAc (50 mL) and washed with brine (50 mL), dried over $MgSO_4$, concentrated in vacuo and purified by silica gel chromatography (eluent: 0-3% MeOH/DCM), affording tert-butyl 1-(5-(5-(2,6-difluorophenyl)-1-(tetrahydro-2H-pyran-2-yl)-1H-indazol-3-yl)pyridin-3-yl)piperidin-4-ylcarbamate (120 mg, 89%). MS (ESI, pos. ion) m/z: 590.3 (M+1).

Preparation of Compound 35: 1-(5-(5-(2,6-difluorophenyl)-1H-indazol-3-yl)pyridin-3-yl)piperidin-4-amine A solution of tert-butyl 1-(5-(5-(2,6-difluorophenyl)-1-(tetrahydro-2H-pyran-2-yl)-1H-indazol-3-yl)pyridin-3-yl)piperidin-4-ylcarbamate (120 mg, 0.204 mmol) in dioxane (5 mL) was treated with concentrated HCl (0.113 mL, 2.035 mmol). The reaction was heated to 85° C. After 1 h, the reaction was cooled to 23° C. and concentrated. The residue (as HCl salt) was free-based using a Silicycle Si-propylsulfonic acid ion exchange column (catalog # R51230B). The compound was diluted in MeOH and added to a pad of the resin (wetted and flushed with 10 mL MeOH). It was flushed with MeOH (50 mL), and then the product was "released" using 2.0 M $NH_3$ in MeOH solution (50 ml). The final filtrate was concentrated, affording 1-(5-(5-(2,6-difluorophenyl)-1H-indazol-3-yl)pyridin-3-yl)piperidin-4-amine. MS (ESI, pos. ion) m/z: 406.2 (M+1).

The compounds of examples 36-230 shown in Table 1 were made in accordance with exemplary methods shown above. The compound examples were named according to the ACD naming convention, as associated with ISIS software. The mass spectral data is recorded M+1, which is the positive ion as measured by an electrospray ionization method.

TABLE 1

| Ex# | IUPAC Name | M + 1 | Method |
|---|---|---|---|
| 36 | 3-(3-(6-(4-amino-1-piperidinyl)-2-pyrazinyl)-1H-indazol-5-yl)-N-benzyl-4-fluorobenzamide | 523 | Example 3 |
| 37 | 3-(3-(6-(4-amino-1-piperidinyl)-2-pyrazinyl)-1H-indazol-5-yl)-N-tert-butyl-4-fluorobenzamide | 489 | Example 3 |
| 38 | 3-(3-(6-(4-amino-1-piperidinyl)-2-pyrazinyl)-1H-indazol-5-yl)-N-butyl-4-fluorobenzamide | 489 | Example 3 |
| 39 | 3-(3-(6-(4-amino-1-piperidinyl)-2-pyrazinyl)-1H-indazol-5-yl)-4-fluoro-N-propylbenzamide | 475 | Example 3 |
| 40 | 3-(3-(6-(4-amino-1-piperidinyl)-2-pyrazinyl)-1H-indazol-5-yl)-4-fluoro-N,N-dimethylbenzamide | 461 | Example 3 |

TABLE 1-continued

| Ex# | IUPAC Name | M + 1 | Method |
|---|---|---|---|
| 41 | 1-(6-(5-(2-fluoro-5-(1-piperidinylcarbonyl)phenyl)-1H-indazol-3-yl)-2-pyrazinyl)-4-piperidinamine | 501 | Example 3 |
| 42 | 1-(6-(5-(2-fluoro-5-(4-morpholinylcarbonyl)phenyl)-1H-indazol-3-yl)-2-pyrazinyl)-4-piperidinamine | 503 | Example 3 |
| 43 | 3-(3-(6-(4-amino-1-piperidinyl)-2-pyrazinyl)-1H-indazol-5-yl)-N-ethyl-4-fluorobenzamide | 461 | Example 3 |
| 44 | 3-(3-(6-(4-amino-1-piperidinyl)-2-pyrazinyl)-1H-indazol-5-yl)-4-fluoro-N-(1-methylethyl)benzamide | 475 | Example 4 |
| 45 | 3-(3-(6-(4-amino-1-piperidinyl)-2-pyrazinyl)-1H-indazol-5-yl)-4-fluoro-N-phenylbenzamide | 509 | Example 6 |
| 46 | 3-(3-(6-(4-amino-1-piperidinyl)-2-pyrazinyl)-1H-indazol-5-yl)-N,N-diethyl-4-fluorobenzamide | 489 | Example 6 |
| 47 | 3-(3-(6-(4-amino-1-piperidinyl)-2-pyrazinyl)-1H-indazol-5-yl)-N,N-diethyl-2-fluorobenzamide | 489 | Example 6 |
| 48 | 1-(6-(5-(2-chloro-3-quinolinyl)-1H-indazol-3-yl)-2-pyrazinyl)-4-piperidinamine | 457 | Example 2 |
| 49 | 6-(3-(6-(4-amino-1-piperidinyl)-2-pyrazinyl)-1H-indazol-5-yl)-2-methyl-1(2H)-isoquinolinone | 453 | Example 2 |
| 50 | 4-(3-(6-(4-amino-1-piperidinyl)-2-pyrazinyl)-1H-indazol-5-yl)-1-methyl-2(1H)-quinolinone | 453 | Example 2 |
| 51 | 5-(3-(6-(4-amino-1-piperidinyl)-2-pyrazinyl)-1H-indazol-5-yl)-1-methyl-1,3-dihydro-2H-indol-2-one | 441 | Example 2 |
| 52 | 1-(6-(5-(1,3-benzothiazol-6-yl)-1H-indazol-3-yl)-2-pyrazinyl)-4-piperidinamine | 429 | Example 2 |
| 53 | 1-(6-(5-(1,3-benzothiazol-5-yl)-1H-indazol-3-yl)-2-pyrazinyl)-4-piperidinamine | 429 | Example 2 |
| 54 | 3-(3-(6-(4-amino-1-piperidinyl)-2-pyrazinyl)-1H-indazol-5-yl)-2-quinolinol | 439 | Example 4 |
| 55 | 1-(6-(5-(3-quinolinyl)-1H-indazol-3-yl)-2-pyrazinyl)-4-piperidinamine | 423 | Example 6 |
| 56 | 1-(6-(5-(6-quinoxalinyl)-1H-indazol-3-yl)-2-pyrazinyl)-4-piperidinamine | 424 | Example 7 |
| 57 | 1-(6-(5-(1H-pyrrolo[2,3-b]pyridin-5-yl)-1H-indazol-3-yl)-2-pyrazinyl)-4-piperidinamine | 412 | Example 7 |
| 58 | 1-(6-(5-(4-methyl-3,4-dihydro-2H-pyrido[3,2-b][1,4]oxazin-7-yl)-1H-indazol-3-yl)-2-pyrazinyl)-4-piperidinamine | 444 | Example 7 |
| 59 | 1-(6-(5-(4-(methylsulfonyl)phenyl)-1H-indazol-3-yl)-2-pyrazinyl)-4-piperidinamine | 450 | Example 3 |
| 60 | 2-(3-(6-(4-amino-1-piperidinyl)-2-pyrazinyl)-1H-indazol-5-yl)benzonitrile | 397 | Example 4 |
| 61 | 1-(6-(5-(2-fluoro-5-methoxyphenyl)-1H-indazol-3-yl)-2-pyrazinyl)-4-piperidinamine | 420 | Example 4 |
| 62 | 3-(3-(6-(4-amino-1-piperidinyl)-2-pyrazinyl)-1H-indazol-5-yl)benzonitrile | 397 | Example 4 |
| 63 | 1-(6-(5-(6-methoxy-2-pyridinyl)-1H-indazol-3-yl)-2-pyrazinyl)-4-piperidinamine | 403 | Example 5 |
| 64 | 1-(6-(5-(6-(1-methylethoxy)-2-pyridinyl)-1H-indazol-3-yl)-2-pyrazinyl)-4-piperidinamine | 431 | Example 5 |
| 65 | 1-(6-(5-(6-ethoxy-2-pyridinyl)-1H-indazol-3-yl)-2-pyrazinyl)-4-piperidinamine | 417 | Example 5 |
| 66 | 1-(6-(5-(6-fluoro-2-pyridinyl)-1H-indazol-3-yl)-2-pyrazinyl)-4-piperidinamine | 391 | Example 5 |
| 67 | 1-(6-(5-(2-fluorophenyl)-1H-indazol-3-yl)-2-pyrazinyl)-4-piperidinamine | 390 | Example 6 |
| 68 | 3-(3-(6-(4-amino-1-piperidinyl)-2-pyrazinyl)-1H-indazol-5-yl)-2-pyridinol | 389 | Example 6 |
| 69 | 1-(6-(5-(3-fluorophenyl)-1H-indazol-3-yl)-2-pyrazinyl)-4-piperidinamine | 390 | Example 7 |
| 70 | 1-(6-(5-(5-fluoro-2-methoxy-4-pyridinyl)-1H-indazol-3-yl)-2-pyrazinyl)-4-piperidinamine | 421 | Example 7 |
| 71 | 1-(6-(5-(2,3-difluorophenyl)-1H-indazol-3-yl)-2-pyrazinyl)-4-piperidinamine | 408 | Example 7 |
| 72 | 2-(3-(6-(4-amino-1-piperidinyl)-2-pyrazinyl)-1H-indazol-5-yl)phenol | 388 | Example 7 |
| 73 | 5-(3-(6-(4-amino-1-piperidinyl)-2-pyrazinyl)-1H-indazol-5-yl)-3-pyridinamine | 388 | Example 7 |
| 74 | 4-(3-(6-(4-amino-1-piperidinyl)-2-pyrazinyl)-1H-indazol-5-yl)-5-chloro-2(1H)-pyridinone | 423 | Example 7 |
| 75 | 1-(6-(5-phenyl-1H-indazol-3-yl)-2-pyrazinyl)-4-piperidinamine | 372 | Example 7 |

TABLE 1-continued

| Ex# | IUPAC Name | M + 1 | Method |
|---|---|---|---|
| 76 | 1-(6-(5-(3-(methylsulfonyl)phenyl)-1H-indazol-3-yl)-2-pyrazinyl)-4-piperidinamine | 450 | Example 7 |
| 77 | 1-(6-(5-(3-methoxyphenyl)-1H-indazol-3-yl)-2-pyrazinyl)-4-piperidinamine | 402 | Example 7 |
| 78 | 3-(3-(6-(4-amino-1-piperidinyl)-2-pyrazinyl)-1H-indazol-5-yl)phenol | 388 | Example 7 |
| 79 | 1-(6-(5-(5-methoxy-3-pyridinyl)-1H-indazol-3-yl)-2-pyrazinyl)-4-piperidinamine | 403 | Example 7 |
| 80 | 1-(6-(5-(1H-pyrazol-5-yl)-1H-indazol-3-yl)-2-pyrazinyl)-4-piperidinamine | 362 | Example 7 |
| 81 | 1-(6-(5-(3-aminophenyl)-1H-indazol-3-yl)-2-pyrazinyl)-4-piperidinamine | 387 | Example 7 |
| 82 | 1-(6-(5-(3-pyridinyl)-1H-indazol-3-yl)-2-pyrazinyl)-4-piperidinamine | 373 | Example 7 |
| 83 | 1-(6-(5-(2-chlorophenyl)-1H-indazol-3-yl)-2-pyrazinyl)-4-piperidinamine | 406 | Example 7 |
| 84 | 1-(6-(5-(2-fluoro-5-nitrophenyl)-1H-indazol-3-yl)-2-pyrazinyl)-4-piperidinamine | 435 | Example 7 |
| 85 | 1-(6-(5-(5-fluoro-3-pyridinyl)-1H-indazol-3-yl)-2-pyrazinyl)-4-piperidinamine | 391 | Example 7 |
| 86 | 1-(6-(5-(3,5-dimethoxyphenyl)-1H-indazol-3-yl)-2-pyrazinyl)-4-piperidinamine | 432 | Example 7 |
| 87 | 1-(6-(5-(5-pyrimidinyl)-1H-indazol-3-yl)-2-pyrazinyl)-4-piperidinamine | 374 | Example 7 |
| 88 | 1-(6-(5-(2-pyridinyl)-1H-indazol-3-yl)-2-pyrazinyl)-4-piperidinamine | 373 | Example 7 |
| 89 | 1-(6-(5-(4-morpholinyl)-1H-indazol-3-yl)-2-pyrazinyl)-4-piperidinamine | 381 | Example 8 |
| 90 | 1-(6-(5-(1-piperidinyl)-1H-indazol-3-yl)-2-pyrazinyl)-4-piperidinamine | 379 | Example 8 |
| 91 | 1-(3-(6-(4-amino-1-piperidinyl)-2-pyrazinyl)-1H-indazol-5-yl)-2-piperidinone | 393 | Example 8 |
| 92 | 1-(3-(6-(4-amino-1-piperidinyl)-2-pyrazinyl)-1H-indazol-5-yl)-3-methyl-2-imidazolidinone | 394 | Example 8 |
| 93 | N-(6-(3-(6-(4-amino-1-piperidinyl)-2-pyrazinyl)-1H-indazol-5-yl)-2-pyridinyl)-2,2-dimethylpropanamide | 472 | Example 9 |
| 94 | 2-(3-(6-(4-amino-1-piperidinyl)-2-pyrazinyl)-1H-indazol-5-yl)-3-pyridinamine | 388 | Example 9 |
| 95 | 1-(6-(5-(1H-pyrrolo[2,3-b]pyridin-6-yl)-1H-indazol-3-yl)-2-pyrazinyl)-4-piperidinamine | 412 | Example 9 |
| 96 | 5-(3-(6-(4-amino-1-piperidinyl)-2-pyrazinyl)-1H-indazol-5-yl)-N~4~-cyclopentyl-2,4-pyrimidinediamine | 472 | Example 9 |
| 97 | 5-(3-(6-(4-amino-1-piperidinyl)-2-pyrazinyl)-1H-indazol-5-yl)-2-pyrimidinamine | 389 | Example 9 |
| 98 | 1-(6-(5-(2-(4-morpholinyl)-4-pyrimidinyl)-1H-indazol-3-yl)-2-pyrazinyl)-4-piperidinamine | 459 | Example 9 |
| 99 | 1-(6-(5-imidazo[1,2-a]pyrazin-6-yl-1H-indazol-3-yl)-2-pyrazinyl)-4-piperidinamine | 413 | Example 9 |
| 100 | 4-(3-(6-(4-amino-1-piperidinyl)-2-pyrazinyl)-1H-indazol-5-yl)-2-pyridinamine | 388 | Example 9 |
| 101 | 1-(6-(5-(7-methoxy-4-quinolinyl)-1H-indazol-3-yl)-2-pyrazinyl)-4-piperidinamine | 453 | Example 9 |
| 102 | 1-(6-(5-(4-pyridinyl)-1H-indazol-3-yl)-2-pyrazinyl)-4-piperidinamine | 373 | Example 9 |
| 103 | 1-(6-(5-(3-amino-2-methylphenyl)-1H-indazol-3-yl)-2-pyrazinyl)-4-piperidinamine | 401 | Example 9 |
| 104 | 6-(3-(6-(4-amino-1-piperidinyl)-2-pyrazinyl)-1H-indazol-5-yl)-4-pyridazinamine | 389 | Example 9 |
| 105 | 1-(6-(5-(3-amino-4-(4-morpholinyl)phenyl)-1H-indazol-3-yl)-2-pyrazinyl)-4-piperidinamine | 472 | Example 9 |
| 106 | 1-(6-(5-(1,2,2',3',5',6'-hexahydrospiro[indole-3,4'-pyran]-4-yl)-1H-indazol-3-yl)-2-pyrazinyl)-4-piperidinamine | 483 | Example 9 |
| 107 | 1-(6-(5-(5-amino-2-(trifluoromethoxy)phenyl)-1H-indazol-3-yl)-2-pyrazinyl)-4-piperidinamine | 471 | Example 9 |
| 108 | 1-(6-(5-(3-(dimethylamino)phenyl)-1H-indazol-3-yl)-2-pyrazinyl)-4-piperidinamine | 415 | Example 9 |
| 109 | 1-(6-(5-(6-cyclopropyl-2-pyrazinyl)-1H-indazol-3-yl)-2-pyrazinyl)-4-piperidinamine | 414 | Example 9 |
| 110 | 1-(6-(5-(7-fluoro-4-quinolinyl)-1H-indazol-3-yl)-2-pyrazinyl)-4-piperidinamine | 441 | Example 9 |
| 111 | 1-(6-(5-(7-(trifluoromethoxy)-4-quinolinyl)-1H-indazol-3-yl)-2-pyrazinyl)-4-piperidinamine | 507 | Example 9 |
| 112 | 4-(3-(6-(4-amino-1-piperidinyl)-2-pyrazinyl)-1H-indazol-5-yl)-7-quinolinecarbonitrile | 448 | Example 9 |

TABLE 1-continued

| Ex# | IUPAC Name | M + 1 | Method |
|---|---|---|---|
| 113 | 4-(6-(3-(6-(4-amino-1-piperidinyl)-2-pyrazinyl)-1H-indazol-5-yl)-2,3-dihydro-1H-indol-1-yl)-2-pyrimidinamine | 506 | Example 9 |
| 114 | 5-(5-methoxy-3-pyridinyl)-3-(6-((3R)-3-piperidinyloxy)-2-pyrazinyl)-1H-indazole | 404 | Example 10 |
| 115 | 5-(5-fluoro-3-pyridinyl)-3-(6-((3R)-3-piperidinyloxy)-2-pyrazinyl)-1H-indazole | 392 | Example 10 |
| 116 | N-tert-butyl-4-fluoro-3-(3-(6-((3R)-3-piperidinyloxy)-2-pyrazinyl)-1H-indazol-5-yl)benzamide | 490 | Example 10 |
| 117 | 5-(5-chloro-2-fluoro-3-pyridinyl)-3-(6-((3R)-3-piperidinyloxy)-2-pyrazinyl)-1H-indazole | 426 | Example 11 |
| 118 | 5-(6-cyclopropyl-2-pyrazinyl)-3-(6-((3R)-3-piperidinyloxy)-2-pyrazinyl)-1H-indazole | 415 | Example 13 |
| 119 | 5-(6-(1-methylethoxy)-2-pyrazinyl)-3-(6-((3R)-3-piperidinyloxy)-2-pyrazinyl)-1H-indazole | 433 | Example 3 |
| 120 | 5-(5-(1-methylethoxy)-3-pyridinyl)-3-(6-((3R)-3-piperidinyloxy)-2-pyrazinyl)-1H-indazole | 432 | Example 10 |
| 121 | 3-(6-((3R)-3-piperidinyloxy)-2-pyrazinyl)-5-(1H-pyrrolo[2,3-b]pyridin-5-yl)-1H-indazole | 413 | Example 11 |
| 122 | 4-fluoro-N-(1-methylethyl)-3-(3-(6-((3R)-3-piperidinyloxy)-2-pyrazinyl)-1H-indazol-5-yl)benzamide | 476 | Example 10 |
| 123 | 4-methyl-7-(3-(6-((3R)-3-piperidinyloxy)-2-pyrazinyl)-1H-indazol-5-yl)-3,4-dihydro-2H-1,4-benzoxazine | 444 | Example 10 |
| 124 | 5-(3-fluoro-2-pyridinyl)-3-(6-((3R)-3-piperidinyloxy)-2-pyrazinyl)-1H-indazole | 392 | Example 13 |
| 125 | 5-(3-(6-((3R)-3-piperidinyloxy)-2-pyrazinyl)-1H-indazol-5-yl)-4(3H)-pyrimidinone | 391 | Example 13 |
| 126 | 5-(4-(1-methylethyl)-2-pyrimidinyl)-3-(6-((3R)-3-piperidinyloxy)-2-pyrazinyl)-1H-indazole | 417 | Example 13 |
| 127 | 5-(4-cyclopropyl-2-pyrimidinyl)-3-(6-((3R)-3-piperidinyloxy)-2-pyrazinyl)-1H-indazole | 415 | Example 13 |
| 128 | 5-chloro-4-(3-(6-((3R)-3-piperidinyloxy)-2-pyrazinyl)-1H-indazol-5-yl)-2(1H)-pyridinone | 424 | Example 10 |
| 129 | 5-(1-methyl-1H-pyrazol-4-yl)-3-(6-((3R)-3-piperidinyloxy)-2-pyrazinyl)-1H-indazole | 377 | Example 11 |
| 130 | 4-methyl-7-(3-(6-((3R)-3-piperidinyloxy)-2-pyrazinyl)-1H-indazol-5-yl)-3,4-dihydro-2H-pyrido[3,2-b][1,4]oxazine | 445 | Example 11 |
| 131 | 5-(2-fluoro-3-methoxyphenyl)-3-(6-((3R)-3-piperidinyloxy)-2-pyrazinyl)-1H-indazole | 421 | Example 11 |
| 132 | N-cyclopropyl-3-(3-(6-((3R)-3-piperidinyloxy)-2-pyrazinyl)-1H-indazol-5-yl)benzamide | 456 | Example 10 |
| 133 | 5-(2-fluorophenyl)-3-(6-((3R)-3-piperidinyloxy)-2-pyrazinyl)-1H-indazole | 391 | Example 10 |
| 134 | 5-phenyl-3-(6-((3R)-3-piperidinyloxy)-2-pyrazinyl)-1H-indazole | 373 | Example 10 |
| 135 | 5-bromo-3-(6-((3R)-3-piperidinyloxy)-2-pyrazinyl)-1H-indazole | 375 | Example 10 |
| 136 | 5-(6-cyclopropyl-2-pyridinyl)-3-(6-((3R)-3-piperidinyloxy)-2-pyrazinyl)-1H-indazole | 414 | Example 13 |
| 137 | 5-(6-methoxy-2-pyridinyl)-3-(6((3R)-3-piperidinyloxy)-2-pyrazinyl)-1H-indazole | 404 | Example 10 |
| 138 | 6-(3-(6-((3R)-3-piperidinyloxy)-2-pyrazinyl)-1H-indazol-5-yl)imidazo[1,2-a]pyrazine | 414 | Example 13 |
| 139 | N-cyclopropyl-4-fluoro-3-(3-(6-((3R)-3-piperidinyloxy)-2-pyrazinyl)-1H-indazol-5-yl)benzamide | 474 | Example 10 |
| 140 | 5-(2,3-dihydro-1,4-benzodioxin-6-yl)-3-(6-((3R)-3-piperidinyloxy)-2-pyrazinyl)-1H-indazole | 431 | Example 10 |
| 141 | 5-(4-cyclopropyl-2-pyridinyl)-3-(6-((3R)-3-piperidinyloxy)-2-pyrazinyl)-1H-indazole | 414 | Example 13 |
| 142 | 3-(6-((3R)-3-piperidinyloxy)-2-pyrazinyl)-5-(6-(trifluoromethyl)-2-pyridinyl)-1H-indazole | 442 | Example 13 |
| 143 | 5-(2-(1-methylethoxy)-4-pyridinyl)-3-(6-((3R)-3-piperidinyloxy)-2-pyrazinyl)-1H-indazole | 432 | Example 13 |
| 144 | 5-(6-(1-methylethoxy)-2-pyridinyl)-3-(6-((3R)-3-piperidinyloxy)-2-pyrazinyl)-1H-indazole | 432 | Example 10 |
| 145 | 6-(3-(6-((3R)-3-piperidinyloxy)-2-pyrazinyl)-1H-indazol-5-yl)[1,2,4]triazolo[4,3-a]pyridine | 414 | Example 13 |
| 146 | 5-(3-(1-methylethoxy)phenyl)-3-(6-((3R)-3-piperidinyloxy)-2-pyrazinyl)-1H-indazole | 431 | Example 13 |
| 147 | 5-((E)-2-cyclopropylethenyl)-3-(6-((3R)-3-piperidinyloxy)-2-pyrazinyl)-1H-indazole | 363 | Example 11 |

TABLE 1-continued

| Ex# | IUPAC Name | M + 1 | Method |
|---|---|---|---|
| 148 | 5-(3,6-dihydro-2H-pyran-4-yl)-3-(6-((3R)-3-piperidinyloxy)-2-pyrazinyl)-1H-indazole | 379 | Example 11 |
| 149 | 3-(6-((3R)-3-piperidinyloxy)-2-pyrazinyl)-5-(3-pyridazinyl)-1H-indazole | 375 | Example 13 |
| 150 | 3-(6-((3R)-3-piperidinyloxy)-2-pyrazinyl)-5-(3-(trifluoromethoxy)phenyl)-1H-indazole | 457 | Example 10 |
| 151 | 3-(6-((3R)-3-piperidinyloxy)-2-pyrazinyl)-5-(tetrahydro-2H-pyran-4-yl)-1H-indazole | 381 | Example 11 |
| 152 | 5-(2-methoxy-4-pyrimidinyl)-3-(6-((3R)-3-piperidinyloxy)-2-pyrazinyl)-1H-indazole | 405 | Example 13 |
| 153 | 5-(2-(1-methylethoxy)-4-pyrimidinyl)-3-(6-((3R)-3-piperidinyloxy)-2-pyrazinyl)-1H-indazole | 433 | Example 13 |
| 154 | 5-(5,6-dihydro-2H-pyran-3-yl)-3-(6-((3R)-3-piperidinyloxy)-2-pyrazinyl)-1H-indazole | 379 | Example 10 |
| 155 | 4-(3-(6-((3R)-3-piperidinyloxy)-2-pyrazinyl)-1H-indazol-5-yl)-2-pyrimidinol | 391 | Example 13 |
| 156 | 3-(6-((3R)-3-piperidinyloxy)-2-pyrazinyl)-5-(tetrahydro-2H-pyran-3-yl)-1H-indazole | 381 | Example 10 |
| 157 | N-cyclopropyl-2-(3-(6-((3R)-3-piperidinyloxy)-2-pyrazinyl)-1H-indazol-5-yl)-4-pyridinecarboxamide | 457 | Example 13 |
| 158 | N-cyclopropyl-6-(3-(6-((3R)-3-piperidinyloxy)-2-pyrazinyl)-1H-indazol-5-yl)-2-pyrazinamine | 430 | Example 13 |
| 159 | N-cyclopropyl-5-(3-(6-((3R)-3-piperidinyloxy)-2-pyrazinyl)-1H-indazol-5-yl)-3-pyridinecarboxamide | 457 | Example 13 |
| 160 | 5-(2-methoxy-4-pyridinyl)-3-(6-((3R)-3-piperidinyloxy)-2-pyrazinyl)-1H-indazole | 404 | Example 13 |
| 161 | 1-(6-(5-(2,6-difluorophenyl)-1H-indazol-3-yl)-2-pyrazinyl)-4-piperidinamine | 407 | Example 15 |
| 162 | (3R)-1-(6-(5-(2,6-difluorophenyl)-1H-indazol-3-yl)-2-pyrazinyl)-3-pyrrolidinamine | 393 | Example 15 |
| 163 | (3S)-1-(6-(5-(2,6-difluorophenyl)-1H-indazol-3-yl)-2-pyrazinyl)-3-piperidinol | 408 | Example 15 |
| 164 | 6-(5-(2,6-difluorophenyl)-1H-indazol-3-yl)-N-((3S)-3-piperidinyl)-2-pyrazinamine | 407 | Example 15 |
| 165 | 5-(2,6-difluorophenyl)-3-(6-(1-piperazinyl)-2-pyrazinyl)-1H-indazole | 393 | Example 15 |
| 166 | 5-(2,6-difluorophenyl)-3-(6-(1-piperidinyl)-2-pyrazinyl)-1H-indazole | 392 | Example 15 |
| 167 | 6-(5-(2,6-difluorophenyl)-1H-indazol-3-yl)-N-((3S)-3-piperidinyl)-2-pyrazinamine | 407 | Example 15 |
| 168 | 6-(5-(2,6-difluorophenyl)-1H-indazol-3-yl)-N-((3R)-3-piperidinyl)-2-pyrazinamine | 407 | Example 15 |
| 169 | 5-(2,6-difluorophenyl)-3-(6-(4-morpholinyl)-2-pyrazinyl)-1H-indazole | 394 | Example 15 |
| 170 | 5-(2,6-difluorophenyl)-3-(6-(1-pyrrolidinyl)-2-pyrazinyl)-1H-indazole | 378 | Example 15 |
| 171 | 3-(6-(1,4-diazepan-1-yl)-2-pyrazinyl)-5-(2,6-difluorophenyl)-1H-indazole | 407 | Example 15 |
| 172 | 6-(5-(2,6-difluorophenyl)-1H-indazol-3-yl)-N-4-piperidinyl-2-pyrazinamine | 407 | Example 15 |
| 173 | 1-(6-(5-(2,6-difluorophenyl)-1H-indazol-3-yl)-2-pyrazinyl)-4-piperidinol | 408 | Example 15 |
| 174 | 6-(5-(2,6-difluorophenyl)-1H-indazol-3-yl)-N-((3S)-3-pyrrolidinyl)-2-pyrazinamine | 393 | Example 15 |
| 175 | (3S)-1-(6-(5-(2,6-difluorophenyl)-1H-indazol-3-yl)-2-pyrazinyl)-3-pyrrolidinol | 394 | Example 15 |
| 176 | N-3-azetidinyl-6-(5-(2,6-difluorophenyl)-1H-indazol-3-yl)-2-pyrazinamine | 379 | Example 15 |
| 177 | 6-(5-(2,6-difluorophenyl)-1H-indazol-3-yl)-N-((3S)-3-pyrrolidinyl)-2-pyrazinamine | 393 | Example 16 |
| 178 | 6-(5-(2,6-difluorophenyl)-1H-indazol-3-yl)-N-methyl-N-3-piperidinyl-2-pyrazinamine | 421 | Example 17 |
| 179 | 6-(5-(2,6-difluorophenyl)-1H-indazol-3-yl)-N-methyl-2-pyrazinamine | 338 | Example 15 |
| 180 | 6-(5-(2,6-difluorophenyl)-1H-indazol-3-yl)-N-ethyl-2-pyrazinamine | 352 | Example 15 |
| 181 | 6-(5-(2,6-difluorophenyl)-1H-indazol-3-yl)-N,N-dimethyl-2-pyrazinamine | 352 | Example 15 |
| 182 | 6-(5-(2,6-difluorophenyl)-1H-indazol-3-yl)-N-(1-methylethyl)-2-pyrazinamine | 366 | Example 15 |
| 183 | N-tert-butyl-6-(5-(2,6-difluorophenyl)-1H-indazol-3-yl)-2-pyrazinamine | 380 | Example 15 |
| 184 | 6-(5-(2,6-difluorophenyl)-1H-indazol-3-yl)-N-phenyl-2-pyrazinamine | 400 | Example 15 |

TABLE 1-continued

| Ex# | IUPAC Name | M + 1 | Method |
|---|---|---|---|
| 185 | 5-(2,6-difluorophenyl)-3-(6-((3R)-3-piperidinyloxy)-2-pyrazinyl)-1H-indazole | 408 | Example 15 |
| 186 | 5-(2,6-difluorophenyl)-3-(6-(4-piperidinyloxy)-2-pyrazinyl)-1H-indazole | 408 | Example 15 |
| 187 | 5-(2,6-difluorophenyl)-3-(6-(3-pyrrolidinyloxy)-2-pyrazinyl)-1H-indazole | 394 | Example 15 |
| 188 | 5-(2,6-difluorophenyl)-3-(6-((3R)-3-piperidinyloxy)-2-pyrazinyl)-1H-indazole | 408 | Example 15 |
| 189 | 5-(2,6-difluorophenyl)-3-(6-((3S)-3-piperidinyloxy)-2-pyrazinyl)-1H-indazole | 408 | Example 15 |
| 190 | 5-(2,6-difluorophenyl)-3-(2-((3R)-3-piperidinyloxy)-4-pyrimidinyl)-1H-indazole | 408 | Example 20 |
| 191 | 4-(5-(2,6-difluorophenyl)-1H-indazol-3-yl)-N-((3R)-3-piperidinyl)-2-pyrimidinamine | 407 | Example 20 |
| 192 | 4-(5-(2,6-difluorophenyl)-1H-indazol-3-yl)-N-methyl-2-pyrimidinamine | 338 | Example 20 |
| 193 | 4-(5-(2,6-difluorophenyl)-1H-indazol-3-yl)-N-(1-methylethyl)-2-pyrimidinamine | 366 | Example 20 |
| 194 | 1-(4-(5-(2,6-difluorophenyl)-1H-indazol-3-yl)-2-pyrimidinyl)-4-piperidinamine | 407 | Example 20 |
| 195 | 5-(2,6-difluorophenyl)-3-(6-(((3R,4S)-4-methyl-3-piperidinyl)oxy)-2-pyrazinyl)-1H-indazole | 422 | Example 18 |
| 196 | 5-(2,6-difluorophenyl)-3-(6-(((3R,5S)-5-fluoro-3-piperidinyl)oxy)-2-pyrazinyl)-1H-indazole | 426 | Example 18 |
| 197 | 5-(2,6-difluorophenyl)-3-(6-(((3S,4R)-4-methyl-3-piperidinyl)oxy)-2-pyrazinyl)-1H-indazole | 422 | Example 18 |
| 198 | 5-(2,6-difluorophenyl)-3-(6-(((3R,4S)-4-methyl-3-piperidinyl)oxy)-2-pyrazinyl)-1H-indazole | 422 | Example 18 |
| 199 | 5-(2,6-difluorophenyl)-3-(6-(((3S,4S)-4-methyl-3-piperidinyl)oxy)-2-pyrazinyl)-1H-indazole | 422 | Example 18 |
| 200 | 5-(2,6-difluorophenyl)-3-(6-(((3S)-4-methylidene-3-piperidinyl)oxy)-2-pyrazinyl)-1H-indazole | 420 | Example 18 |
| 201 | (3S)-1-(6-(5-(2,6-difluorophenyl)-1H-indol-3-yl)-2-pyrazinyl)-3-piperidinamine | 406 | Example 21 |
| 202 | N-cyclohexyl-6-(5-(2,6-difluorophenyl)-1H-indol-3-yl)-2-pyrazinamine | 405 | Example 22 |
| 203 | (3R)-1-(6-(5-(2,6-difluorophenyl)-1H-indol-3-yl)-2-pyrazinyl)-3-piperidinamine | 406 | Example 22 |
| 204 | 4-(6-(5-(2,6-difluorophenyl)-1H-indol-3-yl)-2-pyrazinyl)-2-piperazinone | 406 | Example 22 |
| 205 | 6-(5-(2,6-difluorophenyl)-1H-indol-3-yl)-N-4-piperidinyl-2-pyrazinamine | 406 | Example 21 |
| 206 | 5-(2,6-difluorophenyl)-3-(6-(4-piperidinyloxy)-2-pyrazinyl)-1H-indole | 407 | Example 21 |
| 207 | 6-(5-(2,6-difluorophenyl)-1H-indol-3-yl)-N-((3R)-3-piperidinyl)-2-pyrazinamine | 406 | Example 21 |
| 208 | 6-(5-(2,6-difluorophenyl)-1H-indol-3-yl)-N-((3R)-3-pyrrolidinyl)-2-pyrazinamine | 392 | Example 21 |
| 209 | 5-(2,6-difluorophenyl)-3-(4-((3R)-3-piperidinyloxy)-2-pyrimidinyl)-1H-indole | 407 | Example 24 |
| 210 | 2-(5-(2,6-difluorophenyl)-1H-indol-3-yl)-N-4-piperidinyl-4-pyrimidinamine | 406 | Example 24 |
| 211 | 5-(2,6-difluorophenyl)-3-(4-(4-piperidinyloxy)-2-pyrimidinyl)-1H-indole | 407 | Example 24 |
| 212 | (3R)-1-(6-(5-(2,6-difluorophenyl)-1H-indol-3-yl)-2-pyrazinyl)-3-pyrrolidinamine | 392 | Example 21 |
| 213 | 5-(6-(1-methylethoxy)-2-pyrazinyl)-3-(6-((3R)-3-piperidinyloxy)-2-pyrazinyl)-1H-indole | 431 | Example 25 |
| 214 | 5-(2,6-difluorophenyl)-3-(6-((3S)-3-piperidinyloxy)-2-pyrazinyl)-1H-indole | 407 | Example 23 |
| 215 | 3-(5-fluoro-2-pyridinyl)-5-(6-(1-methylethoxy)-2-pyrazinyl)-1H-indole | 349 | Example 28 |
| 216 | 5-(6-(1-methylethoxy)-2-pyrazinyl)-3-(4-methyl-2-pyridinyl)-1H-indole | 345 | Example 28 |
| 217 | 6-(5-(6-(1-methylethoxy)-2-pyrazinyl)-1H-indol-3-yl)-2-pyridinamine | 346 | Example 28 |
| 218 | 2-(5-(6-(1-methylethoxy)-2-pyrazinyl)-1H-indol-3-yl)-4-pyridinamine | 346 | Example 28 |
| 219 | 5-(6-(1-methylethoxy)-2-pyrazinyl)-3-(5-methyl-2-pyridinyl)-1H-indole | 345 | Example 28 |
| 220 | 5-(6-(1-methylethoxy)-2-pyrazinyl)-3-(6-(4-morpholinyl)-2-pyridinyl)-1H-indole | 416 | Example 28 |
| 221 | 6-(5-(6-(1-methylethoxy)-2-pyrazinyl)-1H-indol-3-yl)-1H-indazole | 370 | Example 28 |

TABLE 1-continued

| Ex# | IUPAC Name | M + 1 | Method |
|---|---|---|---|
| 222 | 3-(5-methoxy-2-pyrazinyl)-5-(6-(1-methylethoxy)-2-pyrazinyl)-1H-indole | 362 | Example 28 |
| 223 | 5-(6-(1-methylethoxy)-2-pyrazinyl)-3-(6-(1H-pyrazol-1-yl)-2-pyridinyl)-1H-indole | 397 | Example 28 |
| 224 | 3-(6-methoxy-2-pyrazinyl)-5-(6-(1-methylethoxy)-2-pyrazinyl)-1H-indole | 362 | Example 28 |
| 225 | 5-(6-(1-methylethoxy)-2-pyrazinyl)-3-(6-(4-morpholinyl)-2-pyrazinyl)-1H-indole | 417 | Example 28 |
| 226 | 5-(6-(1-methylethoxy)-2-pyrazinyl)-3-(6-(1-methylethoxy)-2-pyridinyl)-1H-indole | 389 | Example 28 |
| 227 | 1-(4-(5-(6-(1-methylethoxy)-2-pyrazinyl)-1H-indol-3-yl)-1,3-thiazol-2-yl)-2(1H)-pyridinone | 430 | Example 28 |
| 228 | 3-(2-(1H-imidazol-1-yl)-1,3-thiazol-4-yl)-5-(6-(1-methylethoxy)-2-pyrazinyl)-1H-indole | 403 | Example 28 |
| 229 | 1-(6-(5-(6-(1-methylethoxy)-2-pyrazinyl)-1H-indol-3-yl)-2-pyridinyl)-2-pyrrolidinone | 414 | Example 28 |
| 230 | N,N-dimethyl-6-(5-(6-(1-methylethoxy)-2-pyrazinyl)-1H-indol-3-yl)-2-pyrazinamine | 375 | Example 28 |

Example 231

R)-3-(6-(6-azaspiro[2.5]octan-4-yloxy)pyrazin-2-yl)-5-(2,6-difluorophenyl)-1H-indazole

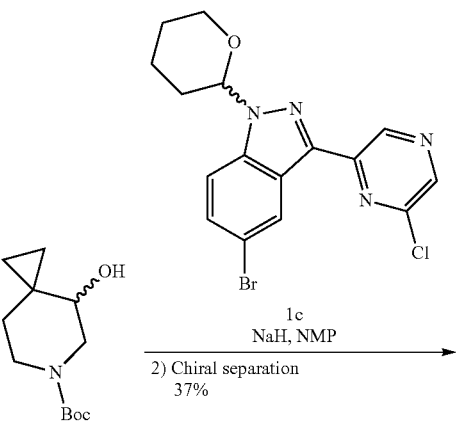

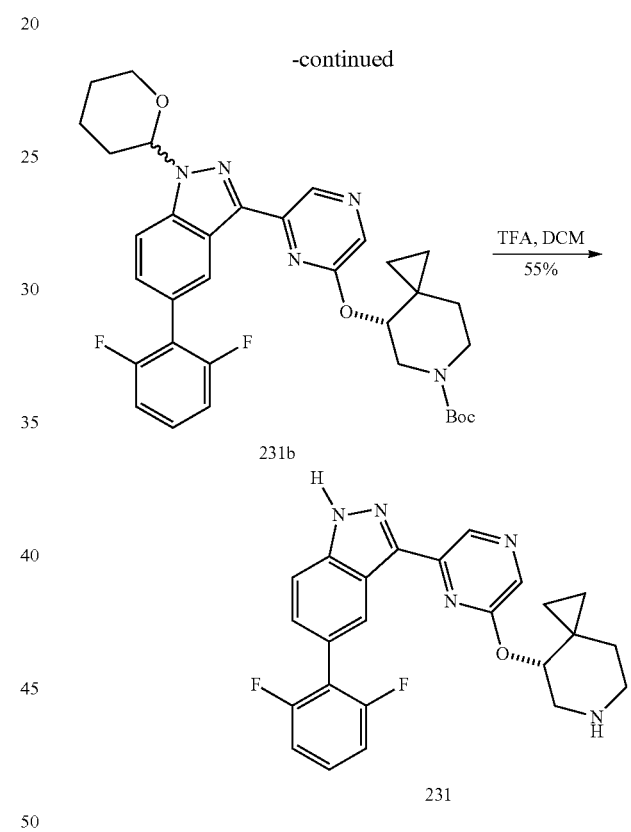

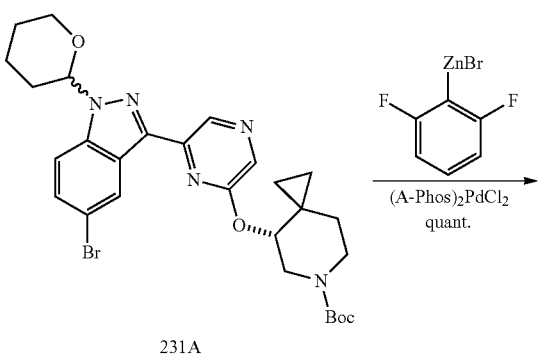

Preparation of Compound 231a: (R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate To a slurry of NaH (60% in mineral oil) (1.981 g, 49.5 mmol) in 60 mL NMP in a 500 mL rbf in an ice-water bath under nitrogen was added racemic tert-butyl 4-hydroxy-6-azaspiro[2.5]octane-6-carboxylate (10.39 g, 45.7 mmol, prepared from tert-butyl 4-methylenepiperidine-1-carboxylate in two steps following *J. Org. Chem.* 2001, 66, 2487 and WO 2010006938) in five 1 g portions and one 5.4 g portion over about 30 min. The reaction was warmed to RT for 15 min, then recooled in an ice/water bath. 5-Bromo-3-(6-chloropyrazin-2-yl)-1-(tetrahydro-2H-pyran-2-yl)-1H-indazole (15.0 g, 38.1 mmol) was added. After 3 h stirring at RT, the reaction was cooled in an ice/water bath and ice was added carefully. The reaction was partitioned between water and EtOAc. The layers were separated and the aqueous layer was extracted 1×EtOAc, and the combined organic layers were washed with water once, saturated NaCl once, and the organics were dried over anhydrous $Na_2SO_4$, filtered, and concentrated in vacuo. The material was treated with DCM and purified by silica gel chromatography (240 g column) using 0-40% EtOAc/hexane. The product-containing fractions were concentrated to afford 20.8 g of a light yellow solid. This material was purified by preparative SFC chromatography (Column: Chiralpak IC (250×21 mm, 5 μm); Mobile Phase: 78:22 (A:B) A: Liquid $CO_2$ B: Methanol (40 mM $NH_3$); Flow Rate: 75 mL/min; Oven Temp: 40° C.; Inlet Pressure: 100 bar; ~20 mg/injection; 230 nm). Under these conditions, the first two eluting compounds were a mixture of epimers at C1 of the tetrahydropyranyl protecting group with a single configuration (R) at the piperidine-alkoxide and the third eluting peak was a mixture of epimers at C1 of the tetrahydropyranyl protecting group with a single configuration (S) at the piperidine-alkoxide. The first two eluting peaks were combined and concentrated in vacuo to give (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (8.3 g, 14.20 mmol, 37% yield) as a white solid: MS (ESI, pos. ion) m/z: 584 (M+1).

Preparation of Compound 231b: (R)-tert-butyl 4-(6-(5-(2,6-difluorophenyl)-1-(tetrahydro-2H-pyran-2-yl)-1H-indazol-3-yl)pyrazin-2-yloxy)-6-azaspiro[2.5]octane-6-carboxylate A 75 mL threaded pressure vessel was flushed with argon and was charged with a stir bar, bis(4-(di-tert-butylphosphino)-N,N-dimethyl-benzenamine) palladium dichloride (0.061 g, 0.086 mmol) and (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (1.00 g, 1.711 mmol). (2,6-Difluorophenyl)zinc(II) bromide 0.5 M in THF (Rieke metals) (5.13 mL, 2.57 mmol) was added, the reaction was sealed, and the slurry was heated to 70° C. After ~10 min, a clear solution resulted. After 3 h the reaction was cooled and judged complete by LCMS. The reaction was treated with sodium 2,2'-(2-((carboxylatomethyl)(2-hydroxyethyl)amino)ethylazanediyl)diacetate hydrate 10 wt % in water (10.23 mL, 2.82 mmol) (10% aqueous EDTA-H) and DCM. An additional 2-3 mL of 10% EDTA-H solution was added to break up emulsion. The layers were separated, and the aqueous layer was extracted 3×DCM. The combined organics were dried over $Na_2SO_4$, filtered, and concentrated in vacuo. The material was treated with DCM and purified by silica gel chromatography (80 g column) eluting with 0-40% EtOAc/hexane. The product-containing fractions were concentrated to afford (4R)-tert-butyl 4-(6-(5-(2,6-difluorophenyl)-1-(tetrahydro-2H-pyran-2-yl)-1H-indazol-3-yl)pyrazin-2-yloxy)-6-azaspiro[2.5]octane-6-carboxylate (1.10 g, 1.781 mmol, quant.) as a light-yellow foam: MS (ESI, pos. ion) m/z: 618 (M+1)

Preparation of Compound 231: (R)-3-(6-(6-azaspiro[2.5]octan-4-yloxy)pyrazin-2-yl)-5-(2,6-difluorophenyl)-1H-indazole*1.5 TFA To a solution of (4R)-tert-butyl 4-(6-(5-(2,6-difluorophenyl)-1-(tetrahydro-2H-pyran-2-yl)-1H-indazol-3-yl)pyrazin-2-yloxy)-6-azaspiro[2.5]octane-6-carboxylate (0.983 g, 1.591 mmol) in 8 mL DCM was added TFA (3.68 mL, 47.7 mmol). After 6 h at RT, the orange reaction was placed in the freezer overnight, and in the morning was warmed and stirred at RT for 3 h. The reaction was concentrated in vacuo, then taken up in DMSO (6 mL total), filtered, and purified by RPHPLC, 20-70% ACN/$H_2O$ with 0.1% TFA; product-containing fractions were combined and concentrated in vacuo to give (R)-3-(6-(6-azaspiro[2.5]octan-4-yloxy)pyrazin-2-yl)-5-(2,6-difluorophenyl)-1H-indazole*1.5 TFA (0.530 g, 0.88 mmol, 55% yield) yellow solid: MS (ESI, pos. ion) m/z: 434 (M+1).

Example 232

1-(6-(5-nitro-1H-indol-3-yl)pyrazin-2-yl)piperidin-4-amine

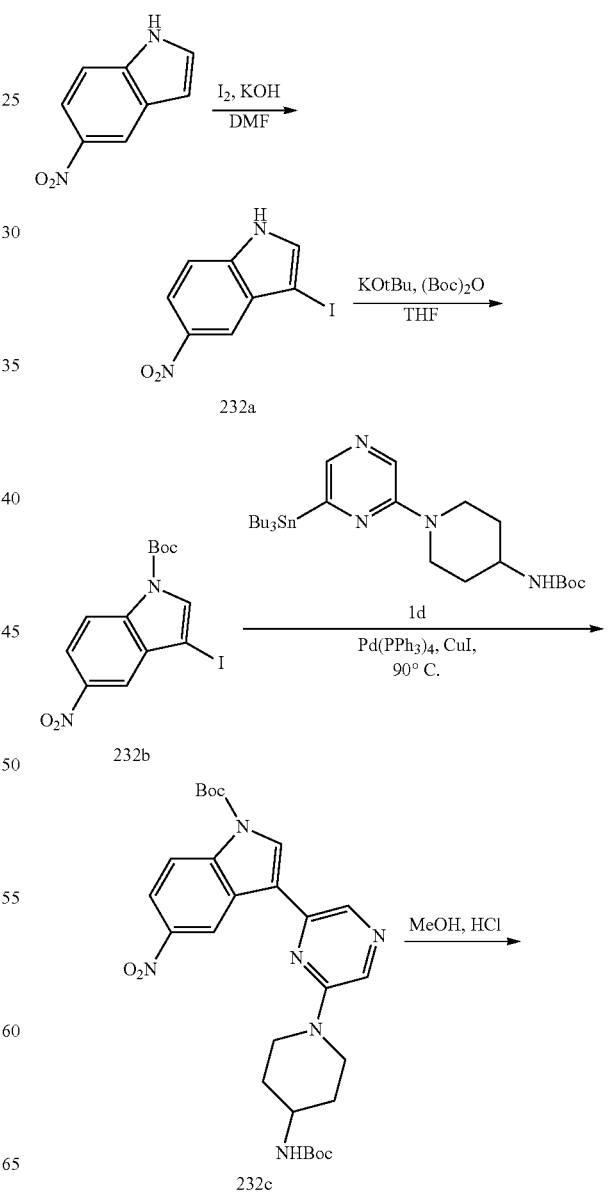

-continued

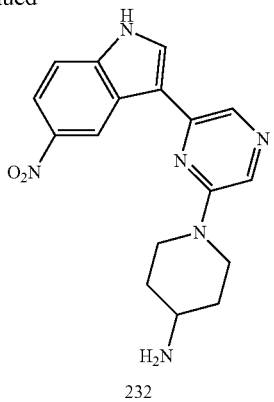

232

Preparation of Compound 232a: 3-iodo-5-nitro-1H-indole

To a solution of 5-nitro-1H-indole (5 g, 30.86 mmol) in DMF (50 mL) was added KOH (5 g, 92.58 mmol), followed by addition of $I_2$ (15.7 g, 61.74 mmol). The reaction mixture was stirred at RT for 2 h and then added 10% aqueous sodium bisulfate (50 mL) solution. The resulting precipitate was collected by filtration, washed with water and dried under vacuum to obtain the title compound as a pale yellow solid (8.0 g, 91%). MS (ESI, pos. ion) m/z: 286.9 (M−1)

Preparation of Compound 232b: tert-butyl 3-iodo-5-nitro-1H-indole-1-carboxylate To a solution of 3-iodo-5-nitro-1H-indole (7.5 g, 26.04 mmol) in THF (75 mL) was added potassium tert-but oxide (5.8 g, 52.08 mmol) and followed by addition of di-tert-butyl-dicarbonate (11.5 g, 52.08 mmol). The reaction mixture was stirred at RT for 2 h and then added ice water (200 mL). THF was evaporated and the resulting precipitate was collected by filtration, washed with water and dried under vacuum to obtain the title compound as a white solid (8.5 g, 84%).

Preparation of Compound 232c: tert-butyl 3-(6-(4-(tert-butoxycarbonylamino)piperidin-1-yl)pyrazin-2-yl)-5-nitro-1H-indole-1-carboxylate To a mixture of 3-Iodo-5-nitro-indole-1-carboxylic acid tert-butyl ester (480 mg, 1.23 mmol) and tert-butyl 1-(6-(tributylstannyl)pyrazin-2-yl)piperidin-4-ylcarbamate 1d (700 mg, 1.23 mmol) in DMF (4.8 mL) was purged with argon gas for 5 min and added CuI (352 mg, 1.84 mmol) and palladium tetrakis (171 mg, 0.15 mmol). The resulting mixture was purged with argon gas for 5 min and stiffed under nitrogen atmosphere at 90° C. for 1 h. The reaction mixture was then poured into water. The resulting precipitate was collected by filtration. The filtrate was extracted with diethyl ether. The organic layer was concentrated and combined with the above precipitate to give the crude product. Purification was carried out by column chromatography to obtain the title compound as a white solid (200 mg, 30%). MS (ESI, pos. ion) m/z: 539.3 (M+1).

Preparation of Compound 232: 1-(6-(5-nitro-1H-indol-3-yl)pyrazin-2-yl)piperidin-4-amine To tert-butyl 3-(6-(4-(tert-butoxycarbonylamino)piperidin-1-yl)pyrazin-2-yl)-5-nitro-1H-indole-1-carboxylate (170 mg, 0.32 mmol) was added 3N MeOH—HCl (3.5 mL) and then heated at 60° C. overnight. The reaction mixture was quenched with water and neutralized with $K_2CO_3$. The resulting precipitate was filtered, washed with water and dried to obtain the crude compound. This crude compound was re-crystallized in ethanol to obtain the title compound as a pale yellow solid (25 mg). MS (ESI, pos. ion) m/z: 339.1 (M+1).

Example 233 and 234

3-(6-(4-aminopiperidin-1-yl)pyrazin-2-yl)-1H-indol-5-amine (233) and N-(3-(6-(4-aminopiperidin-1-yl)pyrazin-2-yl)-1H-indol-5-yl)propionamide (234)

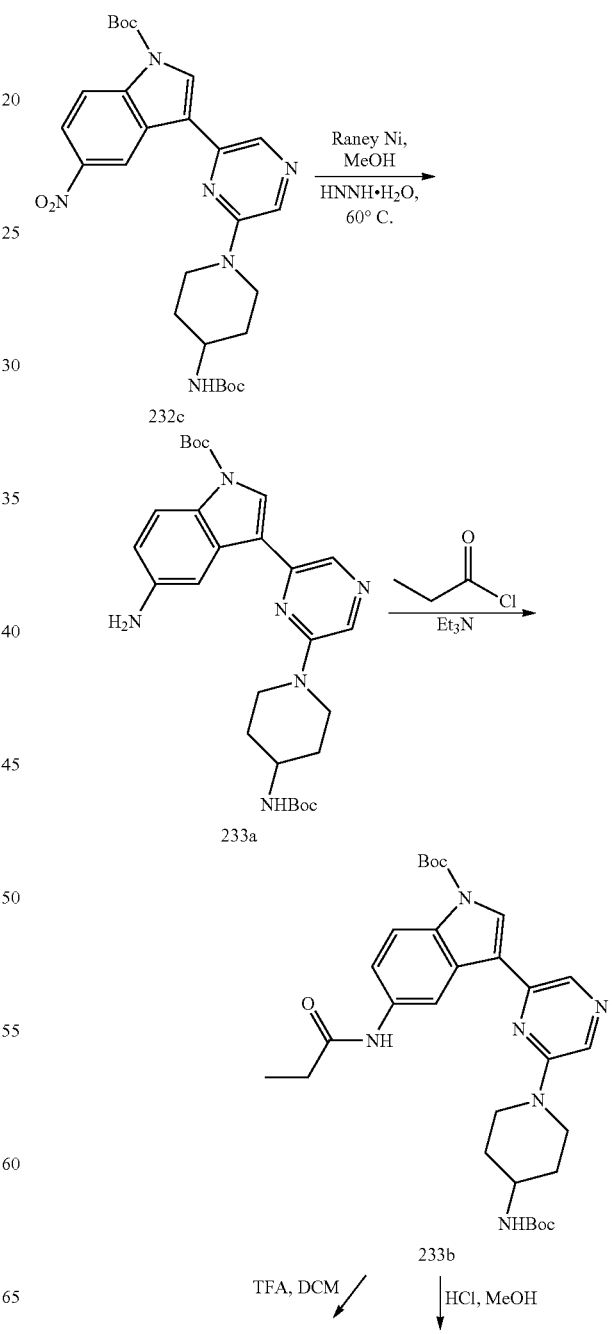

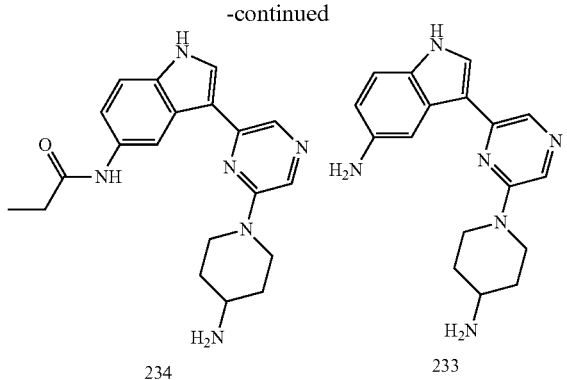

Preparation of Compound 233a: tert-butyl 5-amino-3-(6-(4-(tert-butoxycarbonylamino)piperidin-1-yl)pyrazin-2-yl)-1H-indole-1-carboxylate To a solution of tert-butyl 3-(6-(4-(tert-butoxycarbonylamino)piperidin-1-yl)pyrazin-2-yl)-5-nitro-1H-indole-1-carboxylate (200 mg, 0.37 mmol) in MeOH (2 mL) was added Raney Ni (30 mg) and then heated at 50° C. for 5 min. Hydrazine hydrate (0.2 mL) was added and the resulting mixture was stirred at the same temperature for another 10 min. The reaction mixture was cooled to RT and filtered off the Raney Ni through Celite. The filtrate was concentrated to obtain the title compound as a pale brown solid (160 mg, 85%). MS (ESI, pos. ion) m/z: 509.3 (M+1).

Preparation of Compound 233b: tert-butyl 3-(6-(4-(tert-butoxycarbonylamino)piperidin-1-yl)pyrazin-2-yl)-5-propionamido-1H-indole-1-carboxylate To solution of propionyl chloride (52.5 mg, 0.708 mmol) in DCM (7 mL) at 0° C. was added Et$_3$N (0.2 mL, 1.47 mmol), HBTU (292 mg, 0.75 mmol), tert-butyl 5-amino-3-(6-(4-(tert-butoxycarbonylamino)piperidin-1-yl)pyrazin-2-yl)-1H-indole-1-carboxylate (300 mg, 0.59 mmol) The resulting reaction mixture was stirred at RT for 3 h. The reaction mixture was extracted with DCM (14 mL), washed with brine, dried over Na$_2$SO$_4$, and concentrated to dryness. The crude product was purified by column chromatography to obtain the title compound (150 mg, 45%) as an off white solid. MS (ESI, pos. ion) m/z: 565.2 (M+1).

Preparation of Compound 233: 3-(6-(4-aminopiperidin-1-yl)pyrazin-2-yl)-1H-indol-5-amine A mixture of tert-butyl 3-(6-(4-(tert-butoxycarbonylamino)piperidin-1-yl)pyrazin-2-yl)-5-propionamido-1H-indole-1-carboxylate (150 mg, 0.26 mmol) and 3 N MeOH—HCl (3 mL) was stirred at 60° C. overnight. The reaction mixture was quenched with water and neutralized with K$_2$CO$_3$. The resulting precipitate was filtered, washed with water and dried to obtain the crude product. The crude product was purified by prep HPLC (column: Zorbax Eclipse XDBC Prep C18 5 μm 21.2*150 mm; flow rate: 15.0 mL/min; mobile phase: A: 0.1% TFA in water. B: ACN+MeOH (1:1); gradient: % B, 10% to 50%) to obtain the title compound (25 mg, 28%). MS (ESI, pos. ion) m/z: 309.1 (M+1).

Preparation of Compound 234: N-(3-(6-(4-aminopiperidin-1-yl)pyrazin-2-yl)-1H-indol-5-yl)propionamide To a solution of tert-butyl 3-(6-(4-(tert-butoxycarbonylamino)piperidin-1-yl)pyrazin-2-yl)-5-propionamido-1H-indole-1-carboxylate (200 mg, 0.35 mmol) in DCM (2 mL) was treated with TFA (2 mL) and stirred at RT for 12 h. The reaction mixture was quenched with water and neutralized with K$_2$CO$_3$. The resulting precipitate was filtered, washed with water and dried to obtain the crude product. The crude product was purified by prep HPLC (column: Zorbax Eclipse XDBC Prep C18 5 μm 21.2*150 mm; flow rate: 15.0 mL/min; mobile phase: A: 0.1% TFA in water. B: ACN+MeOH (1:1); gradient: % B, 10% to 50%) to N-(3-(6-(4-aminopiperidin-1-yl)pyrazin-2-yl)-1H-indol-5-yl)propionamide (234) (50 mg, 39%). MS (ESI, pos. ion) m/z: 413.2 (M+1).

Example 235

N-(3-(6-(4-aminopiperidin-1-yl)pyrazin-2-yl)-1H-indol-5-yl)benzamide

The title compound was prepared analogously to Example 234, using tert-butyl 5-amino-3-(6-(4-(tert-butoxycarbonylamino)piperidin-1-yl)pyrazin-2-yl)-1H-indole-1-carboxylate (233a) (250 mg, 0.49 mmol) gave the title compound (25 mg). MS (ESI, pos. ion) m/z: 413.2 (M+1).

Example 236 methyl 3-(6-(4-aminopiperidin-1-yl)pyrazin-2-yl)-1H-indole-5-carboxylate

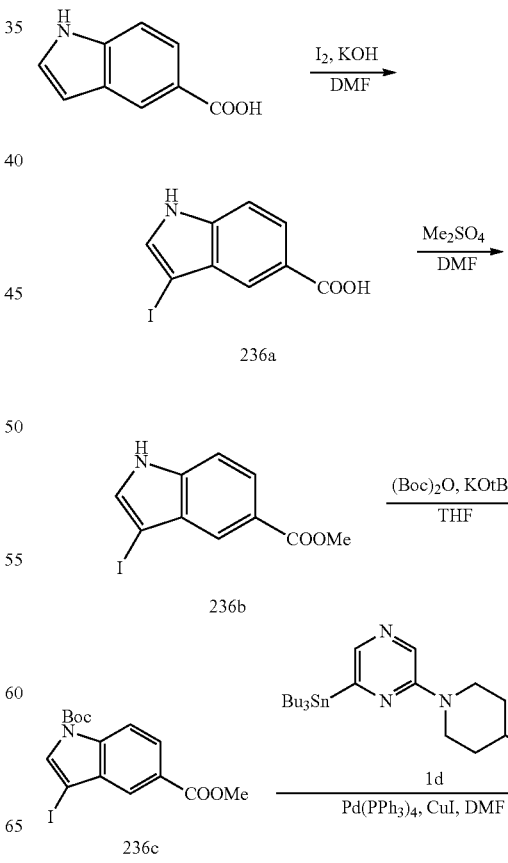

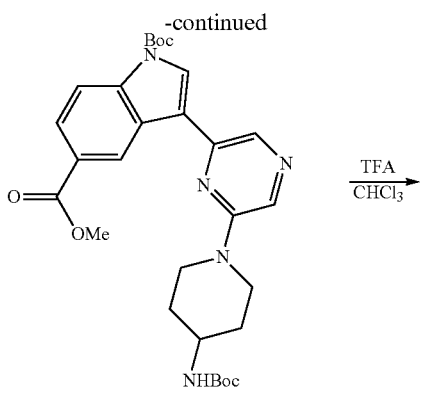

236d

236

Preparation of Compound 236a: 3-iodo-1H-indole-5-carboxylic acid

To a solution of 1H-Indole-5-carboxylic acid (5 g, 31.05 mmol) in DMF (50 mL) was added KOH (5 g, 93.15 mmol) and $I_2$ (15.7 g, 62.11 mmol). The reaction mixture was stirred at RT for 2 h and added 10% aqueous sodium bisulfate solution (25 mL). The resulting precipitate was collected by filtration, washed with water and dried under vacuum to obtain the title compound (8.0 g, 91%) as a brown solid. MS (ESI, pos. ion) m/z: 285.9 (M−1).

Preparation of Compound 236b: methyl 3-iodo-1H-indole-5-carboxylate

To a solution of 3-Iodo-1H-indole-5-carboxylic acid (8.0 g, 27.68 mmol) in DMF (80 mL) was added potassium carbonate (4.2 g, 30.44 mmol) and heated at 60° C. for 5 min. Dimethylsulphite (3.5 g, 27.68 mmol) was added and the resulting mixture was stirred at 80° C. for 1 h. The reaction mixture was then added ice cold water and extracted with EtOAc (240 mL). The organic layer was dried over $Na_2SO_4$, filtered, concentrated to dryness. The crude solid was washed with n-pentane to obtain the title compound (8.0 g, 95%) as a white solid. MS (ESI, pos. ion) m/z: 299.9 (M−1).

Preparation of Compound 236c: 1-tert-butyl 5-methyl 3-iodo-1H-indole-1,5-dicarboxylate To a solution of methyl 3-iodo-1H-indole-5-carboxylate (8 g, 26.57 mmol) in THF (80 mL) was added potassium tert-butoxide (6 g, 53.15 mmol) and di-tert-butyl-dicarbonate (11.6 ml, 53.15 mmol). The resulting mixture was stirred at 80° C. for 1 h and then added ice cold water. The resulting precipitate was collected by filtration, washed with water and dried under vacuum to obtain the title compound (7.0 g, 66%) as a white solid. MS (ESI, pos. ion) m/z: 299.9.

Preparation of Compound 236d: 1-tert-butyl 5-methyl 3-(6-(4-(tert-butoxycarbonylamino)piperidin-1-yl)pyrazin-2-yl)-1H-indole-1,5-dicarboxylate A mixture of 1-tert-butyl 5-methyl 3-iodo-1H-indole-1,5-dicarboxylate (6 g, 14.96 mmol) and tert-butyl 1-(6-(tributylstannyl)pyrazin-2-yl)piperidin-4-ylcarbamate (1d) (10.2 g, 17.95 mmol) in DMF (60 mL) was purged with argon gas for 5 min, added CuI (4.27 g, 22.44 mmol), palladium tetrakis (1.7 g, 1.5 mmol) and again purged with argon gas for 5 min. The reaction mixture was stirred at 90° C. under nitrogen atmosphere for 1 h. The reaction mixture was then poured into water. The resulting precipitate was collected by filtration. The filtrate was extracted with diethyl ether. The organic layer was concentrated and combined with the above precipitate to give the crude product. Purification was carried out by column chromatography to obtain the title compound as a brown solid (2.5 g, 30%). MS (ESI, pos. ion) m/z: 552.2 (M+1).

Preparation of Compound 236: methyl 3-(6-(4-aminopiperidin-1-yl)pyrazin-2-yl)-1H-indole-5-carboxylate To a mixture of 1-tert-butyl 5-methyl 3-(6-(4-(tert-butoxycarbonylamino)piperidin-1-yl)pyrazin-2-yl)-1H-indole-1,5-dicarboxylate (300 mg, 0.53 mmol) in chloroform (3.0 mL) was added TFA (3.0 mL) at 0° C. The reaction mixture was heated at 50° C. for 12 h. After removal of TFA the crude product was purified by preparative HPLC to obtain title compound (90 mg, 47%) as a brown solid. MS (ESI, pos. ion) m/z: 352.1 (M+1).

Example 237

3-(6-(4-aminopiperidin-1-yl)pyrazin-2-yl)-1H-indole-5-carboxylic acid

To mixture of methyl 3-(6-(4-aminopiperidin-1-yl)pyrazin-2-yl)-1H-indole-5-carboxylate (236) (60 mg, 0.17 mmol) in THF (1 mL) was added 10% NaOH solution (1 mL). The reaction mixture was heated at 60° C. for 24 h and cooled to 0° C. 1N HCl solution was added to the mixture to attain pH7. The resulting mixture was stirred at RT for 2 h. The resulting precipitate was collected by filtration, washed with water and dried under vacuum to obtain the title compound (30 mg, 57%). MS (ESI, pos. ion) m/z: 337.9 (M+1).

Example 238

3-(6-(4-aminopiperidin-1-yl)pyrazin-2-yl)-1H-indole-5-carboxamide

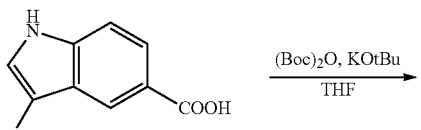

236a

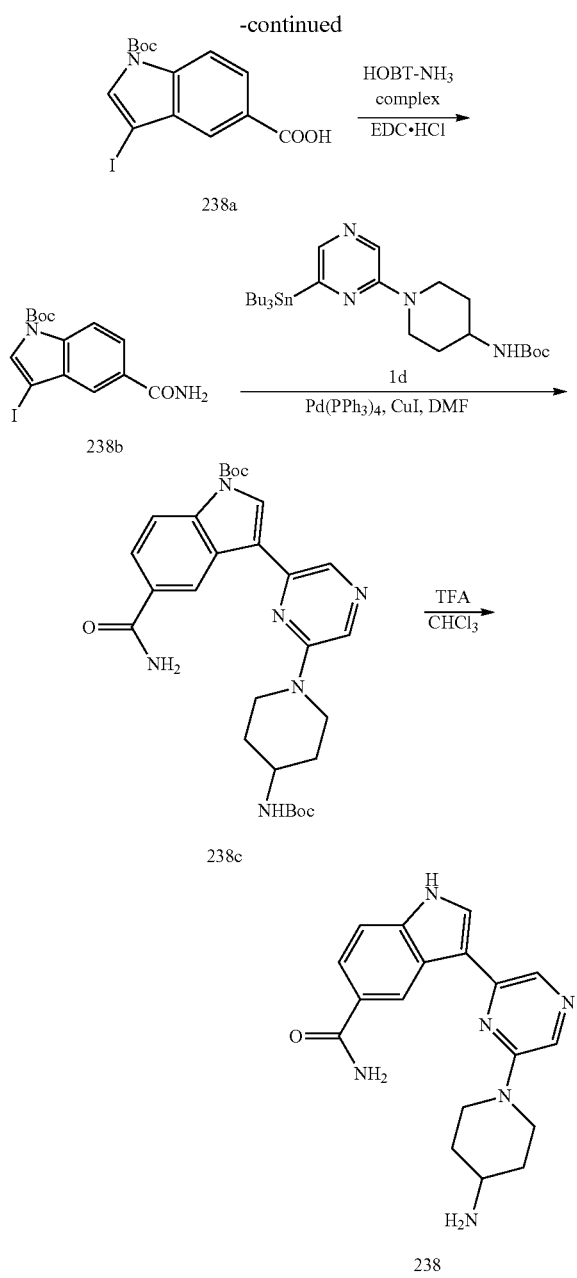

Preparation of Compound 238a: 1-(tert-butoxycarbonyl)-3-iodo-1H-indole-5-carboxylic acid To a solution of 3-iodo-1H-indole-5-carboxylic acid (3 g, 10.41 mmol) in THF (30 mL) was added potassium tert-butoxide (2.3 g, 20.83 mmol) and followed by addition of di-tert-butyl-dicarbonate (4.56 ml, 20.83 mmol). The reaction mixture was stirred at RT for 2 h and then added ice water (30 mL). The resulting precipitate was collected by filtration, washed with water and dried under vacuum to obtain the title compound as a white solid (3 g, 75%). MS (ESI, pos. ion) m/z: 385.8 (M−1).

Preparation of Compound 238b: tert-butyl 5-carbamoyl-3-iodo-1H-indole-1-carboxylate To solution of 1-(tert-butoxycarbonyl)-3-iodo-1H-indole-5-carboxylic acid (1 g, 2.57 mmol) in DMF (10 mL) at 0° C. was added EDC.HCl (741 mg, 3.86 mmol) and HOBT-NH$_3$ complex (825 mg, 5.15 mmol). The reaction mixture was stirred at RT for 3 h and then extracted with DCM (15 mL). The organic layer was washed with brine, dried over Na$_2$SO$_4$, filtered, and concentrated to dryness. The crude product was purified by column chromatography to obtain title compound as an off white solid (550 mg, 50%). MS (ESI, Neg. ion) m/z: 286.9 (M+1).

Preparation of Compound 238c: tert-butyl 3-(6-(4-(tert-butoxycarbonylamino)piperidin-1-yl)pyrazin-2-yl)-5-carbamoyl-1H-indole-1-carboxylate A mixture of tert-butyl 5-carbamoyl-3-iodo-1H-indole-1-carboxylate (460 mg, 1.42 mmol) and tert-butyl 1-(6-(tributylstannyl)pyrazin-2-yl)piperidin-4-ylcarbamate (1d) (807 mg, 1.42 mmol) in DMF (4.6 mL) was purged with argon gas for 5 min, added CuI (405 mg, 2.13 mmol), palladium tetrakis (170 mg, 0.14 mmol) and again purged with argon gas for 5 min. The reaction mixture was stirred at 90° C. under nitrogen atmosphere for 1 h. The reaction mixture was then poured into water. The resulting precipitate was collected by filtration. The filtrate was extracted with diethyl ether. The organic layer was concentrated and combined with the above precipitate to give the crude product, which was purified by column chromatography to obtain the title compound as a brown solid (200 mg, 31%). MS (ESI, pos. ion) m/z: 537.0 (M+1).

Preparation of Compound 238: 3-(6-(4-aminopiperidin-1-yl)pyrazin-2-yl)-1H-indole-5-carboxamide To a mixture of tert-butyl 3-(6-(4-(tert-butoxycarbonylamino)piperidin-1-yl)pyrazin-2-yl)-5-carbamoyl-1H-indole-1-carboxylate (200 mg, 0.37 mmol) in chloroform was added TFA at 0° C. The reaction mixture was heated at 50° C. for 12 h. After removal of TFA the crude product was purified by preparative HPLC to obtain title compound (25 mg, 20%) as a brown solid. MS (ESI, pos. ion) m/z: 337.1 (M+1).

Example 239

3-(6-(4-aminopiperidin-1-yl)pyrazin-2-yl)-N-isopropyl-1H-indole-5-carboxamide

The title compound was prepared analogously to Example 238, using 1-(tert-butoxycarbonyl)-3-iodo-1H-indole-5-carboxylic acid (500 mg, 1.28 mmol) and propan-2-amine (500 mg, 1.28 mmol) in 3 steps gave the title compound (25 mg). MS (ESI, pos. ion) m/z: 379.0 (M+1).

Example 240

3-(6-(4-amino-1-piperidinyl)-2-pyrazinyl)-N-phenyl-1H-indole-5-carboxamide

The title compound was prepared analogously to Example 238, using 1-(tert-butoxycarbonyl)-3-iodo-1H-indole-5-carboxylic acid (1.50 g, 3.86 mmol) and phenylmethanamine (496 mg, 4.63 mmol) in 3 steps gave the title compound (180 mg). MS (ESI, pos. ion) m/z: 427.1 (M+1).

Example 241

3-(6-(4-amino-1-piperidinyl)-2-pyrazinyl)-N-benzyl-1H-indole-5-carboxamide

The title compound was prepared analogously to Example 238, using 1-(tert-butoxycarbonyl)-3-iodo-1H-indole-5-carboxylic acid (1.50 g, 3.86 mmol) and aniline (422 mg, 4.63 mmol) in 3 steps gave the title compound (99 mg). MS (ESI, pos. ion) m/z: 413.1 (M+1).

Example 242

N-cyclopropyl-4-(3-(6-((3R)-3-piperidinyloxy)-2-pyrazinyl)-1H-indazol-5-yl)-2-pyrimidinamine

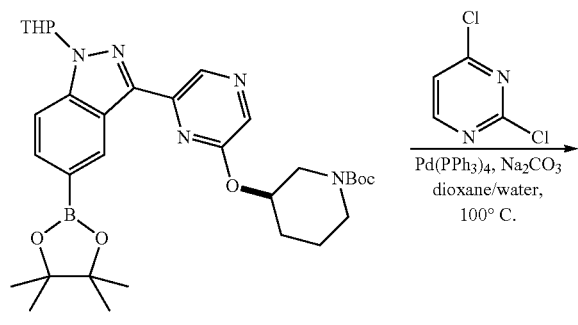

13a

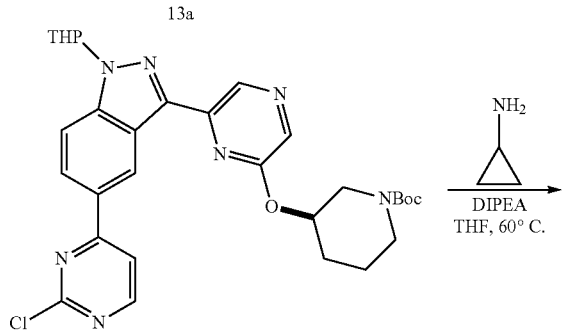

242a

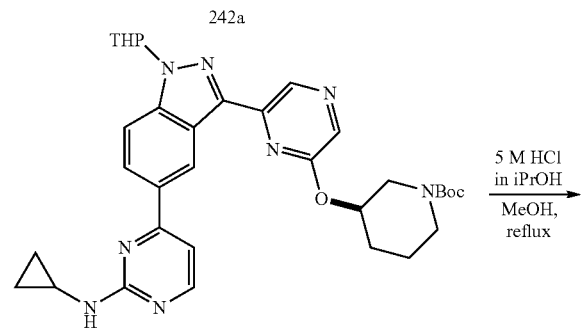

242b

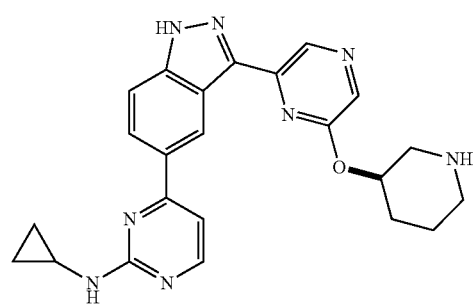

242

Preparation of Compound 242a: (3R)-tert-butyl 3-(6-(5-(2-chloropyrimidin-4-yl)-1-(tetrahydro-2H-pyran-2-yl)-1H-indazol-3-yl)pyrazin-2-yloxy)piperidine-1-carboxylate A glass microwave reaction vessel was charged with (3R)-tert-butyl 3-(6-(1-(tetrahydro-2H-pyran-2-yl)-5-(4,4,5,5-tetramethyl-1,3,2-dioxaborolan-2-yl)-1H-indazol-3-yl)pyrazin-2-yloxy)piperidine-1-carboxylate (600 mg, 0.99 mmol), 2,4-dichloropyrimidine (192 mg, 1.29 mmol, Fluka) and Pd(PPh$_3$)$_4$ (57 mg, 0.050 mmol). The tube was sealed and evacuated under vacuum and back-filled with N$_2$ three times. 2 M Na$_2$CO$_3$ (2.48 mL, 4.95 mmol) and dioxane (5 mL) were added. The reaction was stirred and heated in at 100° C. for 3 h. After cooling to RT, the organic layer was separated and dried over anhydrous Na$_2$SO$_4$, filtered and concentrated. The crude was purified by silica gel chromatography, eluting with a gradient of 0-60% EtOAc in hexanes, to provide (3R)-tert-butyl 3-(6-(5-(2-chloropyrimidin-4-yl)-1-(tetrahydro-2H-pyran-2-yl)-1H-indazol-3-yl)pyrazin-2-yloxy)piperidine-1-carboxylate (505 mg, 0.85 mmol, 86% yield) as a pale yellow solid. MS (ESI, pos. ion) m/z: 592.1 (M+1).

Preparation of Compound 242b: (3R)-tert-butyl 3-(6-(5-(2-(cyclopropylamino)pyrimidin-4-yl)-1-(tetrahydro-2H-pyran-2-yl)-1H-indazol-3-yl)pyrazin-2-yloxy)piperidine-1-carboxylate A mixture of (3R)-tert-butyl 3-(6-(5-(2-chloropyrimidin-4-yl)-1-(tetrahydro-2H-pyran-2-yl)-1H-indazol-3-yl)pyrazin-2-yloxy)piperidine-1-carboxylate (172 mg, 0.290 mmol), cyclopropylamine (0.12 mL, 1.74 mmol) and DIPEA (0.25 mL, 1.45 mmol) in THF (1.5 mL) was stirred and heated in a Initiator microwave reactor (Personal Chemistry, Biotage AB, Inc., Upssala, Sweden) at 120° C. for 30 min and heated at 140° C. for an additional 1 h. 1 M HCl (aq.) was added and the mixture was extracted with EtOAc (3×). The combined organic layers were dried over anhydrous Na$_2$SO$_4$, filtered and concentrated. The crude was purified by silica gel chromatography, eluting with a gradient of 0-50% EtOAc in hexanes, to provide (3R)-tert-butyl 3-(6-(5-(2-(cyclopropylamino)pyrimidin-4-yl)-1-(tetrahydro-2H-pyran-2-yl)-1H-indazol-3-yl)pyrazin-2-yloxy)piperidine-1-carboxylate (116 mg, 0.19 mmol, 65% yield) as a clear oil. MS (ESI, pos. ion) m/z: 613.3 (M+1).

Preparation of Compound 242: (R)—N-cyclopropyl-4-(3-(6-(piperidin-3-yloxy)pyrazin-2-yl)-1H-indazol-5-yl)pyrimidin-2-amine A solution of (3R)-tert-butyl 3-(6-(5-(2-(cyclopropylamino)pyrimidin-4-yl)-1-(tetrahydro-2H-pyran-2-yl)-1H-indazol-3-yl)pyrazin-2-yloxy)piperidine-1-carboxylate (116 mg, 0.19 mmol) and HCl (5-6 M in IPA, 3.8 mL, 18.9 mmol) was heated at 80° C. for 1 h. The reaction was cooled to RT and concentrated to a yellow solid that was slurried with a 1\1 mixture of DCM/MeOH (2 mL) and applied to a pre-washed (5 mL MeOH) of Si-propylsulfonic acid (Silicycle, Cat# R51230B). The column was washed with MeOH (10 mL). The compound was released with 10 mL of 2 M NH$_3$ in MeOH to afford the title compound (75 mg, 0.18 mmol, 92% yield) as a yellow solid. MS (ESI, pos. ion) m/z: 429.2 (M+1). $^1$H NMR (400 MHz, DMSO-d$_6$) δ ppm 9.28 (br. s., 1H), 8.96 (s, 1H), 8.40 (d, J=5.28 Hz, 1H), 8.16-8.26 (m, 2H), 7.74 (d, J=8.80 Hz, 1H), 7.36 (d, J=5.09 Hz, 1H), 5.25-5.35 (m, 1H), 3.36-3.44 (m, 1H), 2.86-2.93 (m, 1H), 2.75-2.82 (m, 1H), 2.67-2.75 (m, 1H), 2.52-2.58 (m, 2H), 2.21-2.32 (m, 1H), 1.55-1.76 (m, 2H), 0.67-0.76 (m, 2H), 0.45-0.59 (m, 2H).

Example 243

6-(5-(6-cyclopropyl-2-pyrazinyl)-1H-indazol-3-yl)-N-((3R)-3-piperidinyl)-2-pyrazinamine

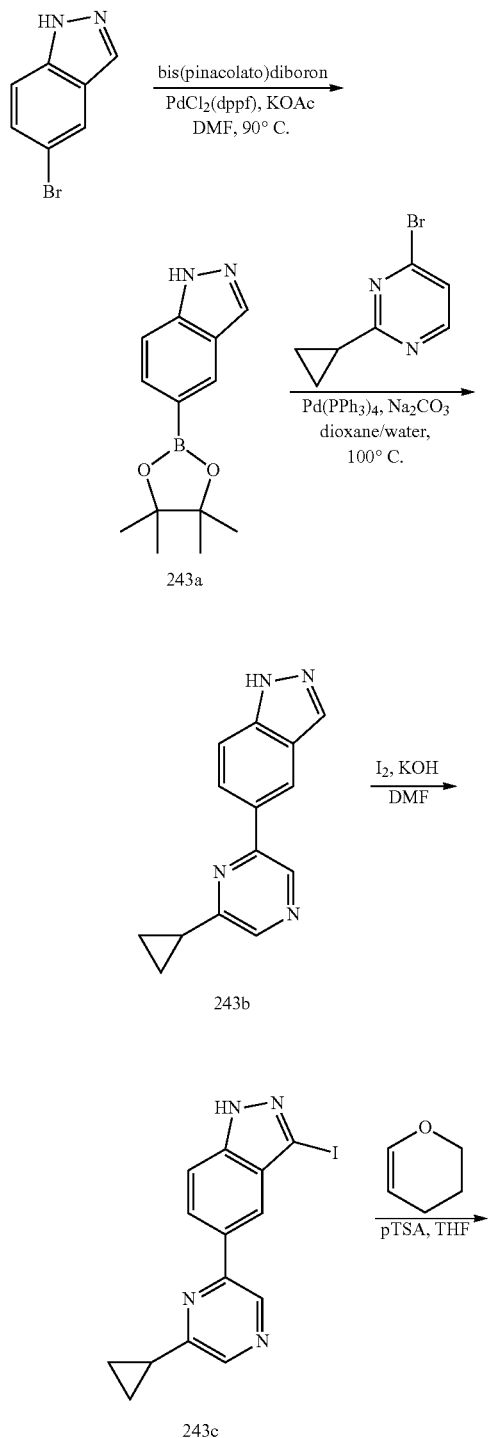

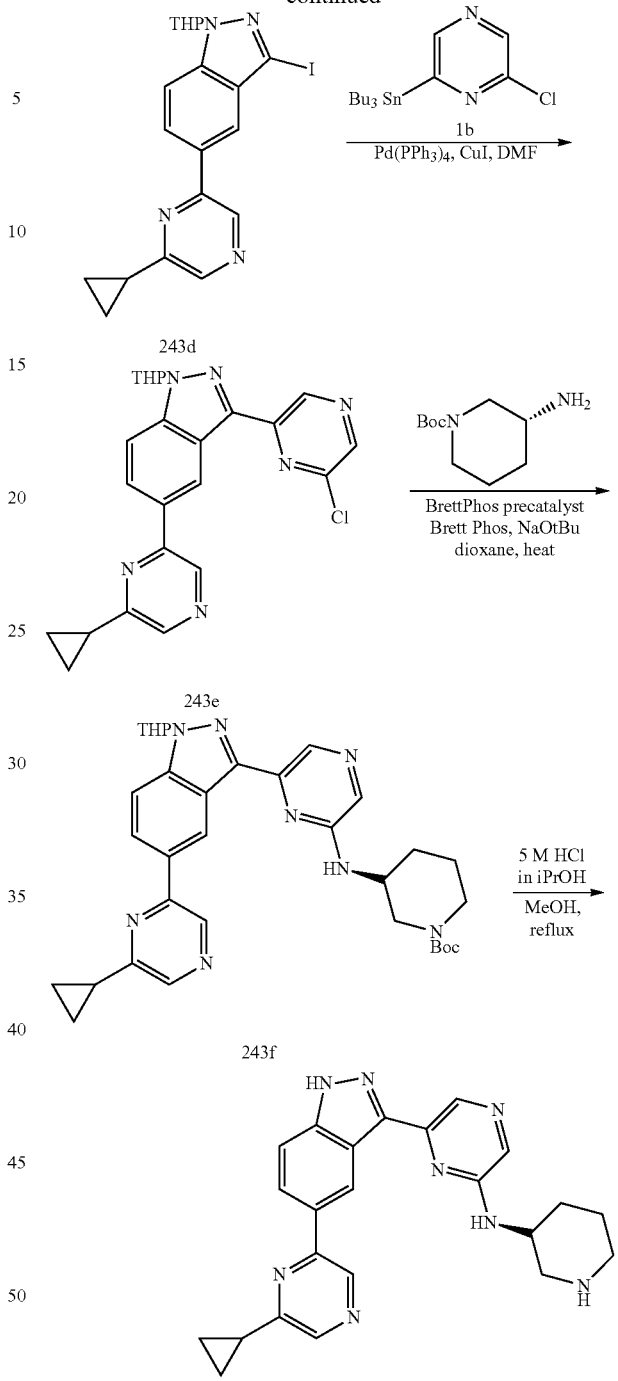

Preparation of Compound 243a: 5-(4,4,5,5-tetramethyl-1,3,2-dioxaborolan-2-yl)-1H-indazole A mixture of 5-bromo-1 h-indazole (3.00 g, 15.2 mmol, Maybridge), bis(pinacolato)diboron (5.80 g, 22.8 mmol), PdCl$_2$(dppf) (1.24 g, 1.52 mmol) and KOAc (7.47 g, 76 mmol) in DMF (38 mL) was stirred at 90° C. for 4 h. The reaction was cooled to RT and concentrated. The thick oil was taken up in EtOAc and water and filtered through celite. The layers were separated and the aqueous layer was extracted with EtOAc (2×). The combined organic layers were dried over anhydrous Na$_2$SO$_4$, filtered and concentrated. The crude was purified by silica gel chromatography, eluting with a gradient of 0-50% EtOAc in hexanes, to provide 5-(4,4,5,5-tetramethyl-1,3,2-dioxaborolan-2-yl)-1H-indazole (3.45 g, 14.1 mmol, 93% yield) as a pale yellow oil that solidified upon standing. MS (ESI, pos. ion) m/z: 245.2 (M+1).

Preparation of Compound 243b:
5-(6-cyclopropylpyrazin-2-yl)-1H-indazole

A reaction vessel was charged with 2-bromo-6-cyclopropylpyrazine (1.27 g, 6.39 mmol, Combi-Phos Catalysts Inc.) and Pd(PPh$_3$)$_4$ (308 mg, 0.27 mmol). The tube was sealed. A solution of 5-(4,4,5,5-tetramethyl-1,3,2-dioxaborolan-2-yl)-1H-indazole (1.30 g, 5.33 mmol) in dioxane (18 mL) and 2 M Na$_2$CO$_3$ (aq.) (8.0 mL, 16.0 mmol) were added. The reaction was stirred and heated at 100° C. overnight. After cooling to RT, the organic layer was separated and dried over anhydrous Na$_2$SO$_4$, filtered and concentrated. The crude was purified by silica gel chromatography, eluting with a gradient of 0-50% EtOAc in hexanes, to provide 5-(6-cyclopropylpyrazin-2-yl)-1H-indazole (575 mg, 2.43 mmol, 46% yield) as an off-white solid. MS (ESI, pos. ion) m/z: 237.2 (M+1).

Preparation of Compound 243c:
5-(6-cyclopropylpyrazin-2-yl)-3-iodo-1H-indazole

I$_2$ (269 mg, 1.06 mmol) followed by powdered KOH (111 mg, 1.98 mmol) was added to a solution of 5-(6-cyclopropylpyrazin-2-yl)-1H-indazole (125 mg, 0.53 mmol) in 1 mL of DMF at RT overnight. The mixture was added to 5 mL of 10% NaHSO$_3$ (aq.). The mixture was extracted with EtOAc (3×). The combined organic layers were dried over anhydrous Na$_2$SO$_4$, filtered and concentrated to give 5-(6-cyclopropylpyrazin-2-yl)-3-iodo-1H-indazole (192 mg, 0.53 mmol, 100% yield) as an orange solid. MS (ESI, pos. ion) m/z: 362.9 (M+1).

Preparation of Compound 243d: 5-(6-cyclopropylpyrazin-2-yl)-3-iodo-1-(tetrahydro-2H-pyran-2-yl)-1H-indazole A mixture of 5-(6-cyclopropylpyrazin-2-yl)-3-iodo-1H-indazole (192 mg, 0.53 mmol), 3,4-dihydro-2 h-pyran (96 μL, 1.06 mmol) and p-toluenesulfonic acid monohydrate (20 mg, 0.106 mmol) in THF (3 mL) was heated at reflux overnight (9 h). After cooling to RT, the mixture was concentrated to about 1 mL. The mixture was diluted with EtOAc and saturated NaHCO$_3$ (aq.) and the layers were separated. The aqueous layer was extracted with EtOAc (3×). The combined organic layers were dried over anhydrous Na$_2$SO$_4$, filtered and concentrated. The crude was purified by silica gel chromatography, eluting with a gradient of 0-30% EtOAc in hexanes, to provide 5-(6-cyclopropylpyrazin-2-yl)-3-iodo-1-(tetrahydro-2H-pyran-2-yl)-1H-indazole (140 mg, 0.31 mmol, 59% yield) as a pale yellow foam. MS (ESI, pos. ion) m/z: 447.0 (M+1).

Preparation of Compound 243e: 3-(6-chloropyrazin-2-yl)-5-(6-cyclopropylpyrazin-2-yl)-1-(tetrahydro-2H-pyran-2-yl)-1H-indazole A glass microwave reaction vessel was charged with 5-(6-cyclopropylpyrazin-2-yl)-3-iodo-1-(tetrahydro-2H-pyran-2-yl)-1H-indazole (140 mg, 0.31 mmol), 2-chloro-6-(tributylstannyl)pyrazine (190 mg, 0.47 mmol), Pd(PPh$_3$)$_4$ (18 mg, 0.016 mmol) and CuI (6 mg, 0.031 mmol) in DMF (1 mL). Argon was bubbled through the mixture for 5 min. The tube was sealed and the mixture was heated to 105° C. for 2 h. The reaction was diluted with EtOAc and water and filtered through celite. The crude was purified by silica gel chromatography, eluting with a gradient of 0-50% EtOAc in hexanes, to provide 3-(6-chloropyrazin-2-yl)-5-(6-cyclopropylpyrazin-2-yl)-1-(tetrahydro-2H-pyran-2-yl)-1H-indazole (48 mg, 0.11 mmol, 35% yield) as a light-yellow solid. MS (ESI, pos. ion) m/z: 433.0 (M+1).

Preparation of Compound 243f: (3R)-tert-butyl 3-(6-(5-(6-cyclopropylpyrazin-2-yl)-1-(tetrahydro-2H-pyran-2-yl)-1H-indazol-3-yl)pyrazin-2-ylamino) piperidine-1-carboxylate A glass microwave reaction vessel was charged with 3-(6-chloropyrazin-2-yl)-5-(6-cyclopropylpyrazin-2-yl)-1-(tetrahydro-2H-pyran-2-yl)-1H-indazole (200 mg, 0.46 mmol), dicyclohexyl(2',4',6'-triisopropyl-4,6-dimethoxybiphenyl-2-yl)phosphine (Brett-Phos) (12 mg, 0.023 mmol), chloro[2-(dicyclohexylphosphino)-3,6-dimethoxy-2'-4'-6'-tri-1,1'-biphenyl]2-(2-amino-ethyl)Ph]Pd(II) (Brett-Phos Precatalyst) (18 mg, 0.023 mmol) and NaOtBu (89 mg, 0.92 mmol). The vessel was sealed, evacuated under vacuum and back-filled with N$_2$ (3×). (R)-tent-Butyl 3-aminopiperidine-1-carboxylate (139 mg, 0.69 mmol, CNH Technologies) and dioxane (1.8 mL) were added and the mixture was heated to 85° C. for 5 h. The crude was purified by silica gel chromatography, eluting with a gradient of 0-100% EtOAc in hexanes, to provide (3R)-tert-butyl 3-(6-(5-(6-cyclopropylpyrazin-2-yl)-1-(tetrahydro-2H-pyran-2-yl)-1H-indazol-3-yl)pyrazin-2-ylamino)piperidine-1-carboxylate (179 mg, 0.30 mmol, 65% yield) as an orange oil. MS (ESI, pos. ion) m/z: 597.4 (M+1).

Preparation of Compound 243: 6-(5-(6-cyclopropyl-2-pyrazinyl)-1H-indazol-3-yl)-N-((3R)-3-piperidinyl)-2-pyrazinamine A solution of (3R)-tert-butyl 3-(6-(5-(6-cyclopropylpyrazin-2-yl)-1-(tetrahydro-2H-pyran-2-yl)-1H-indazol-3-yl)pyrazin-2-ylamino)piperidine-1-carboxylate (179 mg, 0.30 mmol) and HCl (5-6 M in IPA, 6.00 mL, 30.0 mmol) in 4 mL of MeOH was heated at 80° C. for 90 min. The crude reaction was cooled to RT and concentrated to a yellow solid that was slurried with a 1\1 mixture of DCM\MeOH (12 mL) and applied to a pre-washed (45 mL MeOH) of Si-propylsulfonic acid (12 g, Silicycle, Cat# R51230B). The column was washed with MeOH (35 mL). The compound was released with 35 mL of 2 M NH$_3$ in MeOH to afford 120 mg of crude material, which was purified by HPLC (5-100% MeCN in H$_2$O with 0.1% TFA over 15 min) to afford the title compound (56 mg, 0.14 mmol, 45% yield) as a pale yellow solid. MS (ESI, pos. ion) m/z: 413.1 (M+1). $^1$H NMR (400 MHz, DMSO-d$_6$) δ ppm 9.15 (s, 2H), 8.55 (s, 1H), 8.47 (s, 1H), 8.16 (dd, J=8.80, 1.76 Hz, 1H), 7.95 (s, 1H), 7.75 (d, J=8.80 Hz, 1H), 7.13 (d, J=7.63 Hz, 1H), 4.03-4.16 (m, 1H), 3.14-3.25 (m, 1H), 2.78-2.87 (m, 1H), 2.53-2.62 (m, 2H), 2.30 (quin, J=6.41 Hz, 1H), 2.00-2.08 (m, 1H), 1.66-1.77 (m, 1H), 1.46-1.63 (m, 2H), 1.05-1.16 (m, 4H).

Example 244

3,5-bis(6-cyclopropyl-2-pyrazinyl)-1H-indazole

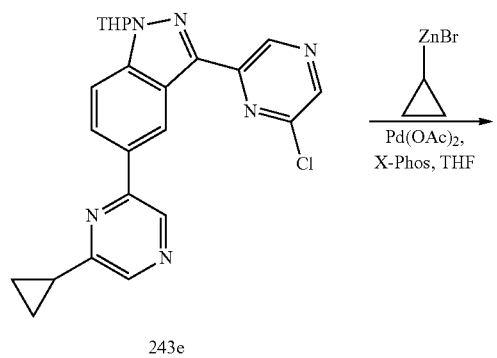

243e

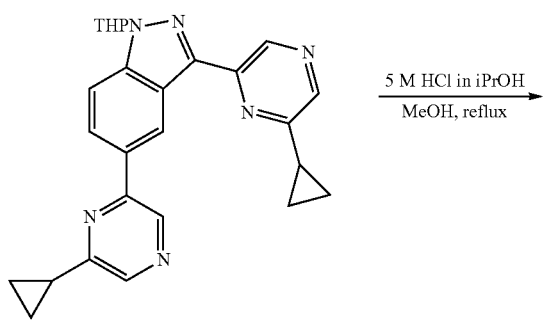

244a

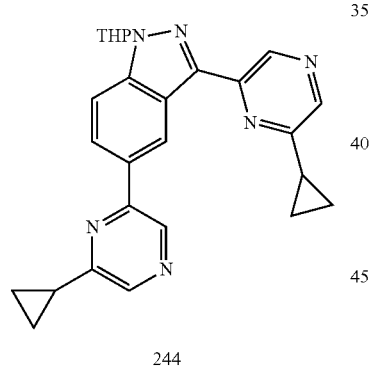

244

Preparation of Compound 244a: 3,5-bis(6-cyclopropylpyrazin-2-yl)-1-(tetrahydro-2H-pyran-2-yl)-1H-indazole A microwave tube was charged with 3-(6-chloropyrazin-2-yl)-5-(6-cyclopropylpyrazin-2-yl)-1-(tetrahydro-2H-pyran-2-yl)-1H-indazole (Ex. 243e, 111 mg, 0.256 mmol), Pd(OAc)$_2$ (3 mg, 0.013 mmol) and 2-(dicyclohexylphosphino)-2',4',6'-tri-1-propyl-1,1'-biphenyl, (X-Phos) (12 mg, 0.026 mmol) and the tube was sealed. The tube was evacuated under vacuum and backfilled with N$_2$ (3×). THF (1.7 mL) was added and the mixture was cooled in an ice-water bath. Cyclopropylzinc bromide solution (0.5 M in THF, 0.62 mL, 0.31 mmol, Sigma-Aldrich) was added and the mixture was warmed to RT and stirred for 2 h. The mixture was filtered and the crude was purified by silica gel chromatography, eluting with a gradient of 0-50% EtOAc in hexanes, to provide 24 mg of 3,5-bis(6-cyclopropylpyrazin-2-yl)-1-(tetrahydro-2H-pyran-2-yl)-1H-indazole. The column was eluted with 2-10% MeOH in CH$_2$Cl$_2$ to afford 50 mg of 3,5-bis(6-cyclopropylpyrazin-2-yl)-1-(tetrahydro-2H-pyran-2-yl)-1H-indazole.

The two portions were combined to give 3,5-bis(6-cyclopropylpyrazin-2-yl)-1-(tetrahydro-2H-pyran-2-yl)-1H-indazole (74 mg, 0.17 mmol, 66% yield) as a yellow foam. MS (ESI, pos. ion) m/z: 439.2 (M+1).

Preparation of Compound 244: 3,5-bis(6-cyclopropyl-2-pyrazinyl)-1H-indazole

A solution of 3,5-bis(6-cyclopropylpyrazin-2-yl)-1-(tetrahydro-2H-pyran-2-yl)-1H-indazole (74 mg, 0.17 mmol) and HCl (5-6 M in IPA, 3.4 mL, 16.9 mmol) in 5 mL of MeOH was heated at 80° C. for 90 min. The crude reaction was cooled to RT and concentrated to a yellow solid that was slurried with a 1\1 mixture of DCM\MeOH (12 mL) and applied to a pre-washed (45 mL MeOH) of Si-propylsulfonic acid (12 g, Silicycle, Cat# R51230B). The column was washed with MeOH (35 mL). The compound was released with 35 mL of 2 M NH$_3$ in MeOH. The crude product was purified by silica gel chromatography, eluting with a gradient of 0-75% EtOAc in hexanes, to provide the title compound (20 mg, 0.056 mmol, 33% yield) as a white solid. MS (ESI, pos. ion) m/z: 355.1 (M+1). $^1$H NMR (400 MHz, DMSO-d$_6$) δ ppm 9.09-9.16 (m, 2H), 8.97 (s, 1H), 8.60 (d, J=16.63 Hz, 2H), 8.15 (dt, J=8.80, 0.88 Hz, 1H), 7.74 (d, J=8.80 Hz, 1H), 2.32-2.38 (m, 1H), 2.25-2.31 (m, 1H), 1.16-1.26 (m, 6H), 1.09-1.15 (m, 2H).

Example 245

3,5-bis(6-cyclopropyl-2-pyrazinyl)-1H-indole

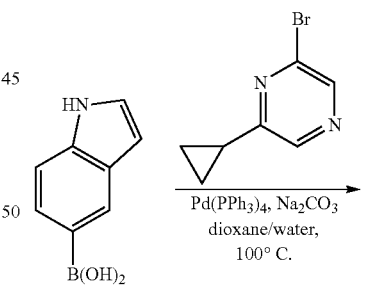

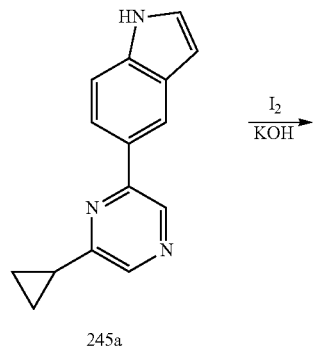

245a

-continued

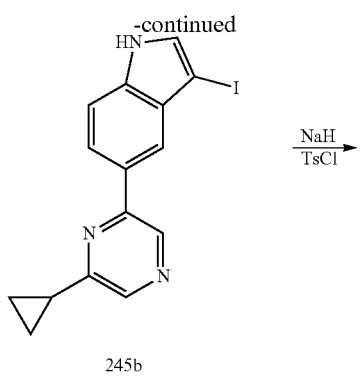

245b

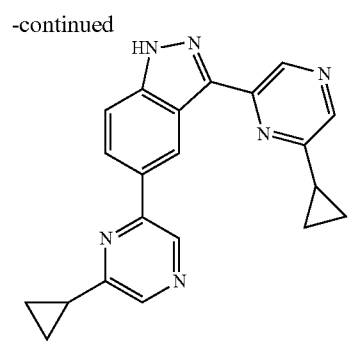

245

Preparation of Compound 245a: 5-(6-cyclopropylpyrazin-2-yl)-1H-indole

A reaction vessel was charged with indole-5-boronic acid (674 mg, 4.19 mmol, Sigma-Aldrich), 2-bromo-6-cyclopropylpyrazine (1.00 g, 5.02 mmol, Combi-Phos Catalysts Inc.) and Pd(PPh$_3$)$_4$ (242 mg, 0.21 mmol). The tube was sealed. Dioxane (14 mL) and 2 M Na$_2$CO$_3$ (aq.) (6.28 mL, 12.56 mmol) were added. The reaction was stirred and heated in at 100° C. for 7 h. After cooling to RT, the organic layer was separated and dried over anhydrous Na$_2$SO$_4$, filtered and concentrated. The crude was purified by silica gel chromatography, eluting with a gradient of 0-40% EtOAc in hexanes, to provide 5-(6-cyclopropylpyrazin-2-yl)-1H-indole (750 mg, 3.19 mmol, 76% yield) as a white solid. MS (ESI, pos. ion) m/z: 236.1 (M+1).

Preparation of Compound 245b: 5-(6-cyclopropylpyrazin-2-yl)-3-iodo-1H-indole I$_2$ (1.62 g, 6.38 mmol) followed by powdered KOH (0.671 g, 11.95 mmol) was added to a solution of 5-(6-cyclopropylpyrazin-2-yl)-1H-indole (750 mg, 3.19 mmol) in 7 mL of DMF at RT overnight. The mixture was added to 30 mL of 10% NaHSO$_3$ (aq.). The mixture was extracted with EtOAc (3×). The combined organic layers were dried over anhydrous Na$_2$SO$_4$, filtered and concentrated. The crude was purified by silica gel chromatography, eluting with a gradient of 0-30% EtOAc in hexanes, to provide 5-(6-cyclopropylpyrazin-2-yl)-3-iodo-1H-indole (280 mg, 0.78 mmol, 24% yield) as an orange solid. MS (ESI, pos. ion) m/z: 362.0 (M+1).

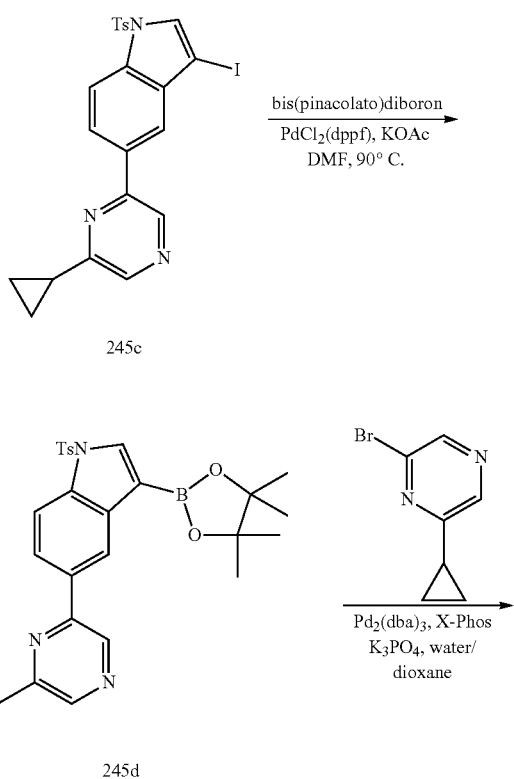

245c

245d

Preparation of Compound 245c: 5-(6-cyclopropylpyrazin-2-yl)-3-iodo-1-tosyl-1H-indole NaH (60% in mineral oil) (34 mg, 0.85 mmol) was added to a solution of 5-(6-cyclopropylpyrazin-2-yl)-3-iodo-1H-indole (280 mg, 0.78 mmol) in THF (4 mL) at 0° C. The mixture was stirred for 10 min at 0° C. and p-toluenesulfonyl chloride (163 mg, 0.85 mmol) was added and the mixture was warmed to RT. After 1 h, water was added and the mixture was extracted with EtOAc (3×). The combined organic layers were dried over anhydrous Na$_2$SO$_4$, filtered and concentrated to afford 5-(6-cyclopropylpyrazin-2-yl)-3-iodo-1-tosyl-1H-indole (394 mg, 0.76 mmol, 99% yield) as a yellow solid. MS (ESI, pos. ion) m/z: 516.0 (M+1).-

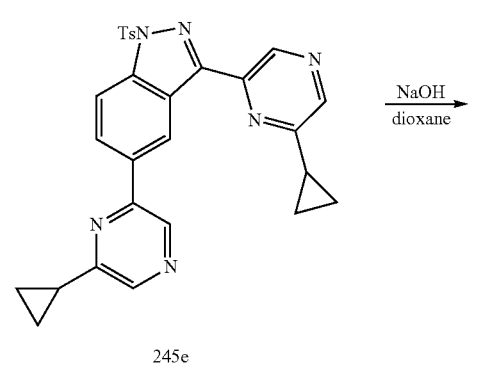

245e

Preparation of Compound 245d: 5-(6-cyclopropy-lpyrazin-2-yl)-3-(4,4,5,5-tetramethyl-1,3,2-dioxaborolan-2-yl)-1-tosyl-1H-indole A mixture of 5-(6-cyclopropylpyrazin-2-yl)-3-iodo-1-tosyl-1H-indole (386 mg, 0.75 mmol), bis(pinacolato)diboron (475 mg, 1.87 mmol), PdCl$_2$(dppf) (61 mg, 0.075 mmol) and KOAc (294 mg, 3.00 mmol) in 4 mL of DMF was heated at 90° C. overnight. The mixture was concentrated, diluted in EtOAc and water and filtered through celite. The layers were separated and the aqueous layer was extracted with EtOAc (2×). The combined organic layers were dried over anhydrous Na$_2$SO$_4$, filtered and concentrated. The crude was purified by silica gel chromatography, eluting with a gradient of 0-50% EtOAc in hexanes, to provide 5-(6-cyclopropylpyrazin-2-yl)-3-(4,4,5,5-tetramethyl-1,3,2-dioxaborolan-2-yl)-1-tosyl-1H-indole (354 mg, 0.69 mmol, 92% yield) as a tan solid. MS (ESI, pos. ion) m/z: 516.1 (M+1).

Preparation of Compound 245e: 3,5-bis(6-cyclopropylpyrazin-2-yl)-1-tosyl-1H-indole A glass microwave reaction vessel was charged with 5-(6-cyclopropylpyrazin-2-yl)-3-(4,4,5,5-tetramethyl-1,3,2-dioxaborolan-2-yl)-1-tosyl-1H-indole (172 mg, 0.33 mmol), 2-bromo-6-cyclopropylpyrazine (80 mg, 0.40 mmol, CombiPhos Catalysis Inc.), Pd$_2$(dba)$_3$ CHCl$_3$ adduct (10 mg, 10.0 μmol), 2-(dicyclohexylphosphino)-2',4',6'-tri-1-propyl-1,1'-biphenyl (X-Phos) (10 mg, 0.020 mmol) and K$_3$PO$_4$ (213 mg, 1.00 mmol). The tube was sealed. The tube was evacuated under vacuum and back-filled with N$_2$ (3×). Dioxane (1.9 mL) and water (0.18 mL) were added. The reaction was stirred and heated in a Initiator microwave reactor (Personal Chemistry, Biotage AB, Inc., Upssala, Sweden) at 130° C. for 20 min. Water was added and the mixture was extracted with EtOAc (3×). The combined organic layers were dried over anhydrous Na$_2$SO$_4$, filtered and concentrated. The crude was purified by silica gel chromatography, eluting with a gradient of 0-50% EtOAc in hexanes, to provide 3,5-bis(6-cyclopropylpyrazin-2-yl)-1-tosyl-1H-indole (72 mg, 0.14 mmol, 43% yield) as a red oil. MS (ESI, pos. ion) m/z: 508.1 (M+1).

Preparation of Compound 245: 3,5-bis(6-cyclopropyl-2-pyrazinyl)-1H-indole

A glass microwave reaction vessel was charged with 3,5-bis(6-cyclopropylpyrazin-2-yl)-1-tosyl-1H-indole (72 mg, 0.14 mmol) and 1 M NaOH (aq., 0.71 mL, 0.71 mmol) in dioxane (1.5 mL). The reaction was stirred and heated in a Initiator microwave reactor (Personal Chemistry, Biotage AB, Inc., Upssala, Sweden) at 120° C. for 20 min. Saturated NaCl (aq.) was added and the mixture was extracted with EtOAc (3×). The combined organic layers were dried over anhydrous Na$_2$SO$_4$, filtered and concentrated. The crude product was purified by silica gel chromatography, eluting with a gradient of 0-70% EtOAc in hexanes, to the title compound (25 mg, 0.07 mmol, 50% yield) as a light-yellow solid. MS (ESI, pos. ion) m/z: 354.1 (M+1). $^1$H NMR (400 MHz, DMSO-d$_6$) δ ppm 11.90 (s, 1H), 9.07-9.14 (m, 1H), 8.95 (d, J=6.46 Hz, 2H), 8.53 (s, 1H), 8.37 (d, J=3.91 Hz, 2H), 7.89-7.97 (m, 1H), 7.60 (s, 1H), 2.22-2.33 (m, 2H), 1.06-1.26 (m, 8H).

Example 246

5-(2,6-difluorophenyl)-3-(6-(3-pyridinyloxy)-2-pyrazinyl)-1H-indazole

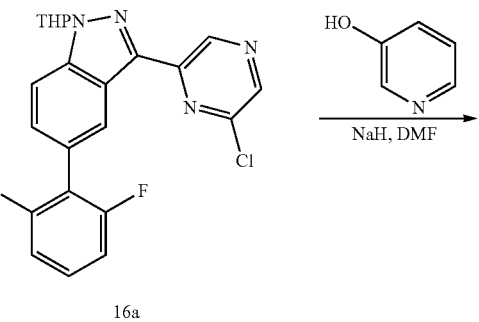

16a

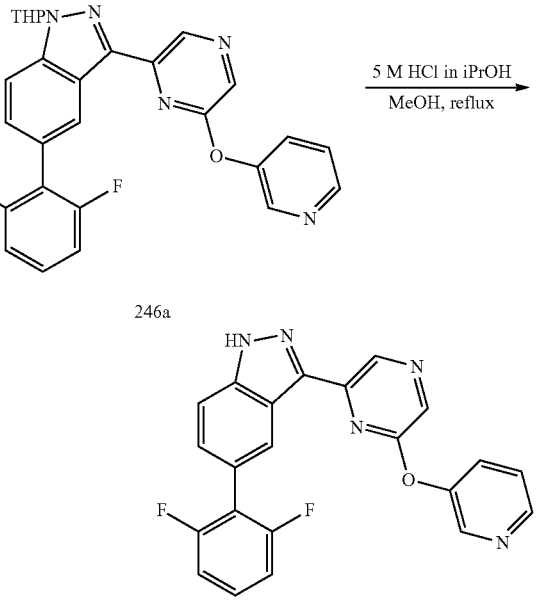

246a

246

Preparation of Compound 246a: 5-(2,6-difluorophenyl)-3-(6-(pyridin-3-yloxy)pyrazin-2-yl)-1-(tetrahydro-2H-pyran-2-yl)-1H-indazole To a solution of 3-hydroxypyridine (40 mg, 0.42 mmol) in DMF (1.2 mL) at 0° C. was added NaH (60% in mineral oil) (28 mg, 0.70 mmol). The heterogenous mixture was stirred for 10 min at 0° C., 3-(6-chloropyrazin-2-yl)-5-(2,6-difluorophenyl)-1-(tetrahydro-2H-pyran-2-yl)-1H-indazole (Ex. 16a, 150 mg, 0.35 mmol) was added. The mixture was warmed to RT and stirred overnight. The mixture was then heated at 60° C. for 6 h. Ice was added and the mixture was extracted with EtOAc (3×) and CH$_2$Cl$_2$ (2×). The combined organic layers were dried over anhydrous Na$_2$SO$_4$, filtered and concentrated. The crude was purified by silica gel chromatography, eluting with a gradient of 0-75% EtOAc in hexanes, to provide 5-(2,6-difluorophenyl)-3-(6-(pyridin-3- yloxy)pyrazin-2-yl)-1-(tetrahydro-2H-pyran-2-yl)-1H-indazole (74 mg, 0.15 mmol, 43% yield) as a white solid. MS (ESI, pos. ion) m/z: 486.0 (M+1).

Preparation of Compound 246: 5-(2,6-difluorophenyl)-3-(6-(3-pyridinyloxy)-2-pyrazinyl)-1H-indazole A solution of 5-(2,6-difluorophenyl)-3-(6-(pyridin-3-yloxy)pyrazin-2-yl)-1-(tetrahydro-2H-pyran-2-yl)-1H-indazole (74 mg, 0.15 mmol) and HCl (5-6 M in IPA, 3.0 mL, 15.2 mmol) in 4 mL of MeOH was heated at 80° C. for 90 min. The reaction was cooled to RT and concentrated. The residue was diluted with CH$_2$Cl$_2$ and saturated NaHCO$_3$ (aq.) was added slowly. The mixture was extracted with CH$_2$Cl$_2$ (3×). The combined organic layers were dried over anhydrous Na$_2$SO$_4$, filtered and concentrated to give the title compound (55 mg, 0.14 mmol, 90% yield) as a yellow solid. MS (ESI, pos. ion) m/z: 402.0 (M+1). $^1$H NMR (400 MHz, DMSO-d$_6$) δ ppm 13.77 (s, 1H), 9.15 (s, 1H), 8.60 (s, 1H), 8.56 (d, J=2.15 Hz, 1H), 7.99 (d, J=4.30 Hz, 1H), 7.82 (dd, J=8.22, 1.37 Hz, 1H), 7.69 (d, J=8.61 Hz, 1H), 7.53-7.62 (m, 1H), 7.49 (s, 1H), 7.37 (d, J=8.61 Hz, 1H), 7.25-7.33 (m, 2H), 7.23 (dd, J=8.41, 4.69 Hz, 1H).

Example 247

3-(3-(6-((4R)-6-azaspiro[25]oct-4-yloxy)-2-pyrazinyl)-1H-indazol-5-yl)-N-cyclopropylbenzamide

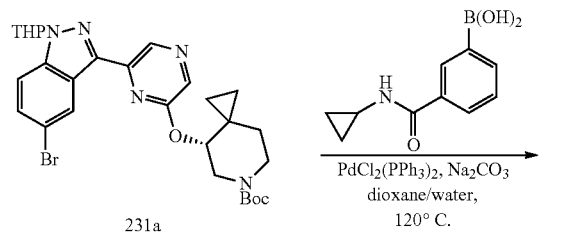

231a

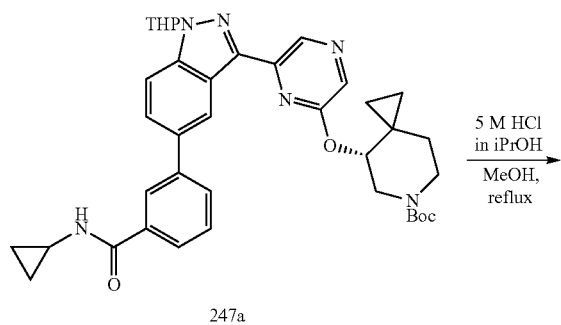

247a

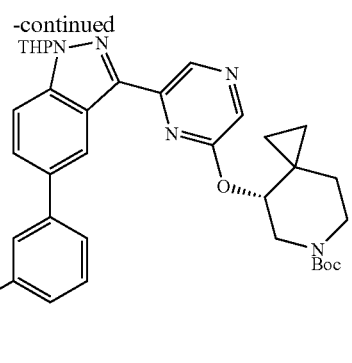

247

Preparation of Compound 247a: (4R)-tert-butyl 4-(6-(5-(3-(cyclopropylcarbamoyl)phenyl)-1-(tetrahydro-2H-pyran-2-yl)-1H-indazol-3-yl)pyrazin-2-yloxy)-6-azaspiro[2.5]octane-6-carboxylate A glass microwave reaction vessel was charged with (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (115 mg, 0.20 mmol), 3-(cyclopropylcarbamoyl)phenylboronic acid (81 mg, 0.39 mmol), PdCl$_2$(PPh$_3$)$_2$ (11 mg, 0.016 mmol) and Na$_2$CO$_3$ (104 mg, 0.98 mmol) in dioxane (0.8 mL) and water (0.2 mL). The reaction was stirred and heated in a Initiator microwave reactor (Personal Chemistry, Biotage AB, Inc., Upssala, Sweden) at 120° C. for 20 min. The layers were separated and the organic phase was dried over anhydrous Na$_2$SO$_4$, filtered and concentrated. The crude was purified by silica gel chromatography, eluting with a gradient of 0-75% EtOAc in hexanes, to provide (4R)-tert-butyl 4-(6-(5-(3-(cyclopropylcarbamoyl)phenyl)-1-(tetrahydro-2H-pyran-2-yl)-1H-indazol-3-yl)pyrazin-2-yloxy)-6-azaspiro[2.5]octane-6-carboxylate (107 mg, 0.16 mmol, 82% yield) as a clear, colorless oil. MS (ESI, pos. ion) m/z: 665.3 (M+1).

Preparation of Compound 247: 3-(3-(6-((4R)-6-azaspiro[25]oct-4-yloxy)-2-pyrazinyl)-1H-indazol-5-yl)-N-cyclopropylbenzamide A solution of (4R)-tert-butyl 4-(6-(5-(3-(cyclopropylcarbamoyl)phenyl)-1-(tetrahydro-2H-pyran-2-yl)-1H-indazol-3-yl)pyrazin-2-yloxy)-6-azaspiro[2.5]octane-6-carboxylate (107 mg, 0.16 mmol) and HCl (5-6 M in IPA, 3.2 mL, 16.10 mmol) in 4 mL of MeOH was heated at 80° C. for 90 min. The crude reaction was cooled to RT and concentrated. The yellow residue was put into solution with 10% MeOH in CH$_2$Cl$_2$. Saturated NaHCO$_3$ (aq.) was added and the layers were separated. The aqueous layer was extracted with 10% MeOH in CH$_2$Cl$_2$ (2×). The combined organic layers were dried over anhydrous Na$_2$SO$_4$, filtered and concentrated. The crude was purified by silica gel chromatography, eluting with a gradient of 0-10% MeOH in CH$_2$Cl$_2$, to provide the title compound (21 mg, 0.04 mmol, 27% yield) as a light-yellow solid. MS (ESI, pos. ion) m/z: 481.2 (M+1). $^1$H NMR (400 MHz, DMSO-d$_6$) δ ppm 8.74 (s, 1H), 8.44 (s, 1H), 8.32-8.38 (m, 1H), 8.04 (s, 1H), 7.94 (t, J=1.96 Hz, 1H), 7.53-7.70 (m, 4H), 7.37 (t, J=7.73 Hz, 1H), 5.55 (s, 1H), 4.53 (t, J=3.13 Hz, 1H), 2.99 (dd, J=12.81, 4.01 Hz, 1H), 2.76-2.85 (m, 1H), 2.61-2.74 (m, 2H), 2.42-2.53 (m, 1H), 1.67-1.78 (m, 1H), 0.80 (d, J=13.11 Hz, 1H), 0.49-0.57 (m, 2H), 0.37-0.47 (m, 3H), 0.25-0.33 (m, 1H), 0.09-0.21 (m, 2H).

Example 248

Racemic cis-1-(6-(5-(2,6-difluorophenyl)-1H-indazol-3-yl)-2-pyrazinyl)-3,4-piperidinediol-1-(6-(5-(2,6-difluorophenyl)-1-(tetrahydro-2H-pyran-2-yl)-1H-indazol-3-yl)pyrazin-2-yl)piperidine-3,4-diol

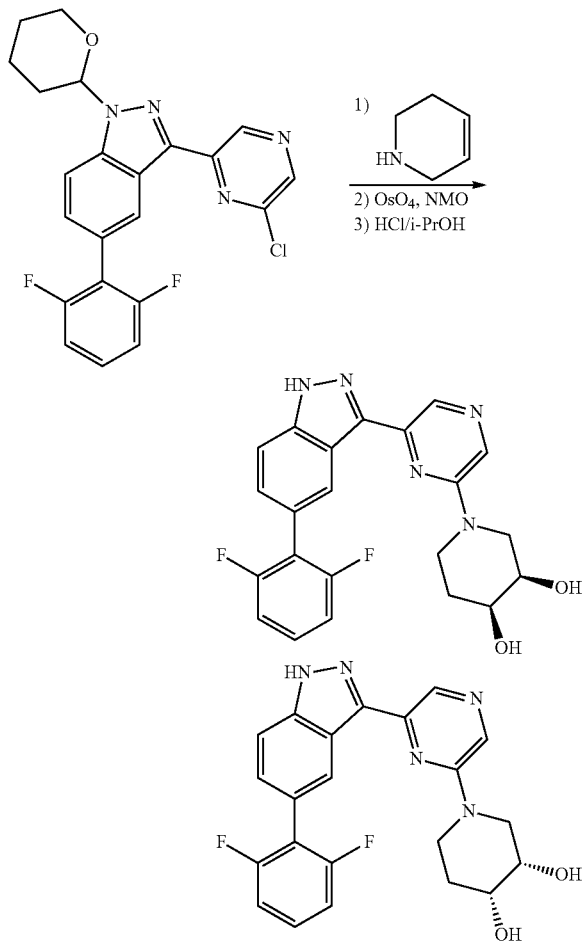

Preparation of Compound 248a: 5-(2,6-difluorophenyl)-3-(6-(5,6-dihydropyridin-1(2H)-yl)pyrazin-2-yl)-1-(tetrahydro-2H-pyran-2-yl)-1H-indazole A slurry of 3-(6-chloropyrazin-2-yl)-5-(2,6-difluorophenyl)-1-(tetrahydro-2H-pyran-2-yl)-1H-indazole (0.500 g, 1.171 mmol) and 5-(2,6-difluorophenyl)-3-(6-(5,6-dihydropyridin-1(2H)-yl)pyrazin-2-yl)-1-(tetrahydro-2H-pyran-2-yl)-1H-indazole (0.461 g, 0.974 mmol, 83% yield) in 2 mL NMP was sealed and heated to 120° C. The reaction became an orange/brown solution. After 1 h, the reaction was complete. The reaction was partitioned between water and EtOAc. The organic layer was washed with water once, saturated aqueous NaCl once, and the organics were dried over anhydrous $Na_2SO_4$, filtered, and concentrated in vacuo. The material was treated with DCM and purified by silica gel chromatography using 0-40% EtOAc/hexane. The desired fractions were concentrated to afford 5-(2,6-difluorophenyl)-3-(6-(5,6-dihydropyridin-1(2H)-yl)pyrazin-2-yl)-1-(tetrahydro-2H-pyran-2-yl)-1H-indazole (0.461 g, 0.974 mmol, 83% yield) as a yellow solid. MS (ESI, pos. ion) m/z: 474 (M+1).

Preparation of Compound 248b: racemic cis-1-(6-(5-(2,6-difluorophenyl)-1-(tetrahydro-2H-pyran-2-yl)-1H-indazol-3-yl)pyrazin-2-yl)piperidine-3,4-diol To a bright yellow slurry of 5-(2,6-difluorophenyl)-3-(6-(5,6-dihydropyridin-1(2H)-yl)pyrazin-2-yl)-1-(tetrahydro-2H-pyran-2-yl)-1H-indazole (0.225 g, 0.475 mmol) and NMO (aldrich) (0.083 g, 0.713 mmol) in 3 mL acetone and 1 mL water was added osmium tetroxide 4% solution in water (aldrich) (0.151 mL, 0.024 mmol). The reaction was sealed and stirred rapidly over the weekend. The heterogeneous reaction was refreshed with NMO (aldrich) (0.083 g, 0.713 mmol) and osmium tetroxide 4% solution in water (aldrich) (0.151 mL, 0.024 mmol) and stirred rapidly for 36 h. The heterogeneous reaction was refreshed with NMO (aldrich) (0.083 g, 0.713 mmol) and osmium tetroxide 4% solution in water (Aldrich) (0.151 mL, 0.024 mmol) and stirred rapidly 48 h. The reaction was treated with 2 mL sat'd aqueous $NaHSO_3$, and partitioned between water and DCM. The aqueous layer was extracted with DCM 4 times, and the combined organics were dried over anhydrous $Na_2SO_4$, filtered, and concentrated in vacuo. The material was treated with 10% MeOH in DCM and adsorbed onto 2 g silica gel, then purified by silica gel chromatography (40 g column) using 0-75% 90/10 DCM/MeOH in DCM. The product-containing fractions were concentrated to afford racemic cis-1-(6-(5-(2,6-difluorophenyl)-1-(tetrahydro-2H-pyran-2-yl)-1H-indazol-3-yl)pyrazin-2-yl)piperidine-3,4-diol (0.10 g, 0.197 mmol, 41.5% yield) as a yellow solid: MS (ESI, pos. ion) m/z: 508 (M+1).

Preparation of Compound 248: Racemic cis-1-(6-(5-(2,6-difluorophenyl)-1H-indazol-3-yl)-2-pyrazinyl)-3,4-piperidinediol-1-(6-(5-(2,6-difluorophenyl)-1-(tetrahydro-2H-pyran-2-yl)-1H-indazol-3-yl)pyrazin-2-yl)piperidine-3,4-diol A slurry of racemic cis-1-(6-(5-(2,6-difluorophenyl)-1-(tetrahydro-2H-pyran-2-yl)-1H-indazol-3-yl)pyrazin-2-yl)piperidine-3,4-diol (0.100 g, 0.197 mmol) in 3 mL 5-6 N HCl in IPA (acros organics) was sealed and the slurry was heated to 70° C. After 1.5 h, the reaction was cooled and concentrated in vacuo. This material was dissolved in DMSO and purified by shimadzu RPHPLC, 15-70% ACN/H2O with 0.1% TFA; product-containing fractions were concentrated in vacuo. The material was partitioned between sat'd aq $NaHCO_3$ and DCM, and the aq. layer was extracted 3×10% MeOH/DCM. The combined organics were dried over anhydrous $Na_2SO_4$, filtered, and concentrated in vacuo to give the title compound (0.024 g, 29% yield) as an off-white solid: MS (ESI, pos. ion) m/z: 424 (M+1).

Example 249 and 250

Non racemic cis-1-(6-(5-(2,6-difluorophenyl)-1H-indazol-3-yl)-2-pyrazinyl)-3,4-piperidinediol-1-(6-(5-(2,6-difluorophenyl)-1-(tetrahydro-2H-pyran-2-yl)-1H-indazol-3-yl)pyrazin-2-yl)piperidine-3,4-diol, enantiomer 1 and 2

A portion of the racemic cis-1-(6-(5-(2,6-difluorophenyl)-1H-indazol-3-yl)-2-pyrazinyl)-3,4-piperidinediol-1-(6-(5-

(2,6-difluorophenyl)-1-(tetrahydro-2H-pyran-2-yl)-1H-indazol-3-yl)pyrazin-2-yl)piperidine-3,4-diol was resolved by chiral SFC: Chiralcel ADH (21×250 mm, 5um), supercritical fluid CO2+27% EtOH with 20 mM NH₃, column temperature was 40° C. and outlet pressure was 100 bar. Non racemic cis-1-(6-(5-(2,6-difluorophenyl)-1H-indazol-3-yl)-2-pyrazinyl)-3,4-piperidinediol-1-(6-(5-(2,6-difluorophenyl)-1-(tetrahydro-2H-pyran-2-yl)-1H-indazol-3-yl)pyrazin-2-yl)piperidine-3,4-diol, enantiomer 1 and 2 were obtained.

Example 251

3-(6-((4R)-6-azaspiro[25]oct-4-yloxy)-2-pyrazinyl)-N-phenyl-1H-indazol-5-amine bis(2,2,2-trifluoroacetate)

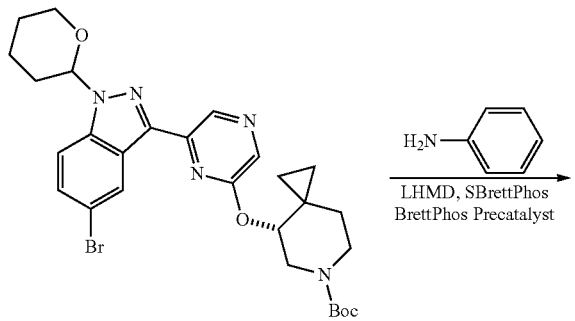

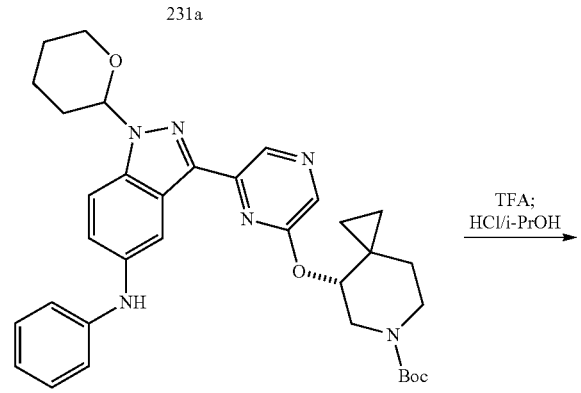

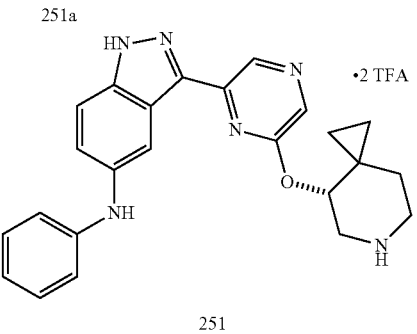

251

Preparation of Compound 251a: (4R)-tert-butyl 4-((6-(5-(phenylamino)-1-(tetrahydro-2H-pyran-2-yl)-1H-indazol-3-yl)pyrazin-2-yl)oxy)-6-azaspiro[2.5]octane-6-carboxylate Aniline (0.019 ml, 0.205 mmol), dicyclohexyl(2',4',6'-triisopropoxy-3,6-dimethoxy-[1,1'-biphenyl]-2-yl)phosphine (brettphos) (5.00 mg, 8.55 μmol), brettphosprecatalyst (7.24 mg, 8.55 μmol), and (4R)-tert-butyl 4-((6-(5-bromo-1-(tetrahydro-2H-pyran-2-yl)-1H-indazol-3-yl)pyrazin-2-yl)oxy)-6-azaspiro[2.5]octane-6-carboxylate (0.100 g, 0.171 mmol) were combined in 0.37 mL THF under argon. Lithium bis(trimethylsilyl)amide, 1.0 m solution in THF (0.376 ml, 0.376 mmol) was added. The dark red solution was sealed and heated in a 70° C. bath for 5 h. The reaction was cooled partitioned between saturated aqueous NH₄Cl and DCM. The aqueous layer was extracted with DCM 3 times, and the combined organics were dried over anhydrous Na₂SO₄, filtered, and concentrated in vacuo. The material was treated with DCM and purified by silica gel chromatography (25 g column) using 0-30% EtOAc/hexane. The product-containing fractions were combined and concentrated to give (4R)-tert-butyl 4-((6-(5-(phenylamino)-1-(tetrahydro-2H-pyran-2-yl)-1H-indazol-3-yl)pyrazin-2-yl)oxy)-6-azaspiro[2.5]octane-6-carboxylate (0.061 g, 0.102 mmol, 59.8% yield) as a sticky brown oil. MS (ESI, pos. ion) m/z: 597 (M+1).

Preparation of Compound 251: 3-(6-((4R)-6-azaspiro[25]oct-4-yloxy)-2-pyrazinyl)-N-phenyl-1H-indazol-5-amine bis(2,2,2-trifluoroacetate)

To a solution of (4R)-tert-butyl 4-((6-(5-(phenylamino)-1-(tetrahydro-2H-pyran-2-yl)-1H-indazol-3-yl)pyrazin-2-yl)oxy)-6-azaspiro[2.5]octane-6-carboxylate (0.061 g, 0.102 mmol) in 1.5 mL DCM was added TFA (0.236 ml, 3.07 mmol). The reaction became dark red and was stirred for 2 h. Additional TFA (0.236 ml, 3.07 mmol) was added. After 2 h the reaction was concentrated under a stream of N₂ and 1 mL 5-6 M HCl/IPA (acros organics) was added and the reaction stirred for 1 h. The reaction was treated with 1 mL DMSO and filtered, and purified by RPHPLC, 10-80% ACN/H2O with 0.1% TFA; product-containing fractions were concentrated in vacuo to give the title compound (0.019 g, 0.030 mmol, 29.0% yield) as an orange solid. MS (ESI, pos. ion) m/z: 413 (M+1).

Example 252

3-(6-((4R)-6-azaspiro[2.5]oct-4-yloxy)-2-pyrazinyl)-5-(1-methyl-1H-pyrazol-5-yl)-1H-indazole

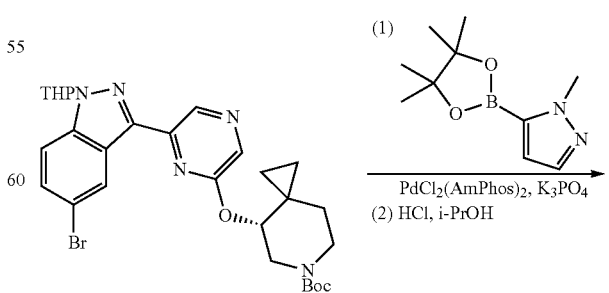

231a

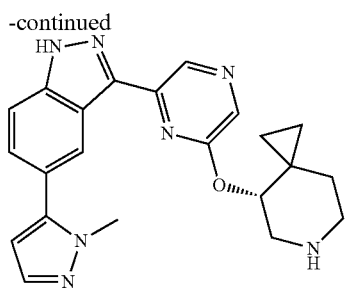

252

Preparation of Compound 252a: (4R)-tert-butyl 4-(6-(5-(1-methyl-1H-pyrazol-5-yl)-1-(tetrahydro-2H-pyran-2-yl)-1H-indazol-3-yl)pyrazin-2-yloxy)-6-azaspiro[2.5]octane-6-carboxylate (4R)-tert-Butyl 4-(6-(5-bromo-1-(tetrahydro-2H-pyran-2-yl)-1H-indazol-3-yl)pyrazin-2-yloxy)-6-azaspiro[2.5]octane-6-carboxylate (158 mg, 0.270 mmol), 1-methyl-5-(4,4,5,5-tetramethyl-1,3,2-dioxaborolan-2-yl)-1H-pyrazole (Aldrich, St. Louis, Mo.; 84 mg, 0.405 mmol), PdCl$_2$(Amphos) (Aldrich, St. Louis, Mo.; 19.14 mg, 0.027 mmol), and potassium phosphate (172 mg, 0.811 mmol) in a mixture of dioxane (2.5 mL) and water (0.250 mL) was heated by microwave at 150° C. for 5 min. The resulting mixture was heated at 100° C. for 3 h. The mixture was subsequently concentrated onto silica gel and chromatographically purified (ISCO, 12 g silica gel column, 0-80% EtOAc/hexanes, 15 min, 254 nm) to provide (4R)-tert-butyl 4-(6-(5-(1-methyl-1H-pyrazol-5-yl)-1-(tetrahydro-2H-pyran-2-yl)-1H-indazol-3-yl)pyrazin-2-yloxy)-6-azaspiro[2.5]octane-6-carboxylate (158 mg, 0.270 mmol, 100% yield) as a light-yellow oil: $^1$H NMR (400 MHz, CDCl$_3$) δ ppm 9.06 (1 H, s), 8.43 (1 H, s), 8.21 (1H, br. s.), 7.76 (1 H, d, J=8.6 Hz), 7.58 (1 H, s), 7.49 (1 H, d, J=8.4 Hz), 6.33 (1H, s), 5.86 (1 H, d, J=7.6 Hz), 4.57 (1 H, br. s.), 4.31-4.40 (1 H, m), 4.19-4.29 (1 H, m), 4.06 (1 H, d, J=11.0 Hz), 3.93 (3 H, s), 3.75-3.87 (1 H, m), 3.15 (1 H, d, J=14.1 Hz), 2.92 (1 H, br. s.), 2.60-2.74 (1 H, m), 2.43 (1 H, br. s.), 2.25 (1 H, m, J=9.0, 4.1 Hz), 2.17 (1 H, d, J=14.9 Hz), 1.76-1.91 (2 H, m), 1.74 (2 H, br. s.), 1.13 (9 H, br. s.), 0.78-0.88 (2 H, m), 0.62-0.73 (2 H, m). MS (ESI, pos. ion) m/z: 586.4 (M+1).

Preparation of Compound 252: 3-(6-((4R)-6-azaspiro[2.5]oct-4-yloxy)-2-pyrazinyl)-5-(1-methyl-1H-pyrazol-5-yl)-1H-indazole 2,2,2-trifluoroacetate A solution of (4R)-tert-butyl 4-(6-(5-(1-methyl-1H-pyrazol-5-yl)-1-(tetrahydro-2H-pyran-2-yl)-1H-indazol-3-yl)pyrazin-2-yloxy)-6-azaspiro[2.5]octane-6-carboxylate (158 mg, 0.270 mmol) in HCl (5.0M in IPA; 6.0 mL, 30.0 mmol) was stirred under argon at 25° C. for 16 h. The reaction was cooled to RT and concentrated in vacuo. The residue was taken up in DMSO (3.0 mL) and purified by rpHPLC (Phenomenex Gemini C18 column (150×30 mm, 10 µm), 35 mL/min, 5-100% CH$_3$CN/H$_2$O+0.1% TFA, 15 min, 254 nm) to provide 3-(6-((4R)-6-azaspiro[2.5]oct-4-yloxy)-2-pyrazinyl)-5-(1-methyl-1H-pyrazol-5-yl)-1H-indazole 2,2,2-trifluoroacetate (104.7 mg, 0.203 mmol, 75% yield) as a light-yellow solid: $^1$H NMR (400 MHz, DMSO-d$_6$) δ ppm 13.82 (1 H, br. s.), 9.01 (1 H, s), 8.94 (1 H, d, J=10.4 Hz), 8.60 (1 H, d, J=10.8 Hz), 8.34 (1 H, s), 8.31 (1H, s), 7.78 (1 H, d, J=8.8 Hz), 7.62 (1 H, dd, J=8.7, 1.5 Hz), 7.52 (1 H, d, J=1.8 Hz), 6.47 (1 H, d, J=2.0 Hz), 4.85 (1 H, s), 3.88 (3 H, s), 3.74 (1 H, d, J=12.9 Hz), 3.32 (2 H, d, J=12.1 Hz), 3.11 (1 H, q, J=11.3 Hz), 2.38-2.48 (1 H, m), 0.78-0.86 (1 H, m), 0.58-0.65 (2 H, m), 0.48-0.58 (2 H, m). $^{19}$F NMR (377 MHz, DMSO-d$_6$) δ ppm -74.51 (3 F, s). MS (ESI, pos. ion) m/z: 402.2 (M+1).

Example 253

3-(6-((4R)-6-azaspiro[2.5]oct-4-yloxy)-2-pyrazinyl)-5-(1-methylethyl)-1H-indazole

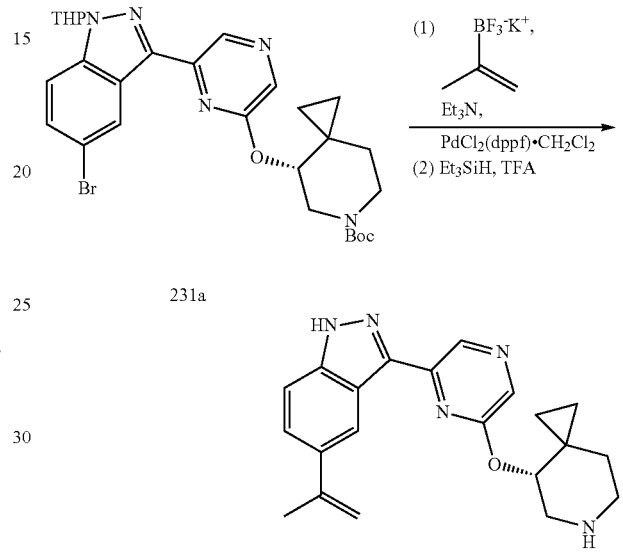

253

Preparation of Compound 253a: (4R)-tert-butyl 4-(6-(5-(prop-1-en-2-yl)-1-(tetrahydro-2H-pyran-2-yl)-1H-indazol-3-yl)pyrazin-2-yloxy)-6-azaspiro[2.5]octane-6-carboxylate A mixture of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (201.3 mg, 0.345 mmol), potassium isopropenyltrifluoroborate (Frontier Scientific, Inc., Logan, Utah; 61.1 mg, 0.413 mmol), PdCl$_2$(dppf)-CH$_2$Cl$_2$ adduct (Acros Organics, Geel, Belgium; 14.28 mg, 17.48 µmol), and Et$_3$N (0.048 mL, 0.350 mmol) in IPA (4.0 mL) was stirred under argon at 90° C. for 2 h. Additional potassium isopropenyltrifluoroborate (20.0 mg, 0.136 mmol) was added, and the resulting mixture was stirred at 90° C. for 1 h. The reaction was cooled to RT and diluted with EtOAc (150 mL). The resulting solution was sequentially washed with water (2×90 mL) and brine (60 mL), dried over Na$_2$SO$_4$, filtered, and concentrated onto silica gel. Chromatographic purification (ISCO, 12 g silica gel column, 0-30% EtOAc/hexanes, 15 min, 254 nm) provided (4R)-tert-butyl 4-(6-(5-(prop-1-en-2-yl)-1-(tetrahydro-2H-pyran-2-yl)-1H-indazol-3-yl)pyrazin-2-yloxy)-6-azaspiro[2.5]octane-6-carboxylate (175.4 mg, 0.321 mmol, 93% yield) as a colorless oil: $^1$H NMR (400 MHz, CDCl$_3$) δ ppm 9.05 (1 H, s), 8.45 (1 H, s), 8.19 (1 H, br. s.), 7.63-7.68 (1 H, m), 7.58-7.62 (1 H, m), 5.80 (1 H, d, J=8.6 Hz), 5.42 (1 H, s), 5.14 (1 H, s), 4.63 (1 H, br. s.), 4.47 (1 H, br. s.), 4.25 (1 H, d, J=8.4 Hz), 4.03 (1 H, d, J=11.2 Hz), 3.73-3.84 (1 H, m), 3.25 (1 H, d, J=13.7 Hz), 2.90-3.05 (1 H, m), 2.56-2.72 (1 H, m), 2.45 (1 H, br. s.), 2.24 (3 H, s), 2.21 (1 H, d, J=4.3 Hz), 2.12 (2 H, d, J=12.7 Hz), 1.75-1.87 (3 H, m), 1.11 (9 H, br. s.), 0.86 (2 H, br. s.), 0.72 (2 H, br. s.). MS (ESI, pos. ion) m/z: 546.3 (M+1).

Preparation of Compound 253: 3-(6-((4R)-6-azaspiro [2.5]oct-4-yloxy)-2-pyrazinyl)-5-(1-methylethyl)-1H-indazole Triethylsilane (0.087 mL, 0.543 mmol) and TFA (1.0 mL, 12.98 mmol) were sequentially added to a solution of (4R)-tert-butyl 4-(6-(5-(prop-1-en-2-yl)-1-(tetrahydro-2H-pyran-2-yl)-1H-indazol-3-yl)pyrazin-2-yloxy)-6-azaspiro[2.5]octane-6-carboxylate (141.2 mg, 0.259 mmol) in $CH_2Cl_2$ (1.0 mL) and the resulting solution was stirred at 25° C. for 30 min. Additional triethylsilane (0.044 mL, 0.275 mmol) was added, the reaction was stirred at 25° C. for 5 min, and the mixture was concentrated in vacuo. The residue was azeotropically dried by concentration from toluene (2×1 mL) and taken up in DMSO (5.0 mL) and purified by rpHPLC (Phenomenex Gemini C18 column (150×30 mm, 10 μm), 35 mL/min, 5-100% $CH_3CN/H_2O$+0.1% TFA, 15 min, 254 nm) to provide 3-(6-((4R)-6-azaspiro[25]oct-4-yloxy)-2-pyrazinyl)-5-(1-methylethyl)-1H-indazole 2,2,2-trifluoroacetate (83.5 mg, 0.175 mmol, 68% yield) as a yellow solid: $^1H$ NMR (400 MHz, DMSO-$d_6$) δ ppm 13.51 (1 H, br. s.), 8.98 (1 H, s), 8.91-8.96 (1 H, m), 8.60 (1 H, d, J=13.9 Hz), 8.28 (1 H, s), 8.04-8.09 (1 H, m), 7.57 (1 H, d, J=8.6 Hz), 7.38 (1 H, d, J=8.3 Hz), 4.85-4.91 (1 H, m), 3.81 (1 H, d, J=14.1 Hz), 3.40-3.51 (1 H, m), 3.30-3.39 (1 H, m), 3.11-3.22 (1 H, m), 3.03-3.11 (1 H, m), 2.40-2.47 (1 H, m), 1.30 (3 H, s), 1.28 (3 H, s), 1.14 (1 H, d, J=12.7 Hz), 0.83-0.90 (1 H, m), 0.62-0.73 (2 H, m), 0.52-0.61 (1 H, m). $^{19}F$ NMR (377 MHz, DMSO-$d_6$) δ ppm −74.28 (3 F, s). MS (ESI, pos. ion) m/z: 364.3 (M+1).

Example 254

3-(6-((4R)-6-azaspiro[2.5]oct-4-yloxy)-2-pyrazinyl)-1H-indazole-5-carbonitrile

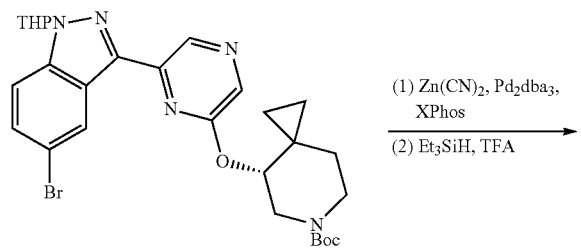

231a

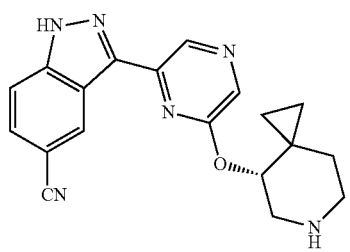

254

Preparation of Compound 254a: (4R)-tert-butyl 4-(6-(5-cyano-1-(tetrahydro-2H-pyran-2-yl)-1H-indazol-3-yl)pyrazin-2-yloxy)-6-azaspiro[2.5]octane-6-carboxylate (4R)-tert-Butyl 4-(6-(5-bromo-1-(tetrahydro-2H-pyran-2-yl)-1H-indazol-3-yl)pyrazin-2-yloxy)-6-azaspiro[2.5]octane-6-carboxylate (124 mg, 0.212 mmol), dicyanozinc (Aldrich, St. Louis, Mo.; 32.4 mg, 0.276 mmol), $Pd_2(dba)_3$ (Aldrich, St. Louis, Mo.; 9.71 mg, 10.61 μmol), and XPhos (Strem, Newburyport, Mass.; 10.11 mg, 0.021 mmol) in a mixture of DMF (2.0 mL) and water (0.020 mL) was heated at 100° C. for 19 h. The mixture was concentrated onto silica gel and chromatographically purified (ISCO, 12 g silica gel column, 0-60% EtOAc/hexanes, 15 min, 254 nm) to provide (4R)-tert-butyl 4-(6-(5-cyano-1-(tetrahydro-2H-pyran-2-yl)-1H-indazol-3-yl)pyrazin-2-yloxy)-6-azaspiro[2.5]octane-6-carboxylate (102.8 mg, 0.194 mmol, 91% yield) as an off-white solid: $^1H$ NMR (400 MHz, CDCl$_3$) δ ppm 9.04 (1 H, s), 8.74 (1 H, br. s.), 8.25 (1 H, br. s.), 8.02 (1 H, s), 7.78 (1 H, s), 7.64 (1 H, s), 5.84 (1 H, d, J=6.8 Hz), 4.63 (1 H, br. s.), 4.35-4.44 (1 H, m), 4.21-4.33 (1 H, m), 3.90-4.10 (2 H, m), 3.73-3.85 (2 H, m), 3.34 (2 H, d, J=14.1 Hz), 2.53-2.70 (2 H, m), 2.45 (1 H, m), 2.09-2.30 (2 H, m), 1.68-1.90 (4 H, m), 1.14 (9 H, br. s.). MS (ESI, pos. ion) m/z: 531.3 (M+1).

Preparation of Compound 254: 3-(6-((4R)-6-azaspiro [2.5]oct-4-yloxy)-2-pyrazinyl)-1H-indazole-5-carbonitrile Triethylsilane (0.075 mL, 0.468 mmol) and TFA (1.0 mL, 12.98 mmol) were sequentially added to a solution of (4R)-tert-butyl 4-(6-(5-cyano-1-(tetrahydro-2H-pyran-2-yl)-1H-indazol-3-yl)pyrazin-2-yloxy)-6-azaspiro[2.5]octane-6-carboxylate (99.4 mg, 0.187 mmol) in $CH_2Cl_2$ (1.0 mL) and the resulting solution was stirred at 25° C. for 2.5 h. The mixture was concentrated in vacuo and the residue was taken up in DMSO (3.0 mL) and purified by rpHPLC (Phenomenex Gemini C18 column (150×30 mm, 10 μm), 35 mL/min, 5-100% $CH_3CN/H_2O$+0.1% TFA, 15 min, 254 nm) to provide 3-(6-((4R)-6-azaspiro[2.5]oct-4-yloxy)-2-pyrazinyl)-1H-indazole-5-carbonitrile 2,2,2-trifluoroacetate (63.2 mg, 0.137 mmol, 73% yield) as a white solid: $^1H$ NMR (400 MHz, DMSO-$d_6$) δ ppm 9.01 (1 H, s), 8.99 (1 H, d, J=11.2 Hz), 8.71 (1 H, s), 8.65 (1 H, d, J=8.2 Hz), 8.35 (1 H, s), 7.86 (1 H, d, J=8.7 Hz), 7.79 (1 H, dd, J=8.6, 1.4 Hz), 5.00 (1 H, s), 3.75 (1 H, d, J=12.9 Hz), 3.47 (1 H, t, J=12.0 Hz), 3.34 (1 H, d, J=12.7 Hz), 3.10-3.22 (1 H, m), 2.37-2.47 (1 H, m), 1.17 (1 H, d, J=14.5 Hz), 0.78-0.90 (2 H, m), 0.61-0.69 (1 H, m), 0.55 (1 H, dd, J=8.7, 4.2 Hz). $^{19}F$ NMR (377 MHz, DMSO-$d_6$) δ ppm −73.67 (3 F, s). MS (ESI, pos. ion) m/z: 347.1 (M+1).

Example 255

3-(6-((4R)-6-azaspiro[2.5]oct-4-yloxy)-2-pyrazinyl)-5-(1-methyl-1H-imidazol-5-yl)-1H-indazole

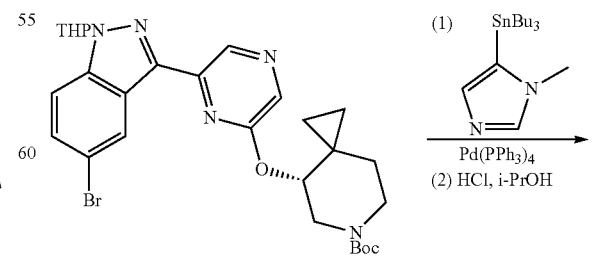

231a

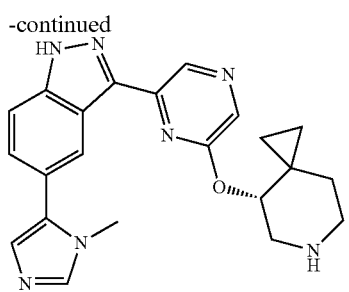

255

Preparation of Compound 255a: (4R)-tert-butyl 4-(6-(5-(1-methyl-1H-imidazol-5-yl)-1-(tetrahydro-2H-pyran-2-yl)-1H-indazol-3-yl)pyrazin-2-yloxy)-6-azaspiro[2.5]octane-6-carboxylate A solution of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (147 mg, 0.251 mmol), 1-methyl-5-(tributylstannyl)-1H-imidazole (Synthonix, Inc., Wake Forest, N.C.; 0.099 mL, 0.327 mmol), and Pd(PPh$_3$)$_4$ (14.53 mg, 0.013 mmol) in DMF (2.0 mL) was heated under argon at 100° C. for 2.5 h. The reaction was cooled to RT, concentrated onto silica gel, and chromatographically purified (ISCO, 12 g silica gel column, 0-10% MeOH/DCM, 20 min, 254 nm) to provide crude (4R)-tert-butyl 4-(6-(5-(1-methyl-1H-imidazol-5-yl)-1-(tetrahydro-2H-pyran-2-yl)-1H-indazol-3-yl)pyrazin-2-yloxy)-6-azaspiro[2.5]octane-6-carboxylate (270.3 mg; contaminated with PPh$_3$ and DMF) as a yellow-orange foam: MS (ESI, pos. ion) m/z: 586.2 (M+1). This material was used without further purification in the subsequent step.

Preparation of Compound 255: 3-(6-((4R)-6-azaspiro[2.5]oct-4-yloxy)-2-pyrazinyl)-5-(1-methyl-1H-imidazol-5-yl)-1H-indazole A solution of (4R)-tert-butyl 4-(6-(5-(1-methyl-1H-imidazol-5-yl)-1-(tetrahydro-2H-pyran-2-yl)-1H-indazol-3-yl)pyrazin-2-yloxy)-6-azaspiro[2.5]octane-6-carboxylate (147 mg, 0.251 mmol) in HCl (5.0M in IPA; 3.0 mL, 15.00 mmol) was stirred under argon at 50° C. for 2 h. The reaction was cooled to RT and concentrated in vacuo. The residue was taken up in DMSO (3.0 mL) and purified by rpHPLC (Phenomenex Gemini C18 column (150×30 mm, 10 μm), 35 mL/min, 5-100% CH$_3$CN/H$_2$O+0.1% TFA, 15 min, 254 nm) to provide 3-(6-((4R)-6-azaspiro[25]oct-4-yloxy)-2-pyrazinyl)-5-(1-methyl-1H-imidazol-5-yl)-1H-indazole 2,2,2-trifluoroacetate (92.0 mg, 0.178 mmol, 71% yield) as a light-yellow solid (following titrituration of initially obtained yellow oil with Et$_2$O): $^1$H NMR (400 MHz, DMSO-d$_6$) δ ppm 13.93 (1H, s), 9.16 (1 H, br. s.), 9.02 (1 H, s), 8.98 (1 H, d, J=12.9 Hz), 8.60 (1 H, d, J=10.2 Hz), 8.38 (1 H, s), 8.34 (1 H, s), 7.90 (1 H, s), 7.85 (1 H, d, J=8.8 Hz), 7.68 (1 H, dd, J=8.7, 1.5 Hz), 4.85 (1 H, s), 3.84-3.86 (3 H, m), 3.84 (1 H, br. s.), 3.71 (1 H, d, J=14.7 Hz), 3.28-3.36 (2 H, m), 2.97-3.10 (1 H, m), 2.39-2.46 (1 H, m), 1.13 (1 H, br. s.), 0.78-0.86 (1 H, m), 0.60 (2 H, d, J=8.2 Hz). $^{19}$F NMR (377 MHz, DMSO-d$_6$) δ ppm −73.94 (3 F, s). MS (ESI, pos. ion) m/z: 402.4 (M+1).

Example 256

3-(6-((4R)-6-azaspiro[2.5]oct-4-yloxy)-2-pyrazinyl)-5-(1-methylethenyl)-1H-indazole

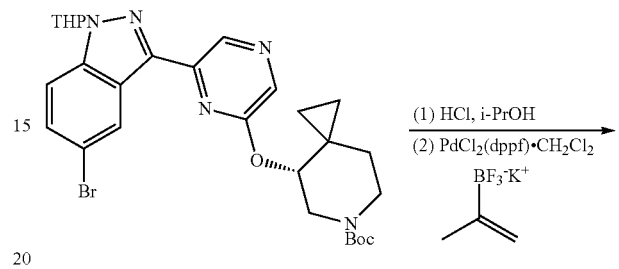

231a

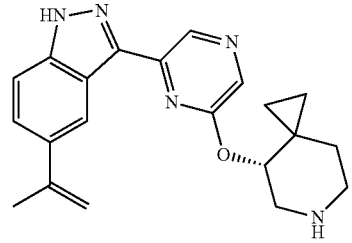

256

Preparation of Compound 256a: (R)-3-(6-(6-azaspiro[2.5]octan-4-yloxy)pyrazin-2-yl)-5-bromo-1H-indazole dihydrochloride A solution of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (314.5 mg, 0.538 mmol) in HCl (5.0M in IPA; 3.0 mL, 15.00 mmol) was stirred under argon at 80° C. for 1 h. The reaction was cooled to RT, diluted with CH$_3$CN (3.0 mL), and vacuum filtered. The collected solid was washed with CH$_3$CN (2×2 mL) and dried in vacuo to provide (R)-3-(6-(6-azaspiro[2.5]octan-4-yloxy)pyrazin-2-yl)-5-bromo-1H-indazole dihydrochloride (256a 205.2 mg, 0.434 mmol, 81% yield) as a yellow solid: MS (ESI, pos. ion) m/z: 400.1/402.1 (M+1).

Preparation of Compound 256: 3-(6-((4R)-6-azaspiro[2.5]oct-4-yloxy)-2-pyrazinyl)-5-(1-methylethenyl)-1H-indazole An orange suspension of (R)-3-(6-(6-azaspiro[2.5]octan-4-yloxy)pyrazin-2-yl)-5-bromo-1H-indazole dihydrochloride (80.2 mg, 0.169 mmol), potassium isopropenyltrifluoroborate (Frontier Scientific, Inc., Logan, Utah; 32.6 mg, 0.220 mmol), PdCl$_2$(dppf)-CH$_2$Cl$_2$ adduct (Acros Organics, Geel, Belgium; 6.92 mg, 8.47 μmol), and Et$_3$N (0.076 mL, 0.542 mmol) in IPA (2.0 mL) was stirred under argon at 90° C. for 3 d. Additional PdCl$_2$(dppf)-CH$_2$Cl$_2$ adduct (6.92 mg, 8.47 μmol) and potassium isopropenyltrifluoroborate (32.6 mg, 0.220 mmol) were added, and the resulting mixture was heated at 90° C. for 3 h. Additional PdCl$_2$(dppf)-CH$_2$Cl$_2$ adduct (6.92 mg, 8.47 μmol) and potassium isopropenyltrifluoroborate (32.6 mg, 0.220 mmol) were added, and the resulting mixture was stirred at 90° C. for 1.5 h. Et₃N (0.076 mL, 0.542 mmol) was added, and the reaction was stirred under argon at 90° C. for 18 h. Additional PdCl₂(dppf)-CH₂Cl₂ adduct (6.92 mg, 8.47 μmol) and potassium isopropenyltrifluoroborate (32.6 mg, 0.220 mmol) were added, and the resulting mixture was stirred at 90° C. for 24 h. The reaction was cooled to RT, diluted with MeOH (3 mL), and filtered through Celite. The filtrate was concentrated in vacuo, and the residue was taken up in DMSO (4.0 mL) and purified by rpHPLC (Phenomenex Gemini C18 column (150×30 mm, 10 μm), 35 mL/min, 5-100% $CH_3CN/H_2O$+0.1% TFA, 15 min, 254 nm) to provide 3-(6-((4R)-6-azaspiro[2.5]oct-4-yloxy)-2-pyrazinyl)-5-(1-methylethenyl)-1H-indazole 2,2,2-trifluoroacetate (31.1 mg, 0.065 mmol, 39% yield) as a yellow solid (following trituration of the initially obtained oil with Et₂O): $^1$H NMR (400 MHz, DMSO-d₆) (~4:1 mixture of rotamers; only peaks from major rotamer reported) δ ppm 13.64 (1 H, s), 8.99 (1 H, s), 8.96 (1 H, br. s.), 8.59 (1 H, br. s.), 8.31 (1 H, br. s.), 8.30 (1H, s), 7.72 (1 H, dd, J=8.7, 1.3 Hz), 7.60 (1 H, s), 5.51 (1 H, s), 5.16 (1 H, s), 4.86 (1 H, s), 3.74-3.85 (1 H, m), 3.52 (1 H, d, J=11.0 Hz), 3.46 (1 H, d, J=11.7 Hz), 3.33 (1 H, br. s.), 3.07-3.19 (1 H, m), 2.22 (3 H, s), 1.89-1.94 (1 H, m), 1.13 (1 H, d, J=14.2 Hz), 0.79-0.89 (1 H, m), 0.65 (1 H, dd, J=8.3, 4.6 Hz), 0.52-0.61 (1 H, m). $^{19}$F NMR (377 MHz, DMSO-d₆) δ ppm −73.62 (3 F, s). MS (ESI, pos. ion) m/z: 362.3 (M+1).

Example 257

3-(6-((4R)-6-azaspiro[2.5]oct-4-yloxy)-2-pyrazinyl)-5-(1-(trifluoromethyl)ethenyl)-1H-indazole

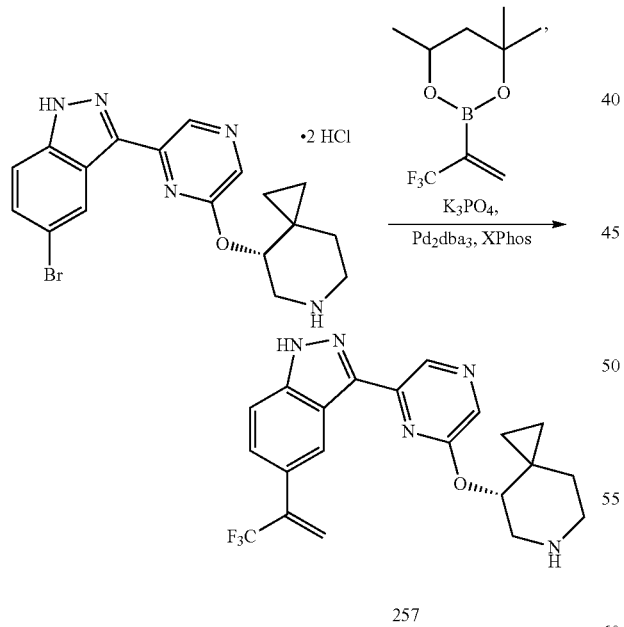

A suspension of (R)-3-(6-(6-azaspiro[2.5]octan-4-yloxy)pyrazin-2-yl)-5-bromo-1H-indazole dihydrochloride (Example 256a (step 1); 104.7 mg, 0.221 mmol), 4,4,6-trimethyl-2-(3,3,3-trifluoroprop-1-en-2-yl)-1,3,2-dioxaborinane (Frontier Scientific, Inc., Logan, Utah; 0.138 mL, 0.664 mmol), dicyclohexyl(2',4',6'-triisopropylbiphenyl-2-yl)phosphine (Xphos; Strem, Newburyport, Mass.; 10.55 mg, 0.022 mmol), Pd₂(dba)₃ (Aldrich, St. Louis, Mo.; 10.13 mg, 0.011 mmol), and potassium phosphate (235 mg, 1.106 mmol) in a mixture of dioxane (2.0 mL) and water (0.200 mL) was stirred under argon at 95° C. for 16 h. Additional XPhos (10.55 mg, 0.022 mmol), Pd₂(dba)₃ (10.13 mg, 0.011 mmol), and 4,4,6-trimethyl-2-(3,3,3-trifluoroprop-1-en-2-yl)-1,3,2-dioxaborinane (0.069 mL, 0.332 mmol) were added, and the resulting mixture was sparged with argon and heated at 95° C. for 2 h. The reaction was cooled to RT, diluted with MeOH (5 mL), and filtered through Celite. The filtrate was concentrated in vacuo, and the residue was taken up in DMSO (4.0 mL) and purified by rpHPLC (Phenomenex Gemini C18 column (150×30 mm, 10 μm), 35 mL/min, 5-100% $CH_3CN/H_2O$+0.1% TFA, 15 min, 254 nm) to provide 3-(6-((4R)-6-azaspiro[25]oct-4-yloxy)-2-pyrazinyl)-5-(1-(trifluoromethyl)ethenyl)-1H-indazole tris(2,2,2-trifluoroacetate) (35.7 mg, 0.047 mmol, 21% yield) as a yellow solid (following trituration of the initially obtained oil with Et₂O): $^1$H NMR (400 MHz, MeOH) δ ppm 9.06 (1 H, s), 8.43-8.49 (1 H, m), 8.28-8.35 (1 H, m), 7.67 (1 H, d, J=8.8 Hz), 7.63 (1 H, dd, J=8.9, 1.1 Hz), 6.09 (1 H, s), 6.03 (1 H, d, J=1.6 Hz), 4.92-4.98 (1 H, m), 3.87 (1 H, d, J=13.2 Hz), 3.50 (2 H, s), 2.71 (1 H, td, J=14.1, 4.2 Hz), 1.16-1.28 (2 H, m), 0.84-0.91 (1 H, m), 0.71-0.81 (2 H, m), 0.63-0.69 (1 H, m). $^{19}$F NMR (376 MHz, MeOH) δ ppm −65.15 (3 F, s), −77.26 (9 F, br. s.). MS (ESI, pos. ion) m/z: 416.1 (M+1).

Example 258

Racemic 3-(6-((4R)-6-azaspiro[25]oct-4-yloxy)-2-pyrazinyl)-5-(2,2,2-trifluoro-1-methylethyl)-1H-indazole

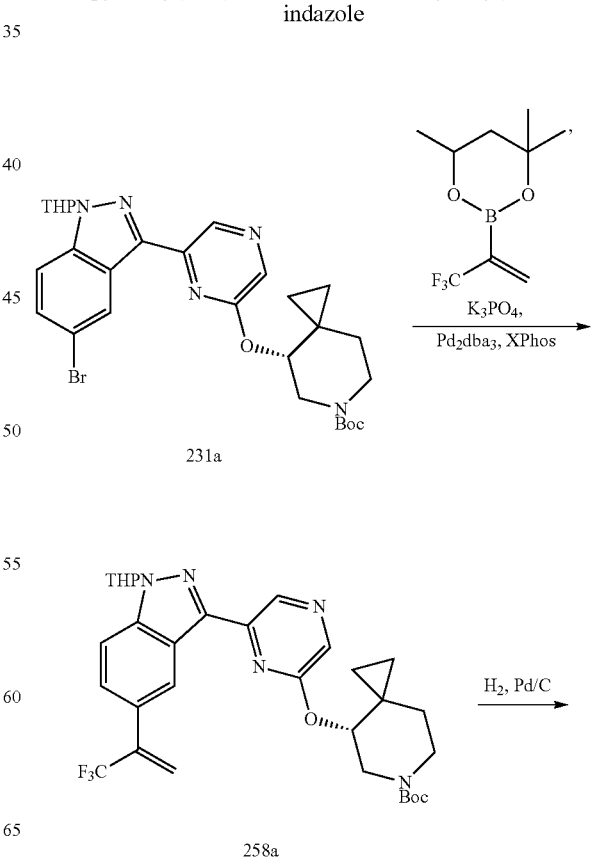

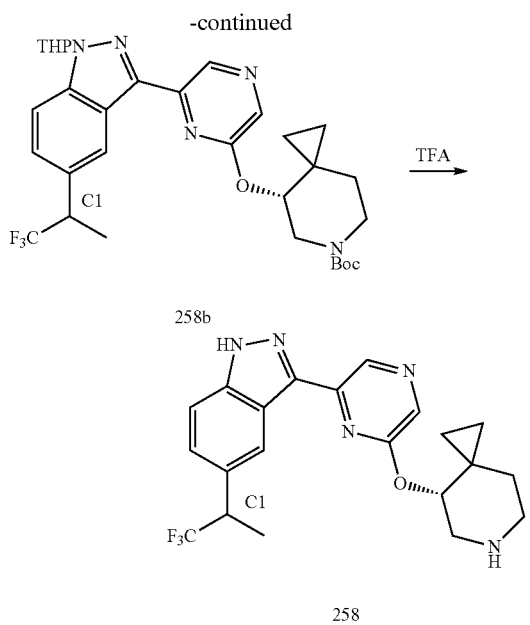

Preparation of Compound 258a: (4R)-tert-butyl 4-(6-(1-(tetrahydro-2H-pyran-2-yl)-5-(3,3,3-trifluoroprop-1-en-2-yl)-1H-indazol-3-yl)pyrazin-2-yloxy)-6-azaspiro[2.5]octane-6-carboxylate A brown solution of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (469.5 mg, 0.803 mmol), 4,4,6-trimethyl-2-(3,3,3-trifluoroprop-1-en-2-yl)1,3,2-dioxaborinane (Frontier Scientific, Inc., Logan, Utah; 0.250 mL, 1.205 mmol), dicyclohexyl(2',4',6'-triisopropylbiphenyl-2-yl)phosphine (Xphos; Strem, Newburyport, Mass.; 38.3 mg, 0.080 mmol), $Pd_2(dba)_3$ (36.8 mg, 0.040 mmol), and potassium phosphate (853 mg, 4.02 mmol) in a mixture of dioxane (7.0 mL) and water (0.700 mL) was stirred under argon at 95° C. for 1.5 h. The reaction was cooled to RT, concentrated onto silica gel, and chromatographically purified (ISCO, 40 g silica gel column, 0-50% EtOAc/hexanes, 15 min, 254 nm) to provide (4R)-tert-butyl 4-(6-(1-(tetrahydro-2H-pyran-2-yl)-5-(3,3,3-trifluoroprop-1-en-2-yl)-1H-indazol-3-yl)pyrazin-2-yloxy)-6-azaspiro[2.5]octane-6-carboxylate (438.7 mg, 0.732 mmol, 91% yield) as a white foam: MS (ESI, pos. ion) m/z: 600.3 (M+1).

Preparation of Compound 258b: (4R)-tert-butyl 4-(6-(1-(tetrahydro-2H-pyran-2-yl)-5-(1,1,1-trifluoropropan-2-yl)-1H-indazol-3-yl)pyrazin-2-yloxy)-6-azaspiro[2.5]octane-6-carboxylate A suspension of (4R)-tert-butyl 4-(6-(1-(tetrahydro-2H-pyran-2-yl)-5-(3,3,3-trifluoroprop-1-en-2-yl)-1H-indazol-3-yl)pyrazin-2-yloxy)-6-azaspiro[2.5]octane-6-carboxylate (100 mg, 0.167 mmol) and palladium on carbon (Aldrich, St. Louis, Mo.; 10% w/w; 17.75 mg, 0.017 mmol) in THF (2.0 mL) was cycled under a $H_2$ atmosphere (1 atm; 3× evacuation/refill cycles) and stirred at 25° C. for 16 h. The mixture was filtered through Celite (washing with THF (3×5 mL) to quantitate the transfer) and the filtrate was concentrated in vacuo to provide (4R)-tert-butyl 4-(6-(1-(tetrahydro-2H-pyran-2-yl)-5-(1,1,1-trifluoropropan-2-yl)-1H-indazol-3-yl)pyrazin-2-yloxy)-6-azaspiro[2.5]octane-6-carboxylate (100 mg, 0.166 mmol, 100% yield; mixture of epimers at C1) as a white foam: $^1H$ NMR (400 MHz, $CDCl_3$) δ ppm 9.03 (1 H, s), 8.39 (1 H, br. s.), 8.20 (1 H, br. s.), 7.64 (1 H, t, J=4.3 Hz), 7.36 (1 H, d, J=8.4 Hz), 5.81 (1 H, d, J=7.2 Hz), 4.66 (1 H, br. s.), 4.41 (1 H, br. s.), 4.28 (1 H, br. s.), 4.03 (1 H, d, J=11.3 Hz), 3.78 (1 H, br. s.), 3.57 (1H, quin, J=8.1 Hz), 3.23 (1 H, d, J=12.5 Hz), 2.95 (1 H, br. s.), 2.57-2.71 (1 H, m), 2.49 (1 H, br. s.), 2.17-2.25 (1 H, m), 2.13 (1 H, br. d, J=12.5 Hz), 1.80 (2 H, d, J=7.4 Hz), 1.71 (1 H, br. s.), 1.58 (3 H, dd, J=7.0, 3.1 Hz), 1.12 (9 H, br. s.), 0.85 (1 H, d, J=12.7 Hz), 0.70 (1 H, br. s.), 0.56-0.62 (1 H, m), 0.54 (2 H, br. s.). $^{19}F$ NMR (377 MHz, $CDCl_3$) δ ppm −71.44 (3 F, d, J=8.0 Hz). MS (ESI, pos. ion) m/z: 602.3 (M+1).

Preparation of Compound 258: racemic 3-(6-((4R)-6-azaspiro[2.5]oct-4-yloxy)-2-pyrazinyl)-5-(2,2,2-trifluoro-1-methylethyl)-1H-indazole 2,2,2-trifluoroacetate TFA (1.0 mL, 12.98 mmol) was added to a solution of (4R)-tert-butyl 4-(6-(1-(tetrahydro-2H-pyran-2-yl)-5-(1,1,1-trifluoropropan-2-yl)-1H-indazol-3-yl)pyrazin-2-yloxy)-6-azaspiro[2.5]octane-6-carboxylate (100 mg, 0.166 mmol; mixture of epimers at C0 in DCM (1.0 mL) and the resulting solution was stirred at 25° C. for 2 h. The mixture was concentrated in vacuo and the residue was taken up in DMSO (2.0 mL) and purified by rpHPLC (Phenomenex Gemini C18 column (150×30 mm, 10 μm), 35 mL/min, 5-100% $CH_3CN/H_2O$+0.1% TFA, 15 min, 254 nm) to provide racemic 3-(6-((4R)-6-azaspiro[2.5]oct-4-yloxy)-2-pyrazinyl)-5-(2,2,2-trifluoro-1-methylethyl)-1H-indazole 2,2,2-trifluoroacetate (52.5 mg, 0.099 mmol, 59% yield; mixture of epimers at C1) as a light-yellow solid (following trituration of the initially obtained oil in hexanes): $^1H$ NMR (400 MHz, MeOH) δ ppm 9.06 (1 H, d, J=2.3 Hz), 8.28-8.40 (2 H, m), 7.65 (1H, d, J=8.8 Hz), 7.49 (1 H, d, J=8.8 Hz), 5.05 (1 H, d, J=19.4 Hz), 3.86-3.98 (1 H, m), 3.77-3.85 (1 H, m), 3.59 (1 H, ddd, J=13.4, 3.9, 1.9 Hz), 3.49-3.56 (1 H, m), 3.30-3.39 (1 H, m), 2.69-2.79 (1 H, m), 1.62 (3 H, d, J=7.2 Hz), 1.24 (1 H, d, J=14.7 Hz), 0.90-1.02 (1 H, m), 0.74-0.86 (2 H, m), 0.65-0.72 (1 H, m). $^{19}F$ NMR (377 MHz, MeOH) δ ppm −72.61 (3 F, dd, J=19.1, 9.5 Hz), −77.16 (3 F, s). MS (ESI, pos. ion) m/z: 418.2 (M+1).

Example 259 and 260 non-racemic 3-(6-((4R)-6-azaspiro[2.5]oct-4-yloxy)-2-pyrazinyl)-5-(2,2,2-trifluoro-1-methylethyl)-1H-indazole, enantiomer 1 and 2

Separation of the C1 epimers of 3-(6-((4R)-6-azaspiro[2.5]oct-4-yloxy)-2-pyrazinyl)-5-(2,2,2-trifluoro-1-methylethyl)-1H-indazole 2,2,2-trifluoroacetate by supercritical-fluid chromatography (Chiralpak AD-H (250×21 mm, 5 μm), 70% liquid $CO_2$/30% IPA (+20 mM ammonia), 50 mL/min) separately afforded non-racemic 3-(6-((4R)-6-azaspiro[2.5]oct-4-yloxy)-2-pyrazinyl)-5-(2,2,2-trifluoro-1-methylethyl)-1H-indazole, enantiomer 1 (259); first compound eluted) as a white solid: $^1H$ NMR (400 MHz, MeOH) δ ppm 8.95 (1 H, s), 8.38-8.44 (1 H, s) m), 8.24 (1 H, s) s), 7.60 (1 H, s) d, J=8.6 Hz), 7.45 (1 H, s) d, J=8.8 Hz), 4.73 (1 H, s) br. s.), 3.69-3.84 (1 H, s) m), 3.51 (1 H, s) d, J=12.9 Hz), 3.15-3.20 (1 H, s) m), 3.10-3.15 (1 H, s) m), 2.91 (1 H, s) td, J=12.4, 2.9 Hz), 2.36-2.49 (1 H, m), 1.60 (3 H, d, J=7.2 Hz), 0.99 (1 H, d, J=13.1 Hz), 0.68-0.75 (1 H, m), 0.62-0.68 (1 H, m), 0.56-0.62 (1 H, m), 0.45-0.53 (1 H, m). $^{19}F$ NMR (377 MHz, MeOH) δ ppm −72.79 (3 F, d, J=10.3 Hz). MS (ESI, pos. ion) m/z: 418.2

(M+1). and non-racemic 3-(6-((4R)-6-azaspiro[2.5]oct-4-yloxy)-2-pyrazinyl)-5-(2,2,2-trifluoro-1-methylethyl)-1H-indazole, enantiomer 2 (260); second compound eluted) as a white solid: ¹H NMR (400 MHz, MeOH) δ ppm 8.97 (1 H, s), 8.43 (1 H, s), 8.25 (1 H, s), 7.62 (1 H, d, J=8.4 Hz), 7.47 (1 H, d, J=9.4 Hz), 4.80 (1 H, br. s.), 3.72-3.86 (1 H, m), 3.45 (1 H, dd, J=13.7, 2.2 Hz), 3.15-3.20 (1 H, m), 3.12 (1 H, br. s.), 2.92 (1 H, td, J=12.2, 2.5 Hz), 2.33-2.47 (1 H, m), 1.62 (3 H, d, J=7.2 Hz), 1.02 (1 H, d, J=12.9 Hz), 0.72-0.80 (1 H, m), 0.64-0.70 (1 H, m), 0.56-0.63 (1 H, m), 0.45-0.54 (1 H, m). ¹⁹F NMR (377 MHz, MeOH) δ ppm −72.83 (3 F, d, J=9.5 Hz). MS (ESI, pos. ion) m/z: 418.2 (M+1).

Examples 261

3-(6-((4R)-6-azaspiro[2.5]oct-4-yloxy)-2-pyrazinyl)-5-(1-(trifluoromethyl)cyclopropyl)-1H-indazole

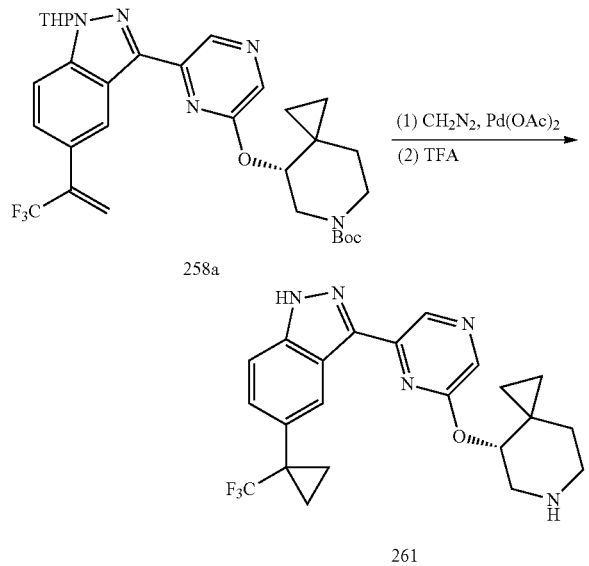

Preparation of Compound 261a: (4R)-tert-butyl 4-(6-(1-(tetrahydro-2H-pyran-2-yl)-5-(1-(trifluoromethyl)cyclopropyl)-1H-indazol-3-yl)pyrazin-2-yloxy)-6-azaspiro[2.5]octane-6-carboxylate Diazomethane (~0.25M in Et₂O (prepared according to Aldrich Technical Bulletin AL-180, Aldrich, St. Louis, Mo.); 1.0 mL, 0.250 mmol) was added (dropwise) to a solution of (4R)-tert-butyl 4-(6-(1-(tetrahydro-2H-pyran-2-yl)-5-(3,3,3-trifluoroprop-1-en-2-yl)-1H-indazol-3-yl)pyrazin-2-yloxy)-6-azaspiro[2.5]octane-6-carboxylate (41.8 mg, 0.070 mmol) and palladium(II) acetate (1.565 mg, 6.97 μmol) in DCM (1.0 mL) at 0° C., and the resulting solution was stirred at 0° C. for 30 min. Additional diazomethane (~0.25M in Et₂O; 2.0 mL, 0.500 mmol) was added, and the resulting solution was stirred at 0° C. for 30 min. Additional palladium(II) acetate (4.54 mg, 0.020 mmol) and diazomethane (~0.25M in Et₂O; 2×2.0 mL, 2×0.500 mmol) were sequentially added, and the reaction was stirred at 0° C. for 5 min. Additional diazomethane (~0.25M in Et₂O; 2.0 mL, 0.500 mmol) was added, the reaction was stirred at 0° C. for 5 min. HOAc (0.160 mL, 2.79 mmol) was added to quench excess diazomethane, and the resulting mixture was stirred at 25° C. for 12 h. The mixture was concentrated onto silica gel and chromatographically purified (ISCO, 12 g silica gel column, 0-60% EtOAc/hexanes, 15 min, 254 nm) to provide (4R)-tert-butyl 4-(6-(1-(tetrahydro-2H-pyran-2-yl)-5-(1-(trifluoromethyl)cyclopropyl)-1H-indazol-3-yl)pyrazin-2-yloxy)-6-azaspiro[2.5]octane-6-carboxylate (25.2 mg, 0.041 mmol, 59% yield) as a colorless oil: ¹H NMR (400 MHz, CDCl₃) δ ppm 9.03 (1 H, s), 8.52 (1 H, s), 8.21 (1 H, br. s.), 7.63 (1 H, s), 7.53 (1 H, d, J=8.8 Hz), 5.80 (1 H, d, J=9.0 Hz), 4.69 (1 H, d, J=11.5 Hz), 4.44 (1 H, br. s.), 4.24-4.36 (1 H, m), 4.03 (1 H, d, J=11.5 Hz), 3.71-3.84 (1 H, m), 3.24 (1 H, d, J=14.7 Hz), 2.88-3.03 (1 H, m), 2.56-2.71 (1 H, m), 2.42-2.55 (1 H, m), 2.17-2.29 (1 H, m), 2.12 (1 H, d, J=7.8 Hz), 1.65-1.88 (5 H, m), 1.37-1.55 (9 H, m), 0.81-0.92 (2 H, m), 0.72 (1 H, br. s.), 0.48-0.63 (4 H, m). ¹⁹F NMR (377 MHz, CDCl₃) δ ppm −70.26 (3 F, br. s.). MS (ESI, pos. ion) m/z: 614.3 (M+1).

Preparation of Compound 261: 3-(6-((4R)-6-azaspiro[2.5]oct-4-yloxy)-2-pyrazinyl)-5-(1-(trifluoromethyl)cyclopropyl)-1H-indazole TFA (0.5 mL, 6.49 mmol) was added to a solution of (4R)-tert-butyl 4-((6-(1-(tetrahydro-2H-pyran-2-yl)-5-(1-(trifluoromethyl)cyclopropyl)-1H-indazol-3-yl)pyrazin-2-yl)oxy)-6-azaspiro[2.5]octane-6-carboxylate (25.2 mg, 0.041 mmol) in DCM (0.5 mL) and the resulting solution was stirred at 25° C. for 2 h. The mixture was concentrated in vacuo and the residue was taken up in DMSO (2.0 mL) and purified by rpHPLC (Phenomenex Gemini C18 column (150×30 mm, 10 μm), 35 mL/min, 5-100% CH₃CN/H₂O+ 0.1% TFA, 15 min, 254 nm) to provide 3-(6-((4R)-6-azaspiro[2.5]oct-4-yloxy)-2-pyrazinyl)-5-(1-(trifluoromethyl)cyclopropyl)-1H-indazole tris(2,2,2-trifluoroacetate) (12.0 mg, 0.016 mmol, 38% yield) as a yellow foam: ¹H NMR (400 MHz, MeOH-d₄) δ ppm 9.04 (1 H, s), 8.42-8.46 (1 H, m), 8.31 (1 H, s), 7.60-7.64 (1 H, m), 7.55-7.59 (1 H, m), 5.07 (1 H, s), 3.89 (1 H, d, J=12.7 Hz), 3.57 (1 H, m, J=13.3, 1.0 Hz), 3.47-3.54 (1 H, m), 3.34-3.39 (1 H, m), 2.72 (1 H, td, J=13.9, 4.5 Hz), 1.45-1.49 (2 H, m), 1.22-1.27 (1 H, m), 1.17-1.22 (2 H, m), 0.99 (1 H, dt, J=8.9, 5.6 Hz), 0.77-0.85 (2 H, m), 0.67-0.73 (1 H, m). ¹⁹F NMR (377 MHz, MeOH) δ ppm −71.41 (3 F, s), −77.45 (9 F, br. s.). MS (ESI, pos. ion) m/z: 430.1 (M+1).

Examples 262

3-(6-((4R)-6-azaspiro[2.5]oct-4-yloxy)-2-pyrazinyl)-5-(1-methylcyclopropyl)-1H-indazole

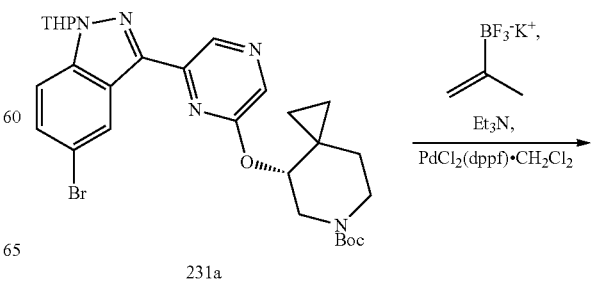

-continued

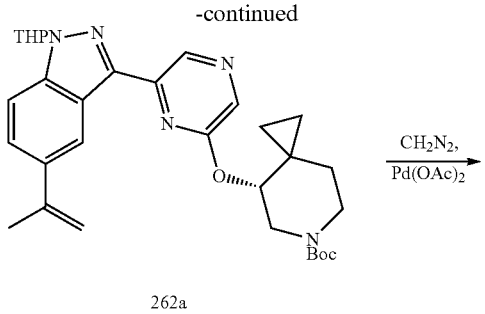

262a

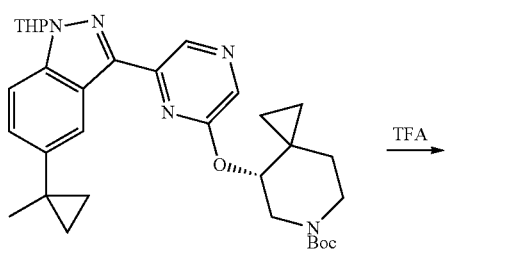

262b

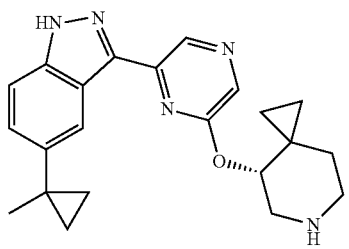

262

Preparation of Compound 262a: (4R)-tert-butyl 4-(6-(5-(prop-1-en-2-yl)-1-(tetrahydro-2H-pyran-2-yl)-1H-indazol-3-yl)pyrazin-2-yloxy)-6-azaspiro[2.5]octane-6-carboxylate A mixture of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (500 mg, 0.855 mmol), potassium isopropenyltrifluoroborate (Frontier Scientific, Inc., Logan, Utah; 152 mg, 1.027 mmol), PdCl$_2$(dppf)·CH$_2$Cl$_2$ adduct (Acros Organics, Geel, Belgium; 34.9 mg, 0.043 mmol), and Et$_3$N (0.119 mL, 0.855 mmol) in IPA (8.0 mL) was stirred under argon at 90° C. for 1 h. Additional potassium isopropenyltrifluoroborate (76 mg, 0.513 mmol) was added to the reaction and the resulting mixture was stirred under argon at 90° C. for 1 h. The reaction was subsequently cooled to RT and concentrated onto silica gel. Chromatographic purification (ISCO, 40 g silica gel column, 0-50% EtOAc/hexanes, 15 min, 254 nm) furnished (4R)-tert-butyl 4-(6-(5-(prop-1-en-2-yl)-1-(tetrahydro-2H-pyran-2-yl)-1H-indazol-3-yl)pyrazin-2-yloxy)-6-azaspiro[2.5]octane-6-carboxylate (411.1 mg, 0.753 mmol, 88% yield) as a white foam: MS (ESI, pos. ion) m/z: 546.3 (M+1).

Preparation of Compound 262b: (4R)-tert-butyl 4-(6-(5-(1-methylcyclopropyl)-1-(tetrahydro-2H-pyran-2-yl)-1H-indazol-3-yl)pyrazin-2-yloxy)-6-azaspiro[2.5]octane-6-carboxylate Diazomethane (~0.25M in Et$_2$O (prepared according to Aldrich Technical Bulletin AL-180, Aldrich, St. Louis, Mo.); 2.0 mL, 0.500 mmol) was added dropwise to a solution of (4R)-tert-butyl 4-(6-(5-(prop-1-en-2-yl)-1-(tetrahydro-2H-pyran-2-yl)-1H-indazol-3-yl)pyrazin-2-yloxy)-6-azaspiro[2.5]octane-6-carboxylate (110.4 mg, 0.202 mmol) and palladium(II) acetate (4.54 mg, 0.020 mmol) in DCM (2.0 mL) at 0° C. and the resulting solution was stirred at 0° C. for 30 min. Additional diazomethane (~0.25M in Et$_2$O; 2.0 mL, 0.500 mmol) was added, and the resulting solution was stirred at 0° C. for 30 min. HOAc (0.069 mL, 1.214 mmol) was added to quench excess diazomethane, and the resulting mixture was stirred at 25° C. for 12 h. The mixture was concentrated onto silica gel and chromatographically purified (ISCO, 12 g silica gel column, 0-60% EtOAc/hexanes, 15 min, 254 nm) to provide (4R)-tert-butyl 4-(6-(5-(1-methylcyclopropyl)-1-(tetrahydro-2H-pyran-2-yl)-1H-indazol-3-yl)pyrazin-2-yloxy)-6-azaspiro[2.5]octane-6-carboxylate (96.3 mg, 0.172 mmol, 85% yield) as a colorless oil: $^1$H NMR (400 MHz, CDCl$_3$) δ ppm 9.04 (1 H, s), 8.28 (1 H, s), 8.19 (1 H, br. s.), 7.57 (1H, d, J=8.8 Hz), 7.37 (1 H, d, J=8.4 Hz), 5.78 (1 H, d, J=9.0 Hz), 4.68 (1 H, d, J=8.0 Hz), 4.49 (1 H, br. s.), 4.28 (1 H, d, J=11.9 Hz), 4.03 (1 H, d, J=11.3 Hz), 3.70-3.84 (1 H, m), 3.28 (1 H, d, J=13.7 Hz), 2.97 (1 H, t, J=11.2 Hz), 2.57-2.73 (1 H, m), 2.41-2.54 (1 H, m), 2.16-2.28 (1 H, m), 2.07-2.15 (1 H, m), 1.63-1.86 (3 H, m), 1.47 (4 H, s), 1.12 (9H, br. s.), 0.85-0.93 (2 H, m), 0.80 (2 H, br. s.), 0.73 (1 H, br. s.), 0.62 (1 H, br. s.), 0.56 (2 H, br. s.). MS (ESI, pos. ion) m/z: 560.3 (M+1).

Preparation of Compound 262: 3-(6-((4R)-6-azaspiro[2.5]oct-4-yloxy)-2-pyrazinyl)-5-(1-methylcyclopropyl)-1H-indazole 2,2,2-trifluoroacetate TFA (1.7 mL, 22.07 mmol) was added to a solution of (4R)-tert-butyl 4-(6-(5-(1-methylcyclopropyl)-1-(tetrahydro-2H-pyran-2-yl)-1H-indazol-3-yl)pyrazin-2-yloxy)-6-azaspiro[2.5]octane-6-carboxylate (96.3 mg, 0.172 mmol) in DCM (1.7 mL) and the resulting solution was stirred at 25° C. for 2 h. The mixture was concentrated in vacuo and the residue was taken up in DMSO (2.0 mL) and purified by rpHPLC (Phenomenex Gemini C18 column (150×30 mm, 10 µm), 35 mL/min, 5-100% CH$_3$CN/H$_2$O+0.1% TFA, 15 min, 254 nm) to provide 3-(6-((4R)-6-azaspiro[2.5]oct-4-yloxy)-2-pyrazinyl)-5-(1-methylcyclopropyl)-1H-indazole 2,2,2-trifluoroacetate (64.6 mg, 0.132 mmol, 77% yield) as a yellow solid: $^1$H NMR (400 MHz, MeOH) δ ppm 9.02 (1 H, s), 8.26-8.33 (1H, m), 8.17-8.22 (1 H, m), 7.54 (1 H, d, J=8.8 Hz), 7.43 (1 H, dd, J=8.7, 1.5 Hz), 5.09 (1H, s), 3.90 (1 H, d, J=13.1 Hz), 3.60 (1 H, d, J=12.3 Hz), 3.47-3.55 (1 H, m), 3.33-3.39 (1 H, m), 2.65-2.77 (1 H, m), 1.49 (3 H, s), 1.23 (1 H, J=14.7 Hz), 1.01 (1 H, dt, J=9.7, 5.1 Hz), 0.90-0.95 (2 H, m), 0.82-0.90 (3 H, m), 0.75-0.81 (1 H, m), 0.64-0.73 (1 H, m). $^{19}$F NMR (377 MHz, MeOH) δ ppm −77.48 (3 F, s). MS (ESI, pos. ion) m/z: 376.3 (M+1).

Example 263

3-(6-((4R)-6-azaspiro[25]oct-4-yloxy)-2-pyrazinyl)-5-(3,6-dihydro-2H-pyran-4-yl)-1H-indazole 2,2,2-trifluoroacetate salt

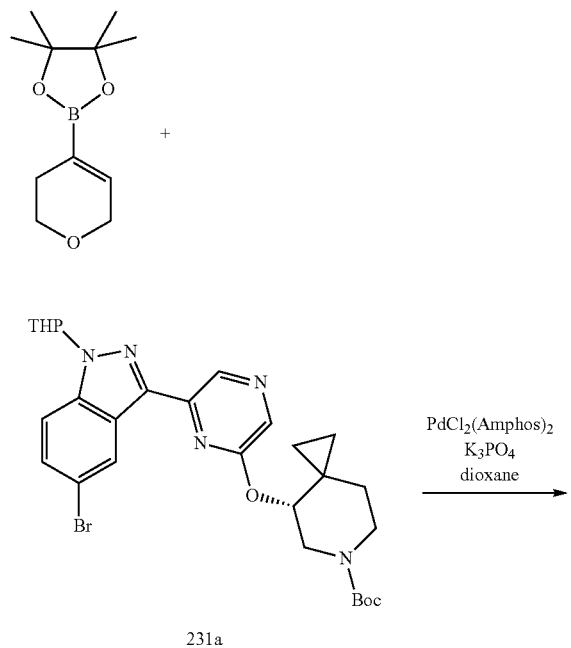

Preparation of 263a: (4R)-tert-butyl 4-(6-(5-(3,6-dihydro-2H-pyran-4-yl)-1-(tetrahydro-2H-pyran-2-yl)-1H-indazol-3-yl)pyrazin-2-yloxy)-6-azaspiro[2.5]octane-6-carboxylate A mixture of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (260 mg, 0.445 mmol), 2-(3,6-dihydro-2H-pyran-4-yl)-4,4,5,5-tetramethyl-1,3,2-dioxaborolane (140 mg, 0.667 mmol), potassium phosphate (283 mg, 1.334 mmol), and PdCl$_2$(Amphos) (31.5 mg, 0.044 mmol) in dioxane (4044 μL) and water (404 μL) was heated in the microwave for 10 min at 150° C. The crude was purified via automated flash chromatography (silica gel) with 100% hexanes to 40% EtOAc/hexanes to give (4R)-tert-butyl 4-(6-(5-(3,6-dihydro-2H-pyran-4-yl)-1-(tetrahydro-2H-pyran-2-yl)-1H-indazol-3-yl)pyrazin-2-yloxy)-6-azaspiro[2.5]octane-6-carboxylate (210 mg, 0.357 mmol, 80% yield) as a colorless oil. MS (ESI, pos. ion) m/z: 588.2 (M+1).

Preparation of 263: 3-(6-((4R)-6-azaspiro[25]oct-4-yloxy)-2-pyrazinyl)-S-(3,6-dihydro-2H-pyran-4-yl)-1H-indazole 2,2,2-trifluoroacetate A solution of (4R)-tert-butyl 4-(6-(5-(3,6-dihydro-2H-pyran-4-yl)-1-(tetrahydro-2H-pyran-2-yl)-1H-indazol-3-yl)pyrazin-2-yloxy)-6-azaspiro[2.5]octane-6-carboxylate (47 mg, 0.080 mmol) in HCl in IPA (7997 μL, 40.0 mmol) was stirred at 100° C. for 1 h before the mixture was concentrated, dissolved in MeOH (~20 mg/ml) and injected (3×1.000 ml) onto the Gilson preparatory LC (Protocol A) before the pure fractions were combined and concentrated via rotary evaporation to give (R)-3-(6-(6-azaspiro[2.5]octan-4-yloxy)pyrazin-2-yl)-5-(3,6-dihydro-2H-pyran-4-yl)-1H-indazole 2,2,2-trifluoroacetate (18 mg, 0.035 mmol, 43.5% yield) as a dark amber oil. MS (ESI, pos. ion) m/z: 404.3 (M+1). $^1$H NMR (400 MHz, MeOH-d$_4$) δ ppm 0.67-0.74 (m, 1 H) 0.79 (dquin, J=9.48, 4.77, 4.77, 4.77, 4.77 Hz, 2H) 0.95-1.04 (m, 1 H) 1.17-1.30 (m, 1H) 1.37 (d, J=6.26 Hz, 1 H) 2.64 (br. s., 2H) 2.68-2.80 (m, 1 H) 3.52 (d, J=11.74 Hz, 1H) 3.57-3.67 (m, 1 H) 3.89 (d, J=13.11 Hz, 1 H) 4.03 (t, J=5.38 Hz, 2H) 4.39 (d, J=2.15 Hz, 2H) 5.07 (s, 1 H) 6.27 (s, 1 H) 7.55-7.63 (m, 1 H) 7.63-7.72 (m, 1 H) 8.30 (d, J=13.69 Hz, 2H) 9.03 (s, 1 H).

Example 264

3-(6-((4R)-6-azaspiro[25]oct-4-yloxy)-2-pyrazinyl)-5-(tetrahydro-2H-pyran-4-yl)-1H-indazole-2,2,2-trifluoroacetate

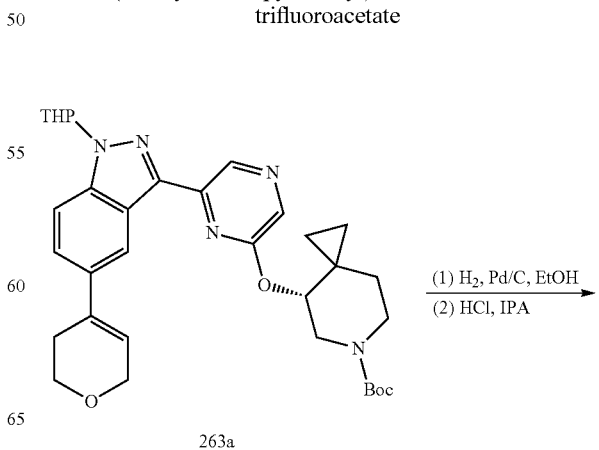

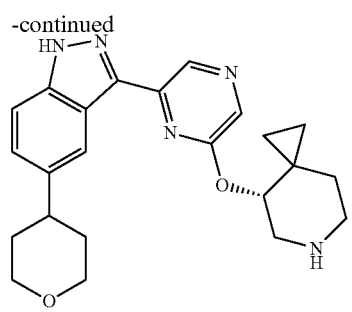

264

Preparation of Compound 264a: (4R)-tert-butyl 4-(6-(1-(tetrahydro-2H-pyran-2-yl)-5-(tetrahydro-2H-pyran-4-yl)-1H-indazol-3-yl)pyrazin-2-yloxy)-6-azaspiro[2.5]octane-6-carboxylate Palladium on carbon, 10% (35.1 mg, 0.330 mmol) was added to a solution of (4R)-tert-butyl 4-(6-(5-(3,6-dihydro-2H-pyran-4-yl)-1-(tetrahydro-2H-pyran-2-yl)-1H-indazol-3-yl)pyrazin-2-yloxy)-6-azaspiro[2.5]octane-6-carboxylate (194 mg, 0.330 mmol) in EtOH (3.3 mL) at RT in a portable hydrogen reactor; the reaction was stirred under 45 psi of $H_2$ for 1.5 h. The mixture was filtered through a pad of Celite, washed with DCM and MeOH, and concentrated to give (4R)-tert-butyl 4-(6-(1-(tetrahydro-2H-pyran-2-yl)-5-(tetrahydro-2H-pyran-4-yl)-1H-indazol-3-yl)pyrazin-2-yloxy)-6-azaspiro[2.5]octane-6-carboxylate (180 mg, 0.305 mmol, 92% yield) as an amber oil. MS (ESI, pos. ion) m/z: 590.4 (M+1).

Preparation of Compound 264: 3-(6-((4R)-6-azaspiro [25]oct-4-yloxy)-2-pyrazinyl)-5-(tetrahydro-2H-pyran-4-yl)-1H-indazole 2,2,2-trifluoroacetate A solution of (4R)-tert-butyl 4-(6-(1-(tetrahydro-2H-pyran-2-yl)-5-(tetrahydro-2H-pyran-4-yl)-1H-indazol-3-yl)pyrazin-2-yloxy)-6-azaspiro[2.5]octane-6-carboxylate (180 mg, 0.305 mmol) in hydrogen chloride in IPA (30.5 mL, 153 mmol) was stirred at 80° C. for 1 h. The crude product was concentrated and was dissolved in MeOH (~20 mg/ml) and injected (5×1.000 ml) onto the Shimadzu (Protocol B) preparatory LC before the pure fractions were combined and concentrated via rotary evaporation to give 3-(6-((4R)-6-azaspiro [25]oct-4-yloxy)-2-pyrazinyl)-5-(tetrahydro-2H-pyran-4-yl)-1H-indazole 2,2,2-trifluoroacetate (45 mg, 0.087 mmol, 28.4% yield). MS (ESI, pos. ion) m/z: 406.2 (M+1). $^1$H NMR (400 MHz, MeOH-$d_4$) δ ppm 0.59-0.72 (m, 1 H) 0.75-0.89 (m, 2H) 0.96-1.05 (m, 1 H) 1.23 (d, J=14.67 Hz, 1 H) 1.75-1.94 (m, 4H) 2.72 (td, J=13.89, 3.72 Hz, 1 H) 2.91-3.04 (m, 1 H) 3.33-3.35 (m, 1 H) 3.52 (d, J=12.32 Hz, 1 H) 3.59-3.70 (m, 3H) 3.89 (d, J=13.30 Hz, 1 H) 4.12 (dd, J=11.05, 3.03 Hz, 2 H) 5.09 (s, 1 H) 7.40 (d, J=8.61 Hz, 1 H) 7.56 (d, J=8.61 Hz, 1 H) 8.13 (s, 1 H) 8.29 (s, 1 H) 9.01 (s, 1 H).

Example 265 methyl 3-(6-((4R)-6-azaspiro[25]oct-4-yloxy)-2-pyrazinyl)-1H-indazole-5-carboxylate bis(2,2,2-trifluoroacetate)

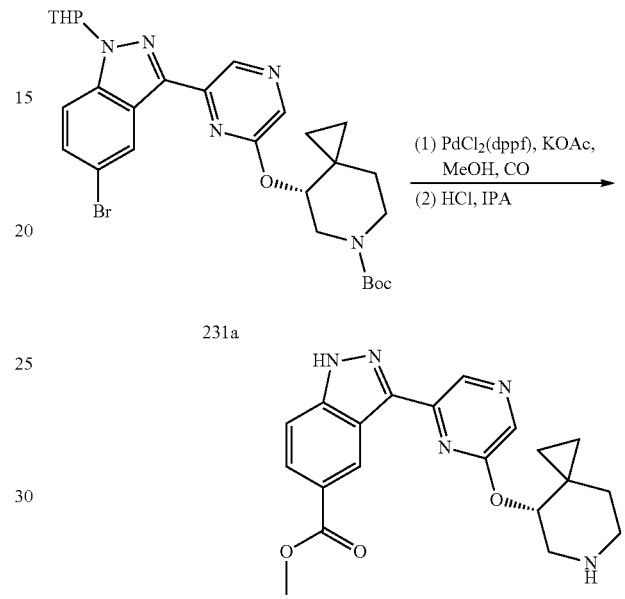

231a

265

Preparation of Compound 265a: methyl 3-(6-((R)-6-(tert-butoxycarbonyl)-6-azaspiro[2.5]octan-4-yloxy) pyrazin-2-yl)-1-(tetrahydro-2H-pyran-2-yl)-1H-indazole-5-carboxylate A mixture of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (150 mg, 0.257 mmol), PdCl$_2$dppf (20.96 mg, 0.026 mmol), and potassium acetate (76 mg, 0.770 mmol) in MeOH (2566 μL) was placed in a Symyx/Argonaut reactor for 16 h at 90° C. under CO (70 psi) when clean conversion was observed via 1 cms. The crude was purified via automated flash chromatography (silica gel) with 100% hexanes to 20% EtOAc/hexanes to give methyl 3-(6-((R)-6-(tert-butoxycarbonyl)-6-azaspiro[2.5]octan-4-yloxy)pyrazin-2-yl)-1-(tetrahydro-2H-pyran-2-yl)-1H-indazole-5-carboxylate (120 mg, 0.213 mmol, 83% yield) as a colorless oil. MS (ESI, pos. ion) m/z: 564.2 (M+1).

Preparation of Compound 265: methyl 3-(6-((4R)-6-azaspiro[25]oct-4-yloxy)-2-pyrazinyl)-1H-indazole-5-carboxylate bis(2,2,2-trifluoroacetate)

A solution of methyl 3-(6-((R)-6-(tert-butoxycarbonyl)-6-azaspiro[2.5]octan-4-yloxy)pyrazin-2-yl)-1-(tetrahydro-2H-pyran-2-yl)-1H-indazole-5-carboxylate (120 mg, 0.213 mmol) in HCl in dioxane (5323 μL, 21.29 mmol) was stirred at 80° C. for 30 min at which time a yellow solid had crashed out. The crude product was concentrated and was dissolved in MeOH (~20 mg/ml) and injected (3×1.000 ml) onto the Shimadzu preparatory LC (Protocol B) before the pure fractions were combined and concentrated via rotary evaporation to give methyl 3-(6-((4R)-6-azaspiro[25]oct-4-yloxy)-2-pyrazinyl)-1H-indazole-5-carboxylate bis(2,2,2-trifluoroacetate)bis(2,2,2-trifluoroacetate) (77 mg, 0.127 mmol, 59.5% yield) as a yellow solid. MS (ESI, pos. ion) m/z: 380.3 (M+1). $^1$H NMR (400 MHz, CDCl$_3$) δ ppm 0.70 (s, 2H) 0.84 (q, J=9.13 Hz, 2H) 1.35 (d, J=13.89 Hz, 1 H) 2.64 (t, J=11.64 Hz, 1 H) 3.41 (d, J=9.19 Hz, 1 H) 3.63 (d, J=10.76 Hz, 1 H) 3.68-3.78 (m, 1 H) 3.89 (s, 3H) 4.06 (d, J=11.93 Hz, 1 H) 4.59 (s, 1H) 7.05 (d, J=8.61 Hz, 1 H) 7.61 (d, J=8.80 Hz, 1 H) 7.98 (s, 1 H) 8.11 (s, 1 H) 8.45 (s, 1 H) 9.03 (br. s., 1 H) 9.60 (br. s., 1 H).

Example 266

3-(6-((4R)-6-azaspiro[25]oct-4-yloxy)-2-pyrazinyl)-5-(2-ethynylphenyl)-1H-indazole bis(2,2,2-trifluoroacetate)

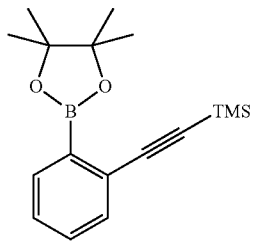

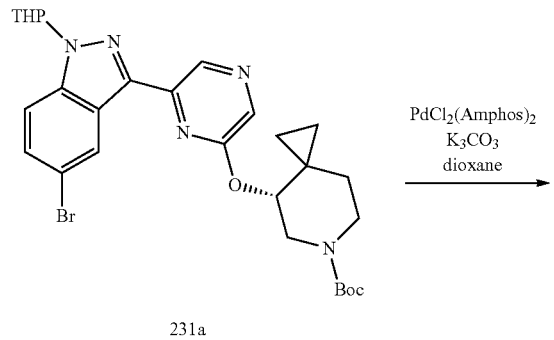

231a

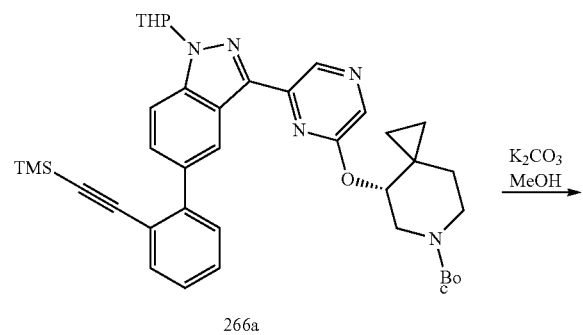

266a

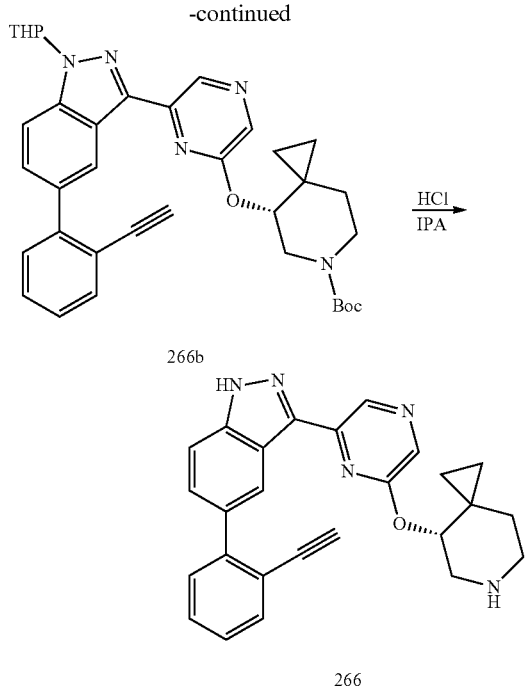

266b

266

Preparation of 266a: (4R)-tert-butyl 4-(6-(1-(tetrahydro-2H-pyran-2-yl)-5-(2-((trimethylsilyl)ethynyl)phenyl)-1H-indazol-3-yl)pyrazin-2-yloxy)-6-azaspiro[2.5]octane-6-carboxylate A mixture of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (159 mg, 0.272 mmol), trimethyl((2-(4,4,5,5-tetramethyl-1,3,2-dioxaborolan-2-yl)phenyl)ethynyl)silane (123 mg, 0.408 mmol), PdCl$_2$ (Amphos) (19.26 mg, 0.027 mmol), and potassium carbonate (408 µL, 0.816 mmol) in dioxane (2720 µL) was heated in the microwave for 10 min at 160° C. The crude was purified via automated flash chromatography (silica gel) with 100% hexanes to 20% EtOAc/hexanes to give (4R)-tert-butyl 4-(6-(1-(tetrahydro-2H-pyran-2-yl)-5-(2-((trimethylsilyl)ethynyl)phenyl)-1H-indazol-3-yl)pyrazin-2-yloxy)-6-azaspiro[2.5]octane-6-carboxylate (110 mg, 0.162 mmol, 59.7% yield) as a yellowish oil. MS (ESI, pos. ion) m/z: 678.2 (M+1).

Preparation of 266b: (4R)-tert-butyl 4-(6-(5-(2-ethynylphenyl)-1-(tetrahydro-2H-pyran-2-yl)-1H-indazol-3-yl)pyrazin-2-yloxy)-6-azaspiro[2.5]octane-6-carboxylate A mixture of (4R)-tert-butyl 4-(6-(1-(tetrahydro-2H-pyran-2-yl)-5-(2-((trimethylsilyl)ethynyl)phenyl)-1H-indazol-3-yl)pyrazin-2-yloxy)-6-azaspiro[2.5]octane-6-carboxylate (110 mg, 0.162 mmol) and potassium carbonate (112 mg, 0.811 mmol) in MeOH (1623 µL) was stirred at RT for 2 h. The mixture was diluted with EtOAc (150 ml), added to a separatory funnel, and washed with water (2×100 ml) before the organic layer was separated, dried over Na$_2$SO$_4$, and concentrated to give (4R)-tert-butyl 4-(6-(5-(2-ethynylphenyl)-1-(tetrahydro-2H-pyran-2-yl)-1H-indazol-3-yl)pyrazin-2-yloxy)-6-azaspiro[2.5]octane-6-carboxylate (80 mg, 0.132 mmol, 81% yield) as a yellowish oil. MS (ESI, pos. ion) m/z: 606.2 (M+1).

Preparation of 266: 3-(6-((4R)-6-azaspiro[25]oct-4-yloxy)-2-pyrazinyl)-5-(2-ethynylphenyl)-1H-indazole bis(2,2,2-trifluoroacetate)

A solution of (4R)-tert-butyl 4-(6-(5-(2-ethynylphenyl)-1-(tetrahydro-2H-pyran-2-yl)-1H-indazol-3-yl)pyrazin-2-yloxy)-6-azaspiro[2.5]octane-6-carboxylate (80 mg, 0.132 mmol) in HCl in IPA (1.32E+04 µL, 66.0 mmol) was stirred at 80° C. for 30 min. The crude product was concentrated and was dissolved in MeOH (~20 mg/ml) and injected (2×1.000 ml) onto the Shimadzu preparatory LC (Protocol B) before the pure fractions were combined and concentrated via rotary evaporation to give impure products; these were run again to give 3-(6-((4R)-6-azaspiro[25]oct-4-yloxy)-2-pyrazinyl)-5-(2-ethynylphenyl)-1H-indazole bis(2,2,2-trifluoroacetate) (1.56 mg, 2.402 µmol, 1.818% yield). MS (ESI, pos. ion) m/z: 422.3 (M+1). $^1$H NMR (400 MHz, MeOH-d$_4$) δ ppm 0.61-0.70 (m, 2 H) 0.71-0.76 (m, 1 H) 0.92-0.97 (m, 1 H) 1.18 (d, J=14.08 Hz, 1 H) 2.70 (d, J=16.04 Hz, 1 H) 3.21-3.30 (m, 1 H) 3.37-3.49 (m, 2 H) 3.52 (s, 1 H) 3.83 (d, J=13.69 Hz, 1 H) 5.12 (s, 1 H) 7.38-7.43 (m, 1 H) 7.53 (d, J=3.91 Hz, 2 H) 7.64-7.72 (m, 3 H) 8.30 (s, 1 H) 8.63 (s, 1 H) 9.08 (s, 1 H).

Example 267

3-(6-((4R)-6-azaspiro[25]oct-4-yloxy)-2-pyrazinyl)-5-(2-(1-chloroethenyl)phenyl)-1H-indazole bis(2,2,2-trifluoroacetate)

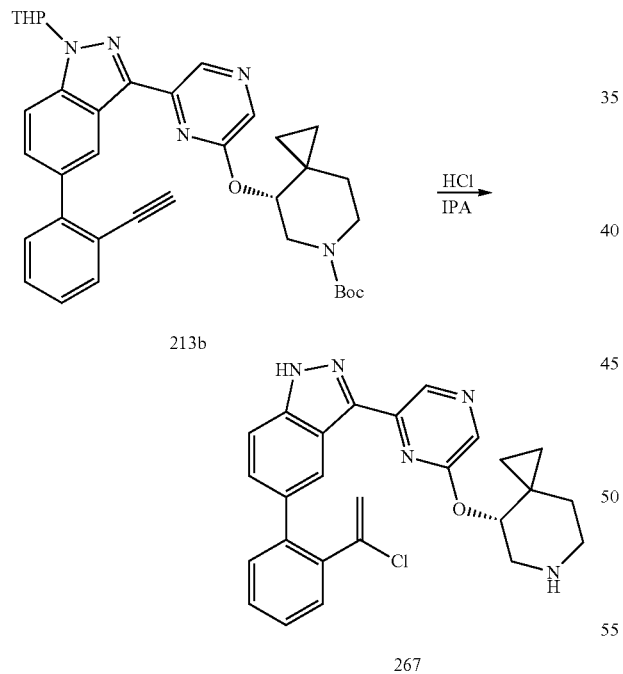

A solution of (4R)-tert-butyl 4-(6-(5-(2-ethynylphenyl)-1-(tetrahydro-2H-pyran-2-yl)-1H-indazol-3-yl)pyrazin-2-yloxy)-6-azaspiro[2.5]octane-6-carboxylate (80 mg, 0.132 mmol) in HCl in IPA (1.32E+04 µL, 66.0 mmol) was stirred at 80° C. for 30 min. The crude product was concentrated and was dissolved in MeOH (~20 mg/ml) and injected (2×1.000 ml) onto the Shimadzu preparatory LC (Protocol B) before the pure fractions were combined and concentrated via rotary evaporation to give impure products; these were run again to give 3-(6-((4R)-6-azaspiro[25]oct-4-yloxy)-2-pyrazinyl)-5-(2-(1-chloroethenyl)phenyl)-1H-indazole bis(2,2,2-trifluoroacetate) (24 mg, 0.035 mmol, 26.5% yield). MS (ESI, pos. ion) m/z: 458.1 (M+1). $^1$H NMR (400 MHz, MeOH-d$_4$) δ ppm 0.48-0.65 (m, 3 H) 0.92-0.97 (m, 1 H) 1.15 (d, J=14.67 Hz, 1 H) 2.61-2.70 (m, 1 H) 3.20-3.28 (m, 1 H) 3.41 (dd, J=13.40, 1.66 Hz, 1 H) 3.47 (d, J=12.32 Hz, 1 H) 3.78 (d, J=12.72 Hz, 1 H) 5.03 (s, 1 H) 5.25 (d, J=1.37 Hz, 1 H) 5.45 (d, J=1.57 Hz, 1 H) 7.42-7.48 (m, 2 H) 7.49-7.58 (m, 3 H) 7.65 (dd, J=8.61, 0.59 Hz, 1 H) 8.29 (dd, J=1.96, 0.98 Hz, 2 H) 9.04 (s, 1 H).

Example 268

1-(3-(6-((4R)-6-azaspiro[25]oct-4-yloxy)-2-pyrazinyl)-1H-indazol-5-yl)ethanone 2,2,2-trifluoroacetate

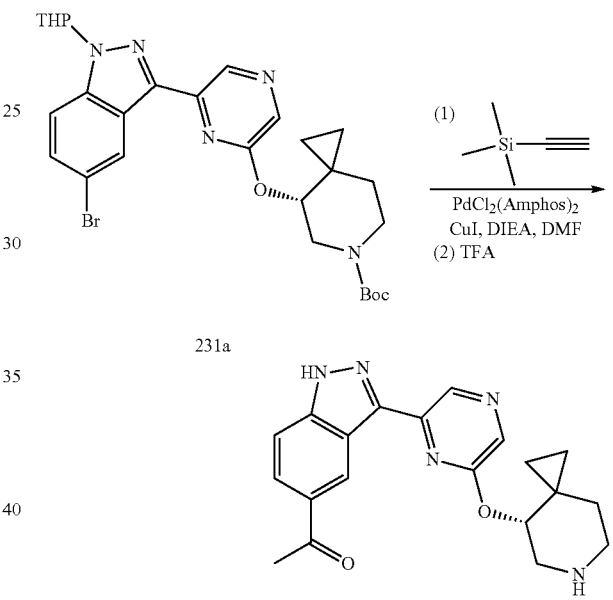

Preparation of Compound 268a: (4R)-tert-butyl 4-(6-(1-(tetrahydro-2H-pyran-2-yl)-5-((trimethylsilyl)ethynyl)-1H-indazol-3-yl)pyrazin-2-yloxy)-6-azaspiro[2.5]octane-6-carboxylate A mixture of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (579 mg, 0.991 mmol), copper(I) iodide (37.7 mg, 0.198 mmol), PdCl$_2$(Amphos) (70.1 mg, 0.099 mmol), N-ethyl-N-isopropylpropan-2-amine (530 µL, 2.97 mmol), and ethynyltrimethylsilane (208 µL, 1.486 mmol) in DMF (9906 µL) was heated in the microwave for 15 min at 160° C. The crude product was adsorbed onto silica and was purified via automated flash chromatography (silica gel) with 100% hexanes to 20% EtOAc/hexanes to give (4R)-tert-butyl 4-(6-(1-(tetrahydro-2H-pyran-2-yl)-5-((trimethylsilyl)ethynyl)-1H-indazol-3-yl)pyrazin-2-yloxy)-6-azaspiro[2.5]octane-6-carboxylate (596 mg, 0.990 mmol, 100% yield) as a yellow foam. MS (ESI, pos. ion) m/z: 602.3 (M+1).

Preparation of Compound 268: 1-(3-(6-((4R)-6-azaspiro[25]oct-4-yloxy)-2-pyrazinyl)-1H-indazol-5-yl)ethanone 2,2,2-trifluoroacetate A solution of (4R)-tert-butyl 4-(6-(1-(tetrahydro-2H-pyran-2-yl)-5-((trimethylsilyl)ethynyl)-1H-indazol-3-yl)pyrazin-2-yloxy)-6-azaspiro[2.5]octane-6-carboxylate (51 mg, 0.085 mmol) in DCM (847 µL) and TFA (326 µL, 4.24 mmol) was stirred at RT for 1 h. The crude was concentrated and was dissolved in MeOH (~20 mg/ml) and injected (2×1.000 ml) onto the Shimadzu preparatory LC (Protocol B) before the pure fractions were combined and concentrated via rotary evaporation to give 1-(3-(6-((4R)-6-azaspiro[25]oct-4-yloxy)-2-pyrazinyl)-1H-indazol-5-yl)ethanone (1 mg, 2% yield) as a yellow solid. MS (ESI, pos. ion) m/z: 364.2 (M+1). $^1$H NMR (400 MHz, MeOH-$d_4$) δ ppm 0.66-0.71 (m, 1 H) 0.76-0.82 (m, 1 H) 0.94-1.02 (m, 2H) 1.25-1.32 (m, 1 H) 2.65-2.79 (m, 1 H) 2.75 (s, 3H) 3.37-3.41 (m, 1 H) 3.48-3.58 (m, 1 H) 3.71 (d, J=13.30 Hz, 1 H) 3.96 (d, J=13.50 Hz, 1 H) 5.14 (s, 1 H) 7.72 (d, J=8.80 Hz, 1H) 8.15 (dd, J=8.90, 1.47 Hz, 1 H) 8.37 (s, 1 H) 9.09 (s, 1 H) 9.11 (s, 1 H).

Example 269

(3-(6-((4R)-6-azaspiro[25]oct-4-yloxy)-2-pyrazinyl)-1H-indazol-5-yl)acetonitrile 2,2,2-trifluoroacetate

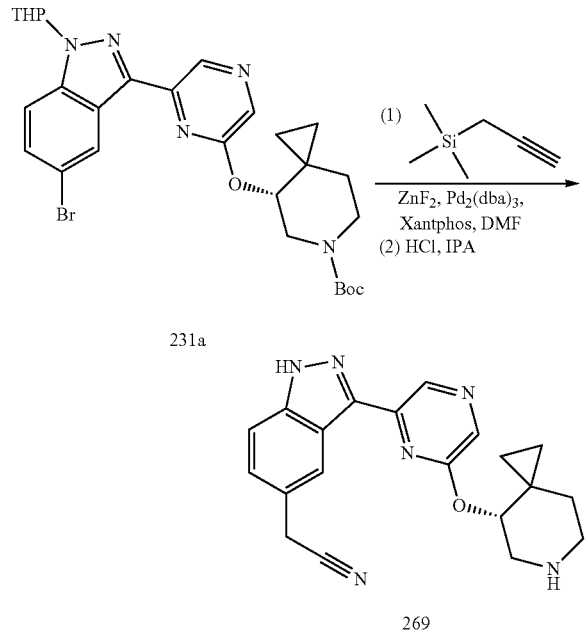

Preparation of Compound 269a: (3-(6-((4R)-6-azaspiro[25]oct-4-yloxy)-2-pyrazinyl)-1-(tetrahydro-2H-pyran-2-yl)-1H-indazol-5-yl)acetonitrile A mixture of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (459 mg, 0.785 mmol), Pd$_2$dba$_3$ (36.0 mg, 0.039 mmol), zinc(II) fluoride (48.7 mg, 0.471 mmol), and 2-(trimethylsilyl)acetonitrile (129 µL, 0.942 mmol) in DMF (1571 µL) was heated to 90° C. for 16 h. The mixture was diluted with DCM (100 ml), added to a separatory funnel, and washed with saturated aqueous NaHCO$_3$ (2×75 ml) before the organic layer was separated, dried over Na$_2$SO$_4$, and concentrated to give the title compound which was used in the next step without further purification. MS (ESI, pos. ion) m/z: 445.2 (M-Boc+1).

Preparation of Compound 269: (3-(6-((4R)-6-azaspiro[25]oct-4-yloxy)-2-pyrazinyl)-1H-indazol-5-yl)acetonitrile 2,2,2-trifluoroacetate A solution of (4R)-tert-butyl 4-(6-(5-(cyanomethyl)-1-(tetrahydro-2H-pyran-2-yl)-1H-indazol-3-yl)pyrazin-2-yloxy)-6-azaspiro[2.5]octane-6-carboxylate (25 mg, 0.046 mmol) in HCl in IPA (459 µL, 2.295 mmol) was heated to 80° C. for 30 min. The crude product was concentrated and was dissolved in DMSO (~20 mg/ml) and injected (2×1.000 ml) onto the Shimadzu preparatory LC (Protocol B) before the pure fractions were combined and concentrated via rotary evaporation to give (3-(6-((4R)-6-azaspiro[25]oct-4-yloxy)-2-pyrazinyl)-1H-indazol-5-yl)acetonitrile 2,2,2-trifluoroacetate (3 mg, 6.32 µmol, 13.78% yield) as a yellow solid. MS (ESI, pos. ion) m/z: 361.2 (M+1). $^1$H NMR (400 MHz, MeOH) δ ppm 0.61-0.71 (m, 2 H) 0.84-0.90 (m, 1 H) 1.04-1.10 (m, 1 H) 1.20 (d, J=14.48 Hz, 1 H) 2.67-2.77 (m, 1 H) 3.22-3.30 (m, 1 H) 3.49 (d, J=12.13 Hz, 1 H) 3.71 (d, J=13.30 Hz, 1 H) 3.93 (d, J=13.69 Hz, 1 H) 4.14 (d, J=2.74 Hz, 2 H) 5.08 (s, 1 H) 7.37 (d, J=8.80 Hz, 1 H) 7.63 (d, J=8.61 Hz, 1 H) 8.30 (s, 1 H) 8.50 (s, 1 H) 9.06 (s, 1 H).

Example 270

2-(3-(6-((4R)-6-azaspiro[25]oct-4-yloxy)-2-pyrazinyl)-1H-indazol-5-yl)ethanol hydrochloride

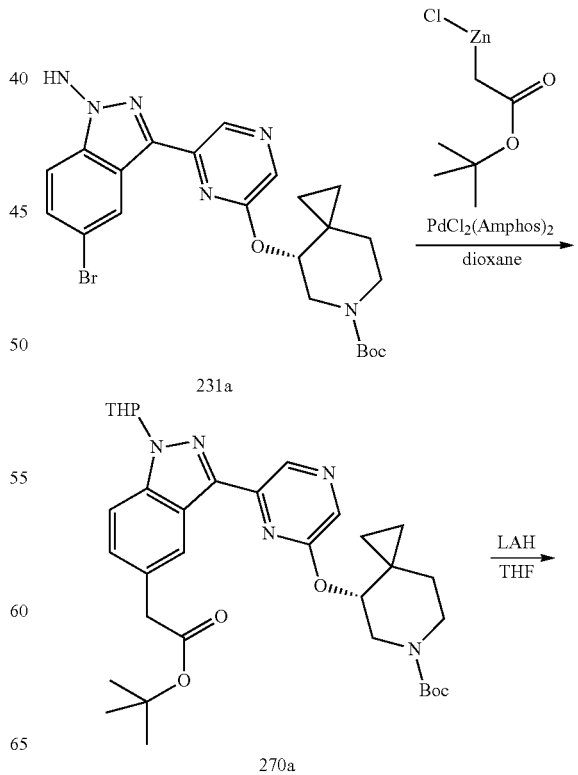

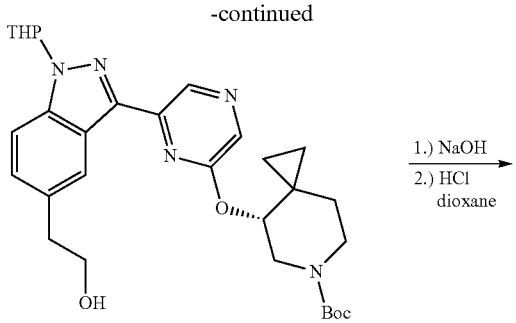

270b

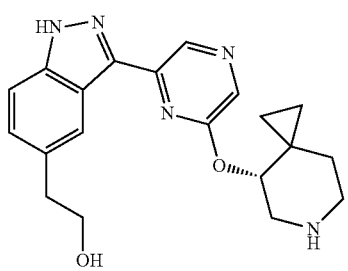

270

Preparation of 270a: (4R)-tert-butyl 4-(6-(5-(2-tert-butoxy-2-oxoethyl)-1-(tetrahydro-2H-pyran-2-yl)-1H-indazol-3-yl)pyrazin-2-yloxy)-6-azaspiro[2.5]octane-6-carboxylate A solution of (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (209 mg, 0.358 mmol), PdCl$_2$(Amphos) (12.66 mg, 0.018 mmol), and (2-tert-butoxy-2-oxoethyl)zinc(II) chloride in Et$_2$O (1073 µL, 0.536 mmol) in dioxane (3576 µL) was heated to 80° C. under a purged stream of N$_2$; the reaction was stirred for 16 h at 80° C. The crude was adsorbed onto silica and was purified via automated flash chromatography (silica gel) with 100% hexanes to 50% EtOAc/hexanes to give (4R)-tert-butyl 4-(6-(5-(2-tert-butoxy-2-oxo ethyl)-1-(tetrahydro-2H-pyran-2-yl)-1H-indazol-3-yl)pyrazin-2-yloxy)-6-azaspiro[2.5]octane-6-carboxylate (137 mg, 0.221 mmol, 61.8% yield) as a yellow oil. MS (ESI, pos. ion) m/z: 620.3 (M+1).

Preparation of 270b: (4R)-tert-butyl 4-(6-(5-(2-hydroxyethyl)-1-(tetrahydro-2H-pyran-2-yl)-1H-indazol-3-yl)pyrazin-2-yloxy)-6-azaspiro[2.5]octane-6-carboxylate Lithium aluminum hydride in THF (181 µL, 0.181 mmol) was added to a solution of (4R)-tert-butyl 4-(6-(5-(2-tert-butoxy-2-oxoethyl)-1-(tetrahydro-2H-pyran-2-yl)-1H-indazol-3-yl)pyrazin-2-yloxy)-6-azaspiro[2.5]octane-6-carboxylate (56 mg, 0.090 mmol) in THF (904 µL) at 0° C.; the reaction was stirred for 1 h. The crude was quenched with EtOAc and was adsorbed onto silica and was purified via automated flash chromatography (silica gel) with 100% hexanes to 40% EtOAc/hexanes to give (4R)-tert-butyl 4-(6-(5-(2-hydroxyethyl)-1-(tetrahydro-2H-pyran-2-yl)-1H-indazol-3-yl)pyrazin-2-yloxy)-6-azaspiro[2.5]octane-6-carboxylate as a pale yellow oil. MS (ESI, pos. ion) m/z: 550.2 (M+1).

Preparation of 270: 2-(3-(6-((4R)-6-azaspiro[25]oct-4-yloxy)-2-pyrazinyl)-1H-indazol-5-yl)ethanol hydrochloride TFA (2.80 µL, 0.036 mmol) was added to a solution of (4R)-tert-butyl 4-(6-(5-(2-hydroxyethyl)-1-(tetrahydro-2H-pyran-2-yl)-1H-indazol-3-yl)pyrazin-2-yloxy)-6-azaspiro[2.5]octane-6-carboxylate (20 mg, 0.036 mmol) in DCM (364 µL) at 40° C. for 1 h when (R)-2-(3-(6-(6-azaspiro[2.5]octan-4-yloxy)pyrazin-2-yl)-1H-indazol-5-yl)ethyl 2,2,2-trifluoroacetate (M+1: 462) and the alcohol (M+1: 366) were observed via 1 cms; the mixture was concentrated and dissolved in THF (3 ml) before a few drops of NaOH (10 N) were added. The crude product was concentrated and was dissolved in DMSO (~20 mg/ml) and injected (2×1.000 ml) onto the Shimadzu preparatory LC (Protocol B) before the pure fractions were combined and concentrated via rotary evaporation to give a mixture of the alcohol and ester. The mixture was diluted with DCM (50 ml), added to a separatory funnel, and washed with 1 N NaOH (2×20 ml) before the organic layer was separated, dried over Na$_2$SO$_4$, and concentrated to give pure alcohol; this was dissolved in MeOH before HCl in dioxane (4 N, 0.5 ml) was added at RT; rotory evaporation afforded 2-(3-(6-((4R)-6-azaspiro[25]oct-4-yloxy)-2-pyrazinyl)-1H-indazol-5-yl)ethanol hydrochloride (8 mg, 0.020 mmol, 54.7% yield) as a yellow solid. MS (ESI, pos. ion) m/z: 366.0 (M+1). $^1$H NMR (400 MHz, MeOH) δ ppm 0.63-0.70 (m, 1 H) 0.74-0.81 (m, 1 H) 0.90-0.97 (m, 1 H) 0.97-1.05 (m, 1 H) 1.26 (d, J=14.67 Hz, 1 H) 2.71 (td, J=13.69, 3.91 Hz, 1 H) 3.02 (t, J=6.65 Hz, 2H) 3.38 (s, 1 H) 3.49-3.57 (m, 1 H) 3.67-3.72 (m, 2 H) 3.86-3.92 (m, 3 H) 5.15 (s, 1 H) 7.40 (dd, J=8.61, 1.37 Hz, 1 H) 7.58 (d, J=8.61 Hz, 1 H) 8.22 (s, 1 H) 8.34 (br. s., 1 H) 9.05 (br. s., 1 H).

Example 271

Racemic 2-(3-(6-((4R)-6-azaspiro[25]oct-4-yloxy)-2-pyrazinyl)-1-methyl-1H-indazol-5-yl)-1-propanol

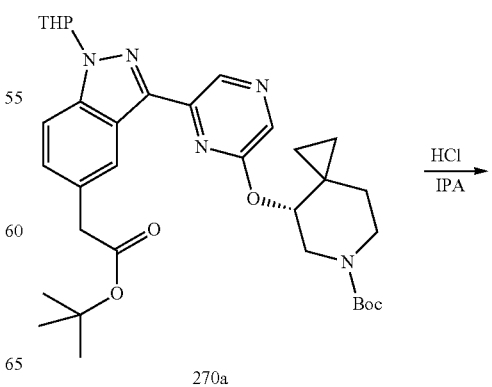

270a

201

-continued

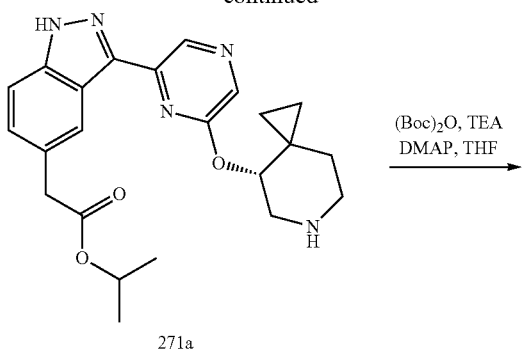

271a

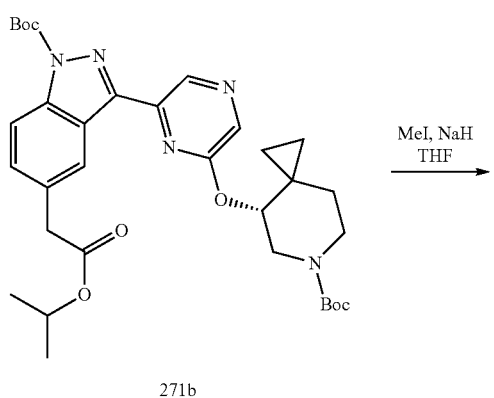

271b

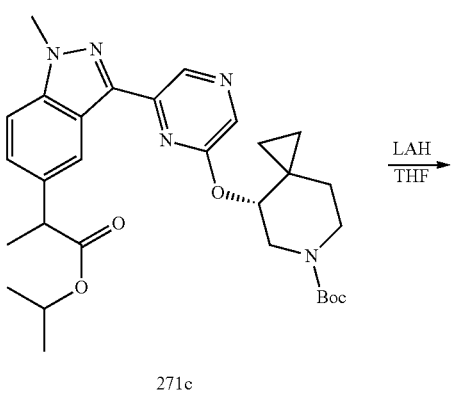

271c

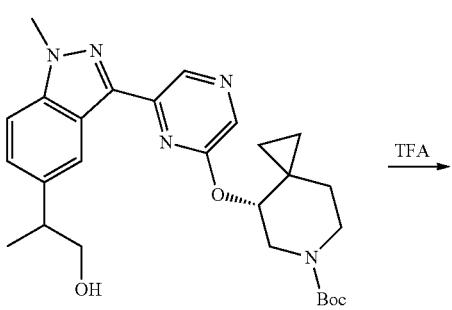

271d

202

-continued

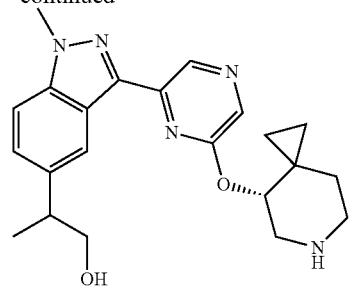

271

Preparation of 271a: (R)-isopropyl 2-(3-(6-(6-azaspiro[2.5]octan-4-yloxy)pyrazin-2-yl)-1H-indazol-5-yl)acetate A solution of (4R)-tert-butyl 4-((6-(5-(2-(tert-butoxy)-2-oxoethyl)-1-(tetrahydro-2H-pyran-2-yl)-1H-indazol-3-yl)pyrazin-2-yl)oxy)-6-azaspiro[2.5]octane-6-carboxylate (280 mg, 0.452 mmol) in hydrogen chloride in IPA (9036 µl, 45.2 mmol) was stirred at 80° C. for 2 h. The mixture was concentrated and was diluted with EtOAc (150 ml), added to a separatory funnel, and washed with 1 N NaOH (2×75 ml) before the organic layer was separated, dried over Na$_2$SO$_4$, and concentrated to give (R)-isopropyl 2-(3-(6-(6-azaspiro[2.5]octan-4-yloxy)pyrazin-2-yl)-1H-indazol-5-yl)acetate (180 mg, 0.427 mmol, 95% yield) and was used as is. MS (ESI, pos. ion) m/z: 422.1 (M+1).

Preparation of 271b: (R)-tert-butyl 3-(6-((6-(tert-butoxycarbonyl)-6-azaspiro[2.5]octan-4-yl)oxy)pyrazin-2-yl)-5-(2-isopropoxy-2-oxoethyl)-1H-indazole-1-carboxylate Di-tert-butyl dicarbonate (215 µl, 0.940 mmol) was added to a solution of (R)-isopropyl 2-(3-(6-(6-azaspiro[2.5]octan-4-yloxy)pyrazin-2-yl)-1H-indazol-5-yl)acetate (180 mg, 0.427 mmol), TEA (179 µl, 1.281 mmol), and DMAP (10.43 mg, 0.085 mmol) in THF (4271 µl) at RT; after stirring for 1 h, starting material was observed to have been consumed. The crude was adsorbed onto silica and was purified via automated flash chromatography (silica gel) with 100% hexanes to 20% EtOAc/hexanes to give (R)-tert-butyl 3-(6-((6-(tert-butoxycarbonyl)-6-azaspiro[2.5]octan-4-yl)oxy)pyrazin-2-yl)-5-(2-isopropoxy-2-oxoethyl)-1H-indazole-1-carboxylate (40 mg, 0.064 mmol, 15.07% yield) as a yellow oil. MS (ESI, pos. ion) m/z: 622.0 (M+1).

Preparation of 271c: (4R)-tert-butyl 4-((6-(5-(1-isopropoxy-1-oxopropan-2-yl)-1-methyl-1H-indazol-3-yl)pyrazin-2-yl)oxy)-6-azaspiro[2.5]octane-6-carboxylate NaH in mineral oil (7.72 mg, 0.193 mmol) was added to a solution of (R)-tert-butyl 3-(6-((6-(tert-butoxycarbonyl)-6-azaspiro[2.5]octan-4-yl)oxy)pyrazin-2-yl)-5-(2-isopropoxy-2-oxoethyl)-1H-indazole-1-carboxylate (40 mg, 0.064 mmol) in THF (643 µl) at 0° C.; this was stirred for 15 min before iodomethane (12.04 µl, 0.193 mmol) was added. After 1 h at 0° C.; the mixture was warmed to RT and stirred for 1.5 h. The mixture was diluted with EtOAc (100 ml), added to a separatory funnel, and washed with saturated aqueous NH₄Cl (2×75 ml) before the organic layer was separated, dried over Na₂SO₄, and concentrated. The crude was adsorbed onto silica and was purified via automated flash chromatography (silica gel) with 100% DCM to 4% MeOH/DCM to give (4R)-tert-butyl 4-((6-(5-(1-isopropoxy-1-oxopropan-2-yl)-1-methyl-1H-indazol-3-yl)pyrazin-2-yl)oxy)-6-azaspiro[2.5]octane-6-carboxylate (30 mg, 0.055 mmol, 85% yield) as a yellow oil. MS (ESI, pos. ion) m/z: 550.0 (M+1).

Preparation of 271d: (4R)-tert-butyl 4-((6-(5-(1-hydroxypropan-2-yl)-1-methyl-1H-indazol-3-yl)pyrazin-2-yl)oxy)-6-azaspiro[2.5]octane-6-carboxylate Lithium aluminum hydride, 1.0 M solution in Et₂O (109 µl, 0.109 mmol) was added to a solution of (4R)-tert-butyl 4-((6-(5-(1-isopropoxy-1-oxopropan-2-yl)-1-methyl-1H-indazol-3-yl)pyrazin-2-yl)oxy)-6-azaspiro[2.5]octane-6-carboxylate (30 mg, 0.055 mmol) in THF (546 µl) at 0° C. for 1 h. The reaction was quenched with EtOAc and triturated with NH₄Cl before it was filtered and concentrated to give (4R)-tert-butyl 4-((6-(5-(1-hydroxypropan-2-yl)-1-methyl-1H-indazol-3-yl)pyrazin-2-yl)oxy)-6-azaspiro[2.5]octane-6-carboxylate (18 mg, 0.036 mmol, 66.8% yield) as a yellow oil. MS (ESI, pos. ion) m/z: 494.0 (M+1).

Preparation of 271: Racemic 2-(3-(6-((4R)-6-azaspiro[2.5]oct-4-yloxy)-2-pyrazinyl)-1-methyl-1H-indazol-5-yl)-1-propanol A solution of (R)-tert-butyl 4-((6-(5-(1-hydroxy-2-methylpropan-2-yl)-1H-indazol-3-yl)pyrazin-2-yl)oxy)-6-azaspiro[2.5]octane-6-carboxylate (18 mg, 0.036 mmol) in TFA (41.6 mg, 0.365 mmol) was stirred at RT for 30 min. The mixture was concentrated and was dissolved in MeOH (~20 mg/ml) and injected (1×1.000 ml) onto the Shimadzu preparatory LC (Protocol B) before the pure fraction was concentrated via rotary evaporation to give impure product. A preparatory TLC plate was loaded with the crude mixture and run 2 times in 20% MeOH/DCM; scraping the plate, extraction with MeOH, filtration, and concentration via rotary evaporation afforded 2-(3-(6-((4R)-6-azaspiro[2.5]oct-4-yloxy)-2-pyrazinyl)-1-methyl-1H-indazol-5-yl)-1-propanol (7.6 mg, 0.019 mmol, 53.0% yield) as a beige solid. MS (ESI, pos. ion) m/z: 394.0 (M+1).

Example 272

Racemic 5-(2,6-difluorophenyl)-3-(6-(3-piperidinylmethyl)-2-pyrazinyl)-1H-indazole ditrifluoroacetate

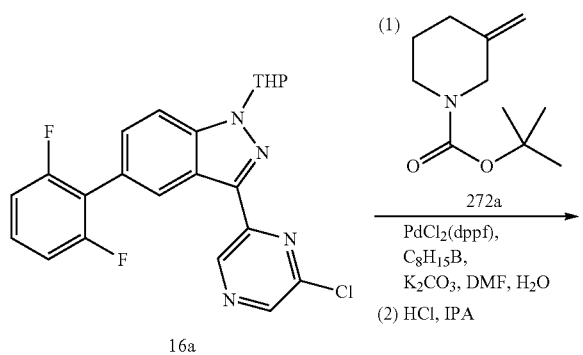

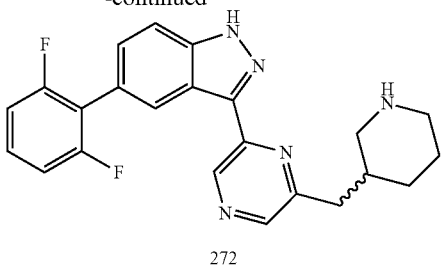

Preparation of Compound 272a: tert-butyl 3-methylenepiperidine-1-carboxylate

A suspension of methyltriphenylphosphonium iodide (15.22 g, 37.6 mmol, Sigma-Aldrich) in THF (75 mL) was stirred at RT before addition of potassium t-butoxide (4.22 g, 37.6 mmol, Sigma-Aldrich) in one portion. The resulting bright yellow solution was stirred at RT for 30 minuets before adding tert-butyl 3-oxopiperidine-1-carboxylate (3 g, 15.06 mmol) and stirring for 3 h. It was poured into ice water, and the mixture was extracted with DCM (4×50 mL) before drying the combined organics over Na₂SO₄, filtering, and concentrating under reduced pressure. The crude material was purified by column chromatography (eluant: 0 to 10% EtOAc/hexanes), affording the product as a clear oil (1.93 g, 65%). ¹H NMR (DMSO-d₆) δ: 4.70-4.81 (m, 2H), 3.80 (s, 2H), 3.30-3.40 (m, 2H), 2.18-2.26 (m, 2H), 1.47-1.56 (m, 2H), 1.38 (s, 9H)

Preparation of Compound 272: 5-(2,6-difluorophenyl)-3-(6-(3-piperidinylmethyl)-2-pyrazinyl)-1H-indazole ditrifluoroacetate A mixture of 0.5 M 9-BBN in THF (2811 µL, 1.406 mmol, Sigma-Aldrich) and tert-butyl 3-methylenepiperidine-1-carboxylate (277 mg, 1.406 mmol) was stirred under N₂ in a sealed tube at 70° C. for 1 h before adding the solution via syringe to a mixture of PdCl₂(dppf) (22.96 mg, 0.028 mmol, Strem Chemicals), K₂CO₃ (259 mg, 1.874 mmol, Sigma-Aldrich), and 3-(6-chloropyrazin-2-yl)-5-(2,6-difluorophenyl)-1-(tetrahydro-2H-pyran-2-yl)-1H-indazole (400 mg, 0.937 mmol) and sealing the mixture under N₂. The reaction was heated to 65° C. for 4 h. The crude material was concentrated under reduced pressure before adding 6N HCl/IPA and stirring for 1 h at 70° C. The mixture was concentrated under reduced pressure before diluting with water (10 mL) and extracting with EtOAc (3×15 mL). The combined organics were dried over Na₂SO₄, filtered, and concentrated under reduced pressure. The residue was purified by reverse-phase preparative HPLC. The product fractions were dried in a Genevac overnight, affording the product as a yellow-orange solid (174 mg, 58.6%). MS (ESI, pos. ion) m/z: 406.2 (M+1)

Example 273 and 274

Non-racemic 5-(2,6-difluorophenyl)-3-(6-(3-piperidinylmethyl)-2-pyrazinyl)-1H-indazole, Enantiomer 1 and 2

The title compounds were prepared according to the procedure for compound 18, using racemic 5-(2,6-difluorophenyl)-3-(6-(3-piperidinylmethyl)-2-pyrazinyl)-1H-indazole.

Example 275

3-(6-((4R)-6-azaspiro[2.5]oct-4-yloxy)-2-pyrazinyl)-5-(6-cyclopropyl-2-pyrazinyl)-1H-indazole

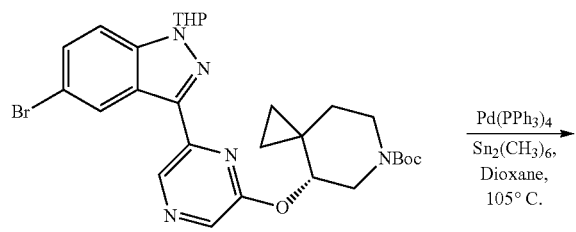

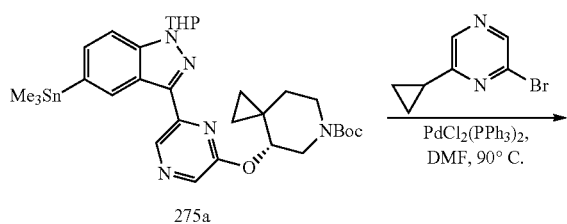

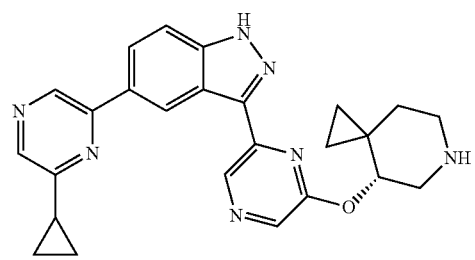

275

Preparation of Compound 275a: (4R)-tert-butyl 4-((6-(1-(tetrahydro-2H-pyran-2-yl)-5-(trimethyl-stannyl)-1H-indazol-3-yl)pyrazin-2-yl)oxy)-6-azaspiro[2.5]octane-6-carboxylate A mixture of Pd(PPh$_3$)$_4$ (0.230 g, 0.199 mmol, Strem Chemicals), 1,1,1,2,2,2-hexamethyldistannane (1.305 g, 3.98 mmol, Sigma-Aldrich), and (4R)-tert-butyl 4-(6-(5-bromo-1-(tetrahydro-2H-pyran-2-yl)-1H-indazol-3-yl)pyrazin-2-yloxy)-6-azaspiro[2.5]octane-6-carboxylate (1.164 g, 1.991 mmol) in dioxane (7.97 mL) was set stirring at 105° C. under N$_2$ for 4 h. The reaction was cooled to RT and concentrated under reduced pressure before adsorbing onto silica and purifying by column chromatography (eluent: 0 to 40% EtOAc/hexanes). The resulting oil was used in the next step.

Preparation of Compound 275: 3-(6-((4R)-6-azaspiro[25]oct-4-yloxy)-2-pyrazinyl)-5-(6-cyclopropyl-2-pyrazinyl)-1H-indazole dihydrochloride A mixture of dichlorobis(triphenyl-phosphine)palladium (II) (21.00 mg, 0.030 mmol, Strem Chemicals), (4R)-tert-butyl 4-(6-(1-(tetrahydro-2H-pyran-2-yl)-5-(trimethylstannyl)-1H-indazol-3-yl)pyrazin-2-yloxy)-6-azaspiro[2.5]octane-6-carboxylate (200 mg, 0.299 mmol), and 2-bromo-6-cyclopropylpyrazine (119 mg, 0.598 mmol, Combi-Blocks) in DMF (2992 µL) was set stirring at 90° C. in a sealed tube for 16 h. The reaction was cooled and concentrated under reduced pressure to a yellow residue that was taken up in DCM and purified by column chromatography (eluent: 0 to 50% EtOAc/hexanes). The product fractions were combined and concentrated before adding 5N HCl in IPA and stirring at 60° C. for 2 h. The reaction was diluted with MeOH (10 mL) and concentrated under reduced pressure to give the product as a yellow solid (37 mg, 24.1% over two steps). MS (ESI, pos. ion) m/z: 440.0 (M+1)

Example 276

1-(4-(5-(2,6-difluorophenyl)-1H-indol-3-yl)-6-methoxypyrimidin-2-yl)piperidin-4-amine

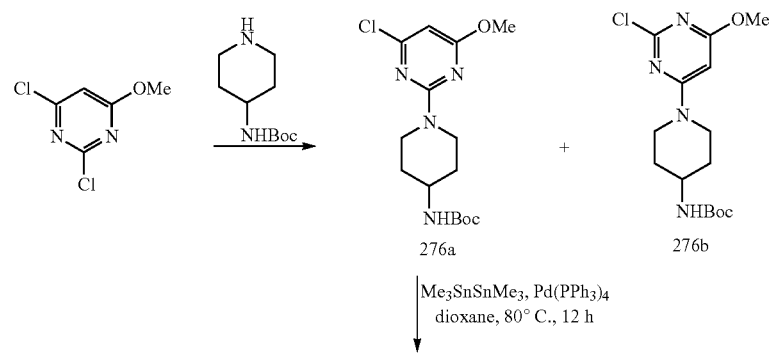

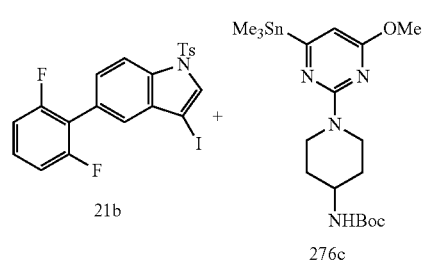
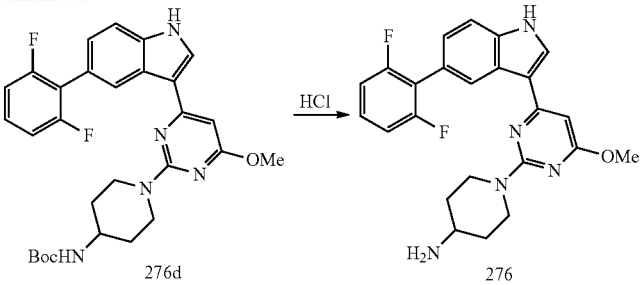

Preparation of Compound 276a and 276b: tert-butyl (1-(4-chloro-6-methoxypyrimidin-2-yl)piperidin-4-yl)carbamate and tert-butyl (1-(2-chloro-6-methoxypyrimidin-4-yl)piperidin-4-yl)carbamate To a solution of 2,4-dichloro-6-methoxypyrimidine (5.0 g, 28.0 mmol) and tert-butyl piperidin-4-ylcarbamate (5.6 g, 28.0 mmol) in DMF (50 mL) was added $K_2CO_3$ (7.74 g, 56.0 mmol) and the mixture was stirred at RT for 6 h. The reaction was quenched with water and the suspension was filtered, washed with water and dried. The crude was purified with silica gel chromatography (eluting with 20% EtOAc in petroleum ether) to give tert-butyl (1-(4-chloro-6-methoxypyrimidin-2-yl)piperidin-4-yl)carbamate 276a (6.0 g, 73% yield). MS (ESI, pos. ion) m/z: 342.8 (M+1); $^1$H-NMR (400 MHz, CDCl$_3$): δ ppm 5.97 (s, 1H), 4.64 (d, 2 H, J=13.2 Hz), 4.49 (brs, 1H), 3.88 (s, 3H), 3.04 (t, 2 H, J=11.6 Hz), 2.03 (d, 2 H, J=10.4 Hz), 1.57 (s, 3H), 1.46 (s, 9H). And tert-butyl (1-(2-chloro-6-methoxypyrimidin-4-yl)piperidin-4-yl)carbamate 276b (1.0 g, 12% yield). MS (ESI, pos. ion) m/z: 343.1 (M+1); $^1$H-NMR (400 MHz, CDCl$_3$): δ ppm 5.70 (s, 1H), 4.49 (brs, 1H), 4.22 (d, 2 H, J=12.4 Hz), 3.91 (s, 3H), 2.96-3.00 (m, 2H), 2.03 (d, 2 H, J=8.4 Hz), 1.45 (s, 9H), 1.3-1.39 (m, 2H).

Preparation of Compound 276c: tert-butyl (1-(4-methoxy-6-(trimethylstannyl)pyrimidin-2-yl)piperidin-4-yl)carbamate To a solution of tert-butyl (1-(4-chloro-6-methoxypyrimidin-2-yl)piperidin-4-yl)carbamate (2.0 g, 5.847 mmol) and hexamethylditin (2.86 g, 8.77 mmol) in dioxane (20 mL) was added Pd(PPh$_3$)$_4$ (338 mg, 0.293 mmol) and the solution was degassed with argon gas for 5 min. The reaction was heated at 90° C. overnight, quenched with water and extracted with EtOAc. The organic layer was dried (Na$_2$SO$_4$), filtered and concentrated. The residue was purified with basic alumina chromatography (eluting with 20% EtOAc in petroleum ether) to give tert-butyl (1-(4-methoxy-6-(trimethylstannyl)pyrimidin-2-yl)piperidin-4-yl)carbamate (800 mg, 29.6%). MS (ESI, pos. ion) m/z: 472.7 (M+1); $^1$H-NMR (400 MHz CDCl$_3$): δ ppm 6.18 (s, 1H), 4.72 (d, J=12 Hz, 2H), 4.47 (brs, 1H), 3.85 (s, 3H), 3.78 (brs, 1H), 3.00 (t, J=12 Hz, 2H), 2.00 (d, J=12 Hz, 2H) 1.30-1.40 (m, 11H), 0.27 (s, 9H).

Preparation of Compound 276d: tert-butyl (1-(4-(5-(2,6-difluorophenyl)-1-tosyl-1H-indol-3-yl)-6-methoxypyrimidin-2-yl)piperidin-4-yl)carbamate To a solution of 5-(2,6-difluorophenyl)-3-iodo-1-tosyl-1H-indole (0.107 g, 0.2 mmol) and tert-butyl (1-(4-methoxy-6-(trimethylstannyl)pyrimidin-2-yl)piperidin-4-yl)carbamate (0.1 g, 0.2 mmol) in DMF (2 mL) was added Pd(PPh$_3$)$_4$ (23 mg, 0.02 mmol) and CuI (42 mg, 0.22 mmol) and argon gas was bubbled for 15 min. The reaction was heated at 90° C. for 1 h then quenched with water. The suspension was extracted with EtOAc and the organic layer was dried (Na$_2$SO$_4$), filtered and concentrated. The residue was purified with basic alumina chromatography (eluting with 50% EtOAc in petroleum ether) to give tert-butyl (1-(4-(5-(2,6-difluorophenyl)-1-tosyl-1H-indol-3-yl)-6-methoxypyrimidin-2-yl)piperidin-4-yl)carbamate (60 mg, 41%). MS (ESI, pos. ion) m/z: 690.2 (M+1); $^1$H-NMR (DMSO-d$_6$, 300 MHz): δ ppm 8.71 (s, 1H), 8.61 (s, 1H), 8.10-8.20 (m, 3H), 7.42-7.52 (m, 4H), 7.20-7.25 (m, 3H), 6.76 (m, 1H), 4.56 (d, J=12.9 Hz, 2H), 3.87 (s, 3H), 3.32 (d, J=9 Hz, 3H), 3.03 (m, 2H) 2.33 (s, 3H), 1.74 (d, J=12.9 Hz, 2H), 1.3 (s, 9H).

Preparation of Compound 276e: tert-butyl (1-(4-(5-(2,6-difluorophenyl)-1H-indol-3-yl)-6-methoxypyrimidin-2-yl)piperidin-4-yl)carbamate To a solution of tert-butyl (1-(4-(5-(2,6-difluorophenyl)-1-tosyl-1H-indol-3-yl)-6-methoxypyrimidin-2-yl)piperidin-4-yl)carbamate (60 mg, 0.087 mmol) in dioxane (0.8 mL) was added 7M aq.NaOH (1 mL) and the mixture was heated at 90° C. for 6 h. The reaction was quenched with water and the suspension was filtered. The resulting solid was washed with water and dried. The crude was purified with basic alumina chromatography to give tert-butyl (1-(4-(5-(2,6-difluorophenyl)-1H-indol-3-yl)-6-methoxypyrimidin-2-yl)piperidin-4-yl)carbamate (25 mg, 54%). $^1$H-NMR (300 MHz, DMSO-d$_6$): δ 11.80 (brs, 1H), 8.58 (s, 1H), 8.26 (s, 1H), 7.40-7.55 (m, 2H), 7.18-7.26 (m, 4H), 6.85 (d, J=7.5 Hz, 1H) 6.49 (s, 1H), 4.66 (d, J=11.7 Hz, 2H), 3.84 (s, 3H), 3.52 (brs, 2H), 2.97-3.05 (m, 2H), 1.7 (brs, 2H), 1.38 (s, 9H).

Preparation of Compound 276: 1-(4-(5-(2,6-difluorophenyl)-1H-indol-3-yl)-6-methoxypyrimidin-2-yl)piperidin-4-amine To solution of tert-butyl (1-(4-(5-(2,6-difluorophenyl)-1H-indol-3-yl)-6-methoxypyrimidin-2-yl)piperidin-4-yl)carbamate (0.1 g, 0.187 mmol) in dioxane (2 mL) was added HCl in dioxane (2 mL) and the mixture was heated at 90° C. for overnight. The reaction was quenched with aq.NaHCO$_3$ and extracted with EtOAc. The organic layer was dried (Na$_2$SO$_4$), filtered and concentrated. The residue was purified with basic alumina column chromatography. (eluting in 1% MeOH in CHCl$_3$) to give 1-(4-(5-(2,6-difluorophenyl)-1H-indol-3-yl)-6-methoxypyrimidin-2-yl)piperidin-4-amine (20 mg, 25%). MS (ESI, pos. ion) m/z: 436.1 (M+1); $^1$H-NMR (DMSO-d$_6$, 400 MHz): δ ppm 11.84 (brs, 1H), 8.58 (s, 1H), 8.29 (s, 1H), 7.56 (d, 1 H, J=8.4 Hz), 7.47-7.43 (m, 1H), 7.19-7.27 (m, 3H), 6.54 (s, 1H), 4.7 (d, J=12 Hz, 2H), 3.8 (s, 3H), 3.0 (t, J=12 Hz, 2H), 1.85-1.89 (m, 3H), 1.38-1.40 (m, 2H).

Example 277

2-(4-aminopiperidin-1-yl)-6-(5-(2,6-difluorophenyl)-1H-indol-3-yl)pyrimidin-4(3H)-one

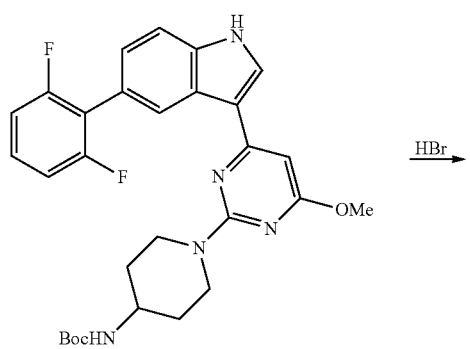

276d

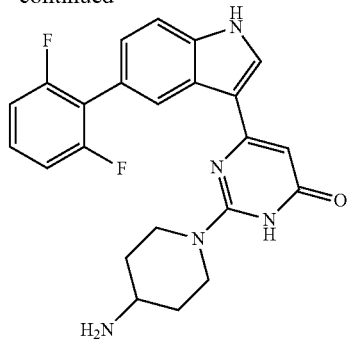

277

A solution of tert-butyl (1-(4-(5-(2,6-difluorophenyl)-1H-indol-3-yl)-6-methoxypyrimidin-2-yl)piperidin-4-yl)carbamate (0.1 g, 0.187 mmol) in 33% HBr in HOAc (1.87 mL) was heated at 90° C. for 14 h. The reaction was quenched with aq. NaHCO$_3$ and extracted with EtOAc. The organic layer was dried (Na$_2$SO$_4$), filtered and concentrated. The residue was purified with treatment of acid-base to give 2-(4-aminopiperidin-1-yl)-6-(5-(2,6-difluorophenyl)-1H-indol-3-yl)pyrimidin-4(3H)-one (15 mg, 20%). MS (ESI, pos. ion) m/z: 422.1 (M+1); $^1$H-NMR (DMSO-d6, 400 MHz): δ ppm 11.80 (brs, 1H), 8.46 (s, 1H), 8.17 (s, 1H), 7.56 (d, J=8.4 Hz, 1H), 7.42-7.46 (m, 1H), 7.19-7.25 (m, 3H), 6.15 (s, 1H), 4.42 (d, J=12.8 Hz, 2H), 2.96-3.05 (m, 3H), 1.88 (s, 1H), 1.77 (d, J=10.8 Hz, 2H), 1.23-1.30 (m, 2H).

Example 278

(R)-4-(5-(2,6-difluorophenyl)-1H-indol-3-yl)-6-methoxy-N-(piperidin-3-yl)pyrimidin-2-amine

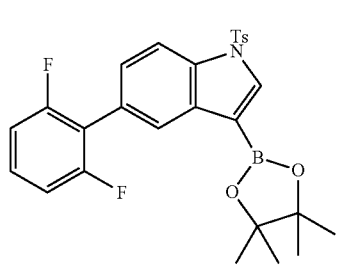

23c

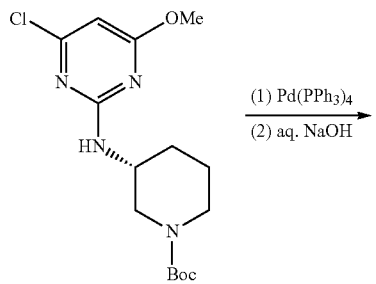

278a

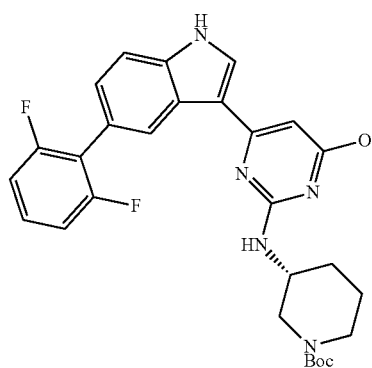

278b

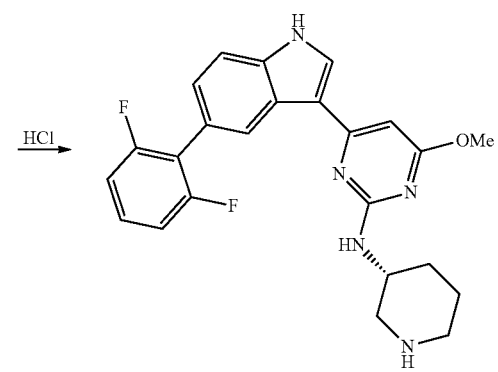

278

Preparation of Compound 278a: (R)-tert-butyl 3-((4-chloro-6-methoxypyrimidin-2-yl)amino)piperidine-1-carboxylate The title compound was prepared according to the procedure for compound 276a, using 2,4-dichloro-6-methoxypyrimidine and (R)-tert-butyl 3-aminopiperidine-1-carboxylate.

Preparation of Compound 278b: (R)-tert-butyl 3-((4-(5-(2,6-difluorophenyl)-1-tosyl-1H-indol-3-yl)-6-methoxypyrimidin-2-yl)amino)piperidine-1-carboxylate To a solution of 5-(2,6-difluorophenyl)-3-(4,4,5,5-tetramethyl-1,3,2-dioxaborolan-2-yl)-1-tosyl-1H-indole (600 mg, 1.17 mmol), and (R)-tert-butyl 3-((4-chloro-6-methoxypyrimidin-2-yl)amino)piperidine-1-carboxylate (483 mg, 1.41 mmol) in DME (12 mL) and water (3 mL) was added Pd(PPh$_3$)$_4$ (270 mg, 0.234 mmol) and Na$_2$CO$_3$ (372 mg, 3.51 mmol) and argon gas was bubbled for 15 min. The above mixture was heated at 90° C. for 8 h. The reaction was quenched with water and extracted with EtOAc. The organic layer was separated, dried over anhydrous Na$_2$SO$_4$, filtered and concentrated. The residue was purified with silica gel chromatography (eluting with 30% EtOAc in petroleum ether) to give (R)-tert-butyl 3-((4-(5-(2,6-difluorophenyl)-1-tosyl-1H-indol-3-yl)-6-methoxypyrimidin-2-yl)amino)piperidine-1-carboxylate (500 mg, 62.5%). MS (ESI, pos. ion) m/z: 690.2 (M+1); $^1$H-NMR (400 MHz CDCl$_3$): δ ppm 8.16 (s, 1H), 8.09 (d, J=8 Hz, 1H), 7.84-7.90 (m, 3H), 7.26-7.46 (m, 6H), 7.02 (m, 2H), 6.41 (s, 1H), 5.07 (brs, 1H), 4.10-4.14 (m, 1H), 3.93 (s, 3H), 2.37 (s, 3H), 1.25-1.60 (m, 15H).

Preparation of Compound 278c: (R)-tert-butyl 3-((4-(5-(2,6-difluorophenyl)-1H-indol-3-yl)-6-methoxypyrimidin-2-yl)amino)piperidine-1-carboxylate To a solution of (R)-tert-butyl 3-((4-(5-(2,6-difluorophenyl)-1-tosyl-1H-indol-3-yl)-6-methoxypyrimidin-2-yl)amino)piperidine-1-carboxylate (500 mg, 0.726 mmol) in dioxane (7 mL) was added 7M aq.NaOH (7 mL) and the mixture was heated at 90° C. for 6 h. The reaction was quenched with water and the suspension was filtered. The resulting solid was washed with water and dried. The crude product was purified with silica gel chromatography (eluting with 50% EtOAc in Hexanes) to give (R)-tert-butyl 3-((4-(5-(2,6-difluorophenyl)-1H-indol-3-yl)-6-methoxypyrimidin-2-yl)amino)piperidine-1-carboxylate (300 mg, 77%). MS (ESI, pos. ion) m/z: 536.0 (M+1); $^1$H-NMR (400 MHz CDCl$_3$): δ ppm: 8.63 (s, 1H), 8.41 (brs, 1H), 7.90 (s, 1H), 7.65-7.77 (m, 1H), 7.48-7.57 (m, 2H), 7.30-7.35 (m, 1H), 6.99-7.03 (m, 2H), 6.43 (s, 1H), 5.00 (s, 1H), 4.09-4.13 (m, 1H), 3.92 (s, 3H), 3.33-3.73 (m, 4H), 2.05 (s, 1H), 1.63-1.72 (m, 1H), 1.38 (s, 9H), 0.86-0.90 (m, 1H).

Preparation of Compound 278: (R)-4-(5-(2,6-difluorophenyl)-1H-indol-3-yl)-6-methoxy-N-(piperidin-3-yl)pyrimidin-2-amine To solution of (R)-tert-butyl 3-((4-(5-(2,6-difluorophenyl)-1H-indol-3-yl)-6-methoxypyrimidin-2-yl)amino)piperidine-1-carboxylate (130 mg, 0.243 mmol) in dioxane (2 mL) was added HCl in dioxane (4 M, 2 mL) and the mixture was heated at 90° C. for overnight. The reaction was quenched with aq.NaHCO$_3$ and extracted with EtOAc. The organic layer was dried (Na$_2$SO$_4$), filtered and concentrated. The residue was washed with 50% EtOAc in petroleum ether to give (R)-4-(5-(2,6-difluorophenyl)-1H-indol-3-yl)-6-methoxy-N-(piperidin-3-yl)pyrimidin-2-amine (22 mg, 22%). MS (ESI, pos. ion) m/z: 436.1 (M+1); $^1$H-NMR (400 MHz DMSO-d$_6$): δ ppm: 11.78 (brs, 1H) 8.66 (s, 1H), 8.25 (s, 1H), 7.54 (d, J=8.4 Hz, 1H), 7.41-7.46 (m, 1H), 7.21-7.22 (m, 3H), 6.70 (s, 1H), 6.48 (s, 1H), 3.80-3.83 (brs, 4H), 2.89-2.99 (m, 1H), 2.33-2.41 (m, 2H), 1.98-1.99 (m, 2H), 1.43-1.50 (m, 2H), 1.12-1.24 (m, 2H).

Example 279

(R)-6-(5-(2,6-difluorophenyl)-1H-indol-3-yl)-2-(piperidin-3-ylamino)pyrimidin-4(3H)-one A solution of (R)-tert-butyl 3-((4-(5-(2,6-difluorophenyl)-1H-indol-3-yl)-6-methoxypyrimidin-2-yl)amino)piperidine-1-carboxylate (0.17 g, 0.318 mmol) in 33% HBr in HOAc (3 mL) was heated at 90° C. for 14 h. The reaction was quenched with aq. NaHCO$_3$ and extracted with EtOAc. The organic layer was dried (Na$_2$SO$_4$), filtered and concentrated. The residue was washed with 50% EtOAc in petroleum ether to give (R)-6-(5-(2,6-difluorophenyl)-1H-indol-3-yl)-2-(piperidin-3-ylamino)pyrimidin-4(3H)-one (30 mg, 22%). MS (ESI, pos. ion) m/z: 422.1 (M+1); $^1$H-NMR (400 MHz DMSO-d$_6$): δ ppm 11.78 (s, 1H), 8.48 (s, 1H), 8.13 (d, J=2.4 Hz, 1H), 7.53 (d, J=8.8 Hz, 1H), 7.40-7.47 (m, 1H), 7.18-7.22 (m, 3H), 6.59 (brs, 1H), 6.00 (s, 1H), 3.93 (brs, 1H), 2.57 (s, 2H), 2.90 (d, J=9.2 Hz, 1H), 1.74 (brs, 1H), 1.50-1.53 (m, 2H), 1.18-1.22 (m, 3H).

Example 280

1-(5-(5-(6-isopropoxypyrazin-2-yl)-1H-indol-3-yl)-1,3,4-oxadiazol-2-yl)piperidin-4-amine

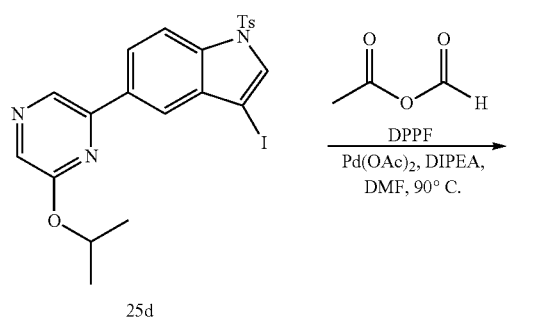

25d

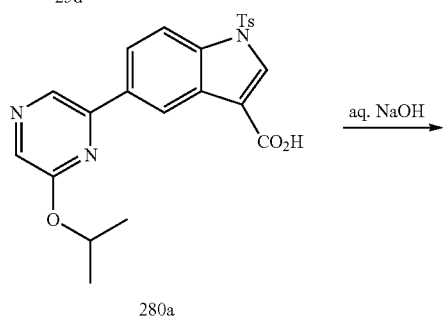

280a

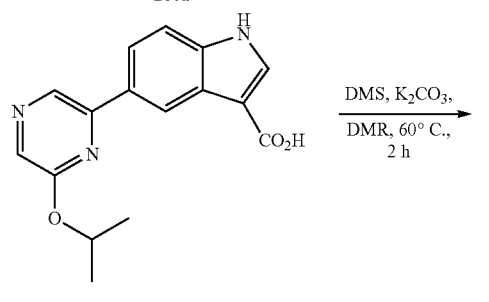

280b

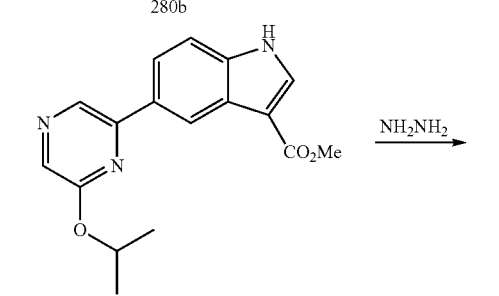

280c

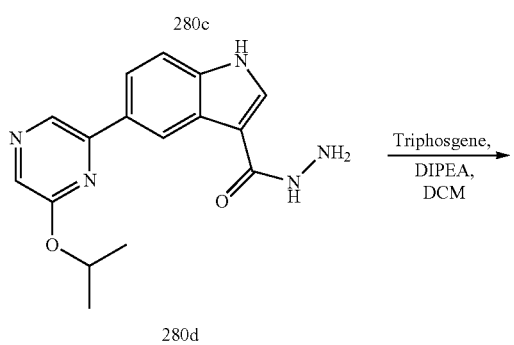

280d

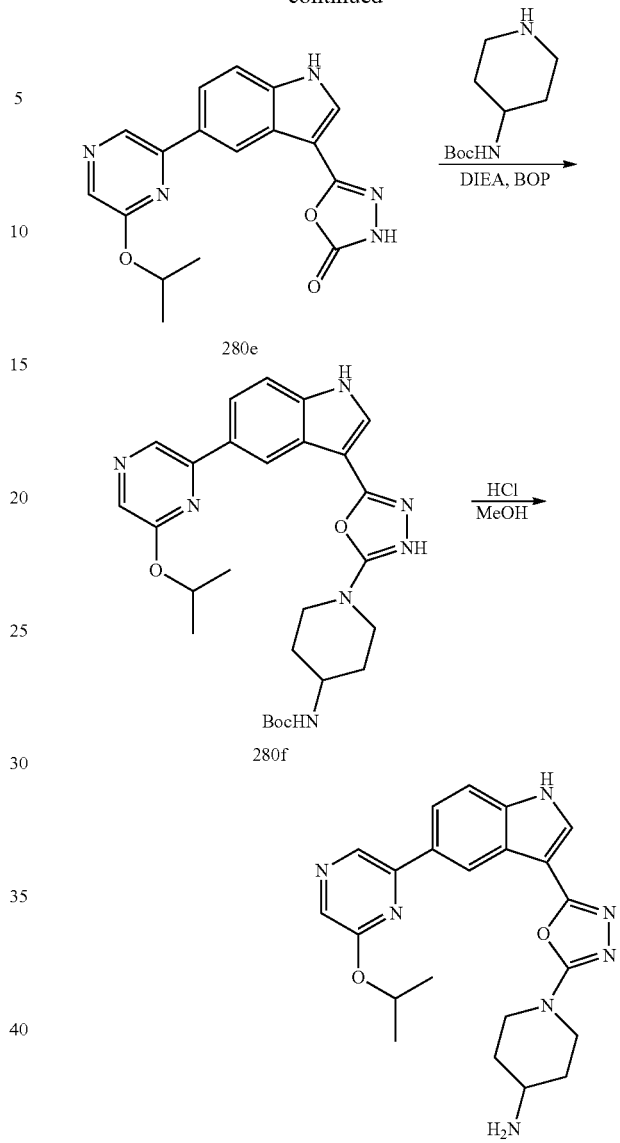

Preparation of Compound 280a: 5-(6-isopropoxypyrazin-2-yl)-1-(toluene-4-sulfonyl)-1H-indole-3-carboxylic acid A solution of 3-iodo-5-(6-isopropoxypyrazin-2-yl)-1-tosyl-1H-indole (0.5 g, 0.93 mmol) in DMF (5 mL) was purged with argon gas for 5-10 min. To the above mixture was added Pd(OAc)$_2$ (10 mg, 0.04 mmol) and dppf (26 mg, 0.046 mmol) and the mixture was again purged with argon for 5-10 min. DIPEA (0.5 mL) was added to the solution followed by dropwise addition of acetic formic anhydride (0.5 mL). The reaction was heated at 90° C. under argon atmosphere for 5 h. The reaction was cooled to RT and partitioned between ice water (5 mL) and EtOAc (5 mL). The organic layer was separated and the aqueous layer was extracted with EtOAc (5 mL×2). The combined organic layers were dried over anhydrous Na$_2$SO$_4$, filtered and concentrated. The residue was taken into 30% NaOH solution (5 mL) and washed with DCM (5 mL×2). The aqueous layer was cooled with ice water and pH was adjusted to neutral with conc. HCl to obtain off white precipitate. The suspension was filtered and the solid was washed with water, dried to give 5-(6-isopropoxy-pyrazin-2-yl)-1-(toluene-4-sulfonyl)-1H-indole-3-carboxylic acid (450 mg) as an off white solid. MS (ESI, pos. ion) m/z: 452.0 (M+1).

Preparation of Compound 280b: 5-(6-isopropoxy-pyrazin-2-yl)-1H-indole-3-carboxylic acid To a solution of 5-(6-isopropoxy-pyrazin-2-yl)-1-(toluene-4-sulfonyl)-1H-indole-3-carboxylic acid (450 mg, 0.99 mmol) in 1,4-dioxane (5 mL) was added of 10% aq. NaOH (5 mL) at RT and the reaction was heated at 90° C. for 1 h. The reaction was cooled to RT and washed with DCM (2×3 mL). The aqueous layer was neutralized with 1N HCl (4 mL) and was extracted with EtOAc (5 mL). The organic layer was dried over anhydrous $Na_2SO_4$, filtered and concentrated in vacuo to give 5-(6-isopropoxypyrazin-2-yl)-1H-indole-3-carboxylic acid (35 mg, 12%) as a brown solid. MS (ESI, pos. ion) m/z: 298.1 (M+1).

Preparation of Compound 280c: methyl 5-(6-isopropoxypyrazin-2-yl)-1H-indole-3-carboxylate To a solution of 5-(6-isopropoxy-pyrazin-2-yl)-1H-indole-3-carboxylic acid (8.0 g, 26.9 mmol) in DMF (80 mL) was added $K_2CO_3$ (4.50 g, 32.3 mmol) and dimethyl sulfate (2.50 mL, 26.9 mmol) at RT and the reaction was heated to 80° C. for 3 h. The mixture was cooled to RT and partitioned between ice water (80 mL) and EtOAc (80 mL). The organic layer was separated and dried over anhydrous $Na_2SO_4$, filtered and concentrated in vacuo. The residue was purified with silica gel chromatography (eluting with 15% EtOAc in petroleum ether) to give methyl 5-(6-isopropoxypyrazin-2-yl)-1H-indole-3-carboxylate (6.5 g, 79%) as an off white solid. MS (ESI, pos. ion) m/z: 311.9 (M+1); $^1$H-NMR (DMSO-$d_6$) δ ppm; 8.70 (d, J=1.6 Hz, 2H), 8.18 (s, 1H), 8.14 (s, 1H), 7.9 (dd, J=2.0 Hz, 1H), 7.62 (d, J=8.4, 1.6 Hz, 1H), 5.39-5.43 (m, 1H), 3.85 (s, 3H), 1.40 (d, J=6.0 Hz, 6H).

Preparation of Compound 280d: 5-(6-isopropoxy-pyrazin-2-yl)-1H-indole-3-carbohydrazide To a stirred solution of methyl 5-(6-isopropoxypyrazin-2-yl)-1H-indole-3-carboxylate (10 g, 30 mmol) in EtOH (50 mL) was added hydrazine hydrate (30 mL) and the reaction was heated to reflux for 48 h. The reaction was cooled to RT and a white precipitate was formed. The suspension was filtered and dried to afford 5-(6-isopropoxypyrazin-2-yl)-1H-indole-3-carbohydrazide (9.0 g, 90.9%) as a white solid. MS (ESI, pos. ion) m/z: 312 (M+1); $^1$H-NMR (DMSO-$d_6$) δ ppm; 11.71 (s, 1H), 9.2 (s, 1H), 8.8 (d, J=1.6 Hz, 1H), 8.71 (s, 1H), 8.1 (s, 1H), 8.0 (s, 1H), 7.90 (dd, J=8.4, 1.6 Hz, 1H), 7.55 (d, J=8.4 Hz, 1H), 5.4 (m, 1H), 4.35 (d, J=2 Hz, 1H), 1.4 (d, J=6.0 Hz, 6H).

Preparation of Compound 280e: 5-(5-(6-isopropoxy-pyrazin-2-yl)-1H-indol-3-yl)-1,3,4-oxadiazol-2(3H)-one To a solution of 5-(6-isopropoxypyrazin-2-yl)-1H-indole-3-carbohydrazide (1 g, 3.2 mmol) in DCM (100 mL) and DIPEA (1.19 mL, 19 mmol) was added a solution triphosgene (1.1 g, 3.7 mmol) in DCM (3 mL) dropwise. The reaction was stirred at RT for 2 h, then the solution was concentrated in vacuo. The residue was purified with silica gel chromatography (eluting with 0-10% MeOH in DCM) to give 5-(5-(6-isopropoxypyrazin-2-yl)-1H-indol-3-yl)-1,3,4-oxadiazol-2(3H)-one (50 mg, 5%) as a white solid. MS (ESI, pos. ion) m/z: 338.0 (M+1); $^1$H NMR (DMSO-d6) δ ppm: 12.32 (s, 1H), 12.1 (s, 1H), 8.75 (s, 1H), 8.69 (s, 1H), 8.00-8.17 (m, 3H), 7.6 (d, J=8.4 Hz, 1H), 5.38-5.45 (m, 1H), 1.49 (d, J=6.0 Hz, 6H).

Preparation of Compound 280f: tert-butyl (1-(5-(5-(6-isopropoxypyrazin-2-yl)-1H-indol-3-yl)-1,3,4-oxadiazol-2-yl)piperidin-4-yl)carbamate To a stirred solution of 5-(5-(6-isopropoxypyrazin-2-yl)-1H-indol-3-yl)-1,3,4-oxadiazol-2(3H)-one (0.25 g, 0.74 mmol) in anhydrous DMF (2.5 mL) was added DIPEA (0.25 mL, 1.48 mmol), $Ph_2O$ (125 mg, 0.74 mmol) and tert-butyl piperidin-4-ylcarbamate (0.295 g, 1.4 mmol) sequentially. The reaction was stirred for 5 min, BOP (360 mg, 0.8 mmol) was added and the reaction was further stirred for 12 h at RT. The mixture was diluted with water (25 mL) and the resulting suspension was filtered. The solid was triturated with 50% EtOAc in petroleum ether to give tert-butyl (1-(5-(5-(6-isopropoxypyrazin-2-yl)-1H-indol-3-yl)-1,3,4-oxadiazol-2-yl) piperidin-4-yl)carbamate (80 mg, 21%) as a solid. MS (ESI, pos. ion) m/z: 520.3 (M+1); $^1$H NMR (400 MHz, DMSO-$d_6$): δ ppm: 12.01 (s, 1H), 8.74 (s, 2H), 8.13 (s, 1H), 8.07 (s, 1H), 7.98 (d, J=8.4 Hz, 1H), 7.63 (d, J=8.4 Hz, 1H), 7.00 (d, J=7.2 Hz, 1H), 5.40-5.46 (m, 1H), 3.73-3.87 (m, 2H), 3.50 (s, 1H), 3.16 (t, J=10.6 Hz, 1H), 2.98 (t, J=9.2 Hz 1H), 1.84 (s, 2H), 1.33 (s, 17H).

Preparation of Compound 280:1-(5-(5-(6-isopropoxypyrazin-2-yl)-1H-indol-3-yl)-1,3,4-oxadiazol-2-yl)piperidin-4-amine To a solution of tert-butyl (1-(5-(5-(6-isopropoxypyrazin-2-yl)-1H-indol-3-yl)-1,3,4-oxadiazol-2-yl)piperidin-4-yl) carbamate (80 mg, 0.15 mmol) in MeOH (1 mL) was added HCl in MeOH (2 mL) and the reaction was stirred for 4 h at RT. The suspension was filtered and the filtrate was washed with $Et_2O$ and basified with saturated $NaHCO_3$ solution. The mixture was extracted in EtOAc (2×3 mL). The combined organic layer were dried over anhydrous $Na_2SO_4$, filtered and concentrated. The residue was triturated with 10% EtOAc in petroleum ether to give 1-(5-(5-(6-isopropoxypyrazin-2-yl)-1H-indol-3-yl)-1,3,4-oxadiazol-2-yl)piperidin-4-amine (20 mg, 31.2%) as a solid. MS (ESI, pos. ion) m/z: 420.3 (M+1); $^1$H NMR (400 MHz, DMSO-$d_6$): δ ppm 8.73 (s, 1H), 7.96-8.13 (m, 3H), 7.63 (d, J=7.6 Hz, 1H), 5.42 (brs, 1H), 3.90 (d, J=10.8 Hz, 3H), 3.13-3.18 (m, 2H), 2.80 (brs, 2H), 1.82 (d, J=10.4 Hz, 3H), 1.23-1.50 (s, 8H).

Example 281

5-(5-(6-isopropoxypyrazin-2-yl)-1H-indol-3-yl)-3-isopropyl-1,3,4-oxadiazol-2(3H)-one

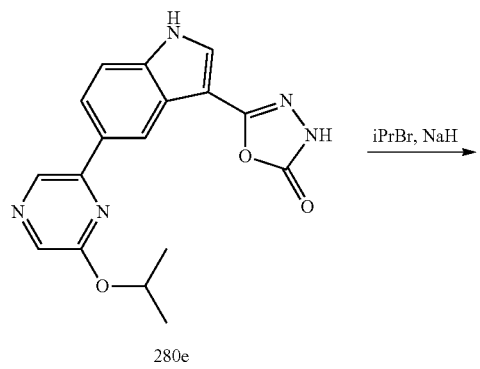

280e iPrBr, NaH

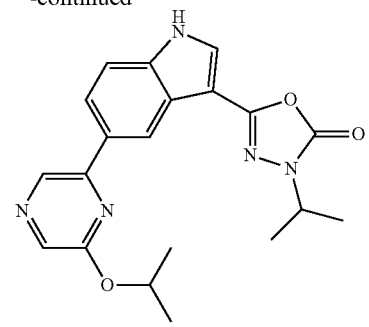

281

To a stirred solution of 5-(5-(6-isopropoxypyrazin-2-yl)-1H-indol-3-yl)-1,3,4-oxadiazol-2(3H)-one (0.2 g, 0.5 mmol) and 2-bromo propane (0.08 g, 0.6 mmol) in DMF (1 mL) at 0° C. was added 60% sodium hydride (in mineral oil) (0.040 g, 0.1 mmol) and the reaction was stirred for 2 h at RT. The reaction was quenched with water (25 mL) and extracted with EtOAc (25 mL). The organic layer was dried over $Na_2SO_4$, filtered and concentrated. The residue was purified with silica gel chromatography (eluting with 20% EtOAc in hexanes) to give 5-(5-(6-isopropoxypyrazin-2-yl)-1H-indol-3-yl)-3-isopropyl-1,3,4-oxadiazol-2(3H)-one (50 mg, 22%) as a white solid. MS (ESI, pos. ion) m/z: 380.0 (M+1); $^1$H NMR (400 MHz, CDCl$_3$): δ ppm 8.86 (br s, 1H), 8.70 (s, 1H), 8.67 (s, 1H), 8.09 (s, 1H), 8.01 (dd, J=8.4, 1.6 Hz, 1H), 7.78 (d, J=2.8 Hz, 1H), 7.56 (d, J=8.4 Hz, 1H), 5.51-5.57 (m, 1H), 4.42-4.49 (m, 1H), 1.50 (d, J=6.8 Hz, 6H), 1.48 (d, J=6.4 Hz, 6H).

Example 282

(R)-6-(5-(2,6-difluorophenyl)-1H-indazol-3-yl)-2-(piperidin-3-ylamino)pyrimidin-4(3H)-one

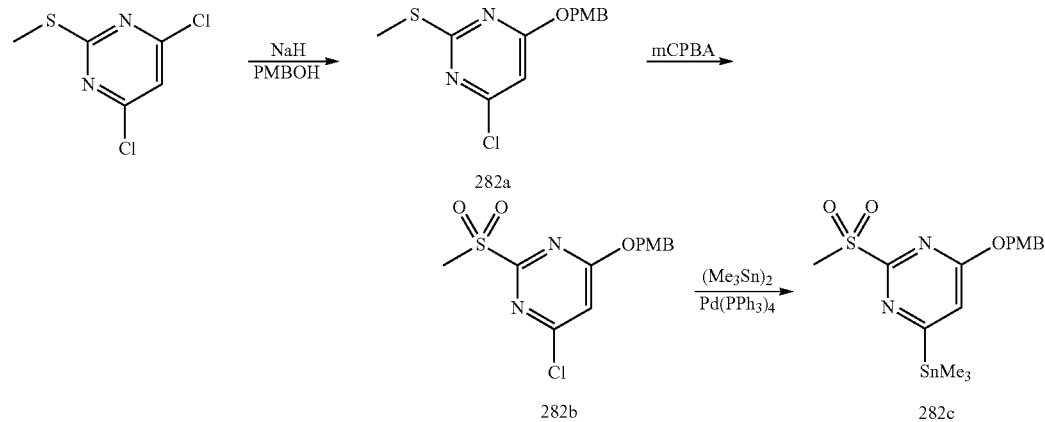

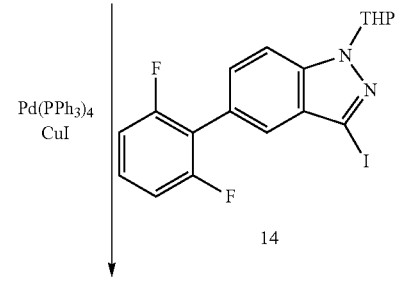

-continued

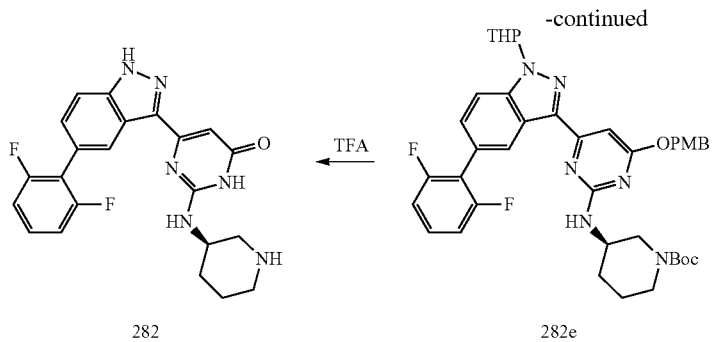

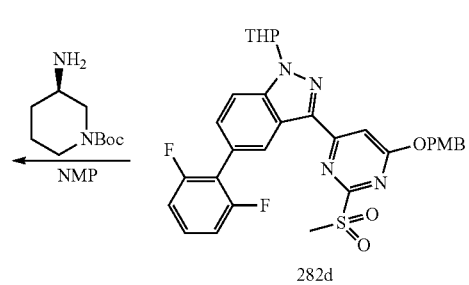

Preparation of Compound 282a: 4-Chloro-6-(4-methoxy-benzyloxy)-2-methylsulfanyl-pyrimidine To a solution of 4,6-dichloro-2-(methyl thio)pyrimidine (75 g, 38.4 mmol, Sigma-Aldrich) in DMF (750 mL) was added p-methoxybenzyl alcohol (58.38 g, 42.1 mmol) and $K_2CO_3$ (212.3 g, 1538 mmol). The reaction was stirred at 60° C. for 12 h, then cooled to RT. Water (500 mL) was added to the mixture and the resulting suspension was filtered. The solid was dried and triturated with Hexanes to give 4-Chloro-6-(4-methoxy-benzyloxy)-2-methylsulfanyl-pyrimidine (75 g, 66.4% yield) as a white solid. MS (ESI, pos. ion) m/z: 297.0 (M+1); $^1$H NMR (400 MHz, $CDCl_3$): δ 7.30-7.37 (m, 3H), 6.89-6.93 (m, 2H), 5.36 (s, 2H), 3.82 (s, 3H), 2.57 (s, 3H).

Preparation of Compound 282b: 4-Chloro-2-methanesulfonyl-6-(4-methoxy-benzyloxy)-pyrimidine To a solution of 4-chloro-6-(4-methoxy-benzyloxy)-2-methylsulfanyl-pyrimidine (75 g, 253 mmol) in DCM (750 mL) was added 3-chloro peroxybenzoic acid (130 g, 760 mmol). The reaction was stirred at RT for 2 h, and quenched with sat $NaHCO_3$. The mixture was extracted with DCM and the combined organic layers were dried with $Na_2SO_4$, filtered and concentrated. The residue was purified with silica gel chromatography (eluting with 12% EtOAc in Petroleum ether) to give 4-Chloro-2-methanesulfonyl-6-(4-methoxy-benzyloxy)-pyrimidine (75 g, 90.3%) as a white solid. MS (ESI, pos. ion) m/z: 350.9 (M+Na); $^1$H NMR (400 MHz, DMSO-$d_6$): δ ppm 7.54 (s, 1H), 7.45 (d, J=8.4 Hz, 2H), 6.96 (d, J=8.4 Hz, 2H), 5.44 (s, 2H), 3.75 (s, 3H), 3.43 (s, 3H).

Preparation of Compound 282c: 2-Methanesulfonyl-4-(4-methoxy-benzyloxy)-6-trimethylstannanyl-pyrimidine A sealed tube was charged with 4-Chloro-2-methanesulfonyl-6-(4-methoxy-benzyloxy)-pyrimidine (10 g, 30.48 mmol), Pd(PPh$_3$)$_4$ (1.7 g, 1.52 mmol) and hexamethylditin (14.97 g, 45.73 mmol) in 1,4 dioxane (100 mL). The reaction was stirred at 110° C. for 12 h. The solvent was removed in vacuo and the residue was purified with neutral alumina chromatography (eluting with 20% EtOAc in Petroleum ether) to give 2-methanesulfonyl-4-(4-methoxy-benzyloxy)-6-trimethylstannanyl-pyrimidine (6.13 g, 43.7%) as a colorless oil. MS (ESI, pos. ion) m/z: 458.9 (M+1); $^1$H NMR (400 MHz, $CDCl_3$): δ ppm 7.42 (dd, J=6.8, 2 Hz, 1H), 7.08 (s, 1H), 6.91 (dd, J=6.8, 2 Hz, 2H), 5.43 (s, 2H), 3.82 (s, 3H), 3.37 (s, 3H), 0.38 (s, 9H)

Preparation of Compound 282d: 5-(2,6-difluorophenyl)-3-(6-(4-methoxybenzyloxy)-2-(methylsulfonyl)pyrimidin-4-yl)-1-(tetrahydro-2H-pyran-2-yl)-1H-indazole A glass microwave reaction vessel was charged with 5-(2,6-difluorophenyl)-3-iodo-1-(tetrahydro-2H-pyran-2-yl)-1H-indazole (347 mg, 0.788 mmol) and 4-(4-methoxybenzyloxy)-2-(methylsulfonyl)-6-(trimethylstannyl)pyrimidine (360 mg, 0.788 mmol) in DMF (3 mL) followed by Pd(PPh$_3$)$_4$ (45.5 mg, 0.039 mmol) and CuI (31 mg, 0.158 mmol). The reaction was stirred and heated in a Initiator microwave reactor (Personal Chemistry, Biotage AB, Inc., Upssala, Sweden) at 100° C. for 30 min. The mixture was diluted with DCM and washed with water, brine, dried with $MgSO_4$, filtered and concentrated. The residue was purified with silica gel chromatography (eluting with 10-30% EtOAc in Hexanes) to give 5-(2,6-difluorophenyl)-3-(6-(4-methoxybenzyloxy)-2-(methylsulfonyl)pyrimidin-4-yl)-1-(tetrahydro-2H-pyran-2-yl)-1H-indazole (422 mg, 0.696 mmol, 88% yield) as a yellow solid. MS (ESI, pos. ion) m/z: 606.5 (M+1).

Preparation of Compound 282e: (3R)-tert-butyl 3-((4-(5-(2,6-difluorophenyl)-1-(tetrahydro-2H-pyran-2-yl)-1H-indazol-3-yl)-6-((4-methoxybenzyl)oxy)pyrimidin-2-yl)amino)piperidine-1-carboxylate A glass microwave reaction vessel was charged with 5-(2,6-difluorophenyl)-3-(6-(4-methoxybenzyloxy)-2-(methylsulfonyl)pyrimidin-4-yl)-1-(tetrahydro-2H-pyran-2-yl)-1H-indazole (200 mg, 0.330 mmol) and (R)-tert-butyl 3-aminopiperidine-1-carboxylate (198 mg, 0.989 mmol) in NMP (2.0 mL). The reaction was stirred and heated in a Initiator microwave reactor (Personal Chemistry, Biotage AB, Inc., Upssala, Sweden) at 125° C. for 2 h. The mixture was diluted with water and the resulting suspension was filtered. The solid was washed with water and dried to give 115 mg of the crude product, which was used in the next step without further purification. MS (ESI, pos. ion) m/z: 727.1 (M+1).

Preparation of Compound 282: (R)-6-(5-(2,6-difluorophenyl)-1H-indazol-3-yl)-2-(piperidin-3-ylamino)pyrimidin-4(3H)-one A glass microwave reaction vessel was charged with (3R)-tert-butyl 3-(4-(5-(2,6-difluorophenyl)-1-(tetrahydro-2H-pyran-2-yl)-1H-indazol-3-yl)-6-(4-methoxybenzyloxy)pyrimidin-2-ylamino)piperidine-1-carboxylate (145 mg, 0.200 mmol) and TFA (1.5 mL, 19.47 mmol). The reaction was stirred and heated in a Initiator microwave reactor (Personal Chemistry, Biotage AB, Inc., Upssala, Sweden) at 120° C. for 20 min. then solvent was removed. The residue was purified with preparative HPLC (10-50% ACN in water with 0.1% TFA) to give (R)-6-(5-(2,6-difluorophenyl)-1H-indazol-3-yl)-2-(piperidin-3-ylamino)pyrimidin-4-ol (54.0 mg, 0.128 mmol, 64.1% yield) as a TFA salt. MS (ESI, pos. ion) m/z: 423 (M+1); $^1$H NMR (400 MHz, DMSO-$d_6$) δ ppm 13.65 (1 H, br. s.), 8.59-8.71 (1 H, m), 8.41-8.56 (2 H, m), 7.73 (1 H, s), 7.41-7.55 (2 H, m), 7.17-7.32 (2 H, m), 6.87 (1 H, br. s.), 6.40 (1 H, br. s.), 4.18 (2 H, br. s.), 3.23 (1 H, d, J=10.4 Hz), 3.01-3.16 (2 H, m), 2.87 (1 H, q, J=10.0 Hz), 2.11 (1 H, d, J=13.1 Hz), 1.70-1.84 (1 H, m), 1.38-1.65 (2 H, m).

Example 283

Racemic 6-(5-(4-chloro-2-fluorophenyl)-1H-indazol-3-yl)-2-((trans-4-fluoropiperidin-3-yl)oxy)pyrimidin-4(3H)-one trifluoroacetate

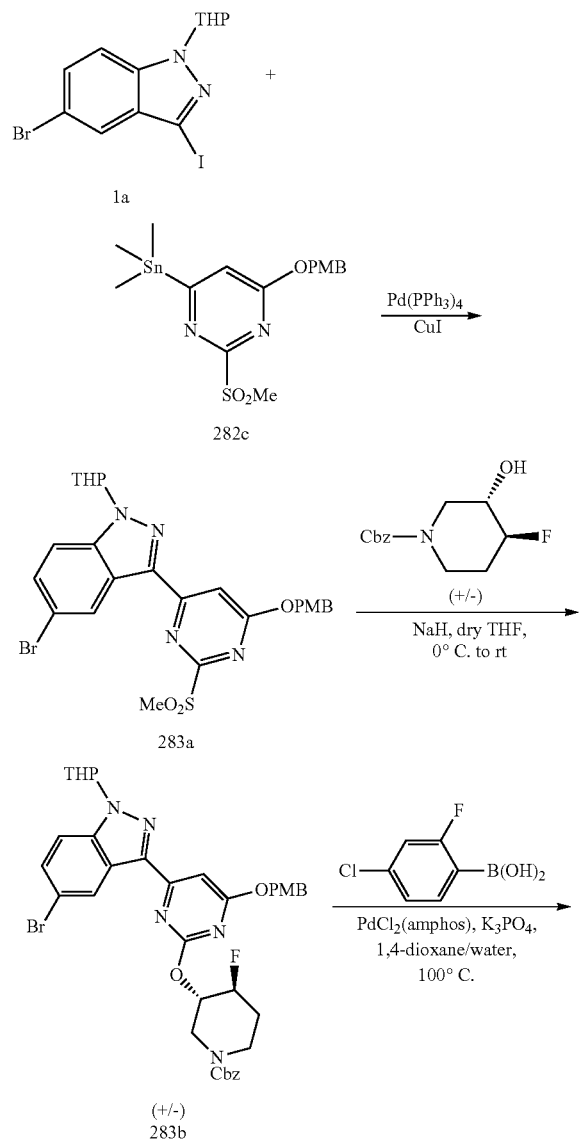

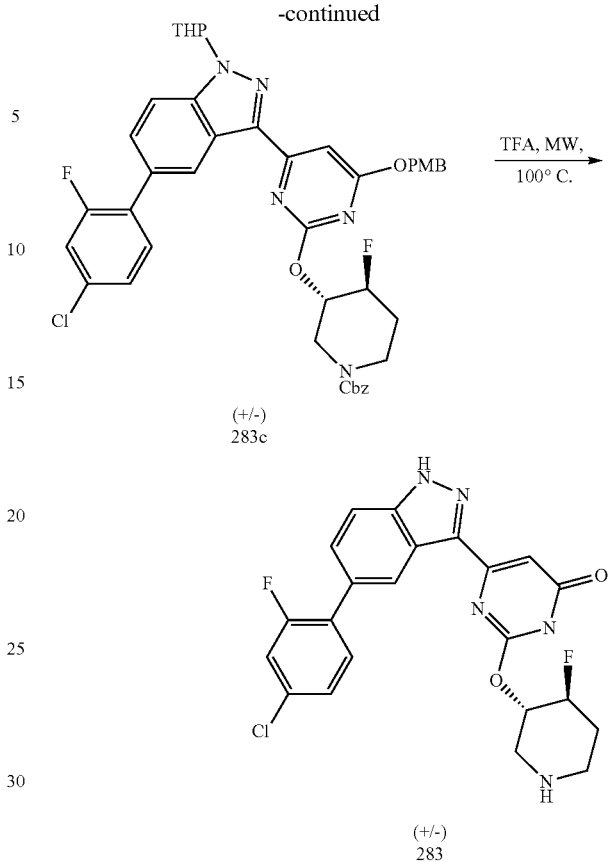

Preparation of Compound 283a: 5-bromo-3-(6-((4-methoxybenzyl)oxy)-2-(methylsulfonyl)pyrimidin-4-yl)-1-(tetrahydro-2H-pyran-2-yl)-1H-indazole A glass microwave reaction vessel was charged with 5-bromo-3-iodo-1-(tetrahydro-2H-pyran-2-yl)-1H-indazole (0.82 g, 2.015 mmol) and 4-((4-methoxybenzyl)oxy)-2-(methylsulfonyl)-6-(trimethylstannyl)pyrimidine (1.013 g, 2.216 mmol) in DMF (5 mL) followed by Pd(PPh$_3$)$_4$ (0.116 g, 0.101 mmol) and CuI (0.017 ml, 0.504 mmol). The reaction was stirred and heated in a Initiator microwave reactor (Personal Chemistry, Biotage AB, Inc., Uppsala, Sweden) at 90° C. for 30 min. The mixture was diluted with DCM (5 mL), filtered through a plug of celite and washed with DCM. The filtrate was washed with water (25 mL×3) and the organic layer was dried, filtered and concentrated. The residue was purified with silica gel chromatography (eluting with 0-10% EtOAc in Hexanes) to give 5-bromo-3-(6-((4-methoxybenzyl)oxy)-2-(methylsulfonyl)pyrimidin-4-yl)-1-(tetrahydro-2H-pyran-2-yl)-1H-indazole (508 mg, 0.886 mmol, 44.0% yield) as a white foam. MS (ESI, pos. ion) m/z: 573/575 (1:1) (M+1); $^1$H NMR (400 MHz, CDCl$_3$) δ ppm 1.67-1.86 (m, 3 H) 2.06-2.26 (m, 2 H) 2.49-2.64 (m, 1 H) 3.48 (s, 3 H) 3.72-3.80 (m, 1 H) 3.82 (s, 3 H) 3.91-4.01 (m, 1H) 5.52 (s, 2 H) 5.79 (dd, J=8.41, 2.93 Hz, 1 H) 6.93 (m, J=8.80 Hz, 2 H) 7.45 (m, J=8.80 Hz, 2 H) 7.51-7.60 (m, 2 H) 7.70 (s, 1 H) 8.68-8.74 (m, 1 H).

Preparation of Compound 283b: Racemic benzyl 3-((4-(5-bromo-1-(tetrahydro-2H-pyran-2-yl)-1H-indazol-3-yl)-6-((4-methoxybenzyl)oxy)pyrimidin-2-yl)oxy)-(trans)-4-fluoropiperidine-1-carboxylate To a solution of benzyl trans-4-fluoro-3-hydroxypiperidine-1-carboxylate (racemic) (0.486 g, 1.92 mmol) in dry THF (10 mL) at 0° C. was added NaH (0.126 g, 5.24 mmol) and the reaction was stirred at RT for 30 min. A solution of 5-bromo-3-(6-((4-methoxybenzyl)oxy)-2-(methylsulfonyl) pyrimidin-4-yl)-1-(tetrahydro-2H-pyran-2-yl)-1H-indazole (1 g, 1.74 mmol) in dry THF (5 mL) was added drop wise to the above mixture and the reaction was stirred for 2 h. The reaction was quenched with ice cold water (10 mL) and extracted with EtOAc (2×20 mL) and the combined organic layers were dried, filtered and concentrated. The residue was purified with silica gel chromatography (eluting with 35% EtOAc in petroleum ether) to give benzyl 3-((4-(5-bromo-1-(tetrahydro-2H-pyran-2-yl)-1H-indazol-3-yl)-6-((4-methoxybenzyl)oxy)pyrimidin-2-yl)oxy)-(trans)-4-fluoropiperidine-1-carboxylate (racemic) (1 g, 77%) as a off white solid. MS (ESI, pos. ion) m/z: 745.7 (M+1).

Preparation of Compound 283c: Racemic benzyl 3-((4-(5-(4-chloro-2-fluorophenyl)-1-(tetrahydro-2H-pyran-2-yl)-1H-indazol-3-yl)-6-((4-methoxybenzyl)oxy)pyrimidin-2-yl)oxy)-(trans)-4-fluoropiperidine-1-carboxylate A 20 mL sealed tube was charged with a mixture of benzyl 3-((4-(5-bromo-1-(tetrahydro-2H-pyran-2-yl)-1H-indazol-3-yl)-6-(4-methoxybenzyl)oxy)pyrimidin-2-yl)oxy)-(trans)-4-fluoropiperidine-1-carboxylate (racemic) (0.4 g, 0.556 mmol), potassium phosphate (341 mg, 1.60 mmol), PdCl$_2$ (AmPhos) (37 mg, 0.053 mmol) and (4-chloro-2-fluorophenyl)boronic acid (121 mg, 0.696 mmol) in dioxane (1069 µl)/water (2140. The reaction was heated to 100° C. for 12 h, then was cooled to RT. The reaction was quenched with water (10 mL) and extracted with EtOAc (20 mL). The organic layer was dried over Na$_2$SO$_4$, filtered and concentrated. The residue was purified with basic alumina chromatography (eluting with 50% EtOAc in petroleum ether) to give benzyl 3-((4-(5-(4-chloro-2-fluorophenyl)-1-(tetrahydro-2H-pyran-2-yl)-1H-indazol-3-yl)-6-((4-ethoxybenzyl)oxy)pyrimidin-2-yl)oxy)-(trans)-4-fluoropiperidine-1-carboxylate (200 mg, 47%) as a off brown solid. MS (ESI, pos. ion) m/z: 796.2 (M+1).

Preparation of Compound 283: Racemic 6-(5-(4-chloro-2-fluorophenyl)-1H-indazol-3-yl)-2-((trans-4-fluoropiperidin-3-yl)oxy)pyrimidin-4(3H)-one trifluoroacetate A glass microwave reaction vessel was charged with benzyl 3-((4-(5-(4-chloro-2-fluorophenyl)-1-(tetrahydro-2H-pyran-2-yl)-1H-indazol-3-yl)-6-((4-ethoxybenzyl)oxy)pyrimidin-2-yl)oxy)-(trans)-4-fluoropiperidine-1-carboxylate (200 mg, 0.25 mmol) and TFA (1 mL). The reaction was stirred and heated in a microwave reactor at 100° C. for 30 min. The solvent was removed in vacuo and the residue was purified with preparative HPLC (eluting with 20-100% MeCN in water with 0.1% TFA) to give 6-(5-(4-chloro-2-fluorophenyl)-1H-indazol-3-yl)-2-((trans-4-fluoropiperidin-3-yl)oxy)pyrimidin-4(3H)-one trifluoroacetate (racemic) (30 mg, 21%) as a off white solid. MS (ESI, pos. ion) m/z: 458.3 (M+1); $^1$H NMR (400 MHz, DMSO-d6): δ ppm 13.81 (s, 1H), 8.82 (bs, 1H), 8.55 (s, 1H), 7.76 (d, 1 H, J=8.8 Hz), 7.62-7.67 (m, 2H), 7.58 (dd, 1 H, J=8.8, 2 Hz), 7.43 (dd, 1 H, J=6.4, 1.6 Hz), 5.64 (s, 1H), 5.24 (s, 1H), 3.41-3.49 (m, 2H), 3.13-3.20 (m, 2H), 2.18-2.32 (m, 1H), 1.95-2.05 (m, 1H).

Example 284

3-(2-(4-aminopiperidin-1-yl)pyrimidin-4-yl)-N,N-dimethyl-1H-indazole-5-carboxamide

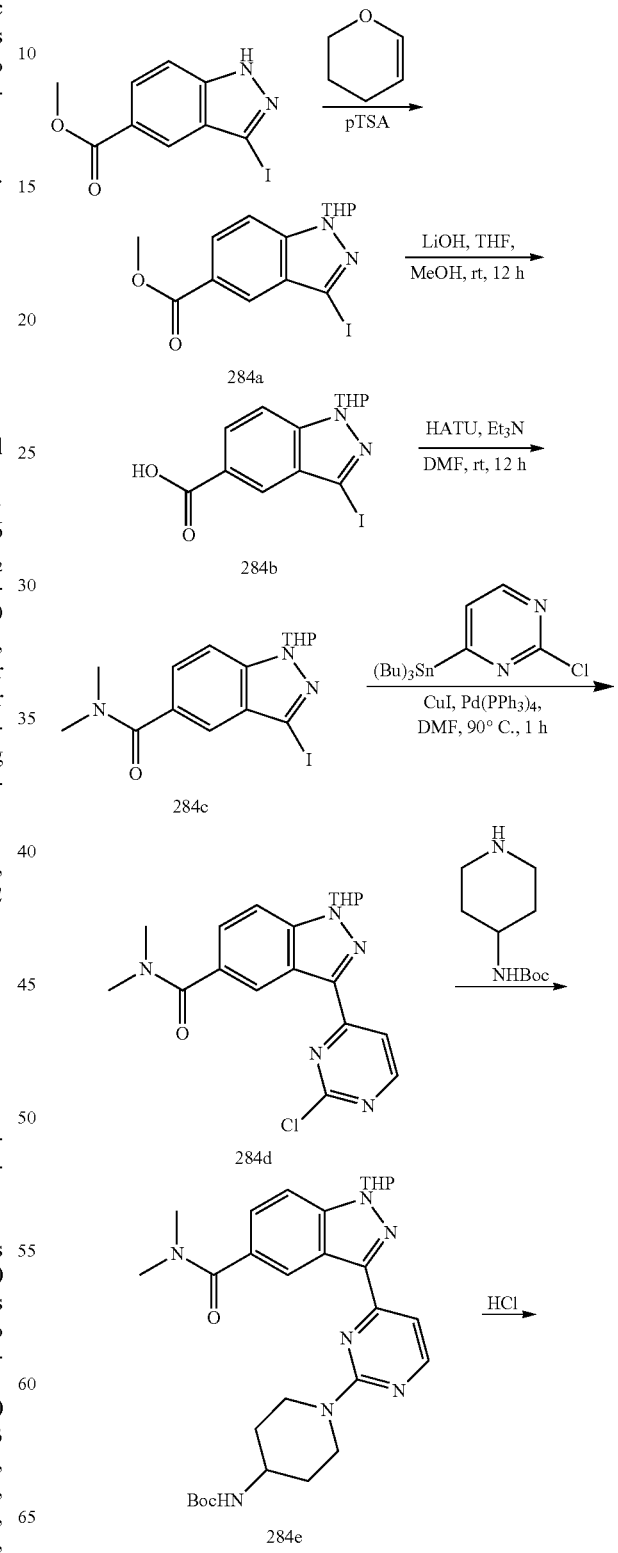

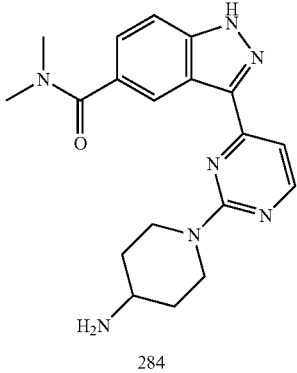 [SMILES: CN(C)C(=O)c1ccc2[nH]nc(-c3ccnc(N4CCC(N)CC4)n3)c2c1]

284

Preparation of Compound 284a: methyl 3-iodo-1-(tetrahydro-2H-pyran-2-yl)-1H-indazole-5-carboxylate In 50 mL R. B. flask, to a solution of 3-iodo-1H-indazole-5-carboxylic acid methyl ester (0.2 g, 0.66 mmol) in DCM (10 mL) was added 3,4-dihydropyran (0.117 g, 1.32 mmol) at 5° C. followed by the addition of PTSA (0.038 g, 0.264 mmol). The reaction was stirred for 2 h at RT, quenched with water (25 mL) and extracted with DCM (50 mL). The organic layer was separated and washed with water (2×25 mL) and dried over anhydrous $Na_2SO_4$, filtered and concentrated. The residue was triturated with n-pentane to give 3-iodo-1-(tetrahydro-pyran-2-yl)-1H-indazole-5-carboxylic acid methyl ester (0.15 g, 58%) as off white solid. MS (ESI, pos. ion) m/z: 302.7 (M-THP+1); $^1$H-NMR (300 MHz DMSO-$d_6$): δ ppm 8.24 (t, 1 H, J=9 Hz), 8.13 (dd, 1 H, J=8.7, 1.5 Hz), 7.60 (d, 1 H, J=9 Hz), 5.73 (dd, 1 H, J=9.6, 2.7 Hz), 4.95 (m, 1H), 3.96-4.04 (m, 4H), 3.75-3.78 (m, 1H), 3.52-3.53 (m, 1H), 2.52-2.56 (m, 1H), 2.05-2.17 (m, 2H), 1.58-1.84 (m, 4H).

Preparation of Compound 284b: 3-iodo-1-(tetrahydro-2H-pyran-2-yl)-1H-indazole-5-carboxylic acid To a solution of methyl 3-iodo-1-(tetrahydro-2H-pyran-2-yl)-1H-indazole-5-carboxylate ((5.0 g, 12.9 mmol) in THF:MeOH (70:30) (50 mL) was added LiOH (3.10 g, 129.0 mmol) in one lot and the reaction was stirred at RT for 12 h. The solvent were removed in vacuo and the residue was diluted with water and quenched with 1N HCl (50 mL) to obtain off white precipitate. The suspension was stirred for 10 min and filtered and dried to give 3-iodo-1-(tetrahydro-2H-pyran-2-yl)-1H-indazole-5-carboxylic acid (4.2 g, 87%) as an off white solid. $^1$H NMR (400 MHz, DMSO-$d_6$) δ ppm 13.09 (s, 1H), 8.03-8.06 (m, 2H), 7.84-7.86 (m, 1H), 5.93 (dd, 1 H, J=9.7, 2.3 Hz), 3.90 (d, 1 H, J=11.9 Hz), 3.74-3.76 (m, 1H), 2.35-2.41 (m, 1H), 1.97-2.00 (m, 2H), 1.69-1.80 (m, 1H), 1.41-1.58 (m, 2H).

Preparation of Compound 284c: 3-iodo-N,N-dimethyl-1-(tetrahydro-2H-pyran-2-yl)-1H-indazole-5-carboxamide To a solution of 3-iodo-1-(tetrahydro-2H-pyran-2-yl)-1H-indazole-5-carboxylic acid (2.5 g, 6.72 mmol) and N,N-dimethylamine hydrochloride (0.8 g, 10.08 mmol) in THF:IPA (7:3) (25 mL) was added EDC. HCl (1.5 g, 8.06 mmol) followed by DMAP (341 mg, 2.80 mmol) in one lot at RT. The reaction was stirred at RT for 12 h, diluted with water (50 mL) and extracted with EtOAc (50 mL). The organic layer was separated and dried over $Na_2SO_4$, filtered and concentrated to give 3-iodo-N,N-dimethyl-1-(tetrahydro-2H-pyran-2-yl)-1H-indazole-5-carboxamide (2.0 g, 75%) as an off white solid. MS (ESI, pos. ion) m/z: 400.1 (M+1); $^1$H NMR (400 MHz, DMSO-$d_6$) δ 7.82 (d, 1 H, J=8.7 Hz), 7.56 (dd, 1 H, J=8.7, 1.3 Hz), 7.48 (s, 1H), 5.91 (dd, 1 H, J=9.7, 2.0 Hz), 3.89 (d, 1 H, J=11.3 Hz), 3.72-3.78 (m, 1H), 2.99 (s, 6H), 2.37 (dd, 1 H, J=12.4, 9.6 Hz), 1.97-2.04 (m, 2H), 1.72-1.77 (m, 1H), 1.59 (s, 2H).

Preparation of Compound 284d: 3-(2-chloropyrimidin-4-yl)-N,N-dimethyl-1-(tetrahydro-2H-pyran-2-yl)-1H-indazole-5-carboxamide To a solution of 3-iodo-N,N-dimethyl-1-(tetrahydro-2H-pyran-2-yl)-1H-indazole-5-carboxamide (3 g, 7.53 mmol) and 2-chloro-4-(tributylstannyl)pyrimidine (3.6 g, 8.04 mmol) in DMF (35 mL) under argon atmosphere was added CuI (1.7 g, 9.02 mmol) and Pd(PPh$_3$)$_4$ (868.5 mg, 0.75 mmol) and argon gas was bubbled for 15 min. The reaction was heated at 100° C. for 1 h. The reaction was quenched with water to give off white precipitate. The suspension filtered, washed with water and dried. The crude was purified by neutral alumina column chromatography (eluting with 100% EtOAc) to give 3-(2-chloropyrimidin-4-yl)-N,N-dimethyl-1-(tetrahydro-2H-pyran-2-yl)-1H-indazole-5-carboxamide (3.0 g, 58%) as an off white solid. MS (ESI, pos. ion) m/z: 386.2 (M+1).

Preparation of Compound 284e: tert-butyl (1-(4-(5-(dimethylcarbamoyl)-1-(tetrahydro-2H-pyran-2-yl)-1H-indazol-3-yl) pyrimidin-2-yl) piperidin-4-yl) carbamate To a solution of 3-(2-chloropyrimidin-4-yl)-N,N-dimethyl-1-(tetrahydro-2H-pyran-2-yl)-1H-indazole-5-carboxamide (0.5 g, 1.29 mmol) in DMSO (5 mL) was added tert-butyl piperidin-4-ylcarbamate (0.311 g, 1.54 mmol) and the reaction was stirred for 12 h at 100° C. The reaction was quenched with ice cold water (5 mL) to give the off white precipitate. The suspension was filtered, washed with ice cold water and dried to give tert-butyl (1-(4-(5-(dimethylcarbamoyl)-1-(tetrahydro-2H-pyran-2-yl)-1H-indazol-3-yl)pyrimidin-2-yl)piperidin-4-yl)carbamate (0.4 g, 48%) as a off white solid. MS (ESI, pos. ion) m/z: 550.3 (M+1); $^1$H NMR (400 MHz, DMSO-$d_6$) δ 8.54 (s, 1H), 8.45 (d, 1 H, J=5.1 Hz), 7.90 (d, 1 H, J=8.8 Hz), 7.35-7.65 (m, 1H), 7.28 (d, 1 H, J=5.1 Hz), 6.89 (d, 1 H, J=7.7 Hz), 6.01 (dd, 1 H, J=7.4, 2.0 Hz), 4.64 (d, 2 H, J=12.9 Hz), 3.90-4.04 (m, 1H), 3.76-3.82 (m, 1H), 3.60 (s, 1H), 3.16 (t, 2 H, J=11.8 Hz), 3.02 (s, 6H), 2.03-2.06 (m, 2H), 1.82-1.86 (m, 3H), 1.62 (bs, 2H), 1.23 (m, 12H).

Preparation of Compound 284: 3-(2-(4-aminopiperidin-1-yl)pyrimidin-4-yl)-N,N-dimethyl-1H-indazole-5-carboxamide To a solution of tert-butyl (1-(4-(5-(dimethylcarbamoyl)-1-(tetrahydro-2H-pyran-2-yl)-1H-indazol-3-yl)pyrimidin-2-yl)piperidin-4-yl)carbamate (0.4 g, 0.728 mmol) in EtOAc (8 mL) was added HCl (4 N in dioxane, 8 mL) and the reaction was stirred at RT for 3 h The mixture was quenched with water and neutralized with NaHCO$_3$ and extracted with EtOAc. The organic layer was separated and dried over Na$_2$SO$_4$, filtered and concentrated. The residue was purified with HPLC (5-50% MeCN in water with 0.1% TFA) to give 3-(2-(4-aminopiperidin-1-yl)pyrimidin-4-yl)-N,N-dimethyl-1H-indazole-5-carboxamide (150 mg, 52%) as an off-white solid. MS (ESI, pos. ion) m/z: 366.2 (M+1); $^1$H NMR (300 MHz, DMSO-d$_6$): –δ 13.88 (s, 1H), 8.53 (s, 1H), 8.48 (d, 2 H, J=5.1 Hz), 7.96 (s, 3H), 7.70 (d, 1 H, J=8.6 Hz), 7.52 (dd, 1 H, J=8.6, 1.4 Hz), 7.38 (d, 1 H, J=5.1 Hz), 4.77 (d, 2 H, J=13.6 Hz), 3.41 (bs, 1H), 3.09-3.20 (m, 2H), 3.03 (s, 6H), 2.03 (d, 2 H, J=10.5 Hz), 1.47-1.58 (m, 2H).

Example 285

6-(5-((2,6-difluorophenyl)amino)-1H-indazol-3-yl)-2-(dimethylamino) pyrimidin-4(3H)-one

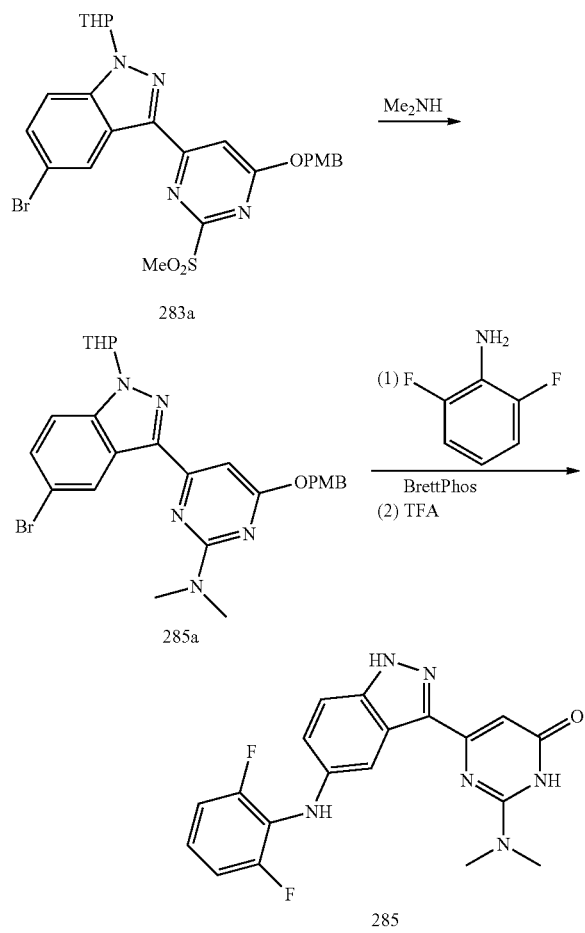

Preparation of Compound 285a: 4-(5-bromo-1-(tetrahydro-2H-pyran-2-yl)-1H-indazol-3-yl)-6-((4-methoxybenzyl)oxy)-N,N-dimethylpyrimidin-2-amine A glass microwave reaction vessel was charged with 5-bromo-3-(6-((4-methoxybenzyl)oxy)-2-(methylsulfonyl)pyrimidin-4-yl)-1-(tetrahydro-2H-pyran-2-yl)-1H-indazole (204 mg, 0.356 mmol) and dimethylamine solution in water (0.4 mL, 3.02 mmol) in NMP (1 ml). The reaction was stirred and heated in a oil bath at 90° C. for 10 min. The mixture was diluted with water. The resulting white ppt was collected by filtration, washed with water, then MeOH, and dried to give the crude product. MS (ESI, pos. ion) m/z: 538/540 (1:1) (M+1).

Preparation of Compound 285b: N-(2,6-difluorophenyl)-3-(2-(dimethylamino)-6-((4-methoxybenzyl)oxy)pyrimidin-4-yl)-1-(tetrahydro-2H-pyran-2-yl)-1H-indazol-5-amine Dicyclohexyl(2',4',6'-triisopropoxy-3,6-dimethoxy-[1,1'-biphenyl]-2-yl)phosphine (brettphos) (4.89 mg, 8.36 μmol), brettphosprecatalyst (7.08 mg, 8.36 μmol), 4-(5-bromo-1-(tetrahydro-2H-pyran-2-yl)-1H-indazol-3-yl)-6-((4-methoxybenzyl)oxy)-N,N-dimethylpyrimidin-2-amine (90 mg, 0.167 mmol) were combined in THF (0.37 mL) under argon. Lithium bis(trimethylsilyl)amide (1 M in THF, 368 μl, 0.368 mmol) was added and the resulting dark red solution was sealed and heated at 70° C. for 4 h. The reaction was cooled to RT then partitioned between satd NH$_4$Cl and CH$_2$Cl$_2$. The aqueous layer was extracted with CH$_2$Cl$_2$ 3 times, and the combined organics were dried over anhydrous Na$_2$SO$_4$, filtered, and concentrated in vacuo. The residue was purified with silica gel chromatography (eluting with 0-30% EtOAc in hexanes) to give N-(2,6-difluorophenyl)-3-(2-(dimethylamino)-6-((4-methoxybenzyl)oxy)pyrimidin-4-yl)-1-(tetrahydro-2H-pyran-2-yl)-1H-indazol-5-amine (44.5 mg, 0.076 mmol, 45.4% yield) as a sticky yellow oil. MS (ESI, pos. ion) m/z: 587.2 (M+1).

Preparation of Compound 285: 6-(5-((2,6-difluorophenyl)amino)-1H-indazol-3-yl)-2-(dimethylamino) pyrimidin-4(3H)-one N-(2,6-Difluorophenyl)-3-(2-(dimethylamino)-6-((4-methoxybenzyl)oxy)pyrimidin-4-yl)-1-(tetrahydro-2H-pyran-2-yl)-1H-indazol-5-amine (260 mg, 0.443 mmol) in DCM (2.0 mL) was treated with TFA, 99% (2.0 mL, 26.9 mmol) at RT and stirred at 50° for 26 h. The mixture was cooled to RT and evaporated to dryness. The residue was diluted with DCM and extracted with sat'd NaHCO$_3$ solution. The aqueous layer was extracted with DCM 3 times, and the combined organics were dried over anhydrous Na$_2$SO$_4$, filtered, and concentrated in vacuo. The crude material was purified with silica gel chromatography (eluting with 0-8% MeOH in DCM with 2 M NH$_3$) to give 6-(5-((2,6-difluorophenyl)amino)-1H-indazol-3-yl)-2-(dimethylamino) pyrimidin-4(3H)-one (85 mg, 0.222 mmol, 50.2% yield) as a yellow solid. MS (ESI, pos. ion) m/z: 383 (M+1); $^1$H NMR (400 MHz, DMSO-d$_6$) δ ppm 2.90 (s, 6 H), 6.28 (br. s., 1 H), 7.05-7.25 (m, 4 H), 7.45 (d, J=8.80 Hz, 1H), 7.51 (br. s., 1 H), 7.74 (s, 1 H), 10.86 (br. s., 1 H), 13.21 (br. s., 1 H).

Example 286

5-(2-fluorophenyl)-3-(5-methoxypyridazin-3-yl)-1H-pyrrolo[3,2-b]pyridine

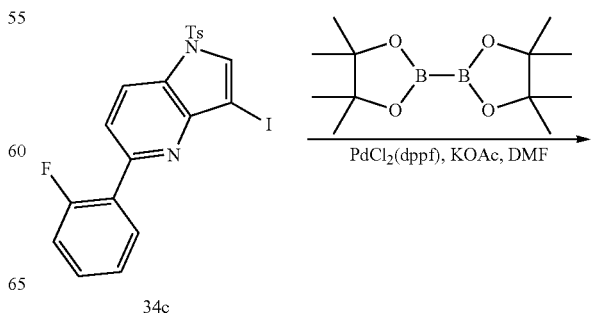

-continued

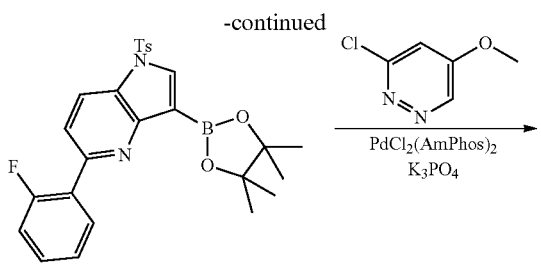

286a

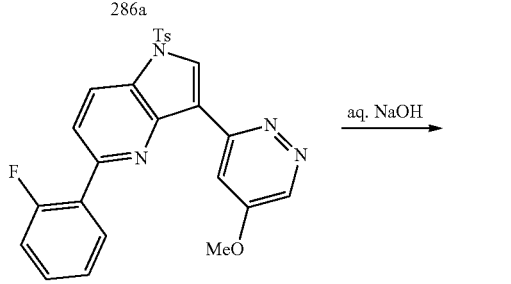

286b

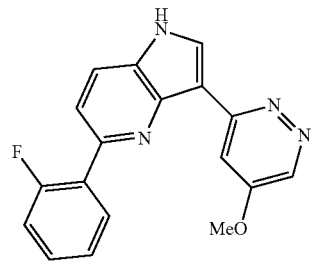

286

Preparation of Compound 286a: 5-(2-fluorophenyl)-3-(4,4,5,5-tetramethyl-1,3,2-dioxaborolan-2-yl)-1-tosyl-1H-pyrrolo[3,2-b]pyridine A glass microwave reaction vessel was charged with 5-(2-fluorophenyl)-3-iodo-1-tosyl-1H-pyrrolo[3,2-b]pyridine (200 mg, 0.406 mmol) and bis(pinacolato)diboron (155 mg, 0.609 mmol) in DMF (1.5 mL) followed by Pd(dppf)Cl$_2$ (16.59 mg, 0.020 mmol) and potassium acetate (50.8 µL, 0.813 mmol). The reaction was stirred and heated in a Initiator microwave reactor (Personal Chemistry, BiotageAB, Inc., Upssala, Sweden) at 100° C. for 2 h. The mixture was diluted with water and filtered. The solid was washed with water, dried to give the crude compound, which was used in the next reaction without further purification. MS (ESI, pos. ion) m/z: 492.8 (M+1).

Preparation of Compound 286b: 5-(2-fluorophenyl)-3-(5-methoxypyridazin-3-yl)-1-tosyl-1H-pyrrolo[3,2-b]pyridine A glass microwave reaction vessel was charged with 5-(2-fluorophenyl)-3-(4,4,5,5-tetramethyl-1,3,2-dioxaborolan-2-yl)-1-tosyl-1H-pyrrolo[3,2-b]pyridine (102 mg, 0.208 mmol) and 3-chloro-5-methoxypyridazine (30 mg, 0.208 mmol) in p-dioxane/H$_2$O (4:1, 1.5 mL) followed by potassium phosphate (88 mg, 0.415 mmol) and bis(di-tert-butyl(4-dimethylaminophenyl)phosphine)dichloropalladium(ii) (7.35 mg, 10.38 µmol). The reaction was stirred and heated in a Initiator microwave reactor (Personal Chemistry, Biotage AB, Inc., Upssala, Sweden) at 105° C. for 1 h. The mixture was diluted with DCM and washed with water. The organic layer was dried, filtered and concentrated. The residue was purified with silica gel chromatography (eluting with 10-35% EtOAc in Hex) to give 5-(2-fluorophenyl)-3-(5-methoxypyridazin-3-yl)-1-tosyl-1H-pyrrolo[3,2-b]pyridine (16 mg, 0.034 mmol, 16.25% yield) as a brown solid. MS (ESI, pos. ion) m/z: 475.0 (M+1).

Preparation of Compound 286: 5-(2-fluorophenyl)-3-(5-methoxypyridazin-3-yl)-1H-pyrrolo[3,2-b]pyridine A glass microwave reaction vessel was charged with 5-(2-fluorophenyl)-3-(5-methoxypyridazin-3-yl)-1-tosyl-1H-pyrrolo[3,2-b]pyridine (16 mg, 0.034 mmol) and NaOH (0.3 mL, 0.300 mmol, 1M) in THF (1 mL). The reaction was stirred and heated in a Initiator microwave reactor (Personal Chemistry, Biotage AB, Inc., Upssala, Sweden) at 85° C. for 20 min. The mixture was diluted with water and extracted with CHCl$_3$/iPrOH (4:1). The combined organic layers were dried, filtered and concentrated. The residue was purified with prep-TLC (eluting with 10% MeOH in DCM) to give 5-(2-fluorophenyl)-3-(5-methoxypyridazin-3-yl)-1H-pyrrolo[3,2-b]pyridine (6.0 mg, 0.019 mmol, 55.6% yield) as a light brown solid. MS (ESI, pos. ion) m/z: 321.0 (M+1); $^1$H NMR (400 MHz, DMSO-d$_6$) δ ppm 12.05 (1 H, br. s.), 8.83 (2 H, s), 8.60 (1 H, s), 8.12 (1H, td, J=8.0, 1.7 Hz), 8.03 (1 H, d, J=8.6 Hz), 7.70 (1 H, dd, J=8.5, 2.1 Hz), 7.43-7.53 (1 H, m), 7.30-7.42 (2 H, m), 4.01 (3 H, s)

Example 287

6-(5-(6-cyclopropylpyrazin-2-yl)-1H-indol-3-yl)-2-(isopropylamino)pyrimidin-4(3H)-one

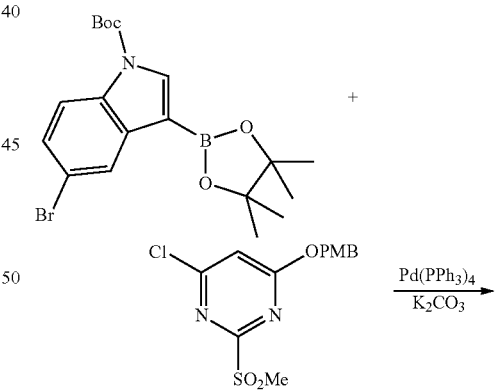

282b

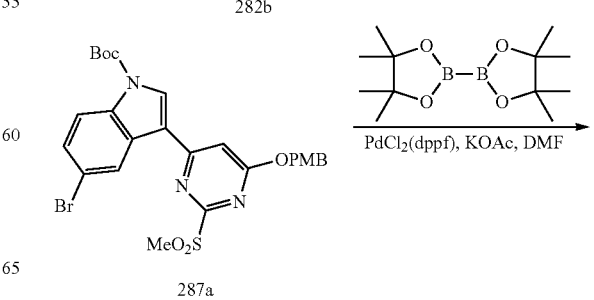

287a

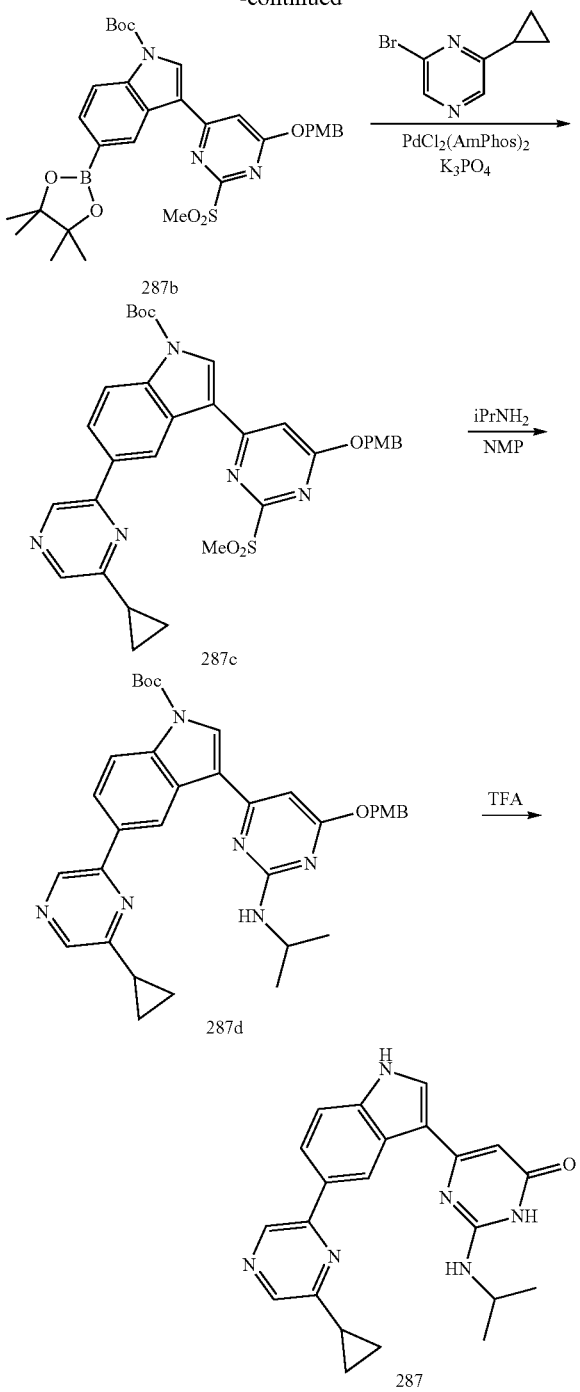

Preparation of Compound 287a: tert-butyl 5-bromo-
3-(6-((4-methoxybenzyl)oxy)-2-(methylsulfonyl)
pyrimidin-4-yl)-1H-indole-1-carboxylate A glass microwave reaction vessel was charged with 4-chloro-6-(4-methoxybenzyloxy)-2-(methylsulfonyl)pyrimidine (600 mg, 1.825 mmol) and tert-butyl 5-bromo-3-(4,4,5,5-tetramethyl-1,3,2-dioxaborolan-2-yl)-1H-indole-1-carboxylate (770 mg, 1.825 mmol) in p-dioxane/H$_2$O (4:1, 6 mL) followed by Pd(PPh$_3$)$_4$ (105 mg, 0.091 mmol) and potassium carbonate (220 μL, 3.65 mmol). The reaction was stirred and heated in a Initiator microwave reactor (Personal Chemistry, Biotage AB, Inc., Upssala, Sweden) at 100° C. for 30 min. The mixture was diluted with water and extracted with DCM. The combined organic layers were dried, filtered and concentrated. The residue was purified with silica gel chromatography (eluting with 10-25% EtOAc in Hexanes) to give tert-butyl 5-bromo-3-(6-(4-methoxybenzyloxy)-2-(methylsulfonyl)pyrimidin-4-yl)-1H-indole-1-carboxylate (445 mg, 0.756 mmol, 41.4% yield) as a half solid. MS (ESI, pos. ion) m/z: 587.8 (M+1).

Preparation of Compound 287b: tert-butyl 3-(6-((4-methoxybenzyl)oxy)-2-(methylsulfonyl)pyrimidin-4-yl)-5-(4,4,5,5-tetramethyl-1,3,2-dioxaborolan-2-yl)-1H-indole-1-carboxylate A glass microwave reaction vessel was charged with tert-butyl 5-bromo-3-(6-(4-methoxybenzyloxy)-2-(methylsulfonyl)pyrimidin-4-yl)-1H-indole-1-carboxylate (435 mg, 0.739 mmol) and bis(pinacolato)diboron (282 mg, 1.109 mmol) in DMF (3 mL) followed by Pd(dppf)Cl$_2$ (30.2 mg, 0.037 mmol) and potassium acetate (145 mg, 1.478 mmol). The reaction was stirred and heated in a Initiator microwave reactor (Personal Chemistry, Biotage AB, Inc., Upssala, Sweden) at 100° C. for 30 min. The mixture was diluted with DCM and washed with water, brine. The organic layer was dried, filtered and concentrated. The residue was purified with silica gel chromatography (eluting with 15-25% EtOAc in Hexanes) to give tert-butyl 3-(6-(4-methoxybenzyloxy)-2-(methylsulfonyl)pyrimidin-4-yl)-5-(4,4,5,5-tetramethyl-1,3,2-dioxaborolan-2-yl)-1H-indole-1-carboxylate (180 mg, 0.283 mmol, 38.3% yield) as a solid. MS (ESI, pos. ion) m/z: 636.0 (M+1).

Preparation of Compound 287c: tert-butyl 5-(6-cyclopropylpyrazin-2-yl)-3-(6-((4-methoxybenzyl)oxy)-2-(methylsulfonyl)pyrimidin-4-yl)-1H-indole-1-carboxylate A glass microwave reaction vessel was charged with tert-butyl 3-(6-(4-methoxybenzyloxy)-2-(methylsulfonyl)pyrimidin-4-yl)-5-(4,4,5,5-tetramethyl-1,3,2-dioxaborolan-2-yl)-1H-indole-1-carboxylate (150 mg, 0.236 mmol) and 2-bromo-6-cyclopropylpyrazine (70.5 mg, 0.354 mmol, CombiPhos) in p-dioxane/H$_2$O (4:1, 2.0 mL) followed by potassium phosphate (100 mg, 0.472 mmol) and 1,1-bis[(di-t-butyl-p-methylaminophenyl]palladium(ii) chloride (8.36 mg, 0.012 mmol). The reaction was stirred and heated in a Initiator microwave reactor (Personal Chemistry, Biotage AB, Inc., Upssala, Sweden) at 100° C. for 20 min. The mixture was diluted with DCM and washed with water. The organic layer was dried, filtered and concentrated. The residue was purified with silica gel chromatography (eluting with 20-60% EtOAc in hexanes) to give tert-butyl 5-(6-cyclopropylpyrazin-2-yl)-3-(6-(4-methoxybenzyloxy)-2-(methylsulfonyl)pyrimidin-4-yl)-1H-indole-1-carboxylate (42 mg, 0.067 mmol, 28.3% yield) as a solid: MS (ESI, pos. ion) m/z: 628.0 (M+1), and 5-(6-cyclopropylpyrazin-2-yl)-3-(6-(4-methoxybenzyloxy)-2-(methylsulfonyl)pyrimidin-4-yl)-1H-indole (28 mg, 0.053 mmol, 22.49% yield) as a solid. MS (ESI, pos. ion) m/z: 528.0 (M+1).

Preparation of Compound 287d: 4-(5-(6-cyclopropylpyrazin-2-yl)-1H-indol-3-yl)-N-isopropyl-6-((4-methoxybenzyl)oxy)pyrimidin-2-amine A glass microwave reaction vessel was charged with 5-(6-cyclopropylpyrazin-2-yl)-3-(6-(4-methoxybenzyloxy)-2-

(methylsulfonyl)pyrimidin-4-yl)-1H-indole (26 mg, 0.049 mmol) and isopropylamine (0.4 ml, 4.66 mmol) in NMP (0.5 mL). The reaction was stirred and heated in a Initiator microwave reactor (Personal Chemistry, Biotage AB, Inc., Upssala, Sweden) at 120° C. for 1 h. The mixture was diluted with water and extracted with $CHCl_3$/iPrOH (4:1). The combined organic layer was washed with water, dried, filtered and concentrated to give the crude compound, which was used in the next step without further purification. MS (ESI, pos. ion) m/z: 507.0 (M+1).

Preparation of Compound 287: 6-(5-(6-cyclopropylpyrazin-2-yl)-1H-indol-3-yl)-2-(isopropylamino)pyrimidin-4(3H)-one A glass microwave reaction vessel was charged with 4-(5-(6-cyclopropylpyrazin-2-yl)-1H-indol-3-yl)-N-isopropyl-6-(4-methoxybenzyloxy)pyrimidin-2-amine (25 mg, 0.049 mmol) and TFA (1 mL, 12.98 mmol). The reaction was stirred and heated in a Initiator microwave reactor (Personal Chemistry, Biotage AB, Inc., Upssala, Sweden) at 120° C. for 20 min, then the solvent was removed and the residue was purified with RP-HPLC (10-50% ACN in water with 0.1% TFA) to give 6-(5-(6-cyclopropylpyrazin-2-yl)-1H-indol-3-yl)-2-(isopropylamino)pyrimidin-4(3H)-one (3.0 mg, 7.76 μmol, 15.73% yield) as a TFA salt. MS (ESI, pos. ion) m/z: 387.0 (M+1); $^1$H NMR (400 MHz, DMSO-$d_6$) δ ppm 11.82 (1 H, br. s.), 8.82-9.07 (2 H, m), 8.48 (1 H, s), 8.14 (1 H, d, J=2.3 Hz), 7.88 (1 H, d, J=8.2 Hz), 7.56 (1 H, d, J=8.8 Hz), 6.10 (1 H, br. s.), 4.20-4.36 (1 H, m), 2.19-2.31 (1 H, m), 1.27 (6 H, d, J=6.5 Hz), 1.04-1.14 (4 H, m)

Example 288

4-(4-aminopiperidin-1-yl)-6-(5-(2-fluorophenyl)-1H-pyrrolo[3,2-b]pyridin-3-yl)pyrimidin-2-ol

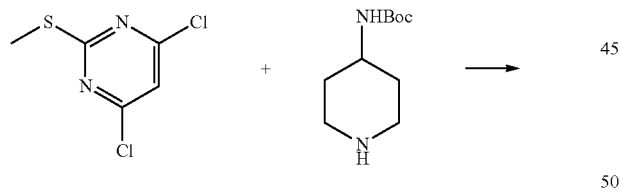

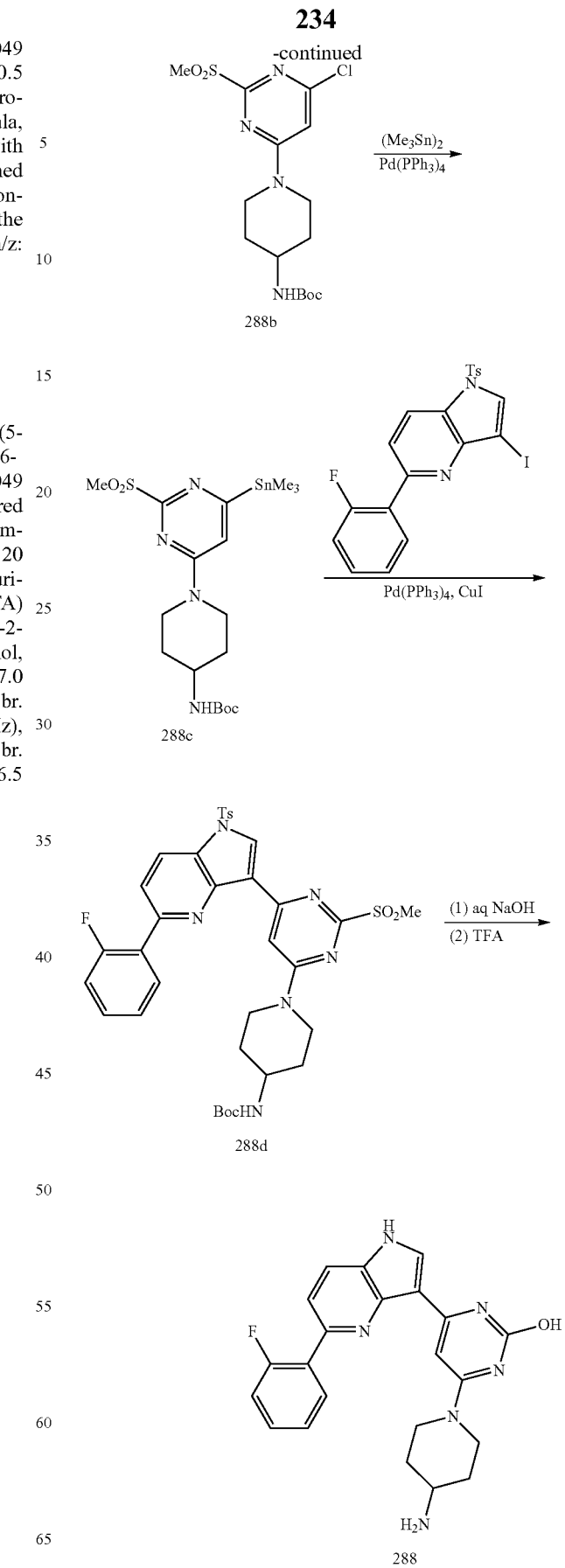

Preparation of Compound 288a: tert-butyl (1-(6-chloro-2-(methylthio)pyrimidin-4-yl)piperidin-4-yl)carbamate To a 100-mL round-bottomed flask was added 4,6-dichloro-2-(methylthio)pyrimidine (2.0 g, 10.25 mmol, Sigma-Aldrich) and 4-(n-boc-amino)-piperidine (2.053 g, 10.25 mmol, Sigma-Aldrich) in DCM (25 mL) followed by Et₃N (2.139 mL, 15.38 mmol). The reaction was stirred at RT for 5 h, then diluted with DCM (100 mL). The mixture was washed with water, brine, dried MgSO₄, filtered and concentrated to give crude tert-butyl 1-(6-chloro-2-(methylthio)pyrimidin-4-yl)piperidin-4-ylcarbamate (3.80 g, 100%) as a white solid. MS (ESI, pos. ion) m/z: 359.0 (M+1).

Preparation of Compound 288b: tert-butyl (1-(6-chloro-2-(methylsulfonyl)pyrimidin-4-yl)piperidin-4-yl)carbamate To a 150-mL round-bottomed flask was added tert-butyl 1-(6-chloro-2-(methylthio)pyrimidin-4-yl)piperidin-4-ylcarbamate (2.0 g, 5.57 mmol) and 3-chloroperoxybenzoic acid (4.12 g, 16.72 mmol) in DCM (25 ml). The reaction was stirred at RT for 4 h. The reaction was quenched with sat NaHCO₃ and the mixture was extracted with DCM. The combined organic layers were washed with sat. NaHCO₃, brine, dried with MgSO₄, filtered and concentrated to give tert-butyl 1-(6-chloro-2-(methylsulfonyl)pyrimidin-4-yl)piperidin-4-ylcarbamate (2.17 g, 5.55 mmol, 100% yield) as a white solid. MS (ESI, pos. ion) m/z: 391.0 (M+1).

Preparation of Compound 288c: tert-butyl (1-(2-(methylsulfonyl)-6-(trimethyl-stannyl)pyrimidin-4-yl)piperidin-4-yl)carbamate A glass microwave reaction vessel was charged with tert-butyl 1-(6-chloro-2-(methylsulfonyl)pyrimidin-4-yl)piperidin-4-ylcarbamate (600 mg, 1.535 mmol) and hexamethylditin (477 µL, 2.302 mmol) in p-dioxane (5 mL) followed by Pd(PPh₃)₄ (89 mg, 0.077 mmol). The reaction was stirred and heated in a Initiator microwave reactor (Personal Chemistry, Biotage AB, Inc., Upssala, Sweden) at 100° C. for 1 h, then solvent was removed. The residue was purified with neutral alumina chromatography (eluting with 20-35% EtOAc in Hex) to give tert-butyl 1-(2-(methylsulfonyl)-6-(trimethylstannyl)pyrimidin-4-yl)piperidin-4-ylcarbamate (251 mg, 0.483 mmol, 31.5% yield) as a white solid. MS (ESI, pos. ion) m/z: 520.8 (M+1).

Preparation of Compound 288d: tert-butyl 1-(6-(5-(2-fluorophenyl)-1-tosyl-1H-pyrrolo[3,2-b]pyridin-3-yl)-2-(methylsulfonyl)pyrimidin-4-yl)piperidin-4-ylcarbamate A glass microwave reaction vessel was charged with 5-(2-fluorophenyl)-3-iodo-1-tosyl-1H-pyrrolo[3,2-b]pyridine (100 mg, 0.203 mmol) and tert-butyl 1-(2-(methylsulfonyl)-6-(trimethylstannyl)pyrimidin-4-yl)piperidin-4-ylcarbamate (105 mg, 0.203 mmol) in DMF (1.5 mL) followed by Pd(PPh₃)₄ (11.74 mg, 10.16 µmol) and CuI (7.8 mg, 0.041 mmol). The reaction was stirred and heated in a Initiator microwave reactor (Personal Chemistry, Biotage AB, Inc., Upssala, Sweden) at 100° C. for 1 h. The mixture was diluted with DCM and washed with water, and brine. The organic layer was dried with MgSO₄, filtered and concentrated. The residue was purified with silica gel chromatography (eluting with 20-80% EtOAc in hexanes) to give tert-butyl 1-(6-(5-(2-fluorophenyl)-1-tosyl-1H-pyrrolo[3,2-b]pyridin-3-yl)-2-(methylsulfonyl)pyrimidin-4-yl)piperidin-4-ylcarbamate (86 mg, 0.119 mmol, 58.7% yield) as a yellow solid. MS (ESI, pos. ion) m/z: 721.0 (M+1).

Preparation of Compound 288: 4-(4-aminopiperidin-1-yl)-6-(5-(2-fluorophenyl)-1H-pyrrolo[3,2-b]pyridin-3-yl)pyrimidin-2-ol A glass microwave reaction vessel was charged with tert-butyl 1-(6-(5-(2-fluorophenyl)-1-tosyl-1H-pyrrolo[3,2-b]pyridin-3-yl)-2-(methylsulfonyl)pyrimidin-4-yl)piperidin-4-ylcarbamate (100 mg, 0.139 mmol) and NaOH (0.3 mL, 0.600 mmol) in p-dioxane (2 mL). The reaction was stirred and heated in a Initiator microwave reactor (Personal Chemistry, Biotage AB, Inc., Upssala, Sweden) at 100° C. for 1 h. The mixture was diluted with CHCl₃/iPrOH (4:1) and washed with water. The organic layer was dried, filtered and concentrated. The residue was dissolved in DCM (1 mL) and TFA (200 µL, 2.60 mmol) was added. The reaction was stirred at RT for 15 min, then the solvent was removed. The residue was purified with preparative HPLC (eluting with 5-30% ACN in water in 30 min) to give 4-(4-aminopiperidin-1-yl)-6-(5-(2-fluorophenyl)-1H-pyrrolo[3,2-b]pyridin-3-yl)pyrimidin-2-ol (36.0 mg, 0.089 mmol, 64.2% yield) as a TFA salt. MS (ESI, pos. ion) m/z: 405.0 (M+1); ¹H NMR (400 MHz, DMSO-d6) δ ppm 12.51 (1 H, br. s.), 8.79 (1 H, d, J=3.1 Hz), 8.12 (1 H, d, J=8.6 Hz), 7.85-8.05 (4 H, m), 7.76 (1 H, dd, J=8.5, 1.9 Hz), 7.46-7.61 (2 H, m), 7.32-7.44 (2 H, m), 4.19-4.55 (2 H, m), 3.37-3.52 (2 H, m), 3.10-3.33 (2 H, m), 2.04 (2 H, d, J=11.2 Hz), 1.47-1.68 (2 H, m).

Example 289

Racemic 2-((trans-4-fluoropiperidin-3-yl)oxy)-6-(5-(thiazol-2-yl)-1H-indazol-3-yl)pyrimidin-4(3H)-one trifluoroacetate

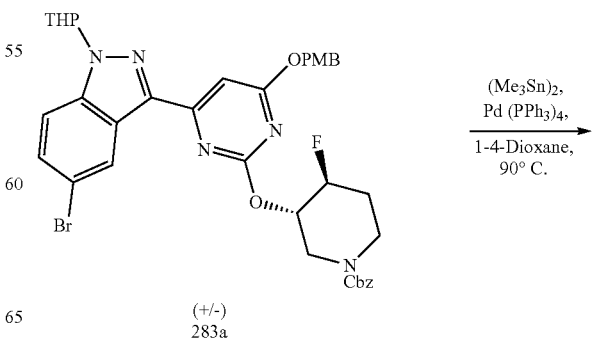

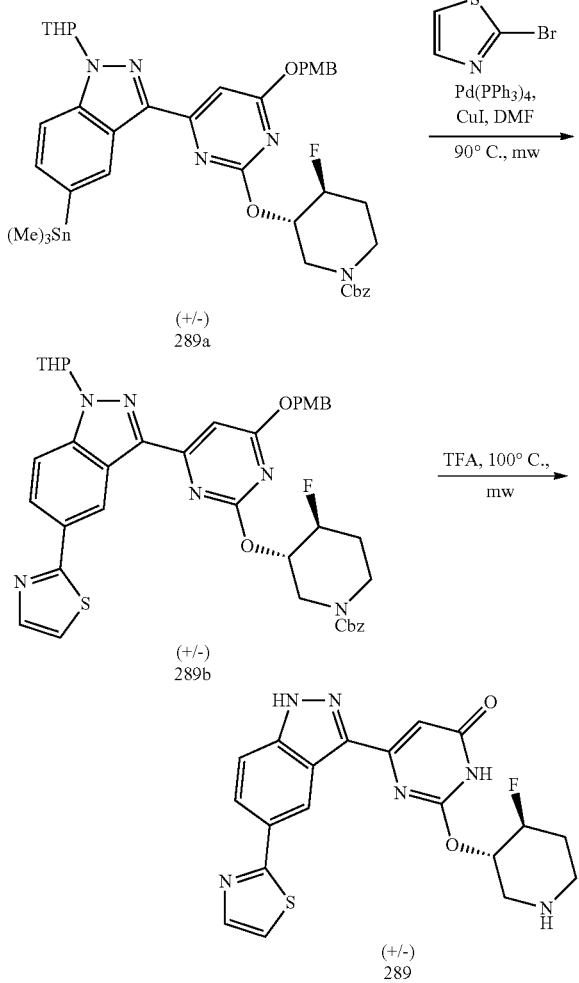

Preparation of Compound 289a: Racemic benzyl trans-4-fluoro-3-((4-((4-methoxybenzyl)oxy)-6-(1-(tetrahydro-2H-pyran-2-yl)-5-(trimethylstannyl)-1H-indazol-3-yl)pyrimidin-2-yl)oxy)piperidine-1-carboxylate A sealed tube was charged with (benzyl 3-((4-(5-bromo-1-(tetrahydro-2H-pyran-2-yl)-1H-indazol-3-yl)-6-(4-methoxybenzyl)oxy)pyrimidin-2-yl)oxy)-(trans)-4-fluoropiperidine-1-carboxylate (racemic) (100 mg, 0.134 mmol), Pd(PPh₃)₄ (0) (7 mg, 0.0134 mmol) and hexamethylditin (45 mg, 0.134 mmol) in toluene (2 mL). The reaction was stirred at 110 C for 12 h, then the solvent was removed in vacuo. The residue was purified with neutral alumina chromatography to give benzyl trans-4-fluoro-3-((4-((4-methoxybenzyl)oxy)-6-(1-(tetrahydro-2H-pyran-2-yl)-5-(trimethylstannyl)-1H-indazol-3-yl)pyrimidin-2-yl)oxy)piperidine-1-carboxylate (racemic) (10 mg, 15%) as a clear oil. MS (ESI, pos. ion) m/z: 831.7 (M+1).

Preparation of Compound 289b: Racemic benzyl trans-4-fluoro-3-((4-((4-methoxybenzyl)oxy)-6-(1-(tetrahydro-2H-pyran-2-yl)-5-(thiazol-2-yl)-1H-indazol-3-yl)pyrimidin-2-yl)oxy)piperidine-1-carboxylate A solution of 2-bromothiazole (20 mg, 0.12 mmol) and benzyl trans-4-fluoro-3-((4-((4-methoxybenzyl)oxy)-6-(1-(tetrahydro-2H-pyran-2-yl)-5-(trimethylstannyl)-1H-indazol-3-yl)pyrimidin-2-yl)oxy)piperidine-1-carboxylate (racemic) (100 mg, 0.12 mmol) in DMF (1 mL) was bubbled with argon for 15 min. To the above mixture was added CuI (11 mg, 0.060 mmol) and Pd(PPh₃)₄ (13 mg, 0.012 mmol) and argon gas was bubbled for another 15 min. The reaction was heated at 100 C for 2 h. The reaction was quenched with water and the suspension was filtered. The solid was dried then purified with basic alumina chromatography (eluting with 30% EtOAc in hexanes) to give benzyl trans-4-fluoro-3-((4-((4-methoxybenzyl)oxy)-6-(1-(tetrahydro-2H-pyran-2-yl)-5-(thiazol-2-yl)-1H-indazol-3-yl)pyrimidin-2-yl)oxy)piperidine-1-carboxylate (racemic) (20 mg, 11%) as a off brown solid. MS (ESI, pos. ion) m/z: 750.8 (M+1).

Preparation of Compound 289: Racemic 2-((trans-4-fluoropiperidin-3-yl)oxy)-6-(5-(thiazol-2-yl)-1H-indazol-3-yl)pyrimidin-4(3H)-one trifluoroacetate A glass microwave reaction vessel was charged with benzyl trans-4-fluoro-3-((4-((4-methoxybenzyl)oxy)-6-(1-(tetrahydro-2H-pyran-2-yl)-5-(thiazol-2-yl)-1H-indazol-3-yl)pyrimidin-2-yl)oxy)piperidine-1-carboxylate (racemic) (200 mg, 0.26 mmol) and TFA (2 mL). The reaction was stirred and heated in a microwave reactor at 100° C. for 30 min, then cooled to RT. The solvent was removed and the residue was purified with preparative HPLC (20-100% MeCN in water with 0.1% TFA) to give 2-((trans-4-fluoropiperidin-3-yl)oxy)-6-(5-(thiazol-2-yl)-1H-indazol-3-yl)pyrimidin-4(3H)-one trifluoroacetate (racemic) (20 mg, 15%) as a off white solid. MS (ESI, pos. ion) m/z: 412.8 (M+1); ¹H NMR (400 MHz, DMSO-d6): δ 13.90 (s, 1 H), 8.96 (brs, 3 H), 8.07 (d, 1 H, J=9.2 Hz), 7.95 (t, 1 H, J=2.4 Hz), 7.75-7.79 (m, 2 H), 5.63 (s, 1 H), 5.05-5.20 (m, 1 H), 3.70-3.72 (m, 1 H), 3.28-3.40 (m, 1 H), 3.16-3.23 (m, 2 H), 2.15-2.30 (m, 3 H).

The compounds of examples 290-569 shown in Table 2 were made in accordance with exemplary methods above. The compound examples were named according to the ACD naming convention, as associated with ISIS software. The mass spectral data is recorded M+1, which is the positive ion as measured by an electrospray ionization method.

TABLE 2

| Example # | IUPAC Name | M + 1 | Method |
|---|---|---|---|
| 290 | 5-(5-fluoro-2-methoxy-4-pyridinyl)-3-(6-((3R)-3-piperidinyloxy)-2-pyrazinyl)-1H-indole | 420 | Example 28 |
| 291 | 5-(1-cyclopropyl-1H-pyrazol-4-yl)-3-(6-((3R)-3-piperidinyloxy)-2-pyrazinyl)-1H-indole | 401 | Example 28 |
| 292 | 5-(3-fluoro-4-methoxyphenyl)-3-(6-((3R)-3-piperidinyloxy)-2-pyrazinyl)-1H-indole | 419 | Example 28 |
| 293 | 5-(3-(6-((3R)-3-piperidinyloxy)-2-pyrazinyl)-1H-indol-5-yl)-2,4-pyrimidinediol | 405 | Example 28 |
| 294 | 5-(3,5-dimethoxyphenyl)-3-(6-((3R)-3-piperidinyloxy)-2-pyrazinyl)-1H-indole | 431 | Example 28 |
| 295 | 2-fluoro-5-(3-(6-((3R)-3-piperidinyloxy)-2-pyrazinyl)-1H-indol-5-yl)benzonitrile | 414 | Example 28 |
| 296 | 2-fluoro-4-(3-(6-((3R)-3-piperidinyloxy)-2-pyrazinyl)-1H-indol-5-yl)benzonitrile | 414 | Example 28 |
| 297 | 5-(3-fluoro-4-pyridinyl)-3-(6-((3R)-3-piperidinyloxy)-2-pyrazinyl)-1H-indole | 390 | Example 28 |
| 298 | 5-(6-(cyclopentyloxy)-2-pyridinyl)-3-(6-((3R)-3-piperidinyloxy)-2-pyrazinyl)-1H-indole | 456 | Example 28 |

TABLE 2-continued

| Example # | IUPAC Name | M + 1 | Method |
|---|---|---|---|
| 299 | 5-(6-(1-piperazinyl)-2-pyridinyl)-3-(6-((3R)-3-piperidinyloxy)-2-pyrazinyl)-1H-indole | 456 | Example 28 |
| 300 | 3-(6-((3R)-3-piperidinyloxy)-2-pyrazinyl)-5-(5-(1H-pyrazol-1-yl)-2-pyridinyl)-1H-indole | 439 | Example 28 |
| 301 | 5-(6-(cyclobutyloxy)-2-pyridinyl)-3-(6-((3R)-3-piperidinyloxy)-2-pyrazinyl)-1H-indole | 442 | Example 28 |
| 302 | 3-(6-((3R)-3-piperidinyloxy)-2-pyrazinyl)-5-(6-(1-pyrrolidinyl)-2-pyrazinyl)-1H-indole | 442 | Example 28 |
| 303 | 5-(2-((2S)-2-methyl-1-piperidinyl)-1,3-thiazol-4-yl)-3-(6-((3R)-3-piperidinyloxy)-2-pyrazinyl)-1H-indole & 5-(2-((2R)-2-methyl-1-piperidinyl)-1,3-thiazol-4-yl)-3-(6-((3R)-3-piperidinyloxy)-2-pyrazinyl)-1H-indole | 475 | Example 28 |
| 304 | 5-(6-(4-methyl-1-piperidinyl)-2-pyridinyl)-3-(6-((3R)-3-piperidinyloxy)-2-pyrazinyl)-1H-indole | 469 | Example 28 |
| 305 | 5-(6-(2-methyl-1H-imidazol-1-yl)-2-pyridinyl)-3-(6-((3R)-3-piperidinyloxy)-2-pyrazinyl)-1H-indole | 452 | Example 28 |
| 306 | 5-(5-((3S)-3-methyl-1-piperidinyl)-2-pyrazinyl)-3-(6-((3R)-3-piperidinyloxy)-2-pyrazinyl)-1H-indole & 5-(5-((3R)-3-methyl-1-piperidinyl)-2-pyrazinyl)-3-(6-((3R)-3-piperidinyloxy)-2-pyrazinyl)-1H-indole | 470 | Example 28 |
| 307 | 5-(6-(3-methyl-1H-pyrazol-1-yl)-2-pyridinyl)-3-(6-((3R)-3-piperidinyloxy)-2-pyrazinyl)-1H-indole | 452 | Example 28 |
| 308 | 5-(1-(1-methylethyl)-1H-pyrazol-4-yl)-3-(6-((3R)-3-piperidinyloxy)-2-pyrazinyl)-1H-indole | 403 | Example 28 |
| 309 | 5-(4-(4-morpholinyl)phenyl)-3-(6-((3R)-3-piperidinyloxy)-2-pyrazinyl)-1H-indole | 456 | Example 28 |
| 310 | 5-(6-methoxy-3-pyridinyl)-3-(6-((3R)-3-piperidinyloxy)-2-pyrazinyl)-1H-indole | 402 | Example 28 |
| 311 | N-(4-(3-(6-((3R)-3-piperidinyloxy)-2-pyrazinyl)-1H-indol-5-yl)phenyl)cyclopropanecarboxamide | 454 | Example 28 |
| 312 | 5-(2,2-dimethylcyclopropyl)-3-(6-((3R)-3-piperidinyloxy)-2-pyrazinyl)-1H-indole | 363 | Example 28 |
| 313 | N-ethyl-4-methyl-3-(3-(6-((3R)-3-piperidinyloxy)-2-pyrazinyl)-1H-indol-5-yl)benzamide | 456 | Example 28 |
| 314 | N-cyclobutyl-4-methyl-3-(3-(6-((3R)-3-piperidinyloxy)-2-pyrazinyl)-1H-indol-5-yl)benzamide | 482 | Example 28 |
| 315 | (3-(3-(6-((3R)-3-piperidinyloxy)-2-pyrazinyl)-1H-indol-5-yl)phenyl)methanol | 401 | Example 28 |
| 316 | (4-(3-(6-((3R)-3-piperidinyloxy)-2-pyrazinyl)-1H-indol-5-yl)phenyl)methanol | 401 | Example 28 |
| 317 | 5-(5-chloro-2-methoxyphenyl)-3-(6-((3R)-3-piperidinyloxy)-2-pyrazinyl)-1H-indole | 435 | Example 28 |
| 318 | 5-(6-(cyclopentyloxy)-2-pyrazinyl)-3-(6-((3R)-3-piperidinyloxy)-2-pyrazinyl)-1H-indole | 457 | Example 28 |
| 319 | N,N-dimethyl-5-(3-(6-((3R)-3-piperidinyloxy)-2-pyrazinyl)-1H-indol-5-yl)-2-pyrazinamine | 416 | Example 28 |
| 320 | 5-(3-methoxyphenyl)-3-(6-((3R)-3-piperidinyloxy)-2-pyrazinyl)-1H-indole | 401 | Example 28 |
| 321 | 5-(4-methoxyphenyl)-3-(6-((3R)-3-piperidinyloxy)-2-pyrazinyl)-1H-indole | 401 | Example 28 |
| 322 | 5-(4-(1-methylethyl)phenyl)-3-(6-((3R)-3-piperidinyloxy)-2-pyrazinyl)-1H-indole | 413 | Example 28 |
| 323 | 5-(6-(cyclopropylmethoxy)-3-pyridinyl)-3-(6-((3R)-3-piperidinyloxy)-2-pyrazinyl)-1H-indole | 442 | Example 28 |
| 324 | 5-(4-(1-methylethoxy)phenyl)-3-(6-((3R)-3-piperidinyloxy)-2-pyrazinyl)-1H-indole | 429 | Example 28 |
| 325 | 3-(3-(6-((3R)-3-piperidinyloxy)-2-pyrazinyl)-1H-indol-5-yl)benzoic acid | 415 | Example 28 |
| 326 | 2-(3-(6-((3R)-3-piperidinyloxy)-2-pyrazinyl)-1H-indol-5-yl)benzonitrile | 396 | Example 28 |
| 327 | N-(4-(3-(6-((3R)-3-piperidinyloxy)-2-pyrazinyl)-1H-indol-5-yl)phenyl)acetamide | 428 | Example 28 |
| 328 | 5-(2-methoxy-3-pyridinyl)-3-(6-((3R)-3-piperidinyloxy)-2-pyrazinyl)-1H-indole | 402 | Example 28 |
| 329 | 5-(2,5-dimethoxyphenyl)-3-(6-((3R)-3-piperidinyloxy)-2-pyrazinyl)-1H-indole | 431 | Example 28 |
| 330 | 5-(2,3-dimethylphenyl)-3-(6-((3R)-3-piperidinyloxy)-2-pyrazinyl)-1H-indole | 399 | Example 28 |
| 331 | 5-(4-methoxy-3,5-dimethylphenyl)-3-(6-((3R)-3-piperidinyloxy)-2-pyrazinyl)-1H-indole | 429 | Example 28 |
| 332 | 5-(4-(2-methylpropyl)phenyl)-3-(6-((3R)-3-piperidinyloxy)-2-pyrazinyl)-1H-indole | 427 | Example 28 |
| 333 | 3-(3-(6-((3R)-3-piperidinyloxy)-2-pyrazinyl)-1H-indol-5-yl)-2-pyridinecarbonitrile | 397 | Example 28 |
| 334 | N-(2-chloro-5-(3-(6-((3R)-3-piperidinyloxy)-2-pyrazinyl)-1H-indol-5-yl)-3-pyridinyl)methanesulfonamide | 499 | Example 28 |
| 335 | 6-(3-(6-((3R)-3-piperidinyloxy)-2-pyrazinyl)-1H-indol-5-yl)-1,2,3,4-tetrahydro-1,8-naphthyridine | 427 | Example 28 |
| 336 | 5-(3-(6-((3R)-3-piperidinyloxy)-2-pyrazinyl)-1H-indol-5-yl)-1H-pyrrolo[2,3-b]pyridine | 411 | Example 28 |
| 337 | 4-((3-(3-(6-((3R)-3-piperidinyloxy)-2-pyrazinyl)-1H-indol-5-yl)-2-pyridinyl)oxy)aniline | 479 | Example 28 |
| 338 | 5-(2-(4-morpholinyl)-3-pyridinyl)-3-(6-((3R)-3-piperidinyloxy)-2-pyrazinyl)-1H-indole | 457 | Example 28 |
| 339 | 3-methyl-5-(3-(6-((3R)-3-piperidinyloxy)-2-pyrazinyl)-1H-indol-5-yl)-1H-pyrazolo[3,4-b]pyridine | 426 | Example 28 |
| 340 | 3-(6-((3R)-3-piperidinyloxy)-2-pyrazinyl)-5-(5-(2-pyrrolidinyl)-3-pyridinyl)-1H-indole | 441 | Example 28 |
| 341 | 4-(3-(6-((3R)-3-piperidinyloxy)-2-pyrazinyl)-1H-indol-5-yl)-2-(trifluoromethoxy)aniline | 470 | Example 28 |
| 342 | 5-methoxy-4-(1-methylethoxy)-2-(3-(6-((3R)-3-piperidinyloxy)-2-pyrazinyl)-1H-indol-5-yl)benzonitrile | 484 | Example 28 |
| 343 | 5-(1,3-benzodioxol-5-yl)-3-(6-((3R)-3-piperidinyloxy)-2-pyrazinyl)-1H-indole | 415 | Example 28 |
| 344 | 5-(3-(difluoromethoxy)phenyl)-3-(6-((3R)-3-piperidinyloxy)-2-pyrazinyl)-1H-indole | 437 | Example 28 |
| 345 | 5-(3,4-dimethoxyphenyl)-3-(6-((3R)-3-piperidinyloxy)-2-pyrazinyl)-1H-indole | 431 | Example 28 |
| 346 | 3,4-dimethoxy-5-(3-(6-((3R)-3-piperidinyloxy)-2-pyrazinyl)-1H-indol-5-yl)benzonitrile | 456 | Example 28 |
| 347 | 4-methyl-7-(3-(6-((3R)-3-piperidinyloxy)-2-pyrazinyl)-1H-indol-5-yl)-3,4-dihydro-2H-1,4-benzoxazine | 442 | Example 28 |
| 348 | 3-methoxy-5-(3-(6-((3R)-3-piperidinyloxy)-2-pyrazinyl)-1H-indol-5-yl)-4-propoxybenzonitrile | 484 | Example 28 |
| 349 | N-(3-(3-(6-((3R)-3-piperidinyloxy)-2-pyrazinyl)-1H-indol-5-yl)-5-(trifluoromethyl)phenyl)acetamide | 496 | Example 28 |
| 350 | 1-(3-(3-(6-((3R)-3-piperidinyloxy)-2-pyrazinyl)-1H-indol-5-yl)phenyl)cyclobutanecarbonitrile | 450 | Example 28 |

TABLE 2-continued

| Example # | IUPAC Name | M + 1 | Method |
|---|---|---|---|
| 351 | 3-(6-((3R)-3-piperidinyloxy)-2-pyrazinyl)-5-(3-(1H-pyrazol-3-yl)phenyl)-1H-indole | 437 | Example 28 |
| 352 | 2-(1-methylethoxy)-5-(3-(6-((3R)-3-piperidinyloxy)-2-pyrazinyl)-1H-indol-5-yl)benzonitrile | 454 | Example 28 |
| 353 | 5-(2-methyl-5-(trifluoromethyl)phenyl)-3-(6-((3R)-3-piperidinyloxy)-2-pyrazinyl)-1H-indole | 453 | Example 28 |
| 354 | 3-methoxy-4-(1-methylethoxy)-5-(3-(6-((3R)-3-piperidinyloxy)-2-pyrazinyl)-1H-indol-5-yl)benzonitrile | 484 | Example 28 |
| 355 | 3-(6-((3R)-3-piperidinyloxy)-2-pyrazinyl)-5-(3-(1H-tetrazol-5-yl)phenyl)-1H-indole | 439 | Example 28 |
| 356 | 5-(3-(5-isoxazolyl)phenyl)-3-(6-((3R)-3-piperidinyloxy)-2-pyrazinyl)-1H-indole | 438 | Example 28 |
| 357 | 5-(3-(2-methyl-1,3-thiazol-4-yl)phenyl)-3-(6-((3R)-3-piperidinyloxy)-2-pyrazinyl)-1H-indole | 468 | Example 28 |
| 358 | 5-phenyl-3-(6-((3R)-3-piperidinyloxy)-2-pyrazinyl)-1H-indole | 371 | Example 28 |
| 359 | (1S)-1-(3-(3-(6-((3R)-3-piperidinyloxy)-2-pyrazinyl)-1H-indol-5-yl)phenyl)ethanol & (1R)-1-(3-(6-((3R)-3-piperidinyloxy)-2-pyrazinyl)-1H-indol-5-yl)phenyl)ethanol | 415 | Example 28 |
| 360 | 5-(3-(1-methylethoxy)phenyl)-3-(6-((3R)-3-piperidinyloxy)-2-pyrazinyl)-1H-indole | 429 | Example 28 |
| 361 | 5-(2-cyclopropyl-4-pyrimidinyl)-3-(6-((3R)-3-piperidinyloxy)-2-pyrazinyl)-1H-indazole | 414.2 | Example 13 |
| 362 | 4-fluoro-N-(1-methylethyl)-3-(3-(6-((3R)-3-piperidinylamino)-2-pyrazinyl)-1H-indazol-5-yl)benzamide | 474.2 | Example 3 |
| 363 | 5-(6-cyclopropyl-2-pyrazinyl)-3-(6-(2,2,2-trifluoroethoxy)-2-pyrazinyl)-1H-indazole | 413.2 | Example 13 |
| 364 | 5-(6-cyclopropyl-2-pyrazinyl)-3-(6-(4-piperidinyloxy)-2-pyrazinyl)-1H-indazole | 414.2 | Example 13 |
| 365 | 5-(6-cyclopropyl-2-pyrazinyl)-3-(6-(((3R,4S)-3-fluoro-4-piperidinyl)oxy)-2-pyrazinyl)-1H-indazole & 5-(6-cyclopropyl-2-pyrazinyl)-3-(6-(((3S,4R)-3-fluoro-4-piperidinyl)oxy)-2-pyrazinyl)-1H-indazole | 432.2 | Example 13 |
| 366 | 5-(6-cyclopropyl-2-pyrazinyl)-3-(6-(((3R,4R)-3-fluoro-4-piperidinyl)oxy)-2-pyrazinyl)-1H-indazole & 5-(6-cyclopropyl-2-pyrazinyl)-3-(6-(((3S,4S)-3-fluoro-4-piperidinyl)oxy)-2-pyrazinyl)-1H-indazole | 432.2 | Example 13 |
| 367 | 1-(3-(3-(6-((3R)-3-piperidinyloxy)-2-pyrazinyl)-1H-indazol-5-yl)phenyl)ethanol | 416 | Example 13 |
| 368 | 6-(5-(6-cyclopropyl-2-pyrazinyl)-1H-indazol-3-yl)-N-(1-methylethyl)-2-pyrazinamine | 372.2 | Example 243 |
| 369 | 6-(5-(6-cyclopropyl-2-pyrazinyl)-1H-indazol-3-yl)-N-4-piperidinyl-2-pyrazinamine | 413.1 | Example 243 |
| 370 | 3-(6-cyclopropyl-2-pyrazinyl)-5-(4-cyclopropyl-2-pyrimidinyl)-1H-indole | 354.2 | Example 245 |
| 371 | 5-(6-cyclopropyl-2-pyrazinyl)-3-(4-cyclopropyl-2-pyrimidinyl)-1H-indole | 354.1 | Example 245 |
| 372 | 3-(6-((8R)-5-azaspiro[2.5]oct-8-yloxy)-2-pyrazinyl)-5-(6-cyclopropyl-2-pyrazinyl)-1H-indazole & 3-(6-((8S)-5-azaspiro[2.5]oct-8-yloxy)-2-pyrazinyl)-5-(6-cyclopropyl-2-pyrazinyl)-1H-indazole | 440.1 | Example 13 |
| 373 | 3-(6-((8R)-5-azaspiro[2.5]oct-8-yloxy)-2-pyrazinyl)-5-(6-cyclopropyl-2-pyrazinyl)-1H-indazole | 440.1 | Example 13 |
| 374 | 3-(6-((8S)-5-azaspiro[2.5]oct-8-yloxy)-2-pyrazinyl)-5-(6-cyclopropyl-2-pyrazinyl)-1H-indazole | 440.1 | Example 13 |
| 375 | 5-(1-methyl-1H-pyrazol-5-yl)-3-(6-((3R)-3-piperidinyloxy)-2-pyrazinyl)-1H-indazole | 376.3 | Example 10 |
| 376 | 3-(6-methoxy-2-pyrazinyl)-5-(4-((3S)-3-methyl-4-morpholinyl)-2-pyrimidinyl)-1H-indazole | 404.9 | Example 13 |
| 377 | 3-(6-methoxy-2-pyrazinyl)-5-(4-(1-methylethyl)-2-pyrimidinyl)-1H-indazole | 347.1 | Example 13 |
| 378 | 3-(6-methoxy-2-pyrazinyl)-5-(4-(trifluoromethyl)-2-pyridinyl)-1H-indazole | 372 | Example 12 |
| 379 | 5-(6-cyclopropyl-2-pyrazinyl)-3-(6-methoxy-2-pyrazinyl)-1H-indazole | 345.2 | Example 13 |
| 380 | 3-(6-(1-methylethoxy)-2-pyrazinyl)-5-(4-((3S)-3-methyl-4-morpholinyl)-2-pyrimidinyl)-1H-indazole | 433 | Example 13 |
| 381 | 5-(6-cyclopropyl-2-pyrazinyl)-3-(6-(1-methylethoxy)-2-pyrazinyl)-1H-indazole | 373.1 | Example 13 |
| 382 | N-cyclopropyl-2-(3-(6-methoxy-2-pyrazinyl)-1H-indazol-5-yl)-4-pyrimidinamine | 360.2 | Example 13 |
| 383 | N-cyclopropyl-6-(3-(6-methoxy-2-pyrazinyl)-1H-indazol-5-yl)-2-pyrazinamine | 360.2 | Example 13 |
| 384 | 5-(6-cyclopropyl-2-pyrazinyl)-3-(6-(2-fluoroethoxy)-2-pyrazinyl)-1H-indazole | 377.1 | Example 13 |
| 385 | 5-(4-cyclopropyl-2-pyrimidinyl)-3-(6-(2-fluoroethoxy)-2-pyrazinyl)-1H-indazole | 377.1 | Example 13 |
| 386 | 6-(3-(6-(2-fluoroethoxy)-2-pyrazinyl)-1H-indazol-5-yl)-2-pyrazinamine | 352.1 | Example 13 |
| 387 | 3-(6-(1-methylethoxy)-2-pyrazinyl)-5-(1-(1-methylethyl)-1H-pyrazol-4-yl)-1H-indazole | 363.2 | Example 10 |
| 388 | 3-(6-methoxy-2-pyrazinyl)-5-(1-(1-methylethyl)-1H-pyrazol-4-yl)-1H-indazole | 335.2 | Example 10 |
| 389 | N-cyclopropyl-4-fluoro-3-(3-(6-(2-fluoroethoxy)-2-pyrazinyl)-1H-indazol-5-yl)benzamide | 436.1 | Example 10 |
| 390 | 4-fluoro-3-(3-(6-(2-fluoroethoxy)-2-pyrazinyl)-1H-indazol-5-yl)benzamide | 396.2 | Example 10 |
| 391 | N-cyclopropyl-6-(5-(6-cyclopropyl-2-pyrazinyl)-1H-indazol-3-yl)-2-pyrazinamine | 370.1 | Example 10 |
| 392 | 1-((6-(5-(6-cyclopropyl-2-pyrazinyl)-1H-indazol-3-yl)-2-pyrazinyl)amino)-2-methyl-2-propanol | 402.2 | Example 243 |
| 393 | 5-(2,6-difluorophenyl)-3-(6-(((3S,4S)-4-(1-methylethyl)-3-piperidinyl)oxy)-2-pyrazinyl)-1H-indazole & 5-(2,6-difluorophenyl)-3-(6-(((3R,4R)-4-(1-methylethyl)-3-piperidinyl)oxy)-2-pyrazinyl)-1H-indazole | 450.2 | Example 18 |
| 394 | Enantiomer 1 of trans-5-(2,6-difluorophenyl)-3-(6-((4-(1-methylethyl)-3-piperidinyl)oxy)-2-pyrazinyl)-1H-indazole | 450.2 | Example 18 |
| 395 | Enantiomer 2 of trans 5-(2,6-difluorophenyl)-3-(6-((4-(1-methylethyl)-3-piperidinyl)oxy)-2-pyrazinyl)-1H-indazole | 450.2 | Example 18 |
| 396 | 5-(2,6-difluorophenyl)-3-(6-(((3S,4R)-4-ethyl-3-piperidinyl)oxy)-2-pyrazinyl)-1H-indazole & 5-(2,6-difluorophenyl)-3-(6-(((3R,4S)-4-ethyl-3-piperidinyl)oxy)-2-pyrazinyl)-1H-indazole | 436.2 | Example 18 |
| 397 | 5-(2,6-difluorophenyl)-3-(6-(((3S,4R)-4-ethyl-3-piperidinyl)oxy)-2-pyrazinyl)-1H-indazole | 436.2 | Example 18 |
| 398 | 5-(2,6-difluorophenyl)-3-(6-(((3R,4S)-4-ethyl-3-piperidinyl)oxy)-2-pyrazinyl)-1H-indazole | 436.2 | Example 18 |

TABLE 2-continued

| Example # | IUPAC Name | M + 1 | Method |
|---|---|---|---|
| 399 | 3-(6-((4S)-6-azaspiro[2.5]oct-4-yloxy)-2-pyrazinyl)-5-(4-morpholinyl)-1H-indazole | 407 | Example 251 |
| 400 | 3-(6-((4R)-6-azaspiro[2.5]oct-4-yloxy)-2-pyrazinyl)-5-(4-morpholinyl)-1H-indazole | 407 | Example 251 |
| 401 | 3-(6-((4R)-6-azaspiro[2.5]oct-4-yloxy)-2-pyrazinyl)-5-((2R)-2-methyl-4-morpholinyl)-1H-indazole | 421 | Example 251 |
| 402 | 3-(6-((4R)-6-azaspiro[2.5]oct-4-yloxy)-2-pyrazinyl)-5-((3S)-3-methyl-4-morpholinyl)-1H-indazole | 421 | Example 251 |
| 403 | 3-(6-((4R)-6-azaspiro[2.5]oct-4-yloxy)-2-pyrazinyl)-5-((3R)-3-methyl-4-morpholinyl)-1H-indazole | 421 | Example 251 |
| 404 | 3-(6-((4R)-6-azaspiro[2.5]oct-4-yloxy)-2-pyrazinyl)-5-(2-methylphenyl)-1H-indazole | 412 | Example 263 |
| 405 | 4-(3-(6-((4R)-6-azaspiro[2.5]oct-4-yloxy)-2-pyrazinyl)-1H-indazol-5-yl)-3-morpholinone | 421 | Example 8 |
| 406 | 3-(6-((4R)-6-azaspiro[2.5]oct-4-yloxy)-2-pyrazinyl)-5-(2-chlorophenyl)-1H-indazole | 432 | Example 263 |
| 407 | 3-(6-((4R)-6-azaspiro[2.5]oct-4-yloxy)-2-pyrazinyl)-5-(2-(trifluoromethyl)phenyl)-1H-indazole | 466 | Example 263 |
| 408 | 2-(3-(6-((4R)-6-azaspiro[2.5]oct-4-yloxy)-2-pyrazinyl)-1H-indazol-5-yl)benzonitrile | 423 | Example 231 |
| 409 | 2-(3-(6-((4R)-6-azaspiro[2.5]oct-4-yloxy)-2-pyrazinyl)-1H-indazol-5-yl)-3-fluorobenzonitrile | 441 | Example 263 |
| 410 | 3-(3-(6-((4R)-6-azaspiro[2.5]oct-4-yloxy)-2-pyrazinyl)-1H-indazol-5-yl)-2-pyridinecarbonitrile | 424 | Example 263 |
| 411 | 3-(3-(6-((4R)-6-azaspiro[2.5]oct-4-yloxy)-2-pyrazinyl)-1H-indazol-5-yl)-4-pyridinecarbonitrile | 424 | Example 263 |
| 412 | 3-(6-((4R)-6-azaspiro[2.5]oct-4-yloxy)-2-pyrazinyl)-5-(2,6-difluorophenyl)-1H-indazole & 3-(6-((4S)-6-azaspiro[2.5]oct-4-yloxy)-2-pyrazinyl)-5-(2,6-difluorophenyl)-1H-indazole | 434 | Example 18 |
| 413 | 5-(2,6-difluorophenyl)-3-(6-(((3R)-4,4-dimethyl-3-piperidinyl)oxy)-2-pyrazinyl)-1H-indazole & 5-(2,6-difluorophenyl)-3-(6-(((3S)-4,4-dimethyl-3-piperidinyl)oxy)-2-pyrazinyl)-1H-indazole | 436 | Example 18 |
| 414 | Enantiomer 1 of 5-(2,6-difluorophenyl)-3-(6-(3-piperidinylsulfanyl)-2-pyrazinyl)-1H-indazole | 424 | Example 18 |
| 415 | Enantiomer 2 of 5-(2,6-difluorophenyl)-3-(6-(3-piperidinylsulfanyl)-2-pyrazinyl)-1H-indazole | 424 | Example 18 |
| 416 | 3-(6-((4S)-6-azaspiro[2.5]oct-4-yloxy)-2-pyrazinyl)-5-(2,6-difluorophenyl)-1H-indazole | 434 | Example 18 |
| 417 | Enantiomer 1 of 5-(2,6-difluorophenyl)-3-(6-((3-methyl-3-piperidinyl)oxy)-2-pyrazinyl)-1H-indazole | 422 | Example 18 |
| 418 | Enantiomer 1 of 5-(2,6-difluorophenyl)-3-(6-(((-4,4-dimethyl-3-piperidinyl)oxy)-2-pyrazinyl)-1H-indazole | 436 | Example 18 |
| 419 | Enantiomer 2 of 5-(2,6-difluorophenyl)-3-(6-((4,4-dimethyl-3-piperidinyl)oxy)-2-pyrazinyl)-1H-indazole | 436 | Example 18 |
| 420 | 3-(6-((4R)-6-azaspiro[2.5]oct-4-yloxy)-2-pyrazinyl)-5-bromo-1H-indazole & 3-(6-((4S)-6-azaspiro[2.5]oct-4-yloxy)-2-pyrazinyl)-5-bromo-1H-indazole | 400 | Example 10 |
| 421 | 3-(6-((4S)-6-azaspiro[2.5]oct-4-yloxy)-2-pyrazinyl)-5-bromo-1H-indazole | 400 | Example 10 |
| 422 | 3-(6-((4R)-6-azaspiro[2.5]oct-4-yloxy)-2-pyrazinyl)-5-bromo-1H-indazole | 400 | Example 10 |
| 423 | Enantiomer 1 of 5-(2,6-difluorophenyl)-3-(6-((4-methyl-3-piperidinyl)oxy)-2-pyrazinyl)-1H-indazole | 422 | Example 18 |
| 424 | Enantiomer 2 of 5-(2,6-difluorophenyl)-3-(6-((4-methyl-3-piperidinyl)oxy)-2-pyrazinyl)-1H-indazole | 422 | Example 18 |
| 425 | 5-(2,6-difluorophenyl)-3-(6-((3R)-1,2,3,6-tetrahydro-3-pyridinyloxy)-2-pyrazinyl)-1H-indazole & 5-(2,6-difluorophenyl)-3-(6-((3S)-1,2,3,6-tetrahydro-3-pyridinyloxy)-2-pyrazinyl)-1H-indazole | 406 | Example 18 |
| 426 | Enantiomer 1 of 5-(2,6-difluorophenyl)-3-(6-(1,2,3,6-tetrahydro-3-pyridinyloxy)-2-pyrazinyl)-1H-indazole | 406 | Example 18 |
| 427 | Enantiomer 2 of 5-(2,6-difluorophenyl)-3-(6-(1,2,3,6-tetrahydro-3-pyridinyloxy)-2-pyrazinyl)-1H-indazole | 406 | Example 18 |
| 428 | 3-(6-((8S)-5-azaspiro[2.5]oct-8-yloxy)-2-pyrazinyl)-5-(2,6-difluorophenyl)-1H-indazole & 3-(6-((8R)-5-azaspiro[2.5]oct-8-yloxy)-2-pyrazinyl)-5-(2,6-difluorophenyl)-1H-indazole | 434 | Example 18 |
| 429 | Enantiomer 1 of 3-(6-(5-azaspiro[2.5]oct-8-yloxy)-2-pyrazinyl)-5-(2,6-difluorophenyl)-1H-indazole | 434 | Example 18 |
| 430 | Enantiomer 2 of 3-(6-(5-azaspiro[2.5]oct-8-yloxy)-2-pyrazinyl)-5-(2,6-difluorophenyl)-1H-indazole | 434 | Example 18 |
| 431 | 5-(2,6-difluorophenyl)-3-(6-(((4R)-3,3-dimethyl-4-piperidinyl)oxy)-2-pyrazinyl)-1H-indazole & 5-(2,6-difluorophenyl)-3-(6-(((4S)-3,3-dimethyl-4-piperidinyl)oxy)-2-pyrazinyl)-1H-indazole | 436 | Example 18 |
| 432 | Enantiomer 1 of 5-(2,6-difluorophenyl)-3-(6-((3,3-dimethyl-4-piperidinyl)oxy)-2-pyrazinyl)-1H-indazole | 436 | Example 18 |
| 433 | Enantiomer 2 of 5-(2,6-difluorophenyl)-3-(6-((3,3-dimethyl-4-piperidinyl)oxy)-2-pyrazinyl)-1H-indazole | 436 | Example 18 |
| 434 | 3-(6-((4R)-6-azaspiro[2.5]oct-4-yloxy)-2-pyrazinyl)-5-(2-fluorophenyl)-1H-indazole | 416 | Example 252 |
| 435 | 6-(5-(2-fluorophenyl)-1H-indazol-3-yl)-2-pyrazinol | 307 | Example 252 |
| 436 | 3-(6-((4R)-6-azaspiro[2.5]oct-4-yloxy)-2-pyrazinyl)-5-phenyl-1H-indazole | 398 | Example 252 |
| 437 | 3-(6-((4R)-6-azaspiro[2.5]oct-4-yloxy)-2-pyrazinyl)-5-(2,6-difluorophenyl)-1H-indole & 3-(6-((4S)-6-azaspiro[2.5]oct-4-yloxy)-2-pyrazinyl)-5-(2,6-difluorophenyl)-1H-indole | 433 | Example 26 |
| 438 | Enantiomer 1 of 3-(6-(6-azaspiro[2.5]oct-4-yloxy)-2-pyrazinyl)-5-(2,6-difluorophenyl)-1H-indole | 433 | Example 26 |
| 439 | Enantiomer 2 of 3-(6-(6-azaspiro[2.5]oct-4-yloxy)-2-pyrazinyl)-5-(2,6-difluorophenyl)-1H-indole | 433 | Example 26 |
| 440 | 3-(6-((4R)-6-azaspiro[2.5]oct-4-yloxy)-2-pyrazinyl)-5-(3-fluoro-4-pyridinyl)-1H-indazole | 417 | Example 252 |
| 441 | 3-(6-((4R)-6-azaspiro[2.5]oct-4-yloxy)-2-pyrazinyl)-5-(2-fluoro-3-pyridinyl)-1H-indazole | 417 | Example 252 |
| 442 | 3-(6-((4R)-6-azaspiro[2.5]oct-4-yloxy)-2-pyrazinyl)-5-(2,5-difluorophenyl)-1H-indazole | 434 | Example 252 |
| 443 | 3-(6-((4R)-6-azaspiro[2.5]oct-4-yloxy)-2-pyrazinyl)-5-(5-chloro-2-fluorophenyl)-1H-indazole | 450 | Example 252 |
| 444 | Racemic 3-(6-(3-azabicyclo[4.1.0]hept-5-yloxy)-2-pyrazinyl)-5-(2,6-difluorophenyl)-1H-indazole | 420 | Example 26 |
| 445 | 5-(2,6-difluorophenyl)-3-(6-((1-methyl-4-piperidinyl)oxy)-2-pyrazinyl)-1H-indazole | 422 | Example 26 |

TABLE 2-continued

| Example # | IUPAC Name | M + 1 | Method |
|---|---|---|---|
| 446 | 3-(6-((4R)-6-azaspiro[2.5]oct-4-yloxy)-2-pyrazinyl)-5-cyclopropyl-1H-indazole | 362 | Example 231 |
| 447 | 3-(6-((4R)-6-azaspiro[2.5]oct-4-yloxy)-2-pyrazinyl)-5-cyclopentyl-1H-indazole | 390 | Example 231 |
| 448 | (3R,4S)-1-(6-(5-(2,6-difluorophenyl)-1H-indazol-3-yl)-2-pyrazinyl)-3,4-pyrrolidinediol | 410 | Example 20 |
| 449 | Enantiomer 1 of 1-(6-(5-(2,6-difluorophenyl)-1H-indazol-3-yl)-2-pyrazinyl)-3,4-pyrrolidinediol | 410 | Example 20 |
| 450 | Enantiomer 2 of 1-(6-(5-(2,6-difluorophenyl)-1H-indazol-3-yl)-2-pyrazinyl)-3,4-pyrrolidinediol | 410 | Example 20 |
| 451 | 3-(6-((4R)-6-azaspiro[2.5]oct-4-yloxy)-2-pyrazinyl)-5-(2,4-difluoro-3-pyridinyl)-1H-indazole | 435 | Example 252 |
| 452 | Racemic 3-(6-(3-azabicyclo[410]hept-5-yloxy)-2-pyrazinyl)-5-(2,6-difluorophenyl)-1H-indazole | 420 | Example 252 |
| 453 | 3-(6-((4R)-6-azaspiro[2.5]oct-4-yloxy)-2-pyrazinyl)-5-cyclobutyl-1H-indazole | 376 | Example 231 |
| 454 | 3-(6-((4R)-6-azaspiro[2.5]oct-4-yloxy)-2-pyrazinyl)-5-(1,3-thiazol-2-yl)-1H-indazole | 405 | Example 231 |
| 455 | 3-(6-((4R)-6-azaspiro[2.5]oct-4-yloxy)-2-pyrazinyl)-5-(3-fluoro-2-pyridinyl)-1H-indazole | 417 | Example 275 |
| 456 | 4-(3-(6-((4R)-6-azaspiro[2.5]oct-4-yloxy)-2-pyrazinyl)-1H-indazol-5-yl)-3-fluorobenzonitrile | 441 | Example 252 |
| 457 | 4-(3-(6-((4R)-6-azaspiro[2.5]oct-4-yloxy)-2-pyrazinyl)-1H-indazol-5-yl)-3-fluoroaniline | 431 | Example 252 |
| 458 | 4-(3-(6-((4R)-6-azaspiro[2.5]oct-4-yloxy)-2-pyrazinyl)-1H-indazol-5-yl)-3-fluorobenzamide | 459 | Example 252 |
| 459 | 3-(6-((4R)-6-azaspiro[2.5]oct-4-yloxy)-2-pyrazinyl)-5-(2-fluoro-4-(methylsulfonyl)phenyl)-1H-indazole | 494 | Example 252 |
| 460 | 3-(6-((4R)-6-azaspiro[2.5]oct-4-yloxy)-2-pyrazinyl)-5-(4-fluoro-3-pyridinyl)-1H-indazole | 417 | Example 252 |
| 461 | 4-(3-(6-((4R)-6-azaspiro[2.5]oct-4-yloxy)-2-pyrazinyl)-1H-indazol-5-yl)-3-fluorophenol | 432 | Example 252 |
| 462 | N-(4-(3-(6-((4R)-6-azaspiro[2.5]oct-4-yloxy)-2-pyrazinyl)-1H-indazol-5-yl)-3-fluorophenyl)acetamide | 473 | Example 252 |
| 463 | 4-(3-(6-((4R)-6-azaspiro[2.5]oct-4-yloxy)-2-pyrazinyl)-1H-indazol-5-yl)-3-fluorobenzenesulfonamide | 495 | Example 252 |
| 464 | 5-(3-(6-((4R)-6-azaspiro[2.5]oct-4-yloxy)-2-pyrazinyl)-1H-indazol-5-yl)-2-pyrimidinamine | 415 | Example 252 |
| 465 | N-(4-(3-(6-((4R)-6-azaspiro[2.5]oct-4-yloxy)-2-pyrazinyl)-1H-indazol-5-yl)-3-fluorophenyl)methanesulfonamide | 509 | Example 252 |
| 466 | 5-(3-(6-((4R)-6-azaspiro[2.5]oct-4-yloxy)-2-pyrazinyl)-1H-indazol-5-yl)-6-fluoro-2-pyridinamine | 432 | Example 252 |
| 467 | 3-(6-((4R)-6-azaspiro[2.5]oct-4-yloxy)-2-pyrazinyl)-5-(2,6-difluoro-4-(methylsulfonyl)phenyl)-1H-indazole | 512 | Example 252 |
| 468 | Enantiomer 1 of cis-5-(2,6-difluorophenyl)-3-(6-((5-methyl-3-piperidinyl)oxy)-2-pyrazinyl)-1H-indazole | 422 | Example 18 |
| 469 | Enantiomer 1 of cis-5-(2,6-difluorophenyl)-3-(6-((5-methyl-3-piperidinyl)oxy)-2-pyrazinyl)-1H-indazole | 422 | Example 18 |
| 470 | 1-methylethyl 3-(6-(4-amino-1-piperidinyl)-2-pyrazinyl)-1H-indazole-5-carboxylate | 381 | Example 238 |
| 471 | N-methyl-3-(6-(4-piperidinylamino)-2-pyrazinyl)-1H-indazole-5-carboxamide | 352.2 | Example 238 |
| 472 | 1-(2-(5-(2,6-difluorophenyl)-1H-indazol-3-yl)-6-methoxy-4-pyrimidinyl)-4-piperidinamine | 437.1 | Example 276 |
| 473 | methyl 3-(6-((3R)-3-piperidinylamino)-2-pyrazinyl)-1H-indazole-5-carboxylate | 353.1 | Example 238 |
| 474 | 1-methylethyl 3-(6-((3R)-3-piperidinylamino)-2-pyrazinyl)-1H-indazole-5-carboxylate | 381.1 | Example 238 |
| 475 | N-methyl-3-(6-((3R)-3-piperidinylamino)-2-pyrazinyl)-1H-indazole-5-carboxamide | 352.2 | Example 238 |
| 476 | methyl 3-(6-((3R)-3-piperidinyloxy)-2-pyrazinyl)-1H-indazole-5-carboxylate | 354 | Example 238 |
| 477 | 1-methylethyl 3-(6-((3R)-3-piperidinyloxy)-2-pyrazinyl)-1H-indazole-5-carboxylate | 382.2 | Example 238 |
| 478 | N-methyl-3-(6-((3R)-3-piperidinyloxy)-2-pyrazinyl)-1H-indazole-5-carboxamide | 353.1 | Example 238 |
| 479 | 2-(5-(2,6-difluorophenyl)-1H-indol-3-yl)-6-methoxy-N-((3R)-3-piperidinyl)-4-pyrimidinamine | 436.2 | Example 278 |
| 480 | 3-(6-(4-amino-1-piperidinyl)-2-pyrazinyl)-N-methyl-1H-indazole-5-carboxamide | 352 | Example 238 |
| 481 | N,N-dimethyl-3-(2-((3R)-3-piperidinylamino)-4-pyrimidinyl)-1H-indazole-5-carboxamide | 366.1 | Example 284 |
| 482 | 6-(4-amino-1-piperidinyl)-2-(5-(2,6-difluorophenyl)-1H-indazol-3-yl)-4-pyrimidinol | 423.1 | Example 277 |
| 483 | 6-(5-(2,6-difluorophenyl)-1H-indol-3-yl)-2-(4-morpholinyl)-4-pyrimidinol | 409.1 | Example 279 |
| 484 | 3-(6-(4-amino-1-piperidinyl)-2-pyrazinyl)-N,N-dimethyl-1H-indazole-5-carboxamide | 366.3 | Example 284 |
| 485 | methyl 3-(4-(4-piperidinylamino)-2-pyrimidinyl)-1H-indazole-5-carboxylate | 353 | Example 284 |
| 486 | methyl 3-(4-((3R)-3-piperidinylamino)-2-pyrimidinyl)-1H-indazole-5-carboxylate | 353.1 | Example 284 |
| 487 | N,N-dimethyl-3-(6-(4-piperidinylamino)-2-pyrazinyl)-1H-indazole-5-carboxamide | 366.2 | Example 284 |
| 488 | methyl 3-(4-(4-amino-1-piperidinyl)-2-pyrimidinyl)-1H-indazole-5-carboxylate | 353.1 | Example 284 |
| 489 | methyl 3-(2-(4-piperidinylamino)-4-pyrimidinyl)-1H-indazole-5-carboxylate | 353 | Example 284 |
| 490 | methyl 3-(2-((3R)-3-piperidinylamino)-4-pyrimidinyl)-1H-indazole-5-carboxylate | 353.1 | Example 284 |
| 491 | methyl 3-(2-(4-amino-1-piperidinyl)-4-pyrimidinyl)-1H-indazole-5-carboxylate | 353.1 | Example 284 |
| 492 | 6-(5-(2,6-difluorophenyl)-1H-indol-3-yl)-2-(dimethylamino)-4(3H)-pyrimidinone | 367 | Example 279 |
| 493 | 5-(2,6-difluorophenyl)-3-(6-methoxy-2-((3R)-3-piperidinyloxy)-4-pyrimidinyl)-1H-indole | 437.1 | Example 278 |
| 494 | N,N-dimethyl-3-(6-((3R)-3-piperidinylamino)-2-pyrazinyl)-1H-indazole-5-carboxamide | 366.1 | Example 284 |
| 495 | 3-(6-((3R)-3-piperidinylamino)-2-pyrazinyl)-1H-indazole-5-carboxylic acid | 339.1 | Example 238 |
| 496 | 2-(5-(2,6-difluorophenyl)-1H-indol-3-yl)-6-(dimethylamino)-4(3H)-pyrimidinone | 367 | Example 279 |
| 497 | methyl 3-(2-((3R)-3-piperidinyloxy)-4-pyrimidinyl)-1H-indazole-5-carboxylate | 354.1 | Example 284 |
| 498 | methyl 3-(4-((3R)-3-piperidinyloxy)-2-pyrimidinyl)-1H-indazole-5-carboxylate | 354.2 | Example 284 |
| 499 | 2-(5-(2,6-difluorophenyl)-1H-indol-3-yl)-6-((1-methylethyl)amino)-4(3H)-pyrimidinone | 380.8 | Example 277 |

TABLE 2-continued

| Example # | IUPAC Name | M + 1 | Method |
|---|---|---|---|
| 500 | 6-(5-(2,6-difluorophenyl)-1H-indol-3-yl)-2-((1-methylethyl)amino)-4(3H)-pyrimidinone | 381.1 | Example 277 |
| 501 | 5-(2-(2-methyl-1-piperidinyl)-1,3-thiazol-4-yl)-3-(6-((3R)-3-piperidinyloxy)-2-pyrazinyl)-1H-indole | 475.1 | Example 2 |
| 502 | N-cyclopropyl-5-(3-(6-((3R)-3-piperidinyloxy)-2-pyrazinyl)-1H-indol-5-yl)-3-pyridinamine | 427 | Example 2 |
| 503 | 1-(6-(5-(6-cyclopropyl-2-pyrazinyl)-1H-indazol-3-yl)-2-pyrazinyl)-4-piperidinamine | 413.1 | Example 9 |
| 504 | 1-(6-(5-(1H-pyrrolo[3,2-c]pyridin-6-yl)-1H-indazol-3-yl)-2-pyrazinyl)-4-piperidinamine | 411 | Example 9 |
| 505 | 5-(5-chloro-3-pyridinyl)-3-(6-((3R)-3-piperidinyloxy)-2-pyrazinyl)-1H-indole | 406 | Example 2 |
| 506 | 1-(4-(5-(2,6-difluorophenyl)-1H-indazol-3-yl)-6-methoxy-2-pyrimidinyl)-4-piperidinamine | 437 | Example 276 |
| 507 | 1-(6-(5-(1H-pyrrolo[3,2-c]pyridin-4-yl)-1H-indazol-3-yl)-2-pyrazinyl)-4-piperidinamine | 410.7 | Example 9 |
| 508 | 6-(3-(6-(4-amino-1-piperidinyl)-2-pyrazinyl)-1H-indazol-5-yl)-2-pyrazinamine | 387.8 | Example 9 |
| 509 | 6-(3-(6-(4-amino-1-piperidinyl)-2-pyrazinyl)-1H-indazol-5-yl)-N-cyclopropyl-2-pyrazinamine | 427.7 | Example 9 |
| 510 | (3S)-1-(5-(5-(6-(1-methylethoxy)-2-pyrazinyl)-1H-indol-3-yl)-1,3,4-oxadiazol-2-yl)-3-piperidinamine | 420.1 | Example 280 |
| 511 | 5-(5-(6-(1-methylethoxy)-2-pyrazinyl)-1H-indol-3-yl)-N-((3S)-3-pyrrolidinyl)-1,3,4-oxadiazol-2-amine | 406.2 | Example 280 |
| 512 | 5-(5-(6-(1-methylethoxy)-2-pyrazinyl)-1H-indol-3-yl)-N-((3R)-3-pyrrolidinyl)-1,3,4-oxadiazol-2-amine | 406 | Example 280 |
| 513 | N-(5-(5-(6-(1-methylethoxy)-2-pyrazinyl)-1H-indol-3-yl)-1,3,4-oxadiazol-2-yl)-4-piperidinamine | 420.2 | Example 280 |
| 514 | (3S)—N-(5-(5-(6-(1-methylethoxy)-2-pyrazinyl)-1H-indol-3-yl)-1,3,4-oxadiazol-2-yl)-3-piperidinamine | 420.2 | Example 280 |
| 515 | 2-(5-(2,6-difluorophenyl)-1H-indol-3-yl)-6-((3R)-3-piperidinylamino)-4-pyrimidinol | 422.1 | Example 277 |
| 516 | 1-(2-(5-(2,6-difluorophenyl)-1H-indazol-3-yl)-4-pyrimidinyl)-4-piperidinamine | 406.7 | Example 16 |
| 517 | 1-(6-(5-(6-cyclopropyl-2-pyrazinyl)-1H-indol-3-yl)-2-pyrazinyl)-4-piperidinamine | 411.8 | Example 9 |
| 518 | (3R)—N-(5-(5-(6-(1-methylethoxy)-2-pyrazinyl)-1H-indol-3-yl)-1,3,4-oxadiazol-2-yl)-3-piperidinamine | 420.2 | Example 280 |
| 519 | 6-(3-(6-(4-amino-1-piperidinyl)-2-pyrazinyl)-1H-indol-5-yl)-N-cyclopropyl-2-pyrazinamine | 426.8 | Example 9 |
| 520 | 5-(6-(1-methylethoxy)-2-pyrazinyl)-3-(5-(1-pyrrolidinyl)-1,3,4-oxadiazol-2-yl)-1H-indole | 391 | Example 280 |
| 521 | 5-(6-cyclopropyl-2-pyrazinyl)-3-(2-pyrazinyl)-1H-indole | 314 | Example 287 |
| 522 | 5-(5-(6-(1-methylethoxy)-2-pyrazinyl)-1H-indol-3-yl)-N-(1-methylethyl)-1,3,4-oxadiazol-2-amine | 379 | Example 280 |
| 523 | 5-(5-(6-(1-methylethoxy)-2-pyrazinyl)-1H-indol-3-yl)-N-phenyl-1,3,4-oxadiazol-2-amine | 413.2 | Example 280 |
| 524 | 6-(5-(2,6-difluorophenyl)-1H-indazol-3-yl)-2-((1-methylethyl)amino)-4(3H)-pyrimidinone | 382.1 | Example 282 |
| 525 | (3R)-1-(5-(5-(6-(1-methylethoxy)-2-pyrazinyl)-1H-indol-3-yl)-1,3,4-oxadiazol-2-yl)-3-piperidinamine | 420.3 | Example 280 |
| 526 | 6-(5-(2,6-difluorophenyl)-1H-indazol-3-yl)-2-(dimethylamino)-4(3H)-pyrimidinone | 368 | Example 282 |
| 527 | 6-(5-(6-cyclopropyl-2-pyrazinyl)-1H-indol-3-yl)-2-(dimethylamino)-4(3H)-pyrimidinone | 373.1 | Example 287 |
| 528 | 6-(5-(2,6-difluorophenyl)-1H-indazol-3-yl)-2-(1-methylethoxy)-4(3H)-pyrimidinone | 383 | Example 282 |
| 529 | 6-(5-(2,6-difluorophenyl)-1H-indazol-3-yl)-2-((3R)-3-piperidinyloxy)-4(3H)-pyrimidinone | 424.1 | Example 282 |
| 530 | 6-(5-(2,6-difluorophenyl)-1H-indazol-3-yl)-4(3H)-pyrimidinone | 325 | Example 278 |
| 531 | methyl 3-(4-((3R)-3-piperidinylamino)-2-pyrimidinyl)-1H-indole-5-carboxylate | 352.1 | Example 236 |
| 532 | methyl 3-(6-((3R)-3-piperidinylamino)-2-pyrazinyl)-1H-indole-5-carboxylate | 352 | Example 236 |
| 533 | methyl 3-(2-((3R)-3-piperidinylamino)-4-pyrimidinyl)-1H-indole-5-carboxylate | 352.2 | Example 236 |
| 534 | 6-(5-(2,6-difluorophenyl)-1H-indazol-3-yl)-2-(((3S,4S)-3-fluoro-4-piperidinyl)oxy)-4(3H)-pyrimidinone & 6-(5-(2,6-difluorophenyl)-1H-indazol-3-yl)-2-(((3R,4R)-3-fluoro-4-piperidinyl)oxy)-4(3H)-pyrimidinone | 442 | Example 282 |
| 535 | 2-butyl-6-(5-(2,6-difluorophenyl)-1H-indazol-3-yl)-4(3H)-pyrimidinone | 381 | Example 282 |
| 536 | 3-(6-((3R)-3-piperidinylamino)-2-pyrazinyl)-1H-indole-5-carbonitrile | 319.1 | Example 232 |
| 537 | 6-(5-(2,6-difluorophenyl)-1H-indazol-3-yl)-2-(((3R,4S)-3-fluoro-4-piperidinyl)oxy)-4(3H)-pyrimidinone & 6-(5-(2,6-difluorophenyl)-1H-indazol-3-yl)-2-(((3S,4R)-3-fluoro-4-piperidinyl)oxy)-4(3H)-pyrimidinone | 442 | Example 282 |
| 538 | 3-(6-((3R)-3-piperidinylamino)-2-pyrazinyl)-1H-indole-5-carboxylic acid | 338.3 | Example 236 |
| 539 | 3-(4-((3R)-3-piperidinylamino)-2-pyrimidinyl)-1H-indole-5-carboxylic acid | 338.1 | Example 236 |
| 540 | 3-(6-((3R)-3-piperidinylamino)-2-pyrazinyl)-1H-indazole-5-carbonitrile | 320.1 | Example 232 |
| 541 | 6-(5-(1,3-oxazol-2-yl)-1H-indazol-3-yl)-N-((3R)-3-piperidinyl)-2-pyrazinamine | 362.1 | Example 2 |
| 542 | 6-(5-(1,3-oxazol-2-yl)-1H-indol-3-yl)-N-((3R)-3-piperidinyl)-2-pyrazinamine | 361.1 | Example 2 |
| 543 | 6-(5-(2,6-difluorophenyl)-1H-indazol-3-yl)-2-((3S)-3-hydroxy-1-pyrrolidinyl)-4(3H)-pyrimidinone | 410 | Example 282 |
| 544 | 6-(5-(2,6-difluorophenyl)-6-fluoro-1H-indazol-3-yl)-2-(((3S,4S)-4-fluoro-3-piperidinyl)oxy)-4(3H)-pyrimidinone | 460 | Example 282 |
| 545 | 6-(5-(2-fluoro-4-(methylsulfonyl)phenyl)-1H-indazol-3-yl)-2-(((3S,4S)-4-fluoro-3-piperidinyl)oxy)-4(3H)-pyrimidinone or 6-(5-(2-fluoro-4-(methylsulfonyl)phenyl)-1H-indazol-3-yl)-2-(((3R,4R)-4-fluoro-3-piperidinyl)oxy)-4(3H)-pyrimidinone | 502.2 | Example 283 |
| 546 | 6-(5-(2,4-difluorophenyl)-1H-indazol-3-yl)-2-(((3S,4S)-4-fluoro-3-piperidinyl)oxy)-4(3H)-pyrimidinone & 6-(5-(2,4-difluorophenyl)-1H-indazol-3-yl)-2-(((3R,4R)-4-fluoro-3-piperidinyl)oxy)-4(3H)-pyrimidinone | 442.3 | Example 283 |
| 547 | 6-(5-(2,6-difluorophenyl)-1H-indazol-3-yl)-2-(((3S,5R)-5-methyl-3-piperidinyl)amino)-4(3H)-pyrimidinone & 6-(5-(2,6-difluorophenyl)-1H-indazol-3-yl)-2-(((3R,5S)-5-methyl-3-piperidinyl)amino)-4(3H)-pyrimidinone | 437 | Example 279 |
| 548 | 6-(5-(2,6-difluorophenyl)-1H-indazol-3-yl)-2-(((3S,5S)-5-methyl-3-piperidinyl)amino)-4(3H)-pyrimidinone & 6-(5-(2,6-difluorophenyl)-1H-indazol- | 437 | Example 279 |

TABLE 2-continued

| Example # | IUPAC Name | M + 1 | Method |
|---|---|---|---|
| | 3-yl)-2-(((3R,5R)-5-methyl-3-piperidinyl)amino)-4(3H)-pyrimidinone | | |
| 549 | 6-(5-(2,6-difluorophenyl)-6-fluoro-1H-indazol-3-yl)-2-(((3S,5R)-5-methyl-3-piperidinyl)amino)-4(3H)-pyrimidinone & 6-(5-(2,6-difluorophenyl)-6-fluoro-1H-indazol-3-yl)-2-(((3R,5S)-5-methyl-3-piperidinyl)amino)-4(3H)-pyrimidinone | 455 | Example 282 |
| 550 | 6-(5-(2,6-difluorophenyl)-6-fluoro-1H-indazol-3-yl)-2-(((3S,5S)-5-methyl-3-piperidinyl)amino)-4(3H)-pyrimidinone & 6-(5-(2,6-difluorophenyl)-6-fluoro-1H-indazol-3-yl)-2-(((3R,5R)-5-methyl-3-piperidinyl)amino)-4(3H)-pyrimidinone | 455 | Example 282 |
| 551 | 3-(3-(2-(((3S,4S)-4-fluoro-3-piperidinyl)oxy)-6-oxo-1,6-dihydro-4-pyrimidinyl)-1H-indazol-5-yl)-4-pyridinecarbonitrile & 3-(3-(2-(((3R,4R)-4-fluoro-3-piperidinyl)oxy)-6-oxo-1,6-dihydro-4-pyrimidinyl)-1H-indazol-5-yl)-4-pyridinecarbonitrile | 431.8 | Example 289 |
| 552 | 2-(((3R,4R)-4-fluoro-3-piperidinyl)oxy)-6-(5-(2-fluoro-3-pyridinyl)-1H-indazol-3-yl)-4(3H)-pyrimidinone & 2-(((3S,4S)-4-fluoro-3-piperidinyl)oxy)-6-(5-(2-fluoro-3-pyridinyl)-1H-indazol-3-yl)-4(3H)-pyrimidinone | 425.3 | Example 289 |
| 553 | 3-(6-((3R)-3-piperidinyloxy)-2-pyrazinyl)-5-(2-(1-pyrrolidinyl)-1,3-thiazol-4-yl)-1H-indole | 447 | Example 231 |
| 554 | Enantiomer 1 of trans-6-(5-(2,6-difluorophenyl)-1H-indazol-3-yl)-2-((4-fluoro-3-piperidinyl)oxy)-4(3H)-pyrimidinone | 442 | Example 282 |
| 555 | Enantiomer 2 of trans-6-(5-(2,6-difluorophenyl)-1H-indazol-3-yl)-2-((4-fluoro-3-piperidinyl)oxy)-4(3H)-pyrimidinone | 442 | Example 282 |
| 556 | N,N-dimethyl-3-(6-((3R)-3-piperidinyloxy)-2-pyrazinyl)-1H-indazole-5-carboxamide | 367 | Example 284 |
| 557 | N,N-dimethyl-3-(2-((3R)-3-piperidinyloxy)-4-pyrimidinyl)-1H-indazole-5-carboxamide | 367.1 | Example 284 |
| 558 | methyl 3-(6-(4-amino-1-piperidinyl)-2-pyrazinyl)-1H-indazole-5-carboxylate | 353.1 | Example 238 |
| 559 | methyl 3-(6-(4-piperidinylamino)-2-pyrazinyl)-1H-indazole-5-carboxylate | 353 | Example 238 |
| 560 | 1-methylethyl 3-(6-(4-piperidinylamino)-2-pyrazinyl)-1H-indazole-5-carboxylate | 380.8 | Example 238 |
| 561 | N,N-dimethyl-3-(2-(4-piperidinylamino)-4-pyrimidinyl)-1H-indazole-5-carboxamide | 366.2 | Example 284 |
| 562 | 5-(2,6-difluorophenyl)-3-(6-methoxy-2-(4-morpholinyl)-4-pyrimidinyl)-1H-indole | 423.1 | Example 276 |
| 563 | 1-(2-(5-(2,6-difluorophenyl)-1H-indol-3-yl)-6-methoxy-4-pyrimidinyl)-4-piperidinamine | 436.1 | Example 277 |
| 564 | 6-(5-(2,6-difluorophenyl)-1H-indol-3-yl)-2-(4-morpholinyl)-4-pyrimidinol | 409.1 | Example 277 |
| 565 | 2-(4-amino-1-piperidinyl)-6-(5-(2,6-difluorophenyl)-1H-indazol-3-yl)-4-pyrimidinol | 423.1 | Example 277 |
| 566 | 6-(4-amino-1-piperidinyl)-2-(5-(2,6-difluorophenyl)-1H-indol-3-yl)-4-pyrimidinol | 422.1 | Example 277 |
| 567 | 6-(5-(2,6-difluorophenyl)-1H-indazol-3-yl)-2-(((3R,5S)-5-methyl-3-piperidinyl)oxy)-4-pyrimidinol & 6-(5-(2,6-difluorophenyl)-1H-indazol-3-yl)-2-(((3S,5R)-5-methyl-3-piperidinyl)oxy)-4-pyrimidinol | 438 | Example 282 |
| 568 | Enantiomer 1 of cis-6-(5-(2,6-difluorophenyl)-1H-indazol-3-yl)-2-((5-methyl-3-piperidinyl)oxy)-4-pyrimidinol | 438 | Example 282 |
| 569 | Enantiomer 2 of cis-6-(5-(2,6-difluorophenyl)-1H-indazol-3-yl)-2-((5-methyl-3-piperidinyl)oxy)-4-pyrimidinol | 438 | Example 282 |

Biological Activity

Pim-1 and Pim-2

Cloning and Expression:

Full-length human cDNAs encoding Pim-1 (MGC ID 3913552) or Pim-2 (IMAGE ID 5092935) were purchased from Invitrogen, Carlsbad, Calif. These cDNAs were used as templates in PCR reactions to produce full-length DNA clones of the PIMs. Oligonucleotide PCR primers for Pim-1 were 5'-TGGCTGATCAATGCTCTTGTCCAAAATC-3' and 5'-ATTAGAATTCTATTTGCTGGGCCCCGGC-3'. Oligonucleotide PCR primers for Pim-2 were 5'-TGCAGGATCCATGTTGACCAAGCCTCTAC-3' and 5'-ACGTGAATTCTATCCCTGTGACATGGCC-3'. PCR products were digested with BelI and EcoRI for Pim-1 and BamHI and EcoRI for Pim-2 and ligated into a modified baculovirus transfer vector (pFastBac1) cleaved with BamHI and EcoRI. For bacterial expression, the same cleaved PCR products encoding Pim-1 or Pim-2 were ligated into a modified E. coli expression vector pET28(a) cleaved with BamHI and EcoRI Amino-terminal hexahistidine tags followed by a thrombin cleavage site were previously added to the vectors using standard methods of molecular biology. Recombinant baculoviruses expressing Pim-1 or Pim-2 were made using standard methods (Fastbac manual, Invitrogen, Carlsbad, Calif.). Infection of Sf9 cells was done at an m.o.i. of greater than 5 for 24-48 h. Cells were harvested by centrifugation and frozen at −80 C. For E. coli expression, cells carrying pET28-His6-Th-Pim-1 or pET28-His6-Th-Pim-2 were picked from a single colony and grown o/n in LB media. The o/n culture was used to inoculate a 2 liter flask with 500 mL media. This was grown o/n and used to inoculate 15-20 liters of Terrific Broth in a New Brunswick Scientific fermentor. The E. coli were grown at 37° C. to and OD600>1.6. The temperature was dropped to 18° C. and o/n expression was induced with 0.5 mM IPTG. Cells were harvested by centrifugation and frozen at −80° C.

Purification

The frozen cell pellets were thawed by stirring in chilled lysis buffer (0.05 M HEPES, pH 8.0, 0.25 M NaCl, 0.01 M 2-mercaptoethanol, 10% (w/v) glycerol, 0.5% (v/v) protease inhibitor cocktail (Sigma P-8340) at a ratio of 1 L/200 g cells until homogeneous. The thawed suspension was applied to a microfluidizer at 10,000 PSI to disrupt the cells and the whole lysates were clarified by centrifugation at 50,000×g for 90 min, 4° C. Imidazole was added to the clarified lysate to a final concentration of 2.5 mM and the lysate was mixed with 10 mL of Talon resin (Clontech) and the slurry rocked gently overnight at 4° C. The slurry was centrifuged at 1,000×g for 5 min, the supernatant decanted, and the resin suspended in 40 mL of lysis wash buffer (lysis buffer at 0.75 M NaCl). This step was repeated 3× and the resin was transferred to a 2.5 cm glass column. Ten column volumes of wash buffer (0.05 M HEPES, pH 8.0, 0.1 M NaCl, 0.01 M 2-mercaptoethanol, 10% (w/v) glycerol) were applied to the resin followed by 10 column volumes of elution buffer (0.05 M HEPES, pH 8.0, 0.25 M NaCl, 0.01 M 2-mercaptoethanol, 10% (w/v) glycerol, 0.1 M imidazole). Fractions were analyzed by SDS-PAGE and those containing the protein of interest were pooled and concentrated. The concentrated protein was applied to an Amersham Superdex 75 (XK 26/60) column equilibrated in 0.025 M Tris-HCl, pH 7.5, 0.1 M NaCl, 0.01 M 2-mercaptoethanol, 10% (w/v) glycerol. The protein eluted at a retention time indicative of it being monomeric and fractions were analyzed by SDS-PAGE. Fractions containing the monomeric protein of interest were pooled, concentrated to ~2 mg/mL, and stored at −80° C.

Pim-3

Pim-3 was purchased from Millipore (UK).

Pim Enzyme Assays

The assay for the determination of Pim activity is based on the formation of phosphorylated biotinylated-BAD peptide at the Serine 112 residue (S112) and employs HTRF® (homogeneous time resolved fluorescence) technology to detect the product in a 96-well plate format. The phosphorylation of biotinylated-BAD (S112) peptide by full length recombinant Pim-1, Pim-2, or Pim-3 protein was detected with streptavidin:Allophycocyanin (APC) conjugate and a europium (Eu) labeled antibody directed against phosphorylated-BAD (S112). Excitation of Eu by a high energy laser light (337 nm) leads to a transfer of energy to the APC molecule, and results in an emission at 665 nm. The fluorescence is directly proportional to the amount of phosphorylated BAD peptide present in the reaction.

Compounds were prepared in DMSO by conducting 3-fold serial dilutions to give a 10-point dosing curve having a high dose of 1 uM. A reference compound was included on each assay plate in order to validate that plate; on one plate of every assay run, two additional reference compounds were included.

The final buffer conditions were as follows: 60 mM Hepes, pH 7.0, 0.05% BSA, 2 mM DTT. Incubations were carried out at RT (22° C.) for 2 h for Pim-1, 1 hour and 30 min for Pim-3, and 45 min for Pim-2. The reaction was stopped by the addition of 3 mM EDTA, and fluorescence was measured by an HTRF® Rubystar microplate reader. For each plate, percent of control (POC) values were calculated for each well. Values for the IC50 IP were estimated using a standard 4-parameter logistic model.

Pim Cell Assay

The cell lines used in the assay were generated by the stable transfection of either Pim-1 or Pim-2 into the U2OS human osteogenic sarcoma line. The assay for determination of the Pim activity in the engineered U2OS cell lines measures levels of phospho-BAD normalized against total BAD protein levels. It was conducted as follows:

The adherent cells were dissociated from the flasks using non-enzymatic cell dissociation solution (Sigma # C5914). Cells were then plated out to 96-well plates at an initial density of 40,000 cells/well in 100 uL of complete growth medium (McCoy's 5A-Invitrogen #16600-082, 10% FBS-Gibco #10099-141, Geneticin/G418 at 500 ug/mL-Invitrogen #10131-027). The cells were then incubated overnight at 37° C., 5% $CO_2$.

Compounds were initially diluted in DMSO by conducting 3-fold serial dilutions to give a 10-point dosing curve having a high dose of 31.6 uM. In addition to the 10-point dosing curve of the test compound, DMSO alone was run as the high control.

This dilution in DMSO was then diluted again into cell growth medium. Aliquots (12 uL) of the compound diluted in growth medium were then transferred to the appropriate wells of the 96-well plates containing cells to yield a final DMSO concentration of 0.3%. The cell plates were then incubated with compound for 29 min at 37° C., 5% $CO_2$.

After a 29 minute incubation, the cell plates had the compound-containing medium removed, and were washed with 150 uL of PBS (Gibco #14040). Following the wash, the cell plates were placed on ice and given 50 uL of ice-cold complete lysis buffer (MSD kit components, Protease Inhibitor Cocktail Tablets-Roche #04 693 116 001). The cell plates containing lysis buffer were then immediately stored at −70° C.

These prepared lysates were then assayed for phospho and total BAD according to the manufacturer's protocols (Meso Scale Diagnostics, Cat# K15103C-3 & # K15103D-3). The plates were read on the MSD Sector Imager 6000, and results were calculated according to the assay protocols ((% Phosphoprotein=((2×Phospho signal)/(Phospho signal+Total signal))×100)).

TABLE 3

IC$_{50}$ Activity of compounds of the Invention

| Ex# | Pim_1_IC50 (uM) | Pim2_IC50 (uM) | Pim3 IC50 (uM) | Pim1_Cell_IC50 (uM) | Pim2_Cell_IC50 (uM) |
|---|---|---|---|---|---|
| 1 | 0.031 | 0.023 | 0.011 | 0.788 | 8.732 |
| 2 | 0.028 | 0.769 | 0.061 | 2.630 | NA |
| 3 | 0.008 | 0.013 | 0.009 | 3.684 | 7.388 |
| 4 | 0.002 | 0.035 | 0.004 | 0.234 | >31.60 |
| 5 | 0.000 | 0.016 | 0.000 | 0.045 | 5.439 |
| 6 | 0.001 | 0.035 | 0.000 | 1.877 | >31.60 |
| 7 | 0.004 | 0.025 | 0.003 | 0.748 | >31.60 |
| 8 | 0.012 | 0.041 | 0.006 | 2.436 | >31.60 |
| 9 | 0.004 | 0.096 | 0.001 | 0.437 | >31.60 |
| 10 | 0.006 | 0.077 | 0.012 | 0.172 | 8.501 |
| 11 | 0.018 | 0.066 | 0.005 | 0.761 | NA |
| 12 | 0.002 | 0.059 | 0.002 | 0.111 | 9.085 |
| 13 | 0.000 | 0.024 | 0.001 | 0.041 | 5.747 |
| 14 | NA | NA | NA | NA | NA |
| 15 | 0.003 | 0.070 | 0.003 | 1.040 | >31.60 |
| 16 | 0.003 | 0.011 | 0.002 | 0.146 | 2.704 |
| 17 | 0.005 | 0.043 | 0.004 | 0.424 | 10.977 |

TABLE 3-continued

IC$_{50}$ Activity of compounds of the Invention

| Ex# | Pim_1_IC50 (uM) | Pim2_IC50 (uM) | Pim3 IC50 (uM) | Pim1_Cell_IC50 (uM) | Pim2_Cell_IC50 (uM) |
|---|---|---|---|---|---|
| 18 | 0.075 | 0.264 | 0.034 | NA | NA |
| 19 | 0.005 | 0.028 | 0.007 | 0.254 | NA |
| 20 | 0.009 | 0.024 | 0.001 | 0.262 | 3.621 |
| 21 | 0.003 | 0.098 | 0.005 | 1.175 | >31.60 |
| 22 | 0.002 | 0.018 | 0.005 | 0.439 | 7.113 |
| 23 | 0.002 | 0.009 | 0.004 | 0.228 | 5.040 |
| 24 | 0.018 | 0.087 | 0.023 | 0.497 | >31.60 |
| 25 | 0.004 | 0.198 | 0.015 | 0.405 | 24.707 |
| 26 | 0.004 | 0.023 | 0.006 | 0.514 | 3.688 |
| 27 | 0.010 | 0.048 | 0.009 | 0.780 | 27.224 |
| 28 | 0.032 | 0.271 | 0.012 | 1.397 | 11.269 |
| 29 | 0.227 | 1.007 | 0.172 | NA | NA |
| 30 | 0.001 | 0.007 | 0.000 | 0.089 | 2.243 |
| 31 | 0.009 | 0.326 | 0.004 | 0.600 | 21.585 |
| 32 | 0.019 | 0.586 | 0.067 | 0.907 | NA |
| 33 | 0.026 | 0.243 | 0.069 | 1.082 | >31.60 |
| 34 | 0.027 | 0.380 | 0.029 | 1.012 | >31.60 |
| 35 | 0.124 | 2.303 | 0.104 | NA | NA |
| 36 | 0.006 | 0.007 | 0.002 | 2.061 | 6.608 |
| 37 | 0.013 | 0.019 | 0.005 | 0.573 | 3.531 |
| 38 | 0.007 | 0.009 | 0.003 | 1.207 | 4.742 |
| 39 | 0.007 | 0.010 | 0.004 | 1.624 | 6.626 |
| 40 | 0.024 | 0.013 | 0.016 | 2.373 | 7.056 |
| 41 | 0.035 | 0.029 | 0.026 | 1.397 | 8.517 |
| 42 | 0.032 | 0.041 | 0.020 | 2.800 | 9.837 |
| 43 | 0.007 | 0.005 | 0.003 | 2.523 | 14.897 |
| 44 | 0.007 | 0.005 | 0.004 | 0.932 | 4.584 |
| 45 | 0.012 | 0.023 | 0.008 | 1.558 | >31.60 |
| 46 | 0.020 | 0.049 | 0.022 | 0.959 | 7.032 |
| 47 | 0.043 | 0.290 | 0.043 | 1.940 | >31.60 |
| 48 | 0.044 | 0.285 | 0.027 | 1.107 | >31.60 |
| 49 | 0.007 | 0.072 | 0.007 | 1.337 | >31.60 |
| 50 | 0.024 | 0.470 | 0.021 | 2.274 | >31.60 |
| 51 | 0.013 | 0.087 | 0.009 | 1.457 | >31.60 |
| 52 | 0.004 | 0.024 | 0.001 | 0.237 | 9.500 |
| 53 | 0.002 | 0.017 | 0.001 | 0.280 | 9.930 |
| 54 | 0.007 | 0.183 | 0.004 | 3.662 | NA |
| 55 | 0.001 | 0.051 | 0.001 | 0.287 | >31.60 |
| 56 | 0.002 | 0.015 | 0.001 | 0.130 | >31.60 |
| 57 | 0.001 | 0.010 | 0.000 | 0.605 | >31.60 |
| 58 | 0.002 | 0.011 | 0.001 | 0.164 | 6.759 |
| 59 | 0.003 | 0.028 | 0.011 | 2.162 | >31.60 |
| 60 | 0.005 | 0.036 | 0.004 | 0.419 | 12.799 |
| 61 | 0.010 | 0.065 | 0.006 | 3.014 | >31.60 |
| 62 | 0.011 | 0.059 | 0.007 | 0.599 | >31.60 |
| 63 | 0.011 | 0.161 | 0.008 | 1.689 | >31.60 |
| 64 | 0.020 | 0.150 | 0.016 | 3.017 | >31.60 |
| 65 | 0.013 | 0.274 | 0.018 | 3.531 | >31.60 |
| 66 | 0.004 | 0.033 | 0.002 | 0.401 | 17.317 |
| 67 | 0.002 | 0.010 | 0.001 | 0.380 | 15.008 |
| 68 | 0.020 | 0.088 | 0.011 | >31.60 | >31.60 |
| 69 | 0.004 | 0.025 | 0.003 | 0.748 | >31.60 |
| 70 | 0.005 | 0.018 | 0.004 | 0.255 | >31.60 |
| 71 | 0.003 | 0.011 | 0.001 | 0.256 | 8.820 |
| 72 | 0.003 | 0.082 | 0.005 | 0.533 | >31.60 |
| 73 | 0.001 | 0.003 | 0.000 | 0.885 | >31.60 |
| 74 | 0.014 | 0.054 | 0.015 | >31.60 | >31.60 |
| 75 | 0.007 | 0.049 | 0.003 | 0.480 | >31.60 |
| 76 | 0.016 | 0.187 | 0.005 | 2.742 | >31.60 |
| 77 | 0.006 | 0.070 | 0.003 | 0.453 | >31.60 |
| 78 | 0.002 | 0.027 | 0.001 | 0.885 | 7.969 |
| 79 | 0.001 | 0.009 | 0.000 | 0.182 | 3.894 |
| 80 | 0.003 | 0.015 | 0.001 | 2.384 | >31.60 |
| 81 | 0.002 | 0.029 | 0.003 | 0.395 | 7.166 |
| 82 | 0.001 | 0.007 | 0.000 | 0.171 | 7.814 |
| 83 | 0.010 | 0.034 | 0.004 | 1.420 | 22.087 |
| 84 | 0.009 | 0.045 | 0.004 | 0.253 | >31.60 |
| 85 | 0.005 | 0.036 | 0.001 | 0.176 | 7.018 |
| 86 | 0.006 | 0.060 | 0.002 | 0.328 | 20.297 |
| 87 | 0.012 | 0.043 | 0.005 | 0.569 | >31.60 |
| 88 | 0.048 | 0.685 | 0.057 | 1.191 | >31.60 |
| 89 | 0.028 | 0.303 | 0.049 | 0.868 | NA |
| 90 | 0.023 | 0.196 | 0.040 | 0.747 | >31.60 |
| 91 | 0.629 | >3.00 | 0.926 | NA | NA |

TABLE 3-continued

IC$_{50}$ Activity of compounds of the Invention

| Ex# | Pim_1_IC50 (uM) | Pim2_IC50 (uM) | Pim3 IC50 (uM) | Pim1_Cell_IC50 (uM) | Pim2_Cell_IC50 (uM) |
|---|---|---|---|---|---|
| 92 | 0.009 | 0.057 | 0.005 | 2.227 | >31.60 |
| 93 | 0.013 | >1.00 | 0.082 | 0.487 | >31.60 |
| 94 | 0.086 | >1.00 | 0.118 | NA | NA |
| 95 | 0.005 | 0.082 | 0.003 | 0.384 | >31.60 |
| 96 | 0.848 | >1.00 | 1.116 | NA | NA |
| 97 | 0.003 | 0.027 | 0.001 | 3.027 | >31.60 |
| 98 | 0.001 | 0.072 | 0.002 |  | >31.60 |
| 99 | 0.003 | 0.057 | 0.005 | 4.719 | >31.60 |
| 100 | 0.001 | 0.018 | 0.002 | 1.250 | >31.60 |
| 101 | 0.004 | 0.055 | 0.010 | 0.269 | >31.60 |
| 102 | 0.002 | 0.020 | 0.003 | 0.199 | 5.003 |
| 103 | 0.034 | 0.224 | 0.068 | NA | NA |
| 104 | 0.000 | 0.001 | 0.000 | 1.923 | >31.60 |
| 105 | 0.002 | 0.043 | 0.005 | 0.484 | NA |
| 106 | 0.499 | 0.897 | 0.278 | NA | NA |
| 107 | 0.030 | 0.192 | 0.067 | NA | NA |
| 108 | 0.009 | 0.153 | 0.006 | 0.866 | NA |
| 109 | 0.000 | 0.002 | 0.000 |  | 1.728 |
| 110 | 0.008 | 0.151 | 0.023 | 0.776 | NA |
| 111 | 0.029 | 0.292 | 0.087 | NA | NA |
| 112 | 0.032 | 0.521 | 0.116 | NA | NA |
| 113 | 0.017 | 0.549 | 0.033 | >15.80 | NA |
| 114 | 0.006 | 0.077 | 0.012 | 0.172 | 8.501 |
| 115 | 0.033 | 0.155 | 0.020 | 0.958 | >31.60 |
| 116 | 0.027 | 0.026 | 0.022 | NA | NA |
| 117 | 0.018 | 0.066 | 0.005 | 0.761 | NA |
| 118 | 0.000 | 0.024 | 0.001 | 0.041 | 5.747 |
| 119 | 0.002 | 0.059 | 0.002 | 0.111 | 9.085 |
| 120 | 0.003 | 0.098 | 0.008 | 0.145 | NA |
| 121 | 0.003 | 0.023 | 0.005 | 0.157 | 3.012 |
| 122 | 0.016 | 0.014 | 0.020 | 0.287 | 1.847 |
| 123 | 0.001 | 0.010 | 0.006 |  | 3.523 |
| 124 | 0.011 | 0.058 | 0.011 | 0.402 | NA |
| 125 | 0.021 | 0.080 | 0.016 | NA | NA |
| 126 | 0.013 | 0.161 | 0.006 | 0.563 | >31.60 |
| 127 | 0.013 | 0.067 | 0.006 | 1.022 | >31.60 |
| 128 | 0.031 | 0.059 | 0.030 | NA | NA |
| 129 | 0.003 | 0.030 | 0.003 | NA | NA |
| 130 | 0.007 | 0.025 | 0.008 | 0.208 | 9.242 |
| 131 | 0.002 | 0.015 | 0.005 | 0.151 | 8.910 |
| 132 | 0.008 | 0.014 | 0.014 | 0.245 | 3.047 |
| 133 | 0.005 | 0.017 | 0.006 | 0.435 | 7.835 |
| 134 | 0.007 | 0.037 | 0.014 | 0.316 | NA |
| 135 | 0.083 | 0.227 | 0.082 | NA | NA |
| 136 | 0.030 | 0.164 | 0.015 | NA | NA |
| 137 | 0.008 | 0.063 | 0.006 | 0.585 | NA |
| 138 | 0.005 | 0.185 | 0.014 | 0.921 | >31.60 |
| 139 | 0.013 | 0.013 | 0.012 | 0.454 | 3.782 |
| 140 | 0.002 | 0.019 | 0.006 |  | 7.777 |
| 141 | 0.042 | 0.435 | 0.032 |  | NA |
| 142 | 0.019 | 0.087 | 0.006 | 0.625 | >31.60 |
| 143 | 0.005 | 0.034 | 0.025 | 0.873 | >31.60 |
| 144 | 0.027 | 0.252 | 0.026 | NA | NA |
| 145 | 0.023 | 0.496 | 0.080 | NA | NA |
| 146 | 0.007 | 0.084 | 0.031 | 0.996 | NA |
| 147 | 0.007 | 0.105 | 0.013 | 0.724 | NA |
| 148 | 0.006 | 0.025 | 0.007 | 0.314 | NA |
| 149 | 0.006 | 0.048 | 0.007 | 0.292 | NA |
| 150 | 0.035 | 0.214 | 0.029 | NA | NA |
| 151 | 0.027 | 0.118 | 0.129 | NA | NA |
| 152 | 0.007 | 0.036 | 0.007 | 1.058 | NA |
| 153 | 0.012 | 0.165 | 0.027 | 0.174 | NA |
| 154 | 0.015 | 0.071 | 0.016 | 0.772 | NA |
| 155 | 0.036 | 0.108 | 0.027 | NA | NA |
| 156 | 0.049 | 0.144 | 0.066 | NA | NA |
| 157 | 0.012 | 0.032 | 0.012 | 1.738 | NA |
| 158 | 0.001 | 0.121 | 0.001 | 0.036 | >15.80 |
| 159 | 0.002 | 0.071 | 0.001 | 0.750 | NA |
| 160 | 0.005 | 0.024 | 0.012 | 0.108 | NA |
| 161 | 0.002 | 0.009 | 0.001 | 0.610 | 5.991 |
| 162 | 0.008 | 0.071 | 0.006 | 0.422 | 29.247 |
| 163 | 0.058 | 0.969 | 0.049 | 1.633 | >31.65 |
| 164 | 0.001 | 0.015 | 0.002 | 0.092 | 5.540 |
| 165 | 0.007 | 0.029 | 0.006 | 0.869 | >31.60 |

TABLE 3-continued

IC$_{50}$ Activity of compounds of the Invention

| Ex# | Pim_1_IC50 (uM) | Pim2_IC50 (uM) | Pim3 IC50 (uM) | Pim1_Cell_IC50 (uM) | Pim2_Cell_IC50 (uM) |
|---|---|---|---|---|---|
| 166 | 0.122 | >3.00 | 0.142 | NA | NA |
| 167 | 0.016 | 0.088 | 0.009 | 1.442 | 11.015 |
| 168 | 0.001 | 0.009 | 0.003 | 0.069 | 3.306 |
| 169 | 0.069 | 1.636 | 0.092 | 2.410 | NA |
| 170 | 0.153 | >3.00 | 0.187 | NA | NA |
| 171 | 0.009 | 0.059 | 0.007 | 1.026 | >31.60 |
| 172 | 0.002 | 0.006 | 0.001 | 0.237 | 3.981 |
| 173 | 0.039 | 0.362 | 0.021 | 0.956 | >31.60 |
| 174 | 0.003 | 0.017 | 0.003 | 0.368 | 7.319 |
| 175 | 0.168 | 1.181 | 0.153 | NA | NA |
| 176 | 0.015 | 0.055 | 0.006 | 2.512 | 20.129 |
| 177 | 0.009 | 0.018 | 0.002 | 0.569 | 5.415 |
| 178 | 0.006 | 0.061 | 0.006 | 0.582 | 14.262 |
| 179 | 0.168 | 0.858 | 0.122 | NA | NA |
| 180 | 0.076 | 0.643 | 0.081 | 2.126 | >31.60 |
| 181 | 0.206 | 2.078 | 0.146 | NA | NA |
| 182 | 0.040 | 0.556 | 0.049 | 2.459 | >31.60 |
| 183 | 0.044 | 0.679 | 0.044 | 4.255 | >31.60 |
| 184 | 0.139 | 1.043 | 0.233 | >31.60 | >31.60 |
| 185 | 0.006 | 0.016 | 0.005 | 0.890 | 10.264 |
| 186 | 0.007 | 0.032 | 0.002 | 0.663 | 13.853 |
| 187 | 0.050 | 0.131 | 0.022 | 1.834 | 24.213 |
| 188 | 0.004 | 0.022 | 0.003 | 0.175 | 5.397 |
| 189 | 0.031 | 0.229 | 0.012 | 1.184 | >31.60 |
| 190 | 0.024 | 0.223 | 0.036 | 1.223 | 18.794 |
| 191 | 0.046 | 0.194 | 0.115 | NA | NA |
| 192 | 0.147 | 1.252 | 0.175 | NA | NA |
| 193 | 0.161 | 1.341 | 0.143 | NA | NA |
| 194 | 0.002 | 0.052 | 0.003 | 0.561 | >31.60 |
| 195 | 0.004 | 0.015 | 0.007 | 0.211 | 7.585 |
| 196 | 0.004 | 0.019 | 0.006 | 0.146 | NA |
| 197 | 0.037 | 0.187 | 0.018 | NA | NA |
| 198 | 0.004 | 0.013 | 0.005 | 0.146 | 5.092 |
| 199 | 0.005 | 0.016 | 0.004 | 0.400 | 3.412 |
| 200 | 0.003 | 0.010 | 0.004 | 0.608 | NA |
| 201 | 0.001 | 0.066 | 0.005 | 0.611 | >31.60 |
| 202 | 0.021 | 0.414 | 0.051 | 8.851 | NA |
| 203 | 0.008 | 0.184 | 0.018 | 3.049 | NA |
| 204 | 0.080 | 0.987 | 0.098 | 2.229 | NA |
| 205 | 0.004 | 0.029 | 0.004 | 0.273 | 4.331 |
| 206 | 0.002 | 0.054 | 0.006 | 0.326 | 20.403 |
| 207 | 0.001 | 0.011 | 0.004 | 0.102 | 3.030 |
| 208 | 0.002 | 0.015 | 0.004 | 0.381 | 4.622 |
| 209 | 0.036 | 0.089 | 0.049 | 1.179 | 30.294 |
| 210 | 0.120 | 0.424 | 0.091 | NA | NA |
| 211 | 0.086 | 0.445 | 0.061 | 3.794 | >31.60 |
| 212 | 0.015 | 0.185 | 0.018 | 0.997 | >31.60 |
| 213 | 0.022 | 0.343 | 0.040 | 1.367 | 18.938 |
| 214 | 0.045 | 0.515 | 0.083 | NA | NA |
| 215 | 1.642 | >3.00 | 0.538 | NA | NA |
| 216 | 0.601 | 2.155 | 0.245 | NA | NA |
| 217 | 0.765 | 2.350 | 0.156 | NA | NA |
| 218 | 0.805 | >3.00 | 0.317 | NA | NA |
| 219 | 1.128 | >3.00 | 0.692 | NA | NA |
| 220 | 0.494 | >3.00 | 0.329 | NA | NA |
| 221 | 0.050 | 0.506 | 0.033 | 1.922 | >31.60 |
| 222 | 0.732 | >3.00 | 0.445 | NA | NA |
| 223 | 0.142 | >3.00 | 0.150 | NA | NA |
| 224 | 0.216 | 2.269 | 0.126 | NA | NA |
| 225 | 0.077 | >3.00 | 0.138 | 1.470 | >31.60 |
| 226 | 2.196 | >3.00 | 0.616 | NA | NA |
| 227 | 0.100 | >3.00 | 0.206 | >15.80 | >15.80 |
| 228 | 0.043 | 1.410 | 0.042 | 3.415 | >31.60 |
| 229 | 0.251 | >3.00 | 0.147 | NA | NA |
| 230 | 0.089 | 2.362 | 0.050 | 2.827 | >31.60 |
| 231 | 0.0004 | 0.001 | 0.0005 |  | 1.811 |
| 232 | 0.047 | 0.065 | 0.028 |  | >15.80 |
| 233 | 0.845 | >3.00 | 1.758 |  |  |
| 235 | 0.121 | 1.868 | 0.151 |  |  |
| 234 | 0.161 | 2.567 | 0.348 |  |  |
| 236 | 0.005 | 0.044 | 0.007 |  | 5.82 |
| 237 | 0.195 | 0.325 | 0.122 |  |  |
| 238 | 0.107 | 0.755 | 0.311 |  |  |
| 239 | 0.166 | >3.00 | 0.347 |  |  |

TABLE 3-continued

IC$_{50}$ Activity of compounds of the Invention

| Ex# | Pim_1_IC50 (uM) | Pim2_IC50 (uM) | Pim3 IC50 (uM) | Pim1_Cell_IC50 (uM) | Pim2_Cell_IC50 (uM) |
|---|---|---|---|---|---|
| 240 | 0.254 | >3.00 | 0.719 | | |
| 241 | 0.376 | 2.477 | 0.538 | | |

TABLE 4

IC$_{50}$ Activity of compounds of the Invention

| Example | Pim_1_IC50 (uM) | Pim2_IC50 (uM) | KMS-Cell-IC50 (uM) | Pim1_Cell_IC50_(uM) | Pim2_Cell_IC50_(uM) |
|---|---|---|---|---|---|
| 242 | 0.005 | 0.108 | | 0.369 | 31.493 |
| 243 | 0.000 | 0.008 | | 0.099 | 5.589 |
| 244 | 0.001 | 0.003 | | 0.169 | >10.00 |
| 245 | 0.028 | 0.345 | | 3.636 | >31.60 |
| 246 | 0.551 | 0.798 | | | |
| 247 | 0.004 | 0.004 | 4.313 | | |
| 248 | 0.017 | 0.043 | >31.60 | | |
| 249 | 0.032 | 0.269 | | | |
| 250 | 0.046 | 0.309 | | | |
| 251 | 0.004 | 0.039 | NA| | | |
| 252 | 0.070 | 0.121 | | | |
| 253 | 0.009 | 0.009 | 5.578 | | |
| 254 | 0.364 | >1.000000 | | | |
| 255 | 0.020 | 0.058 | >31.60 | | |
| 256 | 0.006 | 0.011 | 3.281 | | |
| 257 | 0.004 | 0.002 | 1.172 | | |
| 258 | 0.009 | 0.006 | 3.186 | | |
| 259 | 0.013 | 0.006 | 2.796 | | |
| 260 | 0.009 | 0.005 | 2.187 | | |
| 261 | 0.006 | 0.004 | 1.494 | | |
| 262 | 0.004 | 0.005 | 2.218 | | |
| 263 | 0.004 | 0.008 | | 0.180 | 5.756 |
| 264 | 0.006 | 0.015 | | 0.276 | >10.00 |
| 265 | 0.009 | 0.035 | 5.776 | | |
| 266 | 0.013 | 0.044 | NA| | | |
| 267 | 0.030 | 0.044 | | | |
| 268 | 0.105 | 0.146 | | | |
| 269 | 0.020 | 0.099 | 7.377 | | |
| 270 | 0.046 | 0.166 | | | |
| 271 | 0.159 | 0.200 | | | |
| 272 | 0.013 | 0.054 | 12.987 | | |
| 273 | 0.070 | 0.287 | | | |
| 274 | 0.020 | 0.090 | NA| | | |
| 275 | 0.009 | 0.099 | NA| | | |
| 276 | 0.344 | 0.929 | | | |
| 277 | 0.001 | 0.002 | | 2.470 | >31.6 |
| 278 | 0.565 | 0.700 | | | |
| 279 | 0.001 | 0.000 | | 2.401 | >31.60 |
| 280 | 0.022 | 0.161 | | | |
| 281 | 0.070 | 0.597 | | | |
| 282 | 0.000 | 0.000 | 2.654 | 1.168 | >10.00 |
| 283 | 0.002 | 0.001 | 1.890 | | |
| 284 | 0.839 | >1.000000 | | | |
| 285 | 0.020 | 0.067 | NA| | | |
| 286 | 0.581 | >1.000000 | | | |
| 287 | 0.006 | 0.087 | | 1.311 | >31.60 |
| 288 | 0.364 | 0.968 | | | |
| 289 | 0.000 | 0.001 | 3.540 | | |
| 290 | 0.004 | 0.011 | | 0.313 | 6.526 |
| 291 | 0.006 | 0.032 | | 0.154 | 11.847 |
| 292 | 0.004 | 0.019 | | 0.649 | 35.165 |
| 293 | 0.016 | 0.060 | | >31.60 | >31.60 |
| 294 | 0.007 | 0.026 | | 0.521 | 9.444 |
| 295 | 0.034 | 0.075 | | | |
| 296 | 0.037 | 0.055 | | | |
| 297 | 0.003 | 0.007 | | 0.166 | 8.447 |
| 298 | 0.031 | 0.234 | | | |
| 299 | 0.003 | 0.231 | | 1.266 | >31.60 |
| 300 | 0.042 | 0.115 | | | |
| 301 | 0.013 | 0.122 | | 2.535 | |
| 302 | 0.009 | 0.189 | | 0.995 | |

TABLE 4-continued

IC$_{50}$ Activity of compounds of the Invention

| Example | Pim_1_IC50 (uM) | Pim2_IC50 (uM) | KMS-Cell-IC50 (uM) | Pim1_Cell_IC50_(uM) | Pim2_Cell_IC50_(uM) |
|---|---|---|---|---|---|
| 303 | 0.158 | 0.733 | | | |
| 304 | 0.052 | 0.619 | | | |
| 305 | 0.007 | 0.127 | | 0.754 | |
| 306 | 0.023 | 0.093 | | | |
| 307 | 0.006 | 0.114 | | 1.599 | |
| 308 | 0.008 | 0.076 | | 0.160 | |
| 309 | 0.004 | 0.018 | | 0.125 | 17.028 |
| 310 | 0.006 | 0.041 | | 0.295 | |
| 311 | 0.008 | 0.025 | | 0.412 | >31.60 |
| 312 | 0.009 | 0.031 | | 1.311 | |
| 313 | 0.234 | 0.515 | | | |
| 314 | 0.288 | 0.428 | | | |
| 315 | 0.007 | 0.024 | | 0.444 | 9.060 |
| 316 | 0.002 | 0.009 | | 0.103 | 3.401 |
| 317 | 0.053 | 0.297 | | | |
| 318 | 0.035 | 0.347 | | | |
| 319 | 0.024 | 0.068 | | | |
| 320 | 0.006 | 0.030 | | 0.592 | |
| 321 | 0.005 | 0.019 | | 0.662 | 23.619 |
| 322 | 0.031 | 0.099 | | | |
| 323 | 0.008 | 0.067 | | 1.308 | |
| 324 | 0.004 | 0.034 | | 0.957 | >31.60 |
| 325 | 0.021 | 0.046 | | | |
| 326 | 0.003 | 0.010 | | 0.314 | 7.187 |
| 327 | 0.005 | 0.019 | | 0.666 | 8.063 |
| 328 | 0.028 | 0.141 | | | |
| 329 | 0.083 | 0.514 | | | |
| 330 | 0.054 | 0.268 | | | |
| 331 | 0.008 | 0.111 | | 1.280 | |
| 332 | 0.043 | 0.156 | | | |
| 333 | 0.011 | 0.040 | | 0.803 | >10.00 |
| 334 | 0.072 | 0.149 | | | |
| 335 | 0.005 | 0.072 | | 1.063 | >31.60 |
| 336 | 0.008 | 0.033 | | 0.857 | >10.00 |
| 337 | 0.056 | 0.592 | | | |
| 338 | 0.069 | 66.569 | | | |
| 339 | 0.014 | 0.092 | | 2.582 | >31.60 |
| 340 | 0.042 | 0.260 | | | |
| 341 | 0.009 | 0.069 | | 1.270 | >15.80 |
| 342 | 0.159 | >1.000000 | | | |
| 343 | 0.004 | 0.019 | | 1.206 | >15.80 |
| 344 | 0.009 | 0.068 | | 3.608 | >15.80 |
| 345 | 0.020 | 0.157 | | 0.729 | >15.80 |
| 346 | 0.105 | 0.363 | | | |
| 347 | 0.002 | 0.016 | | 0.273 | 9.690 |
| 348 | 0.364 | >1.000000 | | | |
| 349 | 0.030 | 0.290 | | | |
| 350 | 0.006 | 0.193 | | 2.365 | >15.80 |
| 351 | 0.020 | 0.178 | >31.595598 | | |
| 352 | 0.030 | 0.133 | | | |
| 353 | 0.159 | 0.889 | | | |
| 354 | 0.834 | >1.000000 | | | |
| 355 | 0.020 | 0.104 | >31.595598 | | |
| 356 | 0.006 | 0.041 | 12.572 | | |
| 357 | 0.013 | 0.179 | >31.595598 | | |
| 358 | 0.004 | 0.020 | 8.517 | | |
| 359 | 0.009 | 0.021 | 4.838 | | |
| 360 | 0.008 | 0.094 | | 2.715 | >15.80 |
| 361 | 0.012 | 0.071 | | 2.067 | >31.60 |
| 362 | 0.003 | 0.007 | | 0.864 | 4.150 |
| 363 | 0.057 | 0.253 | | | |
| 364 | 0.000 | 0.005 | 5.847 | 0.022 | 3.461 |
| 365 | 0.001 | 0.014 | NAI | 0.050 | >15.80 |
| 366 | 0.000 | 0.004 | 2.446 | 0.051 | 4.313 |
| 367 | 0.014 | 0.027 | | 0.868 | 8.801 |
| 368 | 0.006 | 0.037 | | 0.023 | 1.772 |
| 369 | 0.000 | 0.001 | | 0.083 | 3.695 |
| 370 | 0.126 | >1.000000 | | | |
| 371 | 0.026 | 0.113 | | | |
| 372 | 0.001 | 0.007 | | 0.200 | >10.00 |
| 373 | 0.001 | 0.005 | | 0.130 | 3.371 |
| 374 | 0.001 | 0.017 | | 0.312 | 8.089 |
| 375 | 0.075 | 0.243 | | | |
| 376 | 0.021 | 0.275 | | | |
| 377 | 0.055 | 0.231 | | | |

TABLE 4-continued

IC$_{50}$ Activity of compounds of the Invention

| Example | Pim_1_IC50 (uM) | Pim2_IC50 (uM) | KMS-Cell-IC50 (uM) | Pim1_Cell_IC50_(uM) | Pim2_Cell_IC50_(uM) |
|---|---|---|---|---|---|
| 378 | 0.627 | >1.000000 | | | |
| 379 | 0.002 | 0.016 | | 0.657 | >31.60 |
| 380 | 0.067 | >1.000000 | | | |
| 381 | 0.004 | 0.037 | | 0.772 | >31.60 |
| 382 | 0.050 | 0.335 | | | |
| 383 | 0.001 | 0.010 | | 0.044 | 21.843 |
| 384 | 0.004 | 0.027 | | 0.207 | >31.60 |
| 385 | 0.056 | 0.457 | | | |
| 386 | 0.006 | 0.011 | | 0.061 | >31.60 |
| 387 | 0.093 | 0.230 | | | |
| 388 | 0.116 | 0.124 | | | |
| 389 | 0.173 | 0.200 | | | |
| 390 | 0.119 | 0.241 | | | |
| 391 | 0.002 | 0.012 | | 0.114 | >10.00 |
| 392 | 0.013 | 0.066 | | 0.212 | >10.00 |
| 393 | 0.013 | 0.016 | 9.966 | | |
| 394 | 0.030 | 0.203 | | | |
| 395 | 0.006 | 0.009 | 10.025 | | |
| 396 | 0.013 | 0.014 | 8.009 | | |
| 397 | 0.020 | 0.144 | 14.309 | | |
| 398 | 0.009 | 0.012 | 10.664 | | |
| 399 | >1.000000 | >1.000000 | | | |
| 400 | 0.017 | 0.025 | | 1.128 | 8.652 |
| 401 | 0.030 | 0.058 | | | |
| 402 | 0.030 | 0.039 | | | |
| 403 | 0.070 | 0.058 | | | |
| 404 | 0.009 | 0.019 | NAl | 2.575 | >15.80 |
| 405 | 0.159 | 0.447 | | | |
| 406 | 0.002 | 0.001 | 2.362 | 0.460 | 5.307 |
| 407 | 0.020 | 0.051 | | 2.073 | >15.80 |
| 408 | 0.001 | 0.001 | 1.296 | | |
| 409 | 0.001 | 0.001 | 2.675 | | |
| 410 | 0.009 | 0.007 | 1.750 | | |
| 411 | 0.004 | 0.012 | 1.215 | | |
| 412 | 0.001 | 0.003 | | 0.211 | 4.276 |
| 413 | 0.003 | 0.016 | | 0.539 | 10.698 |
| 414 | 0.007 | 0.060 | | 1.545 | |
| 415 | 0.028 | 0.076 | | | |
| 416 | 0.024 | 0.204 | NAl | | |
| 417 | 0.015 | 0.335 | | 1.485 | |
| 418 | 0.019 | 0.104 | | 2.306 | >31.60 |
| 419 | 0.001 | 0.007 | 5.136 | 0.323 | 5.126 |
| 420 | 0.025 | 0.042 | | | |
| 421 | 0.019 | 0.050 | | 1.146 | 31.677 |
| 422 | 0.022 | 0.082 | | | |
| 423 | 0.017 | 0.194 | | 1.660 | >31.60 |
| 424 | 0.001 | 0.004 | 6.275 | 0.433 | 2.469 |
| 425 | 0.013 | 0.046 | | 1.386 | >15.80 |
| 426 | 0.105 | 0.174 | | | |
| 427 | 0.013 | 0.037 | >15.80 | | |
| 428 | 0.001 | 0.006 | 7.874 | | |
| 429 | 0.030 | 0.076 | | | |
| 430 | 0.001 | 0.006 | 7.851 | | |
| 431 | 0.004 | 0.055 | | 1.535 | >31.60 |
| 432 | 0.020 | 0.114 | | 2.415 | >31.60 |
| 433 | 0.002 | 0.022 | | 0.801 | >10.00 |
| 434 | 0.001 | 0.001 | 1.975 | 0.232 | 2.442 |
| 435 | 0.322 | 0.629 | | | |
| 436 | 0.002 | 0.004 | 3.397 | 0.295 | 6.447 |
| 437 | 0.001 | 0.002 | | 0.180 | 2.492 |
| 438 | 0.001 | 0.002 | 11.885 | | |
| 439 | 0.159 | 0.407 | | | |
| 440 | 0.004 | 0.006 | 8.398 | | |
| 441 | 0.004 | 0.004 | 0.827 | | |
| 442 | 0.002 | 0.004 | 6.427 | | |
| 443 | 0.001 | 0.005 | 4.644 | | |
| 444 | 0.004 | 0.028 | 5.052 | | |
| 445 | 0.020 | 0.043 | NAl | | |
| 446 | 0.003 | 0.005 | 1.731 | | |
| 447 | 0.004 | 0.004 | 3.162 | | |
| 448 | 0.105 | 0.137 | | | |
| 449 | 0.159 | 0.639 | | | |
| 450 | 0.159 | 0.453 | | | |
| 451 | 0.003 | 0.009 | 1.472 | | |
| 452 | 0.020 | 0.097 | 9.410 | | |

TABLE 4-continued

IC$_{50}$ Activity of compounds of the Invention

| Example | Pim_1_IC50 (uM) | Pim2_IC50 (uM) | KMS-Cell-IC50 (uM) | Pim1_Cell_IC50_(uM) | Pim2_Cell_IC50_(uM) |
|---|---|---|---|---|---|
| 453 | 0.004 | 0.007 | 4.191 | | |
| 454 | 0.004 | 0.008 | 4.525 | | |
| 455 | 0.006 | 0.006 | 0.687 | | |
| 456 | 0.004 | 0.003 | 5.493 | | |
| 457 | 0.000 | 0.000 | 0.118 | | |
| 458 | 0.001 | 0.001 | 0.300 | | |
| 459 | 0.002 | 0.002 | 0.207 | | |
| 460 | 0.003 | 0.005 | 3.200 | | |
| 461 | 0.000 | 0.001 | 0.210 | | |
| 462 | 0.000 | 0.001 | 0.560 | | |
| 463 | 0.002 | 0.001 | 1.610 | | |
| 464 | 0.004 | 0.017 | NAI | | |
| 465 | 0.000 | 0.001 | 0.377 | | |
| 466 | 0.000 | 0.001 | 0.346 | | |
| 467 | 0.003 | 0.003 | 0.546 | | |
| 468 | 0.070 | 0.196 | | | |
| 469 | 0.002 | 0.004 | 3.050 | | |
| 470 | 0.002 | 0.008 | | 0.204 | 8.787 |
| 471 | 0.171 | 0.329 | | | |
| 472 | 0.112 | 0.617 | | | |
| 473 | 0.004 | 0.044 | NAI | 0.221 | 9.634 |
| 474 | 0.002 | 0.052 | | 0.108 | 14.611 |
| 475 | 0.030 | 0.192 | | | |
| 476 | 0.018 | 0.144 | | 0.588 | 31.635 |
| 477 | 0.008 | 0.126 | | 0.348 | 20.342 |
| 478 | 0.180 | >1.000000 | | | |
| 479 | 0.112 | 0.077 | | | |
| 480 | 0.106 | 0.203 | | | |
| 481 | 0.444 | 0.719 | | | |
| 482 | 0.001 | 0.004 | | 1.203 | >31.60 |
| 483 | 0.004 | 0.032 | | 0.219 | >31.60 |
| 484 | 0.374 | >1.00 | | | |
| 485 | 0.026 | 0.026 | | | |
| 486 | 0.072 | 0.543 | | | |
| 487 | 0.159 | 0.217 | | | |
| 488 | 0.046 | 0.055 | | | |
| 489 | 0.002 | 0.003 | 1.687 | 0.202 | 4.476 |
| 490 | 0.013 | 0.054 | | 0.522 | >15.80 |
| 491 | 0.004 | 0.008 | 1.446 | | |
| 492 | 0.046 | 0.109 | | | |
| 493 | 0.834 | 0.653 | | | |
| 494 | 0.834 | >1.00 | | | |
| 495 | 0.070 | 0.159 | >15.80 | | |
| 496 | 0.159 | >1.00 | | | |
| 497 | 0.046 | 0.207 | | | |
| 498 | 0.070 | 0.726 | | | |
| 499 | 0.364 | >1.00 | | | |
| 500 | 0.009 | 0.019 | NAI | | |
| 501 | 0.091 | 0.812 | | | |
| 502 | 0.020 | 0.424 | | | |
| 503 | 0.000 | 0.002 | | 0.076 | 3.678 |
| 504 | 0.005 | 0.127 | | 7.564 | |
| 505 | 0.029 | 0.225 | | | |
| 506 | 0.015 | 0.033 | | 3.736 | >31.60 |
| 507 | 0.003 | 0.065 | | >31.60 | >31.60 |
| 508 | 0.000 | 0.001 | | 1.372 | >31.60 |
| 509 | 0.000 | 0.006 | | 0.051 | 4.228 |
| 510 | 0.017 | 0.078 | | 1.007 | >31.60 |
| 511 | 0.098 | 0.480 | | | |
| 512 | 0.047 | 0.093 | | | |
| 513 | 0.048 | 0.218 | | | |
| 514 | 0.052 | 0.194 | | | |
| 515 | 0.003 | 0.007 | | 12.027 | >31.60 |
| 516 | 0.006 | 0.142 | | 0.861 | >31.60 |
| 517 | 0.002 | 0.065 | | 0.176 | >31.60 |
| 518 | 0.025 | 0.097 | | 6.921 | >31.60 |
| 519 | 0.001 | 0.128 | | 0.338 | >31.60 |
| 520 | 0.052 | 0.527 | | | |
| 521 | 0.425 | >1.00 | | | |
| 522 | 0.090 | 0.446 | | | |
| 523 | 0.359 | >1.00 | | | |
| 524 | 0.005 | 0.018 | | 1.007 | >31.60 |
| 525 | 0.070 | NAI | | | |
| 526 | 0.034 | 0.091 | | | |
| 527 | 0.013 | 0.079 | >15.80 | 0.354 | >31.60 |

TABLE 4-continued

IC$_{50}$ Activity of compounds of the Invention

| Example | Pim_1_IC50 (uM) | Pim2_IC50 (uM) | KMS-Cell-IC50 (uM) | Pim1_Cell_IC50_(uM) | Pim2_Cell_IC50_(uM) |
|---|---|---|---|---|---|
| 528 | 0.013 | 0.036 | | 0.779 | >15.80 |
| 529 | 0.002 | 0.002 | 2.621 | | |
| 530 | 0.834 | 0.565 | | | |
| 531 | 0.020 | 0.182 | NA| | | |
| 532 | 0.004 | 0.056 | NA| | | |
| 533 | 0.105 | 0.237 | | | |
| 534 | 0.001 | 0.003 | 1.497 | | |
| 535 | 0.070 | 0.262 | | | |
| 536 | 0.030 | 0.208 | | | |
| 537 | 0.003 | 0.009 | 4.684 | | |
| 538 | 0.241 | >1.00 | | | |
| 539 | 0.834 | >1.00 | | | |
| 540 | 0.070 | 0.396 | | | |
| 541 | 0.002 | 0.024 | 6.035 | | |
| 542 | 0.002 | 0.024 | 15.860 | | |
| 543 | 0.030 | 0.058 | | | |
| 544 | 0.000 | 0.001 | 0.633 | | |
| 545 | 0.001 | 0.001 | 3.610 | | |
| 546 | 0.001 | 0.001 | 0.970 | | |
| 547 | 0.001 | 0.003 | 12.000 | | |
| 548 | 0.001 | 0.002 | 4.890 | | |
| 549 | 0.001 | 0.005 | 11.200 | | |
| 550 | 0.001 | 0.004 | 6.690 | | |
| 551 | 0.005 | 0.012 | >31.60 | | |
| 552 | 0.001 | 0.003 | 2.740 | | |
| 553 | 0.077 | 0.520 | | | |
| 554 | 0.007 | 0.010 | 6.263 | | |
| 555 | 0.000 | 0.000 | 0.307 | | |
| 556 | >1.0 | >1.0 | | | |
| 557 | >1 | >1 | | | |
| 558 | 0.002 | 0.008 | | 0.156 | 3.800 |
| 559 | 0.000 | 0.001 | | 0.202 | 8.120 |
| 560 | 0.000 | 0.005 | | 0.394 | 4.780 |
| 561 | >1 | >1 | | | |
| 562 | >1 | >1 | | | |
| 563 | 0.087 | 0.143 | | | |
| 564 | 0.004 | 0.032 | | 0.219 | >31.6 |
| 565 | 0.001 | 0.002 | | 1.76 | 13.500 |
| 566 | 0.004 | 0.023 | | 5.59 | >31.6 |
| 567 | 0.001 | 0.002 | 1.33 | | |
| 568 | 0.020 | 0.021 | 2.09 | | |
| 569 | 0.001 | 0.001 | 0.282 | | |

The compounds of the present invention may be administered orally, parentally, by inhalation spray, rectally, or topically in dosage unit formulations containing conventional pharmaceutically acceptable carriers, adjuvants, and vehicles.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment.

The dosage regimen for using these compounds diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula 1a

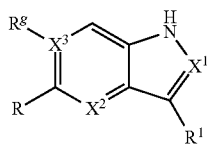

1a wherein $X^1$ is CH or N;

wherein $X^2$ is CH or N;

wherein $X^3$ is C or N;

wherein R is substituted or unsubstituted aryl, substituted or unsubstituted 5-membered heterocyclyl, substituted or unsubstituted 6-membered heterocyclyl, substituted or unsubstituted 9 membered heterocyclyl, substituted or unsubstituted 10 membered heterocyclyl, cycloalkylalkenyl, 1,2,2',3',5',6'-hexahydrospiro[indole-3,4'-pyranyl], alkylcarbonylamino, phenylaminocarbonyl, phenylcarbonylamino, benzylaminocarbonyl, alkylcarbonyl, hydroxyalkyl, haloalkyl, cyanoalkyl, substituted or unsubstituted cycloalkyl, substituted or unsubstituted arylamino, alkenyl, or haloalkenyl;

wherein $R^1$ is

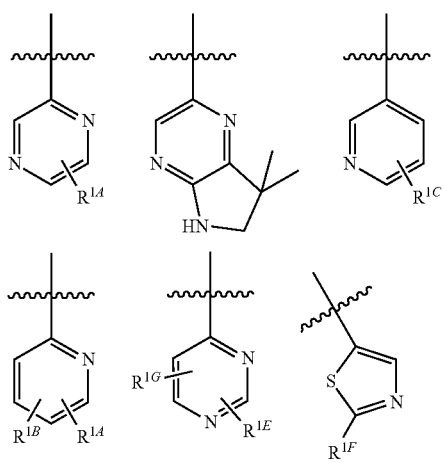

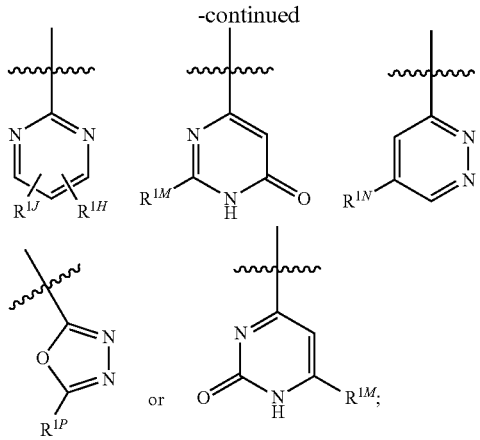

and wherein $R^g$ is H or F;

wherein $R^{1A}$ is H, hydroxy, $C_1$-$C_3$-alkoxy, $C_1$-$C_3$-haloalkoxy, substituted or unsubstituted 5-6-membered heterocyclyl, substituted or unsubstituted 5-6-membered heterocyclyl-amino, substituted or unsubstituted 5-6-membered heterocyclyl-(alkyl)amino, substituted or unsubstituted 5-6-membered heterocyclyloxy, alkylamino, $C_3$-$C_6$ cycloalkylamino, substituted or unsubstituted 5-6-membered heterocyclyl-S—, substituted or unsubstituted phenylamino or 9-10 membered nitrogen containing heterocyclyl;

wherein $R^{1B}$ is H, hydroxy or $C_1$-$C_3$-alkoxy;

wherein $R^{1C}$ is H, hydroxy, $C_1$-$C_3$-alkoxy, substituted or unsubstituted 5-6-membered heterocyclyl, or substituted or unsubstituted 5-6-membered heterocyclyl-amino;

wherein $R^{1E}$ is H, hydroxy, $C_1$-$C_3$-alkoxy, substituted or unsubstituted 5-6-membered heterocyclyl, substituted or unsubstituted 5-6-membered heterocyclyl-amino, substituted or unsubstituted 5-6-membered heterocyclyl-(alkyl)amino, substituted or unsubstituted 5-6-membered heterocyclyloxy or alkylamino;

wherein $R^{1F}$ is H, or substituted or unsubstituted 6-membered heterocyclyl;

wherein $R^{1G}$ is H, hydroxy or $C_1$-$C_3$-alkoxy;

wherein $R^{1J}$ is H, hydroxy, $C_1$-$C_3$-alkoxy, substituted or unsubstituted 5-6-membered heterocyclyl, or substituted or unsubstituted 5-6-membered heterocyclyl-amino or substituted or unsubstituted 5-6-membered heterocyclyl-(alkyl)amino or substituted or unsubstituted 5-6-membered heterocyclyloxy or alkylamino or substituted or unsubstituted 5-6-membered heterocyclyl-S—, or substituted or unsubstituted phenyl or 9-10 membered nitrogen containing heterocyclyl;

wherein $R^{1H}$ is H, hydroxy or $C_1$-$C_3$-alkoxy;

wherein $R^{1M}$ is H, lower alkyl, lower alkoxy, lower alkylamino, lower dialkylamino, substituted or unsubstituted 5-6-membered heterocyclyloxy, substituted or unsubstituted 5-6-membered heterocyclyl or substituted or unsubstituted 5-6-membered heterocyclylamino;

wherein $R^{1N}$ is H, or $C_1$-$C_3$-alkoxy; and wherein $R^{1P}$ substituted or unsubstituted phenylamino, lower alkylamino, substituted or unsubstituted 5-membered nitrogen-containing heterocyclyl, substituted or unsubstituted 5-membered nitrogen-containing heterocyclylamino, substituted or unsubstituted 6-membered nitrogen-containing heterocyclylamino, or substituted or unsubstituted 6-membered nitrogen-containing heterocyclyl;

or a pharmaceutically acceptable salt thereof;

provided $R^1$ is not 4-pyridyl when R is 3-pyridyl, when $X^1$ is CH, $X^2$ is CH and $X^3$ is C; further provided R is not 2,6-dimethyl-3,5-dicyano-dihydropyridyl when $X^1$ is N, $X^2$ is CH and $X^3$ is C; further provided $R^1$ is not 2-(4-morpholinyl-4-phenylamino)-4-pyrimidyl when $X^1$ is CH, $X^2$ is CH and $X^3$ is C; further provided R is not 2-(3-furyl)-(5-phenyl-2-aminopropoxy)-3-pyridyl when $X^1$ is N, $X^2$ is CH and $X^3$ is C; further provided R is not triazolyl or tetrazolyl when $X^1$ is N, $X^2$ is CH and $X^3$ is C; further provided R is not 7,9-dicyano-[1,3,4,8-tetrahydropyrido[2,1-c][1,4]oxazin-8-yl when $X^1$ is N, $X^2$ is CH and $X^3$ is C; further provided R is not 2-methoxypyridyl when Ry is 2-(4-amino-1-piperidyl)-6-pyrazinyl; and further provided R is not 3-cyano-2-methyl-5-oxo-1,4,5,7-tetrahydrofuro[3,4-b]pyridin-4-yl when $X^1$ is N, $X^2$ is CH, $X^3$ is C, $R^g$ is H and $R^1$ is 2-isopropoxypyridin-5-yl.

2. The compound of claim 1 wherein $X^1$ is CH; wherein $X^2$ is CH; wherein $X^3$ is C; and wherein $R^g$ is H; or a pharmaceutically acceptable salt thereof.

3. The compound of claim 1 wherein $X^1$ is N; wherein $X^2$ is CH; wherein $X^3$ is C; and wherein $R^g$ is H; or a pharmaceutically acceptable salt thereof.

4. The compound of claim 1 wherein $X^1$ is CH; wherein $X^2$ is N; wherein $X^3$ is C; and wherein $R^g$ is H; or a pharmaceutically acceptable salt thereof.

5. The compound of claim 1 wherein R is $C_{1-4}$ hydroxyalkyl, $C_{1-4}$ haloalkyl, $C_{1-4}$ cyanoalkyl, $C_3$-$C_6$-cycloalkyl-$C_2$-$C_3$-alkenyl, $C_{1-4}$ alkylcarbonyl, $C_{1-4}$ alkylcarbonylamino, phenylaminocarbonyl, phenylcarbonylamino, benzylaminocarbonyl, substituted or unsubstituted $C_6$-$C_{10}$-arylamino, $C_{2-4}$ alkenyl, or $C_{2-4}$ haloalkenyl; or a pharmaceutically acceptable salt thereof.

6. The compound of claim 1 wherein R is methylcarbonyl, cyanomethyl, 2,6-difluorophenylamino, ethylcarbonylamino, phenylcarbonylamino, phenylaminocarbonyl, benzylaminocarbonyl, hydroxyethyl, 1-hydroxy-2-propyl, isopropyl, 1-methylcyclopropyl, 1-trifluoromethylcyclopropyl, 3,3,3-trifluoroprop-2-yl, prop-1-en-2-yl, 3,3,3-trifluoroprop-1-en-2-yl or cyclopropylethenyl; or a pharmaceutically acceptable salt thereof.

7. The compound of claim 1 wherein R is substituted or unsubstituted $C_3$-$C_6$ cycloalkyl, substituted or unsubstituted phenyl or substituted or unsubstituted 5-membered heterocyclyl or substituted or unsubstituted 6-membered heteroaryl or substituted or unsubstituted 9 membered heteroaryl or substituted or unsubstituted 10 membered heteroaryl; or a pharmaceutically acceptable salt thereof.

8. The compound of claim 1 wherein R is substituted or unsubstituted phenyl, substituted or unsubstituted pyrrolidinyl, substituted or unsubstituted piperidinyl, substituted or unsubstituted pyranyl, substituted or unsubstituted 5,6-dihydro-2H-pyranyl, substituted or unsubstituted 3,6-dihydro-2H-pyranyl, substituted or unsubstituted tetrahydro-pyranyl, substituted or unsubstituted morpholinyl, substituted or unsubstituted imidazolidinyl, substituted or unsubstituted cyclopropyl, substituted or unsubstituted cyclobutyl, substituted or unsubstituted cyclopentyl, substituted or unsubstituted thiazolyl, substituted or unsubstituted pyrazolyl, substituted or unsubstituted imidazolyl, substituted or unsubstituted oxazolyl, substituted or unsubstituted pyrazinyl, substituted or unsubstituted pyridazinyl, substituted or unsubstituted pyrimidinyl, substituted or unsubstituted pyridyl, substituted or unsubstituted indazolyl, substituted or unsubstituted quinoxalinyl, substituted or unsubstituted 1H-pyrazolo[3,4-b]pyridinyl, substituted or unsubstituted 2,3-dihydro-indolyl, substituted or unsubstituted benzothiazolyl, substituted or unsubstituted 3,4-dihydro-2H-pyrido[3,2-b][1,4]oxazinyl, substituted or unsubstituted 3,4-dihydro-2H-1,4-benzoxazinyl, substituted or unsubstituted 1H-pyrrolo[2,3-b]pyridinyl, substituted or unsubstituted 1H-pyrrolo[3,2-c]pyridinyl, substituted or unsubstituted imidazo[1,2-a]pyrazinyl, substituted or unsubstituted [1,2,4]triazolo[4,3-a]pyridinyl, substituted or unsubstituted 1,2,2',3',5',6'-hexahydrospiro[indole-3,4'-pyran]yl, substituted or unsubstituted 2,3-dihydro-1,4-benzodioxinyl, or substituted or unsubstituted quinolyl; or a pharmaceutically acceptable salt thereof.

9. The compound of claim 1 wherein R is phenyl, 2,6-difluorophenyl, 2,5-difluorophenyl, 2,4-difluorophenyl, 2,3-difluorophenyl, 2-fluorophenyl, 3-fluorophenyl, 2-fluoro-5-nitrophenyl, 4-aminocarbonyl-2-fluorophenyl, 3-aminocarbonyl-6-fluorophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(piperidin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-fluoro-4-hydroxyphenyl, 2-hydroxyphenyl, 3-hydroxyphenyl, 3-methoxyphenyl, 3,5-dimethoxyphenyl, 3-isopropoxyphenyl, 3-trifluoromethoxyphenyl, 2-trifluoromethylphenyl, 3-aminophenyl, 3-amino-2-methylphenyl, 3-(1-hydroxyethyl)phenyl, 2-cyanophenyl, 3-cyanophenyl, 4-cyano-2-fluorophenyl, 2-cyano-6-fluorophenyl, 2-chlorophenyl, 2-chloro-6-fluorophenyl, 3-chloro-6-fluorophenyl, 4-chloro-2-fluorophenyl, 3-methylsulfonylphenyl, 2-fluoro-4-methylsulfonylphenyl, 4-methylsulfonylphenyl, 2,6-difluoro-4-methylsulfonylphenyl, 2-fluoro-4-methylsulfonylamino-phenyl, 4-aminosulfonyl-2-fluorophenyl, 3-dimethylaminophenyl, 3-amino-4-morpholinophenyl, 3-amino-6-trifluoromethoxyphenyl, 4-amino-2-fluorophenyl, 2-fluoro 4-methylcarbonylaminophenyl, ethynylphenyl, (1-chlorovinyl)benzene, 2-methylphenyl, 2-pyridyl, 3-pyridyl, 4-pyridyl, 2-hydroxy-3-pyridyl, 2-amino-4-pyridyl, 3-amino-5-pyridyl, 3-amino-2-pyridyl, 2-amino-6-fluoro-5-pyridyl, 4-cyano-3-pyridyl, 2-cyano-3-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 2-fluoro-3-pyridyl, 4-fluoro-3-pyridyl, 2,4-difluoro-3-pyridyl, 3-fluoro-2-pyridyl, 3-fluoro-4-pyridyl, 3-fluoro-5-pyridyl, 3-methyl-2-pyridyl, 2-trifluoromethyl-6-pyridyl, 4-trifluoromethyl-2-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 4-(3-methylmorpholin-4-yl)-pyrimidin-2-yl, 2-amino-4-cyclopentylamino-pyrimidin-5-yl, 4-cyclopropylaminopyrimidin-2-yl, 4-isobuthylpyrimidin-2-yl, 4-cyclopropylpyrimidin-2-yl, 2-cyclopropylpyrimidin-4-yl, 4-oxo-pyrimidin-5-yl, 2-methoxy-pyrimidin-4-yl, 2-isopropoxypyrimidin-4-yl, 3-pyrazinyl, 2-aminopyrazin-6-yl, 2-cyclopropyl-6-pyrazinyl, 2-cyclopropylamino-6-pyrazinyl, 2-isopropoxy-6-pyrazinyl, 3-pyridazinyl, 4-amino-pyridazin-6-yl, 3-quinolyl, 2-hydroxy-3-quinolyl, 2-chloro-3-quinolyl, 7-methoxy-4-quinolyl, 7-fluoro-4-quinolyl, 7-cyano-4-quinolyl, 7-trifluoromethoxy-4-quinolyl, 2-methoxy-3-quinolyl, 1-methyl-2-oxo-quinolin-4-yl, 1-methyl-2-oxo-isoquinolin-6-yl, 6-quinoxalinyl, 3-trifluoromethyl-1H-pyrazolo[3,4-b]pyridin-5-yl, 3-trifluoromethyl-5-indazolyl, 1-methyl-2-oxo-2,3-dihydro-indol-5-yl, 1-(2-aminopyrimidin-4-yl)-2,3-dihydro-indol-6-yl, benzothiazol-5-yl, benzothiazol-6-yl, 4-methyl-3,4-dihydro-2H-pyrido[3,2-b][1,4]oxazin-7-yl, 4-methyl-3,4-dihydro-2H-1,4-benzoxazin-7-yl, 1H-pyrrolo[2,3-b]pyridin-5-yl, 1H-pyrrolo[3,2-c]pyridin-4-yl, 1H-pyrrolo[3,2-c]pyridin-6-yl, 1H-pyrrolo[2,3-b]pyridin-6-yl, imidazo[1,2-a]pyrazin-5-yl, [1,2,4]triazolo[4,3-a]pyridin-5-yl, 1,2,2',3',5',6'-hexahydrospiro[indole-3,4'-pyran]-4-yl and 2,3-dihydro-1,4-benzodioxin-6-yl, 1H-pyrazol-5-yl, 1-methyl-1H-pyrazol-4-yl, 1-methyl-1H-pyrazol-5-yl, 1-isopropyl-1H-pyrazol-4-yl, thiazol-2-yl, 2-(2-methylpiperidin-1-yl)thiazol-4-yl, 2-(pyrrolidin-1-yl)thiazol-4-yl, 1-methyl-5-imidazolyl, 2-oxazolyl, 4-pyranyl, 3-pyranyl, 5,6-dihydro-2H-pyran-3-yl, 3,6-dihydro-2H-pyran-4-yl, tetrahydro-4-pyranyl, tetrahydro-3-pyranyl, 2-oxo-pyrrolidin-1-yl, 2-oxo-piperidin-1-yl, morpholin-4-yl, 1-methyl-2-oxo-imidazolidin-3-yl, 1-piperidinyl, cyclopropyl, cyclobutyl, cyclopentyl, 3-methyl-morpholin-4-yl, 2-methyl-morpholin-4-yl, 3-oxo-morpholin-4-yl, morpholin-4-yl; or a pharmaceutically acceptable salt thereof.

10. The compound of claim 1 wherein $R^{1A}$ is piperidin-3-ylamino, piperidin-4-ylamino, piperidin-4-yl-N-methylamino, piperidin-3-yl-N-methylamino, pyrrolidin-3-ylamino, 3-azetidinylamino, cyclopropylamino, hydroxy, methoxy, isopropoxy, trifluoroethoxy, fluoroethoxy, 3-pyridyloxy, 3-azetidinyloxy, pyrrolidin-3-yloxy, piperidin-3-yloxy, 4-fluoro-piperidin-3-yloxy, 3-fluoro-piperidin-4-yloxy, 3-fluoro-piperidin-5-yloxy, 3-methyl-piperidin-3-yloxy, 3-methyl-piperidin-5-yloxy, 1-methyl-piperidin-4-yloxy, 4-isopropyl-piperidin-3-yloxy, 4-ethyl-piperidin-3-yloxy, 4-methyl-piperidin-3-yloxy, 4,4-dimethyl-piperidin-3-yloxy, 3,3-dimethyl-piperidin-4-yloxy, piperidin-4-yloxy, 1,2,3,6-tetrahydro-3-pyridinyloxy, 6-azaspiro[2.5]oct-4-yloxy, 5-azaspiro[2.5]oct-8-yloxy, 3-azabicyclo[4.1.0]hept-5-yloxy, ((3S)-4-methylidene-3-piperidinyl)oxy, piperidin-3-ylthio, methylamino, ethylamino, isopropylamino, tert-butylamino, dimethylamino, phenylamino, piperidin-3-ylmethyl, piperidin-4-ylmethyl, cyclopropyl, 3-pyridyl, 5-indazolyl, 1,4-diazepan-1-yl, 1-pyrrolidinyl, 3-hydroxypyrrolidin-1-yl, 3,4-dihydroxypyrrolidin-1-yl, 3-aminopyrrolidinyl, 4-aminopiperidin-1-yl, 3-aminopiperidinyl, 3-hydroxypiperidin-1-yl, 3,4-dihydroxypiperidin-1-yl, 4-hydroxypiperidinyl, 4-morpholinyl, 3-pyrazolyl, 3-azetidinyl, 1-piperazinyl, or 1-piperidinyl; $R^{1E}$ is 4-aminopiperidin-1-yl, piperidin-3-ylamino, piperidin-4-ylamino, piperidin-4-yloxy or piperidin-3-yl; $R^{1G}$ is H, hydroxy or methoxy; $R^{1H}$ is H, hydroxy or methoxy; $R^{1J}$ is 4-aminopiperidin-1-yl, piperidin-3-ylamino, piperidin-4-ylamino or piperidin-3-yl; $R^{1M}$ is butyl, dimethylamino, isopropylamino, isopropoxy, 3-fluoro-piperidin-4-yloxy, 4-fluoro-piperidin-3-yloxy, piperidin-3-yloxy, 6-azaspiro[2.5]octan-4-yloxy, 4-aminopiperidin-1-yl, 3-hydroxypyrrolidin-1-yl, piperidin-3-ylamino, piperidin-4-ylamino or 3-methylpiperidin-5-ylamino; wherein $R^{1N}$ is H or methoxy; and wherein $R^{1P}$ phenylamino, isopropylamino, 3-aminopiperidin-1-yl, 4-aminopiperidin-1-yl, piperidin-3-ylamino, pyrrolidin-3-ylamino, or pyrrolidin-1-yl; or a pharmaceutically acceptable salt thereof.

11. A compound of Formula 2'

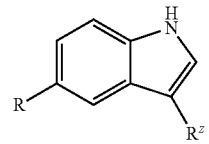

2'

Wherein $R^z$ is substituted or unsubstituted thiazolyl, substituted or unsubstituted oxadiazolyl, substituted or unsubstituted pyrazinyl, substituted or unsubstituted pyridyl, substituted or unsubstituted pyrimidinyl, substituted or unsubstituted oxo-pyrimidinyl or substituted or unsubstituted indazolyl;

Wherein R is substituted or unsubstituted cycloalkyl, substituted or unsubstituted phenyl, substituted or unsubstituted 7-azaindolyl, substituted or unsubstituted 1,2,3,4-tetrahydro-1,8-naphthyridyl, substituted or unsubstituted 1H-pyrazolo[3,4-b]pyridyl, substituted or unsubstituted benzomorpholinyl, substituted or unsubstituted pyrazinyl, substituted or unsubstituted pyridazinyl, substituted or unsubstituted pyrimidinyl, substituted or unsubstituted pyridyl, substituted or unsubstituted thiazolyl, substituted or unsubstituted pyrazolyl, or substituted or unsubstituted oxazolyl;

or a pharmaceutically acceptable salt thereof;

provided $R^z$ is not 4-pyridyl when R is 3-pyridyl.

12. The compound of claim 11 wherein $R^z$ is substituted or unsubstituted thiazol-4-yl or substituted or unsubstituted oxadiazol-2-yl; or a pharmaceutically acceptable salt thereof.

13. The compound of claim 11 wherein R is substituted or unsubstituted phenyl; or a pharmaceutically acceptable salt thereof.

14. The compound of claim 11 wherein R is substituted or unsubstituted pyrazinyl, substituted or unsubstituted pyridazinyl, substituted or unsubstituted pyrimidinyl, or substituted or unsubstituted pyridyl, or a pharmaceutically acceptable salt thereof.

15. The compound of claim 11 wherein $R^z$ is 2-(1-imidazolyl)thiazol-4-yl, 2-(2-oxo-pyrid-1-yl)thiazol-4-yl, 5-isopropylamino-oxadiazol-2-yl, 5-phenylamino-oxadiazol-2-yl, 5-(3-aminopiperidin-1-yl)oxadiazol-2-yl, 5-(4-aminopiperidin-1-yl)oxadiazol-2-yl, 5-(piperidin-3-ylamino)oxadiazol-2-yl, 5-(pyrrolidin-3-ylamino)oxadiazol-2-yl, 5-pyrrolidin-1-yl-oxadiazol-2-yl, pyrazin-2-yl, 2-dimethylaminopyrazin-6-yl, 2-(cyclohexylamino)pyrazin-6-yl, 2-(pyrrolidin-3-ylamino)pyrazin-6-yl, 2-(piperidin-3-ylamino)pyrazin-6-yl, 2-(piperidin-4-ylamino)pyrazin-6-yl, 2-(2-oxopiperazin-4-ylamino)pyrazin-6-yl, 2-(piperidin-3-yloxy)pyrazin-6-yl, 2-(3-amino-pyrrolidin-1-yl)pyrazin-6-yl, 2-(4-aminopiperidin-1-yl)pyrazin-6-yl, 2-isopropylaminopyrazin-6-yl, 2-(3-aminopiperidin-1-yl)pyrazin-6-yl, 2-(morpholin-4-yl)pyrazin-6-yl, 2-methoxy-pyrazin-6-yl, 2-methoxy-pyrazin-5-yl, 2-isopropoxy-pyrazin-6-yl, 2-(piperidin-3-yloxy)pyrazin-6-yl, 2-(piperidin-4-yloxy)pyrazin-6-yl, 2-cyclopropylpyrazin-6-yl, 2-(morpholin-4-yl)pyrid-6-yl, 2-(2-oxo-pyrrolidin-1-yl)pyrid-6-yl, 2-(pyrazol-1-yl)pyrid-6-yl, 3-fluoro-6-pyridyl, 2-amino-6-pyridyl, 2-amino-4-pyridyl, 4-amino-2-pyridyl, 2-amino-3-chloropyrid-5-yl, 4-methyl-2-pyridyl, 3-methyl-6-pyridyl, 2-isopropoxy-pyrid-6-yl, 4-(piperidin-3-ylamino)pyrimidin-2-yl, 4-(piperidin-3-ylamino)-6-methoxypyrimidin-2-yl, 2-(4-aminopiperidin-1-yl)-4-methoxypyrimidin-6-yl, 2-(4-aminopiperidin-1-yl)-4-oxypyrimidin-6-yl, 4-(piperidin-3-yloxy)pyrimidin-2-yl, 4-(piperidin-4-yloxy)pyrimidin-2-yl, 4-(piperidin-4-ylamino)pyrimidin-2-yl, 4-(piperidin-3-ylamino)-6-hydroxypyrimidin-2-yl, 2-(piperidin-3-ylamino)-6-hydroxypyrimidin-4-yl, 2-(morpholinin-4-yl)-6-hydroxypyrimidin-4-yl, 2-(morpholinin-4-yl)-4-hydroxypyrimidin-6-yl, 2-(morpholinin-4-yl)-4-methoxypyrimidin-6-yl, 4-(morpholin-4-yl)-6-methoxypyrimidin-2-yl, 2-(piperidin-3-yloxy)-6-methoxypyrimidin-4-yl, 2-(piperidin-3-ylamino)-6-methoxypyrimidin-4-yl, 2-(4-aminopiperidin-1-yl)-4-methoxypyrimidin-6-yl, 2-(4-aminopiperidin-1-yl)-4-hydroxypyrimidin-6-yl, 4-(4-aminopiperidin-1-yl)-6-hydroxypyrimidin-2-yl, 4-cyclopropylpyrimidin-2-yl, 6-(4-aminopiperidin-1-yl)-2-oxopyrimidin-4-yl, 2-(4-aminopiperidin-1-yl)-4-oxopyrimidin-6-yl, 2-isopropylamino-4-oxopyrimidin-6-yl, 4-isopropylamino-2-oxopyrimidin-6-yl, 2-dimethylamino-4-oxopyrimidin-6-yl, 4-dimethylamino-6-oxopyrimidin-2-yl, or 6-indazolyl; or a pharmaceutically acceptable salt thereof.

16. The compound of claim 11 wherein R is phenyl, 2-fluorophenyl, 2,6-difluorophenyl, 2-chloro-6-fluorophenyl, 3-fluoro-4-methoxyphenyl, 3-fluoro-4-cyanophenyl, 4-fluoro-3-cyanophenyl, 3-chloro-6-methoxyphenyl, 3,4-dimethoxyphenyl, 3,5-dimethoxyphenyl, 2,5-dimethoxyphenyl, 3-methoxyphenyl, 4-methoxyphenyl, 3-cyano-5,6-dimethoxyphenyl, 3-cyano-4-isopropoxyphenyl, 4-isopropoxyphenyl, 3-isopropoxyphenyl, 3-cyano-5-methoxy-6-propoxyphenyl, 3-cyano-6-isopropoxy 5-methoxyphenyl, 2-cyano-5-isopropoxy-4-methoxyphenyl, 4-isopropylphenyl, 4-isobutylphenyl, 2,3-dimethylphenyl, 3,5-dimethyl-4-methoxyphenyl, 3-hydroxymethylphenyl, 4-hydroxymethylphenyl, 3-(2-hydroxyethyl)phenyl, 2-methyl-5-trifluoromethylphenyl, 3-carboxyphenyl, 2-cyanophenyl, 4-(methylcarbonylamino)phenyl, 4-(cyclopropylcarbonylamino)phenyl, 3-(cyclobutylaminocarbonyl)-6-methylphenyl, 3-(methylcarbonylamino)-5-trifluoromethylphenyl, 3-(ethylaminocarbonyl)-6-methylphenyl, 3-difluoromethoxyphenyl, 4-amino-3-trifluoromethoxyphenyl, benzodioxolyl, 3-(pyrazol-3-yl)phenyl, 3-tetrazol-5-ylphenyl, 3-isoxazol-5-ylphenyl, 3-(2-methylthiazol-4-yl)phenyl, 3-(1-cyanocyclobutyl)phenyl, or 4-(morpholin-4-yl)phenyl; or a pharmaceutically acceptable salt thereof.

17. The compound of claim 11 wherein $R^z$ is thiazol-4-yl substituted with substituted or unsubstituted 5-membered nitrogen-containing heterocyclyl or substituted or unsubstituted 6-membered nitrogen-containing heterocyclyl, oxadiazol-2-yl substituted with phenylamino, lower alkylamino, 5-membered nitrogen-containing heterocyclyl, substituted or unsubstituted 5-membered nitrogen-containing heterocyclylamino, substituted or unsubstituted 6-membered nitrogen-containing heterocyclylamino, or substituted or unsubstituted 6-membered nitrogen-containing heterocyclyl, pyrazin-2-yl substituted with alkylamino, dialkylamino, lower cycloalkylamino, substituted or unsubstituted 5-membered nitrogen-containing heterocyclyl, substituted or unsubstituted 6-membered nitrogen-containing heterocyclyl, $C_1$-$C_3$ alkoxy, substituted or unsubstituted 6-membered nitrogen-containing heterocyclyloxy, substituted or unsubstituted 6-membered nitrogen-containing heterocyclylamino, substituted or unsubstituted 5-membered nitrogen-containing heterocyclylamino, substituted or unsubstituted $C_3$-$C_6$ cycloalkyl, pyrid-2-yl substituted with substituted or unsubstituted 5-membered nitrogen-containing heterocyclyl, substituted or unsubstituted 6-membered nitrogen-containing heterocyclyl, $C_1$-$C_3$ alkoxy, $C_1$-$C_3$ alkyl, amino, fluoro, pyrid-4-yl substituted with amino, pyrimidin-2-yl substituted with substituted or unsubstituted 6-membered nitrogen-containing heterocyclyloxy, or substituted or unsubstituted 6-membered nitrogen-containing heterocyclylamino, 2-oxo-pyrimidin-4-yl unsubstituted or substituted with substituted or unsubstituted 6-membered nitrogen-containing heterocyclyloxy, or substituted or unsubstituted 6-membered nitrogen-containing heterocyclylamino, or substituted or unsubstituted indazolyl;

wherein the substituted 5-membered nitrogen-containing heterocyclyl, or substituted 6-membered nitrogen-containing heterocyclyl are substituted with one or more substituents selected from hydroxy, amino, oxo, methyl, fluoro, $=CH_2$, or a pharmaceutically acceptable salt thereof.

18. The compound of claim 11 wherein R is oxazolyl, 1-cyclopropyl-3-pyrazolyl, 2-(2-methylpiperidin-1-yl)thiazol-4-yl, or 1-isopropylpyrazol-4-yl; or a pharmaceutically acceptable salt thereof.

19. The compound of claim 11 wherein R is 2-(isopropoxy)-pyrazin-6-yl, 2-cyclopentyloxypyrazin-6-yl, 2-cyclopropylpyrazin-6-yl, 2-cyclopropylaminopyrazin-6-yl, 2-dimethylamino-pyrazin-5-yl, 2-isopropoxypyrazin-6-yl, 2-(pyrazol-1-yl)pyrazin-5-yl, 2-(pyrrolidin-1-yl)pyrazin-6-yl, 2-(3-methylpiperidin-1-yl)pyrazin-5-yl, 3-chloropyrid-5-yl, 3-chloropyrid-4-yl, 3-cyclopropylaminopyrid-5-yl, 3-fluoro-6-methoxypyrid-4-yl, 2-methoxypyrid-3-yl, 2-methoxypyrid-5-yl, 2-cyclopentyloxy-pyrid-6-yl, 2-cyclobutyloxy-pyrid-6-yl, 2-cyclopropylmethoxy-pyrid-5-yl, 2-(piperazin-1-yl)pyrid-6-yl, 2-(4-methylpiperidin-1-yl)-6-pyridyl, 2-(2-methyl-imidazol-1-yl)pyrid-6-yl, 2-(3-methylpyrazol-1-yl)pyrid-6-yl, 3-(pyrrolidin-2-yl)pyrid-5-yl, 2-cyanopyrid-3-yl, 2-chloro-3-methylsulfonylamino-pyrid-5-yl, 2-(4-aminophenyloxy)pyrid-3-yl, 2-(morpholin-4-yl)pyrid-3-yl, 4-dihydroxypyrimidin-5-yl, or 4-cyclopropylpyrimidin-2-yl;

or a pharmaceutically acceptable salt thereof.

20. The compound of claim 11 wherein R is 2,2-dimethylcyclopropyl; or a pharmaceutically acceptable salt thereof.

21. The compound of claim 11 wherein R is 3-methyl-1H-pyrazolo[3,4-b]pyrid-5-yl, 7-azaindol-5-yl, 4-methylbenzomorpholin-7-yl, or 1,2,3,4-tetrahydro-1,8-naphthyrid-6-yl; or a pharmaceutically acceptable salt thereof.

22. A compound of Formula 3'

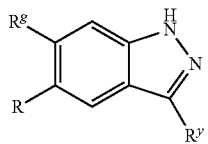

Wherein $R^g$ is H or F;
Wherein $R^y$ is

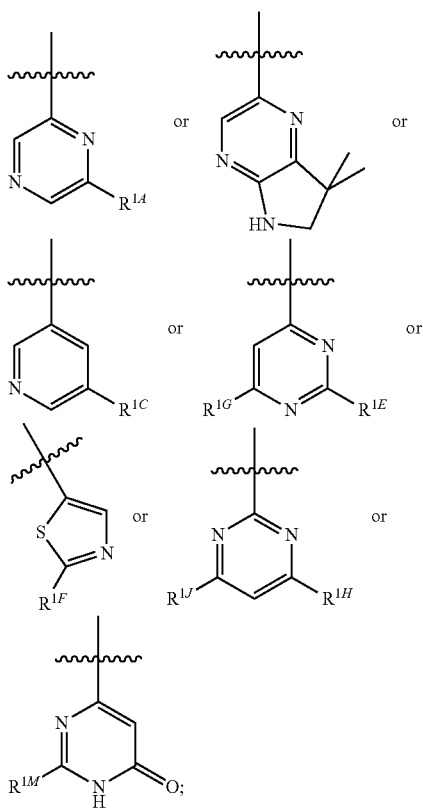

Wherein R is substituted or unsubstituted $C_6$-$C_{10}$-aryl, substituted or unsubstituted 5-6-membered heterocyclyl, substituted or unsubstituted 9-10-membered heterocyclyl, 1,2,2',3',5',6'-hexahydrospiro[indole-3,4'-pyran]-4-yl, halo, $C_{1-4}$ hydroxyalkyl, $C_{1-4}$ haloalkyl, substituted or unsubstituted $C_3$-$C_6$ cycloalkyl, $C_3$-$C_6$-cycloalkyl-$C_2$-$C_3$-alkenyl, $C_{1-4}$ alkylcarbonyl, $C_{1-4}$ alkylcarbonylamino, phenylaminocarbonyl, phenylcarbonylamino, $C_{1-4}$ cyanoalkyl, benzylaminocarbonyl, substituted or unsubstituted $C_6$-$C_{10}$-arylamino, $C_{2-4}$ alkenyl, or $C_{2-4}$ haloalkenyl; provided R is not 2-methoxypyridyl when Ry is 2-(4-amino-1-piperidyl)-6-pyrazinyl;

Wherein $R^{1A}$ is H, hydroxy, $C_1$-$C_3$-alkoxy, $C_1$-$C_3$-haloalkoxy, substituted or unsubstituted 5-6-membered heterocyclyl, substituted or unsubstituted 5-6-membered heterocyclyl-amino, substituted or unsubstituted 5-6-membered heterocyclyl-(alkyl)amino, substituted or unsubstituted 5-6-membered heterocyclyloxy, alkylamino, $C_3$-$C_6$ cycloalkylamino, substituted or unsubstituted 5-6-membered heterocyclyl-S—, or substituted or unsubstituted phenylamino or 9-10 membered nitrogen containing heterocyclyl;

Wherein $R^{1C}$ is H, $C_1$-$C_3$-alkoxy, substituted or unsubstituted 5-6-membered heterocyclyl, or substituted or unsubstituted 5-6-membered heterocyclyl-amino;

Wherein $R^{1E}$ is H, $C_1$-$C_3$-alkoxy, substituted or unsubstituted 5-6-membered heterocyclyl, substituted or unsubstituted 5-6-membered heterocyclyl-amino, substituted or unsubstituted 5-6-membered heterocyclyl-(alkyl)amino, substituted or unsubstituted 5-6-membered heterocyclyloxy or alkylamino;

Wherein $R^{1F}$ is H, or substituted or unsubstituted 6-membered heterocyclyl;

Wherein $R^{1G}$ is H, hydroxy or $C_1$-$C_3$-alkoxy;

Wherein $R^{1H}$ is H, hydroxy or $C_1$-$C_3$-alkoxy;

Wherein $R^{1J}$ is H, hydroxy, $C_1$-$C_3$-alkoxy, substituted or unsubstituted 5-6-membered heterocyclyl, or substituted or unsubstituted 5-6-membered heterocyclyl-amino, or substituted or unsubstituted 5-6-membered heterocyclyl-(alkyl)amino or substituted or unsubstituted 5-6-membered heterocyclyloxy or alkylamino or substituted or unsubstituted 5-6-membered heterocyclyl-S—, or substituted or unsubstituted phenyl or 9-10 membered nitrogen containing heterocyclyl; and Wherein $R^{1M}$ is H, lower alkyl, lower alkoxy, lower alkylamino, lower dialkylamino, substituted or unsubstituted 5-6-membered heterocyclyloxy, substituted or unsubstituted 5-6-membered heterocyclyl or substituted or unsubstituted 5-6-membered heterocyclylamino;

or a pharmaceutically acceptable salt thereof; provided R is not 2,6-dimethyl-3,5-dicyano-dihydropyridyl; further provided R is not 2-(3-furyl)-(5-phenyl-2-aminopropoxy)-3-pyridyl; further provided R is not triazolyl or tetrazolyl; further provided R is not 7,9-dicyano-[1,3,4,8-tetrahydropyrido[2,1-c][1,4]oxazin-8-yl; and further provided R is not 3-cyano-2-methyl-5-oxo-1,4,5,7-tetrahydrofuro[3,4-b]pyridin-4-yl, when $R^g$ is H and $R^1$ is 2-isopropoxypyridin-5-yl.

23. The compound of claim 22 wherein $R^{1A}$ is piperidin-3-ylamino, piperidin-4-ylamino, piperidin-4-yl-N-methylamino, piperidin-3-yl-N-methylamino, pyrrolidin-3-ylamino, 3-azetidinylamino, cyclopropylamino, hydroxy, methoxy, isopropoxy, trifluoroethoxy, fluoroethoxy, 3-pyridyloxy, 3-azetidinyloxy, pyrrolidin-3-yloxy, piperidin-3-yloxy, 4-fluoro-piperidin-3-yloxy, 3-fluoro-piperidin-4-yloxy, 3-fluoro-piperidin-5-yloxy, 3-methyl-piperidin-3-yloxy, 3-methyl-piperidin-5-yloxy, 1-methyl-piperidin-4- yloxy, 4-isopropyl-piperidin-3-yloxy, 4-ethyl-piperidin-3-yloxy, 4-methyl-piperidin-3-yloxy, 4,4-dimethyl-piperidin-3-yloxy, 3,3-dimethyl-piperidin-4-yloxy, piperidin-4-yloxy, 1,2,3,6-tetrahydro-3-pyridinyloxy, 6-azaspiro[2.5]oct-4-yloxy, 5-azaspiro[2.5]oct-8-yloxy, 3-azabicyclo[4.1.0]hept-5-yloxy, ((3S)-4-methylidene-3-piperidinyl)oxy, piperidin-3-ylthio, methylamino, ethylamino, isopropylamino, tert-butylamino, dimethylamino, phenylamino, piperidin-3-ylmethyl, piperidin-4-ylmethyl, cyclopropyl, 3-pyridyl, 5-indazolyl, 1,4-diazepan-1-yl, 1-pyrrolidinyl, 3-hydroxy-pyrrolidin-1-yl, 3,4-dihydroxypyrrolidin-1-yl, 3-aminopyrrolidinyl, 4-aminopiperidin-1-yl, 3-aminopiperidinyl, 3-hydroxypiperidin-1-yl, 3,4-dihydroxypiperidin-1-yl, 4-hydroxypiperidinyl, 4-morpholinyl, 3-pyrazolyl, 3-azetidinyl, 1-piperazinyl, or 1-piperidinyl; $R^{1E}$ is 4-aminopiperidin-1-yl, piperidin-3-ylamino, piperidin-4-ylamino, piperidin-4-yloxy or piperidin-3-yl; $R^{1G}$ is H, hydroxy or methoxy; $R^{1H}$ is H, hydroxy or methoxy; $R^{1J}$ is 4-aminopiperidin-1-yl, piperidin-3-ylamino, piperidin-4-ylamino or piperidin-3-yl; and $R^{1M}$ is butyl, dimethylamino, isopropylamino, isopropoxy, 3-fluoro-piperidin-4-yloxy, 4-fluoro-piperidin-3-yloxy, piperidin-3-yloxy, 6-azaspiro[2.5]octan-4-yloxy, 4-aminopiperidin-1-yl, 3-hydroxypyrrolidin-1-yl, piperidin-3-ylamino, piperidin-4-ylamino or 3-methylpiperidin-5-ylamino;

or a pharmaceutically acceptable salt thereof.

24. The compound of claim 22 wherein R is substituted or unsubstituted Nitrogen containing-6 membered heteroaryl or substituted or unsubstituted phenyl; or a pharmaceutically acceptable salt thereof.

25. The compound of claim 22 wherein R is phenyl substituted or unsubstituted with one or more substituents selected from fluoro, chloro, nitro, amino, cyano, methyl, trifluoromethyl, 1-hydroxyethyl, ethynyl, 1-chlorovinyl, oxo, hydroxy, methoxy, isopropoxy, trifluoromethoxy, methylsulfonyl, dimethylamino, morpholinyl, aminosulfonyl, methylsulfonylamino, aminocarbonyl, methylcarbonylamino, isopropylaminocarbonyl, cyclopropylaminocarbonyl, phenylaminocarbonyl, diethylaminocarbonyl, dimethylaminocarbonyl, benzylaminocarbonyl, tert-butylaminocarbonyl, butylaminocarbonyl, propylaminocarbonyl, ethylaminocarbonyl, cyclopropylaminocarbonyl, cyclohexylaminocarbonyl, piperidinylcarbonyl or morpholinylcarbonyl;

or a pharmaceutically acceptable salt thereof.

26. The compound of claim 22 wherein R is pyridyl, or pyrimidinyl, or pyrazinyl, or pyridazinyl, wherein R is substituted or unsubstituted with one or more substituents selected from hydroxy, amino, cyano, cyclopropyl, fluoro, chloro, methoxy, isopropoxy, ethoxy, methyl, isopropyl, isobutyltrifluoromethyl, tert-butylaminocarbonyl, tert-butylcarbonylamino, 4-cyclopropylaminocarbonyl, oxo, morpholinyl, 3-methylmorpholinyl, cyclopropylamino or cyclopentylamino; and a pharmaceutically acceptable salt thereof.

27. The compound of claim 22 wherein R is quinolyl, isoquinolinyl, quinoxalinyl, pyrazolo[3,4-b]pyridinyl, 2,3-dihydro-indolyl, indazolyl, benzothiazolyl, 3,4-dihydro-2H-pyrido[3,2-b][1,4]oxazinyl, 3,4-dihydro-2H-1,4-benzoxazinyl, 1H-pyrrolo[2,3-b]pyridinyl, 1H-pyrrolo[3,2-c]pyridinyl, imidazo[1,2-a]pyrazinyl, [1,2,4]triazolo[4,3-a]pyridinyl, 1,2,2',3',5',6'-hexahydrospiro[indole-3,4'-pyranyl] or 2,3-dihydro-1,4-benzodioxinyl; wherein R is substituted or unsubstituted with one or more substituents selected from hydroxy, cyano, chloro, methoxy, fluoro, trifluoromethoxy, methyl, oxo, trifluoromethyl or 2-aminopyrimidin-4-yl; or a pharmaceutically acceptable salt thereof.

28. The compound of claim 22 wherein R is cyclopropyl, cyclobutyl, cyclopentyl, pyranyl, 5,6-dihydro-2H-pyranyl, 3,6-dihydro-2H-pyranyl, tetrahydropyranyl, pyrrolidinyl, piperidinyl, morpholinyl, or imidazolidinyl; wherein R is substituted or unsubstituted with one or more substituents selected from methyl, or oxo; or a pharmaceutically acceptable salt thereof.

29. The compound of claim 22 wherein R is methylcarbonyl, cyanomethyl, 2,6-difluorophenylamino, ethylcarbonylamino, phenylcarbonylamino, phenylaminocarbonyl, benzylaminocarbonyl, hydroxyethyl, 1-hydroxy-2-propyl, isopropyl, 1-methylcyclopropyl, 1-trifluoromethylcyclopropyl, 3,3,3-trifluoroprop-2-yl, prop-1-en-2-yl, 3,3,3-trifluoroprop-1-en-2-yl or cyclopropylethenyl; or a pharmaceutically acceptable salt thereof.

30. The compound of claim 22 wherein R is phenyl, 2,6-difluorophenyl, 2,5-difluorophenyl, 2,4-difluorophenyl, 2,3-difluorophenyl, 2-fluorophenyl, 3-fluorophenyl, 2-fluoro-5-nitrophenyl, 4-aminocarbonyl-2-fluorophenyl, 3-aminocarbonyl-6-fluorophenyl, 2-fluoro-5-isopropylaminocarbonylphenyl, 2-fluoro-5-cyclopropylaminocarbonylphenyl, 2-fluoro-5-phenylaminocarbonylphenyl, 2-fluoro-3-diethylaminocarbonylphenyl, 2-fluoro-5-diethylaminocarbonylphenyl, 2-fluoro-5-dimethylaminocarbonylphenyl, 2-fluoro-5-benzylaminocarbonylphenyl, 2-fluoro-5-tert-butylaminocarbonylphenyl, 2-fluoro-5-butylaminocarbonylphenyl, 2-fluoro-5-propylaminocarbonylphenyl, 2-fluoro-5-ethylaminocarbonylphenyl, 3-cyclopropylaminocarbonylphenyl, 3-cyclopropylaminocarbonyl-6-fluorophenyl, 2-fluoro-5-cyclohexylaminocarbonylphenyl, 2-fluoro-5-(piperidin-1-ylcarbonyl)phenyl, 2-fluoro-5-(morpholin-4-ylcarbonyl)phenyl, 2-fluoro-3-methoxyphenyl, 2-fluoro-5-methoxyphenyl, 2-fluoro-4-hydroxyphenyl, 2-hydroxyphenyl, 3-hydroxyphenyl, 3-methoxyphenyl, 3,5-dimethoxyphenyl, 3-isopropoxyphenyl, 3-trifluoromethoxyphenyl, 2-trifluoromethylphenyl, 3-aminophenyl, 3-amino-2-methylphenyl, 3-(1-hydroxyethyl)phenyl, 2-cyanophenyl, 3-cyanophenyl, 4-cyano-2-fluorophenyl, 2-cyano-6-fluorophenyl, 2-chlorophenyl, 2-chloro-6-fluorophenyl, 3-chloro-6-fluorophenyl, 4-chloro-2-fluorophenyl, 3-methylsulfonylphenyl, 2-fluoro-4-methylsulfonylphenyl, 4-methylsulfonylphenyl, 2,6-difluoro-4-methylsulfonylphenyl, 2-fluoro-4-methylsulfonylamino-phenyl, 4-aminosulfonyl-2-fluorophenyl, 3-dimethylaminophenyl, 3-amino-4-morpholinophenyl, 3-amino-6-trifluoromethoxyphenyl, 4-amino-2-fluorophenyl, 2-fluoro 4-methylcarbonylaminophenyl, ethynylphenyl, (1-chlorovinyl)benzene, 2-methylphenyl, 2-pyridyl, 3-pyridyl, 4-pyridyl, 2-hydroxy-3-pyridyl, 2-amino-4-pyridyl, 3-amino-5-pyridyl, 3-amino-2-pyridyl, 2-cyclopropyl-6-pyridyl, 4-cyclopropyl-2-pyridyl, 2-fluoro-5-methoxy-4-pyridyl, 5-fluoro-2-methoxy-4-pyridyl, 3-chloro-6-fluoro-5-pyridyl, 2-methoxy-6-pyridyl, 2-methoxy-4-pyridyl, 3-methoxy-5-pyridyl, 2,3-dimethoxy-5-pyridyl, 3-isopropoxy-5-pyridyl, 2-isopropoxy-4-pyridyl, 2-isopropoxy-6-pyridyl, 2-isopropoxy-5-chloro-6-pyridyl, 2-ethoxy-6-pyridyl, 2-fluoro-6-pyridyl, 3-fluoro-2-pyridyl, 3-fluoro-5-pyridyl, 3-methyl-2-pyridyl, 2-trifluoromethyl-6-pyridyl, 3-chloro-2-pyridyl, 2-tert-butylaminocarbonyl-6-pyridyl, 4-cyclopropylaminocarbonyl-2-pyridyl, 3-cyclopropylaminocarbonyl-5-pyridyl, 3-chloro-6-oxo-pyrid-4-yl, 4-isopropyl-2-pyrimidinyl, pyrimidin-5-yl, 2-amino-pyrimidin-5-yl, 2-hydroxypyrimidin-4-yl, 2-methoxypyrimidin-4-yl, 2,4-dimethoxy-pyrimidin-6-yl, 2-cyclopropylpyrimidin-6-yl, 2-(4-morpholinyl)-pyrimidin-4-yl, 2-amino-4-cyclopentylamino-pyrimidin-5-yl, 4-cyclopropylpyrimidin-2-yl, 4-oxo-pyrimidin-5-yl, 2-methoxy-pyrimidin-4-yl, 2-isopropoxypyrimidin-4-yl, 3-pyrazinyl, 2-cyclopropyl-6-pyrazinyl, 2-cyclopropylamino-6-pyrazinyl, 2-isopropoxy-6-pyrazinyl, 3-pyridazinyl, 4-amino-pyridazin-6-yl,
3-quinolyl, 2-hydroxy-3-quinolyl, 2-chloro-3-quinolyl, 7-methoxy-4-quinolyl, 7-fluoro-4-quinolyl, 7-cyano-4-quinolyl, 7-trifluoromethoxy-4-quinolyl, 2-methoxy-3-quinolyl, 1-methyl-2-oxo-quinolin-4-yl, 1-methyl-2-oxo-isoquinolin-6-yl, 6-quinoxalinyl, 3-trifluoromethyl-1H-pyrazolo[3,4-b]pyridin-5-yl, 3-trifluoromethyl-5-indazolyl, 1-methyl-2-oxo-2,3-dihydro-indol-5-yl, 1-(2-aminopyrimidin-4-yl)-2,3-dihydro-indol-6-yl, benzothiazol-5-yl, benzothiazol-6-yl, 4-methyl-3,4-dihydro-2H-pyrido[3,2-b][1,4]oxazin-7-yl, 4-methyl-3,4-dihydro-2H-1,4-benzoxazin-7-yl, 1H-pyrrolo[2,3-b]pyridin-5-yl, 1H-pyrrolo[2,3-b]pyridin-6-yl, imidazo[1,2-a]pyrazin-5-yl, [1,2,4]triazolo[4,3-a]pyridin-5-yl, 1,2,2',3',5',6'-hexahydrospiro[indole-3,4'-pyran]-4-yl and 2,3-dihydro-1,4-benzodioxin-6-yl, 1H-pyrazol-5-yl, 1-methyl-1H-pyrazol-4-yl, thiazol-2-yl, 2-(2-methylpiperidin-1-yl)thiazol-4-yl, 2-(pyrrolidin-1-yl)thiazol-4-yl,
4-pyranyl, 3-pyranyl, 5,6-dihydro-2H-pyran-3-yl, 3,6-dihydro-2H-pyran-4-yl, tetrahydro-4-pyranyl, tetrahydro-3-pyranyl, 2-oxo-pyrrolidin-1-yl, 2-oxo-piperidin-1-yl, morpholin-4-yl, 1-methyl-2-oxo-imidazolidin-3-yl, 1-piperidinyl,
phenylaminocarbonyl, benzylaminocarbonyl, or cyclopropylethenyl; or a pharmaceutically acceptable salt thereof.

31. The compound of claim 22 wherein $R^{1E}$ is H, hydroxy, methoxy, piperidin-3-yloxy, isopropylamino, 4-amino-piperidin-1-yl, methylamino, piperidin-3-ylamino, piperidin-4-ylamino, 4-aminopiperidin-1-yl, piperidin-4-yloxy or piperidin-3-yl; wherein $R^{1G}$ is H, hydroxy, or methoxy; or a pharmaceutically acceptable salt thereof.

32. The compound of claim 22 wherein $R^{1A}$ is piperidin-3-ylamino, piperidin-4-ylamino, piperidin-4-yl-N-methylamino, piperidin-3-yl-N-methylamino, pyrrolidin-3-ylamino, 3-azetidinylamino, cyclopropylamino, hydroxy, methoxy, isopropoxy, trifluoroethoxy, fluoroethoxy, 3-pyridyloxy, 3-azetidinyloxy, pyrrolidin-3-yloxy, piperidin-3-yloxy, 4-fluoro-piperidin-3-yloxy, 3-fluoro-piperidin-4-yloxy, 3-fluoro-piperidin-5-yloxy, 3-methyl-piperidin-3-yloxy, 3-methyl-piperidin-5-yloxy, 1-methyl-piperidin-4-yloxy, 4-isopropyl-piperidin-3-yloxy, 4-ethyl-piperidin-3-yloxy, 4-methyl-piperidin-3-yloxy, 4,4-dimethyl-piperidin-3-yloxy, 3,3-dimethyl-piperidin-4-yloxy, piperidin-4-yloxy, 1,2,3,6-tetrahydro-3-pyridinyloxy, 6-azaspiro[2.5]oct-4-yloxy, 5-azaspiro[2.5]oct-8-yloxy, 3-azabicyclo[4.1.0]hept-5-yloxy, ((3S)-4-methylidene-3-piperidinyl)oxy, piperidin-3-ylthio, methylamino, ethylamino, isopropylamino, tert-butylamino, dimethylamino, phenylamino, piperidin-3-ylmethyl, piperidin-4-ylmethyl, cyclopropyl, 3-pyridyl, 5-indazolyl, 1,4-diazepan-1-yl, 1-pyrrolidinyl, 3-hydroxypyrrolidin-1-yl, 3,4-dihydroxypyrrolidin-1-yl, 3-aminopyrrolidinyl, 4-aminopiperidin-1-yl, 3-aminopiperidinyl, 3-hydroxypiperidin-1-yl, 3,4-dihydroxypiperidin-1-yl, 4-hydroxypiperidinyl, 4-morpholinyl, 3-pyrazolyl, 3-azetidinyl, 1-piperazinyl, or 1-piperidinyl; or a pharmaceutically acceptable salt thereof.

33. The compound of claim 22 wherein $R^{1F}$ is 4-amino-piperidin-1-yl; or a pharmaceutically acceptable salt thereof.

34. The compound of claim 22 wherein $R^y$ is

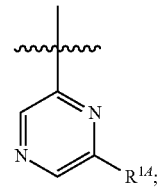

a pharmaceutically acceptable salt thereof.

35. The compound of claim 22 wherein $R^{1C}$ is H, hydroxy, methoxy, piperidin-3-ylamino, piperidin-4-ylamino, piperidin-4-yl-N-methylamino, piperidin-3-yl-N-methylamino, pyrrolidin-3-ylamino, 3-azetidinylamino, 3-pyridyl, 1-pyrrolidinyl, 3-hydroxypyrrolidin-1-yl, 3-aminopyrrolidinyl, 4-aminopiperidinyl, 3-aminopiperidinyl, 3-hydroxypiperidin-1-yl, 4-hydroxypiperidinyl, 4-morpholinyl, 3-pyrazolyl, 3-azetidinyl, 1-piperazinyl, or 1-piperidinyl; or a pharmaceutically acceptable salt thereof.

36. The compound of claim 22 wherein R is unsubstituted or substituted 5-membered heteroaryl; or a pharmaceutically acceptable salt thereof.

37. The compound of claim 22 wherein R is unsubstituted or substituted thiazolyl, unsubstituted or substituted imidazolyl, unsubstituted or substituted oxazolyl or unsubstituted or substituted pyrazolyl; or a pharmaceutically acceptable salt thereof.

38. The compound of claim 22 wherein R is pyrazolyl, thiazolyl, imidazolyl, or oxazolyl; wherein R is substituted or unsubstituted with one or more substituents selected from methyl, isopropyl, 2-methylpiperidin-1-yl, pyrrolidin-1-yl or oxo; or a pharmaceutically acceptable salt thereof.

39. The compound of claim 18 wherein $R^y$ is;

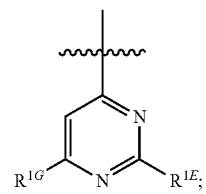

or a pharmaceutically acceptable salt thereof.

40. The compound of claim 22 wherein $R^y$ is

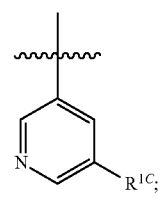

wherein $R^{1C}$ is H, hydroxy, methoxy or 4-aminopiperidin-1-yl; or a pharmaceutically acceptable salt thereof.

41. The compound of claim 22 wherein $R^y$ is

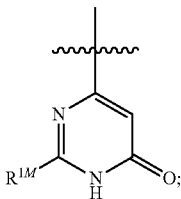

wherein $R^{1M}$ is butyl, dimethylamino, isopropylamino, isopropoxy, 3-fluoro-piperidin-4-yloxy, 4-fluoro-piperidin-3-yloxy, piperidin-3-yloxy, 6-azaspiro[2.5]octan-4-yloxy, 4-aminopiperidin-1-yl, 3-hydroxypyrrolidin-1-yl, piperidin-3-ylamino, piperidin-4-ylamino or 3-methylpiperidin-5-ylamino; or a pharmaceutically acceptable salt thereof.

42. A compound of Formula 4'

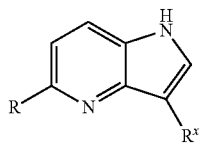

Wherein $R^x$ is

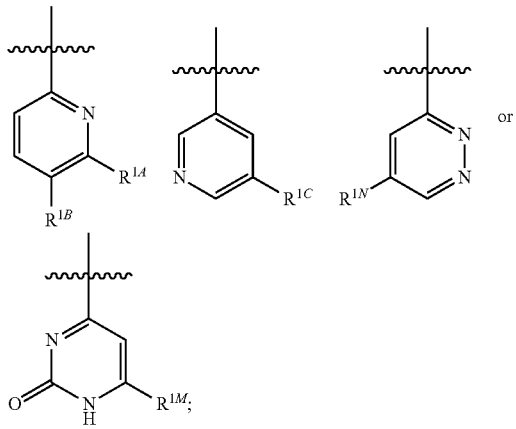

Wherein R is substituted or unsubstituted phenyl or substituted or unsubstituted 5-membered heteroaryl, or substituted or unsubstituted 6-membered heteroaryl;
Wherein $R^{1A}$ is H, methoxy, substituted or unsubstituted 6-membered heterocyclyl-amino or substituted or unsubstituted 6-membered heterocyclyl;
Wherein $R^{1B}$ is H or methoxy;
Wherein $R^{1C}$ is H, methoxy, substituted or unsubstituted 6-membered heterocyclyl, or substituted or unsubstituted 6-membered heterocyclyl-amino;
Wherein $R^{1M}$ is H, methoxy or substituted or unsubstituted 6-membered heterocyclyl; and
Wherein $R^{1N}$ is H or methoxy; and
or a pharmaceutically acceptable salt thereof.

43. The compound of claim 42 wherein R is substituted or unsubstituted phenyl; or a pharmaceutically acceptable salt thereof.

44. The compound of claim 42 wherein R is 2-fluorophenyl, or 2,6-difluorophenyl; or a pharmaceutically acceptable salt thereof.

45. The compound of claim 42 wherein $R^x$ is

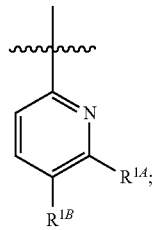

or a pharmaceutically acceptable salt thereof.

46. The compound of claim 42 wherein $R^{1A}$ is H, methoxy, piperid-3-ylamino or 4-amino-piperidyl; wherein $R^{1B}$ is H or methoxy; or a pharmaceutically acceptable salt thereof.

47. The compound of claim 42 wherein $R^x$ is

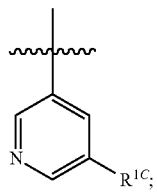

or a pharmaceutically acceptable salt thereof.

48. The compound of claim 42 wherein $R^{1C}$ is piperid-3-ylamino or 4-amino-piperidyl; or a pharmaceutically acceptable salt thereof.

49. A composition comprising a therapeutically effective amount of compound of claim 1, or a stereoisomer, tautomer, or pharmaceutically acceptable salt thereof, together with a pharmaceutically acceptable carrier.

50. A method for treating a cancer disorder in a patient, comprising administering to the patient a composition comprising an amount of a compound of claim 1 wherein the cancer is multiple myeloma or Non Hodgkins Lymphoma, or AML.

51. A compound of claim 1 selected from
5-(6-cyclopropyl-2-pyrazinyl)-3-(6-(4-piperidinyloxy)-2-pyrazinyl)-1H-indazole;
6-(5-(6-cyclopropyl-2-pyrazinyl)-1H-indazol-3-yl)-N-(1-methylethyl)-2-pyrazinamine;
N-cyclopropyl-6-(3-(6-methoxy-2-pyrazinyl)-1H-indazol-5-yl)-2-pyrazinamine;
5-(6-cyclopropyl-2-pyrazinyl)-3-(6-(((3R,4S)-3-fluoro-4-piperidinyl)oxy)-2-pyrazinyl)-1H-indazole;
5-(6-cyclopropyl-2-pyrazinyl)-3-(6-(((3S,4R)-3-fluoro-4-piperidinyl)oxy)-2-pyrazinyl)-1H-indazole;
5-(6-cyclopropyl-2-pyrazinyl)-3-(6-(((3R,4R)-3-fluoro-4-piperidinyl)oxy)-2-pyrazinyl)-1H-indazole;
5-(6-cyclopropyl-2-pyrazinyl)-3-(6-(((3S,4S)-3-fluoro-4-piperidinyl)oxy)-2-pyrazinyl)-1H-indazole;
6-(3-(6-(4-amino-1-piperidinyl)-2-pyrazinyl)-1H-indazol-5-yl)-N-cyclopropyl-2-pyrazinamine;
6-(3-(6-(2-fluoroethoxy)-2-pyrazinyl)-1H-indazol-5-yl)-2-pyrazinamine;
1-(6-(5-(6-cyclopropyl-2-pyrazinyl)-1H-indazol-3-yl)-2-pyrazinyl)-4-piperidinamine;

6-(5-(6-cyclopropyl-2-pyrazinyl)-1H-indazol-3-yl)-N-4-piperidinyl-2-pyrazinamine;
6-(5-(6-cyclopropyl-2-pyrazinyl)-1H-indazol-3-yl)-N-((3R)-3-piperidinyl)-2-pyrazinamine;
(4-(3-(6-((3R)-3-piperidinyloxy)-2-pyrazinyl)-1H-indol-5-yl)phenyl)methanol;
1-(6-(5-(6-cyclopropyl-2-pyrazinyl)-1H-indol-3-yl)-2-pyrazinyl)-4-piperidinamine;
5-(4-(4-morpholinyl)phenyl)-3-(6-((3R)-3-piperidinyloxy)-2-pyrazinyl)-1H-indole;
3-(6-((8R)-5-azaspiro[2.5]oct-8-yloxy)-2-pyrazinyl)-5-(6-cyclopropyl-2-pyrazinyl)-1H-indazole;
5-(1-cyclopropyl-1H-pyrazol-4-yl)-3-(6-((3R)-3-piperidinyloxy)-2-pyrazinyl)-1H-indole;
5-(1-(1-methylethyl)-1H-pyrazol-4-yl)-3-(6-((3R)-3-piperidinyloxy)-2-pyrazinyl)-1H-indole;
5-(3-fluoro-4-pyridinyl)-3-(6-((3R)-3-piperidinyloxy)-2-pyrazinyl)-1H-indole;
3,5-bis(6-cyclopropyl-2-pyrazinyl)-1H-indazole;
1-(6-(5-(6-cyclopropyl-2-pyrazinyl)-1H-indol-3-yl)-2-pyrazinyl)-4-piperidinamine;
3-(6-((4R)-6-azaspiro[2.5]oct-4-yloxy)-2-pyrazinyl)-5-(3,6-dihydro-2H-pyran-4-yl)-1H-indazole;
3-(6-((4R)-6-azaspiro[2.5]oct-4-yloxy)-2-pyrazinyl)-5-(2,6-difluorophenyl)-1H-indole;
3-(6-((4S)-6-azaspiro[2.5]oct-4-yloxy)-2-pyrazinyl)-5-(2,6-difluorophenyl)-1H-indole;
5-(6-cyclopropyl-2-pyrazinyl)-3-(6-(4-piperidinyloxy)-2-pyrazinyl)-1H-indazole;
6-(5-(6-cyclopropyl-2-pyrazinyl)-1H-indazol-3-yl)-N-(1-methylethyl)-2-pyrazinamine;
N-cyclopropyl-6-(3-(6-methoxy-2-pyrazinyl)-1H-indazol-5-yl)-2-pyrazinamine;
5-(6-cyclopropyl-2-pyrazinyl)-3-(6-(((3R,4S)-3-fluoro-4-piperidinyl)oxy)-2-pyrazinyl)-1H-indazole;
5-(6-cyclopropyl-2-pyrazinyl)-3-(6-(((3S,4R)-3-fluoro-4-piperidinyl)oxy)-2-pyrazinyl)-1H-indazole;
5-(6-cyclopropyl-2-pyrazinyl)-3-(6-(((3R,4R)-3-fluoro-4-piperidinyl)oxy)-2-pyrazinyl)-1H-indazole;
5-(6-cyclopropyl-2-pyrazinyl)-3-(6-(((3S,4S)-3-fluoro-4-piperidinyl)oxy)-2-pyrazinyl)-1H-indazole;
6-(3-(6-(4-amino-1-piperidinyl)-2-pyrazinyl)-1H-indazol-5-yl)-N-cyclopropyl-2-pyrazinamine;
6-(3-(6-(2-fluoroethoxy)-2-pyrazinyl)-1H-indazol-5-yl)-2-pyrazinamine;
1-(6-(5-(6-cyclopropyl-2-pyrazinyl)-1H-indazol-3-yl)-2-pyrazinyl)-4-piperidinamine;
6-(5-(6-cyclopropyl-2-pyrazinyl)-1H-indazol-3-yl)-N-4-piperidinyl-2-pyrazinamine;
6-(5-(6-cyclopropyl-2-pyrazinyl)-1H-indazol-3-yl)-N-((3R)-3-piperidinyl)-2-pyrazinamine;
(4-(3-(6-((3R)-3-piperidinyloxy)-2-pyrazinyl)-1H-indol-5-yl)phenyl)methanol;
N-cyclopropyl-6-(5-(6-cyclopropyl-2-pyrazinyl)-1H-indazol-3-yl)-2-pyrazinamine;
5-(4-(4-morpholinyl)phenyl)-3-(6-((3R)-3-piperidinyloxy)-2-pyrazinyl)-1H-indole;
3-(6-((8R)-5-azaspiro[2.5]oct-8-yloxy)-2-pyrazinyl)-5-(6-cyclopropyl-2-pyrazinyl)-1H-indazole;
5-(1-cyclopropyl-1H-pyrazol-4-yl)-3-(6-((3R)-3-piperidinyloxy)-2-pyrazinyl)-1H-indole;
5-(1-(1-methylethyl)-1H-pyrazol-4-yl)-3-(6-((3R)-3-piperidinyloxy)-2-pyrazinyl)-1H-indole;
5-(3-fluoro-4-pyridinyl)-3-(6-((3R)-3-piperidinyloxy)-2-pyrazinyl)-1H-indole;
1-(6-(5-(6-cyclopropyl-2-pyrazinyl)-1H-indol-3-yl)-2-pyrazinyl)-4-piperidinamine;
3-(6-((4R)-6-azaspiro[25]oct-4-yloxy)-2-pyrazinyl)-5-(3,6-dihydro-2H-pyran-4-yl)-1H-indazole;
3-(6-((4R)-6-azaspiro[2.5]oct-4-yloxy)-2-pyrazinyl)-5-(2,6-difluorophenyl)-1H-indole;
3-(6-((4S)-6-azaspiro[2.5]oct-4-yloxy)-2-pyrazinyl)-5-(2,6-difluorophenyl)-1H-indole;
3-(6-((8R)-5-azaspiro[2.5]oct-8-yloxy)-2-pyrazinyl)-5-(6-cyclopropyl-2-pyrazinyl)-1H-indazole;
3,5-bis(6-cyclopropyl-2-pyrazinyl)-1H-indazole; and
3-(6-((8S)-5-azaspiro[2.5]oct-8-yloxy)-2-pyrazinyl)-5-(6-cyclopropyl-2-pyrazinyl)-1H-indazole;
or a pharmaceutically acceptable salt thereof.

* * * * *